US011632922B2

(12) United States Patent
Abdullah et al.

(10) Patent No.: US 11,632,922 B2
(45) Date of Patent: *Apr. 25, 2023

(54) MANTLE PHENOTYPE DETECTION IN PALM

(71) Applicant: Malaysian Palm Oil Board, Kajang Selangor (MY)

(72) Inventors: Meilina Ong Abdullah, Seremban (MY); Ooi Siew Eng, Kuala Lumpur (MY); Leslie Low Eng Ti, Kuala Lumpur (MY); Rajinder Singh, Kuala Lumpur (MY); Rajanaidu Nookiah, Kuala Lumpur (MY); Ravigadevi Sambanthamurthi, Selangor (MY); Nan Jiang, St. Louis, MO (US); Steven W. Smith, Fitchburg, WI (US); Nathan D. Lakey, Chesterfield, MO (US); Rob Martienssen, Cold Spring Harbor, NY (US); Jared Ordway, St. Louis, MO (US); Michael Hogan, Ballwin, MO (US)

(73) Assignee: Malaysian Palm Oil Board, Selangor (MY)

( * ) Notice: Subject to any disclaimer, the term of this patent is extended or adjusted under 35 U.S.C. 154(b) by 549 days.

This patent is subject to a terminal disclaimer.

(21) Appl. No.: 15/962,359

(22) Filed: Apr. 25, 2018

(65) Prior Publication Data

US 2018/0314794 A1 Nov. 1, 2018

Related U.S. Application Data

(63) Continuation of application No. 14/701,425, filed on Apr. 30, 2015, now Pat. No. 9,984,200.

(60) Provisional application No. 61/988,132, filed on May 2, 2014, provisional application No. 62/091,471, filed on Dec. 12, 2014.

(51) Int. Cl.
| | |
|---|---|
| *A01H 1/04* | (2006.01) |
| *C12N 15/113* | (2010.01) |
| *G16B 30/00* | (2019.01) |
| *G16B 20/20* | (2019.01) |
| *C12Q 1/6895* | (2018.01) |
| *G16B 20/00* | (2019.01) |

(52) U.S. Cl.
CPC ............ *A01H 1/04* (2013.01); *C12N 15/113* (2013.01); *C12Q 1/6895* (2013.01); *G16B 20/20* (2019.02); *G16B 30/00* (2019.02); *C12N 2310/14* (2013.01); *C12Q 2537/164* (2013.01); *C12Q 2600/13* (2013.01); *C12Q 2600/154* (2013.01); *C12Q 2600/158* (2013.01); *C12Q 2600/16* (2013.01); *G16B 20/00* (2019.02)

(58) Field of Classification Search
CPC .............................................. C12Q 2537/164
See application file for complete search history.

(56) References Cited

U.S. PATENT DOCUMENTS

| | | |
|---|---|---|
| 4,910,146 A | 3/1990 | Tur-Kaspa et al. |
| 5,786,146 A | 7/1998 | Herman et al. |
| 5,972,602 A | 10/1999 | Hyland et al. |
| 6,033,854 A | 3/2000 | Kurnit et al. |
| 6,180,349 B1 | 1/2001 | Ginzinger et al. |
| 6,307,123 B1 | 10/2001 | Kriz et al. |
| 6,646,264 B1 | 11/2003 | Modiano et al. |
| 6,673,595 B2 | 1/2004 | Barbera-Guillem |
| 6,880,771 B2 | 4/2005 | Deppermann |
| 7,186,512 B2 | 3/2007 | Martienssen et al. |
| 7,367,155 B2 | 5/2008 | Kotyk et al. |
| 7,402,731 B2 | 7/2008 | Penner et al. |
| 7,454,989 B2 | 11/2008 | Deppermann |
| 7,600,642 B2 | 10/2009 | Deppermann |
| 7,673,572 B2 | 3/2010 | Depperman et al. |
| 7,685,768 B2 | 3/2010 | Deppermann |
| 7,901,880 B2 | 3/2011 | Jeddeloh et al. |
| 7,909,276 B2 | 3/2011 | Deppermann et al. |
| 7,910,296 B2 | 3/2011 | Jeddeloh et al. |
| 7,998,669 B2 | 8/2011 | Deppermann et al. |
| 8,076,076 B2 | 12/2011 | Osborn et al. |
| 8,114,669 B2 | 2/2012 | Choo |
| 8,163,485 B2 | 4/2012 | Jeddeloh et al. |
| 8,221,968 B2 | 7/2012 | Becker et al. |
| 8,237,016 B2 | 8/2012 | Ye et al. |
| 8,241,914 B2 | 8/2012 | Durack et al. |
| 8,281,935 B2 | 10/2012 | Depermann |
| 8,312,672 B2 | 11/2012 | Deppermann et al. |

(Continued)

FOREIGN PATENT DOCUMENTS

| | | |
|---|---|---|
| EP | 2787004 A1 | 10/2014 |
| WO | 00/70090 A1 | 11/2000 |

(Continued)

OTHER PUBLICATIONS

Jaligot, Estelle, et al. "DNA methylation and expression of the EgDEF1 gene and neighboring retrotransposons in mantled somaclonal variants of oil palm." PloS one 9.3 (2014): e91896. (Year: 2014).*
GenBank: KF142646.1 (Year: 2014).*
GenBank: KF142645.1 (Year: 2014).*
Adam et al., "Reproductive developmental complexity in the African oil palm (*Elaeis guineensis*, Arecaceae)", *Am J Bot*, 92(11): 1836-1853 (2005).

(Continued)

*Primary Examiner* — Brent T Page
(74) *Attorney, Agent, or Firm* — Kilpatrick Townsend & Stockton LLP

(57) ABSTRACT

Methods, compositions, kits, and computer program code are provided for predicting somaclonal abnormality (e.g., a Mantled phenotype) in a plant and or sorting plants based on the predicted presence or absence of somaclonal abnormality.

10 Claims, 17 Drawing Sheets

Specification includes a Sequence Listing.

(56) References Cited

U.S. PATENT DOCUMENTS

| | | | |
|---|---|---|---|
| 8,361,719 | B2 | 1/2013 | Jeddeloh et al. |
| 8,362,317 | B2 | 1/2013 | Calabotta et al. |
| 8,401,271 | B2 | 3/2013 | Depperman et al. |
| 8,443,545 | B2 | 5/2013 | Deppermann et al. |
| 9,984,200 | B2 * | 5/2018 | Abdullah ............... G16B 30/00 |
| 2005/0069879 | A1 | 3/2005 | Berlin |
| 2006/0112449 | A1 | 5/2006 | Van der Linden et al. |
| 2007/0224626 | A1 | 9/2007 | Jeddeloh et al. |
| 2013/0247249 | A1 | 9/2013 | Singh et al. |
| 2014/0302497 | A1 | 10/2014 | Singh et al. |
| 2015/0315662 | A1 | 11/2015 | Abdullah et al. |

FOREIGN PATENT DOCUMENTS

| | | |
|---|---|---|
| WO | 2011/119390 A1 | 9/2011 |
| WO | 2011/119394 A1 | 9/2011 |
| WO | 2015168470 A2 | 11/2015 |
| WO | 2015168470 A3 | 1/2016 |

OTHER PUBLICATIONS

Adam et al., "MADS Box Genes in Oil Palm (*Elaeis guineensis*): Patterns in the Evolution of the SQUAMOSA, DEFICIENS, GLOBOSA, AGAMOUS, and SEPALLATA Subfamilies", *J Mol Evol*, 62(1):15-31 (2006).

Adam et al., "Determination of flower structure in *Elaeis guineensis*: do palms use the same homeotic genes as other species?", *Ann Bot*, 100(1): 1-12 (2007).

Adam et al., "Functional characterization of MADS box genes involved in the determination of oil palm flower structure", *J Exp Bot*, 58(6):1245-1259 (2007).

Alwee et al., "Characterization of Oil palm MADS box genes to the mantled flower abnormality", *Plant Cell, Tissue and Organ Culture*, 85:331-344 (2006).

Auyong et al., "'MADS-box directed profiling for the detection of oil palm variations", Proceedings of the Pipoc 2005 International Palm Oil Congress, Agriculture, Biotechnology and Sustainability (2005).

Auyong, "MADS box genes and DNA methylation polymorphisms as markers fortissue culture-induced mantled flower abnormalities in oil palm", M.Sc. thesis. University Putra Malaysia (2006), abstract only.

Castilho et al., "Repetitive DNA and the Chromosomes in the Genome of Oil Palm (*Elaeis guineensis*)", *Annals of Botany*, 85(6):837-844 (2000).

Jaligot et al., "Methylation-sensitive RFLPs: characterisation of two oil palm markers showing somaclonal variation-associated polymorphism", *Theor Appl Genet.*, 104(8): 1263-1269 (2002).

Jaligot et al., "Search for methylation-sensitive amplification polymorphisms associated with the mantled variant phenotype in oil palm (*Elaeis guineensis Jacq*).", *Genome*, 47(1): 224-248 (2004).

Jaligot et al., "Somaclonal variation in oil palm (*Elaeis guineensis Jacq*): the DNY methylation hypothesis", *Plant Cell Reports*, 19:684-690 (2000).

Jaligot et al., "DNA methylation and expression of the EgDEF1 gene and neighboring retrotransposons in mantled somaclonal variants of oil palm", *PLos One*, 9(3):e91896 (2014).

Jiang et al., "Regenerant Arabidopsis lineages display a distinct genome-wide spectrum of mutations conferring variant phenotypes", *Curr Biol*, 21 (16):1385-1390 (2011).

Kubis et al., "Retroelements, transposons and methylation status in the genome of oil palm (*Elaeis guineensis*) and the relationship to somaclonal variation", *Plant Mol Biol*, 52(1):69-79 (2003).

Matthes et al., "Variation in oil palm (*Elaeis guineensis Jacq.*) tissue culture-derived regenerants revealed by AFLPs with methylation-sensitive enzymes", *Theoretical and Applied Genetics*, 102: 971-979 (2001).

Miguel et al., "An epigenetic view of plant cells cultured in vitro: somaclonal variation and beyond", *J Exp Bot.*, 62(11):3713-3725 (2011).

Miyao et al., "Molecular spectrum of somaclonal variation in regenerated rice revealed by whole-genome sequencing", *Plant Cell Physiol*, 53(1):256-264 (2012).

Stelpflug et al., "Consistent and heritable alterations of DNA methylation are induced by tissue culture in maize", *Genetics*, 198(1):209-218 (2014).

Stroud et al., "Plants regenerated from tissue culture contain stable epigenome changes in rice", *eLife*, 14 pages (2013).

Tanurdzic et al., "Epigenomic consequences of immortalized plant cell suspension culture", *PLos Biol.*, 6(12):2880-2895 (2008).

Van der Linden et al., "Cloning and characterization of four apple MADS box genes isolated from vegetative tissue", *J Exp Bot.*, 53(371):1025-1036 (2002).

GenBank: KF 142646.1, "Elaeis quineensis disrupted DEF1 gene, partial sequence; and retrotransposons RLB_Koala_Eg133H20-1 and RLC-Rider-Eg133H20-1, complete sequence", 28 pages (2014). http://www.ncbi.hlm.nih.gov/nuccore/KF142S46 (downloaded Aug. 30, 2015).

PCT/US2015/028646, International Search Report and Written Opinion dated Nov. 24, 2015, 19 pages.

PCT/US2015/028646, "International Preliminary Report on Patentability", dated Nov. 17, 2016, 12 pages.

PCT/US2015/028646, "Invitation to Pay Additional Fees and Partial Search Report", dated Sep. 9, 2015, 5 pages.

Jaligot et al. (Mar. 2014, PLoS One 9 (3):e91896).

Rival et al (2009, Acta Horticulturae 829 (Proceedings of the VIth International Symposium on In Vitro Culture and Horticultural Breeding, 2008: 177-181).

U.S. Appl. No. 14/701,425, "Corrected Notice of Allowance", dated Feb. 13, 2018, 6 pages.

U.S. Appl. No. 14/701,425, "Non-Final Office Action", dated May 4, 2017, 14 pages.

U.S. Appl. No. 14/701,425, "Notice of Allowance", dated Jan. 26, 2018, 12 pages.

U.S. Appl. No. 14/701,425, "Restriction Requirement", dated Dec. 30, 2016, 13 pages.

CONC2016/0004468, "Office Action", dated Dec. 14, 2016.

CONC20160004468, "Office Action", dated Sep. 27, 2018, 31 pages.

EP15786526.2, "Office Action", dated May 7, 2020, 4 pages.

* cited by examiner

MANTLE PHENOTYPE DETECTION IN PALM

CROSS-REFERENCE TO RELATED PATENT APPLICATIONS

This application is a continuation of U.S. patent application Ser. No. 14/701,425, filed Apr. 30, 2015, which claims priority to U.S. Provisional Patent Application No. 61/988,132, filed on May 2, 2014, and U.S. Provisional Patent Application No. 62/091,471, filed on Dec. 12, 2014, the contents of each of which are hereby incorporated by reference in the entirety and for all purposes.

REFERENCE TO A "SEQUENCE LISTING," A TABLE, OR A COMPUTER PROGRAM LISTING APPENDIX SUBMITTED AS AN ASCII TEXT FILE

The Sequence Listing written in file SEQ_096380-1083067.txt, created on Apr. 6, 2018, 421,008 bytes, machine format IBM-PC, MS-Windows operating system, is hereby incorporated by reference.

BACKGROUND OF THE INVENTION

The oil palm belongs to the genus *Elaeis* which contains two species, *E. guineensis* and *E. oleifera*. It is regarded as the most efficient oil bearing crop in the world out yielding all other crops of the same genre, e.g., soybean, rapeseed and sunflower. The ability to produce oil at an average yield of 3.74 tonne/ha/year, on land 10 times smaller than the requirement for soybean (Oil World, 2007) and with a productive life cycle of 25-30 years, makes the oil palm a lucrative agricultural crop. However, of late the oil yield has reached stagnation. Nevertheless, demand for edible oils is predicted to escalate to feed the growing world population.

The oil palm has gone through at least two known cycles of yield improvements since its introduction as an oil crop in Malaysia, the first wave being the introduction of the hybrid tenera (DxP), which replaced the dura as commercial planting material. This demonstrated an increase in oil yield of up to 30% by merely manipulating a single gene (Kushairi et al., 2006; Singh et al., 2013). However, the average oil yield in Malaysia has hovered between 3.5 and 3.9 t/ha/yr for the last two decades. Having dropped to the number two spot in palm oil production, Malaysia—and all other palm oil producing countries—is in need of yield improvement. This is further compounded by the fact that agricultural land is becoming a rarity. Therefore increased production by planting larger areas is no longer seen as an alternative.

Through years of breeding and selection, the palm oil industry has already produced palms yielding as high as 13.6 t/ha/yr (Sharma and Tan, 1999) which are close to the theoretical yield of 18.2 t/ha/yr (Corley, 1998). The best experimental plot has produced an average of 9.8 t/ha/yr of palm oil (Musa and Gurmit, 2008) with selected progenies able to achieve up to 12.2 t/ha/yr (Rajanaidu et al., 1990). Cloning these super palms may provide the industry with the much-needed high-yielding planting materials to get it out of the stagnation rut. Hence, clones for commercial use are touted as the second wave of crop improvement for the oil palm.

Due to its biological structure, the oil palm has no natural means of vegetative propagation and conventional hybrid breeding methodology would require at least three generations, or over 20 years, to realize such superior yields (Soh et al., 2005). Successful vegetative propagation of oil palm was first described in the 1970s (Jones, 1974; Rabechault and Martin, 1976). Jones (1995) gave a rather comprehensive and personal account of its development. These successful reports of oil palm cloning prompted the development of tissue culture laboratories to provide clonal oil palm planting material. Encouraging results from early field trials set the pace for more laboratories to follow suit. By the mid-1980's, there were already 10 clonal oil palm laboratories in Malaysia (Wooi, 1990) and others elsewhere (Le Guen et al., 1991).

However, when Corley et al. (1986) reported the mantling phenomenon for the first time, the whole clonal industry led by the pioneering Bakasawit/Unifield and Tropiclone commercial laboratories decided to cut back on production and reverted to research and development. The then, Palm Oil Research Institute of Malaysia (PORIM), now known as Malaysian Palm Oil Board (MPOB), as the custodian of the palm oil industry, was assigned the task of spearheading research in clonal abnormalities.

Through a concerted effort, by the early 1990's, the results obtained suggested that better tissue culture protocols needed to be established, which included subculturing procedures and the use of less devastating types of growth regulators. Alternative methods were also proposed such as suspension and protoplast cultures as a means to avoid subculturing. Cloning of dura and pisifera parents, followed by conventional crossing to circumvent the potential occurrence of somaclonal variants from clonal teneras, was amongst the different methods discussed (Ong-Abdullah, Viva 562/2011). Interestingly, up to 10% of abnormal palms spontaneously reverted to normal and remained normal for some time (Durand-Gasselin et al., 1990). Seedlings developed from Mantled fruits e.g., clone 115E, were normal; refuting the possibility that abnormality is due to a dominant gene effect or to maternally transmitted factors. Through conventional genetic crossings conducted by Rao and Donough (1990), this trait was also shown to behave in a non-Mendelian manner.

Earlier attempts that employed techniques such as flow cytometry, random amplified polymorphic DNA (RAPD) or the classical amplified fragment length polymorphisms (AFLP) analysis failed to yield any detectable differences between Mantled and normal palms (Rival et al. 1997, 1998; Matthes et al. 2001). However, when methylation sensitive or related technologies were utilized, the methylation level of the Mantled genome appeared to be altered (Jaligot et al. 2002, Matthes et al. 2001, Jaligot et al. 2004).

Subsequently, further research concentrated on understanding the underlying molecular cause(s) and epigenetic regulation of mantling. It was also known that in Mantled oil palms, staminodes and stamens of pistillate and functional flowers develop respectively as pseudocarpels (Morcillo et al., 2006). In severe cases, the flowers are sterile with abortive fruits leading to lower yields. It was postulated that since homeotic modifications had taken place, it was highly likely that the B-function homeotic MADS box genes of the ABCDE model for flower organ identity (Murai, 2013) are involved.

Following the MADS box hypothesis, MADS-box containing genes from the oil palm were isolated (Alwee et al., 2006; Auyong, 2006) using the MADS box-directed profiling technique (van der Linden et al. 2002). This method allows the visualization of DNA polymorphisms in restriction sites at the MADS box vicinity among normal, abnormal and reverted oil palms. Two markers, namely MM77 and MM78 (EP Patent Appl. No. 13162130.2) were identified and the latter was widely used for further validation although it was found not to fall in the class of MADS box genes. In the course of validating MM78 and from past experiences with other unrelated markers, it was confirmed that the functional use of these markers is genotype dependent. Therefore, they have little or no use when tested on clones from other genetic backgrounds. This has been the main point of contention in biomarker development for clonal fidelity of the oil palm.

Previous studies have found an overall decrease in DNA methylation in mantled palms relative to ortets and normal ramets (Jaligot et al. 2000; Matthes et al. 2001; Jaligot et al. 2002; Jaligot et al. 2004). These results are similar to observations in *Arabidopsis* and other plant cell cultures, in which transposable elements (TEs) are hypomethylated and expressed (Tanurdzic et al. 2008; Miguel et al. 2011; Castilho et al. 2000; Kubis et al. 2003). In addition to TEs, somaclonal regenerants in rice and maize undergo extensive gene and promoter hypomethylation (Stroud et al. 2013; Stelpflug et al. 2014), which might also contribute to somaclonal variation in oil palm and other crops. The homeotic transformations observed in mantled palms resemble defects in B-function MADS box genes, suggesting that retroelements within one or more MADS box genes, or the MADS box genes themselves are candidates for epigenetic modification (Adam et al. 2005). However, decades of research into DNA methylation changes in candidate retroelements (Castilho et al. 2000; Kubis et al. 2003; Jaligot et al. 2014) and candidate homeotic genes (Syed Alwee et al. 2006; Adam et al. 2007; Jaligot et al. 2014) have yet to identify epigenetic changes that are consistently found in somaclonal mantled palms. And indeed, recent studies of rice and *Arabidopsis* plants regenerated from tissue culture implicate genetic rather than epigenetic mechanisms as being responsible for somaclonal variation (Jiang et al. 2011; Miyao et al. 2012.

BRIEF SUMMARY OF THE INVENTION

Described herein are methods, compositions, and kits for predicting the presence or absence of a somaclonal abnormality (e.g., Mantled) in an oil palm plant, plant cell, or plant tissue. In some embodiments, the present invention provides a method for segregating an oil palm plant comprising: a) obtaining a biological sample from the plant; b) determining the methylation status of at least one cytosine within a differential methylation region (DMR) in the sample from the plant, wherein the DMR is within a sequence of DNA at least 70%, 80%, 90%, 95%, or 99% identical, or identical, to SEQ ID NO:1; c) correlating the methylation status of the at least one cytosine to the presence or absence of a somaclonal abnormality in the plant, wherein the correlation comprises predicting the presence or absence of somaclonal abnormality in the plant; and d) physically separating a plant predicted to have a somaclonal abnormality from one or more plants predicted to lack a somaclonal abnormality.

In some aspects, the DMR is within a DNA meta-region in the sample from the plant, where the DNA meta-region is at least 90%, 95%, or 99% identical, or identical, to a sequence selected from the group consisting of SEQ ID NO:63, 64, 65, 66, 67, 68, 69, and 70. In some aspects, the DMR is within a DNA region in the sample from the plant, where the DNA region is at least 70%, 80%, 90%, 95%, or 99% identical, or identical, to a sequence selected from the group consisting of SEQ ID NO:35, 36, 37, 38, 39, 40, 41, 42, 43, 44, 45, 46, 47, 48, 49, 50, 51, 52, 53, 54, 55, 56, 57, 58, 59, 60, 61, 62, 73, and 74. In some cases, the determining step comprises determining the methylation status of at least one cytosine in a biomarker, wherein the biomarker is at least 90%, 95%, or 99% identical, or identical, to a sequence selected from the group consisting of SEQ ID NO:7, 8, 9, 10, 11, 12, 13, 14, 15, 16, 17, 18, 19, 20, 21, 22, 23, 24, 25, 26, 27, 28, 29, 30, 31, 32, 33, 34, 71, and 72.

In some aspects the method comprises predicting the presence of a somaclonal abnormality when the methylation status of the at least one cytosine is reduced relative to a control locus. In some cases, the presence of a somaclonal abnormality is predicted when the methylation status of the at least one cytosine in the DNA meta-region at least 70%, 80%, 90%, 95%, or 99% identical, or identical, to the sequence selected from the group consisting of SEQ ID NO:63, 64, 65, 66, 67, 69, and 70 (or selected from the group consisting of SEQ ID NO:63, 64, 65, 66, 67, 68, 69, and 70) is reduced relative to a control locus. In some cases, the presence of a somaclonal abnormality is predicted when the methylation status of the at least one cytosine in the DNA region is at least 70%, 80%, 90%, 95%, or 99% identical, or identical, to the sequence selected from the group consisting of SEQ ID NO:35, 36, 39, 40, 42, 43, 44, 45, 46, 48, 49, 51, 52, 57, 58, 59, 60, 61, and 73 is reduced relative to a control locus. In some cases, the presence of a somaclonal abnormality is predicted when the methylation status of the at least one cytosine in the biomarker at least 90%, 95%, or 99% identical, or identical to the sequence selected from the group consisting of SEQ ID NO:7, 8, 11, 12, 14, 15, 16, 17, 18, 20, 21, 23, 24, 29, 30, 31, 32, 33, and 71 is reduced relative to a control locus.

In some aspects, the method comprises predicting the presence of a somaclonal abnormality when the methylation status of the at least one cytosine is increased relative to a control locus. In some cases, the presence of a somaclonal abnormality is predicted when the methylation status of the at least one cytosine in the DNA meta-region at least 70%, 80%, 90%, 95%, or 99% identical, or identical, to the sequence selected from the group consisting of SEQ ID NO:63, 64, 65, 66, 67, 68, and 69 (or selected from the group consisting of SEQ ID NO:63, 64, 65, 66, 67, 68, 69, and 70) is increased relative to a control locus. In some cases, the presence of a somaclonal abnormality is predicted when the methylation status of the at least one cytosine in the DNA region at least 70%, 80%, 90%, 95%, or 99% identical, or identical, to the sequence selected from the group consisting of SEQ ID NO:35, 36, 37, 38, 41, 42, 47, 50, 52, 53, 54, 55, 56, 57, 62, and 74 is increased relative to a control locus. In some cases, the presence of a somaclonal abnormality is predicted when the methylation status of the at least one cytosine in the biomarker at least 90%, 95%, or 99% identical, or identical to the sequence selected from the group consisting of SEQ ID NO:7, 8, 9, 10, 13, 14, 19, 22, 24, 25, 26, 27, 28, 29, 34 and 72 is increased relative to a control locus.

In some aspects, the method comprises predicting the presence of a somaclonal abnormality when the methylation status of the at least one cytosine is either increased or decreased relative to a control locus. In some cases, the control locus is an endogenous control locus. In some cases, the control locus is an exogenous control locus.

In some aspects, the determining step comprises determining the methylation status of at least one cytosine in at least two, three or four different differential methylation regions (DMRs), wherein each DMR is independently within a sequence of DNA at least 70%, 80%, or 90%, 95%, or 99% identical, or identical, to SEQ ID NO:1. In some cases, each DMR is within a DNA meta-region in the sample from the plant, where each DNA meta-region is at least 70%, 80%, 90%, 95%, or 99% identical, or identical, to a sequence independently selected from the group consisting of SEQ ID NO:63, 64, 65, 66, 67, 68, 69, and 70. In some cases, each DMR is within a DNA region in the sample from the plant, where the DNA region is at least 70%, 80%, 90%, 95%, or 99% identical, or identical, to a sequence independently selected from the group consisting of SEQ ID NO:35, 36, 37, 38, 39, 40, 41, 42, 43, 44, 45, 46, 47, 48, 49, 50, 51, 52, 53, 54, 55, 56, 57, 58, 59, 60, 61, 62, 73, and 74. In some cases, the determining step comprises determining the methylation status of at least one cytosine in a biomarker in each DMR, wherein each biomarker is at least 90%, 95%, or 99% identical, or identical, to a sequence independently selected from the group consisting of SEQ ID NO:7, 8, 9, 10, 11, 12, 13, 14, 15, 16, 17, 18, 19, 20, 21, 22, 23, 24, 25, 26, 27, 28, 29, 30, 31, 32, 33, 34, 71, and 72.

In any of the foregoing embodiments, aspects, or cases, the somaclonal abnormality can comprise a reduction in fruit yield, oil yield, growth, or reproduction of the plant relative to a control plant. In some cases, the control plant is a parental plant. In some cases, the control plant is a wild-type plant of the same fruit form phenotype (dura, tenera, or pisifera) as the plant predicted to have a somaclonal abnormality. In some cases, the somaclonal abnormality exhibits a Mantled phenotype.

In any of the foregoing embodiments, aspects, or cases, the determining the methylation status can comprise bisulfite conversion; and/or the determining the methylation status can comprise digesting genomic DNA with a methylation-dependent endonuclease; and/or the determining the methylation status can comprise digesting genomic DNA with a methylation-sensitive endonuclease; and/or the determining of the methylation status can comprise measuring rates of methylated base incorporation during sequencing; and/or the determining of the methylation status can comprise measuring current as molecules including methylated bases pass through a nanopore. In any of the foregoing embodiments, aspects, or cases, the determining the methylation status can comprise methylated DNA immunoprecipitation, methylated DNA capture by affinity purification, or reduced representation bisulfite sequencing. In any of the foregoing embodiments, aspects, or cases, the determining the methylation status can comprise nucleic acid hybridization, e.g., microarray or bead array hybridization.

In any of the foregoing embodiments, aspects, or cases, the physically separating can comprise selecting plants predicted to have a somaclonal abnormality for destruction; and/or selecting plants predicted to lack a somaclonal abnormality for cultivation. In some cases, the plants selected for cultivation are germinated, planted, or transplanted. In some cases, the plants not selected for cultivation are discarded or destroyed.

In some embodiments, the present invention provides a computer program product for determining the presence or absence of a somaclonal abnormality in an oil palm plant, the computer program product comprising: a computer readable medium encoded with program code, the program code including: program code for receiving a methylation value representing a methylation status of at least one cytosine within a differential methylation region (DMR) in a sample from the oil palm plant, wherein the DMR is within a sequence of DNA at least 70%, 80%, 90%, 95%, or 99% identical, or identical, to SEQ ID NO:1; and program code for comparing the methylation value to a control value, wherein the control value distinguishes between plants with and without a somaclonal abnormality, wherein the comparison of the methylation value to the control value is predictive of the presence or absence of a somaclonal abnormality in the plant.

In some aspects, the DMR is within a DNA meta-region in the sample from the plant, where the DNA meta-region is at least 70%, 80%, 90%, 95%, or 99% identical, or identical, to a sequence selected from the group consisting of SEQ ID NO:63, 64, 65, 66, 67, 68, 69, and 70. In some aspects, the DMR is within a DNA region in the sample from the plant, where the DNA region is at least 70%, 80%, 90%, 95%, or 99% identical, or identical, to a sequence selected from the group consisting of SEQ ID NO:35, 36, 37, 38, 39, 40, 41, 42, 43, 44, 45, 46, 47, 48, 49, 50, 51, 52, 53, 54, 55, 56, 57, 58, 59, 60, 61, 62, 73, and 74. In some aspects, the at least one cytosine is in a biomarker, wherein the biomarker is at least 90%, 95%, or 99% identical, or identical, to a sequence selected from the group consisting of SEQ ID NO:7, 8, 9, 10, 11, 12, 13, 14, 15, 16, 17, 18, 19, 20, 21, 22, 23, 24, 25, 26, 27, 28, 29, 30, 31, 32, 33, 34, 71, and 72.

In some aspects, the control value is a methylation value for a control locus exogenous to the plant. In some aspects, the control value is a methylation value for a control locus endogenous to the plant.

In some aspects, wherein the program code comprises program code for receiving the methylation status of at least one cytosine in at least two, three or four different DMRs, wherein each DMR is independently within a sequence of DNA at least 70%, 80%, 90%, 95%, or 99% identical, or identical, to SEQ ID NO:1. In some cases, each DMR is within a DNA meta-region in the sample from the plant, where each DNA meta-region is at least 70%, 80%, 90%, 95%, or 99% identical, or identical, to a sequence independently selected from the group consisting of SEQ ID NO:63, 64, 65, 66, 67, 68, 69, and 70. In some cases, each DMR is within a DNA region in the sample from the plant, where each DNA region is at least 70%, 80%, 90%, 95%, or 99% identical, or identical, to a sequence independently selected from the group consisting of SEQ ID NO:35, 36, 37, 38, 39, 40, 41, 42, 43, 44, 45, 46, 47, 48, 49, 50, 51, 52, 53, 54, 55, 56, 57, 58, 59, 60, 61, 62, 73, and 74. In some cases, each DMR is within a biomarker, wherein each biomarker is at least 90%, 95%, or 99% identical, or identical, to a sequence independently selected from the group consisting of SEQ ID NO:7, 8, 9, 10, 11, 12, 13, 14, 15, 16, 17, 18, 19, 20, 21, 22, 23, 24, 25, 26, 27, 28, 29, 30, 31, 32, 33, 34, 71 and 72.

In any of the foregoing computer program products, the computer program product can, in some cases, predict the presence or absence of a somaclonal abnormality in the plant. In some cases, the somaclonal abnormality exhibits a Mantled phenotype.

In some embodiments, the present invention provides a kit for determining the methylation status of at least one DMR in a biological sample from an oil palm plant, the kit comprising: (1) a polynucleotide (e.g., detectably labeled polynucleotide), or a pair of polynucleotides (e.g., wherein one or both polynucleotides of the pair are detectably labeled), capable of specifically amplifying at least a portion of a DMR, wherein the DMR is within a sequence of DNA at least 70%, 80%, 90%, 95%, or 99% identical, or identical, to SEQ ID NO:1; and a methylation-dependent, a methylation sensitive restriction enzyme, and/or sodium bisulfite; or (2) sodium bisulfite, primers, and adapters for whole genome amplification, and at least one polynucleotide to quantify the presence of the converted methylated and/or the converted unmethylated sequence of at least one cytosine from a DMR, wherein the DMR is within a sequence of DNA at least 70%, 80%, 90%, 95%, or 99% identical, or identical, to SEQ ID NO:1; or (3) methylation sensing restriction enzymes, primers and adapters for whole genome amplification, and at least one polynucleotide to quantify the number of copies of at least a portion of a DMR, wherein the DMR is within a sequence of DNA at least 70%, 80%, 90%, 95%, or 99% identical, or identical, to SEQ ID NO:1; or (4) a methylation sensing binding moiety and at least one polynucleotide to quantify the number of copies of at least a portion of a DMR, wherein the DMR is within a sequence of DNA at least 70%, 80%, 90%, 95%, or 99% identical, or identical, to SEQ ID NO:1.

In some aspects, the DMR is within a DNA meta-region in the sample from the plant, where the DNA meta-region is at least 70%, 80%, 90%, 95%, or 99% identical, or identical, to a sequence selected from the group consisting of SEQ ID NO:63, 64, 65, 66, 67, 68, 69, and 70. In some aspects, the DMR is within a DNA region in the sample from the plant, where the DNA region is at least 70%, 80%, 90%, 95%, or 99% identical, or identical, to a sequence selected from the group consisting of SEQ ID NO:35, 36, 37, 38, 39, 40, 41, 42, 43, 44, 45, 46, 47, 48, 49, 50, 51, 52, 53, 54, 55, 56, 57, 58, 59, 60, 61, 62, 73, and 74. In some cases, the DMR is within a biomarker, wherein the biomarker is at least 90%, 95%, or 99% identical, or identical, to a sequence selected from the group consisting of SEQ ID NO:7, 8, 9, 10, 11, 12, 13, 14, 15, 16, 17, 18, 19, 20, 21, 22, 23, 24, 25, 26, 27, 28, 29, 30, 31, 32, 33, 34, 71, and 72.

In some aspects, the kit comprises at least two, three, or four polynucleotides—or two, three, or four pairs of polynucleotides—capable of specifically amplifying at least a portion of two, three, or four different DMRs, wherein each DMR is independently within a sequence of DNA at least 70%, 80%, 90%, 95%, or 99% identical, or identical, to SEQ ID NO:1. In some cases, each DMR is within a DNA meta-region, where the DNA meta-region is at least 70%, 80%, 90%, 95%, or 99% identical, or identical, to a sequence independently selected from the group consisting of SEQ ID NO:63, 64, 65, 66, 67, 68, 69, and 70. In some cases, each DMR is within a sequence of DNA at least 70%, 80%, 90%, 95%, or 99% identical, or identical, to a sequence independently selected from the group consisting of SEQ ID NO:35, 36, 37, 38, 39, 40, 41, 42, 43, 44, 45, 46, 47, 48, 49, 50, 51, 52, 53, 54, 55, 56, 57, 58, 59, 60, 61, 62, 73 and 74. In some cases, each DMR is within a biomarker, wherein each biomarker is at least 90%, 95%, or 99% identical, or identical, to a sequence independently selected from the group consisting of SEQ ID NO:7, 8, 9, 10, 11, 12, 13, 14, 15, 16, 17, 18, 19, 20, 21, 22, 23, 24, 25, 26, 27, 28, 29, 30, 31, 32, 33, 34, 71 and 72.

In some aspects, the kit further comprises a detectably labeled polynucleotide probe that specifically detects an amplified DMR, or portion thereof. In some cases, the polynucleotide probe specifically detects an amplified DMR, or portion thereof, in a real-time amplification reaction.

In some embodiments, the present invention provides a method of predicting the presence or absence of somaclonal abnormality in an oil palm plant comprising: a) obtaining a biological sample from the plant; b) determining the methylation status of at least one cytosine within a differential methylation region (DMR) in the sample from the plant, wherein the DMR is within a sequence of DNA at least 70%, 80%, 90%, 95%, or 99% identical, or identical, to SEQ ID NO:1; and c) correlating the methylation status of the at least one cytosine to the presence or absence of a somaclonal abnormality in the plant, wherein the correlation comprises predicting the presence or absence of somaclonal abnormality in the plant.

In some aspects, the DMR is within a DNA meta-region in the sample from the plant, where the DNA meta-region is at least 70%, 80%, 90%, 95%, or 99% identical, or identical, to a sequence selected from the group consisting of SEQ ID NO:63, 64, 65, 66, 67, 68, 69, and 70. In some aspects, the DMR is within a DNA region in the sample from the plant, where the DNA region is at least 70%, 80%, 90%, 95%, or 99% identical, or identical, to a sequence selected from the group consisting of SEQ ID NO:35, 36, 37, 38, 39, 40, 41, 42, 43, 44, 45, 46, 47, 48, 49, 50, 51, 52, 53, 54, 55, 56, 57, 58, 59, 60, 61, 62, 73 and 74. In some cases, the determining step comprises determining the methylation status of at least one cytosine in a biomarker, wherein the biomarker is at least 90%, 95%, or 99% identical, or identical, to a sequence selected from the group consisting of SEQ ID NO:7, 8, 9, 10, 11, 12, 13, 14, 15, 16, 17, 18, 19, 20, 21, 22, 23, 24, 25, 26, 27, 28, 29, 30, 31, 32, 33, 34, 71 and 72.

In some aspects, the method comprises predicting the presence of a somaclonal abnormality when the methylation status of the at least one cytosine is reduced relative to a control locus. In some cases, the presence of a somaclonal abnormality is predicted when the methylation status of the at least one cytosine in the DNA meta-region at least 70%, 80%, 90%, 95%, or 99% identical, or identical, to the sequence selected from the group consisting of SEQ ID NO:63, 64, 65, 66, 67, 69, and 70 (or selected from the group consisting of SEQ ID NO: 63, 64, 65, 66, 67, 68, 69, and 70) is reduced relative to a control locus. In some cases, the presence of a somaclonal abnormality is predicted when the methylation status of the at least one cytosine in the DNA region at least 70%, 80%, 90%, 95%, or 99% identical, or identical, to the sequence selected from the group consisting of SEQ ID NO:35, 36, 39, 40, 42, 43, 44, 45, 46, 48, 49, 51, 52, 57, 58, 59, 60, 61, and 73 is reduced relative to a control locus. In some cases, the presence of a somaclonal abnormality is predicted when the methylation status of the at least one cytosine in the biomarker at least 90%, 95%, or 99% identical, or identical to the sequence selected from the group consisting of SEQ ID NO:7, 8, 11, 12, 14, 15, 16, 17, 18, 20, 21, 23, 24, 29, 30, 31, 32, 33, and 71 is reduced relative to a control locus.

In some aspects, the method comprises predicting the presence of a somaclonal abnormality when the methylation status of the at least one cytosine is increased relative to a control locus. In some cases, the presence of a somaclonal abnormality is predicted when the methylation status of the at least one cytosine in the DNA meta-region at least 70%, 80%, 90%, 95%, or 99% identical, or identical, to the sequence selected from the group consisting of SEQ ID NO:63, 64, 65, 66, 67, 68, and 69 (or selected from the group consisting of SEQ ID NO:63, 64, 65, 66, 67, 68, 69, and 70) is increased relative to a control locus. In some cases, the presence of a somaclonal abnormality is predicted when the methylation status of the at least one cytosine in the DNA region at least 70%, 80%, 90%, 95%, or 99% identical, or identical, to the sequence selected from the group consisting of SEQ ID NO:35, 36, 37, 38, 41, 42, 47, 50, 52, 53, 54, 55, 56, 57, 62, and 74 is increased relative to a control locus. In some cases, the presence of a somaclonal abnormality is predicted when the methylation status of the at least one cytosine in the biomarker at least 90%, 95%, or 99% identical, or identical to the sequence selected from the group consisting of SEQ ID NO:7, 8, 9, 10, 13, 14, 19, 22, 24, 25, 26, 27, 28, 29, 34, and 72 is increased relative to a control locus.

In some aspects, the method comprises predicting the presence of a somaclonal abnormality when the methylation status of the at least one cytosine is either increased or decreased relative to a control locus. In some cases, the control locus is an endogenous control locus. In some cases, the control locus is an exogenous control locus.

In some aspects, the determining step comprises determining the methylation status of at least one cytosine in at least two, three or four different differential methylation regions (DMRs), wherein each DMR is independently within a sequence of DNA at least 70%, 80%, 90%, 95%, or 99% identical, or identical, to SEQ ID NO:1. In some cases, each DMR is within a DNA meta-region in the sample from the plant, where each DNA meta-region is at least 70%, 80%, 90%, 95%, or 99% identical, or identical, to a sequence independently selected from the group consisting of SEQ ID NO:63, 64, 65, 66, 67, 68, 69, and 70. In some cases, each DMR is within a DNA region in the sample from the plant, where each DNA region is at least 70%, 80%, 90%, 95%, or 99% identical, or identical, to a sequence independently selected from the group consisting of SEQ ID NO:35, 36, 37, 38, 39, 40, 41, 42, 43, 44, 45, 46, 47, 48, 49, 50, 51, 52, 53, 54, 55, 56, 57, 58, 59, 60, 61, 62, 73, and 74. In some cases, the determining step comprises determining the methylation status of at least one cytosine in a biomarker in each DMR, wherein each biomarker is at least 90%, 90%, 95%, or 99% identical, or identical, to a sequence independently selected from the group consisting of SEQ ID NO:7, 8, 9, 10, 11, 12, 13, 14, 15, 16, 17, 18, 19, 20, 21, 22, 23, 24, 25, 26, 27, 28, 29, 30, 31, 32, 33, 34, 71, and 72.

In some aspects, the somaclonal abnormality comprises a reduction in fruit yield, oil yield, growth, or reproduction of the plant relative to a control plant. In some cases, the control plant is a parental plant. In some cases, the control plant is a wild-type plant of the same fruit form phenotype (dura, tenera, or pisifera) as the plant predicted to have a somaclonal abnormality.

In some aspects, the somaclonal abnormality exhibits a Mantled phenotype.

In some aspects, the determining the methylation status comprises bisulfite conversion; and/or digesting genomic DNA with a methylation-dependent endonuclease; and/or digesting genomic DNA with a methylation-sensitive endonuclease.

In some embodiments, the present invention provides a method comprising: providing a prediction of a presence or absence of a somaclonal abnormality in a plurality of plants, wherein the presence or absence of a somaclonal abnormality is determined by a methylation status of at least one cytosine within a differential methylation region (DMR) in a sample from each plant, wherein the DMR is within a sequence of DNA at least 70%, 80%, 90%, 95%, or 99% identical, or identical, to SEQ ID NO:1; and physically separating a plant predicted to have a somaclonal abnormality from a plant predicted to lack a somaclonal abnormality.

In some aspects, the DMR is within a DNA meta-region in the sample from the plant, where the DNA region is at least 70%, 80%, 90%, 95%, or 99% identical, or identical, to a sequence selected from the group consisting of SEQ ID NO:63, 64, 65, 66, 67, 68, 69, and 70. In some aspects, the DMR is within a DNA region in the sample from the plant, where the DNA region is at least 70%, 80%, 90%, 95%, or 99% identical, or identical, to a sequence selected from the group consisting of SEQ ID NO:35, 36, 37, 38, 39, 40, 41, 42, 43, 44, 45, 46, 47, 48, 49, 50, 51, 52, 53, 54, 55, 56, 57, 58, 59, 60, 61, 62, 73, and 74. In some cases, the determining step comprises determining the methylation status of at least one cytosine in a biomarker, wherein the biomarker is at least 90%, 95%, or 99% identical, or identical, to a sequence selected from the group consisting of SEQ ID NO:7, 8, 9, 10, 11, 12, 13, 14, 15, 16, 17, 18, 19, 20, 21, 22, 23, 24, 25, 26, 27, 28, 29, 30, 31, 32, 33, 34, 71, and 72.

In some aspects, the present invention provides a method for detecting or predicting a somaclonal abnormality for an oil palm plant, the method comprising: a) obtaining a biological sample from the plant; b) determining the methylation status of at least one cytosine within a differential methylation region (DMR) in the sample from the plant, wherein the DMR is within a sequence of DNA at least 90%, 95%, or 99% identical, or identical, to SEQ ID NO:1; and c) correlating the methylation status of the at least one cytosine to the presence or absence of the somaclonal abnormality in the plant. In some embodiments, the method further comprises physically separating a plant predicted to have the somaclonal abnormality from one or more plants predicted to lack a somaclonal abnormality. In some cases, the physically separating comprises selecting plants predicted to have a somaclonal abnormality for destruction.

In some cases, the physically separating comprises selecting plants predicted to lack a somaclonal abnormality for cultivation. In some cases, the plants selected for cultivation are germinated, planted, or transplanted. In some cases, the plants not selected for cultivation are discarded or destroyed. In some cases, the plants not selected for cultivation are treated to reduce the likelihood of a somaclonal abnormality. In some embodiments, the at least one cytosine is a first cytosine in a CHG sequence, wherein H is C, A, or T.

In some embodiments, the DMR is within a DNA meta-region in the sample from the plant, where the DNA meta-region is at least 90%, 95%, or 99% identical, or identical, to a sequence selected from the group consisting of SEQ ID NO:63, 64, 65, 66, 67, 68, 69, and 70. In some embodiments, the DMR is within a DNA region in the sample from the plant, where the DNA region is at least 90%, 95%, or 99% identical, or identical, to a sequence selected from the group consisting of SEQ ID NO:35, 36, 37, 38, 39, 40, 41, 42, 43, 44, 45, 46, 47, 48, 49, 50, 51, 52, 53, 54, 55, 56, 57, 58, 59, 60, 61, 62, 73, and 74.

In some cases, the determining step comprises determining the methylation status of at least one cytosine in a biomarker, wherein the biomarker is at least 90%, 90%, 95%, or 99% identical, or identical, to a sequence selected from the group consisting of SEQ ID NO:7, 8, 9, 10, 11, 12, 13, 14, 15, 16, 17, 18, 19, 20, 21, 22, 23, 24, 25, 26, 27, 28, 29, 30, 31, 32, 33, 34, 71, and 72. In some cases, the DMR is within a DNA region in the sample from the plant, where the DNA region is at least 90%, 95%, or 99% identical, or identical, to SEQ ID NO:84, 87, or 90.

In some cases the at least cytosine is in an AlwNI, BbvI, ScrFI, or RsaI restriction endonuclease recognition site. In some cases, the method comprises determining the methylation status of a first and a second cytosine, wherein the first cytosine is within a DMR within a DNA region in the sample from the plant, where the DNA region is at least 90%, 95%, or 99% identical, or identical, to SEQ ID NO:87, and wherein the second cytosine is within a DMR within a DNA region in the sample from the plant, where the DNA region is at least 90%, 95%, or 99% identical, or identical, to SEQ ID NO: 90. In some cases, the first cytosine is in a BbvI restriction endonuclease site, and the second cytosine is in a RsaI restriction endonuclease site.

In some cases, the method comprises predicting the presence of a somaclonal abnormality when the methylation status of the at least one cytosine is reduced relative to a control locus. In some cases, the method comprises predicting the presence of a somaclonal abnormality when the methylation status of the at least one cytosine is increased relative to a control locus. In some cases, the method comprises predicting the presence of a somaclonal abnormality when the methylation status of the at least one cytosine is either increased or decreased relative to a control locus. In some cases, the control locus is an endogenous control locus. In some cases, the control locus is an exogenous control locus.

In some cases, the determining step comprises determining the methylation status of at least one cytosine in at least two, three or four different differential methylation regions (DMRs), wherein each DMR is independently within a sequence of DNA at least 90%, 95%, or 99% identical, or identical, to SEQ ID NO:1.

In some cases, the somaclonal abnormality comprises a reduction in fruit yield, oil yield, growth, or reproduction of the plant relative to a control plant. In some cases, the control plant is a parental plant. In some cases, the control plant is a wild-type plant of the same fruit form phenotype (dura, tenera, or pisifera) as the plant predicted to have a somaclonal abnormality.

In some cases, the somaclonal abnormality is predicted to exhibit a Mantled phenotype.

In some cases, the determining the methylation status comprises bisulfite conversion. In some cases, the determining the methylation status comprises digesting genomic DNA with a methylation-dependent endonuclease. In some cases, the determining the methylation status comprises digesting genomic DNA with a methylation-sensitive endonuclease. In some cases, the genomic DNA is amplified after digesting.

In some cases, the determining the methylation status comprises bisulfite conversion; and/or the determining the methylation status comprises digesting genomic DNA with a methylation-dependent endonuclease; and/or the determining the methylation status comprises digesting genomic DNA with a methylation-sensitive endonuclease; and/or the determining of the methylation status comprising measuring rates of methylated base incorporation during sequencing; and/or the determining of the methylation status comprising measuring current as molecules including methylated bases pass through a nanopore. In some cases, the determining the methylation status can comprise methylated DNA immunoprecipitation, methylated DNA capture by affinity purification, or reduced representation bisulfite sequencing. In some cases, the determining the methylation status can comprise nucleic acid hybridization, e.g., microarray or bead array hybridization.

In some aspects, the present invention provides a method for detecting or predicting a somaclonal abnormality for an oil palm plant, the method comprising: a) obtaining a biological sample from the plant; b) determining the expression level of at least one small RNA in the sample from the plant, wherein the at least one small RNA is encoded by a sequence comprising a polynucleotide at least 90%, 95%, or 99% identical or identical to SEQ ID NO:91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160 or 161; and c) correlating the expression level of the at least one small RNA to the presence or absence of the somaclonal abnormality in the plant. In some embodiments, the expression level of the at least one small RNA is at least 2-fold increased or decreased relative to expression of the at least one small RNA in a normal control plant.

In some cases, the at least one small RNA in the sample from the plant is encoded by a sequence comprising a polynucleotide at least 90% (e.g., 91%, 92%, 93%, 94%, 95%, 96%, 97%, 98%, 99%, 99.5%, or 100%) identical to any one of SEQ ID NOs: 144-161. In some cases, the expression level of the at least one small RNA that is at least 90% identical to any one of SEQ ID NOs: 144-161 in a sample from a plant predicted to have a somaclonal abnormality is less than 50% of the expression level of the at least one small RNA in a normal control plant. In some cases, the at least one small RNA in the sample from the plant is encoded by a sequence comprising a polynucleotide at least 90% (e.g., 91%, 92%, 93%, 94%, 95%, 96%, 97%, 98%, 99%, 99.5%, or 100%) identical to SEQ ID NO:91. In some cases, the expression level of the at least one small RNA that is at least 90% identical to SEQ ID NO:91 in a sample from a plant predicted to have a somaclonal abnormality is less than 50%, 40%, 30%, or 10% of the expression level of the at least one small RNA in a normal control plant.

In some cases, the biological sample is derived from shoot apex tissue of the plant. In some cases, the biological sample is derived from <2 cm stage inflorescens tissue of the plant. In some cases, the biological sample is derived from at least 2 cm stage inflorescens tissue of the plant. In some cases, the biological sample is derived from an in vitro tissue cultured plant cell, a seed, or a seedling.

In some embodiments, the method further comprises physically separating a plant predicted to have the somaclonal abnormality from one or more plants predicted to lack a somaclonal abnormality. In some embodiments, the physically separating comprises selecting plants predicted to have a somaclonal abnormality for destruction. In some cases, the physically separating comprises selecting plants predicted to lack a somaclonal abnormality for cultivation. In some cases, the plants selected for cultivation are germinated, planted, or transplanted. In some cases, plants not selected for cultivation are discarded or destroyed. In some cases, the plants not selected for cultivation are treated to reduce the likelihood of a somaclonal abnormality. In some cases, the somaclonal abnormality is predicted to exhibit a Mantled phenotype.

In some aspects, the present invention provides, a method for detecting or predicting a somaclonal abnormality for an oil palm plant, the method comprising: a) obtaining a biological sample from the plant; b) determining the expression level of a transcript encoded by SEQ ID NO:5, 75, 78, or 80; and c) correlating the expression level to the presence or absence of the somaclonal abnormality in the plant. In some embodiments, the plant is predicted to have a somaclonal abnormality when the expression level of SEQ ID NO:5 is decreased relative to a wildtype control plant, or when the expression level of SEQ ID NO:75, or 78, or 80 is increased relative to a wildtype control plant. In some embodiments, the plant is predicted to have a somaclonal abnormality when the expression level of SEQ ID NO:75 or 78 or 80 is increased relative to an expression level of SEQ ID NO:5.

In some embodiments, the method further comprises physically separating a plant predicted to have the somaclonal abnormality from one or more plants predicted to lack a somaclonal abnormality. In some cases, the physically separating comprises selecting plants predicted to have a somaclonal abnormality for destruction. In some cases, the physically separating comprises selecting plants predicted to lack a somaclonal abnormality for cultivation. In some cases, the plants selected for cultivation are germinated, planted, or transplanted. In some cases, the plants not selected for cultivation are discarded or destroyed. In some cases, the plants not selected for cultivation are treated to reduce the likelihood of a somaclonal abnormality.

In some embodiments, the somaclonal abnormality is predicted to exhibit the Mantled phenotype.

In some aspects, the present invention provides a computer program product for predicting the presence or absence of a somaclonal abnormality in an oil palm plant, the computer program product comprising: a computer readable medium encoded with program code, the program code including: program code for receiving a methylation value representing the methylation status of at least one cytosine within a differential methylation region (DMR) in the sample from the oil palm plant, wherein the DMR is within a sequence of DNA at least 70%, 80%, 90%, 95%, or 99% identical, or identical, to SEQ ID NO:1; and program code for comparing the methylation value to a control value, wherein the control value distinguishes between plants with and without a somaclonal abnormality, wherein the comparison of the methylation value to the control value is predictive of the presence or absence of a somaclonal abnormality in the plant.

In some embodiments, the DMR is within a DNA meta-region in the sample from the plant, where the DNA meta-region is at least 90%, 95%, or 99% identical, or identical, to a sequence selected from the group consisting of SEQ ID NO:63, 64, 65, 66, 67, 68, 69, and 70. In some cases, the DMR is within a DNA region in the sample from the plant, where the DNA region is at least 90%, 95%, or 99% identical, or identical, to a sequence selected from the group consisting of SEQ ID NO:35, 36, 37, 38, 39, 40, 41, 42, 43, 44, 45, 46, 47, 48, 49, 50, 51, 52, 53, 54, 55, 56, 57, 58, 59, 60, 61, 62, 73, and 74. In some cases, the at least one cytosine is in a biomarker, wherein the biomarker is at least 90% 95%, or 99% identical, or identical, to a sequence selected from the group consisting of SEQ ID NO:7, 8, 9, 10, 11, 12, 13, 14, 15, 16, 17, 18, 19, 20, 21, 22, 23, 24, 25, 26, 27, 28, 29, 30, 31, 32, 33, 34, 71, and 72.

In some cases, the control value is a methylation value for a control locus exogenous to the plant. In some cases, the control value is a methylation value for a control locus endogenous to the plant. In some cases, the program code comprises program code for receiving the methylation status of at least one cytosine in at least two, three or four different DMRs, wherein each DMR is independently within a sequence of DNA at least 90%, 95%, or 99% identical, or identical, to SEQ ID NO:1. In some cases, each DMR is within a DNA meta-region in the sample from the plant, where each DNA meta-region is at least 90%, 95%, or 99% identical, or identical, to a sequence independently selected from the group consisting of SEQ ID NO:63, 64, 65, 66, 67, 68, 69, and 70.

In some cases, each DMR is within a DNA region in the sample from the plant, wherein each DNA region is at least 90%, 95%, or 99% identical, or identical, to a sequence independently selected from the group consisting of SEQ ID NO:35, 36, 37, 38, 39, 40, 41, 42, 43, 44, 45, 46, 47, 48, 49, 50, 51, 52, 53, 54, 55, 56, 57, 58, 59, 60, 61, 62, 73, and 74. In some cases, each DMR is within a biomarker, wherein each biomarker is at least 90%, 95%, or 99% identical, or identical, to a sequence independently selected from the group consisting of SEQ ID NO:7, 8, 9, 10, 11, 12, 13, 14, 15, 16, 17, 18, 19, 20, 21, 22, 23, 24, 25, 26, 27, 28, 29, 30, 31, 32, 33, 34, 71 and 72. In some cases, the somaclonal abnormality is predicted to exhibit a Mantled phenotype.

In some aspects, the present invention provides a computer program product for determining the presence or absence of a somaclonal abnormality in an oil palm plant, the computer program product comprising: a computer readable medium encoded with program code, the program code including: program code for receiving a value representing i). an expression level of a small RNA (e.g., an expression level of a small RNA in a sample from a plant), wherein the small RNA is encoded by a sequence comprising a polynucleotide at least 90%, 95%, or 99% identical, or identical, to SEQ ID NO:91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160 or 161; or ii). an expression level of a transcript at least 90%, 95%, or 99% identical, or identical, to SEQ ID NO:5, 75, 78, or 80; and program code for comparing the expression level value to a control value, wherein the control value distinguishes between plants with and without a somaclonal abnormality, wherein the comparison of the expression level value to the control value is predictive of the presence or absence of a somaclonal abnormality in the plant.

In some cases, the at least one small RNA in the sample from the plant is encoded by a sequence comprising a polynucleotide at least 90% (e.g., 91%, 92%, 93%, 94%, 95%, 96%, 97%, 98%, 99%, 99.5%, or 100%) identical to any one of SEQ ID NOs: 144-161. In some cases, the expression level of the at least one small RNA that is at least 90%, 95%, or 99% identical to any one of SEQ ID NOs: 144-161 in a sample from a plant predicted to have a somaclonal abnormality is less than 50% of the expression level of the at least one small RNA in a normal control plant. In some cases, the at least one small RNA in the sample from the plant is encoded by a sequence comprising a polynucleotide at least 90% (e.g., 91%, 92%, 93%, 94%, 95%, 96%, 97%, 98%, 99%, 99.5%, or 100%) identical to SEQ ID NO:91. In some cases, the expression level of the at least one small RNA that is at least 90%, 95%, or 99% identical to SEQ ID NO:91 in a sample from a plant predicted to have a somaclonal abnormality is less than 50%, 40%, 30%, or 10% of the expression level of the at least one small RNA in a normal control plant.

The computer program product can, in some cases, predict the presence or absence of a somaclonal abnormality in the plant. In some cases, the somaclonal abnormality exhibits a Mantled phenotype. In some cases, a plant predicted to have a somaclonal abnormality by application of the computer program product is physically separated from one or more plants predicted to lack a somaclonal abnormality.

In some aspects, the present invention provides a kit for determining the methylation status of at least one DMR in a biological sample from an oil palm plant, wherein the DMR is within a sequence of DNA at least 90%, 95%, or 99% identical, or identical, to SEQ ID NO:1, the kit comprising: (1) sodium bisulfite, oligonucleotide amplification primers, and at least one polynucleotide to quantify the presence of the unconverted methylated or the converted unmethylated sequence of at least one cytosine from the DMR; (2) a methylation-sensitive or dependent restriction enzyme, oligonucleotide amplification primers, and at least one polynucleotide to quantify the number of copies of at least a portion of the DMR; (3) a methylation sensing binding moiety and at least one polynucleotide to quantify the number of copies of at least a portion of the DMR, wherein the methylation status of the at least one cytosine is predictive of a somaclonal abnormality of the oil palm plant.

In some embodiments, the methylation-sensitive or dependent restriction enzyme is heterologous to the oil palm plant. In some embodiments, the methylation-sensitive or dependent restriction enzyme is selected from the group consisting of AlwNI, BbvI, RsaI, and ScrFI. In some embodiments, the kit comprises BbvI, and RsaI. In some embodiments, the at least one polynucleotide to quantify the presence of the unconverted methylated or the converted unmethylated sequence of at least one cytosine from the DMR comprises a sequence that specifically hybridizes to a sequence from the DMR containing a bisulfite converted cytosine. In some embodiments, the at least one polynucleotide to quantify the number of copies of at least a portion of the DMR comprises a sequence that specifically hybridizes to a sequence from the DMR containing a bisulfite converted cytosine.

In some embodiments, the methylation sensitive binding moiety is an antibody. In some embodiments, the DMR is within a DNA meta-region in the sample from the plant, where the DNA meta-region is at least 90%, 95%, or 99% identical, or identical, to a sequence selected from the group consisting of SEQ ID NO:63, 64, 65, 66, 67, 68, 69, and 70. In some embodiments, the DMR is within a DNA region in the sample from the plant, where the DNA region is at least 90%, 95%, or 99% identical, or identical, to a sequence selected from the group consisting of SEQ ID NO:35, 36, 37, 38, 39, 40, 41, 42, 43, 44, 45, 46, 47, 48, 49, 50, 51, 52, 53, 54, 55, 56, 57, 58, 59, 60, 61, 62, 73, and 74. In some cases, the DMR is within a biomarker, wherein the biomarker is at least 90%, 95%, or 99% identical, or identical, to a sequence selected from the group consisting of SEQ ID NO:7, 8, 9, 10, 11, 12, 13, 14, 15, 16, 17, 18, 19, 20, 21, 22, 23, 24, 25, 26, 27, 28, 29, 30, 31, 32, 33, 34, 71, and 72.

In some embodiments, the kit comprises at least two, three, or four polynucleotides—or two, three, or four pairs of polynucleotides—capable of specifically amplifying at least a portion of two, three, or four different DMRs, wherein each DMR is independently within a sequence of DNA at least 90%, 95%, or 99% identical, or identical, to SEQ ID NO:1. In some cases, each DMR is within a DNA meta-region, where the DNA meta-region is at least 90%, 95%, or 99% identical, or identical, to a sequence independently selected from the group consisting of SEQ ID NO:63, 64, 65, 66, 67, 68, 69, and 70.

In some cases, each DMR is within a sequence of DNA at least 90%, 95%, or 99% identical, or identical, to a sequence independently selected from the group consisting of SEQ ID NO:35, 36, 37, 38, 39, 40, 41, 42, 43, 44, 45, 46, 47, 48, 49, 50, 51, 52, 53, 54, 55, 56, 57, 58, 59, 60, 61, 62, 73 and 74. In some cases, each DMR is within a biomarker, wherein each biomarker is at least 90%, 95%, or 99% identical, or identical, to a sequence independently selected from the group consisting of SEQ ID NO:7, 8, 9, 10, 11, 12, 13, 14, 15, 16, 17, 18, 19, 20, 21, 22, 23, 24, 25, 26, 27, 28, 29, 30, 31, 32, 33, 34, 71 and 72. In some cases, the kit further comprises a detectably labeled polynucleotide probe that specifically detects an amplified DMR, or portion thereof. In some cases, the polynucleotide probe specifically detects an amplified DMR, or portion thereof, in a real-time amplification reaction.

In some aspects, the present invention provides a kit for detecting the expression level of an RNA in an oil palm plant, the kit comprising: a) an oligonucleotide primer capable of specifically hybridizing to a small RNA encoded by a sequence comprising a polynucleotide at least 90%, 95%, or 99% identical, or identical, to SEQ ID NO:91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123,124, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160 or 161; or b) an oligonucleotide primer capable of specifically hybridizing to a transcript encoded by SEQ ID NO:5, 75, 78, or 80, wherein the detected expression level is predictive of a somaclonal abnormality of the oil palm plant. In some cases, the kit further comprises a detectably labeled oligonucleotide probe; or wherein the oligonucleotide primer is detectably labeled. In some cases, the oligonucleotide primer of b) comprises SEQ ID NO:125, 126, 127, 128, or 129. In some cases, the oligonucleotide primer of a) is capable of is capable of specifically hybridizing to a small RNA encoded by a sequence comprising a polynucleotide at least 90% (e.g., 91%, 92%, 93%, 94%, 95%, 96%, 97%, 98%, 99%, 99.5%, or 100%) identical to one of SEQ ID NOs: 144-161.

In some aspects, the present invention provides a method of reducing somaclonal abnormalities an oil palm plant propagated by in vitro tissue culture comprising: exogenously applying to the plant an mRNA encoded by SEQ ID NO:5 or a sequence at least 90%, 95%, or 99% identical to SEQ ID NO:5; or exogenously applying to the plant a small RNA encoded by a sequence comprising a polynucleotide at least 90%, 95%, or 99% identical, or identical, to SEQ ID NO:91, 92, 93, 94, 95, 96, 97, 98, 99, 100, 101, 102, 103, 104, 105, 106, 107, 108, 109, 110, 111, 112, 113, 114, 116, 117, 123, 124, 130, 131, 132, 133, 134, 136, 137, 138, 139, 142, 143, 144, 145, 146, 147, 148, 149, 150, 151, 152, 153, 154, 155, 156, 157, 158, 159, 160 or 161. In some embodiments, the exogenously applying the mRNA or small RNA comprises contacting a cytoplasm or nucleus of the plant with the mRNA or small RNA. In some embodiments, the exogenously applying the mRNA or small RNA comprises contacting the plant with an expression cassette comprising a heterologous promoter operably linked to a polynucleotide at least 90%, 95%, or 99% identical, or identical, to SEQ ID NO:5.

In some embodiments, the exogenously applying the mRNA or small RNA comprises contacting the plant with an expression cassette comprising a heterologous promoter operably linked to a polynucleotide encoding a small RNA, wherein the polynucleotide comprises a sequence at least 90%, 95%, or 99% identical, or identical, to SEQ ID NO:91, 92, 93, 94, 95, 96, 97, 98, 99, 100, 101, 102, 103, 104, 105, 106, 107, 108, 109, 110, 111, 112, 113, 114, 116, 117, 123, 124, 130, 131, 132, 133, 134, 136, 137, 138, 139, 142, 143, 144, 145, 146, 147, 148, 149, 150, 151, 152, 153, 154, 155, 156, 157, 158, 159, 160 or 161. In some embodiments, the exogenously applying the mRNA or small RNA comprises contacting an in vitro tissue cultured plant cell with the mRNA or small RNA.

In some aspects, the present invention provides an expression cassette comprising a heterologous promoter operably linked to: i) a polynucleotide encoding a small RNA, wherein the polynucleotide comprises a sequence at least 90%, 95%, or 99% identical, or identical, to SEQ ID NO:91, 92, 93, 94, 95, 96, 97, 98, 99, 100, 101, 102, 103, 104, 105, 106, 107, 108, 109, 110, 111, 112, 113, 114, 116, 117, 123, 124, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160 or 161; or ii) a polynucleotide encoding an mRNA, wherein the polynucleotide comprises a sequence at least 90%, 95%, or 99% identical, or identical, to SEQ ID NO:5. The expression cassette can be a heterologous expression cassette. In some aspects, the present invention provides a recombinant plant comprising any one of the foregoing expression cassettes.

In some embodiments, the present invention provides a method of predicting the presence or absence of somaclonal abnormality in an oil palm plant comprising: a) obtaining a biological sample from the plant; b) determining a methylation density of a differential methylation region (DMR), or sub-region, in the sample from the plant, wherein the DMR is within a sequence of DNA at least 70%, 80%, 90%, 95%, or 99% identical, or identical, to SEQ ID NO:1; and c) correlating the methylation density to the presence or absence of a somaclonal abnormality in the plant, wherein the correlation comprises predicting the presence or absence of somaclonal abnormality in the plant.

In some aspects, the DMR is within a DNA meta-region in the sample from the plant, where the DNA meta-region is at least 70%, 80%, 90%, 95%, or 99% identical, or identical, to a sequence selected from the group consisting of SEQ ID NO:63, 64, 65, 66, 67, 68, 69, and 70. In some aspects, the DMR is within a DNA region in the sample from the plant, where the DNA region is at least 70%, 80%, 90%, 95%, or 99% identical, or identical, to a sequence selected from the group consisting of SEQ ID NO:35, 36, 37, 38, 39, 40, 41, 42, 43, 44, 45, 46, 47, 48, 49, 50, 51, 52, 53, 54, 55, 56, 57, 58, 59, 60, 61, 62, 73 and 74. In some cases, the determining step comprises determining the methylation density in a biomarker, wherein the biomarker is at least 90%, 95%, or 99% identical, or identical, to a sequence selected from the group consisting of SEQ ID NO:7, 8, 9, 10, 11, 12, 13, 14, 15, 16, 17, 18, 19, 20, 21, 22, 23, 24, 25, 26, 27, 28, 29, 30, 31, 32, 33, 34, 71 and 72.

In some aspects, the method comprises predicting the presence of a somaclonal abnormality when the methylation density is reduced relative to a control locus. In some cases, the presence of a somaclonal abnormality is predicted when the methylation density in a DNA meta-region at least 70%, 80%, 90%, 95%, or 99% identical, or identical, to the sequence selected from the group consisting of SEQ ID NO:63, 64, 65, 66, 67, 69, and 70 (or selected from the group consisting of SEQ ID NO:63, 64, 65, 66, 67, 68, 69, and 70) is reduced relative to a control locus. In some cases, the presence of a somaclonal abnormality is predicted when the methylation density in the DNA region at least 70%, 80%, 90%, 95%, or 99% identical, or identical, to the sequence selected from the group consisting of SEQ ID NO:35, 36, 39, 40, 42, 43, 44, 45, 46, 48, 49, 51, 52, 57, 58, 59, 60, 61, and 73 is reduced relative to a control locus. In some cases, the presence of a somaclonal abnormality is predicted when the methylation density in the biomarker at least 90%, 95%, or 99% identical, or identical to the sequence selected from the group consisting of SEQ ID NO:7, 8, 11, 12, 14, 15, 16, 17, 18, 20, 21, 23, 24, 29, 30, 31, 32, 33, and 71 is reduced relative to a control locus.

In some aspects, the determining step comprises determining the methylation density in at least two, three or four different differential methylation regions (DMRs), wherein each DMR is independently within a sequence of DNA at least 70%, 80%, 90%, 95%, or 99% identical, or identical, to SEQ ID NO:1. In some cases, each DMR is within a DNA meta-region in the sample from the plant, where each DNA meta-region is at least 70%, 80%, 90%, 95%, or 99% identical, or identical, to a sequence independently selected from the group consisting of SEQ ID NO:63, 64, 65, 66, 67, 68, 69, and 70. In some cases, each DMR is within a DNA region in the sample from the plant, where each DNA region is at least 70%, 80%, 90%, 95%, or 99% identical, or identical, to a sequence independently selected from the group consisting of SEQ ID NO:35, 36, 37, 38, 39, 40, 41, 42, 43, 44, 45, 46, 47, 48, 49, 50, 51, 52, 53, 54, 55, 56, 57, 58, 59, 60, 61, 62, 73, and 74. In some cases, the determining step comprises determining the methylation density in a biomarker in each DMR, wherein each biomarker is at least 90%, 90%, 95%, or 99% identical, or identical, to a sequence independently selected from the group consisting of SEQ ID NO:7, 8, 9, 10, 11, 12, 13, 14, 15, 16, 17, 18, 19, 20, 21, 22, 23, 24, 25, 26, 27, 28, 29, 30, 31, 32, 33, 34, 71, and 72.

In some aspects, the somaclonal abnormality comprises a reduction in fruit yield, oil yield, growth, or reproduction of the plant relative to a control plant. In some cases, the control plant is a parental plant. In some cases, the control plant is a wild-type plant of the same fruit form phenotype (dura, tenera, or pisifera) as the plant predicted to have a somaclonal abnormality.

In some aspects, the somaclonal abnormality exhibits a Mantled phenotype.

In some aspects, the determining the methylation density comprises bisulfite conversion; and/or digesting genomic DNA with a methylation-dependent endonuclease; and/or digesting genomic DNA with a methylation-sensitive endonuclease. In some cases, the methylation density is CHG methylation density.

In some embodiments, the present invention provides a method comprising: providing a prediction of a presence or absence of a somaclonal abnormality in a plurality of plants, wherein the presence or absence of a somaclonal abnormality is determined by a methylation density (e.g., CHG methylation density) within a differential methylation region (DMR) in a sample from each plant, wherein the DMR is within a sequence of DNA at least 70%, 80%, 90%, 95%, or 99% identical, or identical, to SEQ ID NO:1; and physically separating a plant predicted to have a somaclonal abnormality from a plant predicted to lack a somaclonal abnormality.

Definitions

As used herein, "plant" refers to any cell, or group of cells, from an organism of the kingdom Plantae. "Oil palm plant" refers to any cell, or group of cells, of an organism of the species *E. guineensis*. Non-limiting examples include whole plants, shoot vegetative organs/structures (e.g., leaves, stems and tubers), roots, flowers and floral organs/structures (e.g., bracts, sepals, petals, stamens, carpels, anthers and ovules), seed (including embryo, endosperm, and seed coat) and fruit (the mature ovary), plant tissue (e.g., vascular tissue, ground tissue, and the like) and cells (e.g., guard cells, egg cells, trichomes and the like), and progeny of same. Non-limiting examples further include a plant cell, or group of plant cells, from in vitro cell culture.

As used herein, "ortet" refers to source palm from which a clone is generated. "Clone" refers to a genetically identical, or substantially identical, copy of a palm from a specimen plant tissue or cell, obtained through asexual reproduction in sterile conditions. "Ramet" refers to plants derived through in vitro propagation. "Explant" refers to excised tissue of a palm for in vitro propagation. "Semiclone" refers to a progeny derived from a cross between a clonal parent and a seedling parent. "Biclone" refers to a progeny derived from a cross where both parents are clones.

As used herein, the term "somaclonal abnormality" refers to any phenotypic or genotypic (e.g., epigenetic) modification that arises from in vitro culture. For example, the Mantled phenotype can arise as a somaclonal abnormality that arises in oil palm plants subjected to in vitro culture.

"Methylation" refers to cytosine methylation and/or hydroxymethylation at positions C5 of cytosine, the N6 position of adenine or other types of nucleic acid methylation. In vitro amplified DNA is unmethylated because in vitro DNA amplification methods do not retain the methylation pattern of the amplification template. However, "unmethylated DNA" or "methylated DNA" can also refer to amplified DNA whose original template was unmethylated or methylated, respectively.

A "methylation profile" refers to a set of data representing the methylation states of one or more loci within a molecule of DNA from e.g., the genome of a plant, e.g., cells or tissues from a plant. The profile can indicate the methylation state of every base in a plant, can comprise information regarding a subset of the base pairs (e.g., the methylation state of specific restriction enzyme recognition sequence) in a genome, or can comprise information regarding regional methylation density of each locus.

"Methylation status" refers to the presence, absence and/or quantity of methylation at a particular nucleotide, or nucleotides within a portion of DNA. The methylation status of a particular DNA sequence (e.g., a DNA biomarker or DNA region as described herein) can indicate the methylation state of every base in the sequence or can indicate the methylation state of a subset of the base pairs (e.g., of cytosines or the methylation state of one or more specific restriction enzyme recognition sequences) within the sequence, or can indicate information regarding regional methylation density within the sequence without providing precise information of where in the sequence the methylation occurs. The methylation status can optionally be represented or indicated by a "methylation value." A methylation value can be generated, for example, by quantifying the amount of intact DNA present following restriction digestion with a methylation dependent restriction enzyme. In this example, if a particular sequence in the DNA is quantified using quantitative PCR, an amount of template DNA approximately equal to a mock treated control indicates the sequence is not highly methylated whereas an amount of template substantially less than occurs in the mock treated sample indicates the presence of methylated DNA at the sequence. Accordingly, a value, i.e., a methylation value, for example from the above described example, represents the methylation status and can thus be used as a quantitative indicator of methylation status. This is of particular use when it is desirable to compare the methylation status of a sequence in a sample to a threshold value.

A "methylation-dependent restriction enzyme" refers to a restriction enzyme that cleaves or digests DNA at or in proximity to a methylated recognition sequence, but does not cleave DNA at or near the same sequence when the recognition sequence is not methylated. Methylation-dependent restriction enzymes include those that cut at a methylated recognition sequence (e.g., DpnI) and enzymes that cut at a sequence near but not at the recognition sequence (e.g., McrBC). For example, McrBC's recognition sequence is 5' RmC (N40-3000) RmC 3' where "R" is a purine and "mC" is a methylated cytosine and "N40-3000" indicates the distance between the two RmC half sites for which a restriction event has been observed. McrBC generally cuts close to one half-site or the other, but cleavage positions are typically distributed over several base pairs, approximately 30 base pairs from the methylated base. McrBC sometimes cuts 3' of both half sites, sometimes 5' of both half sites, and sometimes between the two sites. Exemplary methylation-dependent restriction enzymes include, e.g., McrBC (see, e.g., U.S. Pat. No. 5,405,760), McrA, MrrA, DpnI, MspJI, LpnPI, AspBHI, RlaI and SgrTI. One of skill in the art will appreciate that any methylation-dependent restriction enzyme, including homologs and orthologs of the restriction enzymes described herein, is also suitable for use in the present invention.

A "methylation-sensitive restriction enzyme" refers to a restriction enzyme that cleaves DNA at or in proximity to an unmethylated recognition sequence but does not cleave at or in proximity to the same sequence when the recognition sequence is methylated. Exemplary methylation-sensitive restriction enzymes are described in, e.g., McClelland et al., *Nucleic Acids Res.* 22(17):3640-59 (1994) and http://rebase.neb.com. Suitable methylation-sensitive restriction enzymes that do not cleave DNA at or near their recognition sequence when a cytosine within the recognition sequence is methylated at position $C^5$ include, e.g., Aat II, Aci I, Acl I, Age I, Alu I, Asc I, Ase I, AsiS I, Bbe I, BsaA I, BsaH I, BsiE I, BsiW I, BsrF I, BssH II, BssK I, BstB I, BstN I, BstU I, Cla I, Eae I, Eag I, Fau I, Fse I, Hha I, HinP1 I, HinC II, Hpa II, Hpy99 I, HpyCH4 IV, Kas I, Mbo I, Mlu I, MapA1 I, Msp I, Nae I, Nar I, Not I, Pml I, Pst I, Pvu I, Rsr II, Sac II, Sap I, Sau3A I, Sfl I, Sfo I, SgrA I, Sma I, SnaB I, Tsc I, Xma I, and Zra I. Suitable methylation-sensitive restriction enzymes that do not cleave DNA at or near their recognition sequence when an adenosine within the recognition sequence is methylated at position $N^6$ include, e.g., Mbo I. One of skill in the art will appreciate that any methylation-sensitive restriction enzyme, including homologs and orthologs of the restriction enzymes described herein, is also suitable for use in the present invention. One of skill in the art will further appreciate that a methylation-sensitive restriction enzyme that fails to cut in the presence of methylation of a cytosine at or near its recognition sequence may be insensitive to the presence of methylation of an adenosine at or near its recognition sequence. Likewise, a methylation-sensitive restriction enzyme that fails to cut in the presence of methylation of an adenosine at or near its recognition sequence may be insensitive to the presence of methylation of a cytosine at or near its recognition sequence. For example, Sau3AI is sensitive (i.e., fails to cut) to the presence of a methylated cytosine at or near its recognition sequence, but is insensitive (i.e., cuts) to the presence of a methylated adenosine at or near its recognition sequence. One of skill in the art will also appreciate that some methylation-sensitive restriction enzymes are blocked by methylation of bases on one or both strands of DNA encompassing of their recognition sequence, while other methylation-sensitive restriction enzymes are blocked only by methylation on both strands, but can cut if a recognition site is hemi-methylated.

A "threshold value that distinguishes between plants with and without" a particular somaclonal abnormality refers to a value or range of values of a particular measurement that can be used to distinguish between samples from plants with the abnormality and samples without the abnormality. Ideally, there is a threshold value or values that absolutely distinguishes between the two groups (i.e., values from the abnormal group are always, or nearly always, on one side (e.g., higher) of the threshold value and values from the wild-type group are always, or nearly always, on the other side (e.g., lower) of the threshold value). However, in many instances, threshold values do not absolutely distinguish between abnormal and wild-type samples (for example, when there is some overlap of values generated from abnormal and wild-type samples).

The term "biomarker" refers to a subsequence of a DNA region, differentially methylated region (DMR), or DNA meta-region. In some cases, the biomarker is identical to a portion of the DNA region, DMR, or DNA meta-region. In some cases, the biomarker is substantially identical, or at least 90%, 95%, or 99% identical to a portion of the DNA region, DMR, or DNA meta-region. Sequence comparisons can be performed using any BLAST including BLAST 2.2 algorithm with default parameters, described in Altschul et al., *Nuc. Acids Res.* 25:3389 3402 (1997) and Altschul et al., *J. Mol. Biol.* 215:403 410 (1990), respectively. Thus for example, a DNA region or biomarker described herein can correspond to a DNA sequence in an oil palm plant genome even if there is slight variation between the biomarker or DNA region and the particular oil palm plant genome in question. Such difference can be the result of slight genetic variation between oil palm plants. Consequently, the DMRs, DNA regions, DNA meta-regions, and biomarkers described herein can be at least about 90%, 95%, 99%, 99.9% identical, substantially identical, or identical, to a subsequence of SEQ ID NO:1.

"Sensitivity" of a given biomarker refers to the percentage of somaclonally abnormal samples that report a DNA methylation value different from a threshold value that distinguishes between wild-type and abnormal samples. For example, in some cases, the presence of a somaclonal abnormality is predicted when methylation is increased relative to the threshold value. In such cases, the sensitivity is calculated as follows:

$$\text{Sensitivity} = \left[ \frac{\text{(the number of abnormal samples above the threshold)}}{\text{(the total number of abnormal samples tested)}} \right] \times 100$$

The equation may also be stated as follows:

$$\text{Sensitivity} = \left[ \frac{\text{(the number of true positive samples)}}{\text{(the number of true positive samples) + (the number of false negative samples)}} \right] \times 100$$

where true positive is defined as a sample from a plant confirmed to have a somaclonal abnormality (e.g., a Mantled plant) that reports a DNA methylation value above the threshold value (i.e. the range associated with the phenotype), and false negative is defined as a confirmed somaclonally abnormal sample that reports a DNA methylation value below the threshold value (i.e. the range associated with no somaclonal abnormality). One of skill in the art can readily modify the above equations in cases where somaclonal abnormality is predicted when methylation is below a threshold value. Similarly, where somaclonal abnormality is predicted by either increased or decreased methylation in a DNA region or within a biomarker, the above-equation and its modified version can be combined to obtain a sensitivity value.

The value of sensitivity, therefore, reflects the probability that a DNA methylation measurement for a given biomarker obtained from a known abnormal sample will be in the range of somaclonally abnormal-associated measurements. As defined here, the relevance of the calculated sensitivity value represents an estimation of the probability that a given biomarker would detect the presence of a somaclonal abnormality when applied to a plant with that condition.

"Specificity" of a given biomarker refers to the percentage of wild-type samples that report a DNA methylation value different from a threshold value that distinguishes between somaclonally abnormal and wild-type samples. For example, in some cases, the absence of a somaclonal abnormality is predicted when methylation is reduced relative to the threshold value. In such cases, the specificity is calculated as follows:

$$\text{Specificity} = \left[ \frac{\text{(the number of wild-type samples below the threshold)}}{\text{(the total number of wild-type samples tested)}} \right] \times 100$$

The equation may also be stated as follows:

$$\text{Specificity} = \left[ \frac{\text{(the number of true negative samples)}}{\text{(the number of true negative samples) + (the number of false positive samples)}} \right] \times 100$$

where true negative is defined as a sample from a plant confirmed to be somaclonally normal that reports a DNA methylation value below the threshold value (i.e. the range associated with no abnormality), and false positive is defined as a sample from a plant confirmed to be somaclonally normal that reports DNA methylation value above the threshold value (i.e. the range associated with abnormality). The value of specificity, therefore, reflects the probability that a DNA methylation measurement for a given biomarker obtained from a known non-abnormal sample will be in the range of wild-type associated measurements. One of skill in the art can readily modify the above equations in cases where somaclonal abnormality is predicted when methylation is below a threshold value. Similarly, where somaclonal abnormality is predicted by either increased or decreased methylation in a DNA region or within a biomarker, the above-equation and its modified version can be combined to obtain a specificity value. As defined here, the relevance of the calculated specificity value represents an estimation of the probability that a given biomarker would predict the absence of a somaclonal abnormality when applied to a plant without that condition.

Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, Proc. Natl. Acad. Sci. USA 89:10915 (1989)) alignments (B) of 50, expectation (E) of 10, M=5, N=−4, and a comparison of both strands.

As used herein, the terms "nucleic acid," "polynucleotide" and "oligonucleotide" refer to nucleic acid regions, nucleic acid segments, primers, probes, amplicons and oligomer fragments. The terms are not limited by length and are generic to linear polymers of polydeoxyribonucleotides (containing 2-deoxy-D-ribose), polyribonucleotides (containing D-ribose), and any other N-glycoside of a purine or pyrimidine base, or modified purine or pyrimidine bases. These terms include double- and single-stranded DNA, as well as double- and single-stranded RNA.

A nucleic acid, polynucleotide or oligonucleotide can comprise, for example, phosphodiester linkages or modified linkages including, but not limited to phosphotriester, phosphoramidate, siloxane, carbonate, carboxymethylester, acetamidate, carbamate, thioether, bridged phosphoramidate, bridged methylene phosphonate, phosphorothioate, methylphosphonate, phosphorodithioate, bridged phosphorothioate or sulfone linkages, and combinations of such linkages.

A nucleic acid, polynucleotide or oligonucleotide can comprise the five biologically occurring bases (adenine, guanine, thymine, cytosine and uracil) and/or bases other than the five biologically occurring bases. For example, a polynucleotide of the invention can contain one or more modified, non-standard, or derivatized base moieties or one or more modified sugar moieties.

"Percentage of sequence identity," or "identity" is determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The term "substantial identity" of polypeptide sequences means that a polypeptide comprises a sequence that has at least 75% sequence identity. Alternatively, percent identity can be any integer from 75% to 100%. Exemplary embodiments include at least: 75%, 80%, 85%, 90%, 95%, or 99% compared to a reference sequence using the programs described herein; preferably BLAST using standard parameters, as described below. One of skill will recognize that these values can be appropriately adjusted to determine identity of proteins encoded by two nucleotide sequences by taking into account codon degeneracy, amino acid similarity, reading frame positioning and the like. Polypeptides which are "substantially similar" share sequences as noted above except that residue positions which are not identical may differ by conservative amino acid changes. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, aspartic acid-glutamic acid, and asparagine-glutamine.

Another indication that nucleotide sequences are substantially identical is if two molecules hybridize to each other, or a third nucleic acid, under stringent conditions. Stringent conditions are sequence dependent and will be different in different circumstances. Generally, stringent conditions are selected to be about 5° C. lower than the thermal melting point (Tm) for the specific sequence at a defined ionic strength and pH. The Tm is the temperature (under defined ionic strength and pH) at which 50% of the target sequence hybridizes to a perfectly matched probe. Typically, stringent conditions will be those in which the salt concentration is about 0.02 molar at pH 7 and the temperature is at least about 60° C.

As used herein, the term "specifically hybridizes," in the context of an oligonucleotide, refers to an oligonucleotide that hybridizes under suitable conditions to a sequence, but does not hybridize to other related or unrelated sequences. In some cases, the suitable conditions are stringent hybridization conditions. In some cases, the suitable conditions are nucleic acid amplification conditions, such as PCR amplification conditions. In some cases, oligonucleotides that specifically hybridize to a nucleic acid can hybridize to a bisulfite converted nucleic acid but not to a nucleic acid of the same sequence that is resistant to bisulfite conversion (e.g., a methylated nucleic acid) or has not been subjected to bisulfite conversion. In some cases, oligonucleotides that specifically hybridize to a nucleic acid can hybridize to a nucleic acid sequence but not to a nucleic acid of the same sequence that has been subjected to bisulfite conversion.

The term heterologous, in the context of a heterologous promoter refers to a promoter operably linked to a polynucleotide sequence encoding an RNA or protein, wherein the promoter is not found operably linked to that polynucleotide in a wild-type organism. Similarly, the term "heterologous" in the context of a heterologous expression cassette refers to an expression cassette that differs from any of the expression cassettes found in a wild-type organism. Thus, the term heterologous expression cassette can contain endogenous promoters and endogenous coding sequences, so long as the expression cassette as a whole is not naturally found in the wild-type organism.

DETAILED DESCRIPTION OF THE INVENTION

I. Introduction

Figure 1:
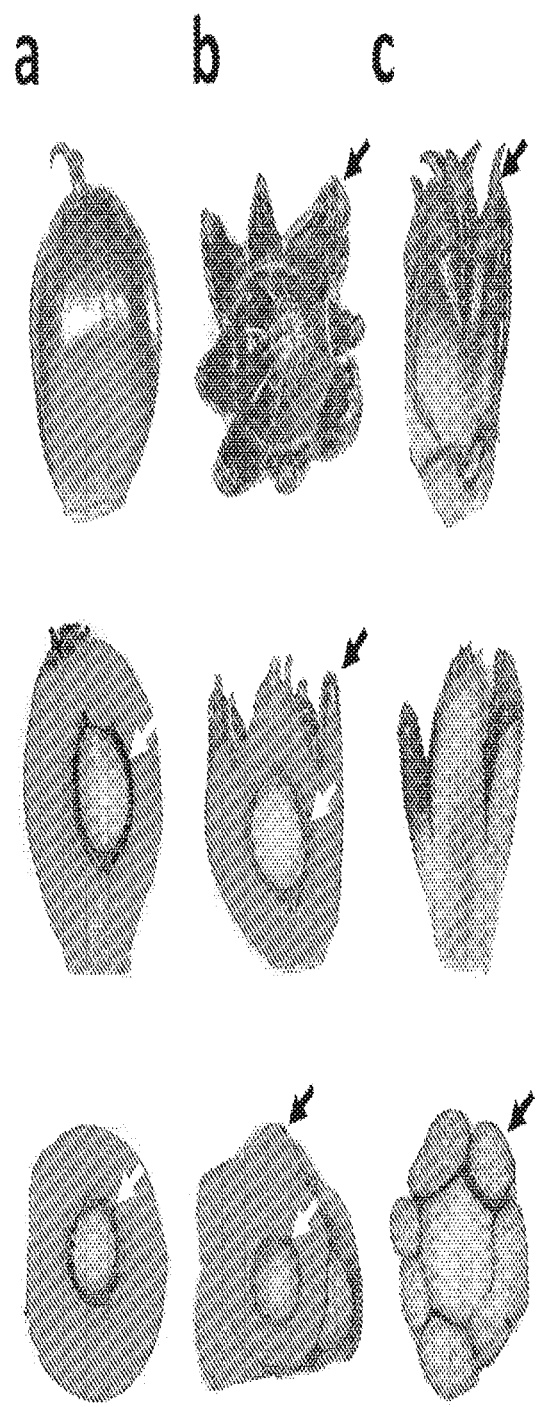
FIG. 1. Normal and mantled fruit forms. a-c, Fruit forms of (a) normal, (b) fertile mantled and (c) parthenocarpic mantled fruit. Images are displayed as whole fruit (top), longitudinal sectioned fruit (middle) and cross sectioned fruit (bottom). Whole fruits are shown as side views of normal and parthenocarpic mantled, and as a top view of fertile mantled so that multiple pseudocarpels are visible. Black arrows indicate one of several pseudocarpels per abnormal fruit. White arrows indicate the lignified shell and kernel of normal and fertile mantled fruit which are absent in parthenocarpic mantled fruit.

The development of oil palm planting material that consistently exhibits high oil yields has been hindered by the emergence of somaclonal abnormalities in plants that have been in vitro cultured. Oil palm plants exhibiting somaclonal abnormality as a result of in vitro culture include, for example, those exhibiting a Mantled phenotype. The present inventors have identified a molecular mechanism underlying somaclonal abnormality in oil palm plants: differential methylation within the oil palm locus corresponding to SEQ ID NO:1. The inventors have also identified DNA regions, meta-regions, and biomarkers within SEQ ID NO:1, where the methylation status is predictive of the presence or absence of a somaclonal abnormality. Methods, compositions, kits, and computer program products, including those described herein, can therefore be utilized to determine the methylation status of one or more DMRs, DNA regions, meta-regions, biomarkers, or cytosine nucleotides (e.g., cytosines in a CHG motif) therein to predict the presence or absence of a somaclonal abnormality in a plant and/or separate plants based on the predicted presence or absence of somaclonal abnormality each plant. For example, a culture of plant cells can be assayed to predict the presence or absence of a somaclonal abnormality (e.g., the Mantled phenotype).

II. DNA Regions

Differential methylation can be detected in a DNA region. A DNA region comprises a nucleic acid having one or more methylation sites of interest (e.g., a cytosine, a "microarray feature," or an amplicon amplified from a select primer or primer pair) and flanking nucleic acid sequences (i.e., "wingspan") of up to 4 kilobases (kb) in either or both of the 3' or 5' direction from the amplicon. This range roughly corresponds to the lengths of DNA fragments obtained by randomly fragmenting the DNA before screening for differential methylation between DNA in two or more samples (e.g., carrying out methods used to initially identify differentially methylated sequences as described in Example 1, below). In some embodiments, the wingspan of the one or more DNA regions is about 0.5 kb, 0.75 kb, 1.0 kb, 1.5 kb, 2.0 kb, 2.5 kb, 3.0 kb, 3.5 kb or 4.0 kb in both 3' and 5' directions relative to the sequence represented by the microarray feature. In some embodiments, the wingspan of the one or more DNA regions is about 2 kb, or 2 kb, in both the 3' and 5' directions relative to centermost nucleotide in the sequence represented by a microarray feature.

The methylation sites in a DNA region can reside in non-coding transcriptional control sequences (e.g., promoters, enhancers, etc.) or in coding sequences, including introns, exons, and retrotransposon elements of the oil palm genome locus corresponding to SEQ ID NO:1. In some embodiments, the methods comprise detecting the methylation status within, at, or near one or more transposable elements (e.g., comprising a nucleic acid sequence that is in, or within about 1.0 kb, 1.5 kb, 2.0 kb, 2.5 kb, 3.0 kb, 3.5 kb or 4.0 kb 3' or 5' of, a transposable element in SEQ ID NO:1).

The DNA regions of the invention also include naturally occurring variants, including for example, variants occurring in different subject populations and variants arising from single nucleotide polymorphisms (SNPs). SNPs encompass insertions and deletions of varying size and simple sequence repeats, such as dinucleotides and trinucleotide repeats. Variants include nucleic acid sequences sharing at least 90%, 95%, 98%, 99% sequence identity, i.e., having one or more deletions, additions, substitutions, inverted sequences, etc., relative to a DNA region described herein. Where the nucleic acid is an siRNA having a length of 21 or 24 nucleotides, variants include nucleic acid sequences sharing at least 15, 16, 17, 18, 19, 20, 21, 22, 23, or 24 identical nucleotides, e.g., having 1, 2, 3, 4, 5, 6, 7, 8, 9 or more deletions, additions, substitutions, inverted sequences, etc., relative to a DNA region described herein.

III. METHODS

In some embodiments, the presence or absence of somaclonal abnormalities (e.g., the Mantled phenotype) can be predicted by determining the methylation status of one or more cytosines within a genomic region of an oil palm plant corresponding to SEQ ID NO:1. SEQ ID NO:1 contains three different retrotransposons (SEQ ID NO:2, Element 1 (Rider); SEQ ID NO:3, Element 2 (Karma); SEQ ID NO:4, Element 3 (Koala)) and the EgDEF1 gene, which is transcribed in at least four different forms (cDEF1, encoded by SEQ ID NO:5; tDEF1, encoded by SEQ ID NO:75; kDEF1, encoded by SEQ ID NO:78; and gDEF1, encoded by SEQ ID NO:80).

The methylation status of one or more cytosines (e.g., cytosines in a CHG motif) of SEQ ID NO:1 can, e.g., be determined and compared to a control, or a threshold value, and the presence or absence of somaclonal abnormalities can thereby be predicted. In some cases, a somaclonal abnormality is predicted when the methylation is increased at one or more specific cytosines (e.g., relative to a control or threshold value). In some cases, a somaclonal abnormality is predicted when the methylation is reduced at one or more specific cytosines (e.g., relative to a control or threshold value). In some cases, a somaclonal abnormality is predicted when the methylation is either increased or reduced at one or more specific cytosines (e.g., relative to a control or threshold value).

In some embodiments, the presence or absence of somaclonal abnormalities (e.g., the Mantled phenotype) can be predicted by determining the expression level of one or more transcripts that are differentially expressed in normal versus mantled plants, plant cells, or tissues. In some cases, a somaclonal abnormality is predicted when expression of one or more transcripts is reduced (e.g., relative to a control or threshold value). In some cases, the transcript is encoded by a sequence within SEQ ID NO:1. In some cases, the transcript is encoded by SEQ ID NO:77. In some cases, the transcript is encoded by a sequence within one or more of SEQ ID NOs: 130-134, 136-139, 142-143, or 144-161. In some cases, the transcript is encoded by a sequence within one or more of SEQ ID NO:144-161. In some cases, the transcript is an siRNA transcript (e.g., a 24mer siRNA). In some cases, a somaclonal abnormality is predicted when expression of one or more transcripts is increased (e.g., relative to a control or threshold value). In some cases, the transcript is encoded by a sequence within one or more of SEQ ID NO: 135, 140, or 141. In some cases, the transcript is an siRNA transcript (e.g., a 24mer siRNA).

A. Methods for Determining Methylation

Any method for detecting DNA methylation can be used in the methods of the present invention.

In some embodiments, methods for detecting methylation include randomly shearing or randomly fragmenting the genomic DNA, cutting the DNA with a methylation-dependent or methylation-sensitive restriction enzyme and subsequently selectively identifying and/or analyzing the cut or uncut DNA. Selective identification can include, for example, separating cut and uncut DNA (e.g., by size) and quantifying a sequence of interest that was cut or, alternatively, that was not cut. See, e.g., U.S. Pat. No. 7,186,512. Alternatively, the method can encompass amplifying intact DNA after restriction enzyme digestion, thereby only amplifying DNA that was not cleaved by the restriction enzyme in the area amplified. See, e.g., U.S. Pat. Nos. 7,910,296; 8,361,719; 7,901,880; and 8,163,485. In some embodiments, amplification can be performed using a primer, or pair of primers, that is gene specific. Alternatively, adaptors can be added to the ends of the randomly fragmented DNA, the DNA can be digested with a methylation-dependent or methylation-sensitive restriction enzyme, intact DNA can be amplified using a primer or primers that hybridize to the adaptor sequences. In this case, a second step can be performed to determine the presence, absence or quantity of a particular gene in an amplified pool of DNA. In some embodiments, the DNA is amplified using real-time, quantitative DNA amplification (e.g., PCR).

In some embodiments, the methods comprise quantifying the average methylation density in a target sequence within a population of genomic DNA. In some embodiments, the method comprises contacting genomic DNA with a methylation-dependent restriction enzyme or methylation-sensitive restriction enzyme under conditions that allow for at least some copies of potential restriction enzyme cleavage sites in the locus to remain uncleaved; quantifying intact copies of the locus; and comparing the quantity of amplified product to a control value representing the quantity of methylation of control DNA, thereby quantifying the average methylation density in the locus compared to the methylation density of the control DNA.

The quantity of methylation of a locus of DNA can be determined by providing a sample of genomic DNA comprising the locus, cleaving the DNA with a restriction enzyme that is either methylation-sensitive or methylation-dependent, and then quantifying the amount of intact (e.g., uncut by the methylation-sensitive or methylation-dependent restriction enzyme) DNA or quantifying the amount of cut DNA at the DNA locus of interest. The amount of intact or cut DNA will depend on the initial amount of genomic DNA containing the locus, the amount of methylation in the locus, and the number (i.e., the fraction) of nucleotides in the locus that are methylated in the genomic DNA. The amount of methylation in a DNA locus can be determined by comparing the quantity of intact DNA or cut DNA to a control value representing the quantity of intact DNA or cut DNA in a similarly-treated DNA sample. The control value can represent a known or predicted number of methylated nucleotides. Alternatively, the control value can represent the quantity of intact or cut DNA from the same locus in another (e.g., normal, wild-type) cell or a second locus.

By using at least one methylation-sensitive or methylation-dependent restriction enzyme under conditions that allow for at least some copies of potential restriction enzyme cleavage sites in the locus to remain uncleaved and subsequently quantifying the remaining intact copies and comparing the quantity to a control, average methylation density of a locus can be determined. If the methylation-sensitive restriction enzyme is contacted to copies of a DNA locus under conditions that allow for at least some copies of potential restriction enzyme cleavage sites in the locus to remain uncleaved due to the presence of methylation at the cleavage site, then the remaining intact DNA will be directly proportional to the methylation density, and thus may be compared to a control to determine the relative methylation density of the locus in the sample. Similarly, if a methylation-dependent restriction enzyme is contacted to copies of a DNA locus under conditions that allow for at least some copies of potential restriction enzyme cleavage sites in the locus to remain uncleaved due to the lack of methylation at the cleavage site, then the remaining intact DNA will be inversely proportional to the methylation density, and thus may be compared to a control to determine the relative methylation density of the locus in the sample. Such assays are disclosed in, e.g., U.S. Pat. No. 7,910,296.

Kits for the above methods can include, e.g., one or more of methylation-dependent restriction enzymes, methylation-sensitive restriction enzymes, amplification (e.g., PCR) reagents, and one or more probes and/or primers. In some cases, the one or more probes and/or primers are specific for, e.g., specifically hybridize to, SEQ ID NO:1, or a portion thereof. In some cases, the one or more probes and/or primers are specific for, e.g., specifically hybridize to, bisulfite converted SEQ ID NO:1, or a portion thereof.

Quantitative amplification methods (e.g., quantitative PCR or quantitative linear amplification) can be used to quantify the amount of intact DNA within a locus selected by one or more amplification primers following restriction digestion. Methods of quantitative amplification are disclosed in, e.g., U.S. Pat. Nos. 6,180,349; 6,033,854; and 5,972,602, as well as in, e.g., Gibson et al., *Genome Research* 6:995-1001 (1996); DeGraves, et al., *Biotechniques* 34(1):106-10, 112-5 (2003); Deiman B, et al., *Mol Biotechnol.* 20(2):163-79 (2002). Amplifications can be monitored in "real time."

Additional methods for detecting DNA methylation can involve genomic sequencing before and after treatment of the DNA with bisulfite. See, e.g., Frommer et al., *Proc. Natl. Acad. Sci. USA* 89:1827-1831 (1992). When sodium bisulfite is contacted to DNA, unmethylated cytosine is converted to uracil, while methylated cytosine is not modified.

In some embodiments, restriction enzyme digestion of PCR products amplified from bisulfite-converted DNA is used to detect DNA methylation. See, e.g., Sadri & Hornsby, *Nucl. Acids Res.* 24:5058-5059 (1996); Xiong & Laird, *Nucleic Acids Res.* 25:2532-2534 (1997).

In some embodiments, a MethyLight assay is used alone or in combination with other methods to detect DNA methylation (see, Eads et al., *Cancer Res.* 59:2302-2306 (1999)). Briefly, in the MethyLight process genomic DNA is converted in a sodium bisulfite reaction (the bisulfite process converts unmethylated cytosine residues to uracil). Amplification of a DNA sequence of interest is then performed using, e.g., PCR primers that hybridize to CpG dinucleotides. By using one or more primers that hybridize only to sequences resulting from bisulfite conversion of unmethylated DNA, (or alternatively to methylated sequences that are not converted) amplification can indicate methylation status of sequences where the one or more primers hybridize. Similarly, the amplification product can be detected with a probe that specifically binds to a sequence resulting from bisulfite treatment of unmethylated (or methylated) DNA. If desired, both primer(s) and probe(s) can be used to detect methylation status. Thus, kits for use with MethyLight can include sodium bisulfite as well as primer(s) or detectably-labeled probe(s) (including but not limited to Taqman or molecular beacon probes) that distinguish between methylated and unmethylated DNA that have been treated with bisulfite. Other kit components can include, e.g., reagents necessary for amplification of DNA including but not limited to, PCR buffers, deoxynucleotides; and a thermostable polymerase.

In some embodiments, a Ms-SNuPE (Methylation-sensitive Single Nucleotide Primer Extension) reaction is used alone or in combination with other methods to detect DNA methylation (see, Gonzalgo & Jones, *Nucleic Acids Res.* 25:2529-2531 (1997)). The Ms-SNuPE technique is a quantitative method for assessing methylation differences at specific CpG sites based on bisulfite treatment of DNA, followed by single-nucleotide primer extension (Gonzalgo & Jones, supra). Briefly, genomic DNA is reacted with sodium bisulfite to convert unmethylated cytosine to uracil while leaving 5-methylcytosine unchanged. Amplification of the desired target sequence is then performed using PCR primers specific for bisulfite-converted DNA, and the resulting product is isolated and used as a template for methylation analysis at the CpG site(s) of interest.

Typical reagents (e.g., as might be found in a typical Ms-SNuPE-based kit) for Ms-SNuPE analysis can include, but are not limited to: PCR primers for specific gene (or methylation-altered DNA sequence or CpG island); optimized PCR buffers and deoxynucleotides; gel extraction kit; positive control primers; Ms-SNuPE primers for a specific gene; reaction buffer (for the Ms-SNuPE reaction); and detectably-labeled nucleotides. Additionally, bisulfite conversion reagents may include: DNA denaturation buffer; sulfonation buffer; DNA recovery regents or kit (e.g., precipitation, ultrafiltration, affinity column); desulfonation buffer; and DNA recovery components.

In some embodiments, a methylation-specific PCR ("MSP") reaction is used alone or in combination with other methods to detect DNA methylation. An MSP assay entails initial modification of DNA by sodium bisulfite, converting all unmethylated, but not methylated, cytosines to uracil, and subsequent amplification with primers specific for methylated versus unmethylated DNA. See, Herman et al., *Proc. Natl. Acad. Sci. USA* 93:9821-9826, (1996); U.S. Pat. No. 5,786,146.

Additional methylation detection methods include, but are not limited to, methylated CpG island amplification (see, Toyota et al., Cancer Res. 59:2307-12 (1999)) and those described in, e.g., U.S. Patent Publication 2005/0069879; Rein, et al. *Nucleic Acids Res.* 26 (10): 2255-64 (1998); Olek, et al. *Nat Genet.* 17(3): 275-6 (1997); and PCT Publication No. WO 00/70090.

In some embodiments, the methods include: obtaining a biological sample from a plant; determining the methylation status of at least one cytosine (e.g., cytosine in a CHG motif) within a differential methylation region (DMR) in the sample from the plant, wherein the DMR is within a sequence of DNA at least 70%, 80%, 90%, 95%, or 99% identical, or identical, to SEQ ID NO:1; and correlating the methylation status of the at least one cytosine to the presence or absence of a somaclonal abnormality in the plant, wherein the correlation comprises predicting the presence or absence of somaclonal abnormality in the plant.

A biological sample can be obtained by any method known in the art. In general, the biological sample is obtained in a manner that preserves the nucleic acid of the sample. In some cases, the biological sample is obtained and treated to preserve the methylation status of genomic DNA therein. In some cases, the biological sample is obtained and treated to preserve RNA integrity.

Alternatively, in some cases, the methods include providing a prediction of a presence or absence of a somaclonal abnormality in a plurality of plants, wherein the presence or absence of a somaclonal abnormality is determined by a methylation status of at least one cytosine within a differential methylation region (DMR) in a sample from each plant, wherein the DMR is within a sequence of DNA at least 70%, 80%, 90%, 95%, or 99% identical, or identical, to SEQ ID NO:1; and physically separating a plant predicted to have a somaclonal abnormality from a plant predicted to lack a somaclonal abnormality.

In some cases, the method further includes physically separating a plant predicted to have a somaclonal abnormality from one or more plants predicted to lack a somaclonal abnormality. In some cases, the plants can be physically separated, e.g., by selecting plants predicted to have a somaclonal abnormality and destroying or discarding them. In some cases, the plants are physically separated by selecting plants predicted to lack a somaclonal abnormality for cultivation. In some cases, plants selected for cultivation are germinated, transplanted, or planted. In some cases, plants not selected for cultivation are discarded or destroyed. In some cases, physically separated plants are treated to reduce, mitigate, eliminate, or prevent the somaclonal abnormality. For example, the physically separated plants can be contacted with an expression cassette containing a promoter operably linked to a polynucleotide encoding a transcript that is reduced in expression in a plant predicted to have a somaclonal abnormality.

In some cases, the DMR is within a DNA meta-region in the sample from the plant. The meta-region contains two or more overlapping DNA regions that exhibit differential methylation. Exemplary DNA meta-regions include overlapping 4 kb wingspan regions (2 kb 5' and 3') centered on biomarkers corresponding (e.g., at least 90%, 95%, or 99% identical, or identical) to SEQ ID NOS: 7, 8, 9, 10, 11, 12, 13, 14, 15, 16, 17, 18, 19, 20, 21, 22, 23, 24, 25, 26, 27, 28, 29, 30, 31, 32, 33, 34, 71, and 72. In some cases, the DNA meta-regions are in SEQ ID NO:1, or are in the locus corresponding to (e.g., at least 70%, 80%, 90%, 95%, or 99% identical, or identical, to) SEQ ID NO:1 in the oil palm genome. Exemplary DNA meta-regions include those at least 70%, 80%, 90%, 95%, or 99% identical, or identical, to a sequence selected from the group consisting of SEQ ID NO:35, 36, 37, 38, 39, 40, 41, 42, 43, 44, 45, 46, 47, 48, 49, 50, 51, 52, 53, 54, 55, 56, 57, 58, 59, 60, 61, 62, 73, and 74. In some cases, the DMR is within a DNA region in the sample from the plant. The DNA region can, e.g., be a 4 kb, wherein the DNA region is at least about 70%, 80%, 90%, 95%, or 99% identical, or identical, to a sequence selected from the group consisting of SEQ ID NO:35, 36, 37, 38, 39, 40, 41, 42, 43, 44, 45, 46, 47, 48, 49, 50, 51, 52, 53, 54, 55, 56, 57, 58, 59, 60, 61, 62, 73, and 74. In some cases, the cytosine is in a biomarker, wherein the biomarker is at least 90%, 95%, or 99% identical, or identical, to a sequence selected from the group consisting of SEQ ID NO:7, 8, 9, 10, 11, 12, 13, 14, 15, 16, 17, 18, 19, 20, 21, 22, 23, 24, 25, 26, 27, 28, 29, 30, 31, 32, 33, 34, 71, and 72.

In some embodiments, the presence of a somaclonal abnormality is predicted when the methylation status of at least one cytosine is reduced relative to a control locus. In some embodiments, the presence of a somaclonal abnormality is predicted when the methylation status of at least one cytosine is increased relative to a control locus. In some cases, either an increase or a decrease in methylation of at least one cytosine predicts the presence of a somaclonal abnormality. In some cases, the at least one cytosine is in a locus, retrotransposon, DNA meta-region, DNA region, or biomarker corresponding (e.g., at least 70%, 80%, 90%, 95%, or 99% identical, or identical) to a sequence selected from SEQ ID NOS: 1-5, and 7-75, 78, or 80.

The methylation status of the at least one cytosine can be compared to a control locus to determine a relative change in methylation. For example, if the methylation status of the cytosine at the test locus indicates a higher degree of methylation as compared to the methylation status of at the control locus, then the methylation status of the test locus is increased. As another example, if the methylation status of the cytosine at the test locus indicates a lower degree of methylation as compared to the methylation status of at the control locus, then the methylation status of the test locus is decreased. Typically, the control locus will have a known, relatively constant, methylation status. For example, the control locus can be previously determined to have no, some, or a high amount of methylation, thereby providing a relative constant value to control for error in detection methods, etc., unrelated to the presence or absence of a somaclonal abnormality. In some embodiments, the control locus is endogenous, i.e., is part of the genome of the individual sampled. Alternatively, the control locus can be an exogenous locus, e.g., a DNA sequence spiked into the sample in a known quantity and having a known methylation status.

In some embodiments, the methylation status of at least one cytosine in 2, 3, 4, 5, 6, 7, 8, 9, 10, 11, 12, 13, 14, 15, 16, 17, 18, 19, 20, 21, 22, 23, 24, 25, 26, 27, or 28 different differential methylation regions (DMRs) are determined to predict the presence or absence of a somaclonal abnormality. In some cases, the DMRs are in a locus, retrotransposon, DNA meta-region, DNA region, or biomarker corresponding (e.g., at least 70%, 80%, 90%, 95%, or 99% identical, or identical) to a sequence independently selected from SEQ ID NOS: 1-5, and 7-75.

In some embodiments, the predicted somaclonal abnormality is an abnormality that reduces fruit yield, oil yield, growth, or reproduction of an oil palm plant. In some cases, the reduction is relative to a control plant, such as a parent plant, or a wild-type plant of the same fruit color (nigrescens or virescens) or shell thickness (dura, tenera, or pisifera) phenotype. In some cases, the somaclonal abnormality exhibits a Mantled phenotype.

B. Predicting Abnormality by Gene Expression Analysis

Methylation of genomic DNA can affect expression (transcription and/or translation) of nearby gene sequences. Therefore, in some embodiments, the methods include the step of correlating the methylation status of at least one cytosine in a DNA region with the expression of nearby coding sequences, such as one or more transcripts of cDEF1 (SEQ ID NO:5), tDEF1 (SEQ ID NO:75), kDEF1 (SEQ ID NO:78), or gDEF1 (SEQ ID NO:80), and/or one or more transcripts of a retrotransposon near the EgDEF1 locus (SEQ ID NO:2, 3, or 4). For example, expression of gene sequences within about 1.0 kb, 1.5 kb, 2.0 kb, 2.5 kb, 3.0 kb, 3.5 kb or 4.0 kb, or more, in either the 3' or 5' direction from the cytosine of interest in the DNA region can be detected. In some embodiments, the methods include the step of detecting or quantifying the expression of nearby coding sequences, such as one or more transcripts of cDEF1 (SEQ ID NO:5), tDEF1 (SEQ ID NO:75), kDEF1 (SEQ ID NO:78), or gDEF1 (SEQ ID NO:80), and/or one or more transcripts of a retrotransposon near the EgDEF1 locus (SEQ ID NO:2, 3, or 4), and correlating the expression with a presence or absence or prediction of a somaclonal abnormality.

In some cases, expression of cDEF1 is correlated with a normal phenotype. For example, in some cases, cDEF1 expression is higher in plants with a normal phenotype, and thus a Mantled phenotype is predicted when a low level (e.g., relative to a threshold or control) of cDEF1 expression is detected. In some cases, expression of tDEF1 is correlated with a Mantled phenotype. For example, in some cases, tDEF1 expression is higher in plants with a Mantled phenotype, and thus a Mantled phenotype is predicted when a high level (e.g., relative to a threshold or control) of tDEF1 expression is detected. In some cases, expression of kDEF1 is correlated with a Mantled phenotype. For example, in some cases, kDEF1 expression is higher in plants with a Mantled phenotype, and thus a Mantled phenotype is predicted when a high level (e.g., relative to a threshold or control) of kDEF1 expression is detected. In some cases, expression of gDEF1 is correlated with a Mantled phenotype. For example, in some cases, gDEF1 expression is higher in plants with a Mantled phenotype, and thus a Mantled phenotype is predicted when a high level (e.g., relative to a threshold or control) of gDEF1 expression is detected. In some cases, the threshold or control is a sample from a normal plant or an expression value for a normal plant. In some cases, the threshold or control is a sample from an abnormal (e.g., Mantled) plant or an expression value for an abnormal (e.g., Mantled) plant.

In some cases, expression of an siRNA encoded within SEQ ID NO:1 is correlated with a normal phenotype, and thus a Mantled phenotype is predicted when a low level (e.g., relative to a threshold or control) of siRNA expression is detected. For example, in some cases, a Mantled phenotype is predicted when a low level (e.g., relative to a threshold or control) of expression of one or more siRNAs encoded by one or more of SEQ ID NOs:144-161 is detected. In some cases, a Mantled phenotype is predicted when expression of one or more siRNAs encoded by one or more of SEQ ID NOs:144-161 is reduced by at least 50% relative to a control or threshold value. As another example, in some cases, a Mantled phenotype is predicted when a low level (e.g., relative to a threshold or control) of expression of an siRNA encoded by SEQ ID NO:91 is detected. In some cases, a Mantled phenotype is predicted when expression of an siRNA encoded by SEQ ID NO:91 is reduced by at least 50%, 60%, 70%, 80%, or 90% relative to a control or threshold value.

Methods for measuring transcription and/or translation of a particular gene sequence are well known in the art. See, for example, Ausubel, *Current Protocols in Molecular Biology*, 1987-2006, John Wiley & Sons; and Sambrook and Russell, *Molecular Cloning: A Laboratory Manual*, 3rd Edition, 2000, Cold Spring Harbor Laboratory Press. In some embodiments, the gene or protein expression of a gene encoded in SEQ ID NO:1, 2, 3, 4, 5, 75, 78, or 80 is compared to a control, for example the expression of a nearby gene sequence from a sample from plant known to be negative for somaclonal abnormality or known to be positive for somaclonal abnormality, or to an expression level that distinguishes between somaclonally abnormal and wild-type states. Such methods involving detection of expression, like the methods of detecting methylation described herein, are useful in predicting the presence or absence of somaclonal abnormality (e.g., useful in predicting the presence or absence of the Mantled phenotype) in a plant.

In some cases, the expression of a regulatory RNA is detected. For example, a regulatory RNA that modulates the expression of cDEF1 (SEQ ID NO:5), tDEF1 (SEQ ID NO:75) can be detected. Exemplary regulatory RNAs include, but are not limited to, microRNAs. In some cases, the expression of one or more regulatory RNAs that are at least partially encoded within a retrotransposon located in the genomic locus corresponding to SEQ ID NO:1 is detected. Differential DNA methylation can result in changes in regulatory RNA expression (e.g., microRNAs, small interfering RNAs and antisense RNAs) which can then result in changes of gene expression in cis or in trans. Likewise, regulatory RNAs themselves can direct the establishment and/or maintenance of DNA methylation state in plants via the RNA-directed DNA methylation (RdDM) system. See Vu, et al. 2013 Development 140: 2953-60, Regulski, et al. 2013 Genome Res 23: 1651. Therefore, in some cases, mechanisms involving regulatory RNAs may be involved in either the establishment of differential DNA methylation associated with the Mantled phenotype, or in the mechanism by which differential DNA methylation regulates the function of genes involved in the Mantled phenotype.

In some embodiments, the methods further comprise the step of correlating the methylation status of one or more cytosines in SEQ ID NO:1, or DNA region, DNA meta-region, or biomarker therein, to expression of one or more of the gene regions identified in SEQ ID NO:1, 2, 3, 4, 5, 75, 78, or 80. In some embodiments, the methods further comprise the step of correlating the methylation status and/or expression level to the Mantled phenotype.

In some embodiments, the expression of a small RNA is detected. Small RNAs are a small non-coding expressed RNA molecules. Small RNAs can be involved in gene regulation and other biological processes. Exemplary small RNAs detected or quantified by the methods of the present invention include one or more small RNAs encoded by a polynucleotide sequence at least 75%, 80%, 85%, 90%, 95%, or 99% identical, or identical, to SEQ ID NO:91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160 or 161. Exemplary small RNAs detected or quantified by the methods of the present invention include one or more small RNAs at least partially encoded by a polynucleotide sequence at least 75%, 80%, 85%, 90%, 95%, or 99% identical, or identical, to SEQ ID NO:91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160 or 161.

In some cases, small RNAs are differentially expressed in normal versus abnormal (e.g., Mantled) plants. Such differential expression can be detected in a plant sample and correlated with a predicted normal or abnormal (e.g., Mantled) phenotype for the plant corresponding to the sample. Such differentially expressed small RNAs include, but are not limited to those encoded by, or at least partially encoded by, a polynucleotide at least 75%, 80%, 85%, 90%, 95%, or 99% identical, or identical, to SEQ ID NO:91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160 or 161.

In some cases, an abnormal (e.g., Mantled) phenotype is predicted when expression of a small RNA encoded by, or at least partially encoded by, a polynucleotide sequence at least 75%, 80%, 85%, 90%, 95%, or 99% identical, or identical, to SEQ ID NO:91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 130, 131, 132, 133, 134, 135, 136, 137, 138, 139, 140, 141, 142, or 143 is increased (e.g., relative to a threshold or control). In some cases, an abnormal (e.g., Mantled) phenotype is predicted when expression of a small RNA encoded by, or at least partially encoded by, a polynucleotide sequence at least 75%, 80%, 85%, 90%, 95%, or 99% identical, or identical, to SEQ ID NO:91, 92, 93, 94, 95, 96, 97, 98, 99, 100, 101, 102, 103, 104, 105, 106, 107, 108, 109, 110, 111, 112, 113, 114, 116, 117, 135 140, or 141 is increased (e.g., relative to a threshold or control). In some cases, the threshold or control is a sample from a normal plant or an expression value for a normal plant. In some cases, the threshold or control is a sample from an abnormal (e.g., Mantled) plant or an expression value for an abnormal (e.g., Mantled) plant.

In some cases, an abnormal (e.g., Mantled) phenotype is predicted when expression of a small RNA encoded by, or at least partially encoded by, a polynucleotide sequence at least 75%, 80%, 85%, 90%, 95%, or 99% identical, or identical, to SEQ ID NO:135, 140, or 141 is detected, or when an increased expression level (e.g., relative to a threshold or control) is detected. In some cases, a normal phenotype is predicted when expression of a small RNA encoded by, or at least partially encoded by, a polynucleotide sequence at least 75%, 80%, 85%, 90%, 95%, or 99% identical, or identical, to SEQ ID NO: 130, 131, 132, 133, 134, 136, 137, 138, 139, 142, or 143 is detected, or when an increased expression level (e.g., relative to a threshold or control) is detected. In some cases, the threshold or control is a sample from a normal plant or an expression value for a normal plant. In some cases, the threshold or control is a sample from an abnormal (e.g., Mantled) plant or an expression value for an abnormal (e.g., Mantled) plant.

In some cases, an abnormal (e.g., Mantled) phenotype is predicted when expression of a small RNA encoded by, or at least partially encoded by, a polynucleotide sequence at least 75%, 80%, 85%, 90%, 95%, or 99% identical, or identical, to SEQ ID NO:91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160 or 161 is decreased (e.g., relative to a threshold or control). In some cases, an abnormal (e.g., Mantled) phenotype is predicted when expression of a small RNA encoded by, or at least partially encoded by, a polynucleotide sequence at least 75%, 80%, 85%, 90%, 95%, or 99% identical, or identical, to SEQ ID NO:97, 115, 118, 119, 120, 121, 122, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160 or 161 is decreased (e.g., relative to a threshold or control).

In some embodiments, the methods include: obtaining a biological sample from a plant; detecting or quantifying expression of one or more of SEQ ID NO:2, 3, 4, 5, 75, 78, 80, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160 or 161; and correlating the expression or expression level to the presence or absence of a somaclonal abnormality in the plant, wherein the correlation comprises predicting the presence or absence of somaclonal abnormality in the plant.

A biological sample can be obtained by any methods known in the art. In general, the biological sample is obtained in a manner that preserves the nucleic acid of the sample. In some cases, the biological sample is obtained and treated to preserve the RNA therein. In some cases, the biological sample is obtained and treated to preserve RNA integrity.

Alternatively, in some cases, the methods include providing a prediction of a presence or absence of a somaclonal abnormality in a plurality of plants, wherein the presence or absence of a somaclonal abnormality is determined by gene expression analysis; and physically separating a plant predicted to have a somaclonal abnormality from a plant predicted to lack a somaclonal abnormality.

In some cases, the method further includes physically separating a plant predicted to have a somaclonal abnormality from one or more plants predicted to lack a somaclonal abnormality. In some cases, the plants can be physically separated, e.g., by selecting plants predicted to have a somaclonal abnormality and destroying or discarding them. In some cases, the plants are physically separated by selecting plants predicted to lack a somaclonal abnormality for cultivation. In some cases, plants selected for cultivation are germinated, transplanted, or planted. In some cases, plants not selected for cultivation are discarded or destroyed. In some cases, physically separated plants are treated to reduce, mitigate, eliminate, or prevent the somaclonal abnormality.

In some embodiments, the predicted somaclonal abnormality is an abnormality that reduces fruit yield, oil yield, growth, or reproduction of an oil palm plant. In some cases, the reduction is relative to a control plant, such as a parent plant, or a wild-type plant of the same fruit color (nigrescens or virescens) or shell thickness (dura, tenera, or pisifera) phenotype. In some cases, the somaclonal abnormality exhibits a Mantled phenotype.

C. Sampling and/or Sorting Oil palm nucleic acid can be obtained from any suitable cell or tissue of an oil palm plant. For example, oil palm nucleic acid can be obtained from a leaf, a stem, a root, a seed, or a plant cell or group of plant cells in, or obtained from, in vitro culture. In some cases, the oil palm nucleic acid is obtained from endosperm tissue of a seed. In some embodiments, nucleic acid is extracted from a plant cell (e.g., a plant cell in, or obtained from, in vitro culture), a seedling, an immature (e.g., non fruit bearing) plant, or a mature plant. In some cases, the oil palm nucleic acid is obtained in such a manner that the oil palm plant is not reduced in viability or is not substantially reduced in viability. For example, in some cases, sample extraction can reduce the number of viable plants or seeds in a population by less than about 20%, 15%, 10%, 5%, 2.5%, 1%, or less. In some cases, nucleic acid is obtained from a population of plant cells, wherein the population of plant cells is of a uniform or substantially uniform genotype and/or epigenotype at one or all genomic loci. For example, a sample of nucleic acid from a portion of plant cells in an in vitro culture can be extracted, assayed, and the results used to sort the in vitro culture. Exemplary tissue types for obtaining a suitable sample include leaf from in vitro plantlets and nursery ramets. Alternatively, tissues such as roots, inflorescence and zygotic embryos can also be used. Tissues from potential ortets can also be screened prior to tissue culture. Seeds from semiclones and biclones can be tested as well.

Sampling can be automated. For example, a machine can be used to pick plant cell colonies or clumps, or portions thereof, in an in vitro culture for analysis. Similarly, a machine can take samples from a plant or seed, or to take samples from a plurality of plant cell colonies, clumps, plants, or seeds. Sampling can also be performed manually. Further sampling methodologies are described herein.

In some embodiments, the sampling is controlled to deter contamination of the sample. For example, washing steps can be employed between sample processing steps. Alternatively, disposable or removable sample handling elements can be utilized, e.g., disposable pipetting tips, disposable receptacles or containers, or disposable blades or grinders.

In some cases, samples are purified prior to detection of the methylation status of one or more cytosines within a DMR of an oil palm plant. For example, samples can be centrifuged, extracted, precipitated (e.g., alcohol precipitated), or purified using a solid support (e.g., using nucleic acid binding beads or membranes). Additional methods for purification of plant nucleic acids are known by those of skill in the art.

In some embodiments, the presence or absence of a somaclonal abnormality (e.g., the Mantled phenotype) is predicted, and the plant is sorted based on the predicted phenotype. The somaclonal abnormality (e.g., the Mantled phenotype) can be predicted, e.g., based on the methylation status of one or more cytosines in SEQ ID NO:1, or one or more DNA regions, DNA meta-regions, or biomarkers therein, and the plant is sorted based on the predicted phenotype. In some cases, the somaclonal abnormality (e.g., the Mantled phenotype) can be predicted, e.g., based on methylation status or gene expression, and the plant is sorted based on the predicted phenotype.

For example, a plurality of plants can be sorted (e.g., physically separated) into Mantled or non-Mantled (e.g., wild-type) plants based on their predicted phenotype (e.g., based on their methylation or expression as described herein). Wild-type plants can be sorted and stored or utilized and planted or otherwise separated from plant propagation material used for the clonal generation of plants lacking one or more somaclonal abnormalities. In some cases plants having one or more somaclonal abnormalities, e.g., Mantled plants, can be discarded or destroyed (e.g., autoclaved) or not cultivated in commercial oil palm production.

In some cases, the plant is a plant cell, a clump of plant cells, or a colony of plant cells from in vitro culture and the in vitro culture is discarded or destroyed when one or more plants from the culture are predicted to have a somaclonal abnormality (e.g., one or more plants are predicted to exhibit a Mantled phenotype). In some cases, the plant is a young ramet and nucleic acid from the plant is assayed to predict the presence or absence of a somaclonal abnormality. In some cases, the young ramet is then sorted before it is planted in the field. For example, young ramet predicted to have a somaclonal abnormality (e.g., the Mantled phenotype) can be discarded. Ramets predicted to lack a somaclonal abnormality can be further cultivated and/or planted in the field. As yet another alternative, oil palm plants that have been planted in the field for optimal palm oil yield, but are not mature enough to verify the absence of a somaclonal abnormality (e.g., a Mantled phenotype) can be assayed and plants predicted to have a somaclonal abnormality can be removed from the field.

In some embodiments, the presence or absence of a somaclonal abnormality and plant fruit color and/or shell thickness phenotype is predicted. Methods for predicting fruit color and/or shell thickness phenotype, and/or sorting based on such predicted phenotypes, are disclosed in, e.g., U.S. patent application Ser. No. 14/226,508, filed on Mar. 26, 2014; and Ser. No. 13/800,652, filed on Mar. 13, 2013. In some cases, fruit color can be predicted and/or sorted based on the genotype of the VIR gene. In some cases, shell thickness can be predicted and/or sorted based on the genotype of the SHELL gene.

In some cases, the fruit color and/or shell thickness prediction is combined with a methylation status or gene expression information to predict the presence or absence of a somaclonal abnormality (e.g., the Mantled phenotype). In some cases, the plant is sorted based on one, two, or all three predicted phenotypes. For example, the plant can be sorted into nigrescens or virescens seeds or plants and dura, tenera, or pisifera seeds or plants based on their predicted phenotypes. The plants can then be verified as predicted to lack a somaclonal abnormality (e.g., the Mantled phenotype). In some cases, the plants can be predicted to lack a somaclonal abnormality (e.g., the Mantled phenotype), and then such plants can be sorted and/or stored based on their predicted, or expected, nigrescens, virescens, dura, tenera, and/or pisifera phenotypes.

In some cases, the prediction of one or more phenotypes is performed in young plants before cultivation in the field. Therefore, in some cases, the samples are young ramets during hardening in the pre-nursery or acclimatization in the nursery. In some embodiments, the samples are obtained from a semiclonal or biclonal plant that has been germinated and then cultivated less than 1, 2, 4, 6, months or less than 1, 2, 3, 4, or 5 years. In some embodiments, the samples are obtained before the plant has been germinated (e.g., from a seed) or shortly thereafter (e.g., less than about 1, 2, 3, 4, or 5 weeks after germination).

In some embodiments, the methylation status of at least one cytosine is determined an combined with DNA fingerprinting methods to aid in cataloging, selecting, maintaining, organizing, identifying, or tracking of clonal material, stocks, strains, or cultures. For example, in vitro cultures can be confirmed to derive from a specified source or lineage suing DNA fingerprinting and methylation status or gene expression used to predict the presence or absence of a somaclonal abnormality. Similarly, the presence or absence of a strain, stock, or varietal protected under a Plant Variety Protection Act (e.g., the Plant Variety Protection Act of Malaysia or Indonesia) can be ascertained and the presence or absence of a somaclonal abnormality predicted. In some embodiments, palms can be identified and/or confirmed using DNA fingerprinting as having, or likely having, one or more desirable phenotypes (e.g., fruit color, shell thickness, pest resistance, etc.) and the presence or absence of a somaclonal abnormality predicted. Methods for DNA fingerprinting are known in the art and include, e.g., those described in Lim & Rao, J Oil Palm Research, 17:136-144 (December 2005); Billotte, et al., Genome, 44(3): 413-425 (2001); Jack & Mayes, Oleagineux, 48(1): 1-8 (1993); Jack, et al., Theor Appl Genet, 90:543-649 (1995); Cheah, et al., Advances in Oil Palm Research p. 332-70 (2000); and Corley, J. Oil Palm Research, 17:64-69 (2005).

Machines can be utilized to carry out one or more methods described herein, prepare plant samples for one or more methods described herein, or facilitate high throughput sorting of oil palm plants.

In some cases, a machine can sort and orient seeds such that the seed are all oriented in a similar manner. The seeds for example, can be oriented such that embryo region of the seed is down and the embryo free region is oriented up. In some cases, the seeds can be placed into an ordered array or into a single line.

In some embodiments, the seed is held in pre-determined orientation to facilitate efficient and accurate sampling. For example, the machine can orient the seeds by seed shape or visual appearance. In some cases, the seed is oriented to facilitate sampling from the 'Crown' of each respective seed, containing the cotyledon and/or endosperm tissue of the seed, so that the germination viability of each seed is preserved.

In some cases, a machine can separately store plants and corresponding extracted samples. For example, a sample may be obtained from an in vitro culture, and the culture stored. In some cases, the extracted samples and stored plants are organized, labeled, or catalogued in such a way that the sample and the plant (e.g., culture) from which it is derived can be determined. In some cases, the extracted samples and stored plants are tracked so that each can be accessed after data is collected. For example, a sample can be extracted from a culture and the presence or absence of a somaclonal abnormality (e.g., the Mantled phenotype) predicted for the sample, and thus the seed. The plant can then be accessed, germinated, planted, stored, or destroyed based on the prediction.

In some cases, the extraction and storing are performed automatically by the machine, but the methylation analysis and/or treatment of analyzed plants performed manually or performed by another machine. As such, in some embodiments, a system is provided consisting of two or more machines for extraction of samples, sorting and storing, and prediction of the presence or absence of a somaclonal abnormality (e.g., the Mantled phenotype).

In some cases, the plants are stored in an array by the machine, such as individually in an array of tubes or wells. The plants can be sampled and/or interrogated in or from each well. The results of the sampling or interrogating can be correlated with the position of the plant in the array.

Sampling can include extraction and/or analysis of nucleic acid (e.g., DNA or RNA). Sampling can further include magnetic resonance imaging, optical dispersion, optical absorption, ELISA, enzymatic assay, or the like.

Systems, machines, methods and compositions for plant culturing, sampling, and/or sorting are further described in, e.g., U.S. Pat. Nos. 4,910,146; 6,307,123; 6,646,264; 6,673,595; 7,367,155; 8,312,672; 7,685,768; 7,673,572; 8,443,545; 7,998,669; 8,114,669; 8,362,317; 8,076,076; 7,402,731; 7,600,642; 8,237,016; 8,401,271; 8,281,935; 8,241,914; 6,880,771; 7,909,276; 8,221,968; and 7,454,989. Systems, machines, methods and compositions for plant culturing, sampling, and/or sorting are also further described in, e.g., U.S. Patent Application Publication NOs: 2012/180386; 2009/070891; 2013/104454, 2012/117865, 2008/289061; 2008/000815; 2011/132721; 2011/195866; 2011/0079544; 2010/0143906; and 2013/079917. Additional systems, machines, methods, and compositions for plant culturing, sampling, and/or sorting are further described in international patent application publications WO2011/119390; and WO2011/119394.

Also provided herein are methods for using the systems, machines, methods, and compositions described herein for plant (e.g., a seed, a seedling, a plant, a plant cell, a plant cell colony, or a clump of plant cells) sampling or sorting. For example, a plant or set of plants can be loaded into a sampler, and a sample obtained. In some cases, the plant can be stored, e.g., in an array. In some cases, the storage is performed by the machine that samples the plant. In other cases, the plant is stored by another machine, or stored manually. In some cases, DNA can be extracted from the sample. In some cases, sample can be obtained and DNA extracted by the same machine. In other cases, the DNA is extracted by another machine, or manually. The extracted DNA can be analyzed and the presence or absence of a somaclonal abnormality (e.g., the Mantled phenotype) predicted. In some cases, the extracted DNA is analyzed by the same machine, by another machine, or manually. In some cases, the presence or absence of a somaclonal abnormality (e.g., the Mantled phenotype) is predicted by the machine, a different machine, or manually. In some cases, stored plants can be disposed of (e.g., cultivated, treated, or destroyed) based on the prediction of the presence or absence of a somaclonal abnormality (e.g., the Mantled phenotype). In some cases, stored plants can be disposed of based on the VIR genotype or predicted fruit color phenotype, based on their predicted shell thickness phenotype, and/or based on the prediction of the presence or absence of a somaclonal abnormality (e.g., the Mantled phenotype). For examples, plants predicted to have a somaclonal abnormality can be discarded or destroyed, or treated. As another example, plants predicted to be pisifera and/or Mantled, or dura and/or Mantled, can be removed from (e.g., separated from) the population of plants that are selected for planting and cultivation in the field for oil production. Similarly, e.g., plants predicted to be tenera and having an absence of somaclonal abnormality (e.g., lacking the Mantled phenotype), can be separated from other plants and/or selected for field cultivation. In some cases, the plant is disposed of by the machine, a different machine, or manually.

In some cases, the plant (e.g., a seed, a seedling, a plant, a plant cell, a plant cell colony, or a clump of plant cells) or plants are shipped from a customer to a service provider, analyzed, and returned. In some cases, only plants with a predicted phenotype or phenotypes are returned. For example, only plants predicted to lack a somaclonal abnormality, or a combination thereof are returned. In other cases, plants are sampled, and the samples are shipped from a customer to a service provider for analysis. The customer can then utilize information provided by the analysis to dispose of the plants.

In some cases, reagents, such as the compositions described herein are provided for sampling of plants manually or automatically. For example, endonucleases, oligonucleotide primers or probes, or a combination thereof as described herein can be provided. As another example, reaction mixtures or kits containing reagents necessary for analysis of nucleic acid from an oil palm plant can be provided, as described herein.

C. Screening Culture Conditions

In vitro culture can produce somaclonal abnormalities in oil palm lines. For example, in vitro culture can give rise to oil palm plants having the Mantled phenotype. In some cases, culture conditions or protocols can screened to identify conditions or protocols that reduce or eliminate the generation of somaclonal variants. Such conditions or protocols can then be used to develop clonally propagated oil palm plant lines having reduced, or no, somaclonal abnormalities. For example, an in vitro culture can be subjected to standard culture conditions as a control. A similar, or identical culture can then be subjected to a test condition. The presence or absence, proportion, or likelihood of a somaclonal abnormality can be determined in the control and test cultures. Test conditions that reduce or eliminate somaclonal abnormalities can then be identified and utilized. In some cases, the experiment can be repeated iteratively to further improve culture conditions. Exemplary culture conditions include, but are not limited to, physiological state of palm during sampling, type of explant, number of subcultures, number of ramets per embryogenic line, auxin hormone level and type, cytokinin hormone level and type, salt concentration, osmolarity, pH, temperature, photoperiod, presence and/or type of feeder cells, media composition, etc.

In some cases, in vitro plant cultures can be screened to identify cultures that have developed somaclonal abnormalities. For example, an in vitro oil palm plant culture, or a set of in vitro oil palm plant cultures can be assayed, the presence or absence of somaclonal abnormalities can be predicted, and then cultures predicted to have a somaclonal abnormality, or a high percentage or likelihood of somaclonal abnormalities, can be separated, discarded or destroyed. In some cases, cultures predicted to have a somaclonal abnormality can be treated to reduce the likelihood of, prevent, or revert the somaclonal abnormality.

IV. Reducing Somaclonal Abnormalities

In some embodiments, plants (e.g., plant cell in vitro tissue cultures) are treated to reduce, prevent, mitigate, eliminate, or revert a somaclonal abnormality or a predicted somaclonal abnormality. In some cases, somaclonal abnormalities are reduced, prevented, mitigated, eliminated, or reverted by exogenously applying to the plant an mRNA encoded by SEQ ID NO:5 or a sequence at least 90%, 95%, or 99% identical to SEQ ID NO:5; or exogenously applying to the plant a small RNA encoded by a sequence comprising a polynucleotide at least 90%, 95%, or 99% identical, or identical, to SEQ ID NO:91, 92, 93, 94, 95, 96, 97, 98, 99, 100, 101, 102, 103, 104, 105, 106, 107, 108, 109, 110, 111, 112, 113, 114, 116, 117, 123, 124, 130, 131, 132, 133, 134, 136, 137, 138, 139, 142, 143, 144, 145, 146, 147, 148, 149, 150, 151, 152, 153, 154, 155, 156, 157, 158, 159, 160 or 161.

In some cases, the exogenously applying the mRNA or small RNA comprises contacting a cytoplasm or nucleus of the plant with the mRNA or small RNA. In some cases, the mRNA or small RNA is produced in an in vitro transcription reaction. In some cases, the exogenously applying the mRNA or small RNA comprises contacting the plant with an expression cassette comprising a heterologous promoter operably linked to a polynucleotide at least 75%, 80%, 85%, 90%, 95%, or 99% identical, or identical, to SEQ ID NO:5. In some cases, the exogenously applying the mRNA or small RNA comprises contacting the plant with an expression cassette comprising a heterologous promoter operably linked to a polynucleotide encoding a small RNA, wherein the polynucleotide comprises a sequence at least 75%, 80%, 85%, 90%, 95%, or 99% identical, or identical, to SEQ ID NO:91, 92, 93, 94, 95, 96, 97, 98, 99, 100, 101, 102, 103, 104, 105, 106, 107, 108, 109, 110, 111, 112, 113, 114, 116, 117, 123, 124, 130, 131, 132, 133, 134, 136, 137, 138, 139, 142, 143, 144, 145, 146, 147, 148, 149, 150, 151, 152, 153, 154, 155, 156, 157, 158, 159, 160 or 161.

In some cases, the exogenously applying the mRNA or small RNA comprises generating a transgenic plant with a heterologous promoter operably linked to one or more of the foregoing polynucleotides and generating an in vitro tissue culture from the transgenic plant. In some cases, such a tissue culture system can reduce or eliminate the generation of somaclonal abnormalities. Thus, oil palm plants having one or more desirable properties such as high oil yield, or a desired dura, tenera, pisifera, virescens, or nigrescens, phenotype, can be generated indefinitely via in vitro tissue culture propagation techniques without, or with less, risk of generating plants with a somaclonal abnormality.

V. Kits

This invention also provides kits for the detection and/or quantification of methylation within the DMRs, DNA regions, DNA meta-regions, or biomarkers of the invention using the methods described herein.

The kits of the invention can comprise at least one polynucleotide that hybridizes to at least one of the diagnostic biomarker sequences of the invention and at least one reagent for detection of methylation. Reagents for detection of methylation can include, e.g., sodium bisulfite, polynucleotides designed to specifically hybridize to sequence that is a produce (e.g., an amplification product) of a biomarker sequence of the invention if the biomarker sequence is not methylated (e.g., containing at least one C→U conversion) or to specifically hybridize if the biomarker sequence is methylated, and/or a methylation-sensitive or methylation-dependent restriction enzyme. The kits can provide solid supports in the form of an assay apparatus that is adapted to use in the assay. The kits may further comprise detectable labels, optionally linked to a polynucleotide, e.g., a probe, in the kit. Other materials useful in the performance of the assays can also be included in the kits, including test tubes, transfer pipettes, and the like. The kits can also include written instructions for the use of one or more of these reagents in any of the assays described herein.

In some embodiments, a kit for determining the methylation status of at least one DMR in a biological sample from an oil palm plant is provided, the kit including: (1) a polynucleotide, or a pair of polynucleotides, capable of specifically amplifying at least a portion of a DMR, wherein the DMR is within a sequence of DNA at least 70%, 80%, 90%, 95%, or 99% identical, or identical, to SEQ ID NO:1; and a methylation-dependent, a methylation sensitive restriction enzyme, and/or sodium bisulfite; or (2) sodium bisulfite, primers, and adapters for whole genome amplification, and at least one polynucleotide to quantify the presence of the converted methylated and/or the converted unmethylated sequence of at least one cytosine from a DMR, wherein the DMR is within a sequence of DNA at least 70%, 80%, 90%, 95%, or 99% identical, or identical, to SEQ ID NO:1; or (3) methylation sensing restriction enzymes, primers and adapters for whole genome amplification, and at least one polynucleotide to quantify the number of copies of at least a portion of a DMR, wherein the DMR is within a sequence of DNA at least 70%, 80%, 90%, 95%, or 99% identical, or identical, to SEQ ID NO:1; or (4) a methylation sensing binding moiety and at least one polynucleotide to quantify the number of copies of at least a portion of a DMR, wherein the DMR is within a sequence of DNA at least 70%, 80%, 90%, 95%, or 99% identical, or identical, to SEQ ID NO:1.

In some cases, the DMR is within a DNA meta-region in the sample from the plant. The meta-region contains two or more overlapping DNA regions that exhibit differential methylation. Exemplary DNA meta-regions include overlapping 4 kb wingspan regions (2 kb 5' and 3') centered on biomarkers corresponding (e.g., at least 90%, 95%, or 99% identical, or identical) to SEQ ID NOS: 7, 8, 9, 10, 11, 12, 13, 14, 15, 16, 17, 18, 19, 20, 21, 22, 23, 24, 25, 26, 27, 28, 29, 30, 31, 32, 33, 34, 71, and 72. In some cases, the DNA meta-regions are in SEQ ID NO:1, or are in the locus corresponding to (e.g., at least 70%, 80%, 90%, 95%, or 99% identical, or identical, to) SEQ ID NO:1 in the oil palm genome. Exemplary DNA meta-regions include those at least 70%, 80%, 90%, 95%, or 99% identical, or identical, to a sequence selected from the group consisting of SEQ ID NO:35, 36, 37, 38, 39, 40, 41, 42, 43, 44, 45, 46, 47, 48, 49, 50, 51, 52, 53, 54, 55, 56, 57, 58, 59, 60, 61, 62, 73, and 74. In some cases, the DMR is within a DNA region in the sample from the plant. The DNA region can, e.g., be a 4 kb, wherein the DNA region is at least about 70%, 80%, 90%, 95%, or 99% identical, or identical, to a sequence selected from the group consisting of SEQ ID NO:35, 36, 37, 38, 39, 40, 41, 42, 43, 44, 45, 46, 47, 48, 49, 50, 51, 52, 53, 54, 55, 56, 57, 58, 59, 60, 61, 62, 73, and 74. In some cases, the cytosine is in a biomarker, wherein the biomarker is at least 90%, 95%, or 95% identical, or identical, to a sequence selected from the group consisting of SEQ ID NO:7, 8, 9, 10, 11, 12, 13, 14, 15, 16, 17, 18, 19, 20, 21, 22, 23, 24, 25, 26, 27, 28, 29, 30, 31, 32, 33, 34, 71, and 72.

In some embodiments, the kit determines the methylation status of at least one cytosine in 2, 3, 4, 5, 6, 7, 8, 9, 10, 11, 12, 13, 14, 15, 16, 17, 18, 19, 20, 21, 22, 23, 24, 25, 26, 27, or 28 different differential methylation regions (DMRs) are determined to predict the presence or absence of a somaclonal abnormality. In some cases, the DMRs are in a locus, retrotransposon, DNA meta-region, DNA region, or biomarker corresponding (e.g., at least 70%, 80%, 90%, 95%, or 99% identical, or identical) to a sequence independently selected from SEQ ID NOS: 1-5, and 7-75.

In some embodiments, the kit contains a detectably labeled polynucleotide probe that specifically detects an amplified DMR, or a portion thereof.

VI. Computer Program Product

The calculations for the methods described herein can involve computer-based calculations and tools to predict the presence or absence of somaclonal abnormalities (e.g., predict the Mantled phenotype) in a plant or plant cells. For example, a methylation value for a DNA region, DNA meta-region, biomarker, a portion thereof, or one or more cytosines therein, can be compared by a computer to a threshold or control value, as described herein. The tools are advantageously provided in the form of computer programs that are executable by a general purpose computer system (referred to herein as a "host computer") of conventional design. The host computer may be configured with many different hardware components and can be made in many dimensions and styles (e.g., desktop PC, laptop, tablet PC, handheld computer, server, workstation, mainframe). Standard components, such as monitors, keyboards, disk drives, CD and/or DVD drives, and the like, may be included. Where the host computer is attached to a network, the connections may be provided via any suitable transport media (e.g., wired, optical, and/or wireless media) and any suitable communication protocol (e.g., TCP/IP); the host computer may include suitable networking hardware (e.g., modem, Ethernet card, WiFi card). The host computer may implement any of a variety of operating systems, including UNIX, Linux, Microsoft Windows, MacOS, or any other operating system.

Computer code for implementing aspects of the present invention may be written in a variety of languages, including PERL, C, C++, Java, JavaScript, VBScript, AWK, or any other scripting or programming language that can be executed on the host computer or that can be compiled to execute on the host computer. Code may also be written or distributed in low level languages such as assembler languages or machine languages.

The host computer system advantageously provides an interface via which the user controls operation of the tools. In the examples described herein, software tools are implemented as scripts (e.g., using PERL), execution of which can be initiated by a user from a standard command line interface of an operating system such as Linux or UNIX. Those skilled in the art will appreciate that commands can be adapted to the operating system as appropriate. In other embodiments, a graphical user interface may be provided, allowing the user to control operations using a pointing device. Thus, the present invention is not limited to any particular user interface.

Scripts or programs incorporating various features of the present invention may be encoded on various computer readable media for storage and/or transmission. Examples of suitable media include magnetic disk or tape, optical storage media such as compact disk (CD) or DVD (digital versatile disk), flash memory, and carrier signals adapted for transmission via wired, optical, and/or wireless networks conforming to a variety of protocols, including the Internet.

In some embodiments, the computer program product contains a computer readable medium encoded with program code, the program code including:

program code for receiving a methylation value representing the methylation status of at least one cytosine within a differential methylation region (DMR) in the sample from the oil palm plant, wherein the DMR is within a sequence of DNA at least 70%, 80%, 90%, 95%, or 99% identical, or identical, to SEQ ID NO:1;

program code for comparing the methylation value to a control value, wherein the control value distinguishes between plants with and without a somaclonal abnormality, wherein the comparison of the methylation value to the control value is predictive of the presence or absence of a somaclonal abnormality in the plant.

In some cases, the DMR is within a DNA meta-region in the sample from the plant. The meta-region contains two or more overlapping DNA regions that exhibit differential methylation. Exemplary DNA meta-regions include overlapping 4 kb wingspan regions (2 kb 5' and 3') centered on biomarkers corresponding (e.g., at least 90%, 95%, or 99% identical, or identical) to SEQ ID NOS: 7, 8, 9, 10, 11, 12, 13, 14, 15, 16, 17, 18, 19, 20, 21, 22, 23, 24, 25, 26, 27, 28, 29, 30, 31, 32, 33, 34, 71, and 72. In some cases, the DNA meta-regions are in SEQ ID NO:1, or are in the locus corresponding to (e.g., at least 70%, 80%, 90%, 95%, or 99% identical, or identical, to) SEQ ID NO:1 in the oil palm genome. Exemplary DNA meta-regions include those at least 70%, 80%, 90%, 95%, or 99% identical, or identical, to a sequence selected from the group consisting of SEQ ID NO:35, 36, 37, 38, 39, 40, 41, 42, 43, 44, 45, 46, 47, 48, 49, 50, 51, 52, 53, 54, 55, 56, 57, 58, 59, 60, 61, 62, 73, and 74. In some cases, the DMR is within a DNA region in the sample from the plant. The DNA region can, e.g., be a 4 kb, wherein the DNA region is at least about 70%, 80%, 90%, 95%, or 99% identical, or identical, to a sequence selected from the group consisting of SEQ ID NO:35, 36, 37, 38, 39, 40, 41, 42, 43, 44, 45, 46, 47, 48, 49, 50, 51, 52, 53, 54, 55, 56, 57, 58, 59, 60, 61, 62, 73, and 74. In some cases, the cytosine is in a biomarker, wherein the biomarker is at least 90%, 95%, or 99% identical, or identical, to a sequence selected from the group consisting of SEQ ID NO:7, 8, 9, 10, 11, 12, 13, 14, 15, 16, 17, 18, 19, 20, 21, 22, 23, 24, 25, 26, 27, 28, 29, 30, 31, 32, 33, 34, 71, and 72.

The methylation status of the at least one cytosine can be compared to a control value, wherein the control value is a methylation value for a control locus to determine a relative change in methylation. For example, if the methylation status of the cytosine at the test locus indicates a higher degree of methylation as compared to the methylation status of at the control locus, then the methylation status of the test locus is increased. As another example, if the methylation status of the cytosine at the test locus indicates a lower degree of methylation as compared to the methylation status of at the control locus, then the methylation status of the test locus is decreased. Typically, the control locus will have a known, relatively constant, methylation status. For example, the control locus can be previously determined to have no, some, or a high amount of methylation, thereby providing a relative constant value to control for error in detection methods, etc., unrelated to the presence or absence of a somaclonal abnormality. In some embodiments, the control locus is endogenous, i.e., is part of the genome of the individual sampled. Alternatively, the control locus can be an exogenous locus, e.g., a DNA sequence spiked into the sample in a known quantity and having a known methylation status.

In some embodiments, the methylation status of at least one cytosine in 2, 3, 4, 5, 6, 7, 8, 9, 10, 11, 12, 13, 14, 15, 16, 17, 18, 19, 20, 21, 22, 23, 24, 25, 26, 27, or 28 different differential methylation regions (DMRs) are determined to predict the presence or absence of a somaclonal abnormality. In some cases, the DMRs are in a locus, retrotransposon, DNA meta-region, DNA region, or biomarker corresponding (e.g., at least 70%, 80%, 90%, 95%, or 99% identical, or identical) to a sequence independently selected from SEQ ID NOS: 1-5, and 7-75.

In some embodiments, the predicted somaclonal abnormality is an abnormality that reduces fruit yield, oil yield, growth, or reproduction of an oil palm plant. In some cases, the reduction is relative to a control plant, such as a parent plant, or a wild-type plant of the same fruit color (nigrescens or viriscens) or shell thickness (dura, tenera, or pisifera) phenotype. In some cases, the somaclonal abnormality exhibits a Mantled phenotype.

In some cases, the computer program product predicts the presence or absence of a somaclonal abnormality (e.g., the Mantled phenotype) in the plant. In some cases, the computer program product provides the data for another computer program product, or a person of skill in the art, to predict the presence or absence of a somaclonal abnormality in the plant. In some cases, the computer program product calculates a statistical confidence (e.g., a p-value, t-statistic, etc.) for a prediction of the presence or absence of a somaclonal abnormality in the plant.

EXAMPLES

The following examples are offered to illustrate, but not to limit the claimed invention.

Example 1: Global DNA Methylation Profiling Reveals Differential DNA Methylation in Mantled Clonally Propagated Materials Microarray features were designed based on a genome build of the pisifera oil palm genome (Singh et al. 2013, *Nature* 500, 340-344). Over 1 million features were designed to unique 61 base sequences across the unique sequence of the oil palm genome. Although repetitive sequences make up approximately 57% of the oil palm genome, unique sequence features could be designed to sequences flanking distinct repetitive elements, as well as unique sequences embedded within specific repetitive elements. Loci that are differentially methylated in Mantled clonal materials relative to phenotypically normal clonal material were identified using a DNA microarray-based technology platform that utilizes the methylation-dependent restriction enzyme McrBC (Ordway et al. 2006 *Carcinogenesis* 27: 2409-2423; Ordway et al. 2007 *PLoS ONE* 2: e1314). See, e.g., U.S. Pat. No. 7,186,512. The genomic region in which a given microarray feature can report DNA methylation status is dependent upon the molecular size of the DNA fragments that were labeled for the microarray hybridizations. In the microarray experiments, DNA in the size range of 1 to 4 kb was purified by agarose gel extraction and used as template for cyanogen dye labeling. Therefore, the genomic region interrogated by each microarray feature is 8 kb (i.e., 4 kb upstream and 4 kp downstream of the sequence represented by the microarray feature).

The fruit form phenotypes associated with the mantled abnormality are shown in FIG. 1. DNA was extracted from spear leaf of 78 clonally propagated palms (ramets), including 37 parthenocarpic mantled ramets, 41 normal ramets and 10 ortets from which clonal ramets are derived. These samples were derived from four industry sources and represented 11 independent clonal propagation events as described in FIG. 2, and each clonal propagation event gave rise to 3 to 5 normal trees and 2 to 5 mantled trees. Genome wide DNA methylation maps were generated from four independent microarray hybridizations representing two technical replicates with a dye-swap reversal hybridization per replicate.

Figure 3:
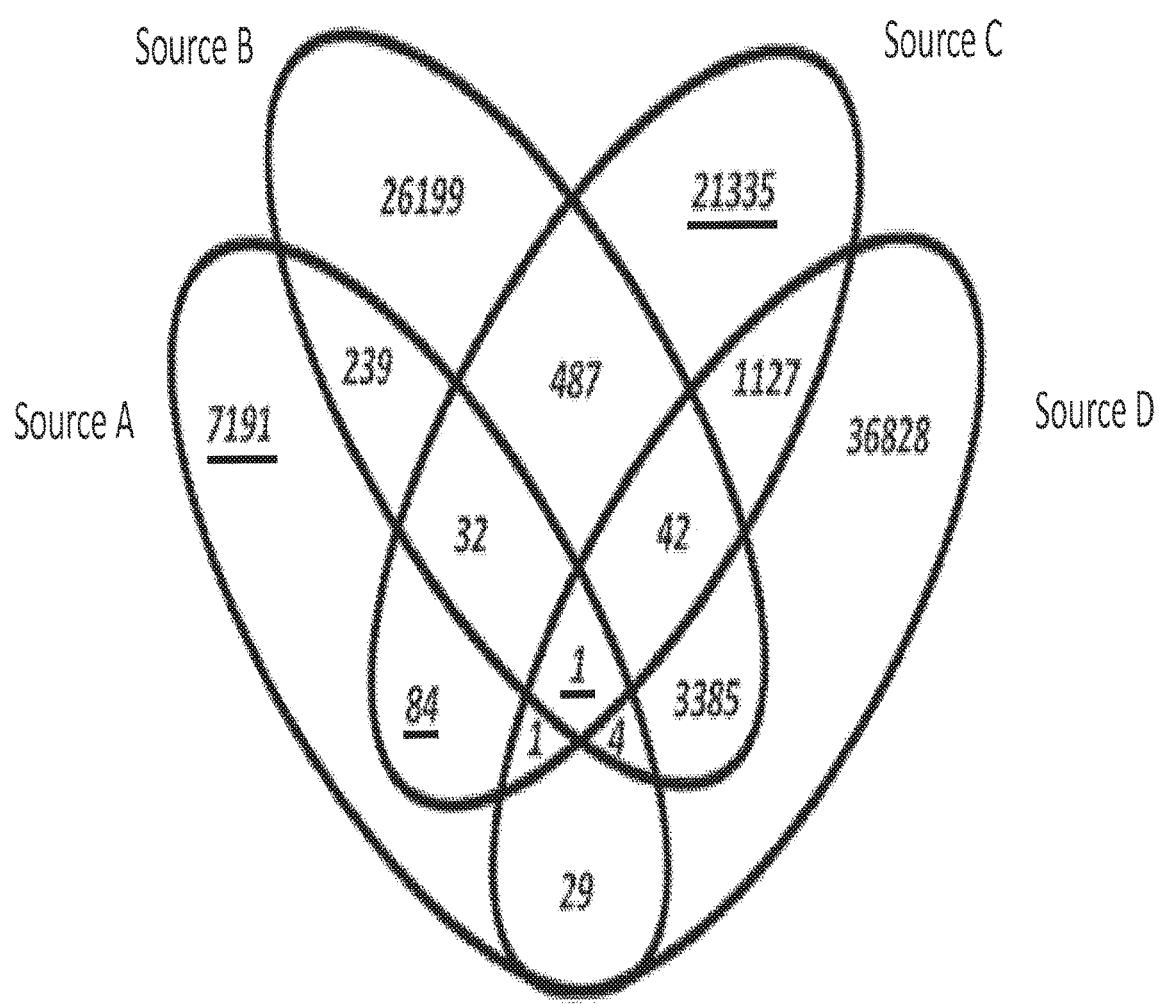
FIG. 3. Venn diagram of microarray features reporting significantly differential methylation between mantled and normal ramet leaf (p<0.05, two-sided Student t-test, Methods). Each oval represents clonal lineages obtained from one source (genotype): Source A (5 mantled and 9 normal ramets), Source B (14 mantled and 15 normal ramets), Source C (10 mantled and 10 normal ramets), and Source D (8 mantled and 7 normal ramets). Relatively few features are shared between genotypes, and only one feature detects hypomethylation in mantled palms from all 4 sources. Underlined numbers indicate subsets that include one of the four microarray features mapping to the Karma LINE element (element 2 as diagrammed in FIG. 2).

Thousands of loci were differentially methylated between genetically identical ortet, parthenocarpic mantled and normal ramet samples, most of which (~90%) were hypomethylated in mantled, consistent with previously reported reductions in total 5mC levels (Matthes et al. 2001; Jaligot et al. 2002; Jaligot et al. 2004). Interestingly, most of these hypomethylated loci (~75%) mapped to transposons and repeats, while less frequent hypermethylated loci mapped to both genic and repetitive sequences. These results were consistent with similar maps of cell cultures of *Arabidopsis* (Vaughn et al. 2007), but differed from epigenomic maps of somaclonal regenerants in rice, in which loss of DNA methylation is largely confined to genes (Stroud et al. 2013), despite the activation of some TEs (Miyao et al. 2012; Cui et al. 2013).). To identify epigenetic differences between mantled and normal clones from multiple clonal lineages, significant differentially methylated regions (DMRs) between normal and fully mantled samples were first identified within each source population independently, based on microarray feature hybridization. Hybridization results were then compared between source populations on a feature by feature basis (FIG. 3). Although tens-of-thousands of significant features were detected between mantled and normal clones in each population, 99.9% of these were exclusive to either one (94.4%) or 2 (5.5%) of the 4 populations, indicating significant genotypic variation in epigenetic response to tissue culture. Only 79 differentially methylated features were common to 3 of the 4 populations (67% of which were associated with a repetitive element), and only a single microarray feature detected differential methylation between normal and mantled clones in all 4 populations (FIG. 3).

Figure 4:
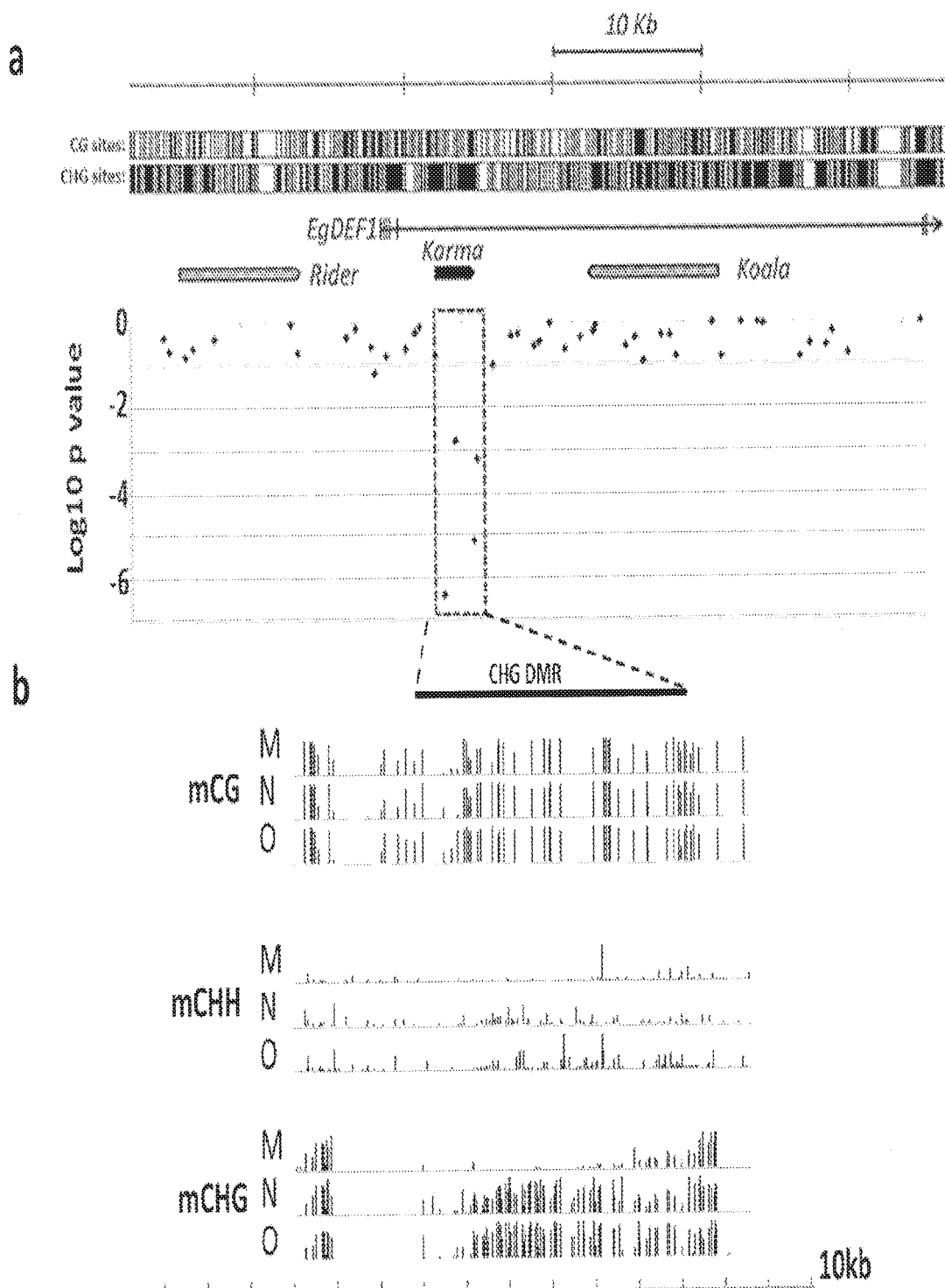
FIG. 4. Epigenetic profile of the EgDEF1/MANTLED gene on chromosome 12. a, Microarray feature data are plotted on a schematic map of the EgDEF1/MANTLED gene including Rider, Karma and Koala retrotransposons. CG and CHG sites are shown above. $\log_{10}$ p values for differential DNA methylation density measurements between normal (n=41) and parthenocarpic mantled (n=37) clonal ramets are plotted on the y-axis (two-sided Student's t-test). b, Genome-wide bisulphite sequencing of ortet (O), normal (N) and parthenocarpic mantled clonal ramet (M) leaf samples. DNA methylation densities of individual cytosines across Karma (boxed in a) are plotted on a 0 to 100% scale and represent the mean of ortet (n=5), normal ramets (n=5) or mantled ramets (n=5). CG, CHG and CHH methylation are plotted separately, as indicated to the left of the histograms. The location of the differentially CHG methylated region (CHG DMR) corresponding to the Karma retrotransposon is highlighted by a horizontal bar.

The single feature that distinguishes mantled from normal clones in all 4 populations lies within the ~35 kb intron 5 of EgDEF1 (FIG. 4a), the oil palm ortholog of the *Antirrhinum majus* DEFICIENS gene, which encodes a floral homeotic MADS box transcription factor similar to *Arabidopsis* APETALA3 (AP3) (Adam et al. 2005). def mutants in *Antirrhinum*, and ap3 mutants in *Arabidopsis*, result in stamen to carpel (B class) homeotic transformations, strongly reminiscent of the mantled phenotype in oil palm (Jaligot et al. 2011). EgDEF1 spans ~40 kb on *E. guineensis* chromosome 12 and includes 7 exons (FIG. 4a). A Ty1/copia retrotransposon lies upstream of the EgDEF1 promoter in the sense orientation, and shares similarity with the Rider element of tomato (*Solanum lycopersicum*), while a Ty3/gypsy retrotransposon, Koala, is located near the center of intron 5 in the antisense orientation. Consistent with a previous report (Jaligot et al. 2014), no DNA methylation difference within either of these retrotransposons was consistently detected in mantled clones across multiple populations (FIG. 4a).

A third, previously unreported, repetitive element lies within intron 5, in the sense orientation, and has homology to rice Karma family LINE elements. Karma elements, along with Tos17 copia-like elements, are activated in rice embryogenic tissue culture, although unlike Tos17, Karma elements only transpose in regenerated plants, in which transgenerational DNA hypomethylation of the element persists (Komatsu et al. 2003). The 3.2 kb oil palm Karma element is flanked by a 13 bp target site duplication (TT-CAAAATGATGA) and encodes a reverse transcriptase open reading frame homologous to rice Karma ORF2. As in mammalian LINE elements, ORF2 is preceded by a splice acceptor sequence (GAACAG^ATGC) immediately adjacent to the target site duplication, and is followed by a polyadenylation signal, resembling 5'truncated Karma elements in rice (Komatsu et al. 2003; Cui et al. 2013). The unique 60 nucleotide microarray feature, which consistently detected hypomethylation in mantled clones, not only maps to the Karma element, but serendipitously includes the predicted splice acceptor site. All three additional microarray features mapping within the Karma element also detected significant hypomethylation in mantled clones, albeit in fewer clonal lineages (FIGS. 3 and 4a).

The identified differentially methylated region of the genome maps to coordinates 58360 to 61400 of scaffold 13008 of the published *E. guineensis* genome build (FIG. 1 of Singh et al. 2014, *Nature* 500, 340-344). The sequences of the four features reporting these differential DNA methylation measurements are provided in SEQ ID NO: 15, 16, 17 and 18. The sequences of 4,061 bp regions spanning the 61mer feature sequence (+/−2 Kb from the 61mer feature sequence) are provided in SEQ ID NO: 43, 44, 45 and 46. A merged sequence from 2 Kb upstream of significant feature 57600 to 2 Kb downstream of significant feature 62840 is provided in SEQ ID NO: 66.

Figure 2:
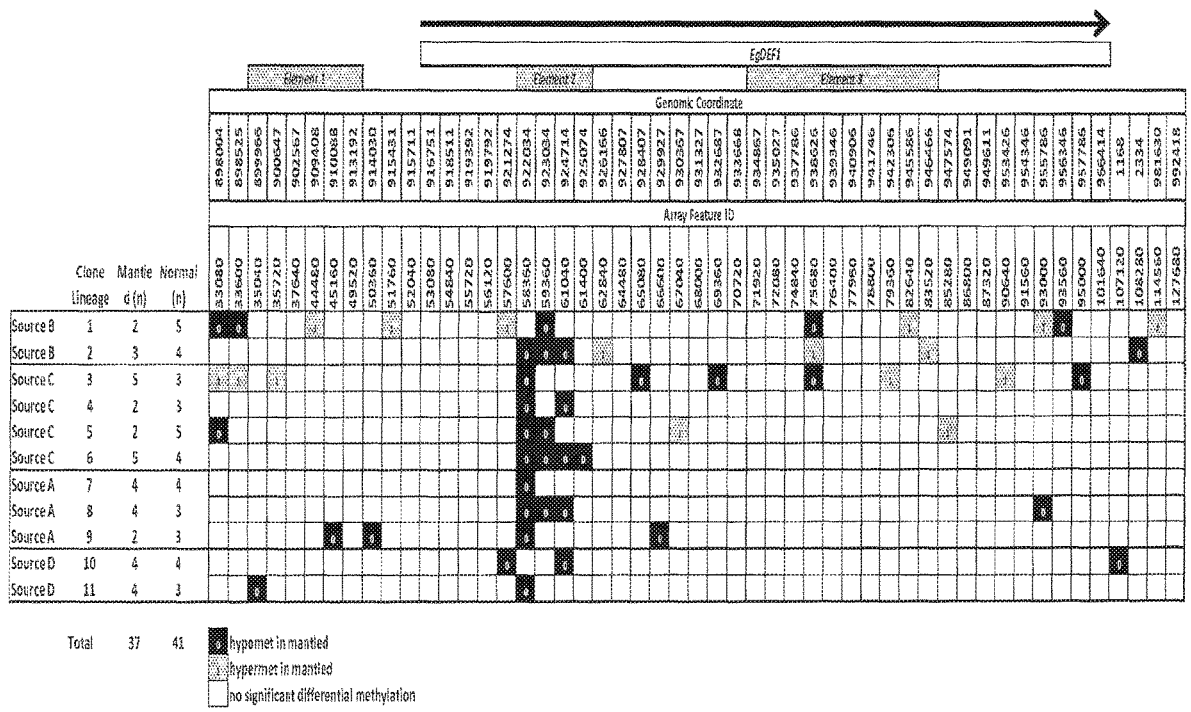
FIG. 2. Summary of significant mantled vs. normal DNA methylation changes. The "EgDEF" box indicates the region from the 5' of exon 1 through the 3' end of the transcript. Element 1 (Rider), 2 (Karma), and 3 (Koala) retrotransposons are indicated by grey boxes, as labeled. Array feature ID numbers are indicated. Genomic coordinates indicate the coordinate of the 5'-most base of each array feature relative to Scaffold p5_sc00322 of the published *E. guineensis* genome (Singh et al., 2013), with the exception of Array feature IDs 107120 and 108280. These two features mapped to Scaffold p5_sc25957 of the published *E. guineensis* genome (Singh et al., 2013) and genomic coordinates are relative to p5_sc25957, as published. This small scaffold has subsequently been mapped to the EgDEF1 interval, as diagrammed. Clonal lineages are indicated in the left-most column and the number of mantled and normal samples within each lineage is indicated. Black boxes represent statistically significant hypomethylation events in mantled relative to normal samples. Grey boxes represent statistically significant hypermethylation events in mantled relative to normal samples (p<0.05, two-tailed Student's t-test). White boxes represent measurements reporting no significant differential DNA methylation. There are statistically significant differentially methylated regions (DMRs) across the entire locus, one of which spans the Karma retrotransposon.

To further analyze DNA methylation across an approximately 95 Kb region spanning the EgDEF1 gene, data generated by microarray features representing from coordinate 33080 to 127680 of scaffold 13008 were analyzed to compare mantled vs. normal clonal material from each clonal propagation event independently (FIG. 2). Within Element 2 (Karma), mantled samples displayed hypomethylation relative to normal samples in samples derived from all 11 clonal propagation lineages. However, as summarized in FIG. 2, other distinct regions displayed differential DNA methylation events in a more lineage-specific manner. For example, lineages 1, 2, 3 and 5 displayed hypermethylation of sequences associated with the 5' end of Element 3 (Koala) in mantled samples. The sequences of the four features reporting these differential DNA methylation measurements are provided in SEQ ID NO: 25, 26 27 and 72. The sequences of 4,061 bp regions spanning the 61mer feature sequence (+/−2 Kb from the 61mer feature sequence) are provided in SEQ ID NO: 53, 54, 55 and 74. A merged sequence from 2 Kb upstream of feature 79360 to 2 Kb downstream of 83520 is provided in SEQ ID NO: 68. Furthermore, regions associated with Element 1 (Rider) displayed differential DNA methylation in mantled samples derived from lineages 1, 3, 5, 9 and 11. The sequences of the eight features reporting these differential DNA methylation measurements are provided in SEQ ID NO: 7, 8, 9, 10, 11, 12, 13 and 71. The sequences of 4,061 bp regions spanning the 61mer feature sequence (+/−2 Kb from the 61mer feature sequence) are provided in SEQ ID NO: 35, 36, 37, 38, 39, 40, 41 and 73. Merged sequence from 2 Kb upstream of feature 33080 to 2 Kb downstream of 35720 is provided in SEQ ID NO: 63. Merged sequence from 2 Kb upstream of feature 44480 to 2 Kb downstream of feature 45160 is provided in SEQ ID NO: 64. Merged sequence from 2 Kb upstream of feature 50360 to 2 Kb downstream of feature 51760 is provided in SEQ ID NO: 65. As shown in FIG. 2, other regions within EgDEF1 intron 5 or downstream of the 3' end of the EgDEF1 gene were occasionally differentially methylated in various clonal lineages. The sequences of all 30 features reporting these differential DNA methylation measurements are provided in SEQ ID NO: 7 to 34, 71 and 72. The sequences of 4,061 bp regions spanning the 61mer feature sequence (+/−2 Kb from the 61mer feature sequence) are provided in SEQ ID NO: 35-62, 73 and 74.

Example 2: Verification and Validation of Differential DNA Methylation in Normal and Abnormal Cloned Trees To verify Karma hypomethylation in mantled clones, sample trios comprising genetically identical ortet, parthenocarpic mantled and normal ramets, from 5 independent clonal lineages (15 samples) were subjected to whole genome bisulfite sequencing. The density of CG methylation was strikingly similar in ortet, normal and mantled samples across the entire EgDEF1 locus, including the Karma element (FIG. 4b), and was higher in introns and flanking regions than in exons. In contrast, the density of CHG methylation was dramatically reduced in mantled clones, revealing a DMR covering ~170 CHG sites throughout the length of the Karma element (FIG. 4b). The density of CHH methylation was much lower than CG and CHG and was only subtly reduced in mantled clones (FIG. 4b).

Figure 5:
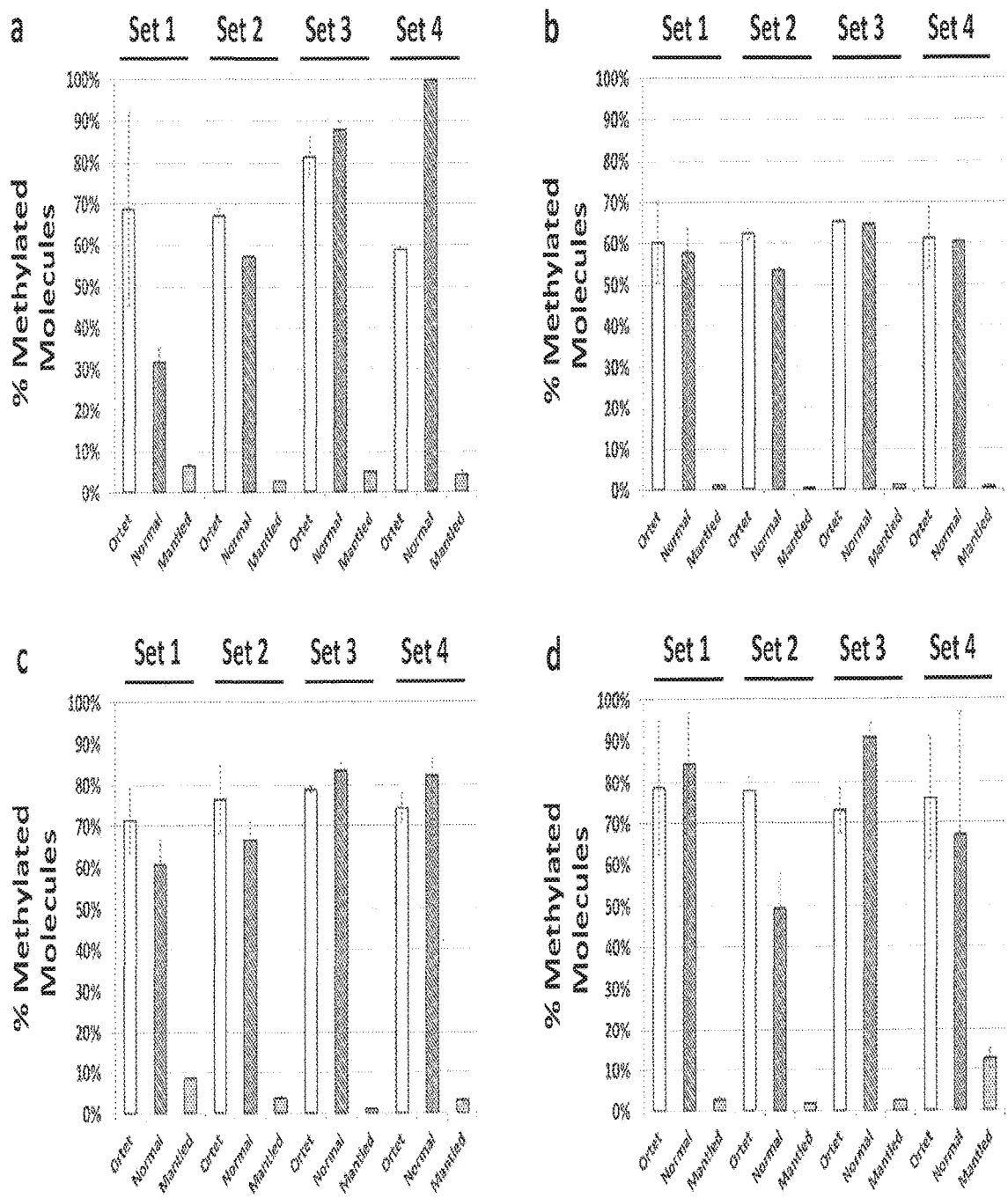
FIG. 5. Differential CHG methylation as measured by four independent MethylScreen assays. Assays were designed as described in Example 2. Each assay monitors methylation of a specific CHG cytosine within the differentially methylated region (CHG DMR). Sets 1, 2, 3 and 4 indicate independent sets of an ortet sample, plus 1 normal and 1 mantled sample from trees derived from the ortet of the same set. The percent densely methylated molecules was calculated as described in Example 2. CHG methylation sensitive restriction enzymes used were AlwNI (a), BbvI (b), ScrFI (c) and RsaI (d). Error bars represent standard deviations for duplicated assays.

To further validate the differential CHG methylation in Element 2, four independent MethylScreen assays (See, e.g., U.S. Pat. Nos. 7,910,296; 8,361,719; 7,901,880; and 8,163, 485) were designed to monitor CHG sites within methylation sensitive restriction enzyme target sequences that are blocked by CHG methylation but are not sensitive to either CHH or CG methylation. A first amplicon was designed to amplify a 576 bp region within Karma that contains a site for the methylation sensitive enzyme, AlwNI. Forward and reverse primer sequences are provided in SEQ ID NO: 82 and 83, respectively. The sequence of the amplicon is provided in SEQ ID NO: 84. The restriction site includes two CHG sites, and methylation of these cytosines blocks digestion by the enzyme. A second amplicon was designed to amplify a 633 bp region within Karma that contains sites for the methylation sensitive enzymes, BbvI and ScrFI. Forward and reverse primer sequences are provided in SEQ ID NO: 85 and 86, respectively. The sequence of the amplicon is provided in SEQ ID NO: 87. Each of these enzyme sites includes a CHG site, and methylation the site blocks digestion by the enzyme. The same amplicon (SEQ ID NO: 87) was used for each of the two enzyme assays separately. Finally, a third amplicon was designed to amplify a 632 bp region within Karma that contains a site for the methylation sensitive restriction enzyme, RsaI. Forward and reverse primer sequences are provided in SEQ ID NO: 88 and 89, respectively. The sequence of the amplicon is provided in SEQ ID NO: 90. The site includes a CHG site, and methylation of the site blocks digestion by the enzyme. Each of the four MethylScreen assays was performed on genomic DNA from four independent sets of ortet, normal and mantled samples that had been whole genome bisulfite sequenced, as described above. Genomic DNA was split into two equal portions. The first portion was mock treated (excluding the restriction enzyme). The second portion was digested with each of the four methylation sensitive restriction enzymes in separate reactions. Quantitative PCR amplification was performed on each portion in duplicate (alternatively, results can be analyzed by gel electrophoresis, without the use of real-time quantitative PCR). The delta Ct of the enzyme digested portion Ct minus the mock treated protion Ct was calculated for each of the two replicated assays. The % densely methylated was calculated as $2^{-dCt}$. The average % densely methylated, and the standard deviation between the duplicated assays, are provided in FIG. 5. These results demonstrate that each of the four MethylScreen assays are capable of detecting the hypomethylation of Mantled clone DNA relative to both ortet DNA and Normal clone DNA.

Figure 6:
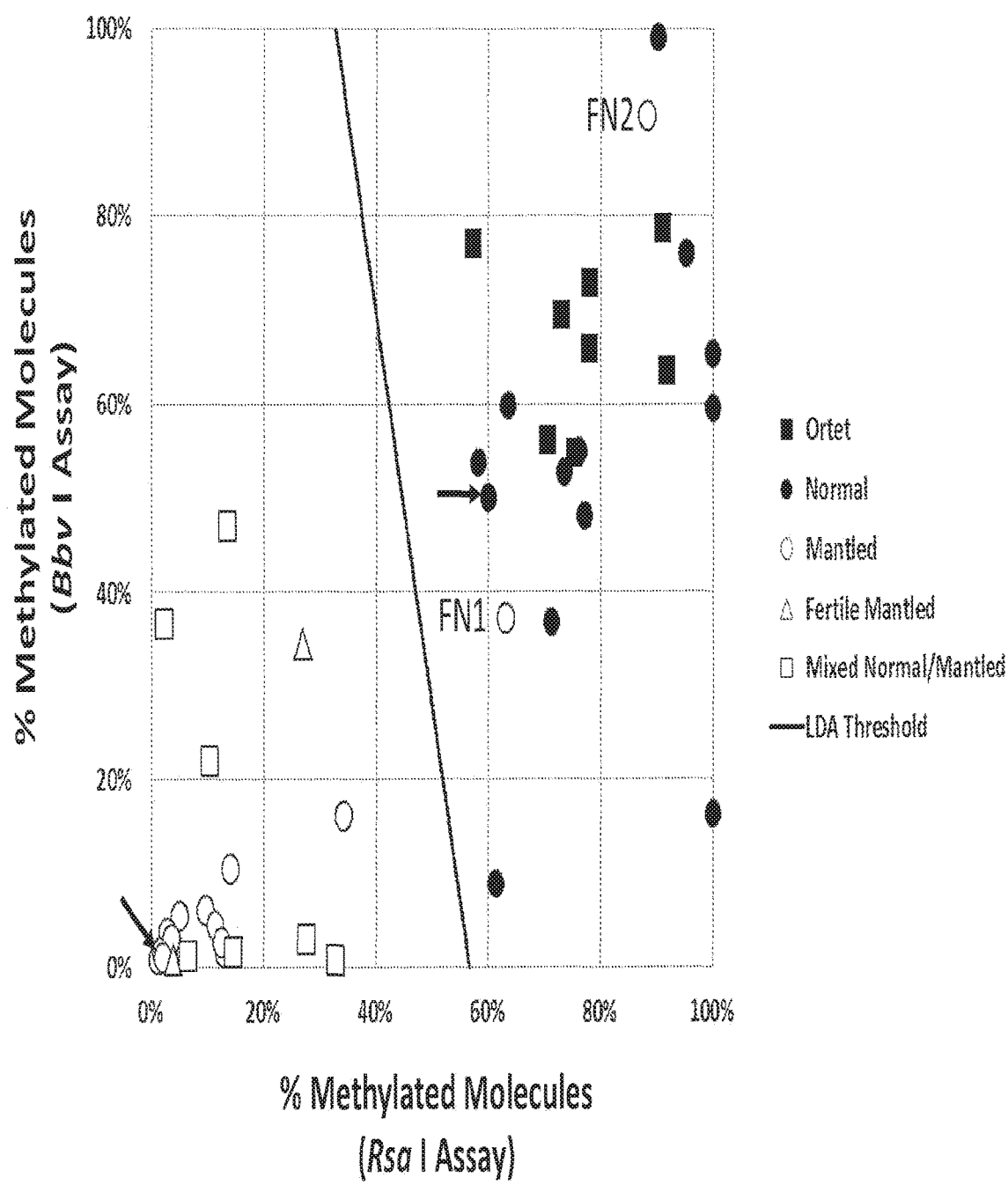
FIG. 6. Linear discriminate analysis (LDA) of CHG methylation in leaf DNA samples from ortet, mantled and normal clones from ramets independent of those represented in FIGS. 2-5. CHG methylation was monitored by digestion with the methylation sensitive restriction enzymes Bbv I or Rsa I, followed by quantitative PCR, as described in Example 2. The diagonal line represents the LDA-determined threshold between normal (ortets (n=8) and normal ramets (n=13)) and mantled (parthenocarpic mantled ramets (n=19), fertile mantled ramets (n=2) and mixed ramets yielding both normal and fertile mantled fruit (n=7)) CHG methylation density predictions. Two false negative parthenocarpic mantled samples are indicated (FN1 and FN2). Arrows indicate normal and mantled control samples further analyzed in FIGS. 7b and 7c, respectively.

To validate differential CHG methylation in unrelated clonal palms, the Bbv I and the Rsa I qPCR assays were performed on mature leaf samples from a panel of 49 palms. These samples represented 21 clonal lineages from 4 independent industry sources and included 8 ortets and 13 normal clones, 19 parthenocarpic mantled clones, 2 fertile mantled clones and 7 partially revertant clones yielding bunches with both mantled and normal fruits. Although the restriction site assays monitored only 2 of ~170 CHG sites in the DMR, a threshold value determined by linear discriminant analysis provided 93% sensitivity and 100% specificity for detection of mantling, reflecting the strong association of Karma hypomethylation with the mantled phenotype (FIG. 6). Fronds taken from all 7 of the revertant palms were scored as mantled, consistent with the observation that normal bunches on mixed palms arise late in development and revert to the normal phenotype (Corely, 1986).

Figure 7:
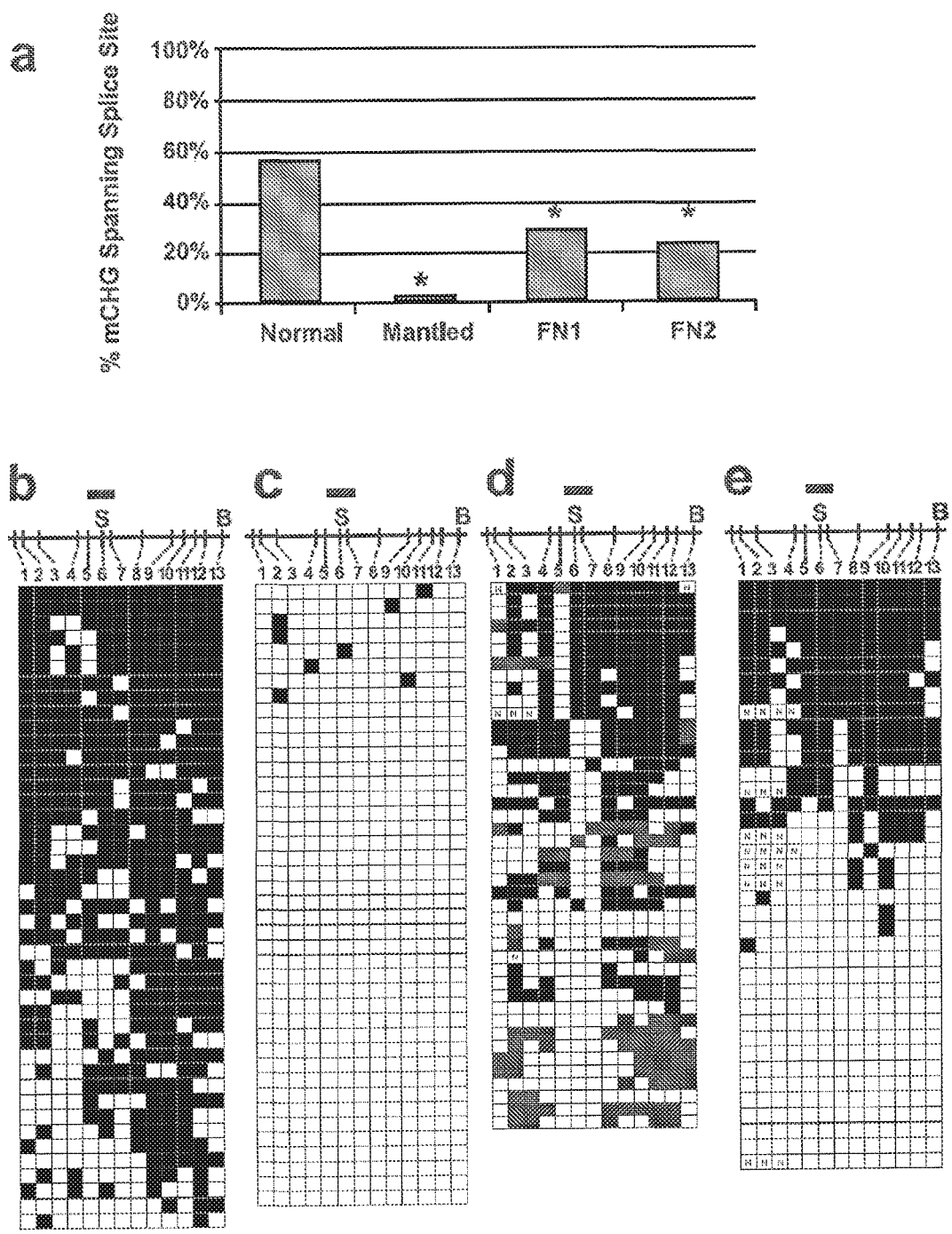
FIG. 7. a, Bisulfite sequencing analyses of the Karma element in leaf samples from normal and mantled clones (ramets), as well as two false negative mantled samples. CHG methylation density (unconverted CHG cytosine base calls/total cytosine base calls) was calculated at the Karma splice acceptor site (site 6 in b-e), plus the two additional CHG positions 27 bp upstream (site 5) and 16 bp downstream of the splice site (site 7), all of which were covered by the unique common microarray feature that detected hypomethylation in mantled palms from all 4 sources in FIG. 3. The mantled control sample and both false negative mantled samples were significantly hypomethylated relative to the normal control, as indicated by asterisks (p<0.0001, two-tailed Fisher's exact test). b-e, Individual bisulphite sequencing reads from the antisense strand of the Karma element in (b) the normal control, (c) mantled control and (d) FN1 and (e) FN2 false negative mantled samples. 13 antisense CHG sites across the sequencing amplicon are shown to scale. "S" indicates the cytosine at the Karma splice acceptor site (CAG/CTG). "B" indicates the Bbv I site. The common microarray feature reported in FIG. 3 is indicated by a bar surrounding the splice site. Methylated and unmethylated CHG sites are indicated by black and white boxes, respectively. Boxes including "N" indicate CHG positions within specific reads that were not high quality DNA sequencing base calls and so the DNA methylation state of those bases was undetermined.

Although CHG methylation density at the two restriction sites was highly predictive, it did not correlate perfectly with the mantled phenotype. The two false negative mantled palms (FN1 an FN2 in FIG. 6), and 2 control palms (arrows in FIG. 6), were further analyzed by bisulfite sequencing of a region spanning the Karma splice acceptor site (FIG. 7). As predicted by qPCR, this region was densely CHG methylated in the normal control sample, while the mantled control sample had lost CHG methylation (FIGS. 7b-c). The false negative mantled samples (predicted to have normal methylation by the restriction site assays) retained substantial CHG methylation in surrounding regions, however CHG methylation near the splice acceptor site was significantly reduced, by 50%, relative to the normal control sample (FIGS. 7a-b and d-e), suggesting that hypomethylation at or adjacent to the splice acceptor CHG site is sufficient to predict the mantled phenotype. Because of their strong predictive properties, we named the MANTLED hyper- and hypo-methylated epialleles Good Karma and Bad Karma, respectively.

Example 3: Phenotype Reversion in Epigenetic Mosaics

Figure 8:
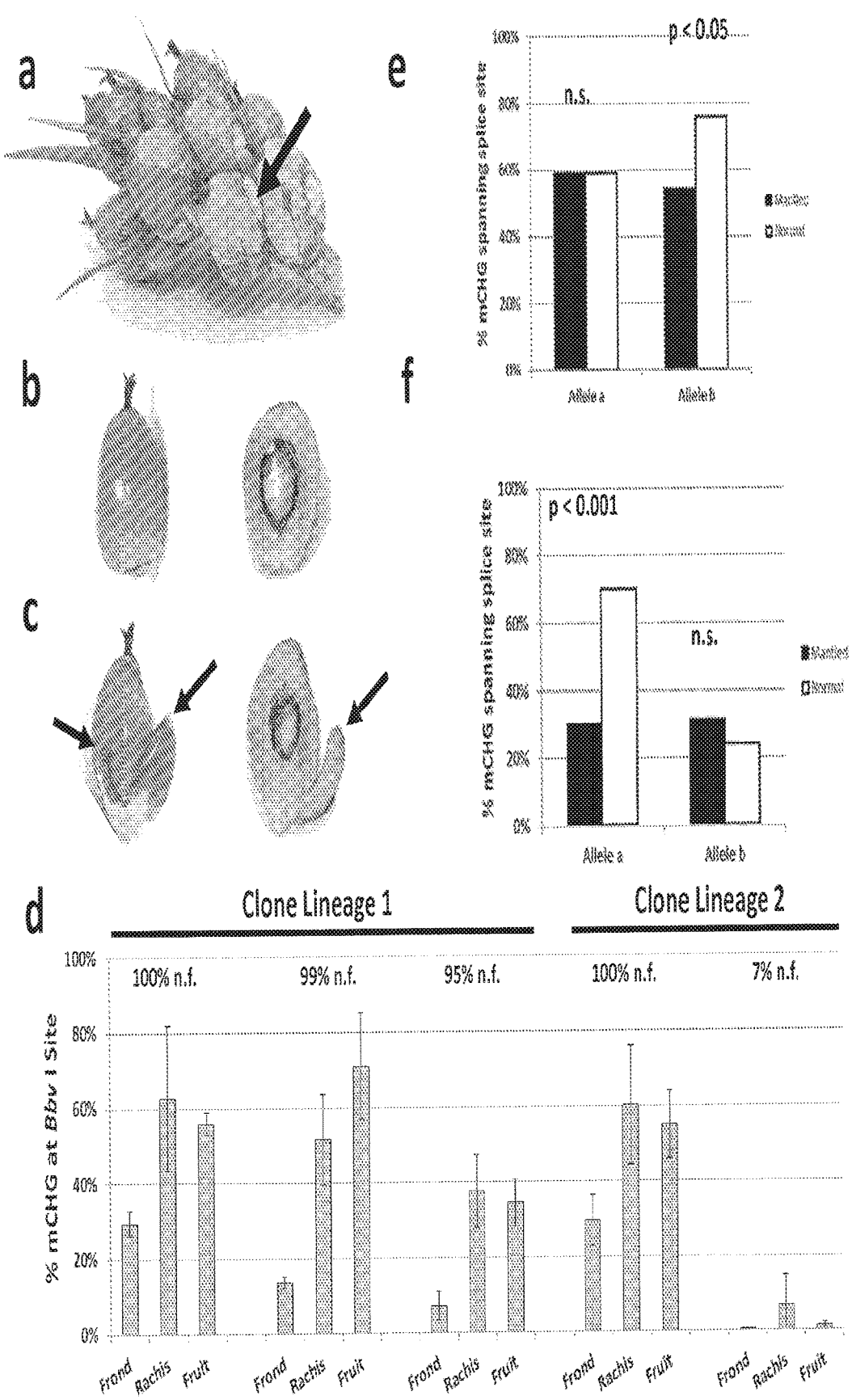
FIG. 8. Karma CHG methylation in revertant palms. a, spikelet from a revertant ramet giving rise to mixed bunches including both normal and fertile mantled fruit with only one or two pseudocarpels per fruit (arrows). b-c, whole (left) and longitudinal sectioned (right) normal (b) and subtly mantled (c) fruit from the bunch represented in (a). d, CHG methylation density at the Bbv I site. Normal ramets yielding 100% normal fruit from each of two independent clonal lineages (1 and 2) are shown, as well as revertant ramets yielding mixed bunches with 99%, 95% or 7% normal fruits (n.f.) per bunch. Error bars indicate standard deviations across biological replicates of fronds (n=4), rachis sections (n=8) or fruits (n=2). e-f, Methylation density at the Karma splice acceptor site, plus the two additional CHG positions 27 bp upstream and 16 bp downstream of the splice site (determined as in FIG. 7) in normal (white bars) and subtly mantled (black bars) fruits from the two revertant ramets in clonal lineage 1 yielding 99% (e) or 95% (f) normal fruit (two-tailed Fisher's exact test, n.s. indicates not significant). For each ramet, normal and subtly mantled fruits were collected from the same bunch. Alleles were analyzed separately by detecting a heterozygous SNP within the bisulfite sequencing amplicon that did not affect a CHG site.

Mantled palms sometimes revert, giving rise to bunches including both normal and mantled fruit (Rao & Donough, 1990). We hypothesized that DNA methylation might sometimes be restored in revertant and mosaic palms, resembling epialleles in maize that are also regulated by transposons (McClintock, 1965; Martienssen et al., 1990; Martienssen & Baron, 1994). Although rare, we identified two clonal lineages giving rise to palms with bunches of both normal and (fertile) mantled fruits. Clone lineage 1 included two revertant clones with 99% and 95% normal fruit per bunch, respectively, in which abnormal fruits had only one or two small pseudocarpels (FIGS. 8a-c). A second lineage (clone lineage 2) included a mosaic clone with a only 7% normal fruits. Relative to normal control clones, CHG methylation at the Bbv I site (FIGS. 5-6) nearest the Karma splice site (FIG. 8d) was low in fronds from revertant and mosaic clones. However, methylation was restored in fruit from the two revertant clones, but not from the mantled mosaic clone (FIGS. 8d-f).

As with similar epialleles in maize, Linnaria, Arabidopsis and tomato (Martienssen et al., 1990; Cubas et al., 1999; Manning et al., 2006; Kinoshita et al., 2007), reversion of the abnormal phenotype during development accompanied by restoration of DNA methylation suggests that methylation of the Karma element is the cause of the mantled phenotype. Differential methylation between individual mantled and normal fruits was not observed, however, likely reflecting non-cell autonomy of the weak mantled phenotype (FIG. 8d). Non-cell autonomy of the DEF and AP3 genes leads to similar reversion in mosaic chimeras of *Antirrhinum* and *Arabidopsis* (Furner et al., 2008; Perbal et al., 1996; Jenik & Irish, 2001). Interestingly, bisulfite sequencing of the region spanning the Karma splice acceptor site in normal and mantled fruits from mosaic clones revealed that CHG methylation at the splice acceptor site was significantly different depending on the phenotype, suggesting that revertant fruits were indeed mosaic for hyper- and hypo-methylated cells (FIGS. 8e-f).

Figure 9:
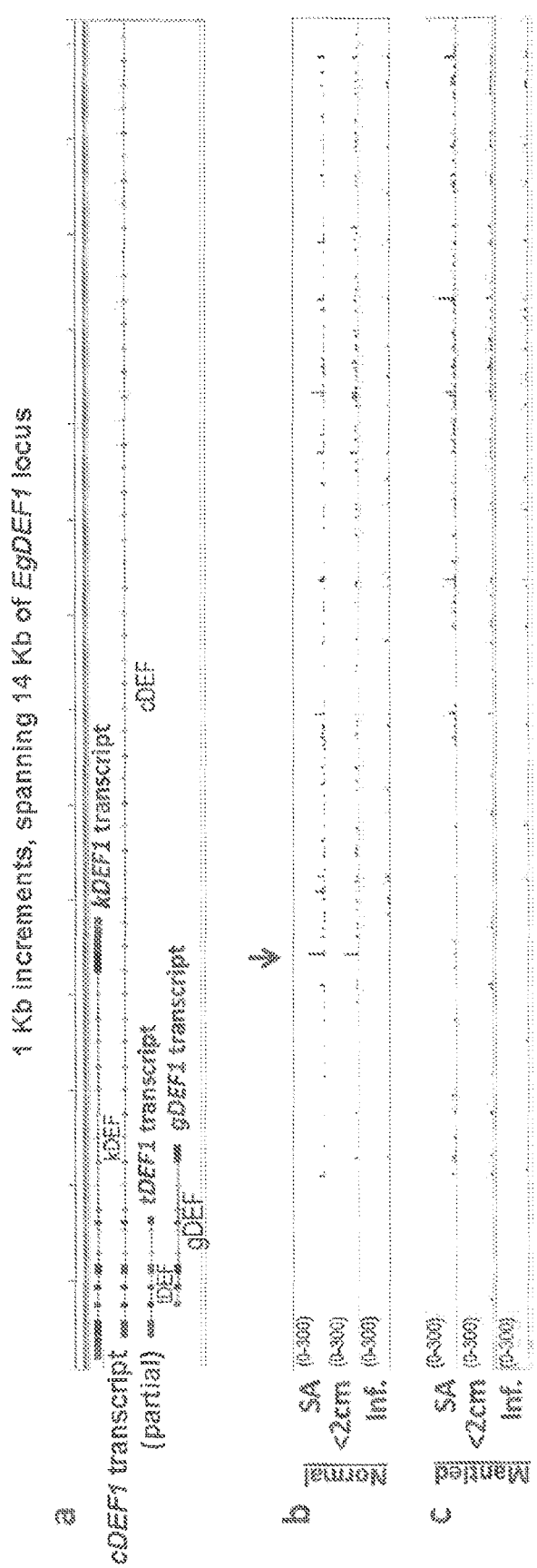
FIG. 9. Differential expression of small non-coding regulatory RNAs in Mantled tissues. a, Transcript models as described in Example 5. b, Distinct 24mer siRNA counts as determined by whole transcriptome small RNA sequencing of Normal shoot apex (SA), <2 cm stage inflorescence tissues (<2 cm) and later stage inflorescence tissues (Inf.). The x-axis is genomic position in scale with the transcript models shown in A. The y-axis is fragments per kilobase per million fragments mapped (FPKM) normalized read counts on a scale of 0 to 3.0. Vertical bars indicate the FPKM normalized read count for distinct 24mers derived from positions across the EgDEF1 locus. Data represent three independent samples per tissue type. c, Distinct 24mer siRNA counts as determined by whole transcriptome small RNA sequencing of mantled shoot apex (SA), <2 cm stage inflorescence tissues (<2 cm) and later stage inflorescence tissues (Inf.). Plots are generated as described in B. The vertical arrow indicates a specific 24mer siRNA (SEQ ID NO: 91) that is expressed 11-fold higher in normal shoot apex relative to mantled shoot apex.

Example 4: The Mantled Phenotype is Correlated with Changes in Non-Coding Regulatory RNA Expression In plants, small noncoding regulatory RNAs can impact DNA methylation and gene expression. To determine the correlation between the Mantled phenotype and expression of small noncoding regulatory RNAs, whole transcriptome small RNA sequencing was performed on shoot apex tissues derived from 3 Normal clonal trees and 3 Mantled clonal trees, <2 cm stage inflorescence tissues derived from 3 Normal clonal trees and 3 Mantled clonal trees, and later stage inflorescence tissues derived from 3 Normal clonal trees and 3 Mantled clonal trees. Small RNA sequencing libraries were generated by standard Illumina technology and each library sample was uniquely barcoded so that the transcriptome of each sample could be analyzed individually. Libraries were sequenced in pools of four libraries per HiSeq 2500 lane. 24 nucleotide sequencing reads (representing the 24mer class of small RNA) were mapped back to the reference oil palm genome (Singh et al. 2013). Reads that had an exact match to the sequence within the EgDEF1 gene interval were identified and mapped to their corresponding sequences of the EgDEF1 reference sequence. The number of mapped reads for each distinct 24mer sequence was calculated for each sample, and the read counts were FPKM normalized within each sample by the calculation: (# exact mapped 24mer reads of a distinct 24 mapped to the EgDEF1 locus)/(# of total 24mer reads mapped to the reference oil palm genome)*1,000,000. FIG. 9 shows plots of 24mer siRNA reads relative to the EgDEF1 genomic locus (FIG. 9A). Individual tracks are shown for normalized counts for shoot apex (SA), <2 cm inflorescence (<2 cm) and later stage inflorescence (Inf.) from Normal (FIG. 8B) and from Mantled (FIG. 8C) cloned trees. As can be seen by comparing tracks for SA and <2 cm tissues between Normal and Mantled phenotypes, there are numerous 24mer siRNAs detected in Normal samples that are either less abundant or not detected in Mantled samples. Substantially fewer distinct 24mer siRNAs are detected in the later stage inflorescences regardless of phenotype, consistent with an important role of small noncoding regulatory RNAs in early floral development. One strong peak (corresponding to the 24mer siRNA provided in SEQ ID NO: 99) in Normal SA and <2 cm that is significantly reduced in Mantled SA and <2 cm maps to a genomic region 152 bp downstream of the splice site of EgDEF1 exon 5 into the Karma element to produce the kDEF1 transcript (see Example 5).

To further address differential 24mer siRNA expression, 24mer siRNAs that displayed at least a 2-fold difference in expression in one phenotype relative to the other were identified for each tissue type: shoot apex, <2 cm stage inflorescences and later stage inflorescences. As predicted by the analysis shown in FIG. 9, shoot apex tissue has the largest number of distinct 24mer siRNAs differentially expressed in Normal relative to Mantled tissues (Table 1).

TABLE 1

24mer siRNAs Differentially Expressed in Shoot Apex

| SEQ ID NO. | Genomic Coordinate | Sequence | Fold Change (Normal/Abnormal) |
|---|---|---|---|
| 91 | 922424 | CTCTAGCAAGGCGATCAGAAGATT | 11.0 |
| 92 | 954273 | TCAGGTGTTATGTCAGTTTGGACT | 5.9 |
| 93 | 935533 | AAGTCTCCACTCTATCTATCCCGA | 5.0 |
| 94 | 948570 | GGGTCAACAAGGTCTGAGAACACT | 4.1 |
| 95 | 933745 | CGCAATCAGAATCAACTGGCCAAT | 3.8 |
| 96 | 926352 | ATGATACACGGTTGCATGCCCTGC | 3.4 |
| 97 | 924957 | GATCTATGGTGCAAGGAGTTAATT | 3.2 |
| 98 | 927895 | AGAGAGAGGGTTAAAGGACAATGC | 2.9 |
| 99 | 933648 | ATAGGGAGAATAGCTTGGCTTCGA | 2.9 |
| 100 | 939466 | TCGGGTTCTTTTATTCGTGGATTT | 2.9 |
| 101 | 932689 | AGGGGAGATTGTTGGCTTAGCTTG | 2.8 |
| 102 | 928308 | AGTAGACTCGATGATGATAAGACT | 2.7 |
| 103 | 928688 | ACCAGCACGGTCAAGGATAGGCAT | 2.7 |
| 104 | 928306 | ATAGTAGACTCGATGATGATAAGA | 2.7 |
| 105 | 937978 | CCTCCAACATCGGCCAAGTTAGTT | 2.7 |
| 106 | 927714 | AAATCCTACTTGTTTCTCTGACCT | 2.5 |
| 107 | 926387 | CATGAGGCATGCAAGGTATTGAAT | 2.4 |
| 108 | 937739 | AAGGCTGGCTAACTCAAAGAAGAG | 2.4 |
| 109 | 932932 | AATGATCGAGAAGGGCTGGAGACA | 2.3 |
| 110 | 933604 | TGACCCACCATCGAGAAGGACCGA | 2.3 |
| 111 | 936422 | ATAACTGACAAGTGGCATTGATCT | 2.3 |
| 112 | 945502 | AGAAGGATGAGAAGAGAGATTGTC | 2.3 |
| 113 | 924825 | AAAGATGTTAGCTCCTGTTCGAGA | 2.0 |
| 114 | 937738 | AAAGGCTGGCTAACTCAAAGAAGA | 2.0 |
| 115 | 935465 | AGAGATTGTGAACAAATGGAGAGA | 0.4 |

The 24mer siRNA (SEQ ID NO: 91) that maps 152 bp downstream of the splice site of EgDEF1 exon 5 into the Karma element is the most differentially expressed and is expressed at 11-fold higher levels in Normal shoot apex tissue relative to Mantled shoot apex tissue. An additional 23 siRNAs (SEQ ID NO: 92-115) also have higher expression in Normal relative to Mantled shoot apex, with fold differences ranging from 2 to 5.9-fold. A single 24mer siRNA was detected as expressed 2.5-fold higher in Mantled relative to Normal shoot apex tissue (SEQ ID NO: 115). Of the 25 siRNAs differentially expressed in Normal relative to Mantled shoot apex tissue, two (SEQ ID NO: 91 and SEQ ID NO: 97) map within the differentially methylated region. These siRNAs may affect DNA methylation and/or differential splicing of the EgDEF1 gene. Furthermore, the other 23 siRNAs may play roles in aspects of EgDEF1 gene expression.

Consistent with the analyses shown in FIG. 9, the later developmental stages (<2 cm stage inflorescence and later stage inflorescence) display progressively fewer 24 siRNA expression differences between Normal and Mantled. In <2 cm stage inflorescence, 10 distinct siRNAs were found to be differentially expressed by at least 2-fold (Table 2).

TABLE 2

24mer siRNAs Differentially Expressed in <2 cm Inflorescens

| SEQ ID NO. | Genomic Coordinate | Sequence | Fold Change (Normal/Abnormal) |
|---|---|---|---|
| 116 | 932666 | ATATTGTCTGCTCTTCACCAAAGA | 4.2 |
| 117 | 951091 | CTCGTAAGGCCCAAGGGTAGTCAT | 3.1 |
| 104 | 928306 | ATAGTAGACTCGATGATGATAAGA | 2.8 |
| 97 | 924957 | GATCTATGGTGCAAGGAGTTAATT | 0.5 |
| 118 | 933595 | AAAATAGCTTGACCCACCATCGAG | 0.5 |
| 119 | 933643 | ATAGAATAGGGAGAATAGCTTGGC | 0.4 |
| 115 | 935465 | AGAGATTGTGAACAAATGGAGAGA | 0.4 |
| 120 | 927834 | TCCTGTCCAGATATTTGCGCCTCT | 0.4 |
| 121 | 932922 | ACAACTAGCCAATGATCGAGAAGG | 0.4 |
| 122 | 933686 | AACACACTGCTGAAAAGGACTAGG | 0.2 |

These include siRNAs represented by SEQ ID NO: 97, 104 and 115 that were also differentially expressed in shoot apex. The siRNA represented by SEQ ID NO: 104 is overexpressed in Normal relative to Mantled shoot apex (2.7-fold) and <2 cm stage inflorescence (2.8-fold). The siRNA represented by SEQ ID NO: 115 is overexpressed in Mantled relative to Normal shoot apex (2.5-fold) and <2 cm stage inflorescence (2.5-fold). The siRNA represented by SEQ ID NO: 97 is overexpressed in Normal relative to Mantled shoot apex (3.2-fold), but is overexpressed in Mantled relative to Normal <2 cm stage inflorescence (2-fold). An additional 7 siRNAs were detected as differentially expressed in <2 cm stage inflorescence (SEQ ID NO: 116-122), as indicated in Table 2. Finally, two siRNAs were detected as overexpressed in Normal relative to Mantled later stage inflorescence (Table 3, SEQ ID NO: 123 and SEQ ID NO: 124).

TABLE 3

24mer siRNAs Differentially Expressed in later stage Inflorescens

| SEQ ID NO. | Genomic Coordinate | Sequence | Fold Change (Normal/Abnormal) |
|---|---|---|---|
| 123 | 951590 | AAACTCATGGTGTCAAGGGACGTG | 3.5 |
| 124 | 951656 | GCTACACAGGCACAATCTCGATTT | 2.3 |

Figure 10:
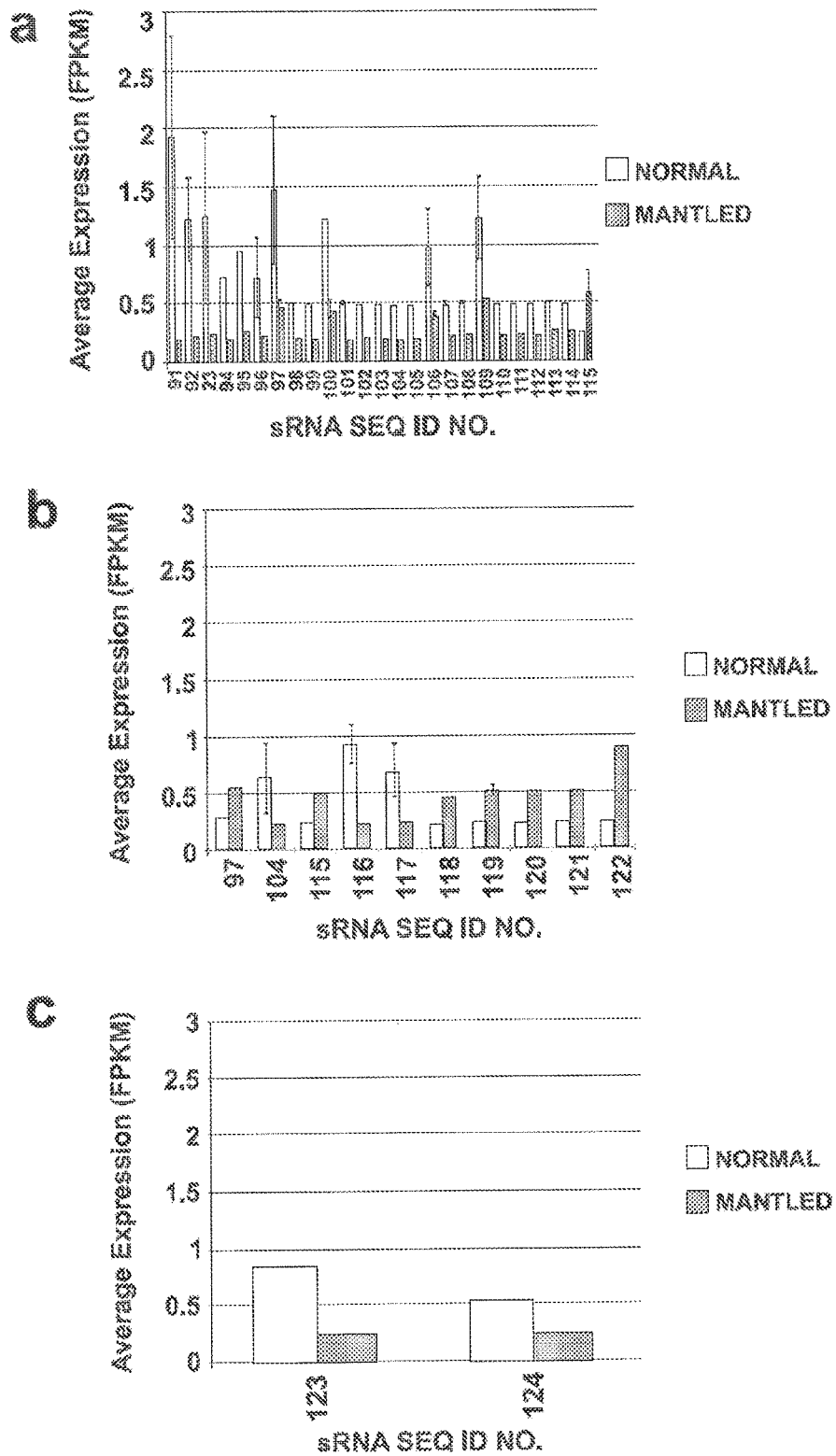
FIG. 10. Differential expression of siRNAs in mantled tissues. a, Average FPKM normalized 24mer siRNA read counts in normal (open bars) and mantled (gray bars) shoot apex samples. Error bars represent standard deviations for three replicates. X-axis labels indicate the SEQ ID NO: for each distinct siRNA. b, Average FPKM normalized 24mer siRNA read counts in normal (open bars) and mantled (gray bars)<2 cm stage inflorescence samples. Error bars represent standard deviations for three replicates. X-axis labels indicate the provided SEQ ID NO for each distinct siRNA. c, Average FPKM normalized 24mer siRNA read counts in normal (open bars) and mantled (gray bars) later stage inflorescence samples. Error bars represent standard deviations for three replicates. X-axis labels indicate the SEQ ID NO for each distinct siRNA.

Normalized siRNA expression levels (FPKM method) of these siRNAs in Normal and Mantled tissues, along with standard deviations across the three replicates per tissue state per phenotype, are shown graphically in FIG. 10. In addition to 24mer siRNAs expressed at quantitatively different levels in Normal relative to Mantled tissues, 24mer siRNAs were identified that are expressed in tissue types of one phenotype but not the other. Table 4 lists 24mer siRNAs that were detected in an average of at least 3 reads for tissue types of one phenotype and no reads were detected in the same tissue of the other phenotype.

TABLE 4

24 mer siRNAs expresses only in tissues of one phenotype and not the other phenotype

| SEQ ID NO. | Genomic Coordinate | Sequence | Tissue type | Phenotype expressing 24 mer siRNA |
|---|---|---|---|---|
| 130 | 667783 | AAATTCTTACTTCTGAGCATACTT | Shoot apex | Normal |
| 131 | 923085 | CGAGGTGGTGTCAATGGATAGAAT | Shoot apex | Normal |
| 132 | 346343 | CTCTTTGTTATACAATCACGGTGT | Shoot apex | Normal |
| 133 | 922431 | CAAGGCGATCAGAAGATTATCGAA | Shoot apex | Normal |
| 134 | 314456 | GTGCCATATGTCATAGTCAACTGT | Shoot apex | Normal |
| 135 | 923490 | AATCTGATATTGGCATCCACATGA | <2 cm Inflorescence | Mantled |
| 136 | 1065423 | CCTGACTTTCGGTTGGETGTCTCT | <2 cm Inflorescence | Normal |
| 137 | 1065863 | AATCCTACTTGTTTCTCTGACCTT | <2 cm Inflorescence | Normal |
| 138 | 1066135 | CTCTAGCAAGGCGATCAGAAGATT | <2 cm Inflorescence | Normal |
| 139 | 1066138 | AAATGGCATACTCTGGCAATTCGA | <2 cm Inflorescence | Normal |

TABLE 4-continued 24 mer siRNAs expresses only in tissues of one phenotype and not the other phenotype

| SEQ ID NO. | Genomic Coordinate | Sequence | Tissue type | Phenotype expressing 24 mer siRNA |
|---|---|---|---|---|
| 140 | 314911 | TCTATCTCATCCTCTCAACCAAT | later stage Inflorescence | Mantled |
| 141 | 314191 | GTAGCCCATGTCTTTGTTTTCCCT | later stage Inflorescence | Mantled |
| 142 | 334759 | TGTGGATGGCTAACGATATGGACT | later stage Inflorescence | Normal |
| 143 | 314753 | ACTAGCACCATGTGTCGTTATGGG | later stage lnflorescence | Normal |

Five distinct siRNAs (SEQ ID NO: 130-134) were detected in Normal shoot apex, but not in Mantled shoot apex. One siRNA (SEQ ID NO: 135) was detected in Mantled <2 cm stage inflorescence, but not in Normal <2 cm stage inflorescence. Four siRNAs (SEQ ID NO:136-139) were detected in Normal <2 cm stage inflorescence, but not in Mantled <2 cm stage inflorescence. Two siRNAs (SEQ ID NO: 140 and 141) were detected in Mantled later stage inflorescence, but not in Normal later stage inflorescence. Finally, 2 siRNAs (SEQ ID NO: 142 and 143) were detected in Normal later stage inflorescence, but not in Mantled later stage inflorescence. Therefore, quantitative detection of expression of one or more of these siRNAs (SEQ ID NO: 82-124) may be useful for the prediction of the Mantled phenotype in somaclonal materials, long before field planting and the development of the Mantled abnormal fruit phenotype. Furthermore, ectopic expression of one or more siRNAs (e.g. SEQ ID NO: 91 and SEQ ID NO: 97) during cell culture stages of somaclonal propagation may be useful to maintain or reset the DNA methylation state of the differentially methylated region within the Karma element and/or the appropriate splicing of mRNAs derived from the EgDEF1 locus, thus inhibiting development of the abnormal Mantled fruit phenotype in clonal derived palms.

Figure 11:
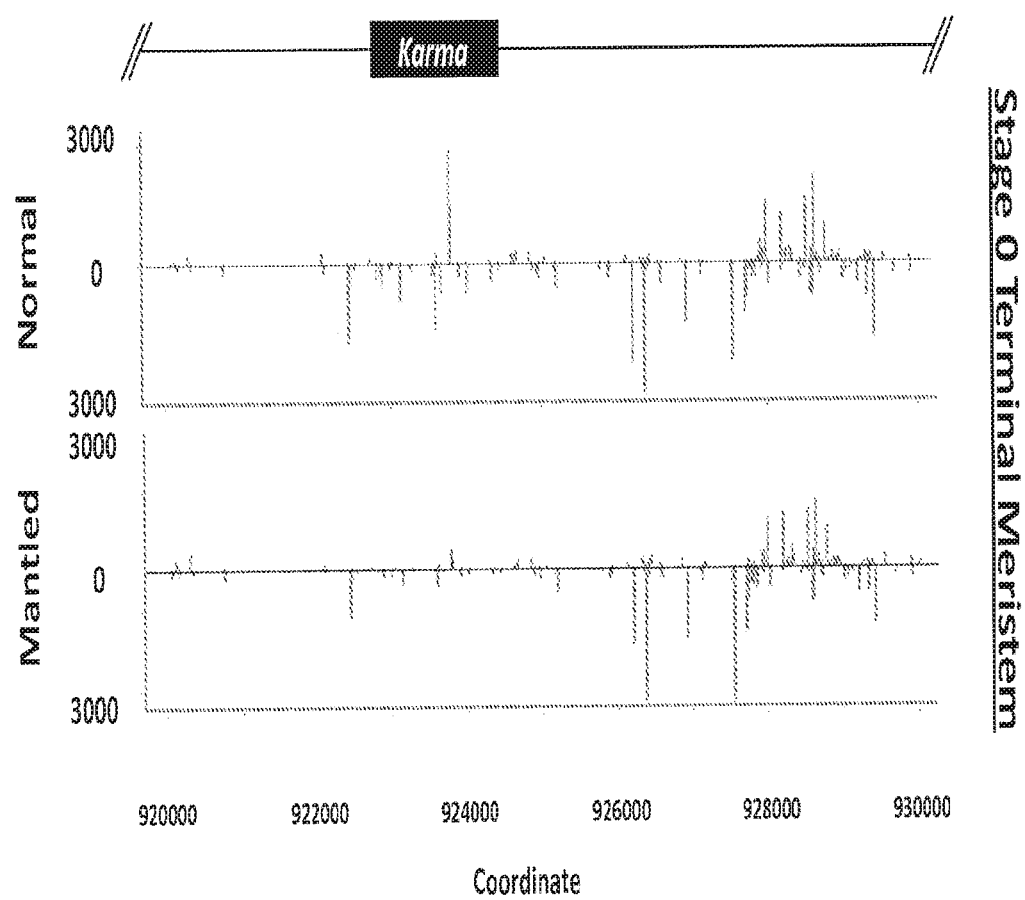
FIG. 11. Repressed 24nt siRNA expression in mantled inflorescences map to Karma. Small RNA sequencing in normal (n=5 biological replicates) and parthenocarpic mantled (n=7 biological replicates) stage 0 Terminal Meristem. Fragments per kilobase per million mapped reads (FPKM) normalized expression values for each 24nt siRNA are plotted on a region of intron 5 including Karma (black box). Bars above and below the zero line represent sense and antisense siRNAs, respectively, and are plotted on the same scale. A cluster of 24nt siRNAs expressed from the Karma region are repressed in mantled relative to normal stage 0 inflorescence tissues.
Figure 12:
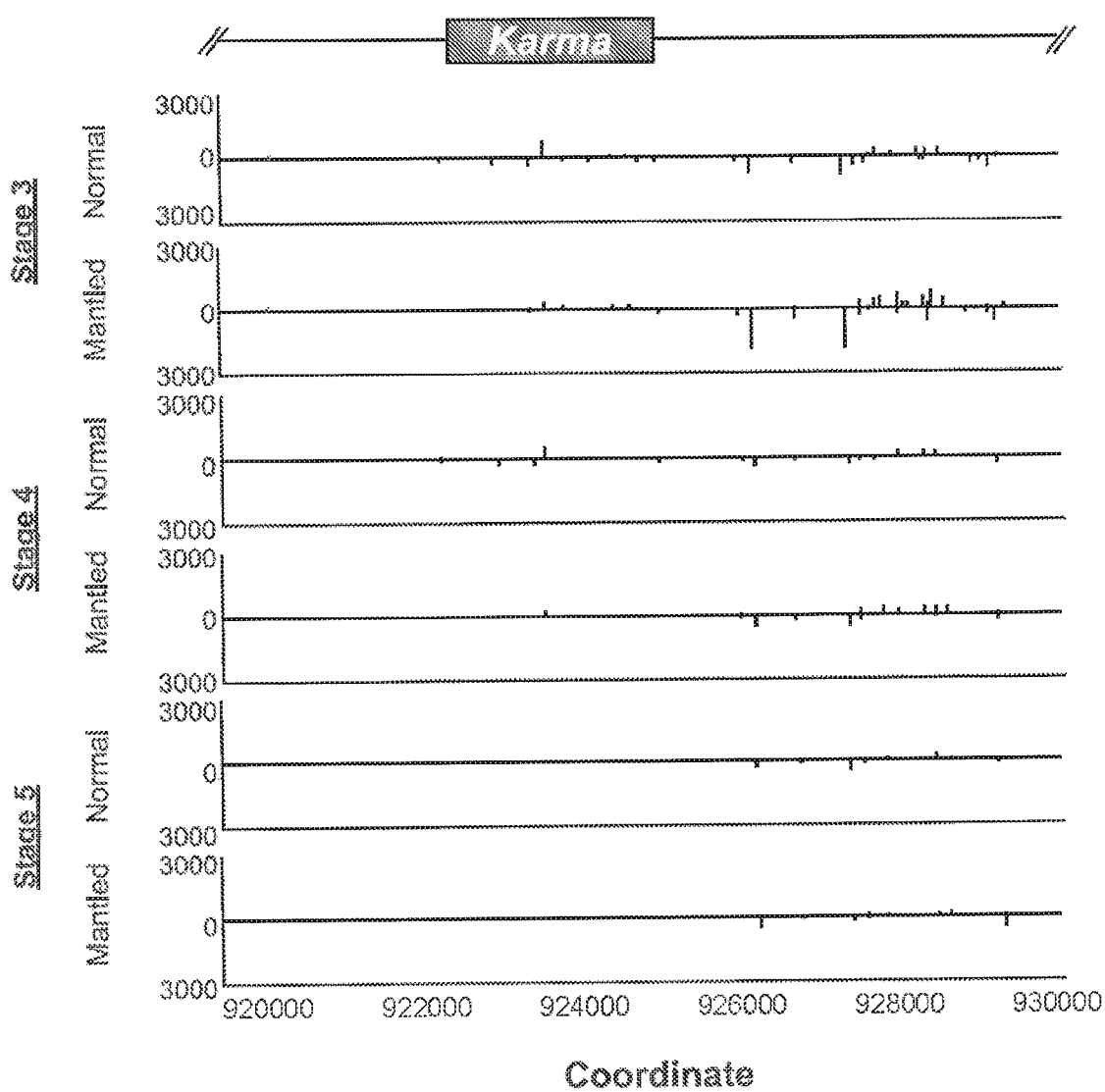
FIG. 12. 24nt small RNA analysis of inflorescence development stages 3-5. FPKM normalized expression values for each measured 24nt siRNA are plotted in scale with the genomic elements diagrammed at the top of the figure. Bars above and below the zero line represent sense and antisense siRNAs, respectively, and are plotted on the same scale in both directions.

Because in Arabidopsis and maize, 24nt small interfering (si)RNAs guide CHH and CHG methylation, and DNA methylation in turn is often required for the biosynthesis of 24nt siRNA by RNA polymerase IV (Regulski et al., 2013; Zhong et al., 2012; Hollick 2012), we further analyzed siRNA expression in a time course of inflorescence development in both normal and mantled female flowers. Small RNA sequencing was performed on female inflorescence tissues at stages 0, 2, 3, 4 and 5 (7 mantled and 5 normal biological replicates at stage 0, 6 mantled and 8 normal biological replicates each at stages 2 and 3, 7 mantled and 5 normal biological replicates at stage 4, and 5 mantled and 4 normal biological replicates at stage 5). Stages were histologically classified as stage 0 (terminal meristem); stage 2 (initiation of perianth organs); stage 3 (development of perianth organs and initiation of reproductive organs); stage 4 (development of reproductive organs); stage 5 (fully formed reproductive organs), as previously defined (Adam et al., 2007). siRNA reads mapping to the genomic scaffold including EgDEF1 were identified and normalized as fragments per 1,000 mapped reads (FPKM) to the entire oil palm reference genome (Singh et al. 2013). FPKM values for each 24mer were compared between biological replicates of normal and mantled samples by Student's t-test, two-tailed assuming equal variance. The analysis identified a cluster of 24nt Karma siRNAs in normal inflorescence at stage 0, which were reduced or absent in mantled inflorescence, while other siRNAs matching the EgDEF1 intron, but outside of Karma, were not significantly differentially expressed (FIG. 11). In summary, several 24nt siRNAs derived from Karma were repressed or silenced in mantled relative to normal stage 0 inflorescence tissues (SEQ ID NO: 144-147, 150-158 and 160-161) (Table 5). Several of these 24nt siRNAs were also repressed or silenced in mantled relative to normal stage 2 inflorescence (SEQ ID NO: 145, 151, 154 and 157), and two 24nt siRNAs were significantly repressed at stage 2 (SEQ ID NO: 148, 149 and 159) (Table 5). Finally, at stage 3, one 24nt siRNA repressed at stage 2 remained repressed in mantled relative to normal (SEQ ID NO: 149). The decrease in the number of differentially expressed siRNAs at later stages of inflorescence development is the consequence of the overall decrease in expression of siRNAs in later development stages, even in normal tissues (FIG. 12). siRNAs derived from near the Karma splice acceptor site were mostly in the antisense orientation (Table 5), raising the interesting possibility that 24nt siRNAs complementary to the alternatively spliced exon cooperate with aberrant DNA methylation in an epigenetic mechanism giving rise to the mantled phenotype. Therefore, quantitative detection of expression of one or more of these siRNAs (SEQ ID NO: 82-124 and 144-161) may be useful for the prediction of the mantled phenotype in somaclonal materials, long before field planting and the development of the mantled abnormal fruit phenotype. Furthermore, ectopic expression of one or more siRNAs (e.g. SEQ ID NO: 144-161) during cell culture stages of somaclonal propagation may be useful to maintain or reset the DNA methylation state of the differentially methylated region within the Karma element and/or the appropriate splicing of mRNAs derived from the EgDEF1 locus, thus inhibiting development of the abnormal mantled fruit phenotype in clonal derived palms.

TABLE 5

24 mer siRNAs downregulated in mantled female inflorescence development

| SEQ ID NO: | Genomic Coordinate[a] | Orientation[b] | Sequence | Mantled Avg.[c] | Normal Avg.[d] | t-test[e] | Stage[f] |
|---|---|---|---|---|---|---|---|
| 144 | 922791 | ANTISENSE | TTCAGTCAGAGACTTCAGGCCAAT | 27.16 | 367.54 | 0.0269 | 0 |
| 145 | 922864 | ANTISENSE | AGGCTCTCACAGAAAATGAATTTG | 159.12 | 565.42 | 0.0362 | 0 |
| 145 | 922864 | ANTISENSE | AGGCTCTCACAGAAAATGAATTTG | 23.29 | 233.70 | 0.0457 | 2 |
| 146 | 923116 | ANTISENSE | TTATACAGCTAAATTCTCAGTCCT | 23.96 | 282.73 | 0.0012 | 0 |
| 147 | 923117 | ANTISENSE | TATACAGCTAAATTCTCAGTCCTT | 13.97 | 442.34 | 0.0000 | 0 |
| 148 | 923120 | ANTISENSE | ACAGCTAAATTCTCAGTCCTTATT | 23.29 | 290.03 | 0.0066 | 2 |
| 149 | 923123 | ANTISENSE | GCTAAATTCTCAGTCCTTATTAAT | 0.00 | 332.96 | 0.0067 | 2 |
| 149 | 923123 | ANTISENSE | GCTAAATTCTCAGTCCTTATTAAT | 67.53 | 257.59 | 0.0295 | 3 |
| 150 | 923545 | ANTISENSE | CATTCTAAACTGAGGAAAACTTAT | 23.96 | 236.90 | 0.0013 | 0 |
| 151 | 923588 | ANTISENSE | AGGTTCAGAAGAAATTGATCGGGT | 397.31 | 1588.90 | 0.0128 | 0 |
| 151 | 923588 | ANTISENSE | AGGTTCAGAAGAAATTGATCGGGT | 41.13 | 278.10 | 0.0138 | 2 |
| 152 | 923601 | SENSE | ATTGATCGGGTAGAAAGGTAAACT | 114.41 | 300.01 | 0.0273 | 0 |
| 153 | 923658 | ANTISENSE | TGCAGTGCTTACAGGGATCCCACT | 22.16 | 719.92 | 0.0000 | 0 |
| 154 | 923765 | SENSE | ACGAGGAGTATAACTAAGGGCACT | 499.49 | 2836.15 | 0.0009 | 0 |
| 154 | 923765 | SENSE | ACGAGGAGTATAACTAAGGGCACT | 130.63 | 647.59 | 0.0301 | 2 |
| 155 | 923780 | SENSE | AAGGGCACTCTAGAATATGTTGGT | 110.50 | 1008.90 | 0.0017 | 0 |
| 156 | 923780 | SENSE | AAGGGCACTTTAGAATATGTTGGT | 88.46 | 517.53 | 0.0005 | 0 |
| 157 | 924004 | ANTISENSE | TGGTTTACAGCACACATGAAATAT | 81.33 | 673.52 | 0.0066 | 0 |
| 157 | 924004 | ANTISENSE | TGGTTTACAGCACACATGAAATAT | 0.00 | 191.09 | 0.0115 | 2 |
| 158 | 924322 | ANTISENSE | GGCATGAAGGATCTACTATTTTCT | 110.20 | 419.35 | 0.0059 | 0 |
| 159 | 924322 | ANTISENSE | GGCATGAAGGATCTACTATTTTCT | 0.00 | 192.51 | 0.0500 | 2 |

TABLE 5-continued 24 mer siRNAs downregulated in mantled female inflorescence development

| SEQ ID NO: | Genomic Coordinate[a] | Orientation[b] | Sequence | Mantled Avg.[c] | Normal Avg.[d] | t-test[e] | Stage[f] |
|---|---|---|---|---|---|---|---|
| 160 | 924604 | SENSE | ACTTTTATGCATGCTTAACACCCT | 73.33 | 257.62 | 0.0235 | 0 |
| 161 | 924610 | SENSE | ATGCATGCTTAACACCCTATGGGA | 30.35 | 240.33 | 0.0018 | 0 |

[a]Genomic coordinate indicates the nucleotide position relative to the reference *pisifera* oil palm genome build (Singh et al. 2013) corresponding to the 5'-most base of the 24 mer siRNA.
[b]Indicates whether the siRNA is expressed from the sense or antisense strand relative to EgDEF1 expression.
[c]The average FPKM normalized expression value for biological replicates of mantled inflorescense tissues at the indicated stage.
[d]The average FPKM normalized expression value for biological replicates of normal inflorescense tissues at the indicated stage.
[e]Significance of differential expression determined by Student's t-test, 2 sided, assuming equal variance.
[f]Indicates the inflorescence development stage at which repressed expression in mantled tissues was detected.

Figure 13:
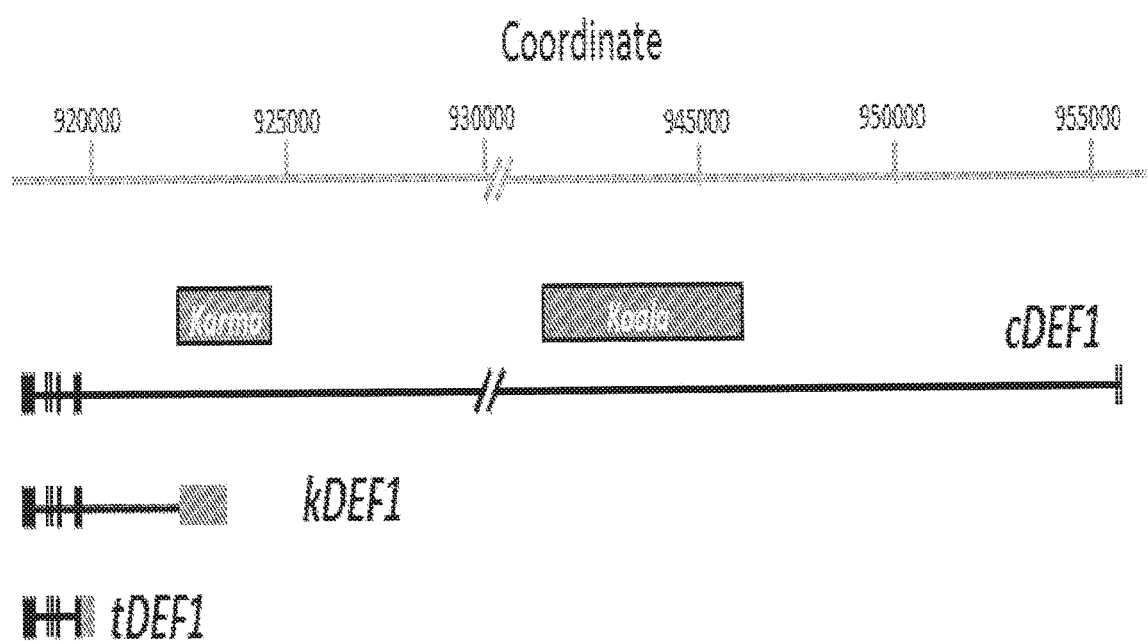
FIG. 13. Alternatively spliced transcripts. EgDEF1/MANTLED transcripts were assembled from transcriptome sequencing of female inflorescences from normal and parthenocarpic mantled palms (3 biological replicates each of shoot apex, <2 cm inflorescence and late stage inflorescence for each phenotype). Black boxes represent exons, Karma and Koala elements are labeled and represented in scale above the transcript model diagrams. Alternative splicing of exon 5 to the splice acceptor site at the beginning of Karma resulted in kDEF1 transcripts in mantled but not normal inflorescence. A third transcript (tDEF1) that does not utilize the exon 5 splice donor site was detected in both normal and mantled inflorescence. Coordinates are relative to the reference pisifera oil palm genome build (Singh et al. 2013).

Example 5: The Mantled Phenotype is Correlated with Changes in Alternatively Spliced Transcript Expression Gene expression in normal and mantled tissues throughout stages of inflorescence development was analyzed by whole transcriptome next-generation sequencing of female inflorescences from normal and parthenocarpic mantled palms (3 biological replicates each of shoot apex, <2 cm inflorescence and late stage inflorescence for each phenotype). Four differentially spliced mRNA transcripts derived from the EgDEF1 locus were detected (FIGS. 9 and 13). First, cDEF1 transcripts (SEQ ID NO: 5) were detected in both normal and mantled tissues. These full-length transcripts include splicing of all EgDEF1 introns so that the mature mRNA includes complete exons 1 through 7 of the EgDEF1 gene and encode the full length EgDEF1 MADS box transcription factor (SEQ ID NO: 6). Second, a shorter transcript, tDEF1 (SEQ ID NO: 75) was detected in both normal and mantled tissues. This transcript includes EgDEF1 exons 1-5, however exon 5 does not splice to exon 6. Instead, the tDEF1 mRNA extends from exon 5 into intron 5 and terminates shortly thereafter. The tDEF1 mRNA encodes a truncated protein due to a frameshift and early translation termination within the predicted K Domain of the MADS box protein (SEQ ID NO: 76). Next, an alternatively spliced transcript was detected exclusively in mantled tissues. This transcript, kDEF1 (SEQ ID NO: 78), splices from EgDEF1 exon 5 to the splice acceptor site of the Karma element within intron 5. The location of this alternative splicing site falls within the differentially methylated region (FIG. 4-8). The alternative splicing event leads to a frame shift following exon 5 coding sequencing and early translation termination with the predicted K Domain of the MADS box protein (SEQ ID NO: 79). Finally, an additional alternatively spliced transcript, gDEF1 (SEQ ID NO: 80) was detected at very low levels in a small number of mantled tissue samples. This transcript splices from EgDEF1 exon 5 into a region of intron 5 that is upstream of Karma and the differentially methylated region. This splicing even also leads to a frameshift following the exon 5 coding sequence and early translational termination within the K Domain of the MADS box transcription factor (SEQ ID NO: 81). It is noted that such expression of truncated MADS box transcription factor proteins (kDEF1, tDEF1 and/or gDEF1), which include the MADS box domain required for protein heterodimerization and DNA binding but lack the C-terminal domains of the protein required for transcriptional activation can have a dominant negative impact on the function of the full length MADS box protein and, thus, lead to homeotic transformation phenotypes such as that displayed in clonal palms with the Mantled fruit abnormality.

Figure 14:
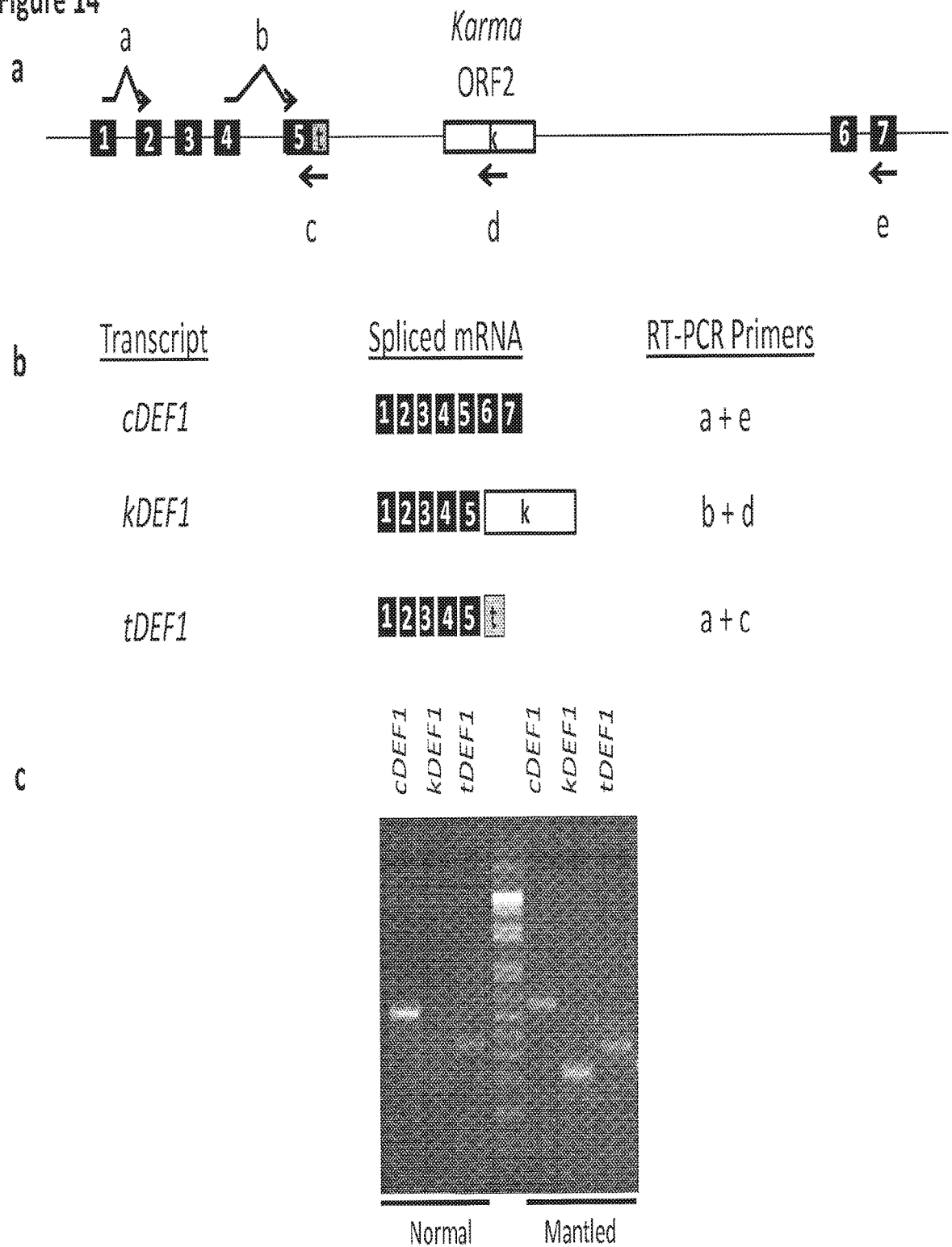
FIG. 14. Design of qRT-PCR assays for cDEF1, kDEF1 and tDEF1. A. Gene model of EgDEF1 indicating relative positions of transcript-specific qRT-PCR primers, as described in Example 5. Black boxes represent EgDEF1 exons. Gray box ('t') represents intron 5 sequence included in the tDEF1 transcript. Open box ('k') represents Karma ORF2 sequence. Arrows indicate qRT-PCR primers. B. Summary of alternatively spliced transcripts and qRT-PCR primers used to specifically detect each transcripts. C. End point RT-PCR results for each assay using normal or mantled total RNA as template.

To quantitatively measure expression of cDEF1, tDEF1 and kDEF1, qRT-PCR assays specific to each transcript were designed and optimized (FIG. 14). To specifically measure cDEF1 expression, a forward PCR primer was designed to span the splice junction of EgDEF1 exons 1 and 2 (a in FIG. 14a, SEQ ID NO: 125), and a reverse primer was designed within EgDEF1 exon 7 (e in FIG. 14a, SEQ ID NO: 126). To specifically measure kDEF1 expression, a forward PCR primer was designed to span the splice junction of EgDEF1 exons 4 and 5 (b in FIG. 14a, SEQ ID NO: 127), and a reverse primer was designed within the Karma element (d in FIG. 14a, SEQ ID NO: 128). To specifically measure tDEF1 expression, a forward PCR primer was designed to span the splice junction of EgDEF1 exons 1 and 2 (a in FIG. 14a, SEQ ID NO: 125), and a reverse primer was designed to span the 3' sequences of exon 5 and the 5' sequences of intron 5 included in the tDEF1 transcript (c in FIG. 14a, SEQ ID NO: 129). Multiple locus-specific reverse oriented primers were designed and pooled for use as RT primers so that all possible transcripts could be amplified as cDNA products from a common reverse transcriptase reaction using stage 4 normal and stage 5 mantled total RNA samples as template. A summary of exon splicing for each analyzed transcript, and the qRT-PCR primers used is provided in FIG. 14b. End-point PCR reactions using these RT products as templates and each primer pair separately are shown in FIG. 14c. cDEF1 primers amplify a band of the predicted size from both normal and mantled RNA templates, although qualitatively more product is amplified from the normal sample relative to the mantled sample. kDEF1 primers amplify a band of the predicted size from mantled, but not normal RNA. tDEF1 primers amplify a band of the predicted size from both normal and mantled RNA, although qualitatively more product is amplified from the mantled sample relative to the normal sample. Quantitative efficiencies of the PCR primers, along with primers for an endogenous housekeeping gene reference qRT-PCR assay, PD00380, for oil palm (Chan et al. (2014) *PLoS ONE* 9: e99774) were determined by amplifying a dilution series of cDNA templates in real-time PCR assays using SYBR green quantification methods.

Figure 15:
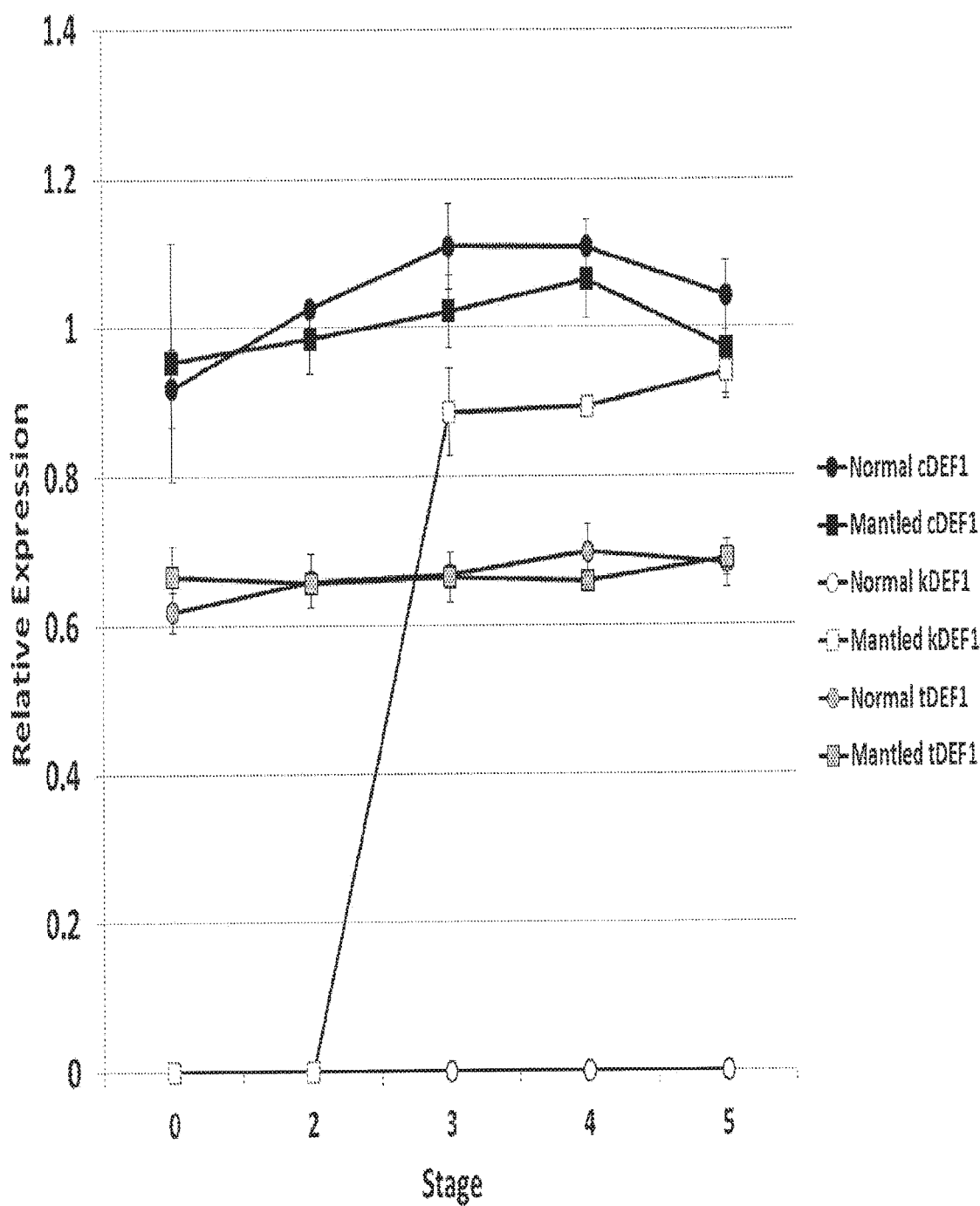
FIG. 15. Quantitative reverse transcriptase PCR (qRT-PCR) analysis of cDEF1, tDEF1 and kDEF1 expression throughout normal and parthenocarpic mantled female inflorescence development. Error bars represent standard deviations between three technical replicate assays of 3 biological replicate tissue samples per phenotype, per stage. Expression relative to an endogenous reference gene is shown.

The qRT-PCR assays were used to quantitatively measure cDEF1, tDEF1 and kDEF expression throughout the female inflorescence time course (FIG. 15). Gene expression was quantified in developing inflorescence stages 0, 2, 3, 4 and 5. All first strand cDNA reverse transcription reactions were performed from 1 µg total RNA using a cocktail of reverse primers specific EgDEF1 exons 6 and 7, as well as 3' regions of Karma. For each stage, three technical replicates were performed for three biological replicates per phenotype, per stage. qRT-PCR reactions were performed using 1 µL first strand cDNA in 1× Roche SYBR Master Mix on a Roche LC480 instrument. Cycle thresholds above 33 cycles were not included in calculations, and detectable expression was calculated only for samples in which expression was detected in at least 2 of 3 technical replicates. Expression levels were quantified by extrapolation from the standard curve for each assay, and expression levels relative to an oil palm gene expression reference gene (Chan et al. 2014) were calculated. In both normal and mantled tissues, cDEF1 expression levels rise subtly from stage 0 through late inflorescence (FIG. 15), while tDEF1 is expressed at a constant, lower level. However, in these results kDEF1 expression is restricted to inflorescence stages 3 to 5, exclusively in mantled tissues. Therefore, unlike tDEF1 expression, the expression of kDEF1 in female inflorescence is, in some cases, only found in mantled, and is predicted to encode a severely truncated form of the EgDEF1 MADS box transcription factor.

In conclusion, the mantled fruit abnormality phenotype of oil palm, which arises as a consequence of somaclonal propagation, is correlated with multiple molecular abnormalities at the EgDEF1 locus. Tissues from mantled palms have significant CHG hypomethylation of a differentially methylated region that covers a Karma family LINE retrotransposon element embedded within intron 5 of the EgDEF1 gene. Hypomethylation of this region is sensitively and specifically diagnostic of the Mantled phenotype, and assays quantitatively measuring methylation content at any of multiple CHG sites within this region have strong diagnostic power for predicting the abnormality. Four alternatively spliced transcripts derived from the EgDEF1 gene have been detected, one of which (cDEF1) encodes a full-length MIKC family MADS box transcription factor and three of which (kDEF1, tDEF1 and gDEF1) encode truncated proteins that include the MADS box, I and partial K domains, but lack the C-terminal transcription activation domain. In normal tissue, the predominantly expressed transcript encodes the full length cDEF1 protein. However, in Mantled tissue, expression is predominantly derived from the alternatively spliced kDEF1 transcript, and to a lesser extent, the alternatively spliced tDEF1 transcript. These findings support a mechanism by which epigenetic deregulation of the EgDEF1 locus leads to expression of truncated dominant negative proteins that interfere with the normal homeotic floral organ specification pathway, thus leading to the mantled fruit phenotype. Moreover, the expression of small non-coding regulatory RNAs from the EgDEF1 locus are significantly altered in tissues from mantled relative to normal palms, especially at early developmental stages.

Figure 16:
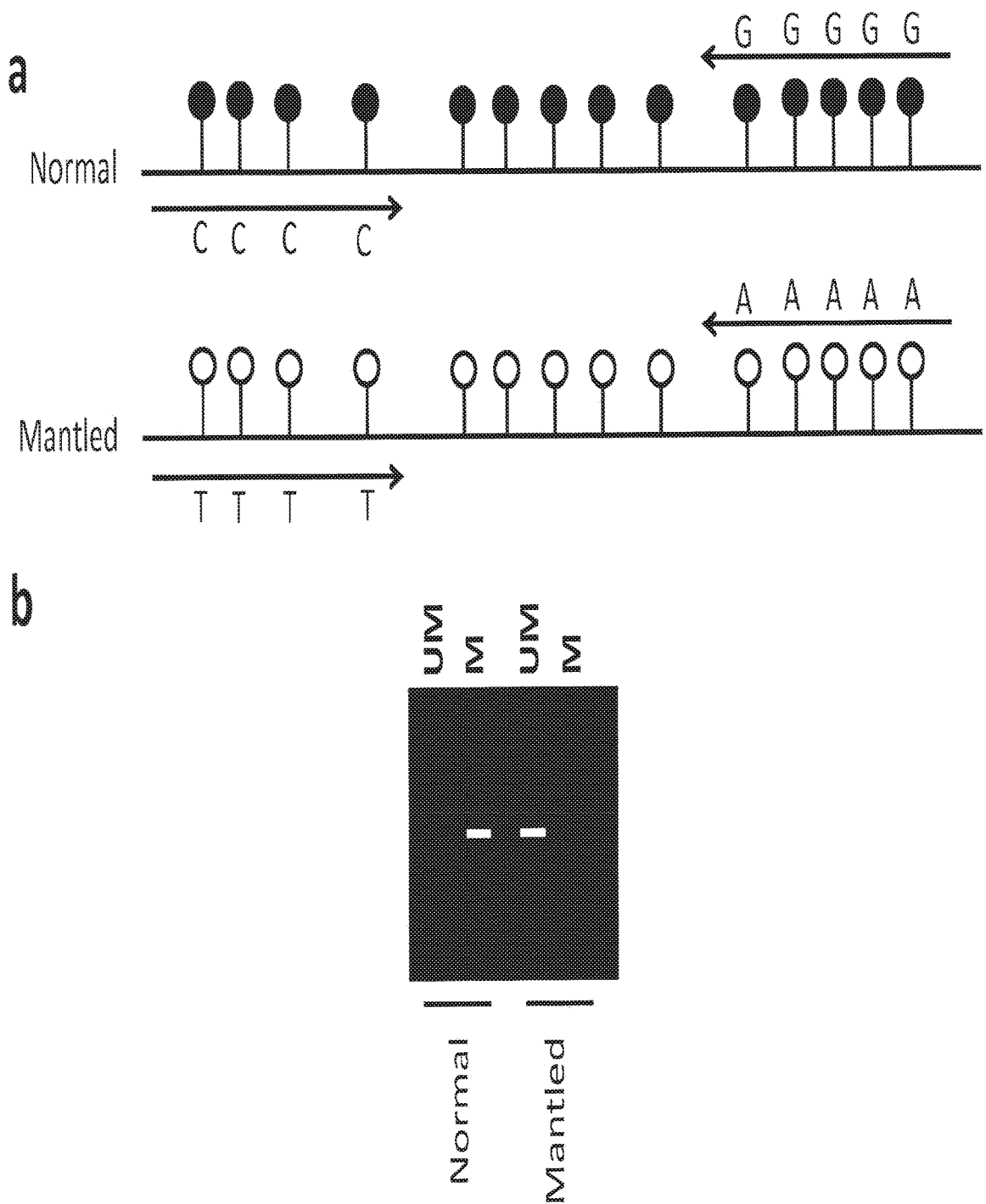
FIG. 16. Example of Methylation Specific PCR assay for detecting differential DNA methylation in DMRs disclosed herein. Details of the assay are described in Example 6.

Example 6: Detection of Differential DNA Methylation by Methylation Specific PCR DNA methylation can be quantified by methylation specific PCR (MSP) methods. Using this method, DNA samples are treated with bisulfite to convert unmethylated cytosines (but not methylated cytosines) to uracil. Primers are designed to cover potential methylated cytosine sites, and different primers are designed for methylated vs. unmethylated configurations. An example of analyzing a DMR identified herein in mantled and normal samples using MSP is shown in FIG. 16. It is noted that such an assay can be performed on clonal material prior to planting in the field, at a time in which the eventual mantled phenotype would be otherwise unknown. For simplicity, all potential DNA methylation sites are indicated as methylated (filled circles) in normal DNA and unmethylated (open circles) in mantled DNA (FIG. 16a). It is noted, however, that a given DNA molecule may include a mixture of methylated and unmethylated cytosines. Primers intended to amplify molecules that are methylated at sites within the primer sequence are designed so that primers have cytosines at potential methylation sites in the primer for one strand and guanines at potential methylation sites in the primer for the other strand. Primers intended to amplify molecules that are unmethylated at sites within the primer sequence are designed so that primers have thymines at potential methylation sites in the primer for one strand and adenines at potential methylation sites in the primer for the other strand. Bases within primers that correspond to cytosines that are not potential methylation sites are designed to base pair with the converted sequence since all unmethylated cytosines are converted to uracil. Normal and mantled DNA samples are treated with bisulfite to convert unmethylated cytosines to uracil, and the converted DNA is used as template for PCR amplification with each primer pair (UM for unmethylated primer pair and M for methylated primer pair) separately. Normal samples, in which the cytosines are predicted to be methylated, amplify with the M primer pair, but not the UM primer pair. Mantled samples, in which the cytosines are predicted to be unmethylated, amplify with the UM primer pair, but not the M primer pair (FIG. 16b). Differential intensities of bands may also be diagnostic of the phenotype, rather than presence or absence of a band.

A modified approach can be applied in which one of the two PCR primers includes only one, two or three potential methylation sites. Following bisulfite conversion, a site behaves similar to a single nucleotide polymorphism in unconverted DNA. For example, following bisulfite conversion, a methylated cytosine remains cytosine and will base pair with guanine. However, an unmethylated cytosine is converted to uracil and will base pair with adenine. Therefore, a method suitable for detection of a single nucleotide polymorphism is also suitable for monitoring the methylation status of a cytosine within the mantled DMR. These methods may provide quantitative or qualitative measurements.

Figure 17:
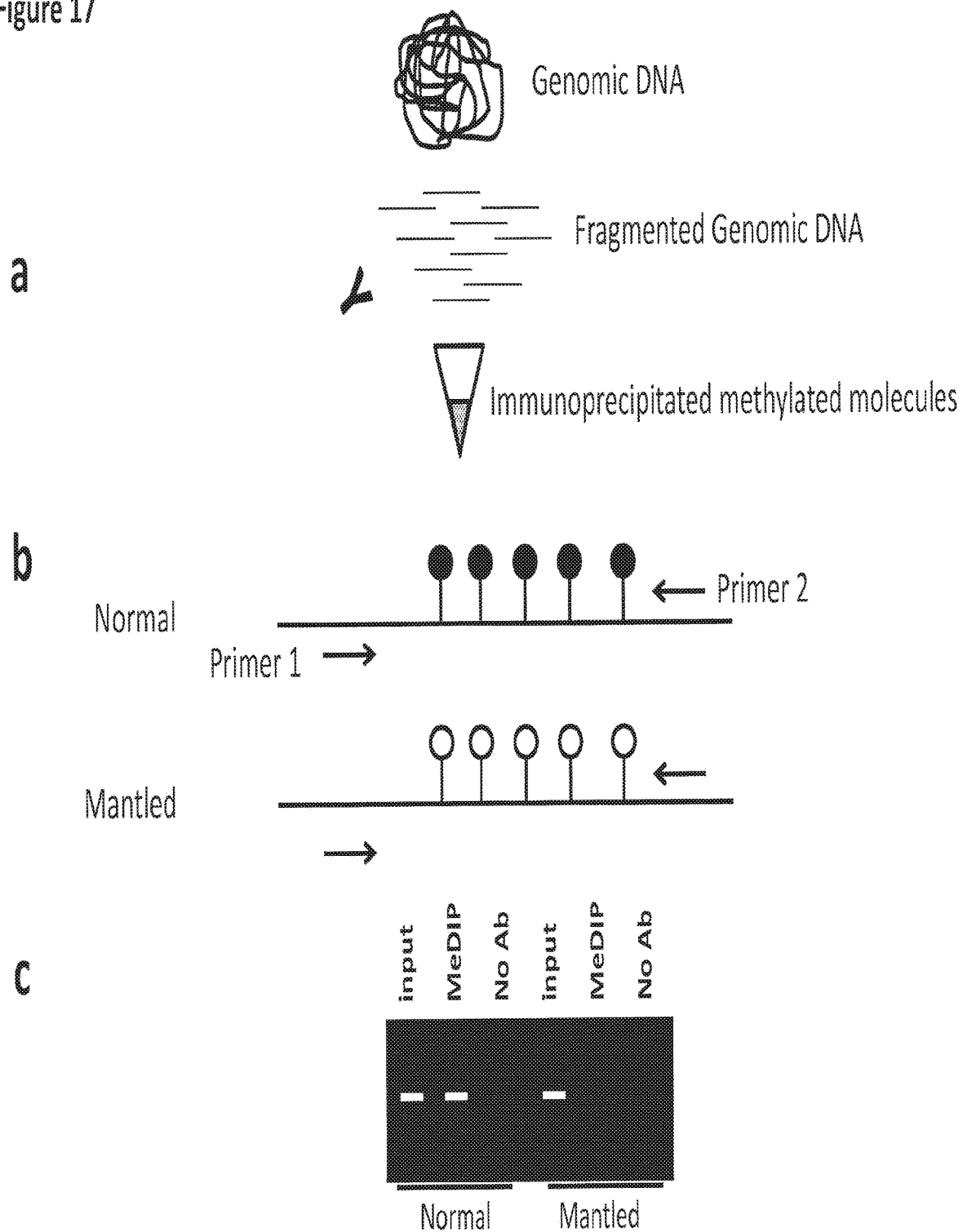
FIG. 17. Prophetic example of Methylation DNA Immunoprecipitation assay for detecting differential DNA methylation in DMRs disclosed herein. Details of the assay are described in Example 7.

Example 7: Detection of Differential DNA Methylation by Methylation Dependent Immunoprecipitation DNA methylation can be quantified by methylation dependent immunoprecipitation (MeDIP) methods. In this method, an antibody specific to methylcytosine is used to immunoprecipitate cytosine methylated DNA molecules, followed by amplification of specific DNA sequences. An example of analyzing a DMR identified herein in Mantled and normal samples using MeDIP is shown in FIG. 17. It is noted that such an assay could be performed on clonal material prior to planting in the field, at a time in which the eventual Mantled phenotype would be otherwise unknown. For simplicity, all potential DNA methylation sites are indicated as methylated (filled circles) in normal DNA and unmethylated (open circles) in Mantled DNA (FIG. 17b). It is noted, however, that a given DNA molecule may include a mixture of methylated and unmethylated cytosines. DNA from normal and Mantled samples is fragmented by restriction enzymes or by sonication or by mechanical shearing (FIG. 17a). An antibody specific to methylcytosine is added, and complexes of antibody and methylated DNA molecules are immunoprecipitated using standard methods (FIG. 17a). Immunoprecipitated fractions are then PCR amplified with primers designed to flank the DMR (FIG. 17b). PCR amplification reactions can be analyzed by agarose gel electrophoresis (FIG. 17c). As a positive control, input DNA (without immunoprecipitation) is amplified. As a negative control, mock immunoprecipitated fractions without antibody is amplified. The 5-methylcytosine specific antibody immunoprecipitated fraction shows amplification of the DMR region in normal samples, but not in Mantled samples.

Differential intensities of bands may also be diagnostic of the phenotype, rather than presence or absence of a band.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

What is claimed is:

1. A method for physically separating the oil palm plant or seed predicted to have the Mantled phenotype from one or more oil palm plants or seeds predicted to lack the Mantled phenotype based on the methylation status, the method comprising:

obtaining genotype information for a sample from the oil palm seeds or plants, wherein the genotype information comprises methylation status of at least one cytosine within a differential methylation region (DMR), wherein the DMR is within a sequence of DNA at least 95% identical to SEQ ID NO:66 and predicting, based on the obtained genotype information, presence or absence of the Mantled phenotype of the palm plants or seeds, or obtaining predicted presence or absence of the Mantled phenotype of palm plants or seeds based on methylation status of at least one cytosine within the DMR; and, physically separating the oil palm plant or seed predicted to have the Mantled phenotype from one or more oil palm plants or seeds predicted to lack the Mantled phenotype based on the methylation status, wherein a reduced methylation status of at least one cytosine within the DMR relative to a control locus indicates presence of the Mantled phenotype.

2. The method of claim 1, wherein the DMR is within a DNA region in the sample from the oil palm seed or plant, where the DNA region is at least 95% identical to SEQ ID NO:43.

3. The method of claim 1, wherein the control locus is an control locus endogenous to the plant.

4. The method of claim 1, wherein the control locus is an control locus exogenous to the plant.

5. The method of claim 1, wherein the method comprises predicting the Mantled phenotype when the methylation status of the at least one cytosine is hypomethylated relative to a sample from oil palm seed or plant having or predicted to have the Mantled phenotype.

6. The method of claim 1, wherein the DMR is within a DNA region in the sample from the oil palm seed or plant, where the DNA region is at least 95% identical to SEQ ID NO:3.

7. The method of claim 1, wherein the at least one cytosine is a first cytosine in a CHG sequence, wherein H is C, A, or T.

8. The method of claim 1, wherein the DMR is within a DNA region in the sample from the oil palm plant or seed, where the DNA region is at least 95% identical to SEQ ID NO:15, 16 or 17.

9. The method of claim 1, wherein the DMR is within a DNA region in the sample from the oil palm plant or seed, where the DNA region is at least 95% identical to a sequence selected from the group consisting of SEQ ID NO:43, 44, 45, and 46.

10. The method of claim 1, wherein the at least one cytosine is in an AlwNI, BbvI, ScrFI, or RsaI restriction endonuclease recognition site.

* * * * *

SEQUENCE LISTING

```
<160> NUMBER OF SEQ ID NOS: 161

<210> SEQ ID NO 1
<211> LENGTH: 78321
<212> TYPE: DNA
<213> ORGANISM: Elaeis guineensis
<220> FEATURE:
<221> NAME/KEY: misc_feature
<222> LOCATION: (14421)..(15355)
<223> OTHER INFORMATION: n is a, c, g, or t
<220> FEATURE:
<221> NAME/KEY: misc_feature
<222> LOCATION: (55950)..(57363)
<223> OTHER INFORMATION: n is a, c, g, or t
<220> FEATURE:
<221> NAME/KEY: misc_feature
<222> LOCATION: (64044)..(65002)
<223> OTHER INFORMATION: n is a, c, g, or t
<220> FEATURE:
<221> NAME/KEY: misc_feature
<222> LOCATION: (65951)..(66637)
<223> OTHER INFORMATION: n is a, c, g, or t

<400> SEQUENCE: 1
aatctattag tatctgacaa aagttaaatt agagtcgaaa cactaaatga caattaggga        60
tcaacttgat caagtagata gagaatatta gaaaagagag aaattaacaa gatagaacat       120
gattaattag gtgacatagc ccgacaatcc aattggtcta agcaagttga tttaatcaaa       180
tcacggttga actaatatat agatagctca ataaaaatca tacataattg aatctaatga       240
tatttggatc tgaccaagat ggaatttgac atgctgtccg atgatcgtga atcaagactc       300
tctttgctaa ttaagatcaa attagaatca ttgaaagaga atcttttact ggatcaagag       360
agagaaatat ataaagagag tgaaatagtc tatagaaaaa aaatttagag agagaaatta       420
agaagaaaaa ataaattttt ttagagaaag aaagtgggta tacaagctca gagaagggag       480
agaggaaaga gagagaaatg ctctcttatt ttctttttt tctttttct tctttctttt        540 ttttttcca ttcttctttc cctttctgc ttaatggaat aggggaccct ccattcccct       600
tctatttcta gagttggggg ctcaaaattg atgatagcta tcattgggga tgtaggctat       660
ggtgatgcag tagaggatca ccgaccgatg atcgatggtg atgttgcaat caaaaaatca       720
agaaagatag atggaaaata aaggaaaata aggagaaata gatctcaact tgtttggatg       780
ctaacccact cactgacgac tccacttcaa ctatggccgg agcttgctat ggaaaagaag       840
ccaaggcctt caaggatgaa caccaatggt gaggaagatg gtcgaaaata gaagaatggc       900 tggctttct aatcgacaaa atagggtatc gcccttctta gcaaatattc ggcaataaat        960
atctagaatc caggatccta ggactatgga agagggagag gagggcaagt caaggatgc      1020 cagattctta tctagcttcc gacaatgatg gggccctatt ttcgataaac acaatcgagg     1080
```

```
atgttcggaa aagggttttt tcgatgatga ttctagtgac caactatgag atttcaaagg    1140
gggtgagggg ggtttaaata agatgggagg gaagtttgaa tcctccttaa atctgaacct    1200
ttttcgacaa agccaagagc gtgaaggaga ctccttcgtg aagtcaaaga tggaatagac    1260
tcccttcggg agtttggttc atcacccaac ttccctagca tgtgcggagt atgtgctagc    1320
cttttctctc ttttttttt cattttttt catcctttaa gatccatgca gtttctaggt    1380
tgagggattg gggtatcaca ttctctctcc taaaaaaaaa ttattttcaa aattttttta    1440
cctatatttt caaaagttgg gattcatggt ccaaatctca tccttgaatt ttttgatat    1500 tctaattctc gaaaaaattt catcgttaaa tcatttcata agagaaaagt caatacctca    1560
agagttgatc tgaatcaaaa ttattatctc tagtaatcga aatcaatatc ttaatttcaa    1620
ataagaatat ccagtttatt gtcaaaatta ttaactactc ttgacttaat tgatctatta    1680
cataatcgta aataaattct aacatactct tgaagtgtag aatataagat tgataaacaa    1740
tcctatatcc gttctaatag atataaaagc ataaacttta aatattttaa atccaagatt    1800
aagaatcaat gatccactta tcctagactc aagatattag aaattttttt ttgtacaata    1860
gatagaggat gtactggtga aaatcatgta gcgatatcca aaataatttt taattaaaaa    1920
tattatcctt ttcattatca atgaatttta tctataagaa agatcaaatc atatgatcca    1980
tcttaaattt ttaactcaaa aaattaatat tgcaaactag ctcaaaataa ttttgatcac    2040
tacatttctg ctgtgcattc taatttaaac cgttcacatt ttttagattc atgaaataat    2100
tttgaccaaa gtattactcc atactatagt caaaaaagat taaaatatta gattctaatt    2160
aaagccaaag ataaactttt gattctcatc cttaattttg cctaaagtat aattattttg    2220 attaacccctt aagcgcaata acacattcaa aaccaacaga taggtttact ataatccaaa    2280
tgaattaaat cttaattctt ttatcaattc atttagacaa tttcaaatca aaattctata    2340
agtaatatca ataaaaaaaa attttgatgc tccaataagt tagaacttaa atcaaaatat    2400
ataagtaaaa ttgatttaat catctcttct aaagtttctt ctattaagat ctttaatatc    2460
tatcaaatac attccacaat aatcatgcaa acctttaaaa aattaaattc tcaatgcctt    2520
tactacattt taacaccaag ctcgataata gtgataaaga aacatctaga tcagctttat    2580
aatcaaaaat tttgacttac aattttacgt gtgtctcaaa atcttgaata aatataaata    2640
agatctttta tcttgatcca aaaatagtaa tcaaggattt cattagtaac ttcaacaaca    2700
atggtaaaaa aattttctat ccattgataa acccaaattt tgaattgaag tttcatgcat    2760
accatatagc ctttaataag atctattatt tggatctaaa gatagtaatt aaaattgtta    2820
atgattccac taagatgaat actttacaat ctcataatta atttcttcaa taaaaataga    2880
cttcttgata atgtctccaa ttgtatattt tttttattt ctacaagaaa acttcataca    2940
ttttttacgt tccaatataa atcttaaaaa gttattccaa tcaaatatca taaaagatct    3000
tcttagtcca accttaaata actttttatga atgaatcttt atcttgccac taaataatga    3060
attttaaaat caagagcaac atcacagcat tctgtcatgt caaatttgtg ttagatgtat    3120
gtcctagaaa tcaattagat tgacaatgta aattttttaa ggataaaatt tatatatttt    3180
gatttattaa taaaataaaa tttaaattaa ttttattca tattttttta tctatgaatc    3240
atctaaagaa ttaataagat gatgatacat attcttaaga gttcaaaatt tgaaatatat    3300
gtcattgatg attaatttct gaatacttt gaattcttaa gagtttagaa gatcttgacc    3360
caagtagtgt gaatagtgaa aaaaagtttt cacatacttc acatcaaaaa tttaagttga    3420
```

```
ataaattgta catatgacag gtattatagt ttgacgagta atctataacc tctatcttat    3480
caaaattctg atagaaagat tgtattgtat gataactgta cttagaggtt cacctttat      3540 tttactggat taccactaca tgttgctaga tgtcactggt ggattgtgag atctacgaag    3600
attatcttga tgatcgataa ttctcattga aaagattgaa actatttaa tgatgttgtg     3660 atagagatca taatatatct tattatcaga cagaatagaa ttctatggga tcatacacaa    3720
taggagatta agactgatca aatagttgaa tgatgattaa gaatcattac ggagttcaga    3780
ttatcaatat aattgataat tagactaact tataattgtt acaagtagca aggacttaac    3840
tgctaaaggt taataggttc aaaaagaact tatgtataaa tgttgtgcat cttaatttga    3900
ttggatcaaa ttagttatgg ctgaattcaa gatgaatcaa ataggaattt ggttcaattg    3960
aatttgggtc aagctttagg cttaggtcac atatacccaa atcatttgg atgcatcagg    4020 tgtgtgacac ctgaatcagg cctttctaaa ctatttgag taagtttgat caagtcaaaa    4080
ggatccacac cctaaggttt cttgaataaa accttaggca ccacattgag gacctatagg    4140
aaactttgac cctctctcat atggggtggc acactgaggt tttataaaaa ccttaggcac    4200
ccattttagc cataaaaaaa aagctccaag ggatggggca gtagccatga agaatccttg    4260
gctgtcagga ctctattcaa aagagttctc aaggttttgg actcttatgg agccctagga    4320
tttgtttgcc tataaataga tggccacccc aaggctttag ataatgttag agacttgtga    4380
agctctcccc tttctcttgg ttgccggcc accctctctc ctctctcttc catgccccaa    4440
gacttctttc ttgtctccat catcttgctg aaatttagat ttcagcaaga aaagtcaagt    4500
agaagtcaaa gttctaatgt agctcacaag atgttgagaa cttcctccat ctggcaaagg    4560
ttctgcaaga gagctagcat cctgagaaac aaaagattg ctgatcagcc ctcatctcca    4620
tatggatatt tgtagagatc agatgcatgc atagctagaa gagaatctta tcacgatcat    4680
cactcgtgaa gatcatctac ctgtgcaaag gtatgagata agaaaaatat tttttttatc    4740
ataattcatg aatcctttgc ttatattata ctgagattct tggaatggat tttttctcta    4800
gtaaaactct agagatcaga tctcgaagtc ttcttcatat aaaggttttg aaagttcttt    4860
atattttcgc tgctttgatt caaaataaat tagatctatt ttgccttca acctttctca    4920 tatttattga catataaagc tttaattaat gagattaatg aaaagcatgt gcgaaatact    4980
gagaaaatcc taacagtgat atcagagcta cttttgtaca taagaaaagg attcaagtta    5040
aataaaatct gtttgattta agtaaatgaa tcaatcaaaa tttatcctaa cataagtttg    5100
tcctggtata atggtcaaga ccattatgtt gaaaggttat cctaggacaa aaagtctaag    5160
taaaatctat tttatttaag taaatgaatc aattaaagtt tattctaata taagattgcc    5220
ttagcataat ggtgaagacc cttatgttga aaggttgtcc taggatggaa agtgattgat    5280
gagacaaata tatcatgaaa gtatttttca cagatggaat aaaatatata tattttgttt    5340
gtgaaaatga gatttcatga atgtgtttgt cattcaatat gtgtggtgat catcttgaat    5400
tgccacaaat cctttttgga ttagggttgt atcatgactc acaaatcctg atggtttgca    5460
aaattttgca ttctgtagtg atagaaacca aaagttaatc cagttttgga ataagattga    5520
tcaattggta tctaaggcaa gtattttata atggtggtta cttaattagt tataaaagta    5580
cgaagagtct cctaccaatc ttacacttat ctagccaatt tggttgattg aattctgaat    5640
ttgggttgct taagtgttaa gttcactaca aatatattgc aaccatgatt ccgacttagt    5700
caaccaagcc tagatctctt gaatagattc atgttaatta tggatttaca taggatataa    5760
ataaataatt aaaacttgaa gagatctaaa tgaaaccttc tcgtacatat taaatcgaat    5820
```

| | | | | |
|---|---|---|---|---|
| gatcttccat | cattgtagat | atacggatac | tctactgatg | ttgatgattt | tcgactagat | 5880 |
| atagtacttt | ggttgcatcg | aaaaagtaca | accactttat | aacatgagat | gttgcagggt | 5940 |
| agagatgggg | ttgggcccaa | taattgttag | gtgaggatcc | aaatgatggc | tgcacttgcg | 6000 |
| tgtgaatggc | gagtctgact | taattaagaa | atagagctaa | taactattag | atgaggcttc | 6060 |
| aggacttaga | gacttatgac | cactacaact | tacttgagaa | gcaatggata | aagagtcgtc | 6120 |
| tatttatcaa | ctgacgcatc | accaataact | atcagatgga | gtgatgtata | attagtggga | 6180 |
| ctatagtatc | cacttgaaat | cttaatcgta | aaaattttg | tttctccacc | tgaagagcat | 6240 |
| gggagattcg | aaaaaatagt | ggggtagtt | tatttttaaa | ataaagctcc | taaaataaac | 6300 |
| taaaataagt | taaatacaaa | gtctaactag | aatcttcttc | tctctgtaga | aaatatctgc | 6360 |
| ttccaacctc | tatttcatat | ccttaagact | aattgtttga | ctagacccag | ttataaagat | 6420 |
| tgactctaaa | acttaaagat | agtcttgagt | tttgaaaaga | tgagctatgt | cctggatcaa | 6480 |
| gatatcctct | ctctaccagc | ttgtcccacc | cctaatcaag | gggcatccta | tgaaaagtgg | 6540 |
| ttaaacgatg | ataacaaggc | ttggtgctgt | gtgctgacat | ctatgtccat | tgaactccaa | 6600 |
| tgccagcata | agggtacaaa | ctgtccaagg | tatattgact | catctacaag | agttatatag | 6660 |
| tgagtagagc | catgtatctc | actaggaagt | atttaagaga | ctcttcaaga | tgaagaagta | 6720 |
| tgatggatag | tctgttaatg | atcattgtct | gataatgatc | aagaacttga | aagaacttga | 6780 |
| gaagctcgat | atgtctatca | ataagaaatt | gcagattgat | ttgatcctac | aattccttac | 6840 |
| tgattcatat | gtgtagttta | ttataaacta | ccatatgaat | aaaatacagt | gcaccaaggt | 6900 |
| tgagttgtta | aatatactga | taactactga | agggacctcg | aagagttcaa | gaggcactgt | 6960 |
| tcttattatg | gagcagacct | catctttcaa | gaaaaagtct | actgaaaaga | agaaaaagtt | 7020 |
| tgtgaagaag | cagaagttag | agaataggcc | aaagaaagaa | gttttcaaga | agaaggccac | 7080 |
| aaaaaaggaa | aagtattttc | actgcaactc | tgatgaccat | tggaagagaa | actattctga | 7140 |
| ttatgtggca | agcttgaaga | acaaaaaaga | tagcatacct | tctgaagata | tgtctgatct | 7200 |
| tctcgttatt | gaaactaatc | ttacaatttc | ttttacttc | agttaggtta | tagactctag | 7260 |
| ctctagtgct | catctatgca | cttctataca | ggatctggag | gaaagtagaa | ggctgaggaa | 7320 |
| agaagaaata | atccaacaag | ttgaaaatga | tgcaagagtt | gttactatgg | ctgtggagat | 7380 |
| ctatcctcta | cgactaccat | ctgatcttag | tttaattctt | agagactgtt | attttatacc | 7440 |
| tactgctagc | aaaaaattga | tctctatttc | atctctagca | taggataatt | atgtattaaa | 7500 |
| ttttaataaa | gattattata | ccatttattt | gaaaaataaa | atggttggac | gtaattttt | 7560 |
| aattgacagt | ctctatcatt | tacatgttga | tgtatctatg | aatgtaacca | agcagaaagt | 7620 |
| gaatgccata | ggatctaaaa | gatctaaaga | tgaaataaat | tatatgtggc | acattaggct | 7680 |
| agatcatata | agagaagaaa | ggattaacag | attggagaaa | gatgggctct | tgggcttatt | 7740 |
| gactactgag | ttatatccga | tctgtgaatt | ctgccttcaa | gaaaaaatga | tcaagctgcc | 7800 |
| ctttatgaaa | caaggagaaa | agaccattaa | gatatttgcc | ctggtacata | ttgatatatg | 7860 |
| tggcccatta | attcgatgcg | ctggtcaaag | aaggttgtct | ctatttcatc | atctttatcg | 7920 |
| ataattattc | acagtatgga | tatgtgtatc | ttatgagata | caaatatgaa | gtctttgaaa | 7980 |
| aatttaaaaa | atttagaaat | gaagtaaaaa | aataaactaa | aattttttta | aagatttttc | 8040 |
| aatcagattg | aaaagttgaa | taccttaatg | gagaatttct | aaattatctc | aaaaaaaata | 8100 |
| gcatagtctt | ataatggact | ccatttggaa | tgtcttaact | caatagagtt | tcgaaataga | 8160 |

```
gaaatcaaac tttattagat atggttcggt ccatgattag tttcattgac cttctcttat    8220
ttctttggag atatagttta cttaccacta attatctatt gaatagggtt tcctctaaaa    8280
tcatttctac cacattgtat gagatatggt attgtagaaa atcaagtctt gatcatatca    8340
agatttaagg atatccgacc catatcaaaa tatttcagac ggacaagtta gaggtcagat    8400
ctatgaaagc tcggttcaaa agtatcttaa ggagtcttta ggatattatt tctactttc    8460 agaggatcac aatatgatta taagccaaca tgctctcttc cttaaaaaat agttcatgca    8520
agatggaagt agtaggaggc agattgagct tgaagagagt ctctgaagag caatgagtct    8580
cagaacttac gtaaaaccta tttaagttga gccaatacac acacctcttc ctccatctcg    8640
tagatccagt aaaattttc attctcctga gagatactta ggtatcatca tagagaatgt    8700
agagaaaata tttctcgtga aaatgagac atatgaaaat gaccccaaaa cctatagcga    8760
ggcaatatca aatatcgact ataagaaatg gttagaggct atgaagttag aaattaactc    8820
aatacactta aaccaagtct gaacctttat ggatccgtca gaaggtatgg tacctattat    8880
gtataaatag atctacaaaa gaaagattgg ttttgatgga aaggtagaga cctttaaggt    8940
aaagcctgtg actaaaggtt atagctgaca cgaaagcatt gactatcaat atattttttc    9000
actagtagtt atgctaagtc catttgaaca ttacttgcga ttgcagcata ttatgattat    9060
aagatatgac agatagatgt gaaaactatt tttctaaatg aatatcttta ggaagttatc    9120
tatatagagt agactttgtg tttcacttcc agtgatggcg atcacaaagt ttacaaattg    9180
taaagatcta tttatgcact caaacaagca tcttggagct ggaatactta tttcaatgat    9240
gtaatcaaat catttagttt catcaaaaat gagaaagaat cgtgtgtgtt taagaaaatc    9300
agtgggagta ctgttacttt tcttgtattg tacgtggatg acatcctcct gatcgaaaat    9360
gatattttta tgttaatttt agtcaaaata tagttgtcta agaaattctc catgaaggat    9420
cttggggaag catcctatat tttggagata aatgtctata gtgataaatc tatgaggatg    9480
ccaggccttt cacagaagat gtacattaag gaagtgctga agaagttcag catgaaaaac    9540
tccaagtgga gacttctatc cttcaggtat gggattcatc tctccaagaa ggtgtgcctc    9600
aacacatctt aagagataca gtacatgagc aaaatcccct tatactgcgg c tataggaagt    9660 ctcatgtatg tcatgttatg tacatgacct gatatagctt atgttgtgag tgtcacaagt    9720
agatatcagt tgaatgcagg tgaaaaacac tggacatcta tgaaatgtat ccttaagtac    9780
ttgagaagga ttaaggatat gttcttgatc tttagaggag gagaattaag ggtgcaagaa    9840
tataccgact taaattttat gtttgatatt gatgatcgaa aattgacatc agattatatt    9900
tttttatgca acggtggtac tgtgagttag aaaagtttca agttgcctat catagcagac    9960
tccattatag aagatgagtt tataatcaca ttggaagcta ccaaagaggc attctggttt   10020
aaaaaattta ttacagagct ggatataatg ccatcagatg tcataccact ctactgcgac   10080
aacaatagtg cctaactct agctaaggag ctgaggtctc accaaaagtc taagcacata   10140
gagcaatgat ttaatctcat tcgcaattat ctcgaaaaaa atatatcaag gtatagaaag   10200
tagatactat ggataatatg acagacccac taactaagta gctgagtcaa taaaaatcg   10260 aagtccatct tgagaagatg ggacttagat ttgtggccaa ttgattttag tgcaaatagg   10320
agattgttag atgtatactc taaaagtcaa ttagactgac aaatataaat tttctaagga   10380
cataatttat atattttgac ttattaataa aataaaattt ggattaattt tttattcata   10440
ttttagtatc catgaattat ccaagagatt aatatgataa tgtatatat tctcaagagt   10500 tgaaaatttg aaacatacgt cattgatgat taatttttga atgctttcga ttaatggatg   10560
```

```
atcataagga tagtaattaa tccgatcaat gtacaaatca cttcttttt gatagacgag    10620 tctcgagtct atactatgga gacactggag caagagtgca ggtatttgtt agagaacaaa    10680
ggtatcgagc gtgactaata cgagaagtca attggatggc tatccactcg ttaatgactt    10740
atttgatact acagtagtat gtctagtcct tagatctgca atgcctcagg tgttcataat    10800
gagactgtta gagtttgact gtacataaac ttgatttcta gccatatgga tctttatagt    10860
gcatgttggc tacagtaggt tcgttgtagg aataggatgt gcacatagat agaatctatc    10920
atccttgata gacaaaaaaa atgatcctat ataatttatg agactgagtt caaaaaatct    10980
tgactaagac agtgtgaata atgaaaagaa gtttccacat atatacttca catcagcaat    11040
tccagttaaa taaatcctac atataatagg tattgtagtt tgatgaataa tctataacct    11100
ccatcttatt gaaactctga tagaaggact gtatcatatg gtaactgtat caagagattc    11160
atctactatt ttgctgaatt gtcactacaa actgctagat gtcactgata gattgtggga    11220
cctatgaaga ttatcttgat gatcgatgat tctcatggag aagattgaaa ctatttcaat    11280
gatgttgtgg tagaaatcac aatatatctt actactagat agaatagaac ctatgaggtc    11340
acacataata aaaatttgag attgatcaga ttgttgaatg atgattaaga attgttacag    11400
gattcagatt atcaatataa ttgataattg gactaacttg taattattat aagtagcaaa    11460 gattaattg ctaaaggtta gcagattcaa ggaggactta tgtgtaaata atgtacatct    11520
taatttgatt ggatcaactt agttatggct aaatttaaga tgaatcaaac agggatttag    11580
tttaatcgaa tttgggtcaa gctttgggct taggtcacat gcactcaaaa gggtttggat    11640
gcatcaagtg tgtgacaccc aaaccaagcc tccctaaact attttgagtt ggttttgacc    11700
aagtcaaaag ggtccacacc ctagggtttc ttgaataaaa ccctaggtgc acattgagg    11760 accaattagg aaactttgac attctttcac acggagcagc acactagggt ttcatgaaaa    11820
ccctaggcac ccatttttagc cataaaagga aagctccaag ggatgggatg gtgccatgaa    11880
gaatccctgg ccattgggac tccattcaaa agttctctag gttttgggct cttatagagc    11940
cctagggttt gtttgcctat aaataggtcg ctaccccaag gctttagata atgctagagg    12000
cttgtgaagc tctctccttt ctcttgtttg ccatcccacc ttctctcctc tctcctccat    12060
gcctcaagac ttctttcttc tctccatcat cttgttgaaa tttagatttc aatgagaagg    12120
atcaagtaga gtcagagttc tactgcagtt ctcaaggtgt tgagaacttt cttcatcagg    12180
caaagattct gcaaggagt tagcacctca aagaaccaag aaagttgcta atctgccctc    12240
atctccatgt ggatacttat agaggccaag catgacgaga agagcttat cacgatcatc    12300 actcgtggag atcatctacc cgcgcaaagg tatgagataa gaaaaaata tttttcttat    12360 catgattcat gaatcctttg cttatgttac attgagactc ttggattaga ttttttctct    12420
aataaaattt caaagattag atctcgaagt cttcttcacc taaaggtatt gaaagttctt    12480
tatattttcg ctactttgat tcaaaataga ttagatttgt tttgcctttc aattttttctc    12540 atatttattg agatatgaag ctttaattaa tgagattaat aaaaagcata tgtgaaatac    12600
tgagaacatc ctaacaattt gagcttacaa ttcacttaaa caactaatga tcaaattaat    12660
aatcacaatg cacaataaaa attcatgata aatcttttg ttgttacttt agatcaaaat    12720
ccaactaatc ataacatgat ccacggattg cctatcatat atcaaaccct ctgaattatt    12780
aatcttaaac gatcttttca ttcatgatca taagatttag ttaaaatca tgaagacaac    12840 ttatattgta atcatcatag atctgtatct taacatcctt agtgtttacc tacctatact    12900
```

-continued

```
catcctatgt ttgattctat atatcataat ttattcacta atactttgat atcatataaa    12960
ttatcgcatc cccaatctaa gatcatattg gtactttaat atttcattag tggggttat     13020
gcattagtac tttgataccc tatcagttga atggttaaac actggtactt tgatatccta    13080
tcagtggagg ttatacgctg gtactttaat atcctatcag taagatggtt aaatactgat    13140
actttgataa cctcccagtg ggtgttgtat gctagtactt tattatccta ccaatggggc    13200
agttaaatgc tactactttg atacgctacc aatgggatag ttaaacgcta gtaatctaat    13260
cttagcttga cataaagtaa cgtcgactcg agtttagggt cgactcgaga gaatgttagg    13320
gttagcttga tatgaaagag ggtcgctcgt caatattttg gagtcaactc ttgtttatgg    13380
atgatctaga aagtgtcaga gtgagctcga gtactgcata tttctgatac attgtctatg    13440
ctagaatgtg ctagaactga ttatcttctt tatcaaagtt gattttgag taacttgatg     13500
atcaattttt ctaggctaga cttgctttgt caaaatgagc acttgttagt ttagagaatc    13560
ttcacctaca catgatctca agcattcatt agtaccaaaa atacttaagt attttgatat    13620
catcaaaatc aattcttggg ttaacacaat acttttcaaa taataagcat acagatataa    13680
tcctataaca atttaaattt tgttcatata tcaatttctt taaaaatatt atattcatct    13740
tgatagctat gaactaaatc aaaatacata ctagtataca acttttactg ggagagtatt    13800
agattaccag catttaacca tcccactggc aaggtatcaa attaccaata cacaacccct    13860
atttataaag tatcaaagta ccagtgttca actgcctcac tggcaggata tcatagtact    13920
agtatttaac taccacattg acaggatatg gaattatcag tatttaacca tcattagtag    13980
aattttgatg catagtcagg ctgcgagtca aaatctatct caaatcaaaa tattgatcac    14040
atgtctaatt ctgtatcata attcattccc ttatgctcta atattatatt aattgtcata    14100
cttctagctc gagatcatga gccaaggatt gcagtaacta ccgcatactt atagagaact    14160
ctttctataa gcatacaaga tattctaaat atactatcaa tatatcatag agaaattaat    14220
ttaataact aaaagttaat attcaattaa taaattcaac tggcaaatgt atttaaaaat    14280
tttacatcaa ataaatcttg attaataaat attaattaat aacaatagat ttaaatcgaa    14340
acaaggttga tattgttaga atttgatgcc tcaagattca gcccacattg agtccacagt    14400
gaggttcgcg acgaaaaatg nnnnnnnnnn nnnnnnnnnn nnnnnnnnnn nnnnnnnnnn    14460
nnnnnnnnnn nnnnnnnnnn nnnnnnnnnn nnnnnnnnnn nnnnnnnnnn nnnnnnnnnn    14520
nnnnnnnnnn nnnnnnnnnn nnnnnnnnnn nnnnnnnnnn nnnnnnnnnn nnnnnnnnnn    14580
nnnnnnnnnn nnnnnnnnnn nnnnnnnnnn nnnnnnnnnn nnnnnnnnnn nnnnnnnnnn    14640
nnnnnnnnnn nnnnnnnnnn nnnnnnnnnn nnnnnnnnnn nnnnnnnnnn nnnnnnnnnn    14700
nnnnnnnnnn nnnnnnnnnn nnnnnnnnnn nnnnnnnnnn nnnnnnnnnn nnnnnnnnnn    14760
nnnnnnnnnn nnnnnnnnnn nnnnnnnnnn nnnnnnnnnn nnnnnnnnnn nnnnnnnnnn    14820
nnnnnnnnnn nnnnnnnnnn nnnnnnnnnn nnnnnnnnnn nnnnnnnnnn nnnnnnnnnn    14880
nnnnnnnnnn nnnnnnnnnn nnnnnnnnnn nnnnnnnnnn nnnnnnnnnn nnnnnnnnnn    14940
nnnnnnnnnn nnnnnnnnnn nnnnnnnnnn nnnnnnnnnn nnnnnnnnnn nnnnnnnnnn    15000
nnnnnnnnnn nnnnnnnnnn nnnnnnnnnn nnnnnnnnnn nnnnnnnnnn nnnnnnnnnn    15060
nnnnnnnnnn nnnnnnnnnn nnnnnnnnnn nnnnnnnnnn nnnnnnnnnn nnnnnnnnnn    15120
nnnnnnnnnn nnnnnnnnnn nnnnnnnnnn nnnnnnnnnn nnnnnnnnnn nnnnnnnnnn    15180
nnnnnnnnnn nnnnnnnnnn nnnnnnnnnn nnnnnnnnnn nnnnnnnnnn nnnnnnnnnn    15240
nnnnnnnnnn nnnnnnnnnn nnnnnnnnnn nnnnnnnnnn nnnnnnnnnn nnnnnnnnnn    15300
```

```
nnnnnnnnnn nnnnnnnnnn nnnnnnnnnn nnnnnnnnnn nnnnnnnnnn nnnnnaagat    15360
attactaaat tttgcttcta atctcactct taaatagtac ttacctttga aactaggcat    15420
ttgaatctga aaagaaaga ggagattatg agcttgatag ttcagtaaat catgaataaa    15480
ttagctaaat aaatctatga ataatagtat attaaaaata aatatgtaag atacaataat    15540
tcaaaaatga attcatatat ataatacttt ccaaataata agtatgtggc tgcaatcctt    15600
tcgtaattca aattttgttc attaattatt tttttcaaaa catcacatgg atagtcatga    15660
actaaatcaa agtaccagtg cataacccct attgataaag aatcaaataa caagtgtttg    15720
actgcctcat tatcaggata tcaaattatt aatgcataac ctccactgct agggtatcaa    15780
agtagcaacc tcaatcacct cactggaagg gcatctagtt tcagtattta actactccac    15840
tggcaaggtg ttaaattatc aatatttaac ctccactgat aggattttga tatatagtca    15900
gactgcgagc caaaattcat ttcaaaccaa atattttttc tcaaagacat attttatgtt    15960
tcacattgaa aaattcacaa aaattatgcg atattgaaat caattggata aaatccacgt    16020
caaatttagt atattcaatc ataaatcatt tactattcta gaaaaggtat attaaaagta    16080
taatgcatca atttcataaa tcataaatat ctcaatataa aaaatatttt attatttatt    16140
aataaatcta ggagaagtga agcattactt atcttgtaag taaaactaac caactgatca    16200
aattaattct gagaatcttt ctcaaaactc atcaccacta tatcaaaaac ttgtgcttct    16260
tgctatgtaa gagcatagac cctttcttcg atctggggtt ccaagtttct atttttatttt   16320 gttcaactat caaattagac tgacttttca tttttttgtg gatattcagc tattttatgg    16380
cctttctaac aataaccaaa gtatgtacca atattccaac aataatcatt tattgcatga    16440
ttttcaccgc atcgaaatat ttgatattat caatcaatcc aaacttgtta ttcactgacc    16500
tcttattcaa acccttagta tatttaatat tctacctttg tgattcattc aatcgatttc    16560
ttttttttta ttttctttcc ctttctatat gctcttcatt aacttttctt tcaattatca    16620
atgctttatt caatacatct gtataagtag ttaactcata tagtaccatt tattttctaa    16680
tttctatcct caattccaac tcaaattat ctactcagtc acattcatct tcaaccaatc    16740
tcgaagcaaa cttgacaagc tccataaatt tagcttcata ttctacaact attatatttc    16800
tttatttcag ataaataaat ttttattctt tctgaatcct catactctaa gaaaaatatt    16860
tttatcataa aatatctttt gaaatcactc ccaagcgagt tgttctccat cttgttcata    16920
tttaggtttc attctctatt atcaattaaa tgtctcatct ttcaacatgt atgatgcata    16980
taagattttt tcatcatcat ggtatctctt aacaataaat gctttctcca tctccataag    17040
ctaattttta gctcctattt catagttttc ttaaaagtca atggagacaa cttcttaaat    17100
tctatgatat tactttattg ctcctattgc tcttatgtcc ttgtggtgac aatatttatt    17160
gttgcacttg ctgtagaggc agttactgtt actgcaattg ctattacgat tccatcaagc    17220
cgactagtgt ctgcattatt tggataatag ttgattttg ctactttatt tagatgttgg    17280
tggcaaaatc aatgacttct ttttgctgag agatgccacc aacctactaa gtatcatcat    17340
cttattggtt gatacctta gcagcacctc gagtggttct ttttatctga tatggaacca    17400
tcttaatctt gcatgaaaaa caacttcgc aaaattttct tttaaaatct aatatctaat    17460
attatacttt tattaaaatt taattatgat tattttaaga ataaaaaatt taaattttga    17520
aatcctcaca aggctggcca agagataatg accatcatcc tagtcggttt gacgtaggac    17580
atccaaagat caactataat tcaagcatca tattgagatg ctaggatata atcgatggtg    17640
```

```
aaatttaatg atgctcgact gatcaagatg ggggccggcc cgatggcctg ttcaacaatc   17700
attgatcaaa attttttaac caaggtctat caagatcatt aaaaagtctt tctaagatct   17760
ataaattgta ataaagagac acaatctaga gagagacact ttttacataa agaaagtaga   17820
aattttaggg agagaaatta gagagaaagg ggaaagagag aggaagctga gaggaagaaa   17880
gaaaagagaa agactctctc tcttttttctt ttctttcttt tctctcttt cttttttcttt   17940 tcttttttt cttcctttc tttctttctt tctttggctc attagaaaaa taggggacct   18000
attgatcccc ttgtttccta aataggggag gaatctcatc ttggtagcta tggccggcga   18060
tgtgagccaa agtggcaaaa tcatgaatct cccaacctgc agccgacatt gacttttggc   18120
actggaaaat caagaaaatt tgacaaaaaa tgggaaaaaa ttgaaaccaa aatagggacc   18180
aaaatccggt aatagctagc aaaaatcctt gatctttgct catggaggat aggaaaaaag   18240
attattcaag agattaaggg aatcttatct cattttttttg ctgtgcttag gccatggtgg   18300
ttgcagaaat cgtttgtgaa agctcgacaa actctgcaat ttcttcgggc ttgggcctcg   18360
atctttaata ggagaagaga gaagtcctct ttcttttaaa tagagtcgga gggaaggagt   18420
ttgattccct ccttatggtg gtttcaaact ctgatcggaa gtccattgga aaagaagact   18480
cccattagtt ttaaaatcta ataagattta ttgattagaa aattgataaa aaatgattat   18540
taaaaaagta gcataattat ttaaatcaat gatgcttaga ttgttggagg taaatagtaa   18600
taaaatcaaa aaattaaaat tcatgggacc aaaaaataat gaacaagatt tgaaagaaat   18660
gtctataaat aagaatttat gaaacagggg aacattgatc aaaggtgtgt taaatagtgt   18720
ccttaaagtg ttattgtccc tctcacgtag actttgtgtg ttgggagaga acatagtaat   18780
tctctcaacc tatgcaacct aaatcttttg aaagaaatt taaaattata gaaaaattgg   18840
caaactagaa ttttggtcat tttctttatt agtaaaaaat atactaagtt atatgtcttt   18900
atttatacta gtgaggtcta tctttgcaca attcagacca aatttatatt ctagttaaaa   18960
gaggtataga ttttttaaaa tagatataac tagtggaaat agtcatagaa aagttaaaaa   19020
tcaatgaaag gtagatttca cttctatatt ggctttattt gtggtcactt tatctaattc   19080
ttttttttga tggagcaata taccctgtta aaatcttctc gattttttttt tcactttaag   19140 caacctattt cgatgcctaa acaatggaat ttagtttaac cacttaatat gctacacttt   19200
taaaaggagc accatattgt agggcttgaa aagttacttg atttaaaaaa agagcatctt   19260
aattggacat catacaagta agttatgacc tccgaaaatt tgatacatga tttatcatct   19320
tgatatggta aatcttgtta agatttcctc atggtgtcta aagtggccgg ttcatactga   19380
gtttggtgat tcttctggtc aatggttaat tgctcgaata ttttttaagat ataactaatc   19440 tccaactctg ccgactcctt agtagtatga gcacatggaa agcttgaccct aattgatttc   19500 ttaaattgct tgaaatcagt acttagaaaa tatgcaaaat ggatgaaatg tttattgcag   19560
cgagagcttt ctgatctgta cgaccgagag cttactagtt ttttatgagc tatacgtttt   19620
gcacttaagc ctaatttaaa tagtgaaata gtttgcaac aattcaaaac aattaaaatc   19680
aaaagacaag ctgctatgca tgttcaactg actcggcttt caatcgcaat atgtcacata   19740
ggctggccta gaatgcagat gcgtgcgtgg tgagcatcct aaaaacctac atatccaata   19800
aattcccact agttggtgaa gtattaaatg taactcgtat taacttttta atgtaggact   19860
aaagtttatt cgactaatta agaactaaat actttaataa ttgaactttt ccaaccagaa   19920
atcagaaaat atttaagtaa ttaaatatta cataataact agatcaaaat atcatggttc   19980
ctctctcgct cgagatcaat tgggatgttg gtttatcttg gtcatccatc gagatgactc   20040
```

```
tatcttagcc tttcaaaacg gcgcggtacc acgggtctca ccgcttcgtt acatcgaatg    20100
ccaccatccc tttttttttt ttttttttat ttatttatgc tttcttgctc ctagattggt    20160
gcggcctcat tacaactcca ctgctacttg atgcttccct ctagcatctc ctttgcagct    20220
ctctcacttc caccactctt cggcctaatg ttgggaaacg acgaaggggc cttacaaaaa    20280
tgtcatccat gatggcagtg gagaagaaaa catcgctggg gctttccttc gatatccttc    20340
gcagccaaag ctcttatagg gttatatggg agaacgctgc attatttggg tgatctttt     20400 ggatggtgtt gttgactgat gctagttttg cttcatgaat tgaatattta cacaagatga    20460
gaatacaatc tagtacaatt ggtaccaatt acctgggttt gactcctgct cgcatctgat    20520
tgaagcttgg ttaatgtgca tctcaattaa ttcagaaaga tcatcggact tcatgtgaat    20580
tattttgact agcatgaata gggctaaata aggctgaaat atgtgttaaa ttttaaaat    20640 tataacttga tcatatgatg tccaattgag atgttttcaa atcaaaattt ttttcgagat    20700
ttatcactta atgttaaact cttagaaggt cgaaacagac tgaaagtttt cttttcaaga    20760 tgtatttga ccgagtatat aacttgatga tcatatgatg cccaattgag atgttttcaa    20820
atgaaaattt tttttgagat ttatgactta atgttaaact cttaaaaggt cgaaacagac    20880
tgaaagtttt cttttcaaga tgtatttga ccaaatatat ctcataatct ataaagaata    20940
tatttcataa tctatgaata attagataga gcgacagaag ataatgctaa tgtaaaaatc    21000
acgatctatt ttttataaaa tttaatattt ttatataatc acttttacta tagtcatatt    21060
tatttttaaa aatttagtta tatttaaaat atcaaaaaaa tttgacttga attatataag    21120
aaaggatctt cctactatta tagatagaag ctttatatca tagtttacag tgtatggatc    21180
atcaatgaaa gaaagaggga tgtaaaacctt acttttgaaa ttttttctatt tgtttctaaa    21240 ttttttaaag gatccaagtt gagaattgag agaattcttt ctttctgcaa atcaaatcat    21300
tagtataatc cacatggaga cgttgtaata gaaagtagaa actatatttt atgaataata    21360
gaaagggagt tgatttacgc caagcctttt gtttgcttga ttaattattt attttatgg     21420 tgttagctgg accccatgaa tagcaaccat cgttgggtca gggtcgtgta tttgttttgg    21480
ggtcttcatt aatatacacg gtggtaaatt gttgggggcg cgtcagatgg aaccaatcct    21540
ggttccttac ggtactgtag tgctctatat gtggacggct gtcattctat ccgtgaaata    21600
agaggtgttg tttttcttta aaaagcagca ctctcctcag caaaaacctc agaatccacc    21660
atgtaatatt actcatcctt ggtcttaaag ctgtagcaat acattacttc caaatgccaa    21720
gcaattaaat aaactacata catcgaacct ctttagtacg tacgtctttt caaaaatatt    21780
tttttcgaag atccgacaaa tgtgaaatgc ttattaactt ctttaatgtc tgtttttgct    21840
tgcatattta cacagacata ccatcaactc catcagttgt tgtttgataa ttcgcttgcc    21900
gagcagagaa gagagagagc aagagagaaa ggaggcatag agagcgtgag atgggaaaag    21960
cgaccgattc ttaaactggc gagacatcac acgttacccg gtacacccaa agctttcacg    22020
aatttggaaa gtgaagccat tatggaagcg ctagcttttt gctctcccctt gccggaatgg    22080 aaaggccccc gaccttcttt accccttcct ccacgccacc cacccaccac tcttctatac    22140
acctttatag ctcccttctc ctttggctttt cttttaagca gagctcagag gaaagagac    22200 cttcctgggt gcttgagaaa tagagaagag agaaaagaga gttggagatg gggaggggga    22260
agatagagat caagaagata gagaatccta caaacaggca ggtgacctac tccaagagga    22320
ggacggggat catgaagaag gctaaggaac tgacggtgct ttgcgatgct gaggtctcgc    22380
```

```
ttatcatgtt ctccagcacc ggcaagttct ccgagtattg cagcccccctt tccgagtgtg    22440 tacacgatat tatccctcct cgtccccctt tttttttttt ttgataaaaa tgaaactcat    22500
atagtcttct tttatgatta tgtgtttgta atgatggatg attgatggct ggatggcagc    22560
accaagacca tatttgatcg ctaccagcag gtgtcaggga tcaacctgtg gagcgcccaa    22620
tacgaggcag aaactcttct tcttcttctt ctcctctctc tctacaaata tgctttttttt   22680 ctaattttc ttttcaaaga aaaagaaaa aaatgatttt ctaatattga tgtatttttct    22740 tgtgggagta gaaaatgcaa aacactttga accatctgag ggagatcaac cagaacctcc    22800
gcagagaaat aaggtggagg gccaaaagag aatattgtaa tattagtact ttctggtaaa    22860
aataagcatg tagtttcttt ttgcctttaa attttgttgt gctggttctg atgagcaggc    22920
agcggatggg tgaagatctc gacagtttgg gcatccatga actgcgcggt cttgagcaaa    22980
atttagatga ggctttgaag gttgttcgtc acagaaaagt aagatccccc atttattcac    23040
tgcacctatt ttaattcctt attctccatg ttttgagagc ttttgagata aatgatgaga    23100
agcgcatcga gatcgagttg tctatattct ggaatgatta attttttaat tctcaattaa    23160
tgctgtttca ttgctaaata ttcagccata tattttgtct ctgcatggga tttctatgct    23220
aaaattcctc agatttcagc atacagaatc catgagactt gccttggctt taccacaagt    23280
actccagaat caaaattgtg aagaaaaat aggataaatc tggttaagct gtaatttatt    23340
tacttacttt ctatctatat taaaattatt cagattattt tgcaaattta tggatatgct    23400
tgaatcacgt atctgatact ttctcttcat ctggatggca gtaccatgtg atcaccacgc    23460
agacggatac ctacaagaaa aaggcaaggc taacatgctt tcttaccatc attctttacg    23520
gtctttgatc cggttttgcg tgtccacttc ttacgtagtc ttttcaaac attcctatct    23580 aagactgaag gtaatgattt gcaaaggaat agctttactg ttttcctcta agtagatgaa    23640
atattactca cgtagaaagg agccatcata attgcagaaa gaataaaact gaatggaata    23700
tgagtagaat tgtcaaaatc ttggtttaag ggttttaata gccagatgag aaagcaacct    23760
acttttcttg aacaacttgt ttgtgactgt cttgttgctc ccatcttgca tctatgatta    23820
gcaaaatata tgataaatag atattcagat ttgatcgaaa agaaggaaga ttttctttaa    23880
tccatttaat ttgaatctca caaaaaaaaa gtagaagatt tggacacgat cgctgggggc    23940
agcacgctct taatagaatg gtgtcacgtt gcagatctcg aaaaattatt caattttttt    24000
taaaaaaaaa agagtcattg aaattagacg ttgtatgacc atgttatgat ctctgaaagt    24060
ttgacttctg actcaacttc ccaatatagc agattttact cctgaaccat gtttaacctc    24120
ctgactcata gtggccaaag tatctacatc gagttcactg gtcttcttgg atcacattca    24180
taagaatact tcccataatt ttgctcaacg ttgttttttct catcaaccaa aggtatatgc    24240 ttttttaaaat tgaaatgccc atgaatatta tggcattctt ttatttgaca ttttggttga    24300
tcctatattg tttgtttggc attcaacact tcttcatggg aacctttgaa atgaggtagg    24360
tgctaggatt tttcttttta cctatccata tcatatttcc aatgtcttct tttacattag    24420
gttctttagt gacaataggg gaaacgaccc aatataatac ccttgaaaat ttgggcaata    24480
tctactaaaa ctaacttgaa taaaatatta acataaaaag ggatttagta acataaaagc    24540
ataactcaaa atcactcacc ttgtgtgcca cgttctcatt gcccttatta ttttttgcatt   24600 gtgaattgtg tccccccaata aagcaacgtg aatggtggaa gagagttgaa tggctttgtt    24660
gagtaattgt tttgagttac tatagcattg ctctactaaa attgaaatct tgctgtgagg    24720
ctatgtatga gaagcaagtt catgcttttt gactgttggg atggaagtat gagcaatctt    24780
```

```
tttaataagaa aatggacgaa tcatgaagtt tttccttttt attgaaaaag atgatcgaaa   24840
aatatgtgca agatagaaaa acactgaaaa gataaaatga gaagtaaaag tggaagtcta   24900
ggagaagaaa atttaagaga aatatcttca atgagaggat gtgtgcacca acaaagccaa   24960 cttttcactaa agaatgtaat gactcacctc tactttcttc gaataagggg ttccagttgt   25020
ggaaagtata tagaatcttc tgaaagactg agtaaatgga gcaattcctt ctaagaaata   25080
ttatggcatt tctctcccac gaaatttcaa agcaaagagc agctagtagt tgatcctcta   25140
atctcttaat tgaagtttgg aatttctctt gcctctattt ggcccaaagg tcatgaagat   25200
ctaccggcca acctcttaag ttgaattaga tcttaataga agtccaaatg cttcttgtag   25260
aagaacatct aataaataaa tgagtgatag attctaatcc agagacaaag agcacacctc   25320
gaattcactt gccatccttt tctagctaga acttctctag catgaaactt gttccttaag   25380
gcaagccaaa taaatactca cattttagga atgactgcct tccaaataat tttataatat   25440
ggacaaatta gaccaccatt attgataaac ttgcaatgaa caattataaa tgagttttca   25500
ggttggcaca ttagcaatat aggatggttt gattattaaa aggatgatat gaagggtttc   25560
aaggtggttt gcctcgttca aatcaaagga ttttgaagat taatattcca agataaggtt   25620
ctccaactcc attaggaaag tgtcttcatg tcatcttaga gaagcagctc gtaccaaact   25680
tgacagatgt tttattttatt tagagtgaca cagataccct ttggcaatac tctccatcct   25740
tgtccgaaca acttctaatc acacctcact tatcttgcat ctaactcaga ggctacaagt   25800
tacacctttc aacaaacctt ttcggtttga aaatttgtga tttcattatt tagagttcga   25860
agagcatatc aagtattggt cggagttggc acccaaagca aacgaaacag ttactgacat   25920
ggtccaaaag ctgagatttc taagatccca acttaagcac tgaataaagc cattatggga   25980
aatatcattt taacgaaaga ggaatttaga gtaagaattg attctcttga taccgaagaa   26040
gaactaatac agctttcatc acttcaaaat gatgaacaga tgcatctcaa gtcagcacta   26100
gaccatcttc taaaatagga agatctatgg aagcaacact cccaaatgca gtggcttcaa   26160
aatggggatt gcaatacgaa gtttatccat gtttgggcaa gtaacaggaa aaaagaata   26220 ctatcactga actctagcaa ggcgatcaga agattatcga atagcagcaa atccaatcca   26280
cattctacaa ctttttttct accctactag gctcgactga ggaatgactc atccaagctg   26340
attagaagat tctttatcca gaaggacctc tggatcttgc tgacattgag tatccattta   26400
tggagaaaga aatccatgat acagtgtatg acttggcttt ggaaaagtca cccggatgat   26460
attttcccat tctccttcta tatgcacttc tagtgtatca tcaaacatga cctgatgaac   26520
ctactgtaaa atcagctaat gtagaccatc tgaactactt gttcatcacc cttatcccaa   26580
aaaaaaattg gtgtgtattc agttagagac ttcaggccaa taagcctgat taatggagta   26640 ataaaaata tttcaaaaac tctatcgaaa aggctctcac agaaaatgaa tttgttaatt   26700
ttatccacag agcttgcttt caacaaagga agaaatatct ctgaatattt tgtaatgact   26760
atggaaacta tacacttctg caaagctgaa gtacacaagg atctcaatta taaagtcgac   26820
ttcgagaaag cttttgacaa tgtggattgg agctttctat tgaaattgct atccagcacg   26880
gggctttgat tcgaggtggt gtcaatggat agaatatctg atttatacag ctaaattctc   26940
agtccttatt aatggtgata aaggtaaact ttttaaattg aggaaagatc tcaggcaagg   27000
agatcctcta ttcgcctagc tcttcttcttt agttgttgat atagaatgat caagggagca   27060
agtaggttca atctttttgt tggaattgga tcatataata tcatgggata acttcaaagc   27120
```

```
ttttagttca ctgatgacac acttatattt tgcagatatg atctaaaata catcaaaact   27180
cttaaatttt tactctatag ttatgagcta ctgatgggtc tcaaaattaa ctttgaaaaa   27240
ttccaatttt ttggcttgag aattgcaaag atgtcagtac agcaagttgc atctatccta   27300
gaaagcaagg tggctacatt ttccattact tatttgggtc tcccactcca tcattctaaa   27360
ctgaggaaaa cttattggaa tccactcctt gagaaggttc agaagaaatt gatcgggtag   27420
aaaggtaaac ttcttaacct ctagggtagg cttatactaa ctaatgcagt gcttacaggg   27480
atcccactac tctggaggga tacattcctt ctccctcaat tcattatcaa ataaattgat   27540
aaaatccatc gatcattcat ttggagagga aacgaggagt ataactaagg gcactctaga   27600
atatgttggt cgaatatttg tcgatcaaaa aaatttggag gactgggggt tcctcaatct   27660
aaaaattttc aatacaattc ttctttgtaa atggtggtgg aagctctact ctaatgctgg   27720
tgacccgtgg tgtagtttta ttgccactat ccacccaact tcacactaga gatctaaagg   27780
tatacacaaa tcaacctctt cattttggaa tggtttacag cacacatgaa atatttctac   27840
tcctaatcca ctttcaagtt agcaactagt attattttgg aaagatagtt ggttacataa   27900
tcatccactg aaggatcgat ttcctcacct ttacacaata gcattgaagt gcaacaactc   27960
agtggcaaag gtattaagca atctacttga taatagctct tttagtactc ctcttcctca   28020
aagataccaa gaagattttc agagtctata ggaaagcatt gaacaaatta cattaacgga   28080
acgacctgat actatacaat ggaaatggtt tagtagcaat atttttttgg catgaaggat   28140
ctactatttt ctgcaagatg gaggagtttg gcctctactg agtaatatta tataaaaact   28200
cctaatacca aagaaagcca agttatttgc ttggctaagt gctcacaaca aaatcccaat   28260
gaaagctaat cttcttaata gaggaataat tggaactgat tactgtacac tttgcgatga   28320
cttatcagaa actaatgatc atctaatgct catctatact ttttcaaaag caatttggaa   28380
tcaagtactt tcagacctgc aattgtcgaa acttttatgc atgcttaaca ccctatggga   28440
tacttggaga ctcatcaata tgcaacacga tagaagacct aaactagctg ctctattcgt   28500
aattggtcaa tggtgtcttt ggaaggaaag aaataaaaga ttattcgact tctatacttt   28560
ttatccacga tcgattgctg aaactgtgtc acttttttctt tcttgggcat cacacctaac   28620
aacggagcaa ctaaagatgt tagctcctgt tcgagaagtt ctcttatcta agaatgaaaa   28680
cacacaatct ttagtgagaa ttacagatgc taacaggcgc agatgaatgt tttatgagca   28740 ttttttatagc tgcagcttat atgtgatcta tggtgcaagg agttaattat aaccatggat   28800
attagttagg ttgactatca gaaatcatct ccaatacatt ctatgtaacc actgatcaat   28860
tccatgttca actagatagg aacctgccta tatacaggta tgtccctgat gtaactatag   28920
tatactatta ttcataaaata aataacgaag gttttacctt cttctcataa aaaaaagta   28980 tcttcatgtc atcctatatg tcatgcatct cctttgctac ttcttttatt tacttcttaa   29040
acttggttct accatatatt atcagcccct tttaaatttg cttttggata ttgcatattc   29100
cactcttcaa tcacctcatg ccaagcaaaa catttattca cacttgaaaa ccaatataag   29160
aataccaaag aatttatcca tgaaattcta gaaactttgg ttttactcct ttctccatca   29220
ttcaaaaagg ttcaaaatga tgataactct atatagctta tttatcaaat ttacgaggtt   29280
ggtgttcaat gttttttgtga aaaaaatatc ttgctatcca catagtttga atccatactt   29340
ttgctatctt gagtttcaaa aatttttaatt tgctacaatt tgttgctatt agcatatgac   29400
tacttttaag aagataagcc aatatactat tttcctaaga atttaaaaaa tcaaaaataa   29460 aaattttttat ttaagatttt ttaagggttg ttttccaaat gtgcaatggg gcttaatctt   29520
```

```
ggcatcattt tctaacttgt agaattttga cccaagtaac atttgtccaa tcacttagaa    29580
cttctataac ttcgtacaat catttgttaa tgttgttcat ctatttatct atattatcta    29640
tctggaatat agttgctctt aattattttt atatatcgcc tattatccac cctaagcttt    29700
catgttcatc ctcatgttgt tggaggtgca tgtcttattc caaactattt accattgctg    29760
tagattttaa aaaatttgct agtttaggac ttttaatct tttgatatca tgttgatgta     29820
agctaaccct ctaaggctag tcataataca ttttaaggat ttatgttata tgagaccaaa    29880
attttaacaa aatgaagtgt tggaaattgg tagaatggaa gtgtaaagat gcttagagac    29940
atagaactag ccctgggcca tgtaaatctt ccaaaagaag aagaaaataa taaaattaag    30000
atcatattca atctctacag aaaagttggt ctttgttgta taataagcca tcttaacata    30060
tgatggacaa taaaatatat aaacttatga gttttaatac ttagatggaa gaaaagggac    30120
agatatgtca caccccatcc tactagcatg agtaggcaca tgatacacgg ttgcatgccc    30180
tgcagagttt gactcatgag gcatgcaagg tattgaatag tagtctaggt aaaattaaaa    30240
aacttggagc attctaaaaa taaatcaagt tcatttata aaatcaatat ttattatgga     30300
ctccatcaaa tattatgcgc ataacatttt atttgcaaat agaagaagat aagtcctaga    30360
tcctaagtct cctactctta gtctcataat tcatccaagc tatccaccaa atatctaaaa    30420
cgaaaaagaa aaacgatagt atgctaatag cttttgtaagt cacctttat ctctaattag    30480 atcaagcata ttagatataa aacaataatt ttcaaagtat atgatttgca attaggaata    30540
aatatttgat aaatacagaa taaatttca taaagcatat ttactaacat tatttataaa     30600
atatataatg cttatatcaa taaatcaatt tctaaatcaa tatatataaa ctatccattc    30660
tgtcttagcc ttacaactat tgctaccatt ccctgtagca tggttaggaa gagactagct    30720
cttgaatact catgtcattt atcaacatat gcgaatgatc attcgactaa tatagtcaaa    30780
aaaaaattac tctgatttat ataaattaaa aattagtaaa taatatatgc tagtaatcac    30840
cttaccagct aagctctaaa gaaaattagc ttttgaatat acatcatgct attgattatt    30900
atatgtcagt gcttgtctca ttttgtggca tgcaagaaga ctagatccta aacttatatg    30960
catagtcaga ttaaagagca aatgttgcat ctgattatat gaacatctat tatgatgtag    31020
agtttgtatc atgtatattt aatttaaaca caaatataat tatacataaa taatattcat    31080 atttttaaatt ttaaatattt agataattat tctagtgcag gtataaaaat aagcaatata    31140
aaattttaaa tcgatttata taacatgcat aataaaaaaa attaaggata gaggtactta    31200
ctgctcaact cataaaacat aagaaatctc tttaactaac tttagtgcaa cctagataga    31260
acatattaat gattaagttt tcatctaaaa taaacataga tatcatttta aaatcttagg    31320
catttaaatg gtctcatgat ttgtgaggct ttcttcagat tctacaattt tgaaatttt    31380 tcaaattata atttttttac cttgattgat aacaaagcca ataatacacc tcaaatccaa    31440
atgtattcct aatagttttc aataaatcta atatcaataa atcataatta agatatcaat    31500
ccattctatg aatttgacca taaatcctac ttgtttctct gaccttcact ataaattaat    31560
catcaaacta aataagtgag gggatcataa ttcttttacg acaatccaag aattcaagtc    31620
tagcatccac attagatggc ttcctgtcca gatatttgcg cctctccaaa attgagatta    31680
tcagattaag aaaaataaaa taagagagag ggttaaagga caatgccttc taggtagtga    31740
tgtccgacat cataatttg atcaaatcta tggggcaacc aataatatta gggaaagagg      31800
attggatttg agcaagaata gcaaagtcat tgtcatcaat ggcctgattc attgagttca    31860
```

```
atgaaggatt ggtggttgag tggtggaggt ggcatctagg aaggagagag aaagaaaaag    31920
atagagagaa agagataaga aaaatagaga gaaggtggca gttaagatcc cttttgtga     31980 ttaatatata gcggtaagat actcaaagat ctcaccttat cgacctcaaa cactaaggga    32040
ggtggaagga gggactacta cccatgaagc tagagaaagg gatgatgatg attggaggaa    32100
ggaagaagga aaaatagtag actcgatgat gataagacta aagaaaagg gtttgactta     32160 gccacttggt atataatgag gtttggtatg gagtcaatag cttgagtaat agcatggaaa    32220
gagagaagga gctgaagaga gtactaagtc ttattagaat aaagaaagat agaatcttag    32280
cgaaaaatag ggcctcaaat ctttcaggta gaggaaaaag agggatcaac gaatgaaaga    32340
ctaaggaaaa ggtgtggagt aggatatact ctcgattagt ctctcaatca tggattctag    32400
tagggcttcg tcagctgctc aatcatggat tctgatagct caaatggtgg taagtagaaa    32460
gagagagatc taaagagatt gatagtggcc ttaaaaccag cacggtcaag gataggcatg    32520
ccttagagag aggaaaagag agagagatta atggaaataa gcgagaaaaa tatattctta    32580
gagaatagat tggcgataag aagaggaggt ggttggggca tgcttaaaga aataaagaaa    32640
attgagtagg cggaaagtgg tgatgcttgg cgatgagaag atttgagaga gagagcaaaa    32700
aaatgtggat gatggtcata ggatagggaa aggaaagaac aaagaagggg gtgctaagct    32760
aactctttct accttcctca caccctgaag caaaggattt ggccaaggat ggacaaatgg    32820
gcgagggctt tggtggatcc atgcctaccc tttctccctc tcacgatgat tctagtcaag    32880
ctatctatct tgatagcctt gagccaagcc aattgacttg atccaatctc tctaaatcca    32940
tacaaactta agagagtgta ttgattcact tattctcttc taagttgata agaaacataa    33000
ttaagtggag ctcattaagt atttcaggta gttgctaact tggcaaaatg gaagcaataa    33060
taaattttaa aagactatag cttggtataa tctcaaccat ccatgattta gaaagatctt    33120
cagactcaat atagattact ttggctacta caggtaagag ctaaatagga tccaaaagta    33180
agatccatca cattagtaag tcaaattata tgtcaaatct tagtaggtat acttagtcct    33240
acgatgccta attaaaatga tcatcatttg aaccttaaaa tggactagtc aactaaaatt    33300
tttctttttg aagaagattt agaccataaa atatcttcta atctgtgaag aattagatag    33360
agcgaggaat ataaaattga tgtagaaatc aagatctatc atatatacaa ttttaatatt    33420
tttttcataa ttttttaaata tttatcttct ttttttatag gtctagtcct atttaaacta    33480
ggaagaggag tccaacttga cttatgcaat aggggatgtc cttctagaag ataagaataa    33540
tttgatcaga attatataag agcaaacctc attattataa ataggggcta tatacatcaa    33600
tttatgagat agagaatcaa tgaaacaaaa gtagacttaa gttttatttt cataattctt    33660
ctatcttcta cttttttct aggagattca agttgagtgg attgaagaaa atctttcatc      33720
ttctcgatcg gatcatattg gtattagagc gttggtcttc tatatttatg gagagcttta    33780
atgtattgtt taaatacgtg aacaatacaa acaatcaaga gaagtgctat ccatgcttca    33840
aatacatcga aatataaaag caaatatggc tactaattct ttttcaatgg acaatgagat    33900
aaaaggatgt cttacacaac tcaaggagaa gattgtgcaa ctcatgaaga ttgtctccag    33960
attgaagata atttcaatac aagcacaaac accagcaact catgttgtga aactgtttcc    34020
tatgtttgga gatgaagatc ttctatctag tgaggagatt gaattaccta aagtatgaa     34080 aaatctttct tcaatcattg aaagttaaag cttgaattga gatcccccata tataatgaa    34140 ccattgatga aaaaaagcta gataattggc taaactaatt acaaacctat tttattatct    34200
atagatatta tggcatctag aagatagctt ttacttatct caagctttct agccatgctc    34260
```

```
ttatctgatg aaattcatat atgagaaata ataatatttt taatatggtg cagagccaat   34320
tcaaaggttt aatcaagaag taattttatc taattggcca taaggaagat cggtggatca   34380
aatgataata cttatgatag aaacataatc aatccactta ggactatacc accaagttcc   34440
acaaacaggc aatctgcctt ggaatcttta tcaacaatta tacaattttt ataaagtatg   34500
ttgaaagtct tcatgagagc atctaaaaaa agatgaaact ctttaaggtt gatgatatca   34560
gtaaagctaa catgaaagtc atagagattg aggagaaaaa tcaaattaga gaagataagg   34620
aaggcaaaaa gcatatcaac ataactcaaa aaaaaaaat tatgatcatt gaaatctttg   34680
aaaatacatc aaggagaagt attgaaagtt tcatcctgaa ttggagctaa agtagaagaa   34740
gcccaaggat gataatttta agaaaaataa aaagtggtcc tcaattctat agagattgag   34800
gagctatctg aacttgagta agcaaacttc aaattgagct tgatggtgag aaaacctaat   34860
acaacaatta aaacggatct agaggtacat gacaactcac ccacttaaag attcaagtga   34920
agcagagtat cattaaggct attataaatc tttgaagcta gaagaacctc attttccaat   34980
atttggttca gaaatcgagg ttgtagatca agcctcatcc atatccttat cctcttagtt   35040
ggattcagaa ggatgtcaag ttaaaaatta tgagatagtg taccttcaag ttagccatca   35100
ctgagaggtt tatttgtgag gtaacttttg aaatagtttc tttggatatt tgtcaagtta   35160
tccttagaaa tgtgtacctt tagaatcaag atgcaatttt ctatagacga tagagaaagt   35220
atcatcttat aagggatgag aaaaagttca tgatcaacac ctcaagaaca taaggtaact   35280
ttgaccttgc aactgttgcc caagtgaagt gatttgttaa tgtttgtgat gagtgcatga   35340
tgatggtata aagaaccgat atcactcatg agaggtcaag gccttgtcct ttggttccat   35400
caatcgatca atagagattg agattaagga ggagtcacta tagtccttgt cgatgaggaa   35460
ggatgacaac aagcattcct accatgaagt ctagatttga gagcaaatga aagtaatcca   35520
ctgagacctg agagcaaaaa aaggcgagac caaaaatcat cttcaagtaa agtcaaatgg   35580
ttcaaccatg agatggggaa gtaagtattt tcccaccttc aattctaact ttgtagaaac   35640
taaatccctt aaacagggga gccctaattt aagaggatcc tcagattcat tgtggactac   35700
tttggctatt acaataagag ctggatagga atcgaaagca aaattcacca cattaggaag   35760
ccaaattgta tggcaaactt caagagacca taacttgatc acatgaaatc caattaagat   35820
gattttattt ttgaatttga atatttttt gagatctata actttagatc taaatcaagc   35880
taaaatttta ttgcttacgc cttcaaaata ggctagtcaa atcaaaactt ttcttttcaa   35940
aaaagacttt gactgaaaga tatctttcaa tctatgaaga atcaagtaga gtgatgaaag   36000 ataagttga tataaaaatt gagatctatc tcttataaaa ttttagtaat tttattttt   36060 ttaatattta tctttattta gagatctatt cctatttaaa ctagaaagaa ttgtccaacc   36120
taacttgttc aatgatcaac atcctcctaa aagataaaaa gaagaatctg actcaaatta   36180
taaaagggcg gacctttttt tttgatgaaa agggaggaaa aaaatccatc aaaatttatt   36240
aagaaaaaaa gagtacaaga aaagaaggat atgaaagagt aagagaagcc ccacaacatc   36300
catcaatatt taaatttaa atttaaatct ccccccatcat tctatcaata tttgatattc   36360
aaatttaaat tcttcgcagc atcccaccaa catttgaaat tcaaatcctt tcatacaaac   36420
aaaataatat ttttcaaatt ctcaactttg agtttcaaaa ttgagaagcc tacatattgt   36480
ctgctcttca ccaaagaggg gagattgttg gcttagcttg gcccaagaga agagaagaag   36540
gccaaggccc aatctgtagc ctagagaagg agggtttggt agctacttaa taatcggatc   36600
```

```
taaccgataa agacactatc tctattagaa gaaaaggtag agagaaaaag aggcaattgg    36660
ttaacttcag aggggagga ggtaagctgt tgaggagatt aatctgacgc aaggaaaaaa    36720
gaagagctga caactagcca atgatcgaga agggctggag acaatccaag cccagcacca    36780
agaagcaaga gaaagaattt ggaggtcaaa ggaggagtcc aggaagagag agcgaaacac    36840
aatgttcgga tctagccgac aacgatacca attatactag gaaagaaggt aaaaagggaa    36900
agagcaatcg atcatcttca gcaaagaaaa ataaaagagg cacccgacag tcaagcccat    36960
ggccaaatca gtcagcaaga ggacctcaca agatctagac gatgctaagg ggaagggagg    37020
aagaaaagag atccagtaac tgtccaacac caggaaaagg aggagataag aggaagggag    37080
aagtcatttt tctatcttgg gccgaaggag ggagaaggaa gaaagaggaa agaacatcct    37140
caaagtcgaa ggaaggaagg aaagagaggg gggaagggt cacagtcaga tataccagaa    37200
gggatagatc cagtgtcaaa gagagaaaag agagaggaga tcagaaaata aaatttgatg    37260
actgactaat tgtcatgaaa ggctaatgac aactcataaa aaagtatag tagtaaagag    37320 aggggatag gcttggttag ggaagagatt ccgacaacaa agagaaagaa agagagagag    37380
agagagaacc ggctcccagc caaaaatagc ttgacccacc atcgagaagg accgacaaag    37440
agagagaaag atagaatagg gagaatagct tggcttcgaa tcaaaaatga tctaacacac    37500
tgctgaaaag gactaggaag agagagagag ggggtagggg agtatctcgg ctcgcaatca    37560
gaatcaactg gccaatgcca gaaaagagag gaagagagag atagagaaga tatagcaaaa    37620
gagaagagat ggacaaaagg agagaggaag ggagggagag agagaaaaaa taggagagag    37680
aggggcttgg tggctgactg tcagaagaag cctcgatgct cgaagattag atggaagaaa    37740
aaaaaatttc tcaaaacttc tcttttctat aagagcaaac ctcactatta taaatagggt    37800
tatgtatctc agtttatgat gtgaagaatt aatgaaaaat tggactttag ctctattttt    37860
gtaattcttt catcttctat ttttatgaaa ttcaagttga gccgattaaa agaaataatc    37920
tttctttccg attggatcaa tccattaact agatacttca aaaatcaaaa tgacctatct    37980
aaaatcctaa atcaaataca aaaccaaaat aactaaatta agatagaaca aactacaatt    38040
acaaaaaact ggctaaagtg tttaaatgct tttactccta agtttcttct tgctcaccat    38100
taatgcttga tctttagctg ggatcatatc agccttatga ccactataag accaacataa    38160
caactcactt gtattgctcc tttaaaatta tacaaaacta gtgtctaata tgtaccatgc    38220
gaatgtctgt ttctcaccag aaaatggatg ggcttcttgt gcaagcacct tcttcctaca    38280
aataataaaa tatgcatccc ttctctcatc ttactaaata aaataattaa aggctttact    38340
atcaggaaat ctggctttat ccatataatt ttggaagttt tatttgaaca taacattacg    38400
agtactagat tacatcagga ggtggttcct cttatttcta ttaagagaaa aatcaatttt    38460
cttttaagaa agatcatttc attttcatca ggtagcgtac tctactaata tacttccaca    38520
acaatatata gggattagat tataggatgg actttaaggc ttcttttcga gagccctgat    38580
ttctcaatca cattcccttt tctttctcat gtaatggcat ttaagagtgc atccagggcc    38640
caacaattag tcacaagtgt tctttttata catggtacat atttgctatt ttttagctta    38700
ttttaacttg attgtgaaga tatcatgaga aaattagatt taaagcctag caatcttgaa    38760
cccataattt caagttaaca ggtggaagag tccattatta tgtgagacca acttagactg    38820
caaaactatc tgatattgga ctatttacta acacccttt tcatgtgcaa tgtttgtaaa    38880
gagaagatat atgatgtagc gagataggat agtttggctc taatattgtg ttaatattca    38940
aaccaaaatc ctaagctaat agatggaaga gaaatgactt atatacatgt gcattattgg    39000
```

| | | | | | |
|---|---|---|---|---|---|
| atatatcttt | atgggagaaa | taatcacatg | gatgtttata | tcacacatct | catatgtgca | 39060 |
| tgttgttgta | aggcttcaaa | agacagacga | tgagattggt | cttggatcaa | attggaatgt | 39120 |
| ttcttagttg | aatttggaga | agtctgcaac | aaatcctata | aagaagtcc | cgaaattggt | 39180 |
| ggggcacctt | tcgatccaag | acccttcgat | ggataagtca | aataaagcct | tgagaacaga | 39240 |
| ttgtggaaat | ggaagaatag | aaggatgaga | aagagattg | tgaacaaatg | gagagaggac | 39300 |
| tcttgtttcc | ttcagtggag | gagttgaaaa | tgattcaaca | aagtctccac | tctatctatc | 39360 |
| ccgacttacc | ttatggaggg | tatgttaccc | tcctttatat | agaggggtga | ggaggcttgc | 39420 |
| tcaagttgtt | aggccgttaa | tttattataa | tagaatggtc | agctatataa | agatcatggg | 39480 |
| atgtttatcc | atgtgatgat | tagctatagg | atagctagaa | aatatctaat | gcttaattag | 39540 |
| atgatagctg | tcagataacc | gtctgcattc | ttatagtaca | tcgatatttt | atcgacgtga | 39600 |
| ctagcttaaa | tcagcaactg | actgaactga | atattatgat | tcttttagtt | aacaatcata | 39660 |
| ttggttagag | accgatgtaa | ttcatagtag | atcgatcaca | agctgagatg | agtatcatat | 39720 |
| tttaagaaca | atactagcaa | gttagatcga | tcaaatgtca | gatgaaaaag | tagatcagta | 39780 |
| aacgttcgat | ggaacctgaa | agaatattta | tgatttagat | aataatctat | catcacgtat | 39840 |
| ccagataatg | agatcatata | acatgtacca | atatatgccc | tccattttc | acaccgaagt | 39900 |
| gaagttcttc | acatcgggtg | tggaaagtct | cttcagaaga | tctcacctga | cctgtattgt | 39960 |
| catcataaat | gctccatacc | acgatggttg | gaagtattaa | ttttttaatc | actcaaagtc | 40020 |
| atacacaatt | tcttgaaaat | gatttgttga | acttagtaat | gatgagcgct | tagaaaatcg | 40080 |
| ggagctcaca | attatttggg | tggctagtcc | ctaatgtgta | tgtgctaggt | gtcatactgt | 40140 |
| aattggccac | ttcagctatc | acatggatcc | tgcttgcatg | gcttaatcaa | gaagaggtgc | 40200 |
| gtcgcaacaa | ctctctgcag | aaccatcgga | taactgacaa | gtggcattga | tctaatggca | 40260 |
| tatcaaatgg | attgagactg | ttagtaaatt | ttataaatag | gtctatactc | tgttcaaaaa | 40320 |
| ttactttact | atttttttca | catgacagtc | ttgctgaaat | tttttcagag | cccctaacat | 40380 |
| cattggtatc | ggagtagaga | cccccccaaag | tcattggagc | cggagaagaa | agaagtaaag | 40440 |
| aagtctttta | aaagcttcct | caaattcctc | tttacatatt | aggcagactc | tttcatcttc | 40500 |
| aacttctttt | ccatgaacat | ctgagatttt | aggttttaca | atctttattt | ttttttttgg | 40560 |
| atagttattc | ccttttctct | cttttttttt | ctgtttctct | tttcccattc | acctttactt | 40620 |
| tcttctttcc | tttcaaaaat | atcttttgat | aggactaatg | agataagtca | ggaccaatgg | 40680 |
| atatctcggt | caacccaacc | actgctcaag | tttgagatgg | aaaatctatc | tcggacaaca | 40740 |
| gctgaagtta | gtacctcagg | ttaggatgat | ctagaatctc | ctataagaga | tttttagat | 40800 |
| tatttcggcc | caagtactga | acaatctgtc | ctgaccaatc | tcgatcttta | ggaacttaag | 40860 |
| aaaaaatatt | cgattcagct | tataactcca | agttgggatg | gtaggattat | tgaacctcca | 40920 |
| gaaggttatg | tcgtattta | tgatgaggca | cttcgatctg | gactttaatt | tctcttacat | 40980 |
| cctttcttca | gtaatgtttt | agacttctat | aaactccatc | caatctaggt | tactcccaat | 41040 |
| gccattagga | tgatcatagt | tttcattatc | tatcgtaaat | ttttgctat | agaactaaga | 41100 |
| atttctctct | ttaggatgct | ggtcatccta | agaaaacatc | cttatgaaaa | agactgatgg | 41160 |
| tatttcttac | cttggcctca | atataaattc | ggtcccactc | ttcctttttc | aatacataat | 41220 |
| tgaaaaaatc | atttttctt | tatttcttct | aatgtttcgt | agggttttat | ttgtaaatag | 41280 |
| tctaagccta | aaaccaaatg | gaactcaaat | aacaaaatat | tatctgagga | tgaggagact | 41340 |

```
tttgtagagc ttttagatat gaaagtatcc aagttgagcc tactggtgtc caatcagtcc    41400
ttgtttgaca ccgacatcag tcagatctct ccttaagata agtctgatgt taattctttt    41460
tctttattgc tttatcattt ttcatcattt ttcttttcta acaatctttt tccttatata    41520
gtagcaataa tgaagttcaa cctacaaagg ctggctaact caaagaagag gaagaaggat    41580
ctaaccgatt gctctcaaga agagtaagga gactgctcct ctaagatcga ttggcccccg    41640
atcatcacct gggccaatat taattgacat agatgctaca tcgatctcca ctataccacc    41700
agcaaaatca actcatcaac ctactaaggt ggcttgtcca cctcctaaag agtctgcaca    41760
tccaaagtag gcatcttccc caacacctcc aacatcggcc aagttagttt ggctgagcaa    41820
tcagcatctg aggtcacaga ctcctgatgt caacccacca actttctcat caaaaaaaaa    41880
ttgacttggc gaaggtatca cttttggaga cacccagact aggcaaggac ttgctctgta    41940
caatgatgcc tcaaaaggac ctagatgctg ataggaggga tctttctttg gagcaaataa    42000
taaattatgg attcaacagt atcatgaacg tgagtcttca ttctcttcca ctctcttctt    42060
tctttttctt ttttttttt acattggcta tttgttgatc tgaatatatc tttcttttg     42120 cagtcggttg tgtatttcaa gttgctcaat gagcacttga catggttctt caaaaataaa    42180
aatttttttg aaagagaggc tcaaggccaa gaaagaggcc aaaaaagcag ttgaggaggt    42240
caagaaggca gtaaagaaga aggctgtcaa agaaagcaaa atgatggagg ggctgaagaa    42300
acagctccaa gaaaaaatag attccattaa ggagactgga caaccaatga cagatgaatg    42360
ataaagatga caagttgtaa aaacagcctg aaaaaaatct caagttgga ggccaagctg     42420 aaggaggtcg agtcaataat tgaaaagcat gatgaagctc ttgtcccata ttagagacaa    42480
cttgataaag acaaagagtg gatgtcaagg attattgaag attataagaa ttccgacact    42540
tttcaagatg acgttactga ggcctcaaaa ggagctttca attatggctt tttgagctac    42600
aggagtttaa ttatcaagct cttttcctaac cttgatctca gcaaggtcat aatagaagca    42660
gctctagaag tagtagccga agtgacttct gcaacaacta ctgagcttgc ttccacttct    42720
atcattggag tttctccgat cgaagtccca acagtccaa tcgaggcctc catcatcgaa      42780
gctatttcga aggaatcagt cggcaaagac cttacctcaa ctcctccaac aaataactcc    42840
caagctaagg cctgaattat cttcttcttt ttttttctaaa catttgtatt agcccgatgt    42900
gggcttctat aaatactttt tacattaatg aatgagtttt tcaatgtcaa tatttttct     42960 ttttaactaa tactaatctt ggatgatccg atctgggttg gatgtctcaa aaaatatcat    43020
tcacgataga tagttatttt ctgacttcgg ttagatgatt atgagtatat gtaattcaac    43080
cttggttagg taagtaatca aatattaact attctcaaac caagtagata acgaagtcaa    43140
tgtgattaac tttaacaagt aagattgtta tggaatgaaa ttgaatcaga tcaactaact    43200
atagataact taatctctca taattcactg taaaggttct aaaagtacct ttatctaagt    43260
tcgaagtgac aagtcgggtt cttttattcg tggatttatg acccatgctg tcttttgtg     43320 atcttcatta ttaatcacct taaatcgata tagcaaaatc cagtttatag atctgagtgc    43380
tttcttgtca gattgagtct atcctattat ctgtgaaacc tgatctagag atcaagtatt    43440
ttaggttttt tatttaaggt ccaattcgaa gattgagtat ccaatgtcat attgttaggt    43500
ccaatttgga gattggatgt ctcactatca tctcgtgagg tccaatccaa agatcgaata    43560
tctcactatc atctcatgag gtccaatcca gagattggat gtctcacatc atcttgtgag    43620
atccaattcg aagattggat gtctcacatc atctcatcct attgtggttg gaattttgt     43680 agccttagtt tgacttttc tgacctcatt tggacaccta aatcttatta tcatcgtttg    43740
```

```
atcgattttt actaatctac tttggatgaa aaagaattct tcaatggaac ttttgattag    43800
aactttatct tcattgggat agaaatcgaa tgctttattg aaagatttta ttgataatac    43860
attctgagat ttttaatatt tcatgttctc gaaatgatcg taccatctaa atttttaatt    43920
cgataagctc ttggatggat cacctcagta atctgataag gtccttccca attcgggatg    43980
agttttcctt actccattgg ttttgagact tcagctcatt ggagaaccaa atctccttat    44040 aaaaatttt aggctttacc tgagagttgt aatatctggc tacttttgt ttataaacta     44100 ccatatgaat ctgggctttt tctcgagttt tctcaaataa attgagatca gtcctcagtt    44160
gatctgaatt attttcttca tgaaaattt ctattctggt tgtaggtaaa ctgatctcga    44220
ctagtattat agcctctgtt ccgaaagtaa gtttaaaaga tatttctcta gttggtctct    44280
gaggtgtagt tctgtatacc cataaaatat tataaaatta ttctaccccg agactttag    44340 cctcaatgag tttattttt aggccttgaa agatagttct ataaataaat ttagcttctc    44400
catttgattg tagatgtcca atcgaagtaa atatatgatc tatgtagagc tcagaataaa    44460 ttttttaaa attttgatta tcaaattatt gctcattatt agtaattata actcaaggca    44520
aaccaaaatg gtaaataatt attttttcaca taaaatctca tatttttct cagtgattta    44580 tgtcagaggt tcaatttcta tccattgggt aaaataatca atagtcacaa ctaaaattt    44640 tctttgctcc atggccatta gaaaggatcc cagaatatcc attctccata tagcaaaagg    44700
ccacagcact gtaatagaaa taagttcagt tgtaggctga tgttatatat tggcgtacct    44760
ttgacactga tcgcagtact tattaataaa gtcggttgaa tcttttgaa tagtaggcca    44820 ataataatct tactgaatta tttcataagc taaaatttta ccccccaaat ggttactaga    44880 gattcccttta tgaacttctc gaaggatgta atcagcttcc gatggcctta ggcataggag    44940
cagtgggagt gaatataacc tctgtatataa ttgattatct tgaacaacat accatggggc    45000
ctgtctttta attcttgttc cttcgactgg atcaaccggt agaggttctt tagtaatata    45060
ctccattaat gggtcaatgg aacttagctc atattaaatt tggacaatta gtaaggcctc    45120
gatactagac tttttaagaa tatcaataag aacaccttga tttagtttga aaaaatctga    45180
tgtggctaaa tgagataggg catcagctca gacattttgt ccttggtatt tgcatgatct    45240
tcagattttc aaagttttt aataattctt tcatattata taaatattga aacatcataa    45300
aatctttagc ttcaaattaa tctcatacct gactgacgat aaattgagaa tcaataaaaa    45360 ttttaattt tttaacatta agctccttag ccattttgag tcctacaatt agcgtttcat    45420
attctactcc attgttgag tgttaaaatt aaatctcaaa gcacgctcac taacaatgcc    45480
ttctagactc gttagaatta aactagttct actttctttc gaatttgagg ctccatcaat    45540
gtacagtatc aaataagaat ctttgatatt tttcaattct tttaagattg gttcttcatt    45600
aggaatagag cattcaataa taaaatcagc taatacttaa actttcaatg aagatcgagg    45660
cccatattga tatcaaattc atttaattca atagcctatt tgaatatcct tcttaaagta    45720
tcaagctact gtaaaattaa ttttaaaggt tgatcgatca gaattataat agaatgagcc    45780
taaaaatacg atcaaagtca tcttgctaat gcaatgaggg tataaattat cttctcaatt    45840
ttagaatatc gagtttcaac atctctaaat aatttatttg tataataaat ggatctttgt    45900
atccctgcat cattcaagc taaaatcgaa ctaacagcat ttgctgaaat agatagatac    45960
atgaataatt tttgaccttt gatcggcttt gatagtaatg gagctgtgcc gagatatttc    46020
ttgagatcat cgaaggctgc ttgacattca tcttatcaat cgaagtcttt gatctgcctt    46080
```

```
agaattttaa agaaaggaag atatttatca gctgatctga aaataaatta actaagcaat    46140
gctactcatc cagtaagttg gtgtacttct ttgatggagc tcggatgctt catttcacat    46200
agagcttgaa tttcttaag attgacttta attcctcttt gagttacaaa aaaatctaaa    46260 aaaattttg aagttacttc aaaagcatat ttgttgggat tgagcttcat ttgatatttt    46320
cgtagtctct aaaggcttct tccagattgg caatatactg atctgactca gtatttttta    46380
ctaatatatc atcaacataa actttgatat taatttcaat ttgttactta aaaatcttat    46440
taatcaagta ttagtatgta gcacctacat ttttaagatc aaaagacatc attttataac    46500
aatgcaaatc tttttcagtg atgaaggcca tattttcttc atcctcaagt gccattttga    46560
tctgatataa ccagaaaaag tatccataaa gcttagtaat ttgtgtcttg aagtagcatc    46620
aacaagctga tcaattttg agagagaaaa actatctttt aggcaagctt tattgagatc    46680
ggtataatca acatagatcc ttcattttc attagccttt ttaaccatga caacatttac    46740
aatccacttt ggatattatg cttctctgat gaatttgtct ttcaagagtt tgtcgacttc    46800
ctcatctatt atttttatc ttttcggggt gaaacttctt ttcttctgtt gcattggttt    46860
atgctttgga tcaacattca gcttatgtac aataagatca gttaaaatct caggcatatt    46920
agagactgac taaacaaaga catcggcatt catccgaaga aaagatatta atttctccct    46980
cagatcaggc ttcaatagag atccaatttg gacagttttt tttggatcat cacacaaaag    47040
aacagtaata agtttctcga ctggttctcc tcgattttg atgatatcaa ctttactttc    47100
ttgatcaagt atttaattg gtagagcttc cacagacctt ttcattttta cagctatcag    47160
aaaatactac ttagcaagta tctgatttcc tcatatttct ccaactccat acttagtttg    47220
gaattggatt agtaaatgat aagtgaagac tatagcctta agggcgttga gcctaggtcg    47280
gtcaagaata gcattataag ctgatggtat tttgacaata aaaaaagtga gtcttacagt    47340
tgactggcat ggttctatcc ctgcagtgac ggacaaagtg acctctcctt ccacagctac    47400
aggatttcta gaaaatccaa ttacgggggt accaacctat ttagctaatt tatcatattc    47460
attctttgga atgtatcata gaacaatata ttagcagagc tttcattatc aataagtatt    47520 cttttatat catatttggc tattgccata aagatgacaa cagcatcatt acgaggagtt    47580
tgaactctaa catcatcatc gaaaaatgaa attatgtgat ccatgcactg atgctttgga    47640
aggctttcag taatctcagc cacctcctca gttccgtcga gatctgagat catattgatg    47700
actgcagcag tagacttgtt gtgatcattc tcattgttgg gcttctatca ttggtcagta    47760
gcttgacttg cccgatctcg aacatatttta ctaaagtaac attagtggat caatacttca    47820
attttatctt ttaattatcg atgctcctca gtatcatggc catagtctcg atggaaatga    47880
cagtattttc tcttatctct ctttgctgga ggggctttca taggattagg ttggcgaata    47940
tatcctaaat cctcgatttc tatcagtatc tgagctcgag gagtagatag tgaggtatag    48000
atgtcgaatc accgaggtgg gcttttgaac ttcagattct tctgaggtcg ttcagagtta    48060
tcctgttggt ttttatgatc ttcttcctag ggccactttt ttccatctct ttttttcttc    48120
acctaacgaa gtatgcatgc tctctttctt ttcagcttga gcatacttac aaacctagat    48180
caatatttgt tcataattgt ttgggtagtt cttattaaga gagaagatca ggcgattact    48240
cttgagtcct tgcttcaaag ctgccattgc aatggactca ttgaagttct tcactttcag    48300
tatggcggca ttaaagcatg ccacatattc ttgaagagat tcaccttcct actatttgat    48360
agtaaaaaga ttgctagtat ttttcaaatg aatccatta ttatcaaaat acgtgatgaa    48420
tatttgctaa ctgtgtgaaa gatgaaatag atcatgtctg gaggtcagag aactagattc    48480
```

```
ttgcagatgt tttgagagtg attggaaaag tgatgcaaaa tagggcatta gatacccctt   48540
gtagtcttat aatggctctg aagccttcaa gatgatttaa gggattgatg gagccatcga   48600
atgtttccac tgtaggtatc ttgaatcgag gaggaactga tttaccaaga attttttgag   48660
aaaaaagaga tcgtaagttg aaatctcttc taccttgaga atggcttcca atctatatct   48720
ccatcatttt cttctcaaga ttttgaatct tttgtccaag accctcctcc atacatggct   48780
tcttatgtgg agcagatttc acttcccaag agtgatcagt atggtcaaga agatgatcat   48840
gatgaagatc ttgaggagtt ggttgctaag tgtgatgtga ttggactact tgggggggcta  48900
cttttttgcta ccgttctgtc gtatactaca gcagtaagag cttggacctg ctgaaccaag  48960
agactaaact attgtggatc aataataatt gaaggttagg tattctcctg aacatcttca   49020
ggagaagatg aagtaggtaa aggatgattt ggtgccttct tgttcaccat ttctactaaa   49080
atattttaag tgcccttcct ctaacactaa tctattactg caaggcttca aaagacaggc   49140
aacgagatgg gtcttgaatc gaactagaat gtttcttggt tgaatttggc gaagtctgta   49200
acaaatcttg caaagaaaat ctcgaaacct acgggtacct tctggttcaa gatcctctga   49260
tggataagtt aggtaaagtc ttgagaatag gttgtgaaaa tagaagaata gaaggatgag   49320
aagagagatt gtcggtaaat ggagagatga ctcttatttc tttcaatggg ggagctgaaa   49380
ataattcagc agagtttcca ctctatcaat cctgacttat tttgtggagg gtaccttggc   49440
cccttcatat ataggggatg aagaggcctg gtaaggttgt tagactatta ggagagtttg   49500
ttagatcgtt aatttattat aatagaatga ccagctatat aaaaatcatg gagtatttac   49560
ccacatggtg attgactgta gtataactga aagatagcta atgcttagct ggatgactgc   49620
tgttagataa ctgtctgcat tcttacggta cattgatatt ttaccaatgt gacatagctt   49680
aaatcggcaa ctggctgaac taaatattat gtatcccttt agttaacaat catgtcggtt   49740
agagatcaat gtaattcgca gcagatcgat cataagctga gatgagtatc atattttaag   49800
aacaacgctg ggcgagttag gccgatcaaa tgtcagactg aaaaagcaga tcaataaacc   49860
tctgatgtga tctgaaagaa tatttatgat ttaaataata atctatcacc acgtatccag   49920
ataatgaggt catataacat gtaccaacag tgcattttc catctagtta agaggttggt    49980
tagtggcatt tgtcttcgat atgtaatgtt cacataacta atgtgcttag tagcattctt   50040
ttgtaaggtt aaatcttcaa tgatcttaag ttcacataat tgcctttgtg ccctattagt   50100
ttatagttga cctttaatt caagagacag tcaccttagc aatcgatgtc tgcttagatt    50160
gggccaatta ggtactcaca ttaatatatt gaatcatgtt tgaatataaa ggattagatt   50220
gatttataag tttcctttta ttgtttacat actgatactt agattgactt actacattat   50280
ttgatatgtt atgttctaat ttttggatta aaattgttgt ttctgatttc tccttacatc   50340
taatactttg tataatttat tatttttttag catgattgag tgtagaggat tagattgatt  50400
tttaagttta ttttgattat ttacatgccg atacttaaat tgacttacta cattattcaa   50460
tatgttatgt ttcaattatt gagttaaaat ttttatttct gatttctact gatgtccagt   50520
gtgtgtgtgt gtacgtatgt gtgtatatat ttatttacat atatatgtat gtatgtatac   50580
agacatacat acatacatac atacatacgt acacacacac acacacacac acacacacac   50640
acacacacac atatatatat atatatatct gtgtgtgtgt gtgtctctct ctctatatat   50700
gtataagtat gtatgtatgt atgtgtatat atatatatat atatatatat atatctatat   50760
gtgtgtatgc atgtatgtat atgtatgtat gtatatacat atatgtatat atatgtatat   50820
```

```
atatgtgtat atatgtatat atatgtgtgt gtgtgtatac atatgtatac atacatatct    50880
atacatacat atgtatacat acatacatat atatgtatat atacatatac atgtatacat    50940
acatgtatac acatacatgt atacatatac atgtatacat atatgtatac atatacatat    51000
atacatatat atatatatat gtatatacgt gtgtgtgtgt gtgtaagtaa ttaagtatgt    51060
agtgtgtgtg tgtgtgtgta tatatattta tatctgtgtg tgtgtgtata tatgtatgta    51120
tgtatgtatg tatatatata taaatacata catacatatt tatacacaca tatctataca    51180
caaatatgta tacatataga cacacacaca cgcgtgcgcg cgcgcgcgca cacacacaca    51240
tatatatata tatatataga tagatagata tatgtatgta tgtatatata tatgtatata    51300
tatgtataca tatgtgtata tatgtatata tatatgtgtg tgtgtgtgtg tgtgtgtaca    51360
tatgtataca tacatatcta tacatatata tatatataca tatatatata catatacata    51420
tatatatata tacataaata tatatacata tacatacata catatatata tatatatata    51480
tatatatata tatatatata tacacataca tacatacata tacatatata catacacaca    51540
cacacataca cacatgtata cgtacatgta tgcatataca tgtatacgta catgtataca    51600
tatacatgta tacatacata tatagatata tatatacaca tatatgtata tatatatata    51660
tatatacaca tatataggtt atttggaacc taagaaactt gcaaagttac tagatgcaat    51720
gttcggaaac catggaccgt aacaactgga gtagtatttg ggtcatgaat tcatggctag    51780
atcatgaatt gagtgggagt caaccgaagt agggccagct cagacacttg tatttaggtc    51840
ccatgcttgc gtgcattctc ttccctgata tcctttggct ttgctgcctc aaatcctcga    51900
gctatcttat catcatcgca ttgagctcca taccttgctc tttcctaact gtcactgtcc    51960
ccatcaaacc tccggagatc ctctttcttc tccaatgttg agatttgttg gagtcttccc    52020
accttctcac ttcaatgggt ggcaatttca agtgccagtt cccttatttg tcccagctat    52080
attgacaatg gggcttattc tagggtttct catggacata gtgataataa taatcaaggg    52140
accaagagag aaaaatcttt ctagtctgtg ttctttaagt ttgagagata ggcagcacat    52200
ttttttaata agccttttc actcatcgga tcctgatttt cagttgttcg acctgaacag    52260
ttcaagcaat tgaactgctt gggtcactat ttttggacgat tttcagccat ttttaagtat    52320
tgtttgactg gatccacgct gcgtagtggg cattgcgttg atcaagtaga cctgtaaggg    52380
tcaacaaggt ctgagaacac tgaatggatg ctccataatc ctcttgttat ctgtcaacca    52440
tttggaatct tttaaaacaa catgtggtga taatatatat gataaactgt gatagattca    52500
tgtatagatt atacatatga aaatgtagag tgcttagtaa aagtgatgaa gagcaatgcg    52560
ttagaatgtg ctagcctttg acctaaaaat tggaatgccc aatgatgagt tatgataaaa    52620
ttgtgacgtg atttatgaag tctaatgttt agttggcttg cagtttcaga tgcgataaag    52680
aattttatga tttagctctt tggttttta acatgcaaac atttaattgt actgaaaaac    52740
atttatttcg aaacatgtag gagactattg gatattgaaa ttaaattga ctttttggtg    52800 tttcacaata tttcttaata aacactacga ctatgtaaat aggtggtgga tcaaagggaa    52860
agaaatgttt ggtgattatt tttagaaaag acaagaagta tttgataaat ggttattttt    52920
caaccgatta atgagagaat gactatgaac ctatgaggtg cacctcttat gatgttgcat    52980
ggatgaagca tctaatccat gggtacaatt tactaaaata taggcccaat tctgagacag    53040
gaacatttac aactcatgta caaagaagaa acttaaagta tcatggatgc cgggatattt    53100
ccttcttcaa atctttcaaa agctgtagtt ttcattataa ggaaaaatga ttataactaa    53160
catcttctat aggtgatgag tggacactag aaggctttcc tataataaca gtagagagag    53220
```

```
tagaaaagcc tgtcagcatg cggtccataa gtatatatac atattttcag cgcttaaagt    53280
aaattttctt gtaccaaaaa aagataaatt ttcaaaataa gaactaaaat caactgaaat    53340
gtttgaaatc tgattcgtag gtacatggag aagagtgtaa gacagcaaat atcataaagg    53400
cagaataaga gctggtaatc ttgtaacctg gcgcaactat gttatgcatg tctatatgtg    53460
tgcatgttta tgtataacaa gtaatatttc ttttcttatt tactcacttc agttaggaag    53520
tcaatccaat ctcccttgc ttgggtgtgt tcagattatc aagggccata acagtagtgc    53580
tggtaagcac ctgtttaatg gataaatggc gacaaattct ctcccttct gctcactcta    53640 ttatcatacc ttccgtctta cccatctgct atatcttata aggaacataa ggatcgacat    53700
agcttcatgc tatcacatta caagctaaga tcggaataat acctaatctt ttcgatctac    53760
tattaggtat tactataggg ttgtaaattg ggtttaggtt ttgaactata ttatattttg    53820
gtgtaagaat atagtgccac actatcttga accagactag ctgttgcact ttttgcagg    53880 catcaatatt ttgttcatcc aaaaaaaaat attgcacatg cacagatgaa gtatgagggc    53940
tgtaatcatg tgagaggaaa cacagatggt tgtgatccta taatgcttga agaatgtgat    54000
ccctctttta gttagtatac ctttcttgtt tttctccctg ataggaaata tgaaatgaag    54060
gtatatcttt atgaaaaaga tggatgcata gaatatacaa atataaattt atacaggata    54120
agagaaaggc ctccagcaat ttgcacaata atagtgaaaa aagattaaat aaattcccaa    54180
caatggcgcc aatatgtgat atgcaactat gagtaggctt tcctgttgca acaatcaata    54240
aatatgtcat gcgaggcttt taaggtagag cactaacatt ctaatctgaa ggcctaggta    54300
caattttgaa tttaggactt gtttggatga ctgagtacaa aatcccataa gaatcattga    54360
tttgggccaa cacaactacc tacatgaggc ttaacctagt ctaattttat aaataccaag    54420
ggaactatta tagtaggcca gcccaaatgc catagggaat aaaagatgaa gtatggaggt    54480 ttttttatt ccttatggga tttggactag tccactgcaa tgattcttta aatatttcta    54540
aataagtcta acctaacctc atttggacag ttgtattagt ccaaatccgt aatttccata    54600
gaattttggc tacagtcatc ccaggcccct aaatttaaaa gatcatattt aaaacatgct    54660
tgaattctag atttttaatct gggcccttta acttccatag ttggtcttga aatagacagc    54720
ccagccccaa gctcatggcc ctactgtatc ttcgtttggc tgtgcccttt agtaggatgt    54780
cttaggtgtg tgaaaagcac ctgaatattt cccacacaat gtgttttttt ttcagtacaa    54840
accggctatc acaccattct aatatgagta cagtccagag aatcagaata caaaatatct    54900
cgtaaggccc aagggtagtc atcgccttca caccaagtcc agtctccgat atgcttcgca    54960
acaaaagagg cagcccaatc catggtgcta ttcgcctccc ggaatacatg ttggacaaac    55020
gacatattgg cgtgatgaag ggacttctag atatcataga acagtgaata ggttttagg    55080 tgtttcacct tgtcctgaat ccaactaatg accatggccg agtcatcctc gataaagatc    55140
ctctccgctc gtagctcata tcttatgcag atgatgtccg cccaaacaac gtggagctct    55200
gccccatgaa cggatgggtc gaagatcttc tagcaaccaa aagcttgaca tctggatctc    55260
aaataatata gcccgcacca cccctaccat ctctgacact actatcaaag ttgaccttga    55320
caaactccaa ggatggagct tctcaagaaa tgaaagagt cctcggagtc actgcaggca    55380
tagcaaggga gtcccagaaa ctcatggtgt caagggacgt ggtggcagta ctcctcagct    55440
aagcaacaag ctctccacca ctcgctacac aggcacaatc tcgatttaa aaatcaagct    55500 gtttctgtac agccaaatct gataggcggt gtacgccatc ctaataccc aaggcaaccc    55560
```

```
ctcaaccata ttctgatgga ccgcatcccg aaaaggcaaa agccatgggc cactatcaac    55620
cttctagatt tggccccccg ccatcctcca aatcagatat gccctcgagc aatggagtaa    55680
ggcatactct attgactcat cctctagttc atagatcaag caagcagtag gaagctccgt    55740
gcttctgtct ttgagaagtg tctgagtagg tagtcgatcc caggcaacct tctagaggaa    55800
aagtctgatc ctagagtgga ctagccatgt gtatatatat atatatatat atgtatgtat    55860
gtatgtatgt atgtatgtat gtgtgtacgt acatacatac atacacacac atacatacat    55920
atacatacat acatatacat acatacatan nnnnnnnnnn nnnnnnnnnn nnnnnnnnnn    55980
nnnnnnnnnn nnnnnnnnnn nnnnnnnnnn nnnnnnnnnn nnnnnnnnnn nnnnnnnnnn    56040
nnnnnnnnnn nnnnnnnnnn nnnnnnnnnn nnnnnnnnnn nnnnnnnnnn nnnnnnnnnn    56100
nnnnnnnnnn nnnnnnnnnn nnnnnnnnnn nnnnnnnnnn nnnnnnnnnn nnnnnnnnnn    56160
nnnnnnnnnn nnnnnnnnnn nnnnnnnnnn nnnnnnnnnn nnnnnnnnnn nnnnnnnnnn    56220
nnnnnnnnnn nnnnnnnnnn nnnnnnnnnn nnnnnnnnnn nnnnnnnnnn nnnnnnnnnn    56280
nnnnnnnnnn nnnnnnnnnn nnnnnnnnnn nnnnnnnnnn nnnnnnnnnn nnnnnnnnnn    56340
nnnnnnnnnn nnnnnnnnnn nnnnnnnnnn nnnnnnnnnn nnnnnnnnnn nnnnnnnnnn    56400
nnnnnnnnnn nnnnnnnnnn nnnnnnnnnn nnnnnnnnnn nnnnnnnnnn nnnnnnnnnn    56460
nnnnnnnnnn nnnnnnnnnn nnnnnnnnnn nnnnnnnnnn nnnnnnnnnn nnnnnnnnnn    56520
nnnnnnnnnn nnnnnnnnnn nnnnnnnnnn nnnnnnnnnn nnnnnnnnnn nnnnnnnnnn    56580
nnnnnnnnnn nnnnnnnnnn nnnnnnnnnn nnnnnnnnnn nnnnnnnnnn nnnnnnnnnn    56640
nnnnnnnnnn nnnnnnnnnn nnnnnnnnnn nnnnnnnnnn nnnnnnnnnn nnnnnnnnnn    56700
nnnnnnnnnn nnnnnnnnnn nnnnnnnnnn nnnnnnnnnn nnnnnnnnnn nnnnnnnnnn    56760
nnnnnnnnnn nnnnnnnnnn nnnnnnnnnn nnnnnnnnnn nnnnnnnnnn nnnnnnnnnn    56820
nnnnnnnnnn nnnnnnnnnn nnnnnnnnnn nnnnnnnnnn nnnnnnnnnn nnnnnnnnnn    56880
nnnnnnnnnn nnnnnnnnnn nnnnnnnnnn nnnnnnnnnn nnnnnnnnnn nnnnnnnnnn    56940
nnnnnnnnnn nnnnnnnnnn nnnnnnnnnn nnnnnnnnnn nnnnnnnnnn nnnnnnnnnn    57000
nnnnnnnnnn nnnnnnnnnn nnnnnnnnnn nnnnnnnnnn nnnnnnnnnn nnnnnnnnnn    57060
nnnnnnnnnn nnnnnnnnnn nnnnnnnnnn nnnnnnnnnn nnnnnnnnnn nnnnnnnnnn    57120
nnnnnnnnnn nnnnnnnnnn nnnnnnnnnn nnnnnnnnnn nnnnnnnnnn nnnnnnnnnn    57180
nnnnnnnnnn nnnnnnnnnn nnnnnnnnnn nnnnnnnnnn nnnnnnnnnn nnnnnnnnnn    57240
nnnnnnnnnn nnnnnnnnnn nnnnnnnnnn nnnnnnnnnn nnnnnnnnnn nnnnnnnnnn    57300
nnnnnnnnnn nnnnnnnnnn nnnnnnnnnn nnnnnnnnnn nnnnnnnnnn nnnnnnnnnn    57360
nnntatatat atatagtata ctatatagta tatatatagt atatatagta tatatatata    57420
tatatatata tagtatatat atatatatat atatatatat gtgtgtgtgt gtgtgtgcgc    57480
gtgcgcgcac gcacgtgtgt atctcgatct gtgtgtgtgt ggtccatctt cacactttt c    57540 cctcaaaaaa acccccttg agattttgtt cagctgaaag gggttcataa aacttgccct    57600
tgcttggtcc tagggtttaa gatttatatg caatattcat taagacgtct aaatgtcata    57660
atattttgag gttacaaata ttaacaaaca gccttggata caaacctttt tctcaaagaa    57720
tcttgtatct gttcttcctc agatgacatg tgatttatgc tacggcctag ttctaaggac    57780
ttttctctgt cattaacata aaaaaaaaac agaaatatat tccttagtaa ggaaatagtt    57840
gtgcactatg attgctatgt ctctcaaaat tataccaaac tttttatgat atagagtgaa    57900
aatcaaatca gcatgtatgg tctatttgcc aaataggggtt gagcataggt cgggttcggt    57960
```

```
cgagttgaga gaaaaatttc atccgatcaa attcaatcgg attgaagaaa attcaatcca   58020
ctgccaatca ttcattatgc ataaactatc taaaactgaa atgaatagtt tgtagcagga   58080
tcaggtgtta tgtcagtttg gacttcaatg ttaacccaat attgatttta aatccaacat   58140
tggtccactt agacttattt atttattttt atcaatttaa tataaaaaag atctaaacct   58200
cataagtcat aaattttgga tttattttg  aacatgtaca aaataaaaca gaaaaaagaa   58260
aaaattactt atctaaaagt aactatatct gaaaactttc actttagaat tgtcttaaat   58320
taatgtactt ccatcaacaa ttcaatgtta atatttttat gaatccaaat ggatgataga   58380
gtatttttta gaatgaagta ttgaagtcta aatgacatcg tcccaaaata aaagtgaatt   58440
tatgaaatac tacatctgtc ggattcggtt tcatacggat taaaagtgta ggaatagaat   58500
ccgattataa ataattattt ttttataaat tctaattcaa ttttattcga tttatatttt   58560
ttaaccggtc aaaattaata tttattaagt aggattggat ggatttattc gtatctcgat   58620
tatttgctca gcccattgcc aaatctaaac tcttttcaga taggttccat gtgaacatga   58680
tacatgagat gcagtgtgat agtacacacc attgctaaga aaactttgga gtttgcgtaa   58740
caatatctgt ttaccattta aaaaatggca gttttgaatt ttaacacgct ctcctccaga   58800
ttcagcttat gaacttttcg aataaaaata cccctggact attttttccaa aaagtaccag   58860 catcttttga acttgaatgg aaattcggcc aataaaatgt tttcatttat tgaagaaata   58920
aacagggtaa cgcagtagct ctatttcctc tgcttttctt ttctatatta ataacatgat   58980
tattcatctc tctcggatca caaaaaaatt aagctattca agctttattt atatttcatt   59040
tttaaatttt ttacttaaat acaaaatctc ccatcccact actacggcag catgttttct   59100
atgtatgatt attttcattc aaatgatatc atttttata  atttatattg tatgtaatta   59160
attcatttat agttcttaca ttttcctgtt tctagtagat acaataaagc ggttttggac   59220
tagtagcttg ttctctgtat cgaagtttaa ctaaagcttt gacaataata tatgaatcca   59280
tatcactggg taggagagga atatgttggg tataaaggat ttaaggaatt agatattttc   59340
atacaattgt attgcattgc agacagtaat tagattacta tgcaattatt ctctctctcc   59400
atgtttgttg cagttgaaga actctaatga agctcacaaa aatttactgc atgaacttgt   59460
aagtggaatt agacgactcc gttgtcctcc attttctttt attttcttta aaatcatctg   59520
ccattcaaat agacagaaaa aaaaggattg attagctatt ggatgcctct tgaattcagg   59580
aaatgaagga cgagcaccca gtttatggtt ttgtggatga tgaccctagc aactacgcag   59640
gtgcactggc tcttgccaat gggcgcttccc acatgtatgc tttccgtgtt cagccgagcc   59700
agccgaatct ccatcgaatg gggtttggct cccatgacct gcgccttgct tgattttatt   59760
gtagcttaaa gaccttacaa cttccagagt ggtgttatat attagtatct taagctatat   59820
gacagtggta agcctctcta tccgctactt gttatccttt aggtactttg catgtggtgc   59880
aaggttataa ttgccttgtg tttctattgt cttcctcatg gtacttactg gactgatgat   59940
gtcaagtgaa atggagttgt tgaatcctg  actgaaattt ctcttggtcc atcaagtgca   60000
agagtaagtt tagacatcac ttgcaagctt ttgctaggaa ataagtagtt tcattgcact   60060
aatgatttcg aatttttgtt ttcgggttag agaaacctag attaatgctg ttattggatg   60120
ctggcagtca gatgaagatt atgtttgatt gtacctcgtt ggacagatgc tcatgcgtag   60180
atccataact ctatttcatt tcatttcct  gtacacaatt gaaacagggc atatatgaat   60240
aggtatagaa cagatgattc ctgcaatatt ggaggtggct agctcagctt agactaaagt   60300
```

```
tggtctagct gggatattct gaacacctga gatgttcaaa taatgtggga taacttggcc    60360
caactcaact aaacattggc tcaaagcata gtcaaggtaa agcttgagca agctcttttg    60420
agcttggttc gagtccgagc tgagcccggg ccgcttgttt agctgatgaa ctgaattcaa    60480
atagccggta ctcagcttgg ctccactcga ttcatgagtt cgaatcccct caagttcaac    60540
ctcgaacttg acggtgtagt cccacaacca tggccacctc ataatgtggg acggccatta    60600
tgcattcctc tagtgcctgc tccatatgac ttttgttctc attataccat gcacctaaat    60660
gagtgctcat agtgacaatg tttagcctcc acgtataatg tgtgccagct aactagaagc    60720
ctaaactttg gtgaaatttc tgcaatgttg tggttgtaaa acgctcctac gttgagacat    60780
gatggtatct aagattatag acaaactatc atgctgaatc aacccaaatc caaggtgaat    60840
aaaacttgat acaagccga gctccattgc aatagtacaa tggattctgc acttgaagaa    60900
cattacaaaa tcattttttc ccaaaagaa acattgcgaa cagaccaaag cgtaaagaaa    60960
ttacatgatt caactaattc aagctttcca tgatgtaggc actcgctaga tgtagtaggg    61020
tgataacttg ctttgtgagg gtggatcata agcttaacct caatctatcc caatctatcc    61080
tttcccttga cctatccatg ccaatctagg ccatttctgc ataaatataa cttaatccca    61140
gtggatccgg cctagtttca ctcactccaa cacattccta ctcaatggta gccaatcctt    61200
tctttagccc tcaaatataa tcctaatcta gcatagccaa ccatcaatca tgcctaataa    61260
agcccgacta caccaacccg atcattcctg atcgtacaca atcaagactt atcctaattg    61320
atcctagctt ttttaggcc tctcttatag aacctgtgcc aattctggac aagctaatcc    61380
aatcttagca gccaaaaata ttacatgttt aattagccaa atcgaaccta tcataaaccc    61440
aatatataat cggaccatac caagatcatc atcctatatt tccttctctt gttataacta    61500
cacctaaaaa ggaatttctt catacttatg aggggtatat tatgataaaa attccttcat    61560
tttagccctc catccttgtc tatttttggg accactagcc aagtaacacc ttaagagccc    61620
tccatcttaa tattccctct aactagctcg atttcttctt cattctttct ttgcgatgtg    61680
tcccctccaa tttaattctt acatgttggg atttgagtac tgaaaaataa tagataaaga    61740
gaaagtaaaa actatgctaa tgataatacc aaaggcataa agaaatcaca gcagtcgcaa    61800
aaacatcaaa ttttttatg gttcggccta agcctatatc tacatagggga cgagagtaag    61860 aagaagcttc cactataata atagtttaga gtacaaaaac ttctctgaca ccatgtaggg    61920
aacatcgctt ctaatacaag aaagaagaaa tccaagatta aacaaacctc tagaaaaatt    61980
cttctcgatg gaataactct aatctgagat tgaacaatct tctccaatcg atgatctcca    62040
atcttctttt cttaaatgaa gcacccttca agcctctctt cttttctctc ttcctatcct    62100
cttttgtggc tcacaacctc ctctcctttt tatgttctat gttcctcaca tcacatccac    62160
agactcattt ttatagataa aaaattagag tctatttcgg actccttttc cacacacaag    62220
atggcttccc acgccattgg ttccgtgcgc atgactttt tcatgccaca aaggattccg    62280
tgctgcaaaa gttttccata tccatgcagt ttccacacac cacaaaaact ttcgcacact    62340
tctcgaaggc ttttcatgct cgacccttt tggttttcaa ttaaattgat ggatcccata    62400
tgaggaggga ccacaccaat aaatctcctc cttctaactc atatggtagg ttccatcaag    62460
cctgtagcac cttttgcattt tatcagtttt gttcctgaag ccggcttcat caatatatta    62520
gaactatttt cttcagtgtc aacttttta agcttgaacc acttcatctc tagcatattg    62580
acatgctttt ggaagtatg tcaaattgct caaaattaat cttacggttc tcttttcgt    62640 tagattctag tgcatattac gcactttaac ataagatcta aggaaggaag aggactgagg    62700
```

```
taaggtgaag tgattttttt ttgagttggt aatggtacaa aagttatact agaccgtggg    62760
tacctaatct cggagattac catttagatt tggttcttga tcatttgtat agtgatgcat    62820
ttaaaaaatt atttgagcaa aacagtgaat gccattgggt ctgagagatc caaaatcaaa    62880
taacctaaag tatatagatg gttcctttag ctaggtcatg tatgagaaaa aatgatctgc    62940
cgactggaga aaatagatct ttgagctcat tgactgttaa gtcatatcta gtctgtgaat    63000
catctctttg aggattaatg atcaagctat cctttatggg ttaaaagaat aggatcactg    63060
aaatacttat cctagtatac ataatgtg catggcctat ttgatgagtc agactagaag       63120
gttatcacta cttcatcacc tttactgatg agcaatcatg atatggatat gtatgtgaga    63180
tacaaatcta aaagattttg aatggttcaa agaattcaga tatgaagtag aaaagataaa    63240
tcaaaaaatt tttaaaggta cttgatcgga tctagaatgc aataccaaat aaaaaatttg    63300
ttgattatct aaaaaagtg atatagtttc atgatggaat tcttcttgta cacctcagct     63360
caacggtata tatatgagga gcaatagcac tatatgagat atggtccggt ccatcatgaa    63420
tatcactaat ttaattatta tttatttaag agcaagattt aattttaaa atttaaatta     63480 gattttttct aaaattggtt tcaccgcacc atatgagata tgatttggtg ataagttag     63540 aggatagatc tgtgagaact catttatagg gtatcccaaa aggtatttaa aatattactt    63600
tttctttcca gtagttgaca atatgattgt gagcaatcat actgttttct taaaaatagt    63660
ggaaggatga actcaaaaag aaagtctcta agaacaacg agtcacaaga cctatacaac      63720
ctatttaaga tgagccagta tatgtagtac ttccttcacc tcatcaattt agtaggatct    63780
cctatctttt agaaagatac tcggtattct tacaaaggat ttagagaaag tgtttcttga    63840
gggagattga gaatataggg atgatctcaa aacctacaat gacataatat aaggaatcat    63900
gtagttacat gaaggtcagt gggagggttc catactgaca tcgattatga tgtggttaca    63960
tatagaattt ttttttcaaa gatctagatc aaacattctg aaaataaaag gtctatagag    64020
ataaatccga aaaggatgtt tgannnnnnn nnnnnnnnnn nnnnnnnnnn nnnnnnnnnn    64080
nnnnnnnnnn nnnnnnnnnn nnnnnnnnnn nnnnnnnnnn nnnnnnnnnn nnnnnnnnnn    64140
nnnnnnnnnn nnnnnnnnnn nnnnnnnnnn nnnnnnnnnn nnnnnnnnnn nnnnnnnnnn    64200
nnnnnnnnnn nnnnnnnnnn nnnnnnnnnn nnnnnnnnnn nnnnnnnnnn nnnnnnnnnn    64260
nnnnnnnnnn nnnnnnnnnn nnnnnnnnnn nnnnnnnnnn nnnnnnnnnn nnnnnnnnnn    64320
nnnnnnnnnn nnnnnnnnnn nnnnnnnnnn nnnnnnnnnn nnnnnnnnnn nnnnnnnnnn    64380
nnnnnnnnnn nnnnnnnnnn nnnnnnnnnn nnnnnnnnnn nnnnnnnnnn nnnnnnnnnn    64440
nnnnnnnnnn nnnnnnnnnn nnnnnnnnnn nnnnnnnnnn nnnnnnnnnn nnnnnnnnnn    64500
nnnnnnnnnn nnnnnnnnnn nnnnnnnnnn nnnnnnnnnn nnnnnnnnnn nnnnnnnnnn    64560
nnnnnnnnnn nnnnnnnnnn nnnnnnnnnn nnnnnnnnnn nnnnnnnnnn nnnnnnnnnn    64620
nnnnnnnnnn nnnnnnnnnn nnnnnnnnnn nnnnnnnnnn nnnnnnnnnn nnnnnnnnnn    64680
nnnnnnnnnn nnnnnnnnnn nnnnnnnnnn nnnnnnnnnn nnnnnnnnnn nnnnnnnnnn    64740
nnnnnnnnnn nnnnnnnnnn nnnnnnnnnn nnnnnnnnnn nnnnnnnnnn nnnnnnnnnn    64800
nnnnnnnnnn nnnnnnnnnn nnnnnnnnnn nnnnnnnnnn nnnnnnnnnn nnnnnnnnnn    64860
nnnnnnnnnn nnnnnnnnnn nnnnnnnnnn nnnnnnnnnn nnnnnnnnnn nnnnnnnnnn    64920
nnnnnnnnnn nnnnnnnnnn nnnnnnnnnn nnnnnnnnnn nnnnnnnnnn nnnnnnnnnn    64980
nnnnnnnnnn nnnnnnnnnn nnactatgta tgttggctat gtaggttccg attcgctgtt    65040
```

```
tggaatatga tatacctaga tgaaatctat cgatcttgat agaaaaagag aagtcctatg    65100
tgattcgtaa gactgagttc agaaaaatct ctgaccagag taagtgtgaa tattgaaaaa    65160
ttttttttac gaaattcaca aatgaactcg agtcgagcca atgtagcata tgactgatga    65220
tagagtttga cgagttctca atgacctccg tcaaattggg actctcgata gagggattgt    65280
atcacacgat aactgcacct agggattcac ttttctattt tgctagcttg ccactatatg    65340
ttgctagacg tcactggtgg atcgtgagaa ctcactaaaa tcattttcgg atcaacgatc    65400
tttgctgagg taagttggaa tcgtttcagt ccatcgaaaa gagtttcgat gatactgtga    65460
tggagatcac gatatgtctc actatcaaac agaatagaac ctgaggagtc acatacaaaa    65520
agagcttaac ctgatcaatg cttggattat atttgaatt atcaattaga ttgatagttt    65580
gaatattaga aactgctaat ttgtaaccgt tacagttttg acaactacta attgttagcg    65640
caaggactta attgcaagta ttataatttt tttgaggctg attaaattat aaattaaatt    65700
ttaattaatt taattcagat ttaatttaat tagacttaat ttaatttaat attaattgga    65760
ttcaattatc caaatcagat ttggatttca agcctgattg gatcaggctt gacagccttt    65820
tcgaatttgg ctcattttag actcgatttg aatccgtttg aggttctatt tggatcagat    65880
aaaccatgac ttagagagct caagtttttt gggactctct ttagaaatca tgtcaaaagg    65940
agaagtagag cnnnnnnnnn nnnnnnnnnn nnnnnnnnnn nnnnnnnnnn nnnnnnnnnn    66000
nnnnnnnnnn nnnnnnnnnn nnnnnnnnnn nnnnnnnnnn nnnnnnnnnn nnnnnnnnnn    66060
nnnnnnnnnn nnnnnnnnnn nnnnnnnnnn nnnnnnnnnn nnnnnnnnnn nnnnnnnnnn    66120
nnnnnnnnnn nnnnnnnnnn nnnnnnnnnn nnnnnnnnnn nnnnnnnnnn nnnnnnnnnn    66180
nnnnnnnnnn nnnnnnnnnn nnnnnnnnnn nnnnnnnnnn nnnnnnnnnn nnnnnnnnnn    66240
nnnnnnnnnn nnnnnnnnnn nnnnnnnnnn nnnnnnnnnn nnnnnnnnnn nnnnnnnnnn    66300
nnnnnnnnnn nnnnnnnnnn nnnnnnnnnn nnnnnnnnnn nnnnnnnnnn nnnnnnnnnn    66360
nnnnnnnnnn nnnnnnnnnn nnnnnnnnnn nnnnnnnnnn nnnnnnnnnn nnnnnnnnnn    66420
nnnnnnnnnn nnnnnnnnnn nnnnnnnnnn nnnnnnnnnn nnnnnnnnnn nnnnnnnnnn    66480
nnnnnnnnnn nnnnnnnnnn nnnnnnnnnn nnnnnnnnnn nnnnnnnnnn nnnnnnnnnn    66540
nnnnnnnnnn nnnnnnnnnn nnnnnnnnnn nnnnnnnnnn nnnnnnnnnn nnnnnnnnnn    66600
nnnnnnnnnn nnnnnnnnnn nnnnnnnccc catcgaaaag agtttcgatg atactgtgat    66660
ggagatcacg atatgtctca ctatcaaaca gaatagaacc tgaggagtca tatacaaaag    66720
gagcttaacc tgatcaatgg cttggattat atttgaatta tcaattagat tgatagtttg    66780
aatattagaa actgctaatt tgtaaccgtt acagttttga caactactaa ttgttagcgc    66840
aaggacttaa ttgcaagtat tgtattttt ttgaggctga ttaaattata aattaaattt    66900
taattaattt aattcagatt taatttaatt agacttaatt taatttaata ttaattaggt    66960
tcaattatcc aaatcagatt tggatttcaa gcctgattgg atcaggcttg acagtctttt    67020
cgaatttggc tcatttaga ctcgatttga atccgtttga ggttctattt ggatcagatg    67080
aaccatgact tagagagctc aagttttttg ggactctctc tagaaatcat gtcaaaagga    67140
gaagtagagt attattttt tcatccttct ttcttcacac gcatgaaagg agaggggca    67200 ccaatagttg gtgccctgcc ttatctggat gtctttttca tccaattttt tttttaattg    67260
aatttgattt aaaatagaat agaaatatct tagattaagg tatagaagta cttttttat    67320 gtgataaaaa aaatagagaa agaggacgtg cgctaattat tggcgtgaga catctttcct    67380
tctttcttcc cttatctcaa cgcacatcta tcctttgatt tgttttgaa caccttggat    67440
```

```
taaaagagat gagatctctt gggcattaag aaggagttgt gcgtgggatt tgagatgtgg   67500
tgcgacaaaa aattaaaaga ggatgcatga agggaggtgg cgtgcgttag atgcgagagg   67560
cttctttctt acatctttct ctcctcccca atgcctcttc cttccttctc cacttcacgt   67620
ccatgcccag attcaataaa gatcagatct aagaaaagaa aagagagaga aaagagaag    67680 aagaagggtt cttcttttct tcatggtgat ctggtataga tcctgttgga tttgtgcgaa   67740
agagtttgag caacgatctg cttctttaag atctgaaaga aaagatcaag atccatggat   67800
gaagagtgag atctgcaagg tgctagcaca ccagtgatct cggtgctccg atcaaatggc   67860
tccgtgtgga tatcagctga ggtcgaacgc gtgcatggct acgatcagaa tctgcgatat   67920
ctgcaggatc cgagatatgg agattcgatc tccattttat ttttctaaca gtttattttt   67980
ctatttcaga tatcagatcg tgggtacata tttgtatcaa gatctttact atggttttca   68040
gatctgattt gatacgtaaa taaattaaaa ttattttaat ttatttattt tcactgtgta   68100
gatgtctaga aaaattttta aactacacgt acgaaatcga agcattttct aacaactctg   68160
actatcacca tagacgacgt atatctcttg cttcccacca aacttcttta ataagttctt   68220
tagccatagc atttctttat cgaccttttgt tatggtgatg tattcaacct ccatcgacga   68280
taatgtgaca cttttatgac tttgattgcc acaacaccgc tccctctgag aatatcatca   68340
gataatctga cgtggatttc tgtatgtcca catcatcgat catgtccgta tctgtgtaag   68400
cctgtagcat aggatctcca ctatcatggc ataaatatat cctggatatc tatttaagat   68460
atcttatttt ccacttcatt gctttccggt gctcctttcc aaagtttgaa agaaaccgat   68520
tgaccatacc atccacttga gcaatattag acctggtgta caccatagca tacataagac   68580
tccccaccac ttagtccttc tcactctttc tgctttgctc tttaatcaat gtaaagtgtc   68640
ctacaagcag acaccaccgg cttcactcta ctcatgttga atcaatccag caccttctca   68700
acataggcct cctatgacaa ccataggacc tggatctcct atctctagca attcttatcc   68760
ttaatatcat tttgacctat cccaagtctt ccgtcataaa tgttcgatcc aactttacct   68820
tcaaatcatt gattttggta atgtggcatc ccacaatcag catgtcatca acatatagca   68880
aaaatttgat aaaattattg tcaaaatatt ttttcatgaa catgcaatgg tcagaactta   68940
ctttcttata tccattctcc attatgatgg aatcaaactt cttgtactac tatcatggtg   69000
cctgcttcag ttcataaaga ttttcttca agcaacacac tatgttctca ttaacctttc    69060
atttcaaact cttctagtta ctctatatat tctcctcctc caagtcgcca tgaaggaatg   69120
ccatcttcac atcaaattgt tccacctcaa catctaaaca gccagcgaga tcgaggataa   69180
ctcgagtaga cgtgagcttt acaacgattg agaaaatctc ttcaaaatcg atactttttc   69240
tctgaccaaa atctttcaca actaatctca tcttgtacct tggttataaa ctattctcct   69300
atggcttcaa tctgaacatc tatttatttt tgagtgcttg cttttttctta ggtatattca   69360 ccaactcata tgtattattt ttctataaag aattcatctc ctctttcatt gccttcatcc   69420
actcctcact atgctggagc tctatggctt cagagtagga ctcaagctct tccacatctg   69480
ttaatagcac ataatcctat ggtggatatc ttatggatgg cgtccactct cttgtgaatc   69540
tctggacctc ttatgcaggt ggttcaacat gcaactcaat ttgaacacca tccgcactct   69600
cctcagcctc atgactatca tatgtaccgt catctgtagt tgctctcctg ttatcaagac   69660
ttctcgaaga ggtatctggg cataagtcta tagggctgct cggggttgac ttcggcttct   69720
taggcttctt aaaatcatcg atcgtctgat cctccaaaaa aataatgtca tagttgcaca   69780
```

```
cgatcttcca ctccatagaa tcccacaatc gatagttgaa ctctccgtcc tcactatagc   69840
tcaggaatat gcactgcttc accttgacat ctagtttgga tctctcatct ttaggaatat   69900
gcacgaatgt cctgcatcca aagattttca ataatcata agaaatatct ttctccaaca   69960
atattctcta tagtgtatca cacttaagag tataagaaaa aaaaagatta atgctatgga   70020
tcacagtcat caatgcctcc ctccagaatg ccttcgatag tttagcataa gagcgcatgc   70080
tcccgatcct ctcgcaaatc atcctgttca ccctctcaac aatctcattt tgttgtggca   70140
tcttaggcac tgtcttctct agtctgatgc catttcattg atagtatttt ttgaaagaac   70200
ccctgtattc acccctgttg tccgtccaaa tatacttcag cttttgccca gtctttcttt   70260
caacagagat gtcaaattac ttgaatatta tcgagcactt gatccttcat ttttaaaata   70320
tatgtccaaa ttttttagaa gtgatcatca ataaaagtca tgaagtaaga acatccataa   70380
aaaattttat cactcagaga acaaacatca ctgtgaataa gatctaatgc accaattttt   70440
cttttagaaa aaaattctaa aaagaaactt ggatttgctt acccatcaag caactttcat   70500
atatcttcaa tccaaaacta tgaataggaa gagcattctt cttagtcaaa attgacattc   70560 cttttttggct tatatgtccc agtcgtcaat gccataattc taaggtagaa gattcttcca   70620
ctacattcac ctcccctta ccgagcttgg cttgtatgaa gtagagaaag ccttgcttga   70680
tacttttggc tactactagc gattttttgg ttagcttcta tttgctgtct ccaaatatat   70740
tgtagtagtc ctcctcatct aatacccta tcgataacaa gttcagatga atatctagta   70800
catgtcgaat attttcaaa aatagcctgt accccaagct cgtgatcagc ataatatctc   70860
caatatcaag gattttaat tctccatcat tctccatctt tattgtccca agttactga    70920 aatgacaaga tgagaataat tttcacctca ctgtaacatg atacgaagtg gccaaatcga   70980
tcacccagat agagtctcaa ccaatagtac ttgcaagatc atcatttgtt gtgccacaag   71040
caacgatcat ctctccatcc gtagctactg ctatcatctt attgttcgag ctggagtcat   71100
cacttgatta tttttgact tctccttttt tagtaatcgg tagtctttct taaagtgatc   71160 cttttttgccg tagttgtaat atctatcact tcgagacttg gatctcttcc gtaatttagt   71220
ggggccatca ttcaagttag attgggagtc cttgtgcttg tttcttccct ttcttttctat   71280 gatgagagcc tcatggtggc tcgagacacc ttgctccttt ctcctagcct cctcattaag   71340
catatagtct ttcaccattg ccaaggctat cgaactatct ggtgaagaat tgcttagaga   71400
caccaccaaa gtctcctaac tatcgagtaa gaaacttaac aatagtaaag cctagagctc   71460
ctcatctaac agcatcttca tcacagtaag ctggttcacc acgttctaaa agttgcttag   71520
atgctccacc atataagctc cctccttata tttcatattt atcagtttgt gaattaggaa   71580
caccttgttc tataccatct ctcttgtata gacttttag tttcaaccaa aggccatgag   71640
cattaacctc cattgaaata tggtggaaga tgctatcatc aatccactgt tggataatcc   71700
caacgatttt atgattcaat ttctcccatt ctttatttga catcttatca aactgaataa   71760
taacatcctc gattggatca tgaaaatctt agcagtaaag gaggtcttcc atgtaaggat   71820
tccagattga gtagttagtt aatgtcagct tgatcgtagt gcccgacgaa gattggttct   71880
ccatctatta gcatcttaat ttcttttttga atacttaga ttttgtaaaa tttggctctg   71940
ataccactta ttgggatttg agtactaaaa gataatagaa aaagcaaaag caaaaatcac   72000
gccaacgata ataccaaagg cacaaagaat catagcaatc gcaagagcac tagaattttt   72060
tatggctcga tcaaagtcta tgtctgcaca gggatgaaaa taaaagaaa cttttactat   72120 aataatagtt tagagtataa aaacttctct gacactacgc cgacaatact acttctaata   72180
```

```
caagaaagaa gaaattcaag attaaacaaa cctccagaag aatccttttt gatggaatat   72240
gaaagaataa tattctacaa gtcaatcgca tgagtaatgc aataagatat tgttctatat   72300
tttatcttcc aaattcatat atttgatatt aattattaat aaaattagat attttatttc   72360
attatatgct gcattttaat acttgtttaa aattataatg aactccatag gttaggacaa   72420
taattttaag gtcatgatga gatcatacca gtgagattta aatctttgat aaccttaatc   72480
taaaatattc tcaatagtag gatcattaag tcaaaaatca atgatactga taaaactggt   72540
acatcctata tattctcgac agagagggtg gttgatgtca taatcacttg tgtggagaca   72600
ctaatacgaa gatgtggtgc tcattagaga ataagttcat tgaatttact gatcgagaga   72660
atatatgatg caagtgatcc tttgacctaa gatcaccatg gtgccttgta tatatgaatc   72720
tatgttttgg ttcattcttt agcttcattt tttgagcctt gtgtggggtg ctccggacat   72780
ggtgcagtat gtatggaggt tgtgagtggt caacaaaaaa tcaatcactc cttgtaaaag   72840
gagcgaatat cttatgtgat cttataggtt gatccaaaaa atctttgacc aaagcagaat   72900
gataattaga aagagttttt aatatatcat taactgaatc aatatcttct gatcgagata   72960
catataaata agtatttgaa tttgacatga ttttatatcc ataactaatc tgaaatattg   73020
tatgattgaa gaattgaatt gtacaatttt ttaccattga aaaaaatttt tgatatttttt   73080 tttcaaattt aatatctttt tgatagtcat gacatgttgc tagacatcaa tcttgacttg   73140
tgggctcaca aaaattaaaa agattttatt tgaaagttaa ttagaaagta ttctgattaa   73200
ttgatgtatt tggactgacc taatctaatt ggattgattt aggtcatgag cttgagccca   73260
ctgctggcta gatgatcgct gtcgtaggca gtcaagaata aaaatcaact caaactatat   73320
agatagggtg agtagggatc atttctatgg agatctagga tgattatctt tttttttaag   73380
aaaaaataaa aagagaattg attgtagaag aattaaaaga aatagaatag caagaattaa   73440
attaaaagta tgaattaatt tatgaaaaaa aataagtcag agaaataact cagaaatttt   73500
gaatccacca tgcaaattag atttattttc ttctttttt tatgttgcaa cattaattct   73560
tgtgattaag gtattagtat agcttatctc taagagatac ggactgtatc agtgagattac   73620 aactcgtcct gttgaagtat aaactatcta aattcaatta caaatataa gattcaatct   73680 aacatactac gatctatctc tccaaagcac gtatcgtatc tagggatcac gatacgtcaa   73740
tagagggtat aagccgtgta ggctggatca atacctcaaa aaaaaataaa aagatatgaa   73800 ataaagtat aatttattta cataaaaatt taatataaaa aaaaccgtt tacaggcttt    73860 atcatatttc tggattgaag agatttagcc acgcatcaag ctctctagct ccataatctc   73920
tcaataattg atccctaaag ctctttaatt tttttttta ttatttttt gtttttctt    73980 taatttttt ctcttcttat ttttgctgcc atctgctgcc tctgttttct ctgctcctgc   74040
tgcctccttt tatagagcac agcttcttcg aattataagc atctatggac tttcaattcc   74100
cactatcttt tattttgatt gggattttaa aacttatcc gcatcccagc atcttgtttc   74160
acgcgagatc ctagcgtcca catgtgtttt gaattcctta tgggccacag accatttaaa   74220
ccaccaaaga ccactttact attttgattt gaatcccatg gaagccggct gcctctggtc   74280
tcattcaccc ttccagtgct tcacatgggt cccattaatt tgaattccta tgagccacat   74340
ccaagctttt gaatccaagc cttccttatt ttttaaatca attaaaactt tgctttaaat   74400
gccttgtaga ccctccctatt tgcatgctac gtgagaacat tgttaagctc ctcttggccc   74460
acttaagaac ttctatgggc tacatgcttt tggctagctt taaaatggtt ttgggcctaa   74520
```

```
ctttggatca ccattcgaag tccatttttga attcaattta tttttatttt ttttttttaac   74580
ctacaaatcg agctctttta ttggtgatca tttttcctat aaaacaaaaa caaaaagcat    74640
caagtcttaa gaaataaaag ttaattaata tatattttga tacttttatt gggatattta   74700
atgtacttat cactagatat gaaatccaat gggtcacaca ctttgaaatt tgatcttagt   74760
ctaatctaac taggatttat tataaatctt atgggttaaa tttacatgct agcacatgaa   74820
ttaactcaag ttttcaattg gatttagttc taaggtgttt gagctaaccc tatcctgata   74880
ccttaaacct aattagatta gatttgaacc tatggttttc ttgatgcctt atgcttatta   74940
catgaaagag tttcatgtga cttaaattcc tccatgccac cacatcttca tccatgccaa   75000
attaatatgg aacaccccat ttaattgtgc atttaagaag gaatagtcct tcttaaacac   75060
tcctcttaat ttcccacact ttcctttgtt ctacacacca tcaaatggct tttggaaata   75120
tgcgggcgca gaagtggagg tgtcctatat gaaggctctt ccacattata agttatcaca   75180
tggtgaatta aattattgtg tgagaaaatc atgcgccaag agttggcacc ccttgggagt   75240
tttaggcact ccttcttatc ctataaataa ggggcacccc atatggataa atacaaggga   75300
attcaagttt aggcatgaga ttgagaggag aaaagacac aaaatctga aaaaagata    75360
agaaaaaaaa agagagaaaa atagaaagaa aagacgagag aaaacgaaag gcaagggttg   75420
ctaatcctag ggttcaattt ttcaatagtt ggatttctga atcaatttgg ggtggtgaga   75480
tttttttgaga aaaagtttct gatgtggccc tagtagaaga ttgaaggcat tcagatgatg   75540
gtgcaatccg tttttgaaaa agaaaagtga gtagtatact tgtgaagaaa gctgcaacac   75600
tacatcaaat tggaaaggac cttgatcaaa cccatatgga tcaccgttgc aggatatcta   75660
ctttggtatc ttgtgaaggt tatttttttt atcagatcat catcttcaaa aaggtataat   75720
tttctaccta atatgcatgc ttgatttgtt tgattaaaat ctataaagtg ttcataaggt   75780
ttgtgttctg attgtattgt tttaagtatt aaaacttact ttaaaaatat aaaaaaattt   75840
gaaaactatc ttctactgtg caactaaaat ccaacagaat aacccctaata tgagattgag   75900
cgatctccgt caaccgatgt tctctgatct tcttttcttg aatgaagcct cttcaagcct   75960
ttcttcttct ctctctctcc ctatcttctt ttgtggccca cggcctcctc ttctttttat   76020
gttttgtatt tctcatgtca catccataaa ctcccttta tagataaaaa attagagtcc   76080
attttggact ccttttccat gcttcccacg ccattggttc tgtgcacacg acttttttcca   76140
tgctacaaaa gtttttcatg tctcacgtag tttccatgcg ccataaaatt ttgcatactt   76200
ctccaagact ttttatgctc gacccttttt ggttttcatt taaatcagtg ggtcccctat   76260
gacgagggat cacaccaaca tcatatgctc tcctcaccat accaaatggt atccccaact   76320
ataagacaaa acattcatca agttgctaac agggttgaag atcagcattc actatagaaa   76380
ttttgttttt ttgctaacag acgaaaagca tcaccaaagg catcaaaacc attggcatag   76440
accctgggt gttttaccga cagacacaaa aagcatcaaa aaatatccct atcagcaaag   76500
agttttgctg atgcttttt tttcatcacc ctttatcgat acttttttac tcgtcgataa   76560
atcatcgaca taactctcaa aaaattgatg atccctattg aatgtcagca taactctaaa   76620
gcctttagtc atgcctgact aaaccatcag caaaaggctt atttttagtg atacctgagc   76680
agtctattac gaaaaatctg aataatatgc tagcaatttt attgtaaatg cacaggagtt   76740
tcatgcatac atttcaaaaa ttttaataa aaaaatatta gattaaatta tttaatctac   76800
aaatgcatgt ataagatctg acccctaaaac tactataaat ggatcgatga catgaattta   76860
tatacataaa aatctgaatc taaaatgaca agcatatgaa ccaaaaacag catttagtaa   76920
```

```
tagatctaat ctaccacttc tagaattccg aatccaatac ctaagtgtgg gtagttgaac   76980
tccatgatca aaaatgtaga tctgaaaatc ttctctggtc gctcatagcc gcacaagcat   77040
ccgacctcta cggatggttc acacgaagct cctcggacct atcagctctc tgcgggagtg   77100
ctagcttgtg cagtcagttt ctgatggtag attgacttga tctccttctt cgattatctc   77160
gaaccttttt aatgttgaag atggatcaga ggaagatgtt ggatggtaga gaaaaaatag   77220
atgaagactc tcttctcttt gattttttc ttacccaaaa atctgaaaca gttctaggtc    77280
tctcacccga gaggagaatg gtctcttctt ttgttcatgc caaggaagaa agaaaaccac   77340
ccaaaccttg caccccaaag aaaaattttg gcccctcttt ctctctagta tcacacaatg   77400
aaaagttctc tcttgttggc acacaaaatt atggtcattt tatggttgtc gcacaaacca   77460
ggtaagacag gataagagcc agagtttgtt gcaattcaaa ccattttaaa tttcaattta   77520
tcttcaactt tttctcactc ttatctgact taaagagaga cttataagag aaaattgggt   77580
ataaaaaacc atcagaaaga cttccttttc ttacacacaa taggccccctt caaaaataac   77640 caacgtgtgg aaggatatgg ataaggtttt aggttgaaat tcaaatcatt ttgaattcaa   77700
atcaaaatca atcaattcct atccttaatg gatgataaaa gaagggttat cttctaattt   77760
tatcatacat aaactaattt tgtacggtga gaaaagacgt aagataattt gggtggtgca   77820
agggagagag tcccattcat ttaggactct agggtttaac caattgaatt ttttttcaaa   77880
cccaatccaa ttagatccaa ttaaaatatg atgaacctaa tctaattagg ctcctataat   77940
ctttattaaa tttaatcaat caataaatta attgagccat agacctgatc aaattaggat   78000
catttctctt ttaccgatta ggtcatctca taacctaatc agacttgacc tgattgaatc   78060
caattcaatc aaacttgata cagacttcaa tgctcaatca aattaagcta attagtgatc   78120
tattcactaa ttaatcttct attaatgata gtgatccaga ctcttctcta gagtctccgt   78180
ccagtgggac tctccagcag agtcccaatc tagtgggact cttcaccaga gtctccattc   78240
attgggactc ttcagattag ccatgtgatt ggagagaaac ttttaatgtg aatccatcat   78300
ccacatttta tgtgaatgac a                                             78321
```

<210> SEQ ID NO 2
<211> LENGTH: 15569
<212> TYPE: DNA
<213> ORGANISM: Elaeis guineensis
<220> FEATURE:
<221> NAME/KEY: misc_feature
<222> LOCATION: (11900)..(12834)
<223> OTHER INFORMATION: n is a, c, g, or t

<400> SEQUENCE: 2

```
actacatttt aacaccaagc tcgataatag tgataaagaa acatctagat cagctttata     60
atcaaaaatt ttgacttaca attttacgtg tgtctcaaaa tcttgaataa atataaataa    120 gatctttttat cttgatccaa aaatagtaat caaggatttc attagtaact tcaacaacaa   180
tggtaaaaaa atttctatc cattgataaa cccaaatttt gaattgaagt ttcatgcata     240
ccatatagcc tttaataaga tctattattt ggatctaaag atagtaatta aaattgttaa    300
tgattccact aagatgaata ctttacaatc tcataattaa tttcttcaat aaaaatagac    360
ttcttgataa tgtctccaat tgtatatttt tttttattc tacaagaaaa cttcatacat     420 ttttacgtt ccaatataaa tcttaaaaag ttattccaat caaatatcat aaaagatctt     480
cttagtccaa ccttaaataa cttttatgaa tgaatcttta tcttgccact aaataatgaa    540
```

```
ttttaaaatc aagagcaaca tcacagcatt ctgtcatgtc aaatttgtgt tagatgtatg    600
tcctagaaat caattagatt gacaatgtaa attttttaag gatataattt atatattttg    660
atttattaat aaaataaaat ttaaattaat ttttattcat atttttttat ctatgaatca    720
tctaaagaat taataagatg atgatacata ttcttaagag ttcaaaattt gaaatatatg    780
tcattgatga ttaatttctg aatacttttg aattcttaag agtttagaag atcttgaccc    840
aagtagtgtg aatagtgaaa aaaagttttc acatacttca catcaaaaat ttaagttgaa    900
taaattgtac atatgacagg tattatagtt tgacgagtaa tctataacct ctatcttatc    960
aaaattctga tagaaagatt gtattgtatg ataactgtac ttagaggttc acctttatt    1020 ttactggatt accactacat gttgctagat gtcactggtg gattgtgaga tctacgaaga   1080
ttatcttgat gatcgataat tctcattgaa aagattgaaa ctattttaat gatgttgtga   1140
tagagatcat aatatatctt attatcagac agaatagaat tctatgggat catacacaat   1200
aggagattaa gactgatcaa atagttgaat gatgattaag aatcattacg gagttcagat   1260
tatcaatata attgataatt agactaactt ataattgtta caagtagcaa ggacttaact   1320
gctaaaggtt aataggttca aaagaacttt atgtataaat gttgtgcatc ttaatttgat   1380
tggatcaaat tagttatggc tgaattcaag atgaatcaaa taggaatttg gttcaattga   1440
atttgggtca agcttaggc ttaggtcaca tatacccaaa atcatttgga tgcatcaggt    1500
gtgtgacacc tgaatcaggc ctttctaaac tattttgagt aagtttgatc aagtcaaaag   1560
gatccacacc ctaaggtttc ttgaataaaa ccttaggcac cacattgagg acctatagga   1620
aactttgacc ctctctcata tggggtggca cactgaggtt ttataaaaac cttaggcacc   1680
cattttagcc ataaaaaaaa agctccaagg gatggggcag tagccatgaa gaatccttgg   1740
ctgtcaggac tctattcaaa agagttctca aggttttgga ctcttatgga gccctaggat   1800
ttgtttgcct ataaatagat ggccacccca aggctttaga taatgttaga gacttgtgaa   1860 gctctccct ttctcttggt tgccggccca ccctctctcc tctctcttcc atgccccaag   1920
acttctttct tgtctccatc atcttgctga aatttagatt tcagcaagaa aagtcaagta   1980
gaagtcaaag ttctaatgta gctcacaaga tgttgagaac ttcctccatc tggcaaaggt   2040
tctgcaagag agctagcatc ctgagaaaca aaaagattgc tgatcagccc tcatctccat   2100
atggatattt gtagagatca gatgcatgca tagctagaag agaatcttat cacgatcatc   2160
actcgtgaag atcatctacc tgtgcaaagg tatgagataa gaaaaatatt ttttttatca   2220
taattcatga atcctttgct tatattatac tgagattctt ggaatggatt ttttctctag   2280
taaaactcta gagatcagat ctcgaagtct tcttcatata aaggttttga aagttcttta   2340
tattttcgct gctttgattc aaaataaatt agatctattt tgcctttcaa cctttctcat   2400
atttattgac atataaagct ttaattaatg agattaatga aaagcatgtg cgaaatactg   2460
agaaaatcct aacagtgata tcagagctac ttttgtacat aagaaaagga ttcaagttaa   2520
ataaaatctg tttgatttaa gtaaatgaat caatcaaaat ttatcctaac ataagtttgt   2580
cctggtataa tggtcaagac cattatgttg aaaggttatc ctaggacaaa aagtctaagt   2640
aaaatctatt ttatttaagt aaatgaatca attaaagttt attctaatat aagattgcct   2700
tagcataatg gtgaagaccc ttatgttgaa aggttgtcct aggatggaaa gtgattgatg   2760 agacaaaatat atcatgaaag tatttttcac agatggaata aaatatatat attttgtttg   2820
tgaaaatgag atttcatgaa tgtgtttgtc attcaatatg tgtggtgatc atcttgaatt   2880
gccacaaatc cttttggat tagggttgta tcatgactca caaatcctga tggtttgcaa    2940
```

```
aattttgcat tctgtagtga tagaaaccaa aagttaatcc agttttggaa taagattgat    3000
caattggtat ctaaggcaag tattttataa tggtggttac ttaattagtt ataaaagtac    3060
gaagagtctc ctaccaatct tacacttatc tagccaattt ggttgattga attctgaatt    3120
tgggttgctt aagtgttaag ttcactacaa atatattgca accatgattc cgacttagtc    3180
aaccaagcct agatctcttg aatagattca tgttaattat ggatttacat aggatataaa    3240
taaataatta aaacttgaag agatctaaat gaaaccttct cgtacatatt aaatcgaatg    3300
atcttccatc attgtagata tacggatact ctactgatgt tgatgatttt cgactagata    3360
tagtactttg gttgcatcga aaagtacaa ccactttata acatgagatg ttgcagggta    3420
gagatggggt tgggcccaat aattgttagg tgaggatcca aatgatggct gcacttgcgt    3480
gtgaatggcg agtctgactt aattaagaaa tagagctaat aactattaga tgaggcttca    3540
ggacttagag acttatgacc actacaactt acttgagaag caatggataa agagtcgtct    3600
atttatcaac tgacgcatca ccaataacta tcagatggag tgatgtataa ttagtgggac    3660
tatagtatcc acttgaaatc ttaatcgtaa aaattttgt ttctccacct gaagagcatg    3720
ggagattcga aaaatagtg ggggtagttt attttaaaa taaagctcct aaaataaact    3780
aaaataagtt aaatacaaag tctaactaga atcttcttct ctctgtagaa aatatctgct    3840
tccaacctct atttcatatc cttaagacta attgtttgac tagacccagt tataaagatt    3900
gactctaaaa cttaaagata gtcttgagtt ttgaaaagat gagctatgtc ctggatcaag    3960
atatcctctc tctaccagct tgtcccaccc ctaatcaagg ggcatcctat gaaaagtggt    4020
taaacgatga taacaaggct tggtgctgtg tgctgacatc tatgtccatt gaactccaat    4080
gccagcataa gggtacaaac tgtccaaggt atattgactc atctacaaga gttatatagt    4140
gagtagagcc atgtatctca ctaggaagta tttaagagac tcttcaagat gaagaagtat    4200
gatggatagt ctgttaatga tcattgtctg ataatgatca agaacttgaa agaacttgag    4260
aagctcgata tgtctatcaa taagaaattg cagattgatt tgatcctaca attccttact    4320
gattcatatg tgtagtttat tataaactac catatgaata aaatacagtg caccaaggtt    4380
gagttgttaa atatactgat aactactgaa gggacctcga agagttcaag aggcactgtt    4440
cttattatgg agcagacctc atcttcaag aaaaagtcta ctgaaaagaa gaaaaagttt    4500
gtgaagaagc agaagttaga gaataggcca agaaagaag ttttcaagaa gaaggccaca    4560
aaaaaggaaa agtattttca ctgcaactct gatgaccatt ggaagagaaa ctattctgat    4620
tatgtggcaa gcttgaagaa caaaaaagat agcataacct tgaagatat gtctgatctt    4680 ctcgttattg aaactaatct tacaatttct tttacttcca gttaggttat agactctagc    4740
tctagtgctc atctatgcac ttctatacag gatctggagg aaagtagaag gctgaggaaa    4800
gaagaaataa tccaacaagt tgaaaatgat gcaagagttg ttactatggc tgtggagatc    4860
tatcctctac gactaccatc tgatcttagt ttaattctta gagactgtta ttttatacct    4920
actgctagca aaaaattgat ctctatttca tctctagcat aggataatta tgtattaaat    4980
tttaataaag attattatac catttatttg aaaaataaaa tggttggacg taatttttta    5040
attgacagtc tctatcattt acatgttgat gtatctatga atgtaaccaa gcagaaagtg    5100
aatgccatag gatctaaaag atctaaagat gaaataaatt atatgtggca cattaggcta    5160
gatcatataa gagaagaaag gattaacaga ttggagaaag atgggctctt gggcttattg    5220
actactgagt tatatccgat ctgtgaattc tgccttcaag aaaaaatgat caagctgccc    5280
```

```
tttatgaaac aaggagaaaa gaccattaag atatttgccc tggtacatat tgatatatgt    5340
ggcccattaa ttcgatgcgc tggtcaaaga aggttgtctc tatttcatca tctttatcga    5400
taattattca cagtatggat atgtgtatct tatgagatac aaatatgaag tctttgaaaa    5460
atttaaaaaa tttagaaatg aagtaaaaaa ataaactaaa attttttttaa agattttttca   5520 atcagattga aaagttgaat accttaatgg agaatttcta aattatctca aaaaaaatag    5580
catagtctta taatggactc catttggaat gtcttaactc aatagagttt cgaaatagag    5640
aaatcaaact ttattagata tggttcggtc catgattagt ttcattgacc ttctcttatt    5700
tctttggaga tatagtttac ttaccactaa ttatctattg aatagggttt cctctaaaat    5760
catttctacc acattgtatg agatatggta ttgtagaaaa tcaagtcttg atcatatcaa    5820
gatttaagga tatccgaccc atatcaaaat atttcgacg gacaagttag aggtcagatc     5880
tatgaaagct cggttcaaaa gtatcttaag gagtctttag gatattattt ctacttttca    5940
gaggatcaca atatgattat aagccaacat gctctcttcc ttaaaaaata gttcatgcaa    6000
gatggaagta gtaggaggca gattgagctt gaagagagtc tctgaagagc aatgagtctc    6060
agaacttacg taaaacctat ttaagttgag ccaatacaca cacctcttcc tccatctcgt    6120
agatccagta aaattttttca ttctcctgag agatacttag gtatcatcat agagaatgta   6180
gagaaaatat ttctcgtgaa aaatgagaca tatgaaaatg accccaaaac ctatagcgag    6240
gcaatatcaa atatcgacta aagaaatgg ttagaggcta tgaagttaga aattaactca     6300
atacacttaa accaagtctg aacctttatg gatccgtcag aaggtatggt acctattatg    6360
tataaataga tctacaaaag aaagattggt tttgatggaa aggtagagac ctttaaggta    6420
aagcctgtga ctaaaggtta tagctgacac gaaagcattg actatcaata tattttttca    6480
ctagtagtta tgctaagtcc atttgaacat tacttgcgat tgcagcatat tatgattata    6540
agatatgaca gatagatgtg aaaactattt ttctaaatga atatctttag gaagttatct    6600
atatagagta gactttgtgt ttcacttcca gtgatggcga tcacaaagtt tacaaattgt    6660
aaagatctat ttatgcactc aaacaagcat cttggagctg gaatacttat ttcaatgatg    6720
taatcaaatc atttagtttc atcaaaaatg agaaagaatc gtgtgtgttt aagaaaatca    6780
gtgggagtac tgttactttt cttgtattgt acgtggatga catcctcctg atcgaaaatg    6840 atattttttat gttaattta gtcaaaatat agttgtctaa gaaattctcc atgaaggatc     6900
ttggggaagc atcctatatt ttggagataa atgtctatag tgataaatct atgaggatgc    6960
caggcctttc acagaagatg tacattaagg aagtgctgaa gaagttcagc atgaaaaact    7020
ccaagtggag acttctatcc ttcaggtatg ggattcatct ctccaagaag gtgtgcctca    7080
acacatctta agagatacag tacatgagca aaatccctta tactgcggct ataggaagtc    7140
tcatgtatgt catgttatgt acatgacctg atatagctta tgttgtgagt gtcacaagta    7200
gatatcagtt gaatgcaggt gaaaaacact ggacatctat gaaatgtatc cttaagtact    7260
tgagaaggat taaggatatg ttcttgatct ttagaggagg agaattaagg gtgcaagaat    7320
ataccgactt aaattttatg tttgatattg atgatcgaaa attgacatca gattatattt    7380
ttttatgcaa cggtggtact gtgagttaga aaagtttcaa gttgcctatc atagcagact    7440
ccattataga agatgagttt ataatcacat tggaagctac caaagaggca ttctggttta    7500
aaaaatttat tacagagctg gatataatgc catcagatgt cataccactc tactgcgaca    7560
acaatagtgc cataactcta gctaaggagc tgaggtctcc ccaaaagtct aagcacatag    7620
agcaatgatt taatctcatt cgcaattatc tcgaaaaaaa tatatcaagg tatagaaagt    7680
```

```
agatactatg gataatatga cagacccact aactaagtag ctgagtcaat aaaaaatcga   7740
agtccatctt gagaagatgg gacttagatt tgtggccaat tgattttagt gcaaatagga   7800
gattgttaga tgtatactct aaaagtcaat tagactgaca aatataaatt ttctaaggac   7860
ataatttata tattttgact tattaataaa ataaaatttg gattaatttt ttattcatat   7920
tttagtatcc atgaattatc caagagatta atatgataat gatatatatt ctcaagagtt   7980
gaaaatttga aacatacgtc attgatgatt aatttttgaa tgctttcgat taatggatga   8040
tcataaggat agtaattaat ccgatcaatg tacaaatcac ttcttttttg atagacgagt   8100
ctcgagtcta tactatggag acactggagc aagagtgcag gtatttgtta gagaacaaag   8160
gtatcgagcg tgactaatac gagaagtcaa ttggatggct atccactcgt taatgactta   8220
tttgatacta cagtagtatg tctagtcctt agatctgcaa tgcctcaggt gttcataatg   8280
agactgttag agtttgactg tacataaact tgatttctag ccatatggat ctttatagtg   8340
catgttggct acagtaggtt cgttgtagga ataggatgtg cacatagata gaatctatca   8400
tccttgatag acaaaaaaaa tgatcctata taatttatga gactgagttc aaaaaatctt   8460
gactaagaca gtgtgaataa tgaaaagaag tttccacata tacttcac atcagcaatt   8520 ccagttaaat aaatcctaca tataataggt attgtagttt gatgaataat ctataacctc   8580
catcttattg aaactctgat agaaggactg tatcatatgg taactgtatc aagagattca   8640 tctactatttt tgctgaattg tcactacaaa ctgctagatg tcactgatag attgtgggac   8700
ctatgaagat tatcttgatg atcgatgatt ctcatggaga agattgaaac tatttcaatg   8760
atgttgtggt agaaatcaca atatatctta ctactagata gaatagaacc tatgaggtca   8820
cacataataa aaatttgaga ttgatcagat tgttgaatga tgattaagaa ttgttacagg   8880
attcagatta tcaatataat tgataattgg actaacttgt aattattata agtagcaaag   8940
atttaattgc taaaggttag cagattcaag gaggacttat gtgtaaataa tgtacatctt   9000
aatttgattg gatcaactta gttatggcta aatttaagat gaatcaaaca gggatttagt   9060
ttaatcgaat ttgggtcaag ctttgggctt aggtcacatg cactcaaaag ggtttggatg   9120
catcaagtgt gtgacaccca aaccaagcct ccctaaacta ttttgagttg gttttgacca   9180
agtcaaaagg gtccacaccc tagggtttct tgaataaaac cctaggtgcc acattgagga   9240
ccaattagga aactttgaca ttcttttcaca cggagcagca cactagggtt tcatgaaaac   9300
cctaggcacc cattttagcc ataaaggaa agctccaagg gatgggatgg tgccatgaag   9360
aatccctggc cattgggact ccattcaaaa gttctctagg ttttgggctc ttatagagcc   9420
ctagggtttg tttgcctata aataggtcgc taccccaagg ctttagataa tgctagaggc   9480
ttgtgaagct ctctccttc tcttgtttgc catcccacct tctctcctct ctcctccatg   9540
cctcaagact tctttcttct ctccatcatc ttgttgaaat ttagatttca atgagaagga   9600
tcaagtagag tcagagttct actgcagttc tcaaggtgtt gagaacttc ttcatcaggc   9660 aaagattctg caaaggagtt agcacctcaa agaaccaaga aagttgctaa tctgccctca   9720
tctccatgtg gatacttata gaggccaagc atgacgagaa gagccttatc acgatcatca   9780
ctcgtggaga tcatctaccc gcgcaaaggt atgagataag aaaaaaatat ttttcttatc   9840
atgattcatg aatcctttgc ttatgttaca ttgagactct tggattagat ttttctcta    9900 ataaaatttc aaagattaga tctcgaagtc ttcttcacct aaaggtattg aaagttcttt   9960
atattttcgc tactttgatt caaaatagat tagatttgtt ttgcctttca attttctca   10020
```

```
tatttattga gatatgaagc tttaattaat gagattaata aaaagcatat gtgaaatact    10080
gagaacatcc taacaatttg agcttacaat tcacttaaac aactaatgat caaattaata    10140
atcacaatgc acaataaaaa ttcatgataa atcttttgt tgttacttta gatcaaaatc     10200
caactaatca taacatgatc cacggattgc ctatcatata tcaaaccctc tgaattatta    10260
atcttaaacg atcttttcat tcatgatcat aagatttagt taaaaatcat gaagacaact    10320
tatattgtaa tcatcataga tctgtatctt aacatcctta gtgtttacct acctatactc    10380
atcctatgtt tgattctata tatcataatt tattcactaa tactttgata tcatataaat    10440
tatcgcatcc ccaatctaag atcatattgg tactttaata tttcattagt gggggttatg    10500
cattagtact ttgatacctt atcagttgaa tggttaaaca ctggtacttt gatatcctat    10560
cagtggaggt tatacgctgg tactttaata tcctatcagt aagatggtta aatactgata    10620
ctttgataac ctcccagtgg gtgttgtatg ctagtacttt attatcctac caatggggca    10680
gttaaatgct actactttga tacgctacca atgggatagt taaacgctag taatctaatc    10740
ttagcttgac ataaagtaac gtcgactcga gtttagggtc gactcgagag aatgttaggg    10800
ttagcttgat atgaaagagg gtcgctcgtc aatattttgg agtcaactct tgtttatgga    10860
tgatctagaa agtgtcagag tgagctcgag tactgcatat ttctgataca ttgtctatgc    10920
tagaatgtgc tagaactgat tatcttcttt atcaaagttg atttttgagt aacttgatga    10980
tcaattttc taggctagac ttgctttgtc aaaatgagca cttgttagtt tagagaatct     11040
tcacctacac atgatctcaa gcattcatta gtaccaaaaa tacttaagta ttttgatatc    11100
atcaaaatca attcttgggt taacacaata cttttcaaat aataagcata cagatataat    11160
cctataacaa tttaaatttt gttcatatat caatttcttt aaaaatatta tattcatctt    11220
gatagctatg aactaaatca aaatacatac tagtatacaa cttttactgg gagagtatta    11280
gattaccagc atttaaccat cccactggca aggtatcaaa ttaccaatac acaacccta     11340
tttataaagt atcaaagtac cagtgttcaa ctgcctcact ggcaggatat catagtacta    11400
gtatttaact accacattga caggatatgg aattatcagt attttaaccat cattagtaga    11460
attttgatgc atagtcaggc tgcgagtcaa aatctatctc aaatcaaaat attgatcaca    11520
tgtctaattc tgtatcataa ttcattccct tatgctctaa tattatatta attgtcatac    11580
ttctagctcg agatcatgag ccaaggattg cagtaactac cgcatactta tagagaactc    11640
tttctataag catacaagat attctaaata tactatcaat atatcataga gaaattaatt    11700
taaataacta aaagttaata ttcaattaat aaattcaact ggcaaatgta tttaaaaatt    11760
ttacatcaaa taaatcttga ttaataaata ttaattaata acaatagatt taaatcgaaa    11820
caaggttgat attgttagaa tttgatgcct caagattcag cccacattga gtccacagtg    11880
aggttcgcga cgaaaaatgn nnnnnnnnn nnnnnnnnnn nnnnnnnnnn nnnnnnnnnn    11940
nnnnnnnnnn nnnnnnnnnn nnnnnnnnnn nnnnnnnnnn nnnnnnnnnn nnnnnnnnnn    12000
nnnnnnnnnn nnnnnnnnnn nnnnnnnnnn nnnnnnnnnn nnnnnnnnnn nnnnnnnnnn    12060
nnnnnnnnnn nnnnnnnnnn nnnnnnnnnn nnnnnnnnnn nnnnnnnnnn nnnnnnnnnn    12120
nnnnnnnnnn nnnnnnnnnn nnnnnnnnnn nnnnnnnnnn nnnnnnnnnn nnnnnnnnnn    12180
nnnnnnnnnn nnnnnnnnnn nnnnnnnnnn nnnnnnnnnn nnnnnnnnnn nnnnnnnnnn    12240
nnnnnnnnnn nnnnnnnnnn nnnnnnnnnn nnnnnnnnnn nnnnnnnnnn nnnnnnnnnn    12300
nnnnnnnnnn nnnnnnnnnn nnnnnnnnnn nnnnnnnnnn nnnnnnnnnn nnnnnnnnnn    12360
nnnnnnnnnn nnnnnnnnnn nnnnnnnnnn nnnnnnnnnn nnnnnnnnnn nnnnnnnnnn    12420
```

```
nnnnnnnnnn nnnnnnnnnn nnnnnnnnnn nnnnnnnnnn nnnnnnnnnn nnnnnnnnnn    12480
nnnnnnnnnn nnnnnnnnnn nnnnnnnnnn nnnnnnnnnn nnnnnnnnnn nnnnnnnnnn    12540
nnnnnnnnnn nnnnnnnnnn nnnnnnnnnn nnnnnnnnnn nnnnnnnnnn nnnnnnnnnn    12600
nnnnnnnnnn nnnnnnnnnn nnnnnnnnnn nnnnnnnnnn nnnnnnnnnn nnnnnnnnnn    12660
nnnnnnnnnn nnnnnnnnnn nnnnnnnnnn nnnnnnnnnn nnnnnnnnnn nnnnnnnnnn    12720
nnnnnnnnnn nnnnnnnnnn nnnnnnnnnn nnnnnnnnnn nnnnnnnnnn nnnnnnnnnn    12780
nnnnnnnnnn nnnnnnnnnn nnnnnnnnnn nnnnnnnnnn nnnnnnnnnn nnnnaagata    12840
ttactaaatt ttgcttctaa tctcactctt aaatagtact tacctttgaa actaggcatt    12900
tgaatctgaa aaagaaagag gagattatga gcttgatagt tcagtaaatc atgaataaat    12960
tagctaaata aatctatgaa taatagtata ttaaaaataa atatgtaaga tacaataatt    13020
caaaaatgaa ttcatatata taatactttc caaataataa gtatgtggct gcaatccttt    13080
cgtaattcaa attttgttca ttaattattt ttttcaaaac atcacatgga tagtcatgaa    13140
ctaaatcaaa gtaccagtgc ataacccta ttgataaaga atcaaataac aagtgtttga    13200
ctgcctcatt atcaggatat caaattatta atgcataacc tccactgcta gggtatcaaa    13260
gtagcaacct caatcacctc actggaaggg catctagttt cagtatttaa ctactccact    13320
ggcaaggtgt taaattatca atatttaacc tccactgata ggattttgat atatagtcag    13380
actgcgagcc aaaattcatt tcaaaccaaa atattttct caaagacata ttttatgttt    13440
cacattgaaa aattcacaaa aattatgcga tattgaaatc aattggataa atccacgtc    13500 aaatttagta tattcaatca taaatcattt actattctag aaaaggtata ttaaaagtat    13560
aatgcatcaa tttcataaat cataaatatc tcaatataaa aatatttta ttatttatta    13620 ataaatctag gagaagtgaa gcattactta tcttgtaagt aaaactaacc aactgatcaa    13680
attaattctg agaatctttc tcaaaactca tcaccactat atcaaaaact tgtgcttctt    13740
gctatgtaag agcatagacc ctttcttcga tctggggttc caagtttcta ttttattttg    13800
ttcaactatc aaattagact gacttttcat ttttttgtgg atattcagct attttatggc    13860 cttctaaca ataaccaaag tatgtaccaa tattccaaca ataatcattt attgcatgat    13920
tttcaccgca tcgaaatatt tgatatattc aatcaatcca aacttgttat tcactgacct    13980
cttattcaaa cccttagtat atttaatatt ctacctttgt gattcattca atcgatttct    14040
ttttttttat tttctttccc tttctatatg ctcttcatta acttttcttt caattatcaa    14100
tgctttattc aatacatctg tataagtagt taactctatat agtaccattt attttctaat    14160
ttctatcctc aattccaact caaatttatc tactcagtca cattcatctt caaccaatct    14220
cgaagcaaac ttgacaagct ccataaattt agcttcatat tctacaacta ttatatttct    14280
ttatttcaga taaataaatt tttattcttt ctgaatcctc atactctaag aaaaatattt    14340
ttatcataaa atatctttg aaatcactcc caagcgagtt gttctccatc ttgttcatat    14400
ttaggtttca ttctctatta tcaattaaat gtctcatctt tcaacatgta tgatgcatat    14460 aagattttt catcatcatg gtatctctta acaataaatg ctttctccat ctccataagc    14520 taattttag ctcctatttc atagttttct taaaagtcaa tggagacaac ttcttaaatt    14580
ctatgatatt actttattgc tcctattgct cttatgtcct tgtggtgaca atatttattg    14640
ttgcacttgc tgtagaggca gttactgtta ctgcaattgc tattacgatt ccatcaagcc    14700
gactagtgtc tgcattattt ggataatagt tgattttgc tactttattt agatgttggt    14760
```

| | | | | |
|---|---|---|---|---|
| ggcaaaatca | atgacttctt | tttgctgaga | gatgccacca | acctactaag tatcatcatc | 14820 |
| ttattggttg | atacctttag | cagcacctcg | agtggttctt | tttatctgat atggaaccat | 14880 |
| cttaatcttg | catgaaaaac | aaacttcgca | aaattttctt | ttaaaatcta atatctaata | 14940 |
| ttatactttt | attaaaattt | aattatgatt | attttaagaa | taaaaatttt aaattttgaa | 15000 |
| atcctcacaa | ggctggccaa | gagataatga | ccatcatcct | agtcggtttg acgtaggaca | 15060 |
| tccaaagatc | aactataatt | caagcatcat | attgagatgc | taggatataa tcgatggtga | 15120 |
| aatttaatga | tgctcgactg | atcaagatgg | gggccggccc | gatggcctgt tcaacaatca | 15180 |
| ttgatcaaaa | tttttaacc | aaggtctatc | aagatcatta | aaagtctttt ctaagatcta | 15240 |
| taaattgtaa | taaagagaca | caatctagag | agagacactt | tttacataaa gaaagtagaa | 15300 |
| attttaggga | gagaaattag | agagaaaggg | gaaagagaga | ggaagctgag aggaagaaag | 15360 |
| aaaagagaaa | gactctctct | ctttttcttt | tctttctttt | ctctcttttc tttttctttt | 15420 |
| cttttttttc | ttccttttct | ttctttcttt | ctttggctca | ttagaaaaat aggggaccta | 15480 |
| ttgatccct | tgtttcctaa | ataggggagg | aatctcatct | tggtagctat ggccggcgat | 15540 |
| gtgagccaaa | gtggcaaaat | catgaatct | | | 15569 |

```
<210> SEQ ID NO 3
<211> LENGTH: 3181
<212> TYPE: DNA
<213> ORGANISM: Elaeis guineensis

<400> SEQUENCE: 3
```

| | | | | |
|---|---|---|---|---|
| ttcaaaatga | tgaacagatg | catctcaagt | cagcactaga | ccatcttcta aaataggaag | 60 |
| atctatggaa | gcaacactcc | caaatgcagt | ggcttcaaaa | tggggattgc aatacgaagt | 120 |
| ttatccatgt | ttgggcaagt | aacaggaaaa | aaagaatact | atcactgaac tctagcaagg | 180 |
| cgatcagaag | attatcgaat | agcagcaaat | ccaatccaca | ttctacaact tttttctac | 240 |
| cctactaggc | tcgactgagg | aatgactcat | ccaagctgat | tagaagattc tttatccaga | 300 |
| aggacctctg | gatcttgctg | acattgagta | tccatttatg | gagaaagaaa tccatgatac | 360 |
| agtgtatgac | ttggctttgg | aaaagtcacc | cggatgtat | tttcccattc tccttctata | 420 |
| tgcacttcta | gtgtatcatc | aaacatgacc | tgatgaacct | actgtaaaat cagctaatgt | 480 |
| agaccatctg | aactacttgt | tcatcaccct | tatcccaaaa | aaaaattggt gtgtattcag | 540 |
| ttagagactt | caggccaata | agcctgatta | atggagtaat | aaaaaatatt tcaaaaactc | 600 |
| tatcgaaaag | gctctcacag | aaaatgaatt | tgttaatttt | atccacagag cttgctttca | 660 |
| acaaggaag | aaatatctct | gaatattttg | taatgactat | ggaaactata cacttctgca | 720 |
| aagctgaagt | acacaaggat | ctcaattata | aagtcgactt | cgagaaagct tttgacaatg | 780 |
| tggattggag | ctttctattg | aaattgctat | ccagcacggg | gctttgattc gaggtggtgt | 840 |
| caatggatag | aatatctgat | ttatacagct | aaattctcag | tccttattaa tggtgataaa | 900 |
| ggtaaacttt | ttaaattgag | gaaagatctc | aggcaaggag | atcctctatt cgcctagctc | 960 |
| tttctcttag | ttgttgatat | agaatgatca | agggagcaag | taggttcaat cttttgttg | 1020 |
| gaattggatc | atataatatc | atgggataac | ttcaaagctt | ttagttcact gatgacacac | 1080 |
| ttatattttg | cagatatgat | ctaaaataca | tcaaaactct | taaatttta ctctatagtt | 1140 |
| atgagctact | gatgggtctc | aaaattaact | ttgaaaaatt | ccatttttt ggcttgagaa | 1200 |
| ttgcaaagat | gtcagtacag | caagttgcat | ctatcctaga | aagcaaggtg gctacatttt | 1260 |
| ccattactta | tttgggtctc | ccactccatc | attctaaact | gaggaaaact tattggaatc | 1320 |

```
cactccttga aaggttcag aagaaattga tcgggtagaa aggtaaactt cttaacctct    1380
agggtaggct tatactaact aatgcagtgc ttacagggat cccactactc tggagggata    1440
cattccttct ccctcaattc attatcaaat aaattgataa atccatcga tcattcattt     1500
ggagaggaaa cgaggagtat aactaagggc actctagaat atgttggtcg aatatttgtc    1560
gatcaaaaaa atttggagga ctggggttc ctcaatctaa aaattttcaa tacaattctt     1620
ctttgtaaat ggtggtggaa gctctactct aatgctggtg acccgtggtg tagttttatt    1680
gccactatcc acccaacttc acactagaga tctaaaggta tacacaaatc aacctcttca    1740
ttttggaatg gtttacagca cacatgaaat atttctactc ctaatccact ttcaagttag    1800
caactagtat tattttggaa agatagttgg ttacataatc atccactgaa ggatcgattt    1860
cctcacctt acacaatagc attgaagtgc aacaactcag tggcaaaggt attaagcaat     1920
ctacttgata atagctcttt tagtactcct cttcctcaaa gataccaaga agattttcag    1980
agtctatagg aaagcattga acaaattaca ttaacggaac gacctgatac tatacaatgg    2040
aaatggttta gtagcaatat ttttttggca tgaaggatct actattttct gcaagatgga    2100
ggagtttggc ctctactgag taatattata taaaaactcc taataccaaa gaaagccaag    2160
ttatttgctt ggctaagtgc tcacaacaaa atcccaatga aagctaatct tcttaataga    2220
ggaataattg gaactgatta ctgtacactt tgcgatgact tatcagaaac taatgatcat    2280
ctaatgctca tctatacttt ttcaaaagca atttggaatc aagtactttc agacctgcaa    2340
ttgtcgaaac ttttatgcat gcttaacacc ctatgggata cttggagact catcaatatg    2400
caacacgata gaagacctaa actagctgct ctattcgtaa ttggtcaatg gtgtctttgg    2460
aaggaaagaa ataaaagatt attcgacttc tatactttt atccacgatc gattgctgaa     2520
actgtgtcac ttttctttc ttgggcatca cacctaacaa cggagcaact aaagatgtta     2580
gctcctgttc gagaagttct cttatctaag aatgaaaaca cacaatcttt agtgagaatt    2640
acagatgcta acaggcgcag atgaatgttt tatgagcatt tttatagctg cagcttatat    2700
gtgatctatg gtgcaaggag ttaattataa ccatggatat tagttaggtt gactatcaga    2760
aatcatctcc aatacattct atgtaaccac tgatcaattc catgttcaac tagataggaa    2820
cctgcctata tacaggtatg tccctgatgt aactatagta tactattatt cataaataaa    2880
taacgaaggt tttaccttct tctcataaaa aaaagtatc ttcatgtcat cctatatgtc     2940
atgcatctcc tttgctactt ctttttatta cttcttaaac ttggttctac catatattat    3000
cagccccttt taaattgct tttggatatt gcatattcca ctcttcaatc acctcatgcc     3060
aagcaaaaca tttattcaca cttgaaaacc aatataagaa taccaagaa tttatccatg     3120
aaattctaga aactttggtt ttactccttt ctccatcatt caaaaggtt caaaatgatg      3180
a                                                                    3181

<210> SEQ ID NO 4
<211> LENGTH: 14184
<212> TYPE: DNA
<213> ORGANISM: Artificial Sequence
<220> FEATURE:
<223> OTHER INFORMATION: synthetic predicted full EgDEF1 cDNA transcript

<400> SEQUENCE: 4
aggagagaga ggggcttggt ggctgactgt cagaagaagc ctcgatgctc gaagattaga     60
tggaagaaaa aaaaatttct caaaacttct cttttctata agagcaaacc tcactattat    120
```

```
aaatagggtt atgtatctca gtttatgatg tgaagaatta atgaaaaatt ggactttagc    180
tctatttttg taattctttc atcttctatt tttatgaaat tcaagttgag ccgattaaaa    240
gaaataatct ttctttccga ttggatcaat ccattaacta gatacttcaa aaatcaaaat    300
gacctatcta aaatcctaaa tcaaatacaa aaccaaaata actaaattaa gatagaacaa    360
actacaatta caaaaaactg gctaaagtgt ttaaatgctt ttactcctaa gtttcttctt    420
gctcaccatt aatgcttgat ctttagctgg gatcatatca gccttatgac cactataaga    480
ccaacataac aactcacttg tattgctcct ttaaaattat acaaaactag tgtctaatat    540
gtaccatgcg aatgtctgtt tctcaccaga aaatggatgg gcttcttgtg caagcacctt    600
cttcctacaa ataataaaat atgcatccct tctctcatct tactaaataa aataattaaa    660
ggctttacta tcaggaaatc tggctttatc catataattt tggaagtttt atttgaacat    720
aacattacga gtactagatt acatcaggag gtggttcctc ttatttctat taagagaaaa    780
atcaattttc ttttaagaaa gatcatttca ttttcatcag gtagcgtact ctactaaatat    840 acttccacaa caatatatag ggattagatt ataggatgga ctttaaggct tcttttcgag    900
agccctgatt tctcaatcac attcccttt ctttctcatg taatggcatt taagagtgca    960
tccagggccc aacaattagt cacaagtgtt ctttttatac atggtacata tttgctattt    1020
tttagcttat tttaacttga ttgtgaagat atcatgagaa aattagattt aaagcctagc    1080
aatcttgaac ccataatttc aagttaacag gtggaagagt ccattattat gtgagaccaa    1140
cttagactgc aaaactatct gatattggac tatttactaa caccctttt catgtgcaat    1200 gtttgtaaag agaagatata tgatgtagcg agataggata gtttggctct aatattgtgt    1260
taatattcaa accaaaatcc taagctaata gatggaagag aaatgactta tatacatgtg    1320
cattattgga tatatcttta tgggagaaat aatcacatgg atgtttatat cacacatctc    1380
atatgtgcat gttgttgtaa ggcttcaaaa gacagacgat gagattggtc ttggatcaaa    1440
ttggaatgtt tcttagttga atttggagaa gtctgcaaca aatcctataa aagaagtccc    1500
gaaattggtg gggcaccttt cgatccaaga cccttcgatg gataagtcaa ataaagcctt    1560
gagaacagat tgtggaaatg gaagaataga aggatgagaa aagagattgt gaacaaatgg    1620
agagaggact cttgtttcct tcagtggagg agttgaaaat gattcaacaa agtctccact    1680
ctatctatcc cgacttacct tatggagggt atgttaccct cctttatata gaggggtgag    1740
gaggcttgct caagttgtta ggccgttaat ttattataat agaatggtca gctatataaa    1800
gatcatggga tgtttatcca tgtgatgatt agctatagga tagctagaaa atatctaatg    1860
cttaattaga tgatagctgt cagataaccg tctgcattct tatagtacat cgatattta    1920 tcgacgtgac tagcttaaat cagcaactga ctgaactgaa tattatgatt cttttagtta    1980
acaatcatat tggttagaga ccgatgtaat tcatagtaga tcgatcacaa gctgagatga    2040
gtatcatatt ttaagaacaa tactagcaag ttagatcgat caaatgtcag atgaaaaagt    2100
agatcagtaa acgttcgatg gaacctgaaa gaatatttat gatttagata taatctatc    2160 atcacgtatc cagataatga gatcatataa catgtaccaa tatatgccct ccattttca    2220 caccgaagtg aagttcttca catcgggtgt ggaaagtctc ttcagaagat ctcacctgac    2280
ctgtattgtc atcataaatg ctccatacca cgatggttgg aagtattaat ttttaatca    2340 ctcaaagtca tacacaattt cttgaaaatg atttgttgaa cttagtaatg atgagcgctt    2400
agaaaatcgg gagctcacaa ttatttgggt ggctagtccc taatgtgtat gtgctaggtg    2460
tcatactgta attggccact tcagctatca catggatcct gcttgcatgg cttaatcaag    2520
```

-continued

```
aagaggtgcg tcgcaacaac tctctgcaga accatcggat aactgacaag tggcattgat    2580
ctaatggcat atcaaatgga ttgagactgt tagtaaattt tataaatagg tctatactct    2640
gttcaaaaat tactttacta tttttttcac atgacagtct tgctgaaatt ttttcagagc    2700
ccctaacatc attggtatcg gagtagagac cccccaaagt cattggagcc ggagaagaaa    2760
gaagtaaaga agtcttttaa aagcttcctc aaattcctct ttacatatta ggcagactct    2820
ttcatcttca acttctttc catgaacatc tgagatttta ggttttacaa tctttatttt    2880 ttttttttgga tagttattcc cttttctctc tttttttttc tgtttctctt ttcccattca    2940
cctttacttt cttctttcct ttcaaaaata tcttttgata ggactaatga gataagtcag    3000
gaccaatgga tatctcggtc aacccaacca ctgctcaagt ttgagatgga aaatctatct    3060
cggacaacag ctgaagttag tacctcaggt taggatgatc tagaatctcc tataagagat    3120
tttttagatt atttcggccc aagtactgaa caatctgtcc tgaccaatct cgatctttag    3180
gaacttaaga aaaatattc gattcagctt ataactccaa gttgggatgg taggattatt    3240
gaacctccag aaggttatgt cgtatttat gatgaggcac ttcgatctgg acttaatt    3300 ctcttacatc ctttcttcag taatgtttta gacttctata aactccatcc aatctaggtt    3360
actcccaatg ccattaggat gatcatagtt ttcattatct atcgtaaatt ttttgctata    3420
gaactaagaa tttctctctt taggatgctg gtcatcctaa gaaaacatcc ttatgaaaaa    3480
gactgatggt atttcttacc ttggcctcaa tataaattcg gtcccactct tccttttca    3540 atacataatt gaaaaaatca ttttttcttt atttcttcta atgtttcgta gggttttatt    3600
tgtaaatagt ctaagcctaa aaccaaatgg aactcaaata acaaaatatt atctgaggat    3660
gaggagactt tgtagagct tttagatatg aaagtatcca agttgagcct actggtgtcc    3720
aatcagtcct tgtttgacac cgacatcagt cagatctctc cttaagataa gtctgatgtt    3780
aattcttttt ctttattgct ttatcatttt tcatcatttt tcttttctaa caatcttttt    3840
ccttatatag tagcaataat gaagttcaac ctacaaaggc tggctaactc aaagaagagg    3900
aagaaggatc taaccgattg ctctcaagaa gagtaaggag actgctcctc taagatcgat    3960
tggcccccga tcatcacctg gccaatatt aattgacata gatgctacat cgatctccac    4020
tataccacca gcaaaatcaa ctcatcaacc tactaaggtg gcttgtccac ctcctaaaga    4080
gtctgcacat ccaaagtagg catcttcccc aacacctcca acatcggcca agttagtttg    4140
gctgagcaat cagcatctga ggtcacagac tcctgatgtc aacccaccaa ctttctcatc    4200
aaaaaaaaat tgacttggcg aaggtatcac ttttggagac acccagacta ggcaaggact    4260
tgctctgtac aatgatgcct caaaaggacc tagatgctga taggagggat cttctctttgg    4320 agcaaataat aaattatgga ttcaacagta tcatgaacgt gagtcttcat tctcttccac    4380
tctcttcttt cttttctttt tttttttta cattggctat tgttgatct gaatatatct    4440 ttcttttgc agtcggttgt gtatttcaag ttgctcaatg agcacttgac atggttcttc    4500
aaaaataaaa atttttttga agagaggct caaggccaag aaagaggcca aaaagcagt    4560 tgaggaggtc aagaaggcag taagaagaa ggctgtcaaa gaaagcaaaa tgatggaggg    4620
gctgaagaaa cagctccaag aaaaaataga ttccattaag gagactggac aaccaatgac    4680
agatgaatga taaagatgac aagttgtaaa aacagcctga aaaaaatctc aaagttggag    4740
gccaagctga aggaggtcga gtcaataatt gaaaagcatg atgaagctct tgtcccatat    4800
tagagacaac ttgataaaga caaagagtgg atgtcaagga ttattgaaga ttataagaat    4860
```

```
tccgacactt ttcaagatga cgttactgag gcctcaaaag gagctttcaa ttatggcttt    4920
ttgagctaca ggagtttaat tatcaagctc tttcctaacc ttgatctcag caaggtcata    4980
atagaagcag ctctagaagt agtagccgaa gtgacttctg caacaactac tgagcttgct    5040
tccacttcta tcattggagt ttctccgatc gaagtcccaa acagtccaat cgaggcctcc    5100
atcatcgaag ctatttcgaa ggaatcagtc ggcaaagacc ttacctcaac tcctccaaca    5160
aataactccc aagctaaggc ctgaattatc ttcttctttt ttttctaaac atttgtatta    5220
gcccgatgtg ggcttctata aatactttt acattaatga atgagttttt caatgtcaat    5280
attttttctt tttaactaat actaatcttg gatgatccga tctgggttgg atgtctcaaa    5340
aaatatcatt cacgatagat agttatttc tgacttcggt tagatgatta tgagtatatg    5400
taattcaacc ttggttaggt aagtaatcaa atattaacta ttctcaaacc aagtagataa    5460
cgaagtcaat gtgattaact ttaacaagta agattgttat ggaatgaaat tgaatcagat    5520
caactaacta tagataactt aatctctcat aattcactgt aaaggttcta aaagtacctt    5580
tatctaagtt cgaagtgaca agtcgggttc ttttattcgt ggatttatga cccatgctgt    5640
cttttgtga tcttcattat taatcacctt aaatcgatat agcaaaatcc agtttataga    5700
tctgagtgct ttcttgtcag attgagtcta tcctattatc tgtgaaacct gatctagaga    5760
tcaagtattt taggttttt atttaaggtc caattcgaag attgagtatc caatgtcata    5820
ttgttaggtc caatttggag attggatgtc tcactatcat ctcgtgaggt ccaatccaaa    5880
gatcgaatat ctcactatca tctcatgagg tccaatccag agattggatg tctcacatca    5940
tcttgtgaga tccaattcga agattggatg tctcacatca tctcatccta ttgtggttgg    6000
aattttgta gccttagttt gactttttct gacctcattt ggacacctaa atcttattat    6060
catcgtttga tcgatttta ctaatctact ttggatgaaa aagaattctt caatggaact    6120
tttgattaga actttatctt cattgggata gaaatcgaat gctttattga aagattttat    6180
tgataataca ttctgagatt tttaatattt catgttctcg aaatgatcgt accatctaaa    6240
tttttaattc gataagctct tggatggatc acctcagtaa tctgataagg tccttcccaa    6300
ttcgggatga gttttttctta ctccattggt tttgagactt cagctcattg gagaaccaaa    6360
tctccttata aaaatttta ggctttacct gagagttgta atatctggct acttttgtt    6420
tataaactac catatgaatc tgggcttttt ctcgagtttt ctcaaataaa ttgagatcag    6480
tcctcagttg atctgaatta ttttcttcat gaaaattttc tattctggtt gtaggtaaac    6540
tgatctcgac tagtattata gcctctgttc cgaaagtaag tttaaaagat atttctctag    6600
ttggtctctg aggtgtagtt ctgtataccc ataaaatatt ataaaattat tctaccccga    6660
gactttagc ctcaatgagt tttatttta ggccttgaaa gatagttcta taaataaatt    6720
tagcttctcc atttgattgt agatgtccaa tcgaagtaaa tatatgatct atgtagagct    6780
cagaataaat tttttaaaa tttttgattat caaattattg ctcattatta gtaattataa    6840
ctcaaggcaa accaaaatgg taaataatta ttttcacat aaaatctcat attttttctc    6900
agtgatttat gtcagaggtt caatttctat ccattgggta aataatcaa tagtcacaac    6960
taaaaatttt ctttgctcca tggccattag aaaggatccc agaatatcca ttctccatat    7020
agcaaaaggc cacagcactg taatagaaat aagttcagtt gtaggctgat gttatatatt    7080
ggcgtacctt tgacactgat cgcagtactt attaataaag tcggttgaat cttttttgaat    7140
agtaggccaa taataatctt actgaattat ttcataagct aaaattttac cccccaaatg    7200
gttactagag attccttat gaacttctcg aaggatgtaa tcagcttccg atggccttag    7260
```

```
gcataggagc agtgggagtg aatataacct ctgatataat tgattatctt gaacaacata   7320
ccatggggcc tgtcttttaa ttcttgttcc ttcgactgga tcaaccggta gaggttcttt   7380
agtaatatac tccattaatg ggtcaatgga acttagctca tattaaattt ggacaattag   7440
taaggcctcg atactagact ttttaagaat atcaataaga acaccttgat ttagtttgaa   7500
aaaatctgat gtggctaaat gagatagggc atcagctcag acattttgtc cttggtattt   7560
gcatgatctt cagattttca aagttttta ataattcttt catattatat aaatattgaa    7620
acatcataaa atctttagct tcaaattaat ctcatacctg actgacgata aattgagaat   7680
caataaaaat tttaattttt ttaacattaa gctccttagc cattttgagt cctacaatta   7740
gcgtttcata ttctactcca ttgtttgagt gttaaaatta aatctcaaag cacgctcact   7800
aacaatgcct tctagactcg ttagaattaa actagttcta ctttctttcg aatttgaggc   7860
tccatcaatg tacagtatca aataagaatc tttgatattt ttcaattctt ttaagattgg   7920
ttcttcatta ggaatagagc attcaataat aaaatcagct aatacttaaa ctttcaatga   7980
agatcgaggc ccatattgat atcaaattca tttaattcaa tagcctattt gaatatcctt   8040
cttaaagtat caagctactg taaaattaat tttaaaggtt gatcgatcag aattataata   8100
gaatgagcct aaaaatacga tcaaagtcat cttgctaatg caatgagggt ataaattatc   8160
ttctcaattt tagaatatcg agtttcaaca tctctaaata atttatttgt ataataaatg   8220
gatctttgta tccctgcatc atttcaagct aaaatcgaac taacagcatt tgctgaaata   8280
gatagataca tgaataattt ttgaccttg atcggctttg atagtaatgg agctgtgccg    8340
agatatttct tgagatcatc gaaggctgct tgacattcat cttatcaatc gaagtctttg   8400
atctgcctta gaattttaaa gaaggaaga tatttatcag ctgatctgaa aataaattaa    8460
ctaagcaatg ctactcatcc agtaagttgg tgtacttctt tgatggagct cggatgcttc   8520
atttcacata gagcttgaat tttcttaaga ttgactttaa ttcctctttg agttacaaaa   8580
aaatctaaaa aaattttga agttacttca aaagcatatt tgttgggatt gagcttcatt    8640
tgatattttc gtagtctcta aaggcttctt ccagattggc aatatactga tctgactcag   8700
tatttttttac taatatatca tcaacataaa ctttgatatt aatttcaatt tgttacttaa   8760
aaatcttatt aatcaagtat tagtatgtag cacctacatt tttaagatca aaagacatca   8820
ttttataaca atgcaaatct ttttcagtga tgaaggccat attttcttca tcctcaagtg   8880
ccattttgat ctgatataac cagaaaaagt atccataaag cttagtaatt tgtgtcttga   8940
agtagcatca acaagctgat caattttga gagagaaaaa ctatctttta ggcaagcttt    9000
attgagatcg gtataatcaa catagatcct tcattttca ttagcctttt taaccatgac    9060
aacatttaca atccactttg gatattatgc ttctctgatg aatttgtctt tcaagagttt   9120
gtcgacttcc tcatctatta ttttttatct tttcggggtg aaacttcttt tcttctgttg   9180
cattggttta tgctttggat caacattcag cttatgtaca ataagatcag ttaaaatctc   9240
aggcatatta gagactgact aaacaaagac atcggcattc atccgaagaa aagatattaa   9300
tttctccctc agatcaggct tcaatagaga tccaatttgg acagttttt ttggatcatc    9360
acacaaaga acagtaataa gtttctcgac tggttctcct cgattttga tgatatcaac    9420
tttactttct tgatcaagta ttttaattgg tagagcttcc acagaccttt tcattttttac  9480
agctatcaga aaatactact tagcaagtat ctgattccct catatttctc caactccata   9540
cttagtttgg aattggatta gtaaatgata agtgaagact atagccttaa gggcgttgag   9600
```

```
cctaggtcgg tcaagaatag cattataagc tgatggtatt ttgacaataa aaaaagtgag   9660
tcttacagtt gactggcatg gttctatccc tgcagtgacg gacaaagtga cctctccttc   9720
cacagctaca ggatttctag aaaatccaat tacgggggta ccaacctatt tagctaattt   9780
atcatattca ttctttggaa tgtatcatag aacaatatat tagcagagct ttcattatca   9840
ataagtattc tttttatatc atatttggct attgccataa agatgacaac agcatcatta   9900
cgaggagttt gaactctaac atcatcatcg aaaaatgaaa ttatgtgatc catgcactga   9960
tgctttggaa ggctttcagt aatctcagcc acctcctcag ttccgtcgag atctgagatc  10020
atattgatga ctgcagcagt agacttgttg tgatcattct cattgttggg cttctatcat  10080
tggtcagtag cttgacttgc ccgatctcga acatatttac taaagtaaca ttagtggatc  10140
aatacttcaa ttttatcttt taattatcga tgctcctcag tatcatggcc atagtctcga  10200
tggaaatgac agtattttct cttatctctc tttgctggag gggctttcat aggattaggt  10260
tggcgaatat atcctaaatc ctcgatttct atcagtatct gagctcgagg agtagatagt  10320
gaggtataga tgtcgaatca ccgaggtggg cttttgaact tcagattctt ctgaggtcgt  10380
tcagagttat cctgttggtt tttatgatct tcttcctagg gccactttt tccatctctt  10440 tttttcttca cctaacgaag tatgcatgct ctctttcttt tcagcttgag catacttaca  10500
aacctagatc aatatttgtt cataattgtt tgggtagttc ttattaagag agaagatcag  10560
gcgattactc ttgagtcctt gcttcaaagc tgccattgca atggactcat tgaagttctt  10620
cactttcagt atggcggcat taaagcatgc cacatattct tgaagagatt caccttccta  10680
ctatttgata gtaaaaagat tgctagtatt tttcaaatga atccatttat tatcaaaata  10740
cgtgatgaat atttgctaac tgtgtgaaag atgaaataga tcatgtctgg aggtcagaga  10800
actagattct tgcagatgtt ttgagagtga ttggaaaagt gatgcaaaat agggcattag  10860 atacccctttg tagtcttata atggctctga agccttcaag atgatttaag ggattgatgg  10920
agccatcgaa tgtttccact gtaggtatct tgaatcgagg aggaactgat ttaccaagaa  10980 tttttttgaga aaaagagat cgtaagttga aatctcttct accttgagaa tggcttccaa  11040
tctatatctc catcattttc ttctcaagat tttgaatctt ttgtccaaga ccctcctcca  11100
tacatggctt cttatgtgga gcagatttca cttcccaaga gtgatcagta tggtcaagaa  11160
gatgatcatg atgaagatct tgaggagttg gttgctaagt gtgatgtgat tggactactt  11220 gggggggctac tttttgctac cgttctgtcg tatactacag cagtaagagc ttggacctgc  11280
tgaaccaaga gactaaacta ttgtggatca ataataattg aaggttaggt attctcctga  11340
acatcttcag gagaagatga agtaggtaaa ggatgatttg gtgccttctt gttcaccatt  11400
tctactaaaa tattttaagt gcccttcctc taacactaat ctattactgc aaggcttcaa  11460
aagacaggca acgagatggg tcttgaatcg aactagaatg tttcttggtt gaatttggcg  11520
aagtctgtaa caaatcttgc aaagaaaatc tcgaaaccta cgggtacctt ctggttcaag  11580
atcctctgat ggataagtta ggtaaagtct tgagaatagg ttgtgaaaat agaagaatag  11640
aaggatgaga agagagattg tcggtaaatg gagagatgac tcttatttct ttcaatgggg  11700
gagctgaaaa taattcagca gagtttccac tctatcaatc ctgacttatt ttgtggaggg  11760
taccttggcc ccttcatata tagggatga agaggcctgg taaggttgtt agactattag  11820
gagagtttgt tagatcgtta atttattata atagaatgac cagctatata aaaatcatgg  11880
agtatttacc cacatggtga ttgactgtag tataactgaa agatagctaa tgcttagctg  11940
gatgactgct gttagataac tgtctgcatt cttacggtac attgatattt taccaatgtg  12000
```

```
acatagctta aatcggcaac tggctgaact aaatattatg tatcccttta gttaacaatc   12060
atgtcggtta gagatcaatg taattcgcag cagatcgatc ataagctgag atgagtatca   12120
tattttaaga acaacgctgg gcgagttagg ccgatcaaat gtcagactga aaaagcagat   12180
caataaacct ctgatgtgat ctgaaagaat atttatgatt taaataataa tctatcacca   12240
cgtatccaga taatgaggtc atataacatg taccaacagt gcatttttcc atctagttaa   12300
gaggttggtt agtggcattt gtcttcgata tgtaatgttc acataactaa tgtgcttagt   12360
agcattcttt tgtaaggtta aatcttcaat gatcttaagt tcacataatt gcctttgtgc   12420
cctattagtt tatagttgac cttttaattc aagagacagt caccttagca atcgatgtct   12480
gcttagattg ggccaattag gtactcacat taatatattg aatcatgttt gaatataaag   12540
gattagattg atttataagt ttccttttat tgtttacata ctgatactta gattgactta   12600
ctacattatt tgatatgtta tgttctaatt tttggattaa aattgttgtt tctgatttct   12660
ccttacatct aatactttgt ataatttatt attttttagc atgattgagt gtagaggatt   12720
agattgattt ttaagtttat tttgattatt tacatgccga tacttaaatt gacttactac   12780
attattcaat atgttatgtt tcaattattg agttaaaatt tttatttctg atttctactg   12840
atgtccagtg tgtgtgtgtg tacgtatgtg tgtatatatt tatttacata tatatgtatg   12900
tatgtataca gacatacata catacataca tacatacgta cacacacaca cacacacaca   12960
cacacacaca cacacacaca tatatatata tatatatctg tgtgtgtgtg tgtctctctc   13020
tctatatatg tataagtatg tatgtatgta tgtgtatata tatatatata tatatatata   13080
tatctatatg tgtgtatgca tgtatgtata tgtatgtatg tatatacata tatgtatata   13140
tatgtatata tatgtgtata tatgtatata tatgtgtgtg tgtgtataca tatgtataca   13200
tacatatcta tacatacata tgtatacata catacatata tatgtatata tacatataca   13260
tgtatacata catgtataca catacatgta tacatataca tgtatacata tatgtataca   13320
tatacatata tacatatata tatatatatg tatatacgtg tgtgtgtgtg tgtaagtaat   13380
taagtatgta gtgtgtgtgt gtgtgtgtat atatatttat atctgtgtgt gtgtgtatat   13440
atgtatgtat gtatgtatgt atatatatat aaatacatac atacatattt atacacacat   13500
atctatacac aaatatgtat acatatagac acacacacac gcgtgcgcgc gcgcgcgcac   13560
acacacacat atatatatat atatatagat agatagatat atgtatgtat gtatatatat   13620
atgtatatat atgtatacat atgtgtatat atgtatatat atatgtgtgt gtgtgtgtgt   13680
gtgtgtacat atgtatacat acatatctat acatatatat atatatacat atatatatac   13740
atatacatat atatatatat acataaatat atatacatat acatacatac atatatatat   13800
atatatatat atatatatat atatatatat acacatacat acatacatat acatatatac   13860
atacacacac acacatacac acatgtatac gtacatgtat gcatatacat gtatacgtac   13920
atgtatacat atacatgtat acatacatat atagatatat atatacacat atatgtatat   13980
atatatatat atatacacat atataggtta tttggaacct aagaaacttg caaagttact   14040
agatgcaatg ttcggaaacc atggaccgta caactggag tagtatttgg gtcatgaatt    14100
catggctaga tcatgaattg agtgggagtc aaccgaagta gggccagctc agacacttgt   14160
atttaggtcc catgcttgcg tgca                                           14184
```

<210> SEQ ID NO 5
<211> LENGTH: 678
<212> TYPE: DNA

<213> ORGANISM: Elaeis guineensis

<400> SEQUENCE: 5

```
atggggaggg ggaagataga gatcaagaag atagagaatc ctacaaacag gcaggtgacc    60
tactccaaga ggaggacggg gatcatgaag aaggctaagg aactgacggt gctttgcgat   120
gctgaggtct cgcttatcat gttctccagc accggcaagt tctccgagta ttgcagcccc   180
ctttccgaca ccaagaccat atttgatcgc taccagcagg tgtcagggat caacctgtgg   240
agcgcccaat acgagaaaat gcaaaacact ttgaaccatc tgagggagat caaccagaac   300
ctccgcagag aaataaggca gcggatgggt gaagatctcg acagtttggg catccatgaa   360
ctgcgcggtc ttgagcaaaa tttagatgag gctttgaagg ttgttcgtca gaaaatac    420
catgtgatca ccacgcagac ggatacctac aagaaaaagt tgaagaactc taatgaagct   480
cacaaaaatt tactgcatga acttgaaatg aaggacgagc acccagttta tggttttgtg   540
gatgatgacc ctagcaacta cgcaggtgca ctggctcttg ccaatggggc ttcccacatg   600
tatgctttcc gtgttcagcc gagccagccg aatctccatc gaatgggggtt tggctcccat   660
gacctgcgcc ttgcttga                                                  678
```

<210> SEQ ID NO 6
<211> LENGTH: 225
<212> TYPE: PRT
<213> ORGANISM: Artificial Sequence
<220> FEATURE:
<223> OTHER INFORMATION: synthetic

<400> SEQUENCE: 6

```
Met Gly Arg Gly Lys Ile Glu Ile Lys Lys Ile Glu Asn Pro Thr Asn
1               5                   10                  15

Arg Gln Val Thr Tyr Ser Lys Arg Thr Gly Ile Met Lys Lys Ala
            20                  25                  30

Lys Glu Leu Thr Val Leu Cys Asp Ala Glu Val Ser Leu Ile Met Phe
        35                  40                  45

Ser Ser Thr Gly Lys Phe Ser Glu Tyr Cys Ser Pro Leu Ser Asp Thr
    50                  55                  60

Lys Thr Ile Phe Asp Arg Tyr Gln Gln Val Ser Gly Ile Asn Leu Trp
65                  70                  75                  80

Ser Ala Gln Tyr Glu Lys Met Gln Asn Thr Leu Asn His Leu Arg Glu
                85                  90                  95

Ile Asn Gln Asn Leu Arg Arg Glu Ile Arg Gln Arg Met Gly Glu Asp
            100                 105                 110

Leu Asp Ser Leu Gly Ile His Glu Leu Arg Gly Leu Glu Gln Asn Leu
        115                 120                 125

Asp Glu Ala Leu Lys Val Val Arg His Arg Lys Tyr His Val Ile Thr
    130                 135                 140

Thr Gln Thr Asp Thr Tyr Lys Lys Lys Leu Lys Asn Ser Asn Glu Ala
145                 150                 155                 160

His Lys Asn Leu Leu His Glu Leu Glu Met Lys Asp Glu His Pro Val
                165                 170                 175

Tyr Gly Phe Val Asp Asp Asp Pro Ser Asn Tyr Ala Gly Ala Leu Ala
            180                 185                 190

Leu Ala Asn Gly Ala Ser His Met Tyr Ala Phe Arg Val Gln Pro Ser
        195                 200                 205

Gln Pro Asn Leu His Arg Met Gly Phe Gly Ser His Asp Leu Arg Leu
    210                 215                 220
```

Ala
225

<210> SEQ ID NO 7
<211> LENGTH: 61
<212> TYPE: DNA
<213> ORGANISM: Artificial Sequence
<220> FEATURE:
<223> OTHER INFORMATION: synthetic

<400> SEQUENCE: 7
aaattaatat tgcaaactag ctcaaaataa ttttgatcac tacatttctg ctgtgcattc    60
t                                                                   61

<210> SEQ ID NO 8
<211> LENGTH: 61
<212> TYPE: DNA
<213> ORGANISM: Artificial Sequence
<220> FEATURE:
<223> OTHER INFORMATION: synthetic

<400> SEQUENCE: 8
actacatttt aacaccaagc tcgataatag tgataaagaa acatctagat cagctttata    60
a                                                                   61

<210> SEQ ID NO 9
<211> LENGTH: 61
<212> TYPE: DNA
<213> ORGANISM: Artificial Sequence
<220> FEATURE:
<223> OTHER INFORMATION: synthetic

<400> SEQUENCE: 9
tgcatgcata gctagaagag aatcttatca cgatcatcac tcgtgaagat catctacctg    60
t                                                                   61

<210> SEQ ID NO 10
<211> LENGTH: 61
<212> TYPE: DNA
<213> ORGANISM: Artificial Sequence
<220> FEATURE:
<223> OTHER INFORMATION: synthetic

<400> SEQUENCE: 10
gctcgagtac tgcatatttc tgatacattg tctatgctag aatgtgctag aactgattat    60
c                                                                   61

<210> SEQ ID NO 11
<211> LENGTH: 61
<212> TYPE: DNA
<213> ORGANISM: Artificial Sequence
<220> FEATURE:
<223> OTHER INFORMATION: synthetic

<400> SEQUENCE: 11
tatattaatt gtcatacttc tagctcgaga tcatgagcca aggattgcag taactaccgc    60
a                                                                   61

<210> SEQ ID NO 12
<211> LENGTH: 61
<212> TYPE: DNA
<213> ORGANISM: Artificial Sequence

```
<220> FEATURE:
<223> OTHER INFORMATION: synthetic

<400> SEQUENCE: 12
ggaatctcat cttggtagct atggccggcg atgtgagcca aagtggcaaa atcatgaatc        60
t                                                                        61

<210> SEQ ID NO 13
<211> LENGTH: 61
<212> TYPE: DNA
<213> ORGANISM: Artificial Sequence
<220> FEATURE:
<223> OTHER INFORMATION: synthetic

<400> SEQUENCE: 13
tataactaat ctccaactct gccgactcct tagtagtatg agcacatgga aagcttgacc        60
t                                                                        61

<210> SEQ ID NO 14
<211> LENGTH: 61
<212> TYPE: DNA
<213> ORGANISM: Artificial Sequence
<220> FEATURE:
<223> OTHER INFORMATION: synthetic

<400> SEQUENCE: 14
ataaatgagt gatagattct aatccagaga caaagagcac acctcgaatt cacttgccat        60
c                                                                        61

<210> SEQ ID NO 15
<211> LENGTH: 61
<212> TYPE: DNA
<213> ORGANISM: Artificial Sequence
<220> FEATURE:
<223> OTHER INFORMATION: synthetic

<400> SEQUENCE: 15
aagaagaact aatacagctt tcatcacttc aaaatgatga acagatgcat ctcaagtcag        60
c                                                                        61

<210> SEQ ID NO 16
<211> LENGTH: 61
<212> TYPE: DNA
<213> ORGANISM: Artificial Sequence
<220> FEATURE:
<223> OTHER INFORMATION: synthetic

<400> SEQUENCE: 16
ttgatataga atgatcaagg gagcaagtag gttcaatctt tttgttggaa ttggatcata        60
t                                                                        61

<210> SEQ ID NO 17
<211> LENGTH: 61
<212> TYPE: DNA
<213> ORGANISM: Artificial Sequence
<220> FEATURE:
<223> OTHER INFORMATION: synthetic

<400> SEQUENCE: 17
ggcgcagatg aatgttttat gagcattttt atagctgcag cttatatgtg atctatggtg        60
c                                                                        61
```

<210> SEQ ID NO 18
<211> LENGTH: 61
<212> TYPE: DNA
<213> ORGANISM: Artificial Sequence
<220> FEATURE:
<223> OTHER INFORMATION: synthetic

<400> SEQUENCE: 18
atttgctttt ggatattgca tattccactc ttcaatcacc tcatgccaag caaaacattt    60
a                                                                   61

<210> SEQ ID NO 19
<211> LENGTH: 61
<212> TYPE: DNA
<213> ORGANISM: Artificial Sequence
<220> FEATURE:
<223> OTHER INFORMATION: synthetic

<400> SEQUENCE: 19
cggttgcatg ccctgcagag tttgactcat gaggcatgca aggtattgaa tagtagtcta    60
g                                                                   61

<210> SEQ ID NO 20
<211> LENGTH: 61
<212> TYPE: DNA
<213> ORGANISM: Artificial Sequence
<220> FEATURE:
<223> OTHER INFORMATION: synthetic

<400> SEQUENCE: 20
cgtcagctgc tcaatcatgg attctgatag ctcaaatggt ggtaagtaga aagagagaga    60
t                                                                   61

<210> SEQ ID NO 21
<211> LENGTH: 61
<212> TYPE: DNA
<213> ORGANISM: Artificial Sequence
<220> FEATURE:
<223> OTHER INFORMATION: synthetic

<400> SEQUENCE: 21
aagattgtgc aactcatgaa gattgtctcc agattgaaga taatttcaat acaagcacaa    60
a                                                                   61

<210> SEQ ID NO 22
<211> LENGTH: 61
<212> TYPE: DNA
<213> ORGANISM: Artificial Sequence
<220> FEATURE:
<223> OTHER INFORMATION: synthetic

<400> SEQUENCE: 22
atcggtggat caaatgataa tacttatgat agaaacataa tcaatccact taggactata    60
c                                                                   61

<210> SEQ ID NO 23
<211> LENGTH: 61
<212> TYPE: DNA
<213> ORGANISM: Artificial Sequence
<220> FEATURE:
<223> OTHER INFORMATION: synthetic

<400> SEQUENCE: 23

```
ttgaggagat taatctgacg caaggaaaaa agaagagctg acaactagcc aatgatcgag    60
a                                                                   61

<210> SEQ ID NO 24
<211> LENGTH: 61
<212> TYPE: DNA
<213> ORGANISM: Artificial Sequence
<220> FEATURE:
<223> OTHER INFORMATION: synthetic

<400> SEQUENCE: 24
tgatctcagc aaggtcataa tagaagcagc tctagaagta gtagccgaag tgacttctgc    60
a                                                                   61

<210> SEQ ID NO 25
<211> LENGTH: 61
<212> TYPE: DNA
<213> ORGANISM: Artificial Sequence
<220> FEATURE:
<223> OTHER INFORMATION: synthetic

<400> SEQUENCE: 25
atattttcgt agtctctaaa ggcttcttcc agattggcaa tatactgatc tgactcagta    60
t                                                                   61

<210> SEQ ID NO 26
<211> LENGTH: 61
<212> TYPE: DNA
<213> ORGANISM: Artificial Sequence
<220> FEATURE:
<223> OTHER INFORMATION: synthetic

<400> SEQUENCE: 26
atagctaatg cttagctgga tgactgctgt tagataactg tctgcattct tacggtacat    60
t                                                                   61

<210> SEQ ID NO 27
<211> LENGTH: 61
<212> TYPE: DNA
<213> ORGANISM: Artificial Sequence
<220> FEATURE:
<223> OTHER INFORMATION: synthetic

<400> SEQUENCE: 27
aattattgag ttaaaatttt tatttctgat ttctactgat gtccagtgtg tgtgtgtgta    60
c                                                                   61

<210> SEQ ID NO 28
<211> LENGTH: 61
<212> TYPE: DNA
<213> ORGANISM: Artificial Sequence
<220> FEATURE:
<223> OTHER INFORMATION: synthetic

<400> SEQUENCE: 28
tcttcctcag atgacatgtg atttatgcta cggcctagtt ctaaggactt ttctctgtca    60
t                                                                   61

<210> SEQ ID NO 29
<211> LENGTH: 61
<212> TYPE: DNA
```

```
<213> ORGANISM: Artificial Sequence
<220> FEATURE:
<223> OTHER INFORMATION: synthetic

<400> SEQUENCE: 29
cctagattaa tgctgttatt ggatgctggc agtcagatga agattatgtt tgattgtacc    60
t                                                                   61

<210> SEQ ID NO 30
<211> LENGTH: 61
<212> TYPE: DNA
<213> ORGANISM: Artificial Sequence
<220> FEATURE:
<223> OTHER INFORMATION: synthetic

<400> SEQUENCE: 30
taaatgagtg ctcatagtga caatgtttag cctccacgta taatgtgtgc cagctaacta    60
g                                                                   61

<210> SEQ ID NO 31
<211> LENGTH: 61
<212> TYPE: DNA
<213> ORGANISM: Artificial Sequence
<220> FEATURE:
<223> OTHER INFORMATION: synthetic

<400> SEQUENCE: 31
atcctctttt gtggctcaca acctcctctc cttttatgt tctatgttcc tcacatcaca     60
t                                                                   61

<210> SEQ ID NO 32
<211> LENGTH: 61
<212> TYPE: DNA
<213> ORGANISM: Artificial Sequence
<220> FEATURE:
<223> OTHER INFORMATION: synthetic

<400> SEQUENCE: 32
atcctttcaa tctcataaga agttaaatga catggatgac atgaagcttt gatatgcatc    60
g                                                                   61

<210> SEQ ID NO 33
<211> LENGTH: 61
<212> TYPE: DNA
<213> ORGANISM: Artificial Sequence
<220> FEATURE:
<223> OTHER INFORMATION: synthetic

<400> SEQUENCE: 33
accatcaaat ggcttttgga aatatgcggg cgcagaagta gaggtgtcct atatgaaggc    60
t                                                                   61

<210> SEQ ID NO 34
<211> LENGTH: 61
<212> TYPE: DNA
<213> ORGANISM: Artificial Sequence
<220> FEATURE:
<223> OTHER INFORMATION: synthetic

<400> SEQUENCE: 34
gacgagggat cacaccaaca tcatatgctc tcctcaccat accaaatggt atccccaact    60
a                                                                   61
```

<210> SEQ ID NO 35
<211> LENGTH: 4061
<212> TYPE: DNA
<213> ORGANISM: Artificial Sequence
<220> FEATURE:
<223> OTHER INFORMATION: synthetic

<400> SEQUENCE: 35

| | | | | | |
|---|---|---|---|---|---|
| aaatctatta | gtatctgaca | aaagttaaat | tagagtcgaa | acactaaatg acaattaggg | 60 |
| atcaacttga | tcaagtagat | agagaatatt | agaaagaga | gaaattaaca agatagaaca | 120 |
| tgattaatta | ggtgacatag | cccgacaatc | caattggtct | aagcaagttg atttaatcaa | 180 |
| atcacggttg | aactaatata | tagatagctc | aataaaaatc | atacataatt gaatctaatg | 240 |
| atatttggat | ctgaccaaga | tggaatttga | catgctgtcc | gatgatcgtg aatcaagact | 300 |
| ctctttgcta | attaagatca | aattagaatc | attgaaagag | aatctttac tggatcaaga | 360 |
| gagagaaata | tataaagaga | gtgaaatagt | ctatagaaaa | aaattttaga gagagaaatt | 420 |
| aagaagaaaa | ataaattttt | ttagagaaag | aaagtgggta | tacaagctca gagaagggag | 480 |
| agaggaaaga | gagagaaatg | ctctcttatt | ttcttttttt | tctttttct tcttttcttt | 540 |
| ttttttcct | attcttcttt | cccttttctg | cttaatggaa | tagggaccct cccattcccc | 600 |
| ttctatttct | agagttgggg | gctcaaaatt | gatgatagct | atcattgggg atgtaggcta | 660 |
| tggtgatgca | gtagaggatc | accgaccgat | gatcgatggt | gatgttgcaa tcaaaaaatc | 720 |
| aagaaagata | gatggaaaat | aaaggaaaat | aaggagaaat | agatctcaac ttgtttggat | 780 |
| gctaacccac | tcactgacga | ctccacttca | actatggccg | gagcttgcta tggaaaagaa | 840 |
| gccaaggcct | tcaaggatga | acaccaatgg | tgaggaagat | ggtcgaaaat agaagaatgg | 900 |
| ctggcttttc | taatcgacaa | aatagggtat | cgcccttctt | agcaaatatt cggcaataaa | 960 |
| tatctagaat | ccaggatcct | aggactatgg | aagagggaga | ggagggcaag tcaaggatg | 1020 |
| ccagattctt | atctagcttc | cgacaatgat | ggggccctat | tttcgataaa cacaattgag | 1080 |
| gatgttcgga | aaagggtttt | ttcgatgatg | attctagtga | ccaactatga gatttcaaag | 1140 |
| ggggtgaggg | gggtttaaat | aagatgggag | ggaagtttga | atcctcctta aatctgaacc | 1200 |
| ttttttcgaca | aagccaagag | cgtgaaggag | actccttcgt | gaagtcaaag atggaataga | 1260 |
| ctcccttcgg | gagtttggtt | catcacccaa | cttccctagc | atgtgcggag tatgtgctag | 1320 |
| cctttttctct | cttttttttt | cattttttt | catccttttaa | gatccatgca gtttctaggt | 1380 |
| tgagggattg | gggtatcaca | ttctctctcc | taaaaaaaaa | ttattttcaa aatttttta | 1440 |
| cctatatttt | caaaagttgg | gattcatggt | ccaaatctca | tccttgaatt tttttgatat | 1500 |
| tctaattctc | gaaaaaattt | catcgttaaa | tcatttcata | agagaaaagt caatacctca | 1560 |
| agagttgatc | tgaatcaaaa | ttattatctc | tagtaatcga | aatcaatatc ttaatttcaa | 1620 |
| ataagaatat | ccagtttatt | gtcaaaatta | ttaactactc | ttgacttaat tgatctatta | 1680 |
| cataatcgta | aataaattct | aacatactct | tgaagtgtag | aatataagat tgataaacaa | 1740 |
| tcctatatcc | gttctaatag | atataaaagc | ataaactta | aatattttaa atccaagatt | 1800 |
| aagaatcaat | gatccactta | tcctagactc | aagatattag | aaatttttt tgtacaata | 1860 |
| gatagaggat | gtactggtga | aaatcatgta | gcgatatcca | aataatttt taattaaaaa | 1920 |
| tattatcctt | tcattatca | atgaattta | tctataagaa | agatcaaatc atatgatcca | 1980 |
| tcttaaattt | ttaactcaaa | aaattaatat | tgcaaactag | ctcaaaataa ttttgatcac | 2040 |

```
tacatttctg ctgtgcattc taatttaaac cgttcacatt ttttagattc atgaaataat    2100
tttgaccaaa gtattactcc atactatagt caaaaaagat taaaatatta gattctaatt    2160
aaagccaaag ataaactttt gattctcatc cttaattttg cctaaagtat aattattttg    2220
attaacccTT aagcgcaata acacattcaa aaccaacaga taggtttact ataatccaaa    2280
tgaattaaat cttaattctt ttatcaattc atttagacaa tttcaaatca aaattctata    2340
agtaatatca ataaaaaaaa ttttgatgc tccataagt tagaacttaa atcaaaatat    2400
ataagtaaaa ttgatttaat catctcttct aaagtttctt ctattaagat ctttaatatc    2460
tatcaaatac attccacaat aatcatgcaa accttttaaa aattaaattc tcaatgcctt    2520
tactacattt taacaccaag ctcgataata gtgataaaga aacatctaga tcagctttat    2580
aatcaaaaat tttgacttac aattttacgt gtgtctcaaa atcttgaata atataaata    2640 agatctttta tcttgatcca aaaatagtaa tcaaggattt cattagtaac ttcaacaaca    2700
atggtaaaaa aattttctat ccattgataa acccaaattt tgaattgaag tttcatgcat    2760
accatatagc ctttaataag atctattatt tggatctaaa gatagtaatt aaaattgtta    2820
atgattccac taagatgaat actttacaat ctcataatta attt cttcaa taaaaataga    2880 cttcttgata atgtctccaa ttgtatattt tttttt tattt ctacaagaaa acttcataca    2940 tttttt acgt tccaatataa atcttaaaaa gttattccaa tcaaatatca taaaagatct    3000
tcttagtcca accttaaata actttt atga atgaatcttt atcttgccac taataatga    3060 atttt aaaat caagagcaac atcacagcat tctgtcatgt caaatttgtg ttagatgtat    3120
gtcctagaaa tcaattagat tgacaatgta aattttttaa ggatataatt tatatatttt    3180
gatttattaa taaaataaaa tttaaattaa ttttt attca tatttttt ta tctatgaatc    3240 atctaaagaa ttaataagat gatgatacat attcttaaga gttcaaaatt tgaaatatat    3300
gtcattgatg attaatttct gaatactttt gaattcttaa gagtttagaa gatcttgacc    3360
caagtagtgt gaatagtgaa aaaaagtttt cacatacttc acatcaaaaa tttaagttga    3420
ataaattgta catatgacag gtattatagt ttgacgagta atctataacc tctatcttat    3480
caaaattctg atagaaagat tgtattgtat gataactgta cttagaggtt caccttttat    3540
tttactggat taccactaca tgttgctaga tgtcactggt ggattgtgag atctacgaag    3600
attatcttga tgatcgataa ttctcattga aaagattgaa actatttt aa tgatgttgtg    3660 atagagatca taatatatct tattatcaga cagaatagaa ttctatggga tcatacacaa    3720
taggagatta agactgatca aatagttgaa tgatgattaa gaatcattac ggagttcaga    3780
ttatcaatat aattgataat tagactaact tataattgtt acaagtagca aggacttaac    3840
tgctaaaggt taataggttc aaaaagaact tatgtataaa tgttgtgcat cttaatttga    3900
ttggatcaaa ttagttatgg ctgaattcaa gatgaatcaa ataggaattt ggttcaattg    3960
aatttgggtc aagctttagg cttaggtcac atatacccaa aatcatttgg atgcatcagg    4020
tgtgtgacac ctgaatcagg cctttctaaa ctattttgag t                        4061
```

<210> SEQ ID NO 36
<211> LENGTH: 4061
<212> TYPE: DNA
<213> ORGANISM: Artificial Sequence
<220> FEATURE:
<223> OTHER INFORMATION: synthetic

<400> SEQUENCE: 36

```
cttttttctt ctttt ctttt tttttt ccta ttcttctttc cctttt ctgc ttaatggaat      60
```

```
aggggacctc ccattcccct tctatttcta gagttggggg ctcaaaattg atgatagcta    120
tcattgggga tgtaggctat ggtgatgcag tagaggatca ccgaccgatg atcgatggtg    180
atgttgcaat caaaaaatca agaaagatag atggaaaata aaggaaaata aggagaaata    240
gatctcaact tgtttggatg ctaacccact cactgacgac tccacttcaa ctatggccgg    300
agcttgctat ggaaaagaag ccaaggcctt caaggatgaa caccaatggt gaggaagatg    360
gtcgaaaata gaagaatggc tggcttttct aatcgacaaa atagggtatc gcccttctta    420
gcaaatattc ggcaataaat atctagaatc caggatccta ggactatgga gagggagag     480 gagggcaagt caaaggatgc cagattctta tctagcttcc gacaatgatg gggccctatt    540
ttcgataaac acaattgagg atgttcggaa aagggttttt tcgatgatga ttctagtgac    600
caactatgag atttcaaagg gggtgagggg ggtttaaata agatgggagg gaagtttgaa    660
tcctccttaa atctgaacct ttttcgacaa agccaagagc gtgaaggaga ctccttcgtg    720
aagtcaaaga tggaatagac tcccttcggg agtttggttc atcacccaac ttccctagca    780
tgtgcggagt atgtgctagc cttttctctc ttttttttc attttttttc atcctttaag     840
atccatgcag tttctaggtt gagggattgg ggtatcacat tctctctcct aaaaaaaaat    900
tattttcaaa attttttttac ctatattttc aaaagttggg attcatggtc caaatctcat   960
ccttgaattt ttttgatatt ctaattctcg aaaaaatttc atcgttaaat catttcataa    1020
gagaaaagtc aatacctcaa gagttgatct gaatcaaaat tattatctct agtaatcgaa   1080
atcaatatct taatttcaaa taagaatatc cagtttattg tcaaaattat taactactct   1140
tgacttaatt gatctattac ataatcgtaa ataaattcta acatactctt gaagtgtaga   1200
atataagatt gataaacaat cctatatccg ttctaataga tataaaagca taaacttaa    1260 atattttaaa tccaagatta agaatcaatg atccacttat cctagactca agatattaga   1320 aattttttt tgtacaatag atagaggatg tactggtgaa aatcatgtag cgatatccaa     1380
aataattttt aattaaaaat attatccttt tcattatcaa tgaatttat ctataagaaa     1440 gatcaaatca tatgatccat cttaaatttt taactcaaaa aattaatatt gcaaactagc   1500
tcaaaataat tttgatcact acatttctgc tgtgcattct aatttaaacc gttcacattt   1560
tttagattca tgaaataatt ttgaccaaag tattactcca tactatagtc aaaaaagatt   1620
aaaatattag attctaatta aagccaaaga taaacttttg attctcatcc ttaattttgc   1680
ctaaagtata attattttga ttaaccctta agcgcaataa cacattcaaa accaacagat   1740
aggtttacta taatccaaat gaattaaatc ttaattcttt tatcaattca tttagacaat   1800
ttcaaatcaa aattctataa gtaatatcaa taaaaaaaat ttttgatgct ccaataagtt   1860
agaacttaaa tcaaaatata taagtaaaat tgatttaatc atctcttcta aagtttcttc   1920
tattaagatc tttaatatct atcaaataca ttccacaata atcatgcaaa ccttttaaaa   1980
attaaattct caatgccttt actacatttt aacaccaagc tcgataatag tgataaagaa   2040
acatctagat cagctttata atcaaaaatt ttgacttaca attttacgtg tgtctcaaaa   2100
tcttgaataa atataaataa gatcttttat cttgatccaa aaatagtaat caaggatttc   2160
attagtaact tcaacaacaa tggtaaaaaa attttctatc cattgataaa cccaaatttt   2220
gaattgaagt tcatgcata  ccatatagcc tttaataaga tctattattt ggatctaaag   2280
atagtaatta aaattgttaa tgattccact aagatgaata ctttacaatc tcataattaa   2340
tttcttcaat aaaaatagac ttcttgataa tgtctccaat tgtatatttt tttttatttc   2400
```

| tacaagaaaa cttcatacat tttttacgtt ccaatataaa tcttaaaaag ttattccaat | 2460 |
| caaatatcat aaaagatctt cttagtccaa ccttaaataa cttttatgaa tgaatcttta | 2520 |
| tcttgccact aaataatgaa ttttaaaatc aagagcaaca tcacagcatt ctgtcatgtc | 2580 |
| aaatttgtgt tagatgtatg tcctagaaat caattagatt gacaatgtaa attttttaag | 2640 |
| gatataattt atatattttg atttattaat aaaataaaat ttaaattaat ttttattcat | 2700 |
| attttttat ctatgaatca tctaaagaat taataagatg atgatacata ttcttaagag | 2760 |
| ttcaaaattt gaaatatatg tcattgatga ttaatttctg aatactttg aattcttaag | 2820 |
| agtttagaag atcttgaccc aagtagtgtg aatagtgaaa aaaagttttc acatacttca | 2880 |
| catcaaaaat ttaagttgaa taaattgtac atatgacagg tattatagtt tgacgagtaa | 2940 |
| tctataacct ctatcttatc aaaattctga tagaaagatt gtattgtatg ataactgtac | 3000 |
| ttagaggttc accttttatt ttactggatt accactacat gttgctagat gtcactggtg | 3060 |
| gattgtgaga tctacgaaga ttatcttgat gatcgataat tctcattgaa aagattgaaa | 3120 |
| ctattttaat gatgttgtga tagagatcat aatatatctt attatcagac agaatagaat | 3180 |
| tctatgggat catacacaat aggagattaa gactgatcaa atagttgaat gatgattaag | 3240 |
| aatcattacg gagttcagat tatcaatata attgataatt agactaactt ataattgtta | 3300 |
| caagtagcaa ggacttaact gctaaaggtt aataggttca aaagaacttt atgtataaat | 3360 |
| gttgtgcatc ttaatttgat tggatcaaat tagttatggc tgaattcaag atgaatcaaa | 3420 |
| taggaatttg gttcaattga atttgggtca agctttaggc ttaggtcaca tatacccaaa | 3480 |
| atcatttgga tgcatcaggt gtgtgacacc tgaatcaggc cttctaaac tattttgagt | 3540 |
| aagtttgatc aagtcaaaag gatccacacc ctaaggtttc ttgaataaaa ccttaggcac | 3600 |
| cacattgagg acctatagga aactttgacc ctctctcata tggggtggca cactgaggtt | 3660 |
| ttataaaaac cttaggcacc cattttagcc ataaaaaaaa agctccaagg gatggggcag | 3720 |
| tagccatgaa gaatccttgg ctgtcaggac tctattcaaa agagttctca aggttttgga | 3780 |
| ctcttatgga gccctaggat ttgtttgcct ataaatagat ggccaccca aggctttaga | 3840 |
| taatgttaga gacttgtgaa gctctccct ttctcttggt tgccggccca ccctctctcc | 3900 |
| tctctcttcc atgccccaag acttcttct tgtctccatc atcttgctga aatttagatt | 3960 |
| tcagcaagaa aagtcaagta gaagtcaaag ttcaatgta gctcacaaga tgttgagaac | 4020 |
| ttcctccatc tggcaaaggt tctgcaagag agctagcatc c | 4061 |

<210> SEQ ID NO 37
<211> LENGTH: 4061
<212> TYPE: DNA
<213> ORGANISM: Artificial Sequence
<220> FEATURE:
<223> OTHER INFORMATION: synthetic

<400> SEQUENCE: 37

| tcttttatct tgatccaaaa atagtaatca aggatttcat tagtaacttc aacaacaatg | 60 |
| gtaaaaaaat tttctatcca ttgataaacc caattttga attgaagttt catgcatacc | 120 |
| atatagcctt taataagatc tattatttgg atctaaagat agtaattaaa attgttaatg | 180 |
| attccactaa gatgaatact ttacaatctc ataattaatt tcttcaataa aaatagactt | 240 |
| cttgataatg tctccaattg tatatttttt tttattccta caagaaaact tcatacattt | 300 |
| tttacgttcc aatataaatc ttaaaaagtt attccaatca aatatcataa aagatcttct | 360 |
| tagtccaacc ttaaataact tttatgaatg aatctttatc ttgccactaa ataatgaatt | 420 |

```
ttaaaatcaa gagcaacatc acagcattct gtcatgtcaa atttgtgtta gatgtatgtc      480
ctagaaatca attagattga caatgtaaat tttttaagga tataatttat atattttgat      540
ttattaataa aataaaattt aaattaattt ttattcatat ttttttatct atgaatcatc      600
taaagaatta ataagatgat gatacatatt cttaagagtt caaaatttga aatatatgtc      660
attgatgatt aatttctgaa tacttttgaa ttcttaagag tttagaagat cttgacccaa      720
gtagtgtgaa tagtgaaaaa aagttttcac atacttcaca tcaaaatttt aagttgaata      780
aattgtacat atgacaggta ttatagtttg acgagtaatc tataacctct atcttatcaa      840
aattctgata gaaagattgt attgtatgat aactgtactt agaggttcac cttttatttt      900
actggattac cactacatgt tgctagatgt cactggtgga ttgtgagatc tacgaagatt      960
atcttgatga tcgataattc tcattgaaaa gattgaaact attttaatga tgttgtgata     1020
gagatcataa tatatcttat tatcagacag aatagaattc tatgggatca tacacaatag     1080
gagattaaga ctgatcaaat agttgaatga tgattaagaa tcattacgga gttcagatta     1140
tcaatataat tgataattag actaacttat aattgttaca agtagcaagg acttaactgc     1200
taaaggttaa taggttcaaa aagaacttat gtataaatgt tgtgcatctt aatttgattg     1260
gatcaaatta gttatggctg aattcaagat gaatcaaata ggaatttggt tcaattgaat     1320
ttgggtcaag ctttaggctt aggtcacata tacccaaaat catttggatg catcaggtgt     1380
gtgacacctg aatcaggcct ttctaaacta ttttgagtaa gtttgatcaa gtcaaaagga     1440
tccacaccct aaggtttctt gaataaaacc ttaggcacca cattgaggac ctataggaaa     1500
ctttgaccct ctctcatatg gggtggcaca ctgaggtttt ataaaaacct taggcaccca     1560
ttttagccat aaaaaaaaag ctccaaggga tggggcagta gccatgaaga atccttggct     1620
gtcaggactc tattcaaaag agttctcaag gttttggact cttatggagc cctaggattt     1680
gtttgcctat aaatagatgg ccaccccaag gctttagata atgttagaga cttgtgaagc     1740
tctccccttt ctcttggttg ccggcccacc ctctctcctc tctcttccat gccccaagac     1800
ttctttcttg tctccatcat cttgctgaaa tttagatttc agcaagaaaa gtcaagtaga     1860
agtcaaagtt ctaatgtagc tcacaagatg ttgagaactt cctccatctg gcaaaggttc     1920
tgcaagagag ctagcatcct gagaaacaaa aagattgctg atcagccctc atctccatat     1980
ggatatttgt agagatcaaa tgcatgcata gctagaagag aatcttatca cgatcatcac     2040
tcgtgaagat catctacctg tgcaaggta tgagataaga aaaatatttt ttttatcata     2100
attcatgaat cctttgctta tattatactg agattcttgg aatggatttt ttctctagta     2160
aaactctaga gatcagatct caaagtcttc ttcacataaa ggttttgaaa gttctttata     2220
tttccgctgc tttgattcaa aataaattag atctattttg cctttcaacc tttctctat     2280 ttattgacat ataaagcttt aattaatgag attaatgaaa agcatgtgcg aaatactgag     2340
aaaatcctaa cagtgatatc agagctactt ttgtacataa gaaaaggatt caagttaaat     2400
aaaatatgtt tgatttaagt aaatgaatca atcaaaattt atcctaacat aagtttgtcc     2460
tggtataatg gtcaagacca ttatgttgaa aggttatcct aggacaaaaa gtctaagtaa     2520
aatctatttt atttaagtaa atgaatcaat taaagtttat tctaatataa gattgcctta     2580
gcataatggt gaagaccctt atgttgaaag gttgtcctag gatggaaagt gattgatgag     2640
acaaatatat catgaaagta ttttcacag atggaataaa atatatat tttgtttgtg       2700 aaaatgagat ttcatgaatg tgtttgtcat tcaatatgtg tggtgatcat cttgaattgc     2760
```

```
cacaaatcct ttttggatta gggttgtatc atgactcaca atcctgatg gtttgcaaaa    2820 ttttgcattc tgtagtgata gaaaccaaaa gttaatccaa ttttggaata agattgatca    2880
attggtatct aaggcaagta ttttataatg gtggttactt aattagttat aaaagtacga    2940
agagtctcct accaatctta cacttatcta gccaatttgg ttgattgaat tctgaatttg    3000
ggttgcttaa gtgttaagtt cactacaaat atattgcaac catgattccg acttagtcaa    3060
ccaagcctag atctcttgaa tagattcatg ttaattatgg atttacatag gatataaata    3120
aataattaaa acttgaagag atctaaatga aaccttctcg tacatattaa atcgaatgat    3180
cttccatcat tgtagatata cggatactct actgatgttg atgattttcg actagatata    3240
gtactttggt tgcatcgaaa aagtacaacc actttataac atgagatgtt gcagggtaga    3300
gatggggttg ggcccaataa ttgttaggtg aggatccaaa tgatggctgc acttgcgtgt    3360
gaatggcgag tctgacttaa ttaagaaata gagctaataa ctattagatg aggcttcagg    3420
acttagagac ttatgaccac tacaacttac ttgagaagca atggataaag agtcgtctat    3480
ttatcaactg acgcatcacc aataactatc agatggagtg atgtataatt agtgggacta    3540
tagtatccac ttgaaatctt aatcgtaaaa attttgtttt ctccacctga agagcatggg    3600
agattcgaaa aaatagtggg ggtagtttat ttttaaaata aagctcctaa aataaactaa    3660
aataagttaa atacaaagtc taactagaat cttcttctct ctgtagaaaa tatctgcttc    3720
caacctctat ttcatatcct taagactaat tgtttgacta gacccagtta taagattga    3780 ctctaaaact taaagatagt cttgagtttt gaaaagatga gctatgtcct ggatcaagat    3840
atcctctctc taccagcttg tcccacccct aatcaagggg catcctatga aaagtggtta    3900
aacgatgata acaaggcttg gtgctgtgtg ctgacatcta tgtccattga actccaatgc    3960
cagcataagg gtacaaactg tccaaggtat attgactcat ctacaagagt tatatagtga    4020
gtagagccat gtatctcact aggaagtatt taagagactc t                        4061
```

<210> SEQ ID NO 38
<211> LENGTH: 4061
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (3017)..(3951)
<223> OTHER INFORMATION: n is a, c, g, or t

<400> SEQUENCE: 38

```
cagattatca atataattga taattggact aacttgtaat tattataagt agcaaagatt     60
taattgctaa aggttagcag attcaaggag gacttatgtg taaataatgt acatcttaat    120
ttgattggat caacttagtt atggctaaat ttaagatgaa tcaaacaggg atttagttta    180
atcgaatttg ggtcaagctt tgggcttagg tcacatgcac tcaaaagggt ttggatacat    240
caagtgtgtg acacccaaac caagcctccc taaactattt tgagttggtt ttgaccaagt    300
caaaagggtc cacacccctag ggtttcttga ataaaccct aggtgccaca ttgaggacca    360
attaggaaac tttgacattc tttcacacgg agcagcacac tagggtttca tgaaaaccct    420
aggcacccat tttagccata aaaggaaagc tccaagggat gggatggtgc catgaagaat    480
ccctggccat tgggactcca ttcaaaagtt ctctaggttt gggctcttta tagagccta    540 gggtttgttt gcctataaat aggtcgctac cccaaggctt tagataatgc tagaggcttg    600
tgaagctctc tcctttctct tgtttgccat cccaccttct ctcctctctc ctccatgcct    660
```

```
caagacttct tcttctctc catcatcttg ttgaaattta gatttcaatg agaaggatca    720
agtagagtca gagttctact gcagttctca aggtgttgag aactttcttc atcaggcaaa    780
gattctgcaa aggagttagc acctcaaaga accaagaaag ttgctaatct gccctcatct    840
ccatgtggat acttatagag gccaagcatg acgagaagag ccttatcacg atcatcactc    900
gtggagatca tctacccgcg caaaggtatg agataagaaa aaatatttt tcttatcatg     960 attcatgaat cctttgctta tgttacattg agactcttgg attagatttt ttctctaata   1020
aaatttcaaa gattagatct cgaagtcttc ttcacctaaa ggtattgaaa gttctttata   1080
ttttcgctac tttgattcaa aatagattag atttgttttg cctttcaatt tttctcatat   1140
ttattgagat atgaagcttt aattaatgag attaataaaa agcatatgtg aaatactgag   1200
aacatcctaa caatttgagc ttacaattca cttaaacaac taatgatcaa attaataatc   1260
acaatgcaca ataaaaattc atgataaatc tttttgttgt tactttagat caaaatccaa   1320
ctaatcataa catgatccac ggattgccta tcatatatca aaccctctga attattaatc   1380
ttaaacgatc ttttcattca tgatcataag atttagttaa aaatcatgaa gacaacttat   1440
attgtaatca tcatagatct gtatcttaac atccttagtg tttacctacc tatactcatc   1500
ctatgtttga ttctatatat cataatttat tcactaatac tttgatatca tataaattat   1560
cgcatcccca atctaagatc atattggtac tttaatattt cattagtggg ggttatgcat   1620
tagtactttg atccttatc agttgaatgg ttaaacactg gtactttgat atcctatcag    1680
tggaggttat acgctggtac tttaatatcc tatcagtaag atggttaaat actgatactt   1740
tgataacctc ccagtgggtg ttgtatgcta gtactttatt atcctaccaa tggggcagtt   1800
aaatgctact actttgatac gctaccaatg ggatagttaa acgctagtaa tctaatctta   1860
gcttgacata agtaacgtc gactcgagtt tagggtcgac tcgagagaat gttagggtta    1920
gcttgatatg aaagagggtc gctcgtcaat attttggagt caactcttgt ttatggacga   1980
tctagaaagt gtcagagtga gctcgagtac tgcatatttc tgatacattg tctatgctag   2040
aatgtgctag aactgattat cttctttatc aaagttgatt tttgagtaac ttgatgatca   2100
atttttctag gctagacttg ctttgtcaaa atgagcactt gttagtttag agaatcttca   2160
cctacacatg atctcaagca ttcattagta ccaaaaatac ttaagtattt tgatatcatc   2220
aaaatcaatt cttgggttaa cacaaatactt ttcaaataat aagcatacag atataatcct   2280
ataacaattt aaattttgtt catatatcaa tttctttaaa aatattatat tcatcttgat   2340
agctatgaac taaatcaaaa tacatactag tatacaactt ttactgggag agtattagat   2400
taccagcatt taaccatccc actggcaagg tatcaaatta ccaatacaca acccctattt   2460
ataaagtatc aaagtaccag tgttcaactg cctcactggc aggatatcat agtactagta   2520
tttaactacc acattgacag gatatggaat tatcagtatt taaccatcat tagtagaatt   2580
ttgatgcata gtcaggctgc gagtcaaaat ctatctcaaa tcaaatatt gatcacatgt    2640 ctaattctgt atcataattc attcccttat gctctaatat tatattaatt gtcatacttc   2700
tagctcgaga tcatgagcca aggattgcag taactaccgc atacttatag agaactcttt   2760
ctataagcat acaagatatt ctaaatatac tatcaatata tcatagagaa attaatttaa   2820
ataactaaaa gttaatattc aattaataaa ttcaactggc aaatgtattt aaaaatttta   2880
catcaaataa atcttgatta ataaatatta attaataaca atagatttaa atcgaaacaa   2940
ggttgatatt gttagaattt gatgcctcaa gattcagccc acattgagtc cacagtgagg   3000
```

| | |
|---|---|
| ttcgcgacga aaaatgnnnn nnnnnnnnnn nnnnnnnnnn nnnnnnnnnn nnnnnnnnnn | 3060 |
| nnnnnnnnnn nnnnnnnnnn nnnnnnnnnn nnnnnnnnnn nnnnnnnnnn nnnnnnnnnn | 3120 |
| nnnnnnnnnn nnnnnnnnnn nnnnnnnnnn nnnnnnnnnn nnnnnnnnnn nnnnnnnnnn | 3180 |
| nnnnnnnnnn nnnnnnnnnn nnnnnnnnnn nnnnnnnnnn nnnnnnnnnn nnnnnnnnnn | 3240 |
| nnnnnnnnnn nnnnnnnnnn nnnnnnnnnn nnnnnnnnnn nnnnnnnnnn nnnnnnnnnn | 3300 |
| nnnnnnnnnn nnnnnnnnnn nnnnnnnnnn nnnnnnnnnn nnnnnnnnnn nnnnnnnnnn | 3360 |
| nnnnnnnnnn nnnnnnnnnn nnnnnnnnnn nnnnnnnnnn nnnnnnnnnn nnnnnnnnnn | 3420 |
| nnnnnnnnnn nnnnnnnnnn nnnnnnnnnn nnnnnnnnnn nnnnnnnnnn nnnnnnnnnn | 3480 |
| nnnnnnnnnn nnnnnnnnnn nnnnnnnnnn nnnnnnnnnn nnnnnnnnnn nnnnnnnnnn | 3540 |
| nnnnnnnnnn nnnnnnnnnn nnnnnnnnnn nnnnnnnnnn nnnnnnnnnn nnnnnnnnnn | 3600 |
| nnnnnnnnnn nnnnnnnnnn nnnnnnnnnn nnnnnnnnnn nnnnnnnnnn nnnnnnnnnn | 3660 |
| nnnnnnnnnn nnnnnnnnnn nnnnnnnnnn nnnnnnnnnn nnnnnnnnnn nnnnnnnnnn | 3720 |
| nnnnnnnnnn nnnnnnnnnn nnnnnnnnnn nnnnnnnnnn nnnnnnnnnn nnnnnnnnnn | 3780 |
| nnnnnnnnnn nnnnnnnnnn nnnnnnnnnn nnnnnnnnnn nnnnnnnnnn nnnnnnnnnn | 3840 |
| nnnnnnnnnn nnnnnnnnnn nnnnnnnnnn nnnnnnnnnn nnnnnnnnnn nnnnnnnnnn | 3900 |
| nnnnnnnnnn nnnnnnnnnn nnnnnnnnnn nnnnnnnnnn nnnnnnnnnn nagatattac | 3960 |
| taaattttgc ttctaatctc actcttaaat agtacttacc tttgaaacta ggcatttgaa | 4020 |
| tctgaaaaag aaagaggaga ttatgagctt gatagttcag t | 4061 |

<210> SEQ ID NO 39
<211> LENGTH: 4061
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (2337)..(3271)
<223> OTHER INFORMATION: n is a, c, g, or t

<400> SEQUENCE: 39

| | |
|---|---|
| catcatcttg ttgaaattta gatttcaatg agaaggatca agtagagtca gagttctact | 60 |
| gcagttctca aggtgttgag aactttcttc atcaggcaaa gattctgcaa aggagttagc | 120 |
| acctcaaaga accaagaaag ttgctaatct gccctcatct ccatgtggat acttatagag | 180 |
| gccaagcatg acgagaagag ccttatcacg atcatcactc gtggagatca tctacccgcg | 240 |
| caaaggtatg agataagaaa aaaatatttt tcttatcatg attcatgaat cctttgctta | 300 |
| tgttacattg agactcttgg attagatttt ttctctaata aaatttcaaa gattagatct | 360 |
| cgaagtcttc ttcacctaaa ggtattgaaa gttctttata ttttcgctac tttgattcaa | 420 |
| aatagattag atttgttttg cctttcaatt tttctcatat ttattgagat atgaagcttt | 480 |
| aattaatgag attaataaaa agcatatgtg aaatactgag aacatcctaa caatttgagc | 540 |
| ttacaattca cttaaacaac taatgatcaa attaataatc acaatgcaca ataaaaattc | 600 |
| atgataaatc tttttgttgt tactttagat caaaatccaa ctaatcataa catgatccac | 660 |
| ggattgccta tcatatatca aaccctctga attattaatc ttaaacgatc ttttcattca | 720 |
| tgatcataag atttagttaa aaatcatgaa gacaacttat attgtaatca tcatagatct | 780 |
| gtatcttaac atccttagtg tttacctacc tatactcatc ctatgtttga ttctatatat | 840 |
| cataatttat tcactaatac tttgatatca tataaattat cgcatcccca atctaagatc | 900 |

```
atattggtac tttaatattt cattagtggg ggttatgcat tagtactttg atacctatc    960
agttgaatgg ttaaacactg gtactttgat atcctatcag tggaggttat acgctggtac  1020
tttaatatcc tatcagtaag atggttaaat actgatactt tgataacctc ccagtgggtg  1080
ttgtatgcta gtactttatt atcctaccaa tggggcagtt aaatgctact actttgatac  1140
gctaccaatg ggatagttaa acgctagtaa tctaatctta gcttgacata agtaacgtc   1200
gactcgagtt tagggtcgac tcgagagaat gttagggtta gcttgatatg aaagagggtc  1260
gctcgtcaat attttggagt caactcttgt ttatggacga tctagaaagt gtcagagtga  1320
gctcgagtac tgcatatttc tgatacattg tctatgctag aatgtgctag aactgattat  1380
cttctttatc aaagttgatt tttgagtaac ttgatgatca atttttctag gctagacttg  1440
ctttgtcaaa atgagcactt gttagtttag agaatcttca cctacacatg atctcaagca  1500
ttcattagta ccaaaaatac ttaagtattt tgatatcatc aaaatcaatt cttgggttaa  1560
cacaatactt ttcaaataat aagcatacag atataatcct ataacaattt aaattttgtt  1620
catatatcaa tttctttaaa aatattatat tcatcttgat agctatgaac taaatcaaaa  1680
tacatactag tatacaactt ttactgggag agtattagat taccagcatt taaccatccc  1740
actggcaagg tatcaaatta ccaatacaca acccctattt ataaagtatc aaagtaccag  1800
tgttcaactg cctcactggc aggatatcat agtactagta tttaactacc acattgacag  1860
gatatggaat tatcagtatt taaccatcat tagtagaatt ttgatgcata gtcaggctgc  1920
gagtcaaaat ctatctcaaa tcaaaatatt gatcacatgt ctaattctgt atcataattc  1980
attcccttat gctctaatat tatattaatt gtcatacttc tagctcgaga tcatgagcca  2040
aggattgcag taactaccgc atacttatag agaactcttt ctataagcat acaagatatt  2100
ctaaatatac tatcaatata tcatagagaa attaatttaa ataactaaaa gttaatattc  2160
aattaataaa ttcaactggc aaatgtattt aaaaatttta catcaaataa atcttgatta  2220
ataaatatta attaataaca atagatttaa atcgaaacaa ggttgatatt gttagaattt  2280
gatgcctcaa gattcagccc acattgagtc cacagtgagg ttcgcgacga aaaatgnnnn  2340
nnnnnnnnnn nnnnnnnnnn nnnnnnnnnn nnnnnnnnnn nnnnnnnnnn nnnnnnnnnn  2400
nnnnnnnnnn nnnnnnnnnn nnnnnnnnnn nnnnnnnnnn nnnnnnnnnn nnnnnnnnnn  2460
nnnnnnnnnn nnnnnnnnnn nnnnnnnnnn nnnnnnnnnn nnnnnnnnnn nnnnnnnnnn  2520
nnnnnnnnnn nnnnnnnnnn nnnnnnnnnn nnnnnnnnnn nnnnnnnnnn nnnnnnnnnn  2580
nnnnnnnnnn nnnnnnnnnn nnnnnnnnnn nnnnnnnnnn nnnnnnnnnn nnnnnnnnnn  2640
nnnnnnnnnn nnnnnnnnnn nnnnnnnnnn nnnnnnnnnn nnnnnnnnnn nnnnnnnnnn  2700
nnnnnnnnnn nnnnnnnnnn nnnnnnnnnn nnnnnnnnnn nnnnnnnnnn nnnnnnnnnn  2760
nnnnnnnnnn nnnnnnnnnn nnnnnnnnnn nnnnnnnnnn nnnnnnnnnn nnnnnnnnnn  2820
nnnnnnnnnn nnnnnnnnnn nnnnnnnnnn nnnnnnnnnn nnnnnnnnnn nnnnnnnnnn  2880
nnnnnnnnnn nnnnnnnnnn nnnnnnnnnn nnnnnnnnnn nnnnnnnnnn nnnnnnnnnn  2940
nnnnnnnnnn nnnnnnnnnn nnnnnnnnnn nnnnnnnnnn nnnnnnnnnn nnnnnnnnnn  3000
nnnnnnnnnn nnnnnnnnnn nnnnnnnnnn nnnnnnnnnn nnnnnnnnnn nnnnnnnnnn  3060
nnnnnnnnnn nnnnnnnnnn nnnnnnnnnn nnnnnnnnnn nnnnnnnnnn nnnnnnnnnn  3120
nnnnnnnnnn nnnnnnnnnn nnnnnnnnnn nnnnnnnnnn nnnnnnnnnn nnnnnnnnnn  3180
nnnnnnnnnn nnnnnnnnnn nnnnnnnnnn nnnnnnnnnn nnnnnnnnnn nnnnnnnnnn  3240
```

```
nnnnnnnnnn nnnnnnnnnn nnnnnnnnnn nagatattac taaattttgc ttctaatctc      3300
actcttaaat agtacttacc tttgaaacta ggcatttgaa tctgaaaaag aaagaggaga      3360
ttatgagctt gatagttcag taaatcatga ataaattagc taaataaatc tatgaataat      3420
agtatattaa aaataaatat gtaagataca ataattcaaa aatgaattca tatatataat      3480
actttccaaa taataagtat gtggctgcaa tcctttcgta attcaaattt tgttcattaa      3540 ttatttttt caaaacatca catggatagt catgaactaa atcaaagtac cagtgcataa       3600
cccctattga taaagaatca aataacaagt gtttgactgc ctcattatca ggatatcaaa      3660
ttattaatgc ataaccttcca ctgctaggggt atcaaagtag caacctcaat cacctcactg    3720
gaagggcatc tagtttcagt atttaactac tccactggca aggtgttaaa ttatcaatat      3780
ttaacctcca ctgataggat tttgatatat agtcagactg cgagccaaaa ttcatttcaa      3840
accaaaatat ttttctcaaa gacatatttt atgtttcaca ttgaaaaatt cacaaaaatt     3900
atgcgatatt gaaatcaatt ggataaaaatc cacgtcaaat ttagtatatt caatcataaa    3960
tcatttacta ttctagaaaa ggtatattaa aagtataatg catcaatttc ataaatcata     4020
aatatctcaa tataaaaaat attttattat ttattaataa a                          4061

<210> SEQ ID NO 40
<211> LENGTH: 4061
<212> TYPE: DNA
<213> ORGANISM: Artificial Sequence
<220> FEATURE:
<223> OTHER INFORMATION: synthetic

<400> SEQUENCE: 40
agtatattca atcataaatc atttactatt ctagaaaagg tatattaaaa gtataatgca       60
tcaatttcat aaatcataaa tatctcaata taaaaaatat tttattattt attaataaat      120
ctaggagaag tgaagcatta cttatcttgt aagtaaaact aaccaactga tcaaattaat      180
tctgagaatc tttctcaaaa ctcatcacca ctatatcaaa aacttgtgct tcttgctatg      240
taagagcata gacccttttct tcgatctggg gttccaagtt tctattttat tttgttcaac    300
tatcaaatta gactgacttt tcattttttt gtggatattc agctatttta tggcctttct     360
aacaataacc aaagtatgta ccaatattcc aacataatc atttattgca tgattttcac      420
cgcatcgaaa tatttgatat tatcaatcaa tccaaacttg ttattcactg acctcttatt     480
caaaccctta gtatatttaa tattctacct ttgtgattca ttcaatcgat ttcttttttt     540
tatttttctt ccctttctat atgctcttca ttaacttttc tttcaattat caatgcttta    600
ttcaatacat ctgtataagt agttaactca tatagtacca tttattttct aatttctatc     660
ctcaattcca actcaaattt atctactcag tcacattcat cttcaaccaa tctcgaagca     720
aacttgacaa gctccataaa tttagcttca tattctacaa ctattatatt tctttatttc     780 agataaaataa attttattc tttctgaatc ctcatactct aagaaaaata ttttatcat      840 aaaatatctt ttgaaatcac tcccaagcga gttgttctcc atcttgttca tatttaggtt      900
tcattctcta ttatcaatta aatgtctcat cttcaacat gtatgatgca tataagattt      960
tttcatcatc atggtatctc ttaacaataa atgcttctc catctccata agctaatttt     1020
tagctcctat ttcatagttt tcttaaaagt caatggagac aacttcttaa attctatgat     1080 attacttttat tgctcctatt gctcttatgt ccttgtggtg acaatattta ttgttgcact    1140
tgctgtagag gcagttactg ttactgcaat tgctattacg attccatcaa gccgactagt    1200
gtctgcatta tttggataat agttgatttt tgctacttta tttagatgtt ggtggcaaaa    1260
```

-continued

```
tcaatgactt cttttgctg agagatgcca ccaacctact aagtatcatc atcttattgg    1320
ttgataccct tagcagcacc tcgagtggtt cttttatct gatatggaac catcttaatc    1380
ttgcatgaaa aacaaacttc gcaaaatttt cttttaaaat ctaatatcta atattatact    1440
tttattaaaa tttaattatg attatttaa gaataaaaaa tttaaatttt gaaatcctca    1500
caaggctggc caagagataa tgaccatcat cctagtcggt ttgacgtagg acatccaaag    1560
atcaactata attcaagcat catattgaga tgctaggata taatcgatgg tgaaatttaa    1620
tgatgctcga ctgatcaaga tggggggccgg cccgatggcc tgttcaacaa tcattgatca    1680
aaatttttta accaaggtct atcaagatca ttaaaaagtc tttctaagat ctataaattg    1740
taataaagag acacaatcta gagagagaca cttttttacat aaagaaagta gaaattttag    1800
ggagagaaat tagagagaaa ggggaaagag agaggaagct gagaggaaga aagaaaagag    1860
aaagactctc tctctttttc ttttctttct tttctttctt ttcttttct tttcttttt    1920
tcttcctttt ctttctttct ttctttggct cattagaaaa ataggggacc tattgatccc    1980
cttgtttcct aaatagggga ggaatctcat cttggtagct atggccggcg atgtgagcca    2040
aagtggcaaa atcatgaatc tcccaacttg cagccgacat tgacttttgg cactggaaaa    2100
tcaaagaaat ttgacaaaaa atgggaaaaa attgaaacca aaatagggac caaaatccgg    2160
taatagctag ccaaaaatcc ttgatctttg ctcatggagg ataggaaaaa agattattca    2220
agagattaag ggaatcttat ctcattttt tgctgtgctt cggccatggt ggttgcagaa    2280
atcgtttgtg aaagctcgac aaactctgca atttcctcgg gcttgggcct cgatcttaa    2340
taggagaaga gagaagtcct ctttctttta aatagagtcg gagggaagga gtttgatttc    2400
ctccttatgg tggtttcaaa ctctgatcgg aagtccattg gaaagaaga ctcccattag    2460
ttttaaaatc taataagatt tattgattag aaaattgata aaaatgatt attaaaaaag    2520
tagcataatt atttaaatca atgatgctta gattgttgga ggtaaatagt aataaaatca    2580
aaaaattaaa attcatggga ccaaaaaata atgaacaaga tttgaaagaa atgtctataa    2640
ataagaattt atgaaacagg ggaacattga tcaaaggtgt gttaaatagt gtccttaaag    2700
tgttattgtc cctctcacgt agactttgtg tgttgggaga gaacatagta attctctcaa    2760
cctatgcaac ctaaatcttt tgaaaagaaa tttaaaatta tagaaaaatt ggcaaactag    2820
aatttttggtc attttcttta ttagtaaaaa atatactaag ttatatgtct ttatttatac    2880
tagtgaggtc tatctttgca caattcagac caaatttata ttctagttaa aagaggtata    2940
gattttttaa aatagatata actagtgaaa atagtcatag aaaagttaaa aatcaatgaa    3000
aggtagattt cacttctata ttggctttat ttgtggtcac tttatctaat tctttttttt    3060
gatggagcaa tataccctgt taaaatcttc tcgattttt tttcacttta agcaacctat    3120
ttcgatgcct aaacaatgga atttagttta accacttaat atgctacact tttaaaagga    3180
gcaccatatt gtagggcttg aaaagttact tgatttaaaa aaagagcatc ttaattggac    3240
atcatacaag taagttatga cctctgaaaa tttgatacat gatttatcat cttgatatgg    3300
taaatcttgt taagatttcc tcatggtgtc taaagtggcc ggttcatact gagtttggtg    3360
attcttctgg tcaatggtta attgctcgaa tatttttaag atataactaa tctccaactc    3420
tgccgactcc ttagtagtat gagcacatgg aaagcttgac ctaattgatt tcttaaattg    3480
cttgaaatca gtacttagaa aatatgcaaa atggatgaaa tgtttattgc agcgagagct    3540
ttctgatctg tacgaccgag agcttactag ttttttatga gctatacgtt ttgcacttaa    3600
```

```
gcctaattta aatagtgaaa tagttttgca acaattcaaa acaattaaaa tcaaaagaca    3660
agctgctatg catgttcaac tgactcggct ttcaatcgca atatgtcaca taggctggcc    3720
tagaatgcag atgcgtgcgt ggtgagcatc ctaaaaacct acatatccaa taaattccca    3780
ctagttggtg aagtattaaa tgtaactcgt attaactttt taatgtagga ctaaagttta    3840
ttcgactaat taagaactaa atactttaat aattgaactt ttccaaccag aaatcagaaa    3900
atatttaagt aattaaatat tacataataa ctagatcaaa atatcatggt tcctctctcg    3960
ctcgagatca attgggatgt tggtttatct tggtcatcca tcgagatgac tctatcttag    4020
cctttcaaaa cggcgcggta ccacgggtct caccgcttcg t                       4061

<210> SEQ ID NO 41
<211> LENGTH: 4061
<212> TYPE: DNA
<213> ORGANISM: Artificial Sequence
<220> FEATURE:
<223> OTHER INFORMATION: synthetic

<400> SEQUENCE: 41
caaaattttc ttttaaaatc taatatctaa tattatactt ttattaaaat ttaattatga      60
ttattttaag aataaaaaat ttaaattttg aaatcctcac aaggctggcc aagagataat     120
gaccatcatc ctagtcggtt tgacgtagga catccaaaga tcaactataa ttcaagcatc     180
atattgagat gctaggatat aatcgatggt gaaatttaat gatgctcgac tgatcaagat     240
gggggccggc ccgatggcct gttcaacaat cattgatcaa aatttttaa ccaaggtcta     300 tcaagatcat taaaaagtct ttctaagatc tataaattgt aataaagaga cacaatctag     360
agagagacac tttttacata agaaagtag aaattttagg gagagaaatt agagagaaag     420
gggaaagaga gaggaagctg agaggaagaa agaaaagaga aagactctct ctcttttttct    480 tttctttctt ttctttcttt tctttttctt ttctttttt cttccttttc tttctttctt     540
tctttggctc attagaaaaa taggggacct attgatcccc ttgtttccta aataggggag     600
gaatctcatc ttggtagcta tggccggcga tgtgagccaa agtggcaaaa tcatgaatct     660
cccaacttgc agccgacatt gacttttggc actggaaaat caagaaaatt tgacaaaaaa     720
tgggaaaaaa ttgaaaccaa aatagggacc aaaatccggt aatagctagc caaaaatcct     780
tgatctttgc tcatggagga taggaaaaaa gattattcaa gagattaagg gaatcttatc     840
tcattttttt gctgtgcttc ggccatggtg gttgcagaaa tcgtttgtga aagctcgaca     900
aactctgcaa tttcctcggg cttgggcctc gatctttaat aggagaagag agaagtcctc     960 tttctttaa atagagtcgg agggaaggag tttgatttcc tccttatggt ggtttcaaac    1020
tctgatcgga agtccattgg aaaagaagac tcccattagt tttaaaatct aataagattt    1080
attgattaga aaattgataa aaaatgatta ttaaaaaagt agcataatta tttaaatcaa    1140
tgatgcttag attgttggag gtaaatagta ataaaatcaa aaaattaaaa ttcatgggac    1200
caaaaaataa tgaacaagat ttgaaagaaa tgtctataaa taagaattta tgaaacaggg    1260
gaacattgat caaaggtgtg ttaaatagtg tccttaaagt gttattgtcc ctctcacgta    1320
gactttgtgt gttgggagag aacatagtaa ttctctcaac ctatgcaacc taaatctttt    1380 gaaagaaat ttaaaattat agaaaaattg gcaaactaga attttggtca ttttctttat    1440
tagtaaaaaa tatactaagt tatatgtctt tatttatact agtgaggtct atctttgcac    1500
aattcagacc aaatttatat tctagttaaa agaggtatag attttttaaa atagatataa    1560
ctagtggaaa tagtcataga aaagttaaaa atcaatgaaa ggtagatttc acttctatat    1620
```

```
tggctttatt tgtggtcact ttatctaatt ctttttttg atggagcaat atacctgtt    1680 aaaatcttct cgattttttt ttcactttaa gcaacctatt tcgatgccta aacaatggaa    1740
tttagtttaa ccacttaata tgctacactt ttaaaaggag caccatattg tagggcttga    1800
aaagttactt gatttaaaaa aagagcatct taattggaca tcatacaagt aagttatgac    1860
ctctgaaaat ttgatacatg atttatcatc ttgatatggt aaatcttgtt aagatttcct    1920
catggtgtct aaagtggccg gttcatactg agtttggtga ttcttctggt caatggttaa    1980
ttgctcgaat attttaaga tataactaat ctccaactct gccgactcct tagtagtatg    2040
agcacatgga aagcttgacc taattgattt cttaaattgc ttgaaatcag tacttagaaa    2100
atatgcaaaa tggatgaaat gtttattgca gcgagagctt tctgatctgt acgaccgaga    2160
gcttactagt ttttatgag ctacgtttt tgcacttaag cctaatttaa atagtgaaat    2220
agttttgcaa caattcaaaa caattaaaat caaaagacaa gctgctatgc atgttcaact    2280
gactcggctt tcaatcgcaa tatgtcacat aggctggcct agaatgcaga tgcgtgcgtg    2340
gtgagcatcc taaaaaccta catatccaat aaattcccac tagttggtga agtattaaat    2400
gtaactcgta ttaacttttt aatgtaggac taaagtttat tcgactaatt aagaactaaa    2460
tactttaata attgaacttt tccaaccaga aatcagaaaa tatttaagta attaaatatt    2520
acataataac tagatcaaaa tatcatggtt cctctctcgc tcgagatcaa ttgggatgtt    2580
ggtttatctt ggtcatccat cgagatgact ctatcttagc ctttcaaaac ggcgcggtac    2640
cacgggtctc accgcttcgt tacatcgaat gccaccatcc ctttttttt tttttttatt    2700 tatttatgct ttcttgctcc tagattggtg cggcctcatt acaactccac tgctacttga    2760
tgcttccctc tagcatctcc tttgcagctc tctcacttcc accactcttc ggcctaatgt    2820
tgggaaacga cgaaggggcc ttacaaaaat gtcatccatg atggcagtgg agaagaaaac    2880
atcgctgggg cttccttcg atatccttcg cagccaaagc tcttataggg ttatatggga    2940
gaacgctgca ttatttgggt gatctttttg gatggtgttg ttgactgatg ctagttttgc    3000
ttcatgaatt gaatatttac acaagatgag aatacaatct agtacaattg gtaccaatta    3060
cctgggtttg actcctgctc gcatctgatt gaagcttggt taatgtgcat ctcaattaat    3120
tcagaaagat catcggactt catgtgaatt attttgacta gcatgaatag ggctaaataa    3180
ggctgaaata tgtgttaaat ttttaaaatt ataacttgat catatgatgt ccaattgaga    3240
tgttttcaaa tcaaaaattt ttttcgagat ttatcactta atgttaaact cttagaaggt    3300
cgaaacagac tgaaagtttt cttttcaaga tgtatttga ccgagtatat aacttgatga    3360
tcatatgatg cccaattgag atgttttcaa atgaaaattt ttttgagat ttatgactta    3420 atgttaaact cttaaaaggt cgaaacagac tgaaagtttt cttttcaaga tgtatttga    3480 ccaaatatat ctcataatct ataagaata tatttcataa tctatgaata attagataga    3540
gcgacagaag ataatgctaa tgtaaaaatc acgatctatt ttttataaaa tttaatattt    3600
ttatataatc acttttacta tagtcatatt tattttaaaa aatttagtta tatttaaaat    3660
atcaaaaaaa tttgacttga attatataag aaaggatctt cctactatta tagatagaag    3720
ctttatatca tagtttacag tgtatggatc atcaatgaaa gaaagaggga tgtaaacctt    3780
acttttgaaa tttttctatt tgtttctaaa tttttaaag gatccaagtt gagaattgag    3840
agaattcttt ctttctgcaa atcaaatcat tagtataatc cacatggaga cgttgtaata    3900
gaaagtagaa actatatttt atgaataata gaaagggagt tgatttacgc caagcctttt    3960
```

-continued

```
gtttgcttga ttaattattt attttttatgg tgttagctgg accccatgaa tagcaaccat    4020
cgttgggtca gggtcgtgta tttgttttgg ggtcttcatt a                         4061
```

<210> SEQ ID NO 42
<211> LENGTH: 4061
<212> TYPE: DNA
<213> ORGANISM: Artificial Sequence
<220> FEATURE:
<223> OTHER INFORMATION: synthetic

<400> SEQUENCE: 42

```
caagtactcc agaatcaaaa ttgtgaaaga aaataggat aaatctggtt aagctgtaat       60
ttatttactt actttctatc tatattaaaa ttattcagat tattttgcaa atttatggat    120
atgcttgaat cacgtatctg atactttctc ttcatctgga tggcagtacc atgtgatcac    180
cacgcagacg gatacctaca agaaaaaggc aaggctaaca tgctttctta ccatcattct    240
ttacggtctt tgatccggtt ttgcgtgtcc acttcttacg tagtcttttt caaacattcc    300
tatctaagac tgaaggtaat gatttgcaaa ggaatagctt tactgttttc ctctaagtag    360
atgaaatatt actcacgtag aaaggagcca tcataattgc agaaagaata aaactgaatg    420
gaatatgagt agaattgtca aatcttggt ttaagggttt aatagccag atgagaaagc     480 aacctacttt tcttgaacaa cttgtttgtg actgtcttgt tgctcccatc ttgcatctat    540
gattagcaaa atatatgata aatagatatt cagatttgat cgaaagaag gaagattttc    600 tttaatccat ttaatttgaa tctcacaaaa aaaagtaga agatttggac acgatcgctg    660
ggggcagcac gctcttaata gaatggtgtc acgttcaga tctcgaaaaa ttattcaatt     720
ttttttaaaa aaaagagtc attgaaatta gacgttgtat gaccatgtta tgatctctga    780
aagtttgact tctgactcaa cttcccaatg tagcagattt tactcctgaa ccatgtttaa    840
cctcctgact catagtggcc aaagtatcta catcgagttc actggtcttc ttggatcaca    900
ttcataagaa tacttcccat aattttgctc aacgttgttt ttctcatcaa ccaaaggtat    960
atgcttttta aaattgaaat gcccatgaat attatggcat tctttattt gacattttgg    1020 ttgatcctat attgtttgtt tggcattcaa cacttcttca tgggaacctt tgaaatgagg   1080
taggtgctag gattttttctt tttacctatc catatcatat ttccaatgtc ttcttttaca   1140
ttaggttctt tagtgacaat aggggaaacg acccaatata ataccttga aaatttgggc     1200 aatatctact aaaactaact tgaataaaat attaacataa aagggattt agtaacataa     1260 aagcataact caaaatcact caccttgtgt gccacgttct cattgcccct attattttg     1320 cattgtgaat tgtgtccccc aataaagcaa cgtgaatggt ggaagagagt tgaatggctt    1380
tgttgagtaa ttgttttgag ttactatagc attgctctac taaaattgaa atcttgctgt    1440
gaggctatgt atgagaagca agttcatgct ttttgactgt tgggatggaa gtatgagcaa    1500 tcttttttaat agaaaatgga cgaatcatga agttttttcct ttttattgaa aaagatgatc    1560
gaaaaatatg tgcaagatag aaaaacactg aaaagataaa atgagaagta aaagtggaag    1620
tctaggagaa gaaaatttaa gagaaatatc ttcaatgaga ggatgtgtgc accaacaaag    1680
ccaactttca ctaagaatg taatgactca cctctacttt cttcgaataa ggggttccca    1740
gttgtggaaa gtatatagaa tcttctgaaa gactgagtaa atggagcaat tccttctaag    1800
aaatattatg gcatttctct cccacgaaat ttcaaagcaa agagcagcta gtagttgatc    1860
ctctaatctc ttaattgaag tttggaattt ctcttgcctc tatttggccc aaaggtcatg    1920
aagatctacc ggccaaccctc ttaagttgaa ttagatctta atagaagtcc aaatgcttct   1980
```

```
tgtagaagaa catctaataa ataaatgagt gatagattct aatccagaga caaagagcac    2040
acctcgaatt cacttgccat cctttctag ctagaacttc tctagcatga aacttgttcc    2100
ttaaggcaag ccaaataaat actcacattt taggaatgac tgccttccaa ataattttat    2160
aatatggaca aattagacca ccattattga taaacttgca atgaacaatt ataaatgagt    2220
tttcaggttg gcacattagc aatataggat ggtttgatta ttaaaaggat gatatgaagg    2280
gtttcaaggt ggtttgcctc gttcaaatca aaggattttg aagattaata ttccaagata    2340
aggttctcca actccattag gaaagtgtct tcatgtcatc ttagagaagc agctcgtacc    2400
aaacttgaca gatgttttat ttatttagag tgacacagat acccttggc aatactctcc     2460 atccttgtcc gaacaacttc taatcacacc tcacttatct tgcatctaac tcagaggcta    2520
caagttacac ctttcaacaa accttttcgg tttgaaaatt tgtgatttca ttatttagag    2580
ttcgaagagc atatcaagta ttggtcggag ttggcaccca aagcaaacga aacagttact    2640
gacatggtcc aaaagctgag atttctaaga tcccaactta agcactgaat aaagccatta    2700
tgggaaatat catttttaacg aaagaggaat ttagagtaag aattgattct cttgataccg    2760
aagaagaact aatacagctt tcatcacttc aaaatgatga acagatgcat ctcaagtcag    2820
cactagacca tcttctaaaa taggaagatc tatggaagca acactcccaa atgcagtggc    2880
ttcaaaatgg ggattgcaat acgaagttta tccatgtttg ggcaagtaac aggaaaaaaa    2940
gaatactatc actgaactct agcaaggcga tcagaagatt atcgaatagc agcaaatcca    3000
atccacattc tacaactttt tttctaccct actaggctcg actgaggaat gactcatcca    3060
agctgattgg aagattcttt atccagaagg acctctggat cttgctgaca ttgagtatcc    3120
atttatggag aaagaaatcc atgatacagt gtatgacttg gctttggaaa agtcacccgg    3180
atgatatttt cccattctcc ttctataagc acttctagtg tatcatcaaa catgacctga    3240
tgaacctact gtaaaatcag ctaatgtaga ccatctgaac tacttgttca tcacccttat    3300
cccaaaaaaa aattggtgtg tattcagtta gagacttcag gccaataagc ctgattaatg    3360
gagtaataaa aaatatttca aaaactctat cgaaaaggct cccacagaaa atgaatttgt    3420
taattttatc cacagagctt gctttcaaca gaggaagaaa tatctctgaa tattttgtaa    3480
tgactatgga aactatacac ttctgcaaag ctgaagtaca caaggatctc aattataaag    3540
tcgacttcga gaaagctttt gacaatgtgg attggagctt tctattgaaa ttgctatcca    3600
gcacggggct ttgattcgag gtggtgtcaa tggatagaat atctgattta tacagctaaa    3660
ttctcagtcc ttattaatgg tgataaaggt aaactttta aattgaggaa agatctcagg    3720
caaggagatc ctctattcgc ctagctcttt ctcttagttg ttgatataga atgatcaagg    3780
gagcaagtag gttcaatctt tttgttggaa ttggatcata taatatcatg ggataacttc    3840
aaagctttta gttcactgat gacacactta tattttgcag atatgatcta aaatacatca    3900
aaactcttaa attttactc tatagttatg agctactgat gggtctcaaa attaactttg    3960
aaaaattcca attttttggc ttgagaattg caaagatgtc agtacagcaa gttgcatcta    4020
tcctagaaag caaggtggct acatttcca ttacttattt g                         4061
```

<210> SEQ ID NO 43
<211> LENGTH: 4061
<212> TYPE: DNA
<213> ORGANISM: Artificial Sequence
<220> FEATURE:
<223> OTHER INFORMATION: synthetic

<400> SEQUENCE: 43

```
gaccatgtta tgatctctga aagtttgact tctgactcaa cttcccaatg tagcagattt        60
tactcctgaa ccatgtttaa cctcctgact catagtggcc aaagtatcta catcgagttc       120
actggtcttc ttggatcaca ttcataagaa tacttcccat aattttgctc aacgttgttt       180
ttctcatcaa ccaaaggtat atgcttttta aaattgaaat gcccatgaat attatggcat       240
tcttttattt gacattttgg ttgatccat attgttgtt tggcattcaa cacttcttca        300
tgggaacctt tgaaatgagg taggtgctag gattttctt tttacctatc catatcatat       360
ttccaatgtc ttcttttaca ttaggttctt tagtgacaat aggggaaacg acccaatata       420
ataccttga aaatttgggc aatatctact aaaactaact tgaataaaat attaacataa       480
aaagggattt agtaacataa aagcataact caaaatcact caccttgtgt gccacgttct       540
cattgccctt attattttg cattgtgaat tgtgtccccc aataaagcaa cgtgaatggt       600
ggaagagagt tgaatggctt tgttgagtaa ttgttttgag ttactatagc attgctctac       660
taaaattgaa atcttgctgt gaggctatgt atgagaagca agttcatgct ttttgactgt       720
tgggatggaa gtatgagcaa tcttttaat agaaaatgga cgaatcatga agttttcct        780
ttttattgaa aaagatgatc gaaaaatatg tgcaagatag aaaacactg aaagataaa        840
atgagaagta aagtggaag tctaggagaa gaaatttaa gagaaatatc ttcaatgaga        900
ggatgtgtgc accaacaaag ccaacttca ctaagaatg taatgactca cctctacttt         960
cttcgaataa ggggttccca gttgtggaaa gtatatagaa tcttctgaaa gactgagtaa      1020
atggagcaat tccttctaag aaatattatg gcatttctct cccacgaaat ttcaaagcaa      1080
agagcagcta gtagttgatc ctctaatctc ttaattgaag tttggaattt ctcttgcctc      1140
tatttggccc aaaggtcatg aagatctacc ggccaacctc ttaagttgaa ttagatctta      1200
atagaagtcc aaatgcttct tgtagaagaa catctaataa ataaatgagt gatagattct      1260
aatccagaga caaagagcac acctcgaatt cacttgccat cctttttctag ctagaacttc     1320
tctagcatga aacttgttcc ttaaggcaag ccaaataaat actcacattt taggaatgac      1380
tgccttccaa ataattttat aatatggaca aattagacca ccattattga taaacttgca      1440
atgaacaatt ataaatgagt tttcaggttg gcacattagc aatataggat ggtttgatta      1500
ttaaaaggat gatatgaagg gtttcaaggt ggtttgcctc gttcaaatca aaggattttg      1560
aagattaata ttccaagata aggttctcca actccattag gaaagtgtct tcatgtcatc      1620
ttagagaagc agctcgtacc aaacttgaca gatgttttat ttatttagag tgacacagat      1680
accctttggc aatactctcc atccttgtcc gaacaacttc taatcacacc tcacttatct      1740
tgcatctaac tcagaggcta caagttacac ctttcaacaa accttttcgg tttgaaaatt      1800
tgtgatttca ttatttagag ttcgaagagc atatcaagta ttggtcggag ttggcaccca      1860
aagcaaacga aacagttact gacatggtcc aaaagctgag atttctaaga tcccaactta      1920
agcactgaat aaagccatta tgggaaatat cattttaacg aaagaggaat ttagagtaag      1980
aattgattct cttgataccg aagaagaact aatacagctt tcatcacttc aaaatgatga      2040
acagatgcat ctcaagtcag cactagacca tcttctaaaa taggaagatc tatgaaagca      2100
acactcccaa atgcagtggc ttcaaaatgg ggattgcaat acgaagttta tccatgtttg      2160
ggcaagtaac aggaaaaaaa gaatactatc actgaactct agcaaggcga tcagaagatt      2220
atcgaatagc agcaaatcca atccacattc tacaactttt tttctaccct actaggctcg      2280
actgaggaat gactcatcca agctgattgg aagattcttt atccagaagg acctctggat      2340
```

| | |
|---|---|
| cttgctgaca ttgagtatcc atttatggag aaagaaatcc atgatacagt gtatgacttg | 2400 |
| gctttggaaa agtcacccgg atgatatttt cccattctcc ttctataagc acttctagtg | 2460 |
| tatcatcaaa catgacctga tgaacctact gtaaaatcag ctaatgtaga ccatctgaac | 2520 |
| tacttgttca tcacccttat cccaaaaaaa aattggtgtg tattcagtta gagacttcag | 2580 |
| gccaataagc ctgattaatg gagtaataaa aaatatttca aaaactctat cgaaaaggct | 2640 |
| cccacagaaa atgaatttgt taattttatc cacagagctt gctttcaaca gaggaagaaa | 2700 |
| tatctctgaa tattttgtaa tgactatgga aactatacac ttctgcaaag ctgaagtaca | 2760 |
| caaggatctc aattataaag tcgacttcga gaaagctttt gacaatgtgg attggagctt | 2820 |
| tctattgaaa ttgctatcca gcacggggct ttgattcgag gtggtgtcaa tggatagaat | 2880 |
| atctgattta tacagctaaa ttctcagtcc ttattaatgg tgataaaggt aaacttttta | 2940 |
| aattgaggaa agatctcagg caaggagatc ctctattcgc ctagctcttt ctcttagttg | 3000 |
| ttgatataga atgatcaagg gagcaagtag gttcaatctt tttgttggaa ttggatcata | 3060 |
| taatatcatg ggataacttc aaagctttta gttcactgat gacacactta tattttgcag | 3120 |
| atatgatcta aaatacatca aaactcttaa attttactc tatagttatg agctactgat | 3180 |
| gggtctcaaa attaactttg aaaaattcca attttttggc ttgagaattg caaagatgtc | 3240 |
| agtacagcaa gttgcatcta tcctagaaag caaggtggct acattttcca ttacttattt | 3300 |
| gggtctccca ctccatcatt ctaaactgag gaaaacttat tggaatccac tccttgagaa | 3360 |
| ggttcagaag aaattgatcg ggtagaaagg taaacttctt aacctctagg gtaggcttat | 3420 |
| actaactaat gcagtgctta cagggatccc actactctgg agggatacat tccttctccc | 3480 |
| tcaattcatt atcaaataaa ttgataaaat ccatcgatca ttcatttgga gaggaaacga | 3540 |
| ggagtataac taagggcact ctagaatatg ttggtcgaat atttgtcgat caaaaaaatt | 3600 |
| tggaggactg ggggttcctc aatctaaaaa ttttcaatac aattcttctt tgtaaatggt | 3660 |
| ggtggaagct ctactctaat gctggtgacc cgtggtgtag ttttattgcc actgtccacc | 3720 |
| caacttcaca ctagagatct aaaggtatac acaaatcaac ctcttcattt tggaatggtt | 3780 |
| tacagcacac atgaaatatt tctactccta atccactttc aagttagcaa ctagtattat | 3840 |
| tttggaaaga tagttggtta cataatcatc cactgaagga tcgatttcct cacctttaca | 3900 |
| caatagcatt gaagtgcaac aactcagtgg caaaggtatt aagcaatcta cttgataata | 3960 |
| gctcttttag tactcctctt cctcaaagat accaagaaga ttttcagagt ctataggaaa | 4020 |
| gcattgaaca aattacatta acggaacgac ctgatactat a | 4061 |

<210> SEQ ID NO 44
<211> LENGTH: 4061
<212> TYPE: DNA
<213> ORGANISM: Artificial Sequence
<220> FEATURE:
<223> OTHER INFORMATION: synthetic

<400> SEQUENCE: 44

| | |
|---|---|
| tcttctgaaa gactgagtaa atggagcaat tccttctaag aaatattatg gcatttctct | 60 |
| cccacgaaat ttcaaagcaa agagcagcta gtagttgatc tctctaatctc ttaattgaag | 120 |
| tttggaatttt ctcttgcctc tatttggccc aaaggtcatg aagatctacc ggccaacctc | 180 |
| ttaagttgaa ttgatctta atagaagtcc aaatgcttct tgtagaagaa catctaataa | 240 |
| ataaatgagt gatagattct aatccagaga caaagagcac acctcgaatt cacttgccat | 300 |

```
ccttttctag ctagaacttc tctagcatga aacttgttcc ttaaggcaag ccaaataaat      360
actcacattt taggaatgac tgccttccaa ataattttat aatatggaca aattagacca      420
ccattattga taaacttgca atgaacaatt ataaatgagt tttcaggttg gcacattagc      480
aatataggat ggtttgatta ttaaaaggat gatatgaagg gtttcaaggt ggtttgcctc      540
gttcaaatca aaggattttg aagattaata ttccaagata aggttctcca actccattag      600
gaaagtgtct tcatgtcatc ttagagaagc agctcgtacc aaacttgaca gatgttttat      660
ttatttagag tgacacagat acccttttggc aatactctcc atccttgtcc gaacaacttc     720
taatcacacc tcacttatct tgcatctaac tcagaggcta caagttacac ctttcaacaa      780
accttttcgg tttgaaaatt tgtgatttca ttatttagag ttcgaagagc atatcaagta     840
ttggtcggag ttggcaccca aagcaaacga aacagttact gacatggtcc aaaagctgag     900
atttctaaga tcccaactta agcactgaat aaagccatta tgggaaatat cattttaacg     960
aaagaggaat ttagagtaag aattgattct cttgataccg aagaagaact aatacagctt    1020
tcatcacttc aaaatgatga acagatgcat ctcaagtcag cactgaccaa tcttctaaaa   1080
taggaagatc tatggaagca acactcccaa atgcagtggc ttcaaaatgg ggattgcaat    1140
acgaagttta tccatgtttg ggcaagtaac aggaaaaaaa gaatactatc actgaactct    1200
agcaaggcga tcagaagatt atcgaatagc agcaaatcca atccacattc tacaactttt    1260 tttctacccct actaggctcg actgaggaat gactcatcca agctgattgg aagattcttt    1320
atccagaagg acctctggat cttgctgaca ttgagtatcc atttatggag aaagaaatcc    1380
atgatacagt gtatgacttg gctttggaaa agtcacccgg atgatatttt cccattctcc    1440
ttctataagc acttctagtg tatcatcaaa catgacctga tgaacctact gtaaaatcag    1500
ctaatgtaga ccatctgaac tacttgttca tcacccttat cccaaaaaaa aattggtgtg    1560
tattcagtta gagacttcag gccaataagc ctgattaatg gagtaataaa aaatatttca    1620
aaaactctat cgaaaaggct cccacagaaa atgaatttgt taattttatc cacagagctt    1680
gctttcaaca gaggaagaaa tatctctgaa tattttgtaa tgactatgga aactatacac    1740
ttctgcaaag ctgaagtaca caaggatctc aattataaag tcgacttcga gaaagctttt    1800
gacaatgtgg attggagctt tctattgaaa ttgctatcca gcacggggct ttgattcgag    1860
gtggtgtcaa tggatagaat atctgattta tacagctaaa ttctcagtcc ttattaatgg    1920
tgataaaggt aaacttttta aattgaggaa agatctcagg caaggagatc ctctattcgc    1980 ctagctctt ctcttagttg ttgatataga atgatcaagg gagcaagtag gttcaatctt     2040
tttgttggaa ttggatcata taatatcatg ggataacttc aaagctttta gttcactgat    2100
gacacactta tattttgcag atatgatcta aaatacatca aaactcttaa attttttactc   2160 tatagttatg agctactgat gggtctcaaa attaactttg aaaaattcca atttttttggc   2220 ttgagaattg caaagatgtc agtacagcaa gttgcatcta tcctagaaag caaggtggct    2280 acatttttcca ttacttattt gggtctccca ctccatcatt ctaaactgag gaaaactat    2340 tggaatccac tccttgagaa ggttcagaag aaattgatcg ggtagaaagg taaacttctt    2400
aacctctagg gtaggcttat actaactaat gcagtgctta cagggatccc actactctgg    2460
agggatacat tccttctccc tcaattcatt atcaaataaa ttgataaaat ccatcgatca    2520
ttcatttgga gaggaaacga ggagtataac taagggcact ctagaatatg ttggtcgaat    2580
atttgtcgat caaaaaaatt tggaggactg ggggttcctc aatctaaaaa ttttcaatac    2640
aattcttctt tgtaaatggt ggtggaagct ctactctaat gctggtgacc cgtggtgtag    2700
```

-continued

```
ttttattgcc actgtccacc caacttcaca ctagagatct aaaggtatac acaaatcaac    2760
ctcttcattt tggaatggtt tacagcacac atgaaatatt tctactccta atccactttc    2820
aagttagcaa ctagtattat tttggaaaga tagttggtta cataatcatc cactgaagga    2880
tcgatttcct cacctttaca caatagcatt gaagtgcaac aactcagtgg caaaggtatt    2940
aagcaatcta cttgataata gctcttttag tactcctctt cctcaaagat accaagaaga    3000
ttttcagagt ctataggaaa gcattgaaca aattacatta acggaacgac ctgatactat    3060
acaatggaaa tggtttagta gcaatatttt tttggcatga aggatctact attttctgca    3120
agatggagga gtttggcctc tactgagtaa tattatataa aaactcctaa taccaaagaa    3180
agccaagtta tttgcttggc taagtgctca caacaaaatc ccaatgaaag ctaatcttct    3240
taatagagga ataattggaa ctgattactg tacactttgc gatgacttat cagaaactaa    3300
tgatcatcta atgctcatct atactttttc aaaagcaatt tggaatcaag tactttcaga    3360
cctgcaattg tcgaaacttt tatgcatgct taacacccta tgggatactt ggagactcat    3420
caatatgcaa cacgatagaa gacctaaact agctgctcta ttcgtaattg gtcaatggtg    3480
tctttggaag gaaagaaata aaagattatt cgacttctat acttttatc cacgatcgat     3540 tgctgaaact gtgtcacttt ttctttcttg gcatcacac ctaacaacgg agcaactaaa     3600
gatgttagct cctgttcgag aagttctctt atctaagaat gaaaacacac aatctttagt    3660
gagaattaca gatgctaaca ggcgcagatg aatgttttat gagcattttt atagctgcag    3720
cttatatgtg atctatggtg caaggagtta attataacca tggatattag ttaggttgac    3780
tatcagaaat catctccaat acattctatg taaccactga tcaattccat gttcaactag    3840
ataggaacct gcctatatac aggtatgtcc ctgatgtaac tatagtatac tattattcat    3900
aaataaataa cgaaggtttt accttcttct cataaaaaaa aagtatcttc atgtcatcct    3960
atatgtcatg catctccttt gctacttctt ttatttactt cttaaacttg gttctaccat    4020
atattatcag ccccttttaa atttgctttt ggatattgca t                        4061
```

<210> SEQ ID NO 45
<211> LENGTH: 4061
<212> TYPE: DNA
<213> ORGANISM: Artificial Sequence
<220> FEATURE:
<223> OTHER INFORMATION: synthetic

<400> SEQUENCE: 45

```
gctttcaaca gaggaagaaa tatctctgaa tattttgtaa tgactatgga aactatacac      60
ttctgcaaag ctgaagtaca caaggatctc aattataaag tcgacttcga gaaagctttt     120
gacaatgtgg attggagctt tctattgaaa ttgctatcca gcacggggct ttgattcgag     180
gtggtgtcaa tggatagaat atctgattta tacagctaaa ttctcagtcc ttattaatgg     240
tgataaaggt aaacttttta aattgaggaa agatctcagg caaggagatc ctctattcgc     300
ctagctcttt ctcttagttg ttgatataga atgatcaagg gagcaagtag gttcaatctt     360
tttgttggaa ttggatcata taatatcatg ggataacttc aaagctttta gttcactgat     420
gacacactta tattttgcag atatgatcta aaatacatca aaactcttaa attttactc      480 tatagttatg agctactgat gggtctcaaa attaactttg aaaaattcca attttttggc     540
ttgagaattg caaagatgtc agtacagcaa gttgcatcta tcctagaaag caaggtggct     600
acattttcca ttacttattt gggtctccca ctccatcatt ctaaactgag gaaaacttat     660
```

```
tggaatccac tccttgagaa ggttcagaag aaattgatcg ggtagaaagg taaacttctt    720
aacctctagg gtaggcttat actaactaat gcagtgctta cagggatccc actactctgg    780
agggatacat tccttctccc tcaattcatt atcaaataaa ttgataaaat ccatcgatca    840
ttcatttgga gaggaaacga ggagtataac taagggcact ctagaatatg ttggtcgaat    900
atttgtcgat caaaaaaatt tggaggactg ggggttcctc aatctaaaaa ttttcaatac    960
aattcttctt tgtaaatggt ggtggaagct ctactctaat gctggtgacc cgtggtgtag   1020
ttttattgcc actgtccacc caacttcaca ctagagatct aaaggtatac acaaatcaac   1080
ctcttcattt tggaatggtt tacagcacac atgaaatatt tctactccta atccactttc   1140
aagttagcaa ctagtattat tttggaaaga tagttggtta cataatcatc cactgaagga   1200
tcgatttcct cacctttaca caatagcatt gaagtgcaac aactcagtgg caaaggtatt   1260
aagcaatcta cttgataata gctcttttag tactcctctt cctcaaagat accaagaaga   1320
ttttcagagt ctataggaaa gcattgaaca aattacatta acggaacgac ctgatactat   1380
acaatggaaa tggtttagta gcaatatttt tttggcatga aggatctact attttctgca   1440
agatggagga gtttggcctc tactgagtaa tattatataa aaactcctaa taccaaagaa   1500
agccaagtta tttgcttggc taagtgctca aacaaaatc ccaatgaaag ctaatcttct   1560
taatagagga ataattggaa ctgattactg tacactttgc gatgactat cagaaactaa   1620
tgatcatcta atgctcatct atactttttc aaaagcaatt tggaatcaag tactttcaga   1680
cctgcaattg tcgaaacttt tatgcatgct taacacccta tgggatactt ggagactcat   1740
caatatgcaa cacgatagaa gacctaaact agctgctcta ttcgtaattg gtcaatggtg   1800
tctttggaag gaaagaaata aaagattatt cgacttctat acttttatc cacgatcgat   1860
tgctgaaact gtgtcacttt ttctttcttg ggcatcacac ctaacaacgg agcaactaaa   1920
gatgttagct cctgttcgag aagttctctt atctaagaat gaaaacacac aatctttagt   1980
gagaattaca gatgctaaca ggcgcagatg aatgttttat gagcattttt atagctgcag   2040
cttatatgtg atctatggtg caaggagtta attataacca tggatattag ttaggttgac   2100
tatcagaaat catctccaat acattctatg taaccactga tcaattccat gttcaactag   2160
ataggaacct gcctatatac aggtatgtcc ctgatgtaac tatagtatac tattattcat   2220
aaataaataa cgaaggtttt accttcttct cataaaaaaa aagtatcttc atgtcatcct   2280
atatgtcatg catctccttt gctacttctt ttatttactt cttaaacttg gttctaccat   2340
atattatcag ccccttttaa atttgctttt ggatattgca tattccactc ttcaatcacc   2400
tcatgccaag caaaacattt attcacactt gaaaaccaat ataagaatac caaagaattt   2460
atccatgaaa ttctagaaac tttggtttta ctcctttctc catcattcaa aaaggttcaa   2520
aatgatgata actctatata gcttatttat caaatttacg aggttggtgt tcaatgtttt   2580
tgtgaaaaaa atatcttgct atccacatag tttgaatcca tacttttgct atcttgagtt   2640
tcaaaaattt taatttgcta caatttgttg ctattagcat atgactactt ttaagaagat   2700
aagccaatat actattttcc taagaattta aaaaatcaaa aataaaaatt tttatttaag   2760
attttttaag ggttgttttc caaatgtgca atggggctta atcttggcat cattttctaa   2820
cttgtagaat tttgacccaa gtaacatttg tccaatcact tagaacttct ataacttcgt   2880
acaatcattt gttaatgttg ttcatctatt tatctatatt atctatctgg aatatagttg   2940
ctcttaatta ttttatatata tcgcctatta tccaccctaa gctttcatgt tcatcctcat   3000
gttgttggag gtgcatgtct tattccaaac tatttaccat tgctgtagat tttaaaaaat   3060
```

```
ttgctagttt aggactttt  aatcttttga tatcatgttg atgtaagcta accctctaag   3120
gctagtcata atacatttta aggatttatg ttatatgaga ccaaatttt  aacaaaatga   3180
agtgttggaa attggtagaa tggaagtgta aagatgctta gagacataga actagccctg   3240
ggccatgtaa atcttccaaa agaagaagaa aataataaaa ttaagatcat attcaatctc   3300
tacagaaaag ttggtctttg ttgtataata agccatctta acatatgatg acaataaaa    3360
tatataaact tatgagtttt aatacttaga tggaagaaaa gggacagata tgtcacaccc   3420
catcctacta gcatgagtag gcacatgata cacggttgca tgccctgcag agtttgactc   3480
atgaggcatg caaggtattg aatagtagtc taggtaaaat taaaaaactt ggagcattct   3540
aaaaataaat caagttcatt ttataaaatc aatatttatt atggactcca tcaaatatta   3600
tgcgcataac attttatttg caaatagaag aagataagtc ctagatccta agtctcctac   3660
tcttagtctc ataattcatc caagctatcc accaaatatc taaaacgaaa aagaaaaacg   3720
atagtatgct aatagctttg taagtcacct tttatctcta attagatcaa gcatattaga   3780
tataaaacaa taattttcaa agtatatgat ttgcaattag gaataaatat ttgataaata   3840
cagaataaat tttcataaag catatttact aacattattt ataaaatata taatgcttat   3900
atcaataaat taatttctaa atcaatatat ataaactatc cattctgtct tagccttaca   3960
actattgcta ccattccctg tagcatggtt aggaagagac tagctcttga atactcatgt   4020
catttatcaa catatgcgaa tgatcattcg actaatatag t                       4061
```

<210> SEQ ID NO 46
<211> LENGTH: 4061
<212> TYPE: DNA
<213> ORGANISM: Artificial Sequence
<220> FEATURE:
<223> OTHER INFORMATION: synthetic

<400> SEQUENCE: 46

```
tttgttggaa ttggatcata taatatcatg ggataacttc aaagctttta gttcactgat     60
gacacactta tattttgcag atatgatcta aatacatca  aaactcttaa attttttactc   120
tatagttatg agctactgat gggtctcaaa attaactttg aaaaattcca attttttggc    180
ttgagaattg caaagatgtc agtacagcaa gttgcatcta tcctagaaag caaggtggct    240
acattttcca ttacttattt gggtctccca ctccatcatt ctaaactgag gaaaacttat    300
tggaatccac tccttgagaa ggttcagaag aaattgatcg ggtagaaagg taaacttctt    360
aacctctagg gtaggcttat actaactaat gcagtgctta cagggatccc actactctgg    420
agggatacat tccttctccc tcaattcatt atcaaataaa ttgataaaat ccatcgatca    480
ttcatttgga gaggaaacga ggagtataac taagggcact ctagaatatg ttggtcgaat    540
atttgtcgat caaaaaaatt tggaggactg ggggttcctc aatctaaaaa ttttcaatac    600
aattcttctt tgtaaatggt ggtggaagct ctactctaat gctggtgacc cgtggtgtag    660
ttttattgcc actgtccacc caacttcaca ctagagatct aaaggtatac acaaatcaac    720
ctcttcattt tggaatggtt tacagcacac atgaaatatt tctactccta atccactttc    780
aagttagcaa ctagtattat tttggaaaga tagttggtta cataatcatc cactgaagga    840
tcgatttcct caccttaca  caatagcatt gaagtgcaac aactcagtgg caaaggtatt    900
aagcaatcta cttgataata gctctttag  tactcctctt cctcaaagat accaagaaga    960
ttttcagagt ctataggaaa gcattgaaca aattacatta acggaacgac ctgatactat   1020
```

```
acaatggaaa tggtttagta gcaatatttt tttggcatga aggatctact attttctgca    1080
agatggagga gtttggcctc tactgagtaa tattatataa aaactcctaa taccaaagaa    1140
agccaagtta tttgcttggc taagtgctca caacaaaatc ccaatgaaag ctaatcttct    1200
taatagagga ataattggaa ctgattactg tacactttgc gatgacttat cagaaactaa    1260
tgatcatcta atgctcatct atacttttc aaaagcaatt tggaatcaag tactttcaga    1320
cctgcaattg tcgaaacttt tatgcatgct taacaccta tgggatactt ggagactcat     1380
caatatgcaa cacgatagaa gacctaaact agctgctcta ttcgtaattg gtcaatggtg    1440
tctttggaag gaaagaaata aaagattatt cgacttctat acttttatc cacgatcgat     1500 tgctgaaact gtgtcacttt ttctttcttg ggcatcacac ctaacaacgg agcaactaaa    1560
gatgttagct cctgttcgag aagttctctt atctaagaat gaaaacacac aatctttagt    1620
gagaattaca gatgctaaca ggcgcagatg aatgttttat gagcattttt atagctgcag    1680
cttatatgtg atctatggtg caaggagtta attataacca tggatattag ttaggttgac    1740
tatcagaaat catctccaat acattctatg taaccactga tcaattccat gttcaactag    1800
ataggaacct gcctatatac aggtatgtcc ctgatgtaac tatagtatac tattattcat    1860 aaaataaataa cgaaggtttt accttcttct cataaaaaaa aagtatcttc atgtcatcct    1920
atatgtcatg catctccttt gctacttctt ttatttactt cttaaacttg gttctaccat    1980
atattatcag cccctttaa atttgcttt ggatattgca tattccactc ttcaatcacc     2040
tcatgccaag caaacatttt attcacactt gaaaccaat ataagaatac caagaatttt     2100
atccatgaaa ttctagaaac tttggtttta ctccttctc catcattcaa aaaggttcaa     2160
aatgatgata actctatata gcttatttat caaatttacg aggttggtgt tcaatgtttt    2220
tgtgaaaaaa atatcttgct atccacatag tttgaatcca tacttttgct atcttgagtt    2280
tcaaaatttt taatttgcta caatttgttg ctattagcat atgactactt ttaagaagat    2340
aagccaatat actattttcc taagaattta aaaaatcaaa aataaaaatt tttatttaag    2400
attttttaag ggttgttttc caaatgtgca atggggctta atcttggcat cattttctaa    2460
cttgtagaat tttgacccaa gtaacatttg tccatcact tagaacttct ataacttcgt     2520
acaatcattt gttaatgttg ttcatctatt tatctatatt atctatctgg aatatagttg    2580
ctcttaatta tttttatata tcgcctatta tccacccta gctttcatgt tcatcctcat     2640
gttgttggag gtgcatgtct tattccaaac tatttaccat tgctgtagat tttaaaaaat    2700
ttgctagttt aggactttt aatcttttga tatcatgttg atgtaagcta accctctaag     2760
gctagtcata atacattta aggatttatg ttatatgaga ccaaaatttt aacaaaatga     2820
agtgttggaa attggtagaa tggaagtgta aagatgctta gagacataga actagccctg    2880
ggccatgtaa atcttccaaa agaagaagaa aataataaaa ttaagatcat attcaatctc    2940
tacagaaaag ttggtctttg ttgtataata agccatctta acatatgatg acaataaaa     3000 tatataaact tatgagtttt aatacttaga tggaagaaaa gggacagata tgtcacaccc    3060
catcctacta gcatgagtag gcacatgata cacggttgca tgccctgcag agtttgactc    3120
atgaggcatg caaggtattg aatagtagtc taggtaaaat taaaaaactt ggagcattct    3180
aaaaataaat caagttcatt ttataaaatc aatatttatt atggactcca tcaaatatta    3240
tgcgcataac atttattttg caaatagaag aagataagtc ctagatccta agtctcctac    3300
tcttagtctc ataattcatc caagctatcc accaaatatc taaaacgaaa aagaaaaacg    3360
atagtatgct aatagctttg taagtcacct tttatctcta attagatcaa gcatattaga    3420
```

```
tataaaacaa taattttcaa agtatatgat ttgcaattag gaataaatat ttgataaata    3480
cagaataaat tttcataaag catatttact aacattattt ataaaatata taatgcttat    3540
atcaataaat taatttctaa atcaatatat ataaactatc cattctgtct tagccttaca    3600
actattgcta ccattccctg tagcatggtt aggaagagac tagctcttga atactcatgt    3660
catttatcaa catatgcgaa tgatcattcg actaatatag tcaaaaaaaa attactctga    3720
tttatataaa ttaaaaatta gtaaataata tatgctagta atcaccttac cagctaagct    3780
ctaaagaaaa ttagcttttg aatatacatc atgctattga ttattatatg tcagtgcttg    3840
tctcattttg tggcatgcaa gaagactaga tcctaaactt atatgcatag tcagattaaa    3900
gagcaaatgt tgcatctgat tatatgaaca tctattatga tgtagagttt gtatcatgta    3960
tatttaattt aaacacaaat ataattatac ataaataata ttcatatttt aaattttaaa    4020
tatttagata attattctag tgcaggtata aaaataagca a                        4061

<210> SEQ ID NO 47
<211> LENGTH: 4061
<212> TYPE: DNA
<213> ORGANISM: Artificial Sequence
<220> FEATURE:
<223> OTHER INFORMATION: synthetic

<400> SEQUENCE: 47
ttggcctcta ctgagtaata ttatataaaa actcctaata ccaaagaaag ccaagttatt      60
tgcttggcta agtgctcaca acaaaatccc aatgaaagct aatcttctta atagaggaat     120
aattggaact gattactgta cactttgcga tgacttatca gaaactaatg atcatctaat     180
gctcatctat acttttttcaa aagcaatttg gaatcaagta ctttcagacc tgcaattgtc     240
gaaactttta tgcatgctta acaccctatg ggatacttgg agactcatca atatgcaaca     300
cgatagaaga cctaaactag ctgctctatt cgtaattggt caatggtgtc tttggaagga     360
aagaaataaa agattattcg acttctatac tttttatcca cgatcgattg ctgaaactgt     420 gtcactttt ctttcttggg catcacacct aacaacggag caactaaaga tgttagctcc     480
tgttcgagaa gttctcttat ctaagaatga aaacacacaa tctttagtga aattacaga      540 tgctaacagg cgcagatgaa tgttttatga gcatttttat agctgcagct tatatgtgat    600
ctatggtgca aggagttaat tataaccatg gatattagtt aggttgacta tcagaaatca    660
tctccaatac attctatgta accactgatc aattccatgt tcaactagat aggaacctgc    720
ctatatacag gtatgtccct gatgtaacta tagtatacta ttattcataa ataaataacg    780
aaggttttac cttcttctca taaaaaaaaa gtatcttcat gtcatcctat atgtcatgca    840
tctcctttgc tacttctttt atttacttct taaacttggt tctaccatat attatcagcc    900
ccttttaaat ttgcttttgg atattgcata ttccactctt caatcacctc atgccaagca    960
aaacatttat tcacacttga aaccaatat aagaatacca aagaatttat ccatgaaatt    1020
ctagaaactt tggttttact cctttctcca tcattcaaaa aggttcaaaa tgatgataac    1080
tctatatagc ttatttatca aatttacgag gttggtgttc aatgttttg tgaaaaaaat    1140 atcttgctat ccacatagtt tgaatccata cttttgctat cttgagtttc aaaaatttta    1200
atttgctaca atttgttgct attagcatat gactactttt aagaagataa gccaatatac    1260
tattttccta agaatttaaa aaatcaaaaa taaaattttt tatttaagat ttttaaggg    1320 ttgttttcca aatgtgcaat ggggcttaat cttggcatca ttttctaact tgtagaattt   1380
```

```
tgacccaagt aacatttgtc caatcactta gaacttctat aacttcgtac aatcatttgt    1440
taatgttgtt catctattta tctatattat ctatctggaa tatagttgct cttaattatt    1500
tttatatatc gcctattatc caccctaagc tttcatgttc atcctcatgt tgttggaggt    1560
gcatgtctta ttccaaacta tttaccattg ctgtagattt taaaaaattt gctagtttag    1620 gacttttaa tcttttgata tcatgttgat gtaagctaac cctctaaggc tagtcataat    1680
acattttaag gatttatgtt atatgagacc aaaattttaa caaatgaag tgttggaaat     1740 tggtagaatg gaagtgtaaa gatgcttaga gacatagaac tagccctggg ccatgtaaat    1800
cttccaaaag aagaagaaaa taataaaatt aagatcatat tcaatctcta cagaaaagtt    1860
ggtctttgtt gtataataag ccatcttaac atatgatgga caataaaata tataaactta    1920
tgagttttaa tacttagatg gaagaaaagg gacagatatg tcacacccca tcctactagc    1980
atgagtaggc acatgataca cggttgcatg ccctgcagag tttgactcat gaggcatgca    2040
aggtattgaa tagtagtcta ggtaaaatta aaaaacttgg agcattctaa aaataaatca    2100
agttcatttt ataaaatcaa tatttattat ggactccatc aaatattatg cgcataacat    2160
tttatttgca aatagaagaa gataagtcct agatcctaag tctcctactc ttagtctcat    2220
aattcatcca agctatccac caaatatcta aaacgaaaaa gaaaaacgat agtatgctaa    2280 tagcttttgta agtcaccttt tatctctaat tagatcaagc atattagata taaaacaata   2340
attttcaaag tatatgattt gcaattagga ataaatattt gataaataca gaataaattt    2400
tcataaagca tatttactaa cattatttat aaaatatata atgcttatat caataaatta    2460
atttctaaat caatatatat aaactatcca ttctgtctta gccttacaac tattgctacc    2520
attccctgta gcatggttag gaagagacta gctcttgaat actcatgtca tttatcaaca    2580
tatgcgaatg atcattcgac taatatagtc aaaaaaaaat tactctgatt tatataaatt    2640
aaaaattagt aaataatata tgctagtaat caccttacca gctaagctct aaagaaaatt    2700
agcttttgaa tatacatcat gctattgatt attatatgtc agtgcttgtc tcattttgtg    2760
gcatgcaaga agactagatc ctaaacttat atgcatagtc agattaaaga gcaaatgttg    2820
catctgatta tatgaacatc tattatgatg tagagtttgt atcatgtata tttaatttaa    2880
acacaaatat aattatacat aaataatatt catattttaa atttttaaata tttagataat    2940 tattctagtg caggtataaa aataagcaat ataaaatttt aaatcgattt atataacatg    3000
cataataaaa aaaattaagg atagaggtac ttactgctca actcataaaa cataagaaat    3060
ctctttaact aactttagtg caacctagat agaacatatt aatgattaag ttttcatcta    3120
aaataaacat agatatcatt ttaaaatctt aggcatttaa atggtctcat gatttgtgag    3180
gctttcttca gattctacaa ttttgaaatt ttttcaaatt ataatttttt taccttgatt    3240
gataacaaag ccaataatac acctcaaatc caaatgtatt cctaatagtt ttcaataaat    3300
ctaatatcaa taaatcataa ttaagatatc aatccattct atgaatttga ccataaatcc    3360
tacttgtttc tctgaccttc actataaatt aatcatcaaa ctaaataagt gaggggatca    3420
taattctttt acgacaatcc aagaattcaa gtctagcatc cacattagat ggcttcctgt    3480
ccagatattt gcgcctctcc aaaattgaga ttatcagatt aagaaaaata aaataagaga    3540
gagggttaaa ggacaatgcc ttctaggtag tgatgtccga catcataatt ttgatcaaat    3600
ctatggggca accaataata ttagggaaag aggattggat ttgagcaaga atagcaaagt    3660
cattgtcatc aatggcctga ttcattgagt tcaatgaagg attggtggtt gagtggtgga    3720
ggtggcatct aggaaggaga gagaaagaaa aagatagaga gaaagagata agaaaaatag    3780
```

```
agagaaggtg gcagttaaga tccctttttg tgattaatat atagccgtaa gatactcaaa    3840
gatctcacct tatcgacctc aaacactaag ggaggtggaa ggaggactac tacccatga     3900 agctagagaa agggatgatg atgattggag gaaggaagaa ggaaaaatag tagactcgat    3960
gatgataaga ctaaaagaaa aggggtttgac ttagccactt ggtatataat gaggtttggt   4020
atggagtcaa tagcttgagt aatagcatgg aaagagagaa g                        4061
```

<210> SEQ ID NO 48
<211> LENGTH: 4061
<212> TYPE: DNA
<213> ORGANISM: Artificial Sequence
<220> FEATURE:
<223> OTHER INFORMATION: synthetic

<400> SEQUENCE: 48

```
aaatatctaa acgaaaaag aaaaacgata gtatgctaat agctttgtaa gtcacctttt      60
atctctaatt agatcaagca tattagatat aaaacaataa ttttcaaagt atatgatttg    120
caattaggaa taaatatttg ataaatacag aataaatttt cataaagcat atttactaac    180
attatttata aaatatataa tgcttatatc aataaaattaa tttctaaatc aatatatata    240
aactatccat tctgtcttag ccttacaact attgctacca ttccctgtag catggttagg    300
aagagactag ctcttgaata ctcatgtcat ttatcaacat atgcgaatga tcattcgact    360
aatatagtca aaaaaaaatt actctgattt atataaatta aaaattagta aataatatat    420
gctagtaatc accttaccag ctaagctcta aagaaaatta gcttttgaat atacatcatg    480
ctattgatta ttatatgtca gtgcttgtct cattttgtgg catgcaagaa gactagatcc    540
taaacttata tgcatagtca gattaaagag caaatgttgc atctgattat atgaacatct    600
attatgatgt agagtttgta tcatgtatat ttaatttaaa cacaaatata attatacata    660
aataatattc atattttaaa ttttaaatat ttagataatt attctagtgc aggtataaaa    720
ataagcaata taaaatttta aatcgattta tataacatgc ataataaaaa aaattaagga    780
tagaggtact tactgctcaa ctcataaaac ataagaaatc tctttaacta actttagtgc    840
aacctagata gaacatatta atgattaagt tttcatctaa aataaacata gatatcattt    900
taaaatctta ggcatttaaa tggtctcatg atttgtgagg ctttcttcag attctacaat    960
tttgaaattt tttcaaatta taattttttt accttgattg ataacaaagc caataataca   1020
cctcaaatcc aaatgtattc ctaatagttt tcaataaatc taatatcaat aaatcataat   1080
taagatatca atccattcta tgaatttgac cataaatcct acttgtttct ctgaccttca   1140
ctataaatta atcatcaaac taaataagtg aggggatcat aattctttta cgacaatcca   1200
agaattcaag tctagcatcc acattagatg gcttcctgtc cagatatttg cgcctctcca   1260
aaattgagat tatcagatta agaaaaataa aataagagag agggttaaag gacaatgcct   1320
tctaggtagt gatgtccgac atcataattt tgatcaaatc tatggggcaa ccaataatat   1380
tagggaaaga ggattggatt tgagcaagaa tagcaaagtc attgtcatca atggcctgat   1440
tcattgagtt caatgaagga ttggtggttg agtggtggag gtggcatcta ggaaggagag   1500
agaaagaaaa agatagagag aaagagataa gaaaaataga gagaaggtgg cagttaagat   1560 cccttttgt gattaatata tagccgtaag atactcaaag atctcacctt atcgacctca   1620
aacactaagg gaggtggaag gagggactac tacccatgaa gctagagaaa gggatgatga   1680
tgattggagg aaggaagaag gaaaaatagt agactcgatg atgataagac taaaagaaaa   1740
```

-continued

```
gggtttgact tagccacttg gtatataatg aggtttggta tggagtcaat agcttgagta    1800
atagcatgga agagagaag gagctgaaga gagtactaag tcttattaga ataaagaaag     1860
atagaatctt agcgaaaaat agggcctcaa atctttcagg tagaggaaaa agagggatca    1920
acgaatgaaa gactaaggaa aaggtgtgga gtaggatata ctctcgatta gtctctcaat    1980
catggattct agtagggctt cgtcagctgc tcaatcatgg attctgatag ctcaaatggt    2040
ggtaagtaga aagagagaga tctaaagaga ttgatagtgg ccttaaaacc agcacggtca    2100
aggataggca tgccttagag agaggaaaag agagagagat taatggaaat aagcgagaaa    2160
aatatattct tagagaatag attggcgata agaagaggag gtggttgggg catgcttaaa    2220
gaaataaaga aaattgagta ggcggaaagt ggtgatgctt ggcgatgaga agatttgaga    2280
gagagagcaa aaaaatgtgg atgatggtca taggataggg aaaggaaaga acaaagaagg    2340
gggtgctaag ctaactcttt ctaccttcct cacaccctga agcaaaggat ttggccaagg    2400
atggacaaat gggcgagggc tttggtggat ccatgcctac cctttctccc tctcacgatg    2460
attctagtca agctatctat ctttgatagc ttgagccaag ccaattgact tgatccaatc    2520
tctctaaatc catacaaact taagagagtg tattgattca cttattctct tctaagttga    2580
taagaaacat aattaagtgg agctcattaa gtatttcagg tagttgctaa cttggcaaaa    2640
tggaagcaat aataaatctt aaaagactat agcttggtat aatctcaacc atccatgatt    2700
tagaaagatc ttcagactca atatagatta ctttggctac tacaggtaag agctaaaatag    2760 gatccaaaag taagatccat cacattagta agtcaaatta tatgtcaaat tttagtaggt    2820
atacttagtc ctacgatgcc taattaaaat gatcatcatt tgaaccttaa aatggactag    2880
tcaactaaaa ttttcttttt tgaagaagat ttagaccata aaatatcttc taatctgtga    2940
agaattagat agagcgagga atataaaatt gatgtagaaa tcaagatcta tcatatatac    3000
aattttaata tttttttcat aattttttaaa tatttatctt cttttttat aggtctagtc    3060 ctatttaaac taggaagagg agtccaactt gacttatgca ataggggatg tccttctaga    3120
agataagaat aatttgatca gaattatata agagcaaacc tcattattat aaatagggc     3180 tatatacatc aatttatgag atagagaatc aatgaaacaa aagtagactt aagttttatt    3240
ttcataattc ttctatcttc tactttttt ctaggagatt caagttgagt ggattgaaga     3300
aaatctttca tcttctcgat cggatcatat tggtattaga gcgttggtct tctatattta    3360
tggagagctt taatgtattg tttaaatacg tgaacaatac aaacaatcaa gagaagtgct    3420
atccatgctt caaatacatc gaaatataaa agcaaatatg gctactaatt cttttttcaat   3480 ggacaatgag ataaaaggat gtcttacaca actcaaggag aagattgtgc aactcatgaa    3540
gattgtctcc agattgaaga taatttcaat acaagcacaa acaccagcaa ctcatgttgt    3600
gaaactgttt cctatgtttg gagatgaaga tcttctatct agtgaggaga ttgaattacc    3660
taaaagtatg aaaaatcttt cttcaatcat tgaaagttaa agcttgaatt gagatcccca    3720
tatataatgg aaccattgat gaaaaaaagc tagataattg gctaaactaa ttacaaacct    3780
attttattat ctatagatat tatggcatct agaagatagc ttttacttat ctcaagcttt    3840
ctagccatgc tcttatctga tgaaattcat atatgagaaa taataatatt tttaatatgg    3900
tgcagagcca attcaaaggt ttaatcaaga agtaatttta tctaattggc cataaggaag    3960
atcggtggat caaatgataa tacttatgat agaaacataa tcaatccact taggactata    4020
ccaccaagtt ccacaaacag gcaatctgcc ttggaatctt t                        4061
```

<210> SEQ ID NO 49
<211> LENGTH: 4061
<212> TYPE: DNA
<213> ORGANISM: Artificial Sequence
<220> FEATURE:
<223> OTHER INFORMATION: synthetic

<400> SEQUENCE: 49

| | | | | | |
|---|---|---|---|---|---|
| aaagagataa | gaaaaataga | gagaaggtgg | cagttaagat | cccttttgt | gattaatata | 60 |
| tagccgtaag | atactcaaag | atctcacctt | atcgacctca | aacactaagg | gaggtggaag | 120 |
| gagggactac | tacccatgaa | gctagagaaa | gggatgatga | tgattggagg | aaggaagaag | 180 |
| gaaaaatagt | agactcgatg | atgataagac | taaaagaaaa | gggtttgact | tagccacttg | 240 |
| gtatataatg | aggtttggta | tggagtcaat | agcttgagta | atagcatgga | aagagagaag | 300 |
| gagctgaaga | gagtactaag | tcttattaga | ataaagaaag | atagaatctt | agcgaaaaat | 360 |
| agggcctcaa | atctttcagg | tagaggaaaa | agagggatca | acgaatgaaa | gactaaggaa | 420 |
| aaggtgtgga | gtaggatata | ctctcgatta | gtctctcaat | catggattct | agtagggctt | 480 |
| cgtcagctgc | tcaatcatgg | attctgatag | ctcaaatggt | ggtaagtaga | aagagagaga | 540 |
| tctaaagaga | ttgatagtgg | ccttaaaacc | agcacggtca | aggataggca | tgccttagag | 600 |
| agaggaaaag | agagagagat | taatggaaat | aagcgagaaa | aatatattct | tagagaatag | 660 |
| attggcgata | agaagaggag | gtggttgggg | catgcttaaa | gaaataaaga | aaattgagta | 720 |
| ggcggaaagt | ggtgatgctt | ggcgatgaga | agatttgaga | gagagagcaa | aaaaatgtgg | 780 |
| atgatggtca | taggataggg | aaaggaaaga | acaaagaagg | gggtgctaag | ctaactcttt | 840 |
| ctaccttcct | cacaccctga | agcaaaggat | ttggccaagg | atggacaaat | gggcgagggc | 900 |
| tttggtggat | ccatgcctac | cctttctccc | tctcacgatg | attctagtca | agctatctat | 960 |
| ctttgatagc | ttgagccaag | ccaattgact | tgatccaatc | tctctaaatc | catacaaact | 1020 |
| taagagagtg | tattgattca | cttattctct | tctaagttga | taagaaacat | aattaagtgg | 1080 |
| agctcattaa | gtatttcagg | tagttgctaa | cttggcaaaa | tggaagcaat | aataaatctt | 1140 |
| aaaagactat | agcttggtat | aatctcaacc | atccatgatt | tagaaagatc | ttcagactca | 1200 |
| atatagatta | ctttggctac | tacaggtaag | agctaaatag | gatccaaaag | taagatccat | 1260 |
| cacattagta | agtcaaatta | tatgtcaaat | tttagtaggt | atacttagtc | ctacgatgcc | 1320 |
| taattaaaat | gatcatcatt | tgaaccttaa | aatggactag | tcaactaaaa | ttttttcttt | 1380 |
| tgaagaagat | ttagaccata | aaatatcttc | taatctgtga | agaattagat | agagcgagga | 1440 |
| atataaaatt | gatgtagaaa | tcaagatcta | tcatatatac | aatttttaata | tttttttcat | 1500 |
| aattttttaaa | tatttatctt | ctttttttat | aggtctagtc | ctatttaaac | taggaagagg | 1560 |
| agtccaactt | gacttatgca | ataggggatg | tccttctaga | agataagaat | aatttgatca | 1620 |
| gaattatata | agagcaaacc | tcattattat | aaataggggc | tatatacatc | aatttatgag | 1680 |
| atagagaatc | aatgaaacaa | aagtagactt | aagtttatt | ttcataattc | ttctatcttc | 1740 |
| tactttttt | ctaggagatt | caagttgagt | ggattgaaga | aaatctttca | tcttctcgat | 1800 |
| cggatcatat | tggtattaga | gcgttggtct | tctatattta | tggagagctt | taatgtattg | 1860 |
| tttaaatacg | tgaacaatac | aaacaatcaa | gagaagtgct | atccatgctt | caaatacatc | 1920 |
| gaaatataaa | agcaaatatg | gctactaatt | cttttttcaat | ggacaatgag | ataaaaggat | 1980 |
| gtcttacaca | actcaaggag | aagattgtgc | aactcatgaa | gattgtctcc | agattgaaga | 2040 |
| taatttcaat | acaagcacaa | acaccagcaa | ctcatgttgt | gaaactgttt | cctatgtttg | 2100 |

```
gagatgaaga tcttctatct agtgaggaga ttgaattacc taaaagtatg aaaaatcttt    2160
cttcaatcat tgaaagttaa agcttgaatt gagatcccca tatataatgg aaccattgat    2220
gaaaaaaagc tagataattg gctaaactaa ttacaaacct attttattat ctatagatat    2280
tatggcatct agaagatagc ttttacttat ctcaagcttt ctagccatgc tcttatctga    2340
tgaaattcat atatgagaaa taataatatt tttaatatgg tgcagagcca attcaaaggt    2400
ttaatcaaga agtaatttta tctaattggc cataaggaag atcggtggat caaatgataa    2460
tacttatgat agaaacataa tcaatccact taggactata ccaccaagtt ccacaaacag    2520
gcaatctgcc ttggaatctt tatcaacaat tatacaattt ttataaagta tgttgaaagt    2580
cttcatgaga gcatctaaaa aaagatgaaa ctctttaagg ttgatgatat cagtaaagct    2640
aacatgaaag tcatagagat tgaggagaaa aatcaaatta gagaagataa ggaaggcaaa    2700
aagcatatca acataactca aaaaaaaaaa ttatgatcat tgaaatcttt gaaaatacat    2760
caaggagaag tattgaaagt ttcatcctga attggagcta agtagaaga agcccaagga    2820 tgataatttt aagaaaaata aaaagtggtc ctcaattcta tagagattga ggagctatct    2880
gaacttgagt aagcaaactt caaattgagc ttgatggtga gaaaacctaa tacaacaatt    2940
aaaacggatc tagaggtaca tgacaactca cccacttaaa gattcaagtg aagcagagta    3000
tcattaaggc tattataaat cttgaagct agaagaacct cattttccaa tatttggttc    3060
agaaatcgag gttgtagatc aagcctcatc catatcctta tcctcttagt tggattcaga    3120
aggatgtcaa gttaaaaatt atgagatagt gtaccttcaa gttagccatc actgagaggt    3180
ttatttgtga ggtaactttt gaaatagttt ctttggatat tgtcaagtt atccttagaa    3240 atgtgtacct ttagaatcaa gatgcaattt tctatagacg atagagaaag tatcatctta    3300
taagggatga gaaaaagttc atgatcaaca cctcaagaac ataaggtaac tttgaccttg    3360
caactgttgc ccaagtgaag tgatttgtta atgtttgtga tgagtgcatg atgatggtat    3420
aaagaaccga tatcactcat gagaggtcaa ggccttgtcc tttggttcca tcaatcgatc    3480
aatagagatt gagattaagg aggagtcact atagtccttg tcgatgagga aggatgacaa    3540
caagcattcc taccatgaag tctagatttg agagcaaatg aaagtaatcc actgagacct    3600
gagagcaaaa aaaggcgaga ccaaaaatca tcttcaagta aagtcaaatg gttcaaccat    3660
gagatgggga agtaagtatt tcccaccctt caattctaac tttgtagaaa ctaaatccct    3720
taaacagggg agccctaatt taagaggatc ctcagattca ttgtggacta ctttggctat    3780
tacaataaga gctggatagg aatcgaaagc aaaattcacc acattaggaa gccaaattgt    3840
atggcaaact tcaagagacc ataacttgat cacatgaaat ccaattaaga tgattttatt    3900
tttgaatttg aatattttt tgagatctat aactttagat ctaaatcaag ctaaaatttt    3960
attgcttatg ccttcaaaat aggctagtca aatcaaaact tttcttttca aaaaagactt    4020
tgactgaaag atatctttca atctatgaag aatcaagtag a                        4061
```

<210> SEQ ID NO 50
<211> LENGTH: 4061
<212> TYPE: DNA
<213> ORGANISM: Artificial Sequence
<220> FEATURE:
<223> OTHER INFORMATION: synthetic

<400> SEQUENCE: 50

```
ctctcgatta gtctctcaat catggattct agtagggctt cgtcagctgc tcaatcatgg      60
attctgatag ctcaaatggt ggtaagtaga aagagagaga tctaaagaga ttgatagtgg     120
```

| | | | | |
|---|---|---|---|---|
| ccttaaaacc | agcacggtca | aggataggca | tgccttagag | agaggaaaag | agagagagat | 180 |
| taatggaaat | aagcgagaaa | aatatattct | tagagaatag | attggcgata | agaagaggag | 240 |
| gtggttgggg | catgcttaaa | gaaataaaga | aaattgagta | ggcggaaagt | ggtgatgctt | 300 |
| ggcgatgaga | agatttgaga | gagagagcaa | aaaatgtgg | atgatggtca | taggataggg | 360 |
| aaaggaaaga | acaaagaagg | gggtgctaag | ctaactcttt | ctaccttcct | cacaccctga | 420 |
| agcaaaggat | ttggccaagg | atggacaaat | gggcgagggc | tttggtggat | ccatgcctac | 480 |
| cctttctccc | tctcacgatg | attctagtca | agctatctat | ctttgatagc | ttgagccaag | 540 |
| ccaattgact | tgatccaatc | tctctaaatc | catacaaact | taagagagtg | tattgattca | 600 |
| cttattctct | tctaagttga | taagaaacat | aattaagtgg | agctcattaa | gtatttcagg | 660 |
| tagttgctaa | cttggcaaaa | tggaagcaat | aataaatctt | aaaagactat | agcttggtat | 720 |
| aatctcaacc | atccatgatt | tagaaagatc | ttcagactca | atatagatta | ctttggctac | 780 |
| tacaggtaag | agctaaatag | gatccaaaag | taagatccat | cacattagta | agtcaaatta | 840 |
| tatgtcaaat | tttagtaggt | atacttagtc | ctacgatgcc | taattaaaat | gatcatcatt | 900 |
| tgaaccttaa | aatggactag | tcaactaaaa | ttttcttt | tgaagaagat | ttagaccata | 960 |
| aaatatcttc | taatctgtga | agaattagat | agagcgagga | atataaaatt | gatgtagaaa | 1020 |
| tcaagatcta | tcatatatac | aatttttaata | tttttttcat | aatttttaaa | tatttatctt | 1080 |
| cttttttat | aggtctagtc | ctatttaaac | taggaagagg | agtccaactt | gacttatgca | 1140 |
| ataggggatg | tccttctaga | agataagaat | aatttgatca | gaattatata | agagcaaacc | 1200 |
| tcattattat | aaataggggc | tatatacatc | aatttatgag | atagagaatc | aatgaaacaa | 1260 |
| aagtagactt | aagttttatt | ttcataattc | ttctatcttc | tactttttt | ctaggagatt | 1320 |
| caagttgagt | ggattgaaga | aaatctttca | tcttctcgat | cggatcatat | tggtattaga | 1380 |
| gcgttggtct | tctatattta | tggagagctt | taatgtattg | tttaaatacg | tgaacaatac | 1440 |
| aaacaatcaa | gagaagtgct | atccatgctt | caaatacatc | gaaatataaa | agcaaatatg | 1500 |
| gctactaatt | cttttcaat | ggacaatgag | ataaaaggat | gtcttacaca | actcaaggag | 1560 |
| aagattgtgc | aactcatgaa | gattgtctcc | agattgaaga | taatttcaat | acaagcacaa | 1620 |
| acaccagcaa | ctcatgttgt | gaaactgttt | cctatgtttg | gagatgaaga | tcttctatct | 1680 |
| agtgaggaga | ttgaattacc | taaaagtatg | aaaaatcttt | cttcaatcat | tgaaagttaa | 1740 |
| agcttgaatt | gagatcccca | tatataatgg | aaccattgat | gaaaaaaagc | tagataattg | 1800 |
| gctaaactaa | ttacaaacct | attttattat | ctatagatat | tatggcatct | agaagatagc | 1860 |
| tttacttat | ctcaagcttt | ctagccatgc | tcttatctga | tgaaattcat | atatgagaaa | 1920 |
| taataatatt | tttaatatgg | tgcagagcca | attcaaggt | ttaatcaaga | agtaatttta | 1980 |
| tctaattggc | cataaggaag | atcggtggat | caaatgataa | tacttatgat | agaaacataa | 2040 |
| tcaatccact | taggactata | ccaccaagtt | ccacaaacag | gcaatctgcc | ttggaatctt | 2100 |
| tatcaacaat | tatacaattt | ttataaagta | tgttgaaagt | cttcatgaga | gcatctaaaa | 2160 |
| aaagatgaaa | ctctttaagg | ttgatgatat | cagtaaagct | aacatgaaag | tcatagagat | 2220 |
| tgaggagaaa | aatcaaatta | gagaagataa | ggaaggcaaa | aagcatatca | acataactca | 2280 |
| aaaaaaaaaa | ttatgatcat | tgaaatcttt | gaaaatacat | caaggagaag | tattgaaagt | 2340 |
| ttcatcctga | attggagcta | agtagaaga | agcccaagga | tgataatttt | aagaaaaata | 2400 |
| aaaagtggtc | ctcaattcta | tagagattga | ggagctatct | gaacttgagt | aagcaaactt | 2460 |

```
caaattgagc ttgatggtga gaaaacctaa tacaacaatt aaaacggatc tagaggtaca    2520
tgacaactca cccacttaaa gattcaagtg aagcagagta tcattaaggc tattataaat    2580
cttttgaagct agaagaacct cattttccaa tatttggttc agaaatcgag gttgtagatc   2640
aagcctcatc catatcctta tcctcttagt tggattcaga aggatgtcaa gttaaaaatt   2700
atgagatagt gtaccttcaa gttagccatc actgagaggt ttatttgtga ggtaactttt   2760
gaaatagttt ctttggatat ttgtcaagtt atccttagaa atgtgtacct ttagaatcaa   2820
gatgcaattt tctatagacg atagagaaag tatcatctta taagggatga gaaaaagttc   2880
atgatcaaca cctcaagaac ataaggtaac tttgaccttg caactgttgc ccaagtgaag   2940
tgatttgtta atgtttgtga tgagtgcatg atgatggtat aaagaaccga tatcactcat   3000
gagaggtcaa ggccttgtcc tttggttcca tcaatcgatc aatagagatt gagattaagg   3060
aggagtcact atagtccttg tcgatgagga aggatgacaa caagcattcc taccatgaag   3120
tctagatttg agagcaaatg aaagtaatcc actgagacct gagagcaaaa aaaggcgaga   3180
ccaaaaatca tcttcaagta aagtcaaatg gttcaaccat gagatgggga agtaagtatt   3240
ttcccaccctt caattctaac tttgtagaaa ctaaatccct taaacagggg agccctaatt   3300
taagaggatc ctcagattca ttgtggacta cttttggctat tacaataaga gctggatagg   3360
aatcgaaagc aaaattcacc acattaggaa gccaaattgt atggcaaact tcaagagacc   3420
ataacttgat cacatgaaat ccaattaaga tgattttatt tttgaatttg aatattttttt  3480
tgagatctat aactttagat ctaaatcaag ctaaaatttt attgcttatg ccttcaaaat   3540
aggctagtca atcaaaact tttcttttca aaaagactt tgactgaaag atatctttca    3600
atctatgaag aatcaagtag agtgatgaaa gataaagttg atataaaat tgagatctat    3660
ctcttataaa attttagtaa ttttattttt tttaatattt atctttattt agagatctat    3720
tcctatttaa actagaaaga attgtccaac ctaacttgtt caatgatcaa catcctccta   3780
aaagataaaa agaagaatct gactcaaatt ataaaagggc ggaccttttt ttttgatgaa   3840
aagggaggaa aaaaatccat caaaatttat taagaaaaaa agagtacaag aaaagaagga   3900
tatgaaagag taagagaagc cccacaacat ccatcaatat ttaaaattta aatttaaatc   3960
tcccccatca ttctatcaat atttgatatt caaatttaaa ttcttcgcag catcccacca   4020
acatttgaaa ttcaaatcct ttcatacaaa caaaataata t                       4061
```

<210> SEQ ID NO 51
<211> LENGTH: 4061
<212> TYPE: DNA
<213> ORGANISM: Artificial Sequence
<220> FEATURE:
<223> OTHER INFORMATION: synthetic

<400> SEQUENCE: 51

```
caaggagaag tattgaaagt ttcatcctga attggagcta agtagaaga agcccaagga      60
tgataatttt aagaaaaata aaagtggtc ctcaattcta tagagattga ggagctatct     120
gaacttgagt aagcaaactt caaattgagc ttgatggtga gaaaacctaa tacaacaatt    180
aaaacggatc tagaggtaca tgacaactca cccacttaaa gattcaagtg aagcagagta    240
tcattaaggc tattataaat cttttgaagct agaagaacct cattttccaa tatttggttc   300
agaaatcgag gttgtagatc aagcctcatc catatcctta tcctcttagt tggattcaga    360
aggatgtcaa gttaaaaatt atgagatagt gtaccttcaa gttagccatc actgagaggt    420
ttatttgtga ggtaactttt gaaatagttt ctttggatat ttgtcaagtt atccttagaa    480
```

```
atgtgtacct ttagaatcaa gatgcaattt tctatagacg atagagaaag tatcatctta      540
taagggatga gaaaaagttc atgatcaaca cctcaagaac ataaggtaac tttgaccttg      600
caactgttgc ccaagtgaag tgatttgtta atgtttgtga tgagtgcatg atgatggtat      660
aaagaaccga tatcactcat gagaggtcaa ggccttgtcc tttggttcca tcaatcgatc      720
aatagagatt gagattaagg aggagtcact atagtccttg tcgatgagga aggatgacaa      780
caagcattcc taccatgaag tctagatttg agagcaaatg aaagtaatcc actgagacct      840
gagagcaaaa aaaggcgaga ccaaaaatca tcttcaagta aagtcaaatg gttcaaccat      900
gagatgggga agtaagtatt tcccaccttc aattctaact ttgtagaaaa ctaaatccct      960
taaacagggg agccctaatt aagaggatcc tcagattcat tgtggactac tttggctat      1020 tacaataaga gctggatagg aatcgaaagc aaaattcacc acattaggaa gccaaattgt     1080
atggcaaact tcaagagacc ataacttgat cacatgaaat ccaattaaga tgattttatt     1140
tttgaatttg aatatttttt tgagatctat aactttagat ctaaatcaag ctaaaatttt     1200
attgcttatg ccttcaaaat aggctagtca aatcaaaact tttcttttca aaaagactt      1260 tgactgaaag atatctttca atctatgaag aatcaagtag agtgatgaaa gataaagttg     1320
atataaaaat tgagatctat ctcttataaa attttagtaa ttttattttt tttaatattt     1380
atctttattt agagatctat tcctatttaa actagaaaga attgtccaac ctaacttgtt     1440
caatgatcaa catcctccta aaagataaaa agaagaatct gactcaaatt ataaaagggc     1500 ggacctttt ttttgatgaa aagggaggaa aaaatccat caaaatttat taagaaaaaa      1560
agagtacaag aaaagaagga tatgaaagag taagagaagc cccacaacat ccatcaatat     1620
ttaaaattta aatttaaatc tcccccatca ttctatcaat atttgatatt caaatttaaa     1680
ttcttcgcag catcccacca acatttgaaa ttcaaatcct ttcatacaaa caaaataata     1740 ttttttcaaat tctcaacttt gagtttcaaa attgagaagc ctacatattg tctgctcttc     1800
accaaagagg ggagattgtt ggcttagctt ggcccaagag aagagaagaa ggccaaggcc     1860
caatctgtag cctagagaag gagggtttgg tagctactta ataatcggat ctaaccgata     1920
aagacactat ctctattaga agaaaaggta gagagaaaaa gaggcaattg gttaacttca     1980 gaggggagg aggtaagctg ttgaggagat taatctgacg caaggaaaaa agaagagctg      2040
acaactagcc aatgatcgag aagggctgga gacaatccaa gcccagcacc aagaagcaag     2100
agaaagaatt tggaggtcaa aggaggagtc caggaagaga gagcgaaaca caatgttcgg     2160
atctagccga caacgatacc aattatacta ggaaagaagg taaaagggga aagagcaatc     2220
gatcatcttc agcaaagaaa aataaaagag gcacccgaca gtcaagccca tggccaaatc     2280
agtcagcaag aggacctcac aagatctaga cggtgctaag gggaagggag gagaaaaga     2340 gatccagtaa ctgtccaaca ccaggaaaag gaggagataa gaggaaggga gaagtcattt     2400
ttctatcttg ggccgaagga gggagaagga agaaagagga agaacatcc tcaaagtcga     2460 aggaaggaag gaaagagagg ggggaagggg tcacagtcag atataccaga agggatagat     2520
ccagtgtcaa agagagaaaa gagagaggag atcagaaaat aaaatttgat gactgactaa     2580
ttgtcatgaa aggctaatga caactcataa aaaagtata gtagtaaaga gaggggata      2640 ggcttggtta gggaagagat tccgacaaca aagagaaaga aagagagaga gagagagaac     2700
cggctcccag ccaaaaatag cttgaccac catcgagaag gaccgacaaa gagagagaaa     2760
gatagaatag ggagaatagc ttggcttcga atcaaaaatg atctaacaca ctgctgaaaa     2820
```

| | | |
|---|---|---|
| ggactaggaa gagagagaga gggggtaggg gagtatctcg gctcgcaatc agaatcaact | 2880 | |
| ggccaatgcc agaaaagaga ggaagagaga gatagagaag atatagcaaa agagaagaga | 2940 | |
| tggacaaaag gagagaggaa gggagggaga gagagaaaaa ataggagaga gaggggcttg | 3000 | |
| gtggctgact gtcagaagaa gcctcgatgc tcgaagatta gatggaagaa aaaaaaattt | 3060 | |
| ctcaaaactt ctcttttcta taagagcaaa cctcactatt ataaataggg ttatgtatct | 3120 | |
| cagtttatga tgtgaagaat taatgaaaaa ttggactttta gctctatttt tgtaattctt | 3180 | |
| tcatcttcta tttttatgaa attcaagttg agccgattaa aagaaataat ctttctttcc | 3240 | |
| gattggatca atccattaac tagatacttc aaaaatcaaa atgacctatc taaaatccta | 3300 | |
| aatcaaatac aaaaccaaaa taactaaatt aagatagaac aaactacaat tacaaaaaac | 3360 | |
| tggctaaagt gtttaaatgc ttttactcct aagtttcttc ttgctcacca ttaatgcttg | 3420 | |
| atctttagct gggatcatat cagccttatg accactataa gaccaacata acaactcact | 3480 | |
| tgtattgctc ctttaaaatt atacaaaact agtgtctaat atgtaccatg cgaatgtctg | 3540 | |
| tttctcacca gaaaatggat gggcttcttg tgcaagcacc ttcttcctac aaataataaa | 3600 | |
| atatgcatcc cttctctcat cttactaaat aaaataatta aaggctttac tatcaggaaa | 3660 | |
| tctggcttta tccatataat tttggaagtt ttatttgaac ataacattac gagtactaga | 3720 | |
| ttacatcagg aggtggttcc tcttatttct attaagagaa aaatcaattt tcttttaaga | 3780 | |
| aagatcattt cattttcatc aggtagcgta ctctactaat atacttccac aacaatatat | 3840 | |
| agggattaga ttataggatg gactttaagg cttcttttcg agagccctga tttctcaatc | 3900 | |
| acattcccct ttctttctca tgtaatggca tttaagagtg catccagggc ccaacaatta | 3960 | |
| gtcacaagtg ttcttttat acatggtaca tatttgctat ttttagctt attttaactt | 4020 | |
| gattgtgaag atatcatgag aaaattagat ttaaagccta g | 4061 | |

<210> SEQ ID NO 52
<211> LENGTH: 4061
<212> TYPE: DNA
<213> ORGANISM: Artificial Sequence
<220> FEATURE:
<223> OTHER INFORMATION: synthetic

<400> SEQUENCE: 52

| | | |
|---|---|---|
| ctttcaaaaa tatcttttga taggactaat gagataagtc aggaccaatg gatatctcgg | 60 | |
| tcaacccaac cactgctcaa gtttgagatg gaaaatctat ctcggacaac agctgaagtt | 120 | |
| agtacctcag gttaggatga tctagaatct cctataagag atttttttaga ttatttcggc | 180 | |
| ccaagtactg aacaatctgt cctgaccaat ctcgatcttt aggaacttaa gaaaaaatat | 240 | |
| tcgattcagc ttataactcc aagttgggat ggtaggatta ttgaacctcc agaaggttat | 300 | |
| gtcgtatttt atgatgaggc acttcgatct ggactttaat ttctcttaca tcctttcttc | 360 | |
| agtaatgttt tagacttcta taaactccat ccaatctagg ttactcccaa tgccattagg | 420 | |
| atgatcatag ttttcattat ctatcgtaaa tttttttgcta tagaactaag aatttctctc | 480 | |
| tttaggatgc tggtcatcct aagaaaacat ccttatgaaa aagactgatg gtatttctta | 540 | |
| ccttggcctc aatataaatt cggtcccact cttcctttt caatacataa ttgaaaaaat | 600 | |
| catttttct ttatttcttc taatgtttcg tagggtttta tttgtaaata gtctaagcct | 660 | |
| aaaaccaaat ggaactcaaa taacaaaata ttatctgagg atgaggagac ttttgtagag | 720 | |
| cttttagata tgaaagtatc caagttgagc ctactggtgt ccaatcagtc cttgtttgac | 780 | |
| accgacatca gtcagatctc tccttaagat aagtctgatg ttaattcttt ttctttattg | 840 | |

```
ctttatcatt tttcatcatt tttcttttct aacaatctttt ttccttatat agtagcaata    900
atgaagttca acctacaaag gctggctaac tcaaagaaga ggaagaagga tctaaccgat    960
tgctctcaag aagagtaagg agactgctcc tctaagatcg attggccccc gatcatcacc   1020
tgggccaata ttaattgaca tagatgctac atcgatctcc actataccac cagcaaaatc   1080
aactcatcaa cctactaagg tggcttgtcc acctcctaaa gagtctgcac atccaaagta   1140
ggcatcttcc ccaacacctc caacatcggc caagttagtt tggctgagca atcagcatct   1200
gaggtcacag actcctgatg tcaacccacc aactttctca tcaaaaaaaa ttgacttggc   1260
gaaggtatca cttttggaga cacccagact aggcaaggac ttgctctgta caatgatgcc   1320
tcaaaaggac ctagatgctg ataggaggga tcttctcttg gagcaaataa taaattatgg   1380
attcaacagt atcatgaacg tgagtcttca ttctcttcca ctctcttctt tcttttttctt   1440
tttttttta cattggctat tgttgatct gaatatatct ttcttttttgc agtcggttgt    1500
gtatttcaag ttgctcaatg agcacttgac atggttcttc aaaataaaaa ttttttttgaa   1560
agagaggctc aaggccaaga agaggccaa aaagcagtt gaggaggtca agaaggcagt    1620
aaagaagaag gctgtcaaag aaagcaaaat gatggcgggg ctgaagaaac agctccaaga   1680
aaaaatagat tccattaagg agactggaca accaatgaca gatgaatgat aaagatgaca   1740
agttgtaaaa acagcctgaa aaaaatctca aagttgagg ccaagctgaa ggaggtcgag    1800
tcaataattg aaaagcatga tgaagctctt gtcccatatt agagacaact tgataaagac   1860
aaagagtgga tgtcaaggat tattgaagat tataagaatt ccgacacttt tcaagatgac   1920
gttactgagg cctcaaaagg agctttcaat tatggctttt tgagctacag gagtttaatt   1980
atcaagctct ttcctaacct tgatctcagc aaggtcataa tagaagcagc tctagaagta   2040
gtagccgaag tgacttctgc aacaactact gagcttgctt ccacttctat cattggagtt   2100
tctccgatcg aagtcccaaa cagtccaatc gaggcctcca tcatcgaagc tatttcgaag   2160
gaatcagtcg gcaaagacct tacctcaact cctccaacaa ataactccca agctaaggcc   2220
tgaattatct tcttcttttt ttctaaacat ttgtattagc ccgatgtggg cttctataaa   2280
tacttttac attaatgaat gagttttca atgtcaatat ttttctttt taactaatac    2340
taatcttgga tgatccgatc tgggttggat gtctcaaaaa atatcattca cgatagatag   2400
ttattttctg acttcggtta gatgattatg agtatatgta attcaacctt ggttaggtaa   2460
gtaatcaaat attaactatt ctcaaaccaa gtagataacg aagtcaatgt gattaacttt   2520
aacaagtaag attgttatgg aatgaaattg aatcagatca actaactata gataacttaa   2580
tctctcataa ttcactgtaa aggttctaaa agtacccttta tctaagttcg aagtgacaag   2640
tcgggttctt ttattcgtgg atttatgacc catgctgtct ttttgtgatc ttcattatta   2700
atcaccttaa atcgatatag caaaatccag tttatagatc tgagtgcttt cttgtcagat   2760
tgagtctatc ctattatctg tgaaacctga tctagagatc aagtatttta ggttttttat   2820
ttaaggtcca attcgaagat tgagtatcca atgtcatatt gttaggtcca atttggagat   2880
tggatgtctc actatcatct cgtgaggtcc aatccaaaga tcgaatatct cactatcatc   2940
tcatgaggtc caatccagag attggatgtc tcacatcatc ttgtgagatc caattcgaag   3000
attggatgtc tcacatcatc tcatcctatt gtggttggaa tttttgtagc cttagtttga   3060
cttttttctga cctcatttgg acacctaaat cttattatca tcgtttgatc gatttttact   3120
aatctacttt ggatgaaaaa gaattcttca atggaacttt tgattagaac tttatcttca   3180
```

```
ttgggataga aatcgaatgc tttattgaaa gattttattg ataatacatt ctgagatttt      3240
taatatttca tgttctcgaa atgatcgtac catctaaatt tttaattcga taagctcttg      3300
gatggatcac ctcagtaatc tgataaggtc cttcccaatt cgggatgagt ttttcttact      3360
ccattggttt tgagacttca gctcattgga gaaccaaatc tccttataaa aaattttagg      3420
ctttacctga gagttgtaat atctggctac ttttttgttta taaactacca tatgaatctg     3480 ggcttttttct cgagttttct caaataaatt gagatcagtc ctcagttgat ctgaattatt    3540
ttcttcatga aaattttcta ttctggttgt aggtaaactg atctcgacta gtattatagc      3600
ctctgttccg aaagtaagtt taaaagatat ttctctagtt ggtctctgag gtgtagttct      3660
gtatacccat aaaatattat aaaattattc taccccgaga cttttagcct caatgagttt      3720
tatttttagg ccttgaaaga tagttctata aataaattta gcttctccat ttgattgtag      3780
atgtccaatc gaagtaaata tatgatctat gtagagctca gaataaattt ttttaaaatt     3840
ttgattatca aattattgct cattattagt aattataact caaggcaaac caaaatggta      3900
aataattatt tttcacataa aatctcatat ttttttctcag tgatttatgt cagaggttca    3960
atttctatcc attgggtaaa ataatcaata gtcacaacta aaaattttct ttgctccatg      4020
gccattagaa aggatcccag aatatccatt ctccatatag c                         4061

<210> SEQ ID NO 53
<211> LENGTH: 4061
<212> TYPE: DNA
<213> ORGANISM: Artificial Sequence
<220> FEATURE:
<223> OTHER INFORMATION: synthetic

<400> SEQUENCE: 53
aaaattattc taccccgaga cttttagcct caatgagttt tatttttagg ccttgaaaga        60
tagttctata aataaattta gcttctccat ttgattgtag atgtccaatc gaagtaaata       120
tatgatctat gtagagctca gaataaattt ttttaaaatt ttgattatca aattattgct       180
cattattagt aattataact caaggcaaac caaaatggta aataattatt tttcacataa       240
aatctcatat ttttttctcag tgatttatgt cagaggttca atttctatcc attgggtaaa     300
ataatcaata gtcacaacta aaaattttct ttgctccatg gccattagaa aggatcccag       360
aatatccatt ctccatatag caaaaggcca cagcactgta atagaaataa gttcagttgt       420
aggctgatgt tatatattgg cgtacctttg acactgatcg cagtacttat taataaagtc       480
ggttgaatct ttttgaatag taggccaata ataatcttac tgaattattt cataagctaa       540 aattttacccc ccaaatggt tactagagat tcctttatga acttctcgaa ggatgtaatc      600
agcttccgat ggcctaggc ataggagcag tgggagtgaa tataacctct gatataattg        660
attatcttga caacatacc atggggcctg tcttttaatt cttgttcctt cgactggatc       720
aaccggtaga ggttctttag taatatactc cattaatggg tcaatggaac ttagctcata      780
ttaaatttgg acaattagta aggcctcgat actagacttt ttaagaatat caataagaac      840
accttgattt agtttgaaaa aatctgatgt ggctaaatga gataggggcat cagctcagac     900 attttgtcct tggtatttgc atgatcttca gattttcaaa gttttttaat aattctttca      960
tattatataa atattgaaac atcataaaat ctttagcttc aaattaatct catacctgac     1020
tgacgataaa ttgagaatca ataaaaattt taattttttt aacattaagc tccttagcca    1080
ttttgagtcc tacaattagc gtttcatatt ctactccatt gtttgagtgt taaaattaaa    1140
tctcaaagca cgctcactaa caatgccttc tagactcgtt agaattaaac tagttctact    1200
```

```
ttctttcgaa tttgaggctc catcaatgta cagtatcaaa taagaatctt tgatatttt    1260
caattctttt aagattggtt cttcattagg aatagagcat tcaataataa aatcagctaa   1320
tacttaaact ttcaatgaag atcgaggccc atattgatat caaattcatt taattcaata   1380
gcctatttga atatccttct taaagtatca agctactgta aaattaattt taaaggttga   1440
tcgatcagaa ttataataga atgagcctaa aaatacgatc aaagtcatct tgctaatgca   1500
atgagggtat aaattatctt ctcaatttta gaatatcgag tttcaacatc tctaaataat   1560
ttatttgtat aataaatgga tctttgtatc cctgcatcat ttcaagctaa aatcgaacta   1620
acagcatttg ctgaaataga tagatacatg aataattttt gacctttgat cggctttgat   1680
agtaatggag ctgtgccgag atatttcttg agatcatcga aggctgcttg acattcatct   1740
tatcaatcga agtctttgat ctgccttaga attttaaaga aaggaagata tttatcagct   1800
gatctgaaaa taaattaact aagcaatgct actcatccag taagttggtg tacttctttg   1860
atggagctcg gatgcttcat ttcacataga gcttgaattt tcttaagatt gactttaatt   1920
cctctttgag ttacaaaaaa atctaaaaaa attttgaag ttacttcaaa agcatatttg    1980
ttgggattga gcttcatttg atattttcgt agtctctaaa ggcttcttcc agattggcaa   2040
tatactgatc tgactcagta ttttttacta atatatcatc aacataaact ttgatattaa   2100
tttcaatttg ttacttaaaa atcttattaa tcaagtatta gtatgtagca cctacatttt   2160
taagatcaaa agacatcatt ttataacaat gcaaatcttt ttcagtgatg aaggccatat   2220
tttcttcatc ctcaagtgcc attttgatct gatataacca gaaaaagtat ccataaagct   2280
tagtaatttg tgtcttgaag tagcatcaac aagctgatca attttgaga gagaaaaact    2340
atcttttagg caagctttat tgagatcggt ataatcaaca tagatccttc attttcatt    2400
agccttttta accatgacaa catttacaat ccactttgga tattatgctt ctctgatgaa   2460
tttgtctttc aagagtttgt cgacttcctc atctattatt ttttatcttt tcggggtgaa   2520
acttcttttc ttctgttgca ttggtttatg ctttggatca acattcagct tatgtacaat   2580
aagatcagtt aaaatctcag gcatattaga gactgactaa acaaagacat cggcattcat   2640
ccgaagaaaa gatattaatt tctccctcag atcaggcttc aatagagatc caatttggac   2700
agttttttt ggatcatcac acaaaagaac aataataagt ttctcgactg gttctcctcg    2760
attttgatg atatcaactt tacttccttg atcaagtatt ttaattggta gagcttccac    2820
agacctttc attttacag ctatcagaaa atactactta gcaagtatct gatttcctca     2880
tatttctcca actccatact tagtttggaa ttggattagt aaatgataag tgaagactat   2940
agccttaagg gcgttgagcc taggtcggtc aagaatagca ttataagctg atggtatttt   3000
gacaataaaa aaagtgagtc ttacagttga ctggcatggt tctatccctg cagtgacgga   3060
caaagtgacc tctccttcca cagctacagg atttctagaa aatccaatta cggggtacc    3120
aacctattta gctaatttat catattcatt ctttggaatg tatcatagaa caatatatta   3180
gcagagcttt cattatcaat aagtattctt tttatatcat atttggctat tgccataaag   3240
atgacaacag catcattacg aggagtttga actctaacat catcatcgaa aaatgaaatt   3300
atgtgatcca tgcactgatg ctttggaagg ctttcagtaa tctcagccac ctcctcagtt   3360
ccgtcgagat ctgagatcat attgatgact gcagcagtag acttgttgtg atcattctca   3420
ttgttgggct tctatcattg gtcagtagct tgacttgccc gatctcgaac atatttacta   3480
aagtaacatt agtggatcaa tacttcaatt ttatctttta attatcgatg ctcctcagta   3540
```

```
tcatggccat agtctcgatg gaaatgacag tattttctct tatctctctt tgctggaggg    3600
gctttcatag gattaggttg gcgaatatat cctaaatcct cgatttctat cagtatctga    3660
gctcgaggag tagatagtga ggtatagatg tcgaatcacc gaggtgggct tttgaacttc    3720
agattcttct gaggtcgttc agagttatcc tgttggtttt tatgatcttc ttcctagggc    3780 cactttttc catctctttt tttcttcacc taacgaagta tgcatgctct ctttcttttc     3840
agcttgagca tacttacaaa cctagatcaa tatttgttca taattgtttg ggtagttctt    3900
attaagagag aagatcaggc gattactctt gagtccttgc ttcaaagctg ccattgcaat    3960
ggactcattg aagttcttca ctttcagtat ggcggcatta aagcatgcca catattcttg    4020
aagagattca ccttcctact atttgatagt aaaaagattg c                       4061
```

<210> SEQ ID NO 54
<211> LENGTH: 4061
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (2978)..(3705)
<223> OTHER INFORMATION: n is a, c, g, or t

<400> SEQUENCE: 54

```
catcatcgaa aaatgaaatt atgtgatcca tgcactgatg ctttggaagg ctttcagtaa      60
tctcagccac ctcctcagtt ccgtcgagat ctgagatcat attgatgact gcagcagtag     120
acttgttgtg atcattctca ttgttgggct tctatcattg gtcagtagct tgacttgccc     180
gatctcgaac atatttacta aagtaacatt agtggatcaa tacttcaatt ttatcttta      240 attatcgatg ctcctcagta tcatggccat agtctcgatg gaaatgacag tattttctct     300
tatctctctt tgctggaggg gctttcatag gattaggttg gcgaatatat cctaaatcct     360
cgatttctat cagtatctga gctcgaggag tagatagtga ggtatagatg tcgaatcacc     420
gaggtgggct tttgaacttc agattcttct gaggtcgttc agagttatcc tgttggtttt    480
tatgatcttc ttcctagggc cactttttc catctctttt tttcttcacc taacgaagta     540
tgcatgctct ctttcttttc agcttgagca tacttacaaa cctagatcaa tatttgttca    600
taattgtttg ggtagttctt attaagagag aagatcaggc gattactctt gagtccttgc    660
ttcaaagctg ccattgcaat ggactcattg aagttcttca ctttcagtat ggcggcatta    720
aagcatgcca catattcttg aagagattca ccttcctact atttgatagt aaaaagattg    780
ctagtatttt tcaaatgaat ccatttatta tcaaaatacg tgatgaatat ttgctaactg    840
tgtgaaagat gaaatagatc atgtctggag gtcagagaac tagattcttg cagatgtttt    900
gagagtgatt ggaaaagtga tgcaaaatag ggcattagat acccccttgta gtcttataat    960 ggctctgaag ccttcaagat gatttaaggg attgatggag ccatcgaatg tttccaatgt   1020
aggtatcttg aatcgaggag gaactgattt accaagaatt ttttgagaaa aaagagatcg   1080
taagttgaaa tctcttctac cttgagaatg gcttccaatc tatatctcca tcatttcttt   1140
ctcaagattt tgaatctttt gtccaagacc ctcctccata catggcttct tatgtgggagc   1200 agatttcact tcccaagagt gatcagtatg gtcaagaaga tgatcatgat gaagatcttg   1260
aggagttggt tgctaagtgt gatgtgattg gactacttgg ggggctactt tttgctaccg   1320
ttctgtcgta tactacagca gtaagagctt ggacctgctg aaccaagaga ctaaactatt   1380
gtggatcaat aataattgaa ggttaggtat tctcctgaac atcttcagga gaagatgaag   1440
```

```
taggtaaagg atgatttggt gccttcttgt tcaccatttc tactaaaata ttttaagtgc   1500
ccttcctcta acactaatct attactgcaa ggcttcaaaa gacaggcaac gagatgggtc   1560
ttgaatcgaa ctagaatgtt tcttggttga atttggcgaa gtctgtaaca aatcttgcaa   1620
agaaaatctc gaaacctacg ggtaccttct ggttcaagat cctctgatgg ataagttagg   1680
taaagtcttg agaataggtt gtgaaaatag aagaatagaa ggatgagaag agagattgtc   1740
ggtaaatgga gagatgactc ttatttcttt caatggggga gctgaaaata attcagcaga   1800
gtttccactc tatcaatcct gacttatttt gtggagggta ccttggcccc ttcatatata   1860
ggggatgaag aggcctggta aggttgttag actattagga gagtttgtta gatcgttaat   1920
ttattataat agaatgacca gctatataaa aatcatggag tatttaccca catggtgatt   1980
gactgtagta taactgaaag atagctaatg cttagctgga tgactgctgt tagataactg   2040
tctgcattct tacggtacat tgatatttta ccaatgtgac atagcttaaa tcggcaactg   2100
gctgaactaa atattatgta tcccttagt taacaatcat gtcggttaga gatcaatgta   2160
attcgcagca gatcgatcat aagctgagat gagtatcata ttttaagaac aacgctgggc   2220
gagttaggcc gatcaaatgt cagactgaaa aagcagatca ataaacctct gatgtgatct   2280
gaaagaatat ttatgattta aataataatc tatcaccacg tatccagata atgaggtcat   2340
ataacatgta ccaacagtgc attttttccat ctagttaaga ggttggttag tggcatttgt   2400
cttcgatatg taatgttcac ataactaatg tgcttagtag cattcttttg taaggttaaa   2460
tcttcaatga tcttaagttc acataattgc ctttgtgccc tattagttta tagttgacct   2520
tttaattcaa gagacagtca ccttagcaat cgatgtctgc ttagattggg ccaattaggt   2580
actcacatta atatattgaa tcatgtttga atataaagga ttagattgat ttataagttt   2640 cctttattg tttacatact gatacttaga ttgacttact acattatttg atatgttatg   2700
ttctaatttt tggattaaaa ttgttgtttc tgatttctcc ttacatctaa tactttgtat   2760
aatttattat tttttagcat gattgagtgt agaggattag attgattttt aagtttattt   2820
tgattattta catgcccata cttaaattga cttactacat tattcaatat gttatgtttc   2880
aattattgag ttaaaatttt tatttctgat ttctactgat gtccagtgtg tgtgtgtgta   2940
cgtatgtgtg tatatattta tttacatata tatgtatnnn nnnnnnnnn nnnnnnnnn   3000 nnnnnnnnnn nnnnnnnnnn nnnnnnnnnn nnnnnnnnnn nnnnnnnnnn nnnnnnnnnn   3060
nnnnnnnnnn nnnnnnnnnn nnnnnnnnnn nnnnnnnnnn nnnnnnnnnn nnnnnnnnnn   3120
nnnnnnnnnn nnnnnnnnnn nnnnnnnnnn nnnnnnnnnn nnnnnnnnnn nnnnnnnnnn   3180
nnnnnnnnnn nnnnnnnnnn nnnnnnnnnn nnnnnnnnnn nnnnnnnnnn nnnnnnnnnn   3240
nnnnnnnnnn nnnnnnnnnn nnnnnnnnnn nnnnnnnnnn nnnnnnnnnn nnnnnnnnnn   3300
nnnnnnnnnn nnnnnnnnnn nnnnnnnnnn nnnnnnnnnn nnnnnnnnnn nnnnnnnnnn   3360
nnnnnnnnnn nnnnnnnnnn nnnnnnnnnn nnnnnnnnnn nnnnnnnnnn nnnnnnnnnn   3420
nnnnnnnnnn nnnnnnnnnn nnnnnnnnnn nnnnnnnnnn nnnnnnnnnn nnnnnnnnnn   3480
nnnnnnnnnn nnnnnnnnnn nnnnnnnnnn nnnnnnnnnn nnnnnnnnnn nnnnnnnnnn   3540
nnnnnnnnnn nnnnnnnnnn nnnnnnnnnn nnnnnnnnnn nnnnnnnnnn nnnnnnnnnn   3600
nnnnnnnnnn nnnnnnnnnn nnnnnnnnnn nnnnnnnnnn nnnnnnnnnn nnnnnnnnnn   3660
nnnnnnnnnn nnnnnnnnnn nnnnnnnnnn nnnnnnnnnn nnnnnatgta tacatataca   3720
tgtatacata catatataga tatatatata tacatatatg tatatatata tatatatata   3780
```

```
cacatatata ggttatttgg aacctaagaa acttgcaaag ttactagatg caatgttcgg   3840
aaaccatgga ccgtaacaac tggagtagta tttgggtcat gaattcatgg ctagatcatg   3900
aattgagtgg gagtcaaccg aagtagggcc agctcagaca cttgtattta ggtcccatgc   3960
ttgcgtgcat tctcttccct gatatccttt ggctttgctg cctcaaatcc tcgagctatc   4020
ttatcatcat cgcattgagc tccataacctt gctctttcct a                      4061

<210> SEQ ID NO 55
<211> LENGTH: 4061
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (2098)..(2825)
<223> OTHER INFORMATION: n is a, c, g, or t

<400> SEQUENCE: 55
tagattcttg cagatgtttt gagagtgatt ggaaaagtga tgcaaaatag ggcattagat     60 acccccttgta gtcttataat ggctctgaag ccttcaagat gatttaaggg attgatggag   120
ccatcgaatg tttccaatgt aggtatcttg aatcgaggag gaactgattt accaagaatt   180
ttttgagaaa aaagagatcg taagttgaaa tctcttctac cttgagaatg gcttccaatc   240
tatatctcca tcattttctt ctcaagattt tgaatctttt gtccaagacc ctcctccata   300
catggcttct tatgtggagc agatttcact tcccaagagt gatcagtatg gtcaagaaga   360
tgatcatgat gaagatcttg aggagttggt tgctaagtgt gatgtgattg gactacttgg   420
ggggctactt tttgctaccg ttctgtcgta tactacagca gtaagagctt ggacctgctg   480
aaccaagaga ctaaactatt gtggatcaat aataattgaa ggttaggtat tctcctgaac   540
atcttcagga gaagatgaag taggtaaagg atgatttggt gccttcttgt tcaccatttc   600
tactaaaata ttttaagtgc ccttcctcta acactaatct attactgcaa ggcttcaaaa   660
gacaggcaac gagatgggtc ttgaatcgaa ctagaatgtt tcttggttga atttggcgaa   720
gtctgtaaca aatcttgcaa agaaaatctc gaaacctacg ggtaccttct ggttcaagat   780
cctctgatgg ataagttagg taaagtcttg agaataggtt gtgaaaatag aagaatagaa   840
ggatgagaag agagattgtc ggtaaatgga gagatgactc ttatttcttt caatggggga   900
gctgaaaata attcagcaga gtttccactc tatcaatcct gacttatttt gtggagggta   960
ccttggcccc ttcatatata ggggatgaag aggcctggta aggttgttag actattagga  1020
gagtttgtta gatcgttaat ttattataat agaatgacca gctatataaa aatcatggag  1080
tatttaccca catggtgatt gactgtagta taactgaaag atagctaatg cttagctgga  1140
tgactgctgt tagataactg tctgcattct tacggtacat tgatattta ccaatgtgac   1200 atagcttaaa tcggcaactg gctgaactaa atattatgta tcccttagt taacaatcat    1260 gtcggttaga gatcaatgta attcgcagca gatcgatcat aagctgagat gagtatcata  1320
ttttaagaac aacgctgggc gagttaggcc gatcaaatgt cagactgaaa aagcagatca  1380
ataaacctct gatgtgatct gaaagaatat ttatgattta aataataatc tatcaccacg  1440
tatccagata atgaggtcat ataacatgta ccaacagtgc attttccat ctagttaaga   1500 ggttggttag tggcatttgt cttcgatatg taatgttcac ataactaatg tgcttagtag  1560
cattcttttg taaggttaaa tcttcaatga tcttaagttc acataattgc ctttgtgccc   1620
tattagttta tagttgacct tttaattcaa gagacagtca ccttagcaat cgatgtctgc  1680
```

```
ttagattggg ccaattaggt actcacatta atatattgaa tcatgtttga atataaagga    1740
ttagattgat ttataagttt cctttttattg tttacatact gatacttaga ttgacttact   1800
acattatttg atatgttatg ttctaattt tggattaaaa ttgttgtttc tgatttctcc    1860
ttacatctaa tactttgtat aatttattat tttttagcat gattgagtgt agaggattag   1920
attgattttt aagtttattt tgattattta catgcccata cttaaattga cttactacat   1980
tattcaatat gttatgtttc aattattgag ttaaaatttt tatttctgat ttctactgat   2040
gtccagtgtg tgtgtgtgta cgtatgtgtg tatatattta tttacatata tatgtatnnn   2100
nnnnnnnnnn nnnnnnnnnn nnnnnnnnnn nnnnnnnnnn nnnnnnnnnn nnnnnnnnnn   2160
nnnnnnnnnn nnnnnnnnnn nnnnnnnnnn nnnnnnnnnn nnnnnnnnnn nnnnnnnnnn   2220
nnnnnnnnnn nnnnnnnnnn nnnnnnnnnn nnnnnnnnnn nnnnnnnnnn nnnnnnnnnn   2280
nnnnnnnnnn nnnnnnnnnn nnnnnnnnnn nnnnnnnnnn nnnnnnnnnn nnnnnnnnnn   2340
nnnnnnnnnn nnnnnnnnnn nnnnnnnnnn nnnnnnnnnn nnnnnnnnnn nnnnnnnnnn   2400
nnnnnnnnnn nnnnnnnnnn nnnnnnnnnn nnnnnnnnnn nnnnnnnnnn nnnnnnnnnn   2460
nnnnnnnnnn nnnnnnnnnn nnnnnnnnnn nnnnnnnnnn nnnnnnnnnn nnnnnnnnnn   2520
nnnnnnnnnn nnnnnnnnnn nnnnnnnnnn nnnnnnnnnn nnnnnnnnnn nnnnnnnnnn   2580
nnnnnnnnnn nnnnnnnnnn nnnnnnnnnn nnnnnnnnnn nnnnnnnnnn nnnnnnnnnn   2640
nnnnnnnnnn nnnnnnnnnn nnnnnnnnnn nnnnnnnnnn nnnnnnnnnn nnnnnnnnnn   2700
nnnnnnnnnn nnnnnnnnnn nnnnnnnnnn nnnnnnnnnn nnnnnnnnnn nnnnnnnnnn   2760
nnnnnnnnnn nnnnnnnnnn nnnnnnnnnn nnnnnnnnnn nnnnnnnnnn nnnnnnnnnn   2820
nnnnnatgta tacatataca tgtatacata catatataga tatatatata tacatatatg   2880
tatatatata tatatatata cacatatata ggttatttgg aacctaagaa acttgcaaag   2940
ttactagatg caatgttcgg aaaccatgga ccgtaacaac tggagtagta tttgggtcat   3000
gaattcatgg ctagatcatg aattgagtgg gagtcaaccg aagtagggcc agctcagaca   3060
cttgtattta ggtcccatgc ttgcgtgcat tctcttccct gatatccttt ggctttgctg   3120
cctcaaatcc tcgagctatc ttatcatcat cgcattgagc tccatacctt gctctttcct   3180
aactgccccc atcaaacctc cggagatcct ctttcttctc caatgttgag atttgttgga   3240
gtcttcccac cttctcactt caatgggtgg caatttcaag tgccagttcc cttatttgtc   3300
ccagctatat tgacaatggg gcttattcta gggtttctca tggacatagt gataataata   3360
atcaagggac caagagagaa aaatctttct agtctgtgtt ctttaagttt gagagatagg   3420
cagcacattt ttttaataag cctttttcac tcatcggatc ctgattttca gttgttcgac   3480
ctgaacagtt caagcaattg aactgcttgg gtcactattt tggacgattt tcagccattt   3540
ttaagtattg tttgactgga tccacgctgc gtagtgggca ttgcgttgat caagtagacc   3600
tgtaagggtc aacaaggtct gagaacactg aatggatgct ccataatcct cttgttatct   3660
gtcaaccatt tggaatcttt taaaacaaca tgtggtgata atatatatga taaactgtga   3720
tagattcatg tatagattat acatatgaaa atgtagagtg cttagtaaaa gtgatgaaga   3780
gcaatgcgtt agaatgtgct agcctttgac ctaaaaattg gaatgcccaa tgatgagtta   3840
tgataaaatt gtgacgtgat ttatgaagtc taatgtttag ttggcttgca gtttcagatg   3900
cgataaagaa tttatgatt tagctctttg gtttttttaac atgcaaacat ttaattgtac   3960
tgaaaaacat ttatttcgaa acatgtagga gactattgga tattgaaatt aaaattgact   4020
```

| | |
|---|---|
| ttttggtgtt tcacaatatt tcttaataaa cactacgact a | 4061 |

<210> SEQ ID NO 56
<211> LENGTH: 4061
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (218)..(1631)
<223> OTHER INFORMATION: n is a, c, g, or t

<400> SEQUENCE: 56

| | |
|---|---|
| aagctccgtg cttctgtctt tgagaagtgt ctgagtaggt agtcgatccc aggcaacctt | 60 |
| ctagaggaaa agtctgatcc tagagtggat agccatgtgt atatatatat atatatatat | 120 |
| gtatgtatgt atgtatgtat gtatgtatgt atgtacgtac atacatacat acacacacat | 180 |
| acatacatat acatacatac atatacatac atacatannn nnnnnnnnnn nnnnnnnnnn | 240 |
| nnnnnnnnnn nnnnnnnnnn nnnnnnnnnn nnnnnnnnnn nnnnnnnnnn nnnnnnnnnn | 300 |
| nnnnnnnnnn nnnnnnnnnn nnnnnnnnnn nnnnnnnnnn nnnnnnnnnn nnnnnnnnnn | 360 |
| nnnnnnnnnn nnnnnnnnnn nnnnnnnnnn nnnnnnnnnn nnnnnnnnnn nnnnnnnnnn | 420 |
| nnnnnnnnnn nnnnnnnnnn nnnnnnnnnn nnnnnnnnnn nnnnnnnnnn nnnnnnnnnn | 480 |
| nnnnnnnnnn nnnnnnnnnn nnnnnnnnnn nnnnnnnnnn nnnnnnnnnn nnnnnnnnnn | 540 |
| nnnnnnnnnn nnnnnnnnnn nnnnnnnnnn nnnnnnnnnn nnnnnnnnnn nnnnnnnnnn | 600 |
| nnnnnnnnnn nnnnnnnnnn nnnnnnnnnn nnnnnnnnnn nnnnnnnnnn nnnnnnnnnn | 660 |
| nnnnnnnnnn nnnnnnnnnn nnnnnnnnnn nnnnnnnnnn nnnnnnnnnn nnnnnnnnnn | 720 |
| nnnnnnnnnn nnnnnnnnnn nnnnnnnnnn nnnnnnnnnn nnnnnnnnnn nnnnnnnnnn | 780 |
| nnnnnnnnnn nnnnnnnnnn nnnnnnnnnn nnnnnnnnnn nnnnnnnnnn nnnnnnnnnn | 840 |
| nnnnnnnnnn nnnnnnnnnn nnnnnnnnnn nnnnnnnnnn nnnnnnnnnn nnnnnnnnnn | 900 |
| nnnnnnnnnn nnnnnnnnnn nnnnnnnnnn nnnnnnnnnn nnnnnnnnnn nnnnnnnnnn | 960 |
| nnnnnnnnnn nnnnnnnnnn nnnnnnnnnn nnnnnnnnnn nnnnnnnnnn nnnnnnnnnn | 1020 |
| nnnnnnnnnn nnnnnnnnnn nnnnnnnnnn nnnnnnnnnn nnnnnnnnnn nnnnnnnnnn | 1080 |
| nnnnnnnnnn nnnnnnnnnn nnnnnnnnnn nnnnnnnnnn nnnnnnnnnn nnnnnnnnnn | 1140 |
| nnnnnnnnnn nnnnnnnnnn nnnnnnnnnn nnnnnnnnnn nnnnnnnnnn nnnnnnnnnn | 1200 |
| nnnnnnnnnn nnnnnnnnnn nnnnnnnnnn nnnnnnnnnn nnnnnnnnnn nnnnnnnnnn | 1260 |
| nnnnnnnnnn nnnnnnnnnn nnnnnnnnnn nnnnnnnnnn nnnnnnnnnn nnnnnnnnnn | 1320 |
| nnnnnnnnnn nnnnnnnnnn nnnnnnnnnn nnnnnnnnnn nnnnnnnnnn nnnnnnnnnn | 1380 |
| nnnnnnnnnn nnnnnnnnnn nnnnnnnnnn nnnnnnnnnn nnnnnnnnnn nnnnnnnnnn | 1440 |
| nnnnnnnnnn nnnnnnnnnn nnnnnnnnnn nnnnnnnnnn nnnnnnnnnn nnnnnnnnnn | 1500 |
| nnnnnnnnnn nnnnnnnnnn nnnnnnnnnn nnnnnnnnnn nnnnnnnnnn nnnnnnnnnn | 1560 |
| nnnnnnnnnn nnnnnnnnnn nnnnnnnnnn nnnnnnnnnn nnnnnnnnnn nnnnnnnnnn | 1620 |
| nnnnnnnnnn ntatatatat atagtatact atatagtata tatatagtat atatagtata | 1680 |
| tatatatata tatatatata gtatatatat atatatatat atatatatgt gtgtgtgtgt | 1740 |
| gtgtgcgcgt gcgcgcacgc acgtgtgtat ctcgatctgt gtgtgtgtgg tccatcttca | 1800 |
| cactttccc tcaaaaaaac cccccttgag attttgttca gctgaaaggg gttcataaaa | 1860 |
| cttgcccttg cttggtccta gggtttaaga tttatatgca atattcatta agacgtctaa | 1920 |

```
atgtcataat attttgaggt tacaaatatt aacaaacagc cttggataca aacctttttc    1980
tcgaagaatc ttgtatctgt tcttcctcag atgacatgtg atttatgcta cggcctagtt    2040
ctaaggactt ttctctgtca ttaacataaa aaaaaacaga atatattcc ttagtaagga     2100
aatagttgtg cactatgatt gctatgtctc tcaaaattat accaaacttt ttatgatata    2160
gagtgaaaat caaatcagca tgtctggtct atttgccaaa tagggttgag cataggtcgg    2220
gttcggtcga gttgagagaa aaatttcatc cgatcaaatt caatcggatt gaagaaaatt    2280
caatccactg ccaatcattc attatgcata aactatctaa aactgaaatg aatagtttgt    2340
agcaggatca ggtgttatgt cagtttggac ttcaatgtta acccaatatt gattttaaat    2400
ccaacattgg tccacttaga cttatttatt tattttatc aatttaatat aaaaaagatc     2460
taaacctcat aagtcataaa ttttggattt attttgaac atgtacaaaa taaacagaa      2520
aaagaaaaa attacttatc taaaagtaac tatatctgaa aactttcact ttagaattgt     2580
cttaaattaa tgtacttcca tcaacaattc aatgttaata tttttatgaa tccaaatgga    2640
tgatagagta tttttagaa tgaagtattg aagtctaaat gacatcgtcc caaaataaaa     2700
gtgaatttat gaaatactac atctgtcgga ttcggtttca tacggattaa aagtgtagga    2760
atagaatccg attataaata attattttt tataaattct aattcaattt tattcgattt     2820
atatttttta accggtcaaa attaatattt attaagtagg attggatgga tttattcgta    2880
tctcgattat ttgctcagcc cattgccaaa tctaaactct tttcagatag gttccatgtg    2940
aacatgatac atgagatgca gtgtgatagt acacaccatt gctaagaaaa ctttggagtt    3000
tgcgtaacaa tatctgttta ccatttaaaa aatggcagtt ttgaatttta acacgctctc    3060
ctccagattc agcttatgaa cttttcgaat aaaaatcccc ctggactatt tttccaaaaa    3120
gtaccagcat cttttgaact tgaatggaaa ttcggccaat aaaatgtttt catttattga    3180
agaaataaac agggtaacgc agtagctcta tttcctctgc ttttcttttc tatattaata    3240
acatgattat tcatctctct cggatcacaa aaaaattaag ctattcaagc tttatttata    3300
tttcatttt aaattttta cttaaataca aaatctccca tcccactact acggcagcat      3360
gttttctatg tatgattatt ttcattcaaa tgatatcatt tttataatt tatattgtat     3420
gtaattaatt catttatagt tcttacattt tcctgtttct agtagataca ataaagcggt    3480
tttggactag tagcttgttc tctgtatcga agtttaacta aagctttgac aataatatat    3540
gaatccatat cactgggtag gagaggaata tgttgggtat aaaggattta aggaattaga    3600
tattttcata caattgtatt gcattgcaga cagtaattag attactatgc aattattctc    3660
tctctccatg tttgttgcag ttgaagaact ctaatgaagc tcacaaaaat ttactgcatg    3720
aacttgtaag tggaattaga cgactccgtt gtcctccatt ttctttatt ttctttaaaa     3780
tcatctgcca ttcaaataga cagaaaaaaa aggattgatt agctattgga tgcctcttga    3840
attcaggaaa tgaaggacga gcacccagtt tatggttttg tggatgatga ccctagcaac    3900
tacgcaggtg cactagctct tgccaatggg gcttcccaca tgtatgcttt ccgtgttcag    3960
ccgagccagc cgaatctcca tcgaatgggg tttggctccc atgacctgcg ccttgcttga    4020
ttttattgta gcttaaagac cttacaactt ccagagtggt g                        4061
```

<210> SEQ ID NO 57
<211> LENGTH: 4061
<212> TYPE: DNA
<213> ORGANISM: Artificial Sequence
<220> FEATURE:

<223> OTHER INFORMATION: synthetic

<400> SEQUENCE: 57

```
cagtttggac ttcaatgtta acccaatatt gattttaaat ccaacattgg tccacttaga        60
cttatttatt tatttttatc aatttaatat aaaaaagatc taaacctcat aagtcataaa       120
ttttggattt atttttgaac atgtacaaaa taaaacagaa aaagaaaaa attacttatc        180
taaaagtaac tatatctgaa aactttcact ttagaattgt cttaaattaa tgtacttcca       240
tcaacaattc aatgttaata tttttatgaa tccaaatgga tgatagagta ttttttagaa       300
tgaagtattg aagtctaaat gacatcgtcc caaaataaaa gtgaatttat gaaatactac       360
atctgtcgga ttcggtttca tacgattaa aagtgtagga atagaatccg attataaata        420
attatttttt tataaattct aattcaattt tattcgattt atattttta accggtcaaa        480
attaatattt attaagtagg attggatgga tttattcgta tctcgattat ttgctcagcc       540
cattgccaaa tctaaactct tttcagatag gttccatgtg aacatgatac atgagatgca       600
gtgtgatagt acacaccatt gctaagaaaa ctttggagtt gcgtaacaa tatctgttta        660
ccatttaaaa aatggcagtt ttgaattta acacgctctc ctccagattc agcttatgaa        720
cttttcgaat aaaaatacc ctggactatt ttccaaaaa gtaccagcat cttttgaact         780
tgaatggaaa ttcggccaat aaaatgtttt catttattga agaaataaac agggtaacgc       840
agtagctcta tttcctctgc ttttcttttc tatattaata acatgattat tcatctctct       900
cggatcacaa aaaattaag ctattcaagc tttatttata tttcattttt aaattttta        960
cttaaataca aatctcccca tcccactact acggcagcat gttttctatg tatgattatt      1020
ttcattcaaa tgatatcatt ttttataatt tatattgtat gtaattaatt catttatagt      1080
tcttacattt tcctgtttct agtagataca ataaagcggt tttggactag tagcttgttc      1140
tctgtatcga agtttaacta aagctttgac aataatatat gaatccatat cactgggtag      1200
gagaggaata tgttgggtat aaaggattta aggaattaga tattttcata caattgtatt      1260
gcattgcaga cagtaattag attactatgc aattattctc tctctccatg tttgttgcag      1320
ttgaagaact ctaatgaagc tcacaaaaat ttactgcatg aacttgtaag tggaattaga      1380
cgactccgtt gtcctccatt ttctttatt ttctttaaaa tcatctgcca ttcaaataga       1440
cagaaaaaaa aggattgatt agctattgga tgcctcttga attcaggaaa tgaaggacga      1500
gcacccagtt tatggttttg tggatgatga ccctagcaac tacgcaggtg cactagctct      1560
tgccaatggg gcttcccaca tgtatgcttt ccgtgttcag ccgagccagc cgaatctcca      1620
tcgaatgggg tttggctccc atgacctgcg ccttgcttga ttttattgta gcttaaagac      1680
cttacaactt ccagagtggt gttatatatt agtatcttaa gctatgacag tggtaagcct      1740
ctctatccgc tacttgttat cctttaggta ctttgcatgt ggtgcaaggt tataattgcc      1800
ttgtgtttct attgtcttcc tcatggtact tactggactg atgatgtcaa gtgaaatgga      1860
gttgtttgaa tcctgactga aatttctctt ggtccatcaa gtgcaagagt aagtttagac      1920
atcactcgca agcttttgct aggaaataag tagtttcatt gcactaatga tttcgaattt      1980
ttgttttcgg gttagagaaa cctagattaa tgctgttatt ggatgctggc agtcagatga      2040
agattatgtt tgattgtacc tcgttggaca gatgctcatg cgtagatcca taactctatt      2100
tcatttcatt tccctgtaca caattgaaac agggcatata tgaataggta tagaacagat      2160
gattcctgca atattggagg tggctagctc agcttagact aaagttggtc tagctgggat      2220
attctgaaca cctgagatgt tcaaataatg tgggataact tggcccaact caactaaaca      2280
```

```
ttggctcaaa gcatagtcaa ggtaaagctt gagcaagctc ttttgagctt ggttcgagtc    2340
cgagctgagc ccgggccgct tgtttagctg atgaactgaa ttcaaatagc cggtactcag    2400
cttggctcca ctcgattcat gagttcgaat cccctcaagt tcaacctcga acttgacggt    2460
gtagtcccac aaccatggcc acctataat gtgggacggc cattatgcat tcctctagtg     2520
cctgctccat atgactttg ttctcattat accatgcacc taaatgagtg ctcatagtga     2580
caatgtttag cctccacgta taatgtgtgc cagctaacta aagcctaaa ctttggtgaa     2640 atttctgcaa tgttgtggtt gtaaaacgct cctacgttga dacatgatgg tatctaagat    2700
tatagacaaa ctatcatgct gaatcaaccc aaatccaagg tgaataaaac ttgatacaaa    2760
gccgagctcc attgaaatag tacaatggat tctgcacttg aagaacatta caaaatcatt    2820 tttcccaaa aagaaacatt gcgaacagac aaagcgtaa agaaattaca tgattcaact     2880
aattcaagct ttccatgatg taggcactcg ctagatgtag tagggtgata acttgctttg    2940
tgagggtgga tcataagctt aacctcaatc tatcccaatc tatcctttcc cttgacctat    3000
ccatgccaat ctaggccatt tctgcataaa tataacttaa tcccagtgga tccggcctag    3060
tttcactcac tccaacacat tcctactcaa tggtagccaa tcctttcttt agccctcaaa    3120
tataatccta atctagcata gccaaccatc aatcatgcct aataaagccc gactacacca    3180
acccgatcat tcctgatcgt acacaatcaa gacttatcct aattgatcct agcttttttt    3240
aggcctctct tatagaacct gtgccaattc tggacaagct aatccaatct tagcagccaa    3300
aaatattaca tgtttaatta gccaaatcga acctatcata aacccaatat ataatcggac    3360
cataccaaga tcatcatcct atatttcctt ctcttgttat aactacacct aaaaaggaat    3420
ttcttcatac ttatgagggg tatattatga taaaaattcc ttcattttag ccctccatcc    3480
ttgtctattt ttgggaccac tagccaagta acaccttaag agccctccat cttaatattc    3540
cctctaacta gctcgatttc ttcttcattc tttctttgcg atgtgtcccc tccaatttaa    3600
ttcttacatg ttgggatttg agtactgaaa aataatagat aaagagaaag taaaaactat    3660
gctaatgata ataccaaagg cataaagaaa tcacagcagt cgcaaaaaca tcaaattttt    3720
ttatggttcg gcctaagcct atatctacat agggacgaga gtaagaagaa gcttccacta    3780
taataatagt ttagagtaca aaaacttctc tgacaccatg tagggaacat cgcttctaat    3840
acaagaaaga agaaatccaa gattaaacaa acctctagaa aaattcttct cgatggaata    3900
actctaatct gagattgaac aatcttctcc aatcgatgat ctccaatctt cttttcttaa    3960
atgaagcacc cttcaagcct ctcttctttt ctctcttcct atcctctttt gtggctcaca    4020
acctcctctc cttttatgt tctatgttcc tcacatcaca t                          4061
```

<210> SEQ ID NO 58  
<211> LENGTH: 4061  
<212> TYPE: DNA  
<213> ORGANISM: Artificial Sequence  
<220> FEATURE:  
<223> OTHER INFORMATION: synthetic

<400> SEQUENCE: 58

```
tttcagatag gttccatgtg aacatgatac atgagatgca gtgtgatagt acacaccatt      60
gctaagaaaa ctttggagtt tgcgtaacaa tatctgttta ccatttaaaa aatggcagtt    120
ttgaatttta acacgctctc ctccagattc agcttatgaa cttttcgaat aaaaatacc     180 ctggactatt tttccaaaaa gtaccagcat cttttgaact tgaatggaaa ttcggccaat    240
```

```
aaaatgtttt catttattga agaaataaac agggtaacgc agtagctcta tttcctctgc      300
ttttcttttc tatattaata acatgattat tcatctctct cggatcacaa aaaaattaag      360
ctattcaagc tttatttata tttcatttt aaatttttta cttaaataca aaatctccca      420
tcccactact acggcagcat gttttctatg tatgattatt tcattcaaa tgatatcatt      480 ttttataatt tatattgtat gtaattaatt catttatagt tcttacattt tcctgtttct      540
agtagataca ataaagcggt tttggactag tagcttgttc tctgtatcga agtttaacta      600
aagctttgac aataatatat gaatccatat cactgggtag gagaggaata tgttgggtat      660
aaaggattta aggaattaga tattttcata caattgtatt gcattgcaga cagtaattag      720
attactatgc aattattctc tctctccatg tttgttgcag ttgaagaact ctaatgaagc      780
tcacaaaaat ttactgcatg aacttgtaag tggaattaga cgactccgtt gtcctccatt      840
ttcttttatt ttctttaaaa tcatctgcca ttcaaataga cagaaaaaaa aggattgatt      900
agctattgga tgcctcttga attcaggaaa tgaaggacga gcacccagtt tatggttttg      960
tggatgatga ccctagcaac tacgcaggtg cactagctct tgccaatggg gcttcccaca     1020
tgtatgcttt ccgtgttcag ccgagccagc cgaatctcca tcgaatgggg tttggctccc     1080
atgacctgcg ccttgcttga ttttattgta gcttaaagac cttacaactt ccagagtggg     1140
gttatatatt agtatcttaa gctatgacag tggtaagcct ctctatccgc tacttgttat     1200
cctttaggta ctttgcatgt ggtgcaaggt tataattgcc ttgtgtttct attgtcttcc     1260
tcatggtact tactggactg atgatgtcaa gtgaaatgga gttgtttgaa tcctgactga     1320
aatttctctt ggtccatcaa gtgcaagagt aagtttagac atcactcgca agcttttgct     1380
aggaaataag tagtttcatt gcactaatga tttcgaattt ttgttttcgg gttagagaaa     1440
cctagattaa tgctgttatt ggatgctggc agtcagatga agattatgtt tgattgtacc     1500
tcgttggaca gatgctcatg cgtagatcca taactctatt tcatttcatt tccctgtaca     1560
caattgaaac agggcatata tgaataggta tagaacagat gattcctgca atattggagg     1620
tggctagctc agcttagact aaagttggtc tagctgggat attctgaaca cctgagatgt     1680
tcaaataatg tgggataact tggcccaact caactaaaca ttggctcaaa gcatagtcaa     1740
ggtaaagctt gagcaagctc ttttgagctt ggttcgagtc cgagctgagc ccgggccgct     1800
tgtttagctg atgaactgaa ttcaaatagc cggtactcag cttggctcca ctcgattcat     1860
gagttcgaat cccctcaagt tcaacctcga acttgacggt gtagtcccac aaccatggcc     1920
accttataat gtgggacggc cattatgcat tcctctagtg cctgctccat atgacttttg     1980
ttctcattat accatgcacc taaatgagtg ctcatagtga caatgtttag cctccacgta     2040
taatgtgtgc cagctaacta aagcctaaa ctttggtgaa atttctgcaa tgttgtggtt      2100
gtaaaacgct cctacgttga gacatgatgg tatctaagat tatagacaaa ctatcatgct     2160
gaatcaaccc aaatccaagg tgaataaaac ttgatacaaa gccgagctcc attgaaatag     2220
tacaatggat tctgcacttg aagaacatta caaaatcatt ttttcccaaa agaaacatt      2280 gcgaacagac caaagcgtaa agaaattaca tgattcaact aattcaagct ttccatgatg     2340
taggcactcg ctagatgtag tagggtgata acttgctttg tgagggtgga tcataagctt     2400
aacctcaatc tatcccaatc tatcctttcc cttgacctat ccatgccaat ctaggccatt     2460
tctgcataaa tataacttaa tcccagtgga tccggcctag tttcactcac tccaacacat     2520
tcctactcaa tggtagccaa tccttctctt agccctcaaa tataatccta atctagcata     2580
gccaaccatc aatcatgcct aataaagccc gactacacca acccgatcat tcctgatcgt     2640
```

```
acacaatcaa gacttatcct aattgatcct agctttttt aggcctctct tatagaacct      2700
gtgccaattc tggacaagct aatccaatct tagcagccaa aaatattaca tgtttaatta      2760
gccaaatcga acctatcata aacccaatat ataatcggac cataccaaga tcatcatcct      2820
atatttcctt ctcttgttat aactacacct aaaaaggaat ttcttcatac ttatgagggg      2880
tatattatga taaaaattcc ttcattttag ccctccatcc ttgtctattt ttgggaccac      2940
tagccaagta acaccttaag agccctccat cttaatattc cctctaacta gctcgatttc      3000
ttcttcattc tttctttgcg atgtgtcccc tccaatttaa ttcttacatg ttgggatttg      3060
agtactgaaa aataatagat aaagagaaag taaaaactat gctaatgata ataccaaagg      3120
cataaagaaa tcacagcagt cgcaaaaaca tcaaattttt ttatggttcg gcctaagcct      3180
atatctacat agggacgaga gtaagaagaa gcttccacta taataatagt ttagagtaca      3240
aaaacttctc tgacaccatg tagggaacat cgcttctaat acaagaaaga agaaatccaa      3300
gattaaacaa acctctagaa aaattcttct cgatggaata actctaatct gagattgaac      3360
aatcttctcc aatcgatgat ctccaatctt cttttcttaa atgaagcacc cttcaagcct      3420
ctcttctttt ctctcttcct atcctctttt gtggctcaca acctcctctc cttttatgt      3480 tctatgttcc tcacatcaca tccacagact catttttata gataaaaaat tagagtctat      3540
ttcggactcc ttttccacac acaagatggc ttcccacgcc attggttccg tgcgcatgac      3600 tttttcatg ccacaaagga ttccgtgctg caaaagtttt ccatatccat gcagtttcca      3660
cacaccacaa aaactttcgc acacttctcg aaggcttttc atgctcgacc ctttttggtt      3720
ttcaattaaa ttgatggatc ccatatgagg agggaccaca ccaataaatc tcctccttct      3780
aactcatatg gtaggttcca tcaagcctgt agcacctttg cattttatca gttttgttcc      3840
tgaagccggc ttcatcaata tattagaact atttttcttca gtgtcaactt ttttaagctt      3900
gaaccacttc atctctagca tattgacatg cttttggaaa gtatgtcaaa ttgctcaaaa      3960
ttaatcttac ggttctcttt ttcgttagat tctagtgcat attacgcact ttaacataag      4020
atctaaggaa ggaagaggac tgaggtaagg tgaagtgatt t                          4061
```

<210> SEQ ID NO 59
<211> LENGTH: 4061
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (3947)..(4061)
<223> OTHER INFORMATION: n is a, c, g, or t

<400> SEQUENCE: 59

```
cctagattaa tgctgttatt ggatgctggc agtcagatga agattatgtt tgattgtacc        60
tcgttggaca gatgctcatg cgtagatcca taactctatt tcatttcatt tccctgtaca       120
caattgaaac agggcatata tgaataggta tagaacagat gattcctgca atattggagg       180
tggctagctc agcttagact aaagttggtc tagctgggat attctgaaca cctgagatgt       240
tcaaataatg tgggataact tggcccaact caactaaaca ttggctcaaa gcatagtcaa       300
ggtaaagctt gagcaagctc ttttgagctt ggttcgagtc cgagctgagc ccgggccgct       360
tgtttagctg atgaactgaa ttcaaatagc cggtactcag cttggctcca ctcgattcat       420
gagttcgaat cccctcaagt tcaacctcga acttgacggt gtagtcccac aaccatggcc       480
```

```
accttataat gtgggacggc cattatgcat tcctctagtg cctgctccat atgactttg      540
ttctcattat accatgcacc taaatgagtg ctcatagtga caatgtttag cctccacgta      600
taatgtgtgc cagctaacta aaagcctaaa ctttggtgaa atttctgcaa tgttgtggtt      660
gtaaaacgct cctacgttga gacatgatgg tatctaagat tatagacaaa ctatcatgct      720
gaatcaaccc aaatccaagg tgaataaaac ttgatacaaa gccgagctcc attgaaatag      780
tacaatggat tctgcacttg aagaacatta caaaatcatt ttttcccaaa aagaaacatt      840
gcgaacagac caaagcgtaa agaaattaca tgattcaact aattcaagct ttccatgatg      900
taggcactcg ctagatgtag tagggtgata acttgctttg tgagggtgga tcataagctt      960
aacctcaatc tatcccaatc tatcctttcc ctttgacctat ccatgccaat ctaggccatt     1020
tctgcataaa tataacttaa tcccagtgga tccggcctag tttcactcac tccaacacat     1080
tcctactcaa tggtagccaa tccttctctt agccctcaaa tataatccta atctagcata     1140
gccaaccatc aatcatgcct aataaagccc gactacacca acccgatcat tcctgatcgt     1200
acacaatcaa gacttatcct aattgatcct agcttttttt aggcctctct tatagaacct     1260
gtgccaattc tggacaagct aatccaatct tagcagccaa aaatattaca tgttttaatta    1320
gccaaatcga acctatcata aacccaatat ataatcggac cataccaaga tcatcatcct     1380
atatttcctt ctcttgttat aactacacct aaaaggaat tcttcatac ttatgagggg       1440
tatattatga taaaaattcc ttcattttag ccctccatcc ttgtctattt ttgggaccac     1500
tagccaagta acaccttaag agccctccat cttaatattc cctctaacta gctcgatttc     1560
ttcttcattc tttctttgcg atgtgtcccc tccaatttaa ttcttacatg ttgggatttg     1620
agtactgaaa aataatagat aaagagaaag taaaaactat gctaatgata ataccaaagg     1680
cataaagaaa tcagcagcagt cgcaaaaaca tcaaattttt ttatggttcg gcctaagcct     1740
atatctacat agggacgaga gtaagaagaa gcttccacta taataatagt ttagagtaca     1800
aaaacttctc tgacaccatg tagggaacat cgcttctaat acaagaaaga agaaatccaa     1860
gattaaacaa acctctagaa aaattcttct cgatggaata actctaatct gagattgaac     1920
aatcttctcc aatcgatgat ctccaatctt ctttttctta atgaagcacc cttcaagcct     1980
ctcttctttt ctctcttcct atcctctttt gtggctcaca acctcctctc cttttatgt       2040
tctatgttcc tcacatcaca tccacagact cattttata gataaaaat tagagtctat       2100
ttcggactcc ttttccacac acaagatggc ttcccacgcc attggttccg tgcgcatgac     2160
tttttcatg ccacaaagga ttccgtgctg caaaagtttt ccatatccat gcagtttcca     2220
cacaccacaa aaactttcgc acacttctcg aaggcttttc atgctcgacc cttttggtt     2280
ttcaattaaa ttgatggatc ccatatgagg agggaccaca ccaataaatc tcctccttct     2340
aactcatatg gtaggttcca tcaagcctgt agcaccttg cattttatca gttttgttcc     2400
tgaagccggc ttcatcaata tattagaact attttcttca gtgtcaactt ttttaagctt     2460
gaaccacttc atctctagca tattgacatg cttttggaaa gtatgtcaaa ttgctcaaaa     2520
ttaatcttac ggttctcttt ttcgttagat tctagtgcat attacgcact ttaacataag     2580
atctaaggaa ggaagaggac tgaggtaagg tgaagtgatt ttttttgagt tggtaatggt     2640
acaaaagtta tactagaccg tgggtaccta atctcggaga ttaccattta gatttggttc     2700
ttgatcattt gtatagtgat gcatttaaaa aattatttga gcaaacagt gaatgccatt      2760
gggtctgaga gatccaaaac caaataacct aaagtatata gatggttcct ttagctagat     2820
catgtatgag aaaaaatgat ctgccgactg gaaaaaatag atctttgagc tcattgattg     2880
```

```
ttaagtcata tctagtctgt gaatcatctc tttgaggatt aatgatcaag ctatctttta    2940
tgggttaaaa gaataggatc actgaaatac ttatcctagt atacatataa tgtgcatggc    3000
ctatttgatg agtcagacta gaaggttatc actacttcat cacctttact gatgagcaat    3060
catgatatag atatgtatgt gagatacaaa tctaaaagat tttgaatggt tcaaagaatt    3120
cagatatgaa gtagaaaaga taaatcaaaa aattttttaaa ggtacttgat cggatctaga    3180
atgcaatacc aaataaaaaa tttgttgatt atctaaaaaa agtgatatag tttcatgatg    3240
gaattcttct tgtacacctc agctcaacgg tatatatatg aggagcaata gcactatatg    3300
agatatggtc cggtccatca tgaatatcac taatttaatt attatttatt taagagcaag    3360
atttaatttt taaaatttaa attagatttt ttctaaaatt ggtttcaccg caccatatga    3420
gatatgattt ggtggataag ttagaggata ggtctgtgag aactcattta tagggtatcc    3480
caaaaggtat ttaaaatatt acttttttctt tctagtagtt gacaatatga ttgtgagcaa    3540
tcatactgtt ttcttaaaaa cagtggaagg atgaactcaa aaagaaagtc tctaaagaac    3600
aacgagtcac aagacctata caacctattt aagatgagcc agtatatgta gtacttcctt    3660
cacctcatca atttagtagg atctcctatc ctttagaaag atactcggta ttcttacaaa    3720
ggatttagag aaagtgtttc ttgagggaga ttgagaatat agggatgatc tcaaaaccta    3780
caatgacata atataaggaa tcatgtagtt acatgaaggt cagtgggagg gttccatact    3840
gacatcgatt atgatgtggt tacatataga atttttttt caaagatcta gatcaaacat    3900
tctgaaaata aaaggtctat agagataaat ccgaaaagga tgtttgnnnn nnnnnnnnn    3960 nnnnnnnnnn nnnnnnnnnn nnnnnnnnnn nnnnnnnnnn nnnnnnnnnn nnnnnnnnnn    4020
nnnnnnnnnn nnnnnnnnnn nnnnnnnnnn nnnnnnnnnn n                       4061

<210> SEQ ID NO 60
<211> LENGTH: 4061
<212> TYPE: DNA
<213> ORGANISM: Artificial Sequence
<220> FEATURE:
<223> OTHER INFORMATION: synthetic

<400> SEQUENCE: 60
tataccatag attttttctgt taaccacatg tcaattcttc tcctccattg attttcatta      60
caatattcag gaacagctgc tttcatcttc tcaacaaata agtcaacatt aaaatggtta     120
gactttagat cattcttcca atgcctccac atagccccta ttttttccag tagagacttt     180
cttatggcat ccatgtactt agataaaaat ataaatatat cctacaccta gaaactgact     240
tttagaaaaa gtgtatatat acctaaataa aatgatttaa gatgaaaata ttcactatac     300
ctctagttca gctatcatct tttccttgaa gcctgatggc acatcatgcc aagagtcata     360
atcgattgga gcattatcaa attgtcttac cattgactgt atataatttg acaaattagt     420
agcttccacc cggattgatt gtccaagttc acttaggttg caacaacat gctctccctc      480 ttttagatca cgtaactcag acatacgtat gtatcctctc cttctaggcc agctagtcga    540
acctacaaat atgtatacac aattaaaaaa atacataaaa tgtaagaaaa tgatccctca    600
aaattaataa ttatcatatg caccatcctt tatttggtta ttagtgatct atttatgcaa    660
ttcattcgaa gaagattata tatgtatacc tagttgactt tcattggtag ctaagggagg    720
tagctcttag gcaactgatt cagttttctc ataattttgg gcttcaagtg actgctccta    780
ttgattatga gatggaggct caccttgatt ctgactttaa gagttttctg taccactaat    840
```

```
attgacaatt gtctgcttgt gttttgccat tattaatgta atttgaaaga aaaaaataga    900
attcatatat ctgaatgtta gtgaccaaaa aaacttgcaa gtatctcccc aaccatctaa    960
agattatacg ctattttatt tttcaaatct taaaaggcta acaaggcaca tagcaattac   1020
atgaagcaaa aaaagaaaat aaataaagca ccaaggaaac cattacactg tcattactga   1080
aattacattc aatagtatta tgcattaaaa caaaaactac attgataaaa taaaattgaa   1140
aataagaaac tacaagctcg tgggtgttcc ctcttgatca aaacatatcc tcaaactcta   1200
aatcttcatc gtgttggtgc acttcttgaa caaccacttc tttaaatggc tcttcacctc   1260
gaatcaaatc tgaaggttga agctgatcct catacatttg ttgtggcaca tgatcactaa   1320
caatagagtt cacatctccc aaatcataat tgtctctaac tttaaccgac ttaacaataa   1380
ccacatcttt atgtctagga gtattaatat agaacatctt tgcttgagat gcaaatacga   1440
aaggatcgtc aagcacacct tcaccagtat gtgctaagta agaaaaattc acaagtacaa   1500
taaaatttat ctttcttgca tcctttattg atatcaaccc aatcgcactt gaataaatca   1560
atcttgattt tgcaatgata atttaattga ataatgtcct ttaatatacc ataatactct   1620
attttttctt tcaacaggct acctatctct agtcctagtg taacccattg attcaactat   1680
caccacaacc ccactatttt gagttctcaa cttcctctca agtgcttttg tgtggaatct   1740
aaagccattc ataacgtaac cggtatatca tcgtgcaaca tcaagtggct ttcgagcaag   1800
gcacctaatt tgtttagtaa tatagacatc accttgttga ttcatgcatg caacctaaat   1860
taacatggat ttcaaatagt atattacaag atagaacatt atgaggtaaa tatatggtgt   1920
ttatatattc aaattataaa ttataaagga gcatataaaa cactcattta tgaaaccact   1980
cgaaaaattc ctgactatga atcctttcaa tctcataaga agttaaatga catggatgac   2040
atgaagcttt gatatgcatc gaaacatatt cacatggtta ttaatgagat gagtgatagt   2100
ttggtagact tgccaactta ataactaact taataacaaa atctccttac tctcgaaata   2160
cggtaattgc atcgtagtta aataggatat atctgtgcgc ttgcatcaac tctttctcat   2220
caagatggac ccttggcact cgacttcacc tttctggcct ccatgacttt tgctacttcc   2280
tttctaaaga ttttttctggc ctaaacattc ttgaatcgac atcaagttgg tcttcaccat   2340
catcgcctac aagttggtct tcaccatcat ctcctacaag tagatcttcg ctattatcat   2400
tccttcatgg ccaattgaac cttatttgaa tcccacttaa gtgtcgtaag cagaatgtac   2460
attatacatt catttgcaag atatgcttct gctattgagc cctctggagg agctctattg   2520
cacacatata tcttaaggta accaagaagc taaataaaaa aattgaaaga atgataaca    2580
taaattaatc atcaaaaaat atcataacac ataatgaacc aaattttaac tataacacat   2640
ccaaaattat acctctcaat aggatacatt catctatgat gaactggatc agtcatctta   2700
gcctcgctcg ctagatgaac cactaagtga accataactg tgaaaaaaga tggtggaaaa   2760
atcttcctat ttgacaaaag gtaagagcag ctcaagattg aagccgctca agattatcca   2820
catccaaaac cttgctataa agttctatga aaaaattgca tagatcaata acagctaaag   2880
aaacatggtc aggaaaagac ccaggggtag caattggaag gatttcttca atcaggacat   2940
gacagtcata cgactaaggg tgagcaagct tgtgttgtct caactacaca cacctctaaa   3000
tgttggatga acactcttct ggaaatttca attccttaat cacattgcaa aaatcatcct   3060
tttcttttgc attcatttga ggcataaact tcaaataagt attgttgggt ataaatacc    3120
ccccggctga agtctgtaaa agaccgaccc ttccaggact ctttcggctt ccgaccttgt   3180
gtgtggcatc actccaaacc cccatgaccg tccggacttc tccgatagag aacttctgca   3240
```

```
ttcgtctacc gagccgcccc aaaatgctct ctgggcctca ccaccagccg accttctaca    3300
gtgatcaact attctccgaa ctccttccga actctgccaa tatccaagct tcttcgacaa    3360
cgagatttct acagtaatca gactccatcc aagtttctac gacggtcgac cgccttcagg    3420
attccaactg ggctcctgtg agagccaaac ttctactacg acagtctac tccgaactca    3480 tacagtgagc ggtctactct ggatatccac tataagcaaa ctccattcga gcctctgctg    3540
taaacaaatt tcttccaaac tttcgttaca ggtagacttc gatcgagctt cttcgtagcc    3600
ggatcccata cgagcttcta cgatggggca ggatccaccg gccaggtcgt tactccgagc    3660
tcccacgaca accgatcttc gatcgagctc aacaataag tggcttcctt tcggcctccc    3720
acaagaacca gactccgtcc gagcttccac agtggatgga ttctggatga gctttcgcaa    3780
tggacgagct ctagcagctg gatttctaca atgactgatc acctccgacg tctgtcgaac    3840
ctccccagcg ccatccgaag tccatcacca gctgacctcc tgccagatcc ttcatgaaat    3900
caaagttctc caatggatca tcttcagatg agcttccaca tcaggtaaat ctcagacgga    3960
ctcctctagc aatcgaactt ctgttgggct tcaccaacga aaagtctcca tccgagcttc    4020
tacaacagat gactcccacc tgtggtatca gcgcctaagg t                        4061
```

<210> SEQ ID NO 61
<211> LENGTH: 4061
<212> TYPE: DNA
<213> ORGANISM: Artificial Sequence
<220> FEATURE:
<223> OTHER INFORMATION: synthetic

<400> SEQUENCE: 61

```
attttaaaat ttttaatagg ataaaaaatt ttagttagct ttgtgatagg cctagcgaat      60
ccacgagcta ccattctttg cttttggaca aattgcagat gcacgaagcc aatcatgata    120
tagttagcaa aactccttca ataggacagg aatgacaaac tggctggcca aagcctcagt    180
cggtgctttc aaagtgtatc gtcacctaac aataaagtag atattagaat caccacaagg    240
taaaaaattt ttaacgataa aattatttgt gatagataaa attttattta taaataataa    300
tgtcaatgat ggtaaaaaat tttcatcgat aataaaaaaa tatttacgat gaataaattt    360
tttcattata aataaaagta attaacgacg aaaatattgc ttacgtcgta acaaacagaa    420
tatttgcgat gaaattttta atcataaata agaaaatatt ttttaaataa aaatatagag    480
atattaccga tgaaattatt tttgttagaa atattaaaag ttttttcgat gaaatcaggt    540
tttgcatcat caataacatt atttacgata aatttttttt gtcactaata aatcaaaaaa    600
aattaaaaat tagatatttt caattatttg tgatgtaaat tttagtcgta ataatttga    660 ctatttgaaa actgagacat acctttaaaa aaaataaata aataaaaatt gatccagctc    720
gagatgatga tatatattta atatattaat tatatctatc tatataacaa taataaaatg    780
atatacaggt attagggta gcattcttta ttgacacata aagattataa gatgatccct    840
aaagtcttct ttaatttttt ttttatttat tttttgtttt tctttaattt tttctcttct    900
tatttttgct gccatctgct gcctctgttt tctctgctcc tgctgcctcc ttttatagag    960
cacagcttct tcgaattata agcatctatg gactttcaat tcccactatc ttttatttg    1020 attgggattt taaaacttta tccgcatccc agcatcttgt ttcacgcgag atcctagcgt   1080
ccacatgtgt tttgaattcc ttatgggcca cagaccattt aaaccaccaa agaccacttt   1140 actatttga tttgaatccc atggaagccg gctgcctctg gtctcattca cccttccagt   1200
```

```
gcttcacatg ggtcccatta atttgaattc ctatgagcca catccaagct tttgaatcca    1260
agccttcctt attttttaaa tcaattaaaa ctttgcttta aatgccttgt agaccctcct    1320
atttgcatgc tacgtgagaa cattgttaag ctcctcttgg cccacttaag aacttctatg    1380
ggctacatgc ttttggctag cttttaaaatg gttttgggcc taactttgga tcaccattcg    1440
aagtccattt tgaattcaat ttatttttat ttttttttt aaccttacaa atcgagctct    1500
tttattggtg atcattttc ctataaaaca aaaacaaaaa gcatcaagtc ttaagaaata    1560
aaagttaatt aatatatatt ttgatacttt tattgggata tttaatgtac ttatcactag    1620
atatgaaatc caatgggtca cacactttga aatttgatct tagtctaatc taactaggat    1680
ttattataaa tcttatgggt taaatttaca tgctagcaca tgaattaact caagttttca    1740
attggattta gttctaaggt gtttgagcta accctatcct gataccttaa acctaattag    1800
attagatttg aacctatggt tttcttgatg ccttatgctt attacatgaa agagtttcat    1860
gtgacttaaa ttcctccatg ccaccacatc ttcatccatg ccaaattaat atggaacgcc    1920
ccatttaatt gtgcatttaa gaaggaatag tccttcttaa acactcctct taatttccca    1980
cactttcctt tgttctacac accatcaaat ggcttttgga aatatgcggg cgcagaagta    2040
gaggtgtcct atatgaaggc tcttccacat tataagttat cacatggtga attaaatcat    2100
tgtgtgagaa aatcatgcgc caagagttgg caccccttgg gagttttagg cactccttat    2160
cctataaata agggcaccc catatggata aatacaaggg aattcaagtt taggcatgag    2220
attgagagga gaaaagaca caaaaatctg agaaaaagat aagaaaaaaa aagagagaaa    2280
aatagaaaga aagacgaga gaaatgaaa ggcaagggtt gctaatccta gggttcaatt    2340
tttcaatagt tggatttctg aatcaatttg gggtggtgag atttttgag aaaaagtttc    2400 tgatgtggcc ctagtagaag attgaaggca ttcagatgat ggtgcaatcc gtttttgaaa    2460
aagaaaagtg agtagtatac ttatgaagaa agctgcaaca ctacatcaaa ttggaaagga    2520
ccttgatcaa acccatatgg atcaccgttg caggatatct actttggtat cttgtgaagg    2580 ttatttttt tatcagatca tcatcttcaa aaaggtataa ttttctacct aatatgcatg    2640
cttgatttgt ttgattaaaa tctataaagt gttcataagg tttgtgttct gattgtattg    2700
ttttaagtat taaaacttac tttaaaaata taaaaaaatt tgaaaactat cttctactgt    2760
gcaactaaaa tccaacagaa taaccctaat atgagattga gcgatctccg ccaatgttct    2820
cgatcttctt ttcttgaatg aagccttttc aagcctctct tcttctctct ctctccctat    2880
cttcttttgt ggcccacggc ctcctcttct ttttatgttt tgtgtttctc atgtcacatc    2940
cataaactcc cttttataga taaaaaatta gagtccattt tggactcctt ttccatgcat    3000
aagaaggctt cccacgccat tggttctgtg cacacgactt tttccatgct acaaaagttt    3060
ttcatgtctc acgtagtttc catgcgccat aaaattttgc atacttctcc aagactttt    3120 atgctcgacc cttttggtt ttcatttaaa tcagtgggtc ccatatgacg agggatcaca    3180
ccaacatcat atgctctcct caccatacca aatggtatcc ccaactataa gacaaaacat    3240
tcatcaaatt gctaacaggg ttgaggatca gcattcacta tagaaatttt gtttttcaat    3300 ctgtaaccc tcccaccatc ctggcctctt ggatatcgga cccatcaagt gggtcccgcg    3360
agcccgcacg gcactgtcag tccccaaact caattttttt tttaggaaaa atgttacctg    3420
cagtagaaga aagagacctc caaaaaaatt atgaaaaaaa agccttaaaa taaaaatgaa    3480
aaggatgaag attaaaaggg gtgcaacagg aggagttccc aggggggtcat ccatccctgt    3540 acgactctcg cccaagcacg ctcgactgtg gagttctgat gggatccggt gcattagtgc    3600
```

```
tggtatgatc gcacccatca tgatctcttc gaaattcata gatataacat agcttccgtt   3660
gcacgccatc cataaccctc ccaccgtccg ggcctgcagg gtaccagact catcaagtgg   3720
gctcgcgagc ccgcacgtca ctataggtct ccagacttag ttttttttga tagagaacat   3780
taaccatggt agaagaaaga gatctccata aaaattatga aaaaaaatat tgaaataaaa   3840
ataaaaggct taaaaattat ggaaaaaaag gcttgaaata gaaataaaaa ggacgaagat   3900
taaaagggat gcaacatgag gtcctcccag gggttcatcc atcttagaac tactctcgcc   3960
caagcatgct taactacgaa gttctgatgg gatctgacgt attggtgctg gcatgatctc   4020
ctcgaaattc ttagatataa cgtagcgacc gtcgcacccc a                      4061

<210> SEQ ID NO 62
<211> LENGTH: 4061
<212> TYPE: DNA
<213> ORGANISM: Artificial Sequence
<220> FEATURE:
<223> OTHER INFORMATION: synthetic

<400> SEQUENCE: 62
gccggctgcc tctggtctca ttcacccttc cagtgcttca catgggtccc attaatttga     60
attcctatga gccacatcca agcttttgaa tccaagcctt ccttattttt taaatcaatt    120
aaaactttgc tttaaatgcc ttgtagaccc tcctatttgc atgctacgtg agaacattgt    180
taagctcctc ttggcccact taagaacttc tatgggctac atgcttttgg ctagctttaa    240
aatggttttg ggcctaactt tggatcacca ttcgaagtcc attttgaatt caatttattt    300 ttatttttt ttttaacctt acaaatcgag ctcttttatt ggtgatcatt tttcctataa    360
aacaaaaaca aaaagcatca agtcttaaga aataaaagtt aattaatata tattttgata    420
cttttattgg gatatttaat gtacttatca ctagatatga aatccaatgg gtcacacact    480
ttgaaatttg atcttagtct aatctaacta ggatttatta taaatcttat gggttaaatt    540
tacatgctag cacatgaatt aactcaagtt ttcaattgga tttagttcta aggtgtttga    600 gctaaccccta tcctgatacc ttaaacctaa ttagattaga tttgaaccta tggttttctt    660
gatgccttat gcttattaca tgaaagagtt tcatgtgact taaattcctc catgccacca    720
catcttcatc catgccaaat taatatggaa cgccccattt aattgtgcat ttaagaagga    780
atagtccttc ttaaacactc ctcttaattt cccacacttt cctttgttct acacaccatc    840
aaatggcttt tggaaatatg cgggcgcaga agtagaggtg tcctatatga aggctcttcc    900
acattataag ttatcacatg gtgaattaaa tcattgtgtg agaaaatcat gcgccaagag    960
ttggcacccc ttgggagttt taggcactcc ttatcctata ataagggc ccccatatg     1020 gataaataca agggaattca agtttaggca tgagattgag aggagaaaaa gacacaaaaa   1080
tctgagaaaa agataagaaa aaaaagaga gaaaataga agaaaagac gagagaaaat     1140 gaaaggcaag ggttgctaat cctagggttc aattttttcaa tagttggatt tctgaatcaa   1200
tttggggtgg tgagattttt tgagaaaaag tttctgatgt ggccctagta gaagattgaa   1260
ggcattcaga tgatggtgca atccgttttt gaaaagaaa agtgagtagt atacttatga   1320
agaaagctgc aacactacat caaattggaa aggaccttga tcaaacccat atggatcacc   1380
gttgcaggat atctactttg gtatcttgtg aaggttattt tttttatcag atcatcatct   1440
tcaaaaaggt ataattttct acctaatatg catgcttgat ttgtttgatt aaaatctata   1500
aagtgttcat aaggtttgtg ttctgattgt attgttttaa gtattaaaac ttactttaaa   1560
```

```
aatataaaaa aatttgaaaa ctatcttcta ctgtgcaact aaaatccaac agaataaccc    1620
taatatgaga ttgagcgatc tccgccaatg ttctcgatct tcttttcttg aatgaagcct    1680
tttcaagcct ctcttcttct ctctctctcc ctatcttctt ttgtggccca cggcctcctc    1740 ttcttttat gttttgtgtt tctcatgtca catccataaa ctccctttta tagataaaaa    1800
attagagtcc attttggact ccttttccat gcataagaag gcttcccacg ccattggttc    1860
tgtgcacacg acttttttcca tgctacaaaa gttttttcatg tctcacgtag tttccatgcg    1920
ccataaaatt ttgcatactt ctccaagact ttttatgctc gaccttttt ggttttcatt    1980 taaatcagtg ggtcccatat gacgagggat cacaccaaca tcatatgctc tcctcaccat    2040
accaaatggt atccccaact ataagacaaa acattcatca aattgctaac agggttgagg    2100
atcagcattc actatagaaa ttttgttttt caatctgtaa cccctcccac catcctggcc    2160
tcttggatat cggacccatc aagtgggtcc cgcgagcccg cacggcactg tcagtcccca    2220
aactcaattt tttttttagg aaaaatgtta cctgcagtag aagaaagaga cctccaaaaa    2280
aattatgaaa aaaaagcctt aaaataaaaa tgaaaaggat gaagattaaa aggggtgcaa    2340
caggaggagt tcccaggggg tcatccatcc ctgtacgact ctcgcccaag cacgctcgac    2400
tgtggagttc tgatgggatc cggtgcatta gtgctggtat gatcgcaccc atcatgatct    2460
cttcgaaatt catagatata acatagcttc cgttgcacgc catccataac cctcccaccg    2520
tccgggcctg cagggtacca gactcatcaa gtgggctcgc gagcccgcac gtcactatag    2580
gtctccagac ttagttttt ttgatagaga acattaacca tggtagaaga aagagatctc    2640
cataaaaatt atgaaaaaa atattgaaat aaaaataaaa ggcttaaaaa ttatggaaaa    2700
aaaggcttga aatagaaata aaaaggacga agattaaaag ggatgcaaca tgaggtcctc    2760
ccaggggttc atccatctta gaactactct cgcccaagca tgcttaacta cgaagttctg    2820
atgggatctg acgtattggt gctggcatga tctcctcgaa attcttagat ataacgtagc    2880
gaccgtcgca ccccatcaat aaccctccca cgtccaggcc tgtagggcac cggacctttc    2940
atgtgcatcc ccataaaaat tgtggaaaaa agtattgaat taaaaataaa atagacaaag    3000
attaaaaaaa atgcaacacg cccatcccag tacaactctc acccaagctc gttcgactgc    3060
ggagttttga tgggatccgg tgcattagtg ctggtatgat cacacccatc acgatctctt    3120
cgaaattcat gtatataacg tagcttcaat tgcacgccat ctgtaaccct cccaccattc    3180
gggcctgtag ggtatcggac ccttcatgcg agctcgtacg gcactgtagg tctccagacc    3240
cagttttttt ttgagagaaa acgttaacct tggcagaaga aagagatctc tataaaaatt    3300
gtagaagaaa gtgtttgaat aaaaataaaa agcataaaaa ttacaaaaaa aatcttgaaa    3360
tagaaataaa aaggatgaag attaaaaggg atgcaacatg tggacctcgc tgggggttac    3420
ccttcctagt tctactctcg atcaagcatg cttaactacg gagttctgat gggatccaat    3480
gtattagtgc tggcatgatc gcacccatca tgatctctta gaattctta gatataacgt    3540 agcggccgtt gcatgccatc agtaaacctc ccacgtccag gcctgtaggg cactagacct    3600
atcaagtgga tccggtgagg ccgcacggca ctgcctgtct ccagactcaa tttatttttt    3660
taagaattgt ggaaagtgat ccccataaaa attatgaaaa aaagtgttga attaaaaata    3720
aaatagatga agattaaaaa agatgcaaca cgaggacttc ccaggggtag atataacgta    3780
gcggccgttg catgccatca gtaaacctcc cacgtccagg cctgtagggc actagaccta    3840
tcaagtggat cccgcgaggc cgcacggcac tgcctgtctc cagactcaat ttatttttt    3900 aagaattgtg gaaagtgatc cccataaaaa ttatggaaaa aagtgttgaa ttaaaaataa    3960
```

-continued

| | |
|---|---|
| aatagatgaa gattaaaaaa gatgcaacaa gaggacttcc caggggttca cccatcctaa | 4020 |
| tattactctc gtccaagcac gcttaactat agagttctga a | 4061 |

<210> SEQ ID NO 63
<211> LENGTH: 6704
<212> TYPE: DNA
<213> ORGANISM: Artificial Sequence
<220> FEATURE:
<223> OTHER INFORMATION: synthetic

<400> SEQUENCE: 63

| | |
|---|---|
| aaatctatta gtatctgaca aaagttaaat tagagtcgaa acactaaatg acaattaggg | 60 |
| atcaacttga tcaagtagat agagaatatt agaaagaga gaaattaaca agatagaaca | 120 |
| tgattaatta ggtgacatag cccgacaatc caattggtct aagcaagttg atttaatcaa | 180 |
| atcacggttg aactaatata tagatagctc aataaaaatc atacataatt gaatctaatg | 240 |
| atatttggat ctgaccaaga tggaatttga catgctgtcc gatgatcgtg aatcaagact | 300 |
| ctctttgcta attaagatca aattagaatc attgaaagag aatcttttac tggatcaaga | 360 |
| gagagaaata tataaagaga gtgaaatagt ctatagaaaa aaattttaga gagagaaatt | 420 |
| aagaagaaaa aataaatttt ttagagaaag aaagtgggta tacaagctca gagaagggag | 480 |
| agaggaaaga gagagaaatg ctctcttatt ttcttttttt tcttttttct tcttttcttt | 540 |
| tttttttcct attcttcttt cccttttctg cttaatggaa taggggacct cccattcccc | 600 |
| ttctatttct agagttgggg gctcaaaatt gatgatagct atcattgggg atgtaggcta | 660 |
| tggtgatgca gtagaggatc accgaccgat gatcgatggt gatgttgcaa tcaaaaaatc | 720 |
| aagaaagata gatggaaaat aaaggaaaat aaggagaaat agatctcaac ttgtttggat | 780 |
| gctaacccac tcactgacga ctccacttca actatggccg gagcttgcta tggaaaagaa | 840 |
| gccaaggcct tcaaggatga acaccaatgg tgaggaagat ggtcgaaaat agaagaatgg | 900 |
| ctggcttttc taatcgacaa ataggggtat cgcccttctt agcaaatatt cggcaataaa | 960 |
| tatctagaat ccaggatcct aggactatgg aagagggaga ggagggcaag tcaaggatg | 1020 |
| ccagattctt atctagcttc cgacaatgat ggggccctat tttcgataaa cacaattgag | 1080 |
| gatgttcgga aaagggtttt ttcgatgatg attctagtga ccaactatga gatttcaaag | 1140 |
| ggggtgaggg gggtttaaat aagatgggag ggaagtttga tcctccttaa atctgaacc | 1200 |
| tttttcgaca aagccaagag cgtgaaggag actccttcgt gaagtcaaag atggaataga | 1260 |
| ctcccttcgg gagtttggtt catcacccaa cttccctagc atgtgcggag tatgtgctag | 1320 |
| ccttttctct cttttttttt catttttttt catcctttaa gatccatgca gtttctaggt | 1380 |
| tgagggattg gggtatcaca ttctctctcc taaaaaaaaa ttattttcaa aattttttta | 1440 |
| cctatatttt caaaagttgg gattcatggt ccaaatctca tccttgaatt tttttgatat | 1500 |
| tctaattctc gaaaaaattt catcgttaaa tcatttcata agagaaaagt caatacctca | 1560 |
| agagttgatc tgaatcaaaa ttattatctc tagtaatcga atcaatatc ttaatttcaa | 1620 |
| ataagaatat ccagtttatt gtcaaaatta ttaactactc ttgacttaat tgatctatta | 1680 |
| cataatcgta aataaattct aacatactct tgaagtgtag aatataagat tgataaacaa | 1740 |
| tcctatatcc gttctaatag atataaaagc ataaacttta aatattttaa atccaagatt | 1800 |
| aagaatcaat gatccactta tcctagactc aagatattag aaattttttt ttgtacaata | 1860 |
| gatagaggat gtactggtga aaatcatgta gcgatatcca aaataatttt taattaaaaa | 1920 |

```
tattatcctt ttcattatca atgaatttta tctataagaa agatcaaatc atatgatcca    1980
tcttaaattt ttaactcaaa aaattaatat tgcaaactag ctcaaaataa ttttgatcac    2040
tacatttctg ctgtgcattc taatttaaac cgttcacatt ttttagattc atgaaataat    2100
tttgaccaaa gtattactcc atactatagt caaaaaagat taaaatatta gattctaatt    2160
aaagccaaag ataaactttt gattctcatc cttaattttg cctaaagtat aattattttg    2220
attaacccct aagcgcaata acacattcaa aaccaacaga taggtttact ataatccaaa    2280
tgaattaaat cttaattctt ttatcaattc atttagacaa tttcaaatca aaattctata    2340
agtaatatca ataaaaaaaa ttttgatgc tccaataagt tagaacttaa atcaaaatat    2400
ataagtaaaa ttgatttaat catctcttct aaagtttctt ctattaagat ctttaatatc    2460
tatcaaatac attccacaat aatcatgcaa acctttaaaa aattaaattc tcaatgcctt    2520
tactacattt taacaccaag ctcgataata gtgataaaga aacatctaga tcagctttat    2580
aatcaaaaat tttgacttac aattttacgt gtgtctcaaa atcttgaata aatataaata    2640
agatctttta tcttgatcca aaaatagtaa tcaaggattt cattagtaac ttcaacaaca    2700
atggtaaaaa aattttctat ccattgataa acccaaattt tgaattgaag tttcatgcat    2760
accatatagc ctttaataag atctattatt tggatctaaa gatagtaatt aaaattgtta    2820
atgattccac taagatgaat actttacaat ctcataatta atttcttcaa taaaaataga    2880
cttcttgata atgtctccaa ttgtatattt ttttttattt ctacaagaaa acttcataca    2940
ttttttacgt tccaatataa atcttaaaaa gttattccaa tcaaatatca taaaagatct    3000
tcttagtcca accttaaata acttttatga atgaatcttt atcttgccac taaataatga    3060
atttttaaaat caagagcaac atcacagcat tctgtcatgt caaatttgtg ttagatgtat    3120
gtcctagaaa tcaattagat tgacaatgta aattttttaa ggataataatt tatatatttt    3180
gattattaa taaaataaaa tttaaattaa tttttattca tatttttta tctatgaatc    3240
atctaaagaa ttaataagat gatgatacat attcttaaga gttcaaaatt tgaaatatat    3300
gtcattgatg attaatttct gaatactttt gaattcttaa gagtttagaa gatcttgacc    3360
caagtagtgt gaatagtgaa aaaaagtttt cacatacttc acatcaaaaa tttaagttga    3420
ataaattgta catatgacag gtattatagt ttgacgagta atctataacc tctatcttat    3480
caaaattctg atagaaagat tgtattgtat gataactgta cttagaggtt cacctttat    3540
tttactggat taccactaca tgttgctaga tgtcactggt ggattgtgag atctacgaag    3600
attatcttga tgatcgataa ttctcattga aaagattgaa actatttttaa tgatgttgtg    3660
atagagatca taatatatct tattatcaga cagaatagaa ttctatggga tcatacacaa    3720
taggagatta agactgatca aatagttgaa tgatgattaa gaatcattac ggagttcaga    3780
ttatcaatat aattgataat tagactaact tataattgtt acaagtagca aggacttaac    3840
tgctaaaggt taataggttc aaaaagaact tatgtataaa tgttgtgcat cttaatttga    3900
ttggatcaaa ttagttatgg ctgaattcaa gatgaatcaa ataggaattt ggttcaattg    3960
aatttgggtc aagctttagg cttaggtcac atatacccaa aatcatttgg atgcatcagg    4020
tgtgtgacac ctgaatcagg cctttctaaa ctattttgag taagtttgat caagtcaaaa    4080
ggatccacac cctaaggttt cttgaataaa accttaggca ccacattgag gacctatagg    4140
aaactttgac cctctctcat atggggtggc acactgaggt tttataaaaa ccttaggcac    4200
ccattttagc cataaaaaaa aagctccaag ggatggggca gtagccatga agaatccttg    4260
gctgtcagga ctctattcaa aagagttctc aaggtttttgg actcttatgg agccctagga    4320
```

```
tttgtttgcc tataaataga tggccacccc aaggctttag ataatgttag agacttgtga    4380
agctctcccc tttctcttgg ttgccggccc accctctctc ctctctcttc catgcccaa     4440
gacttctttc ttgtctccat catcttgctg aaatttagat ttcagcaaga aaagtcaagt    4500
agaagtcaaa gttctaatgt agctcacaag atgttgagaa cttcctccat ctggcaaagg    4560
ttctgcaaga gagctagcat cctgagaaac aaaaagattg ctgatcagcc ctcatctcca    4620
tatgatatt tgtagagatc aaatgcatgc atagctagaa gagaatctta tcacgatcat     4680
cactcgtgaa gatcatctac ctgtgcaaag gtatgagata agaaaaatat ttttttatc     4740
ataattcatg aatcctttgc ttatattata ctgagattct tggaatggat tttttctcta    4800
gtaaaactct agagatcaga tctcaaagtc ttcttcacat aaaggttttg aaagttcttt    4860
atatttccgc tgctttgatt caaaataaat tagatctatt ttgcctttca accttttctca   4920
tatttattga catataaagc tttaattaat gagattaatg aaaagcatgt gcgaaatact    4980
gagaaaatcc taacagtgat atcagagcta cttttgtaca taagaaaagg attcaagtta    5040
aataaaatat gtttgattta agtaaatgaa tcaatcaaaa tttatcctaa cataagtttg    5100
tcctggtata atggtcaaga ccattatgtt gaaaggttat cctaggacaa aaagtctaag    5160
taaaatctat tttatttaag taaatgaatc aattaaagtt tattctaata taagattgcc    5220
ttagcataat ggtgaagacc cttatgttga aaggttgtcc taggatggaa agtgattgat    5280
gagacaaata tatcatgaaa gtattttca cagatggaat aaaatatata tattttgttt      5340
gtgaaaatga gatttcatga atgtgtttgt cattcaatat gtgtggtgat catcttgaat    5400
tgccacaaat ccttttttgga ttagggttgt atcatgactc acaaatcctg atggtttgca   5460
aaattttgca ttctgtagtg atagaaacca aagttaatc caattttgga ataagattga      5520
tcaattggta tctaaggcaa gtattttata atggtggtta cttaattagt tataaaagta    5580
cgaagagtct cctaccaatc ttacacttat ctagccaatt tggttgattg aattctgaat    5640
ttgggttgct taagtgttaa gttcactaca aatatattgc aaccatgatt ccgacttagt    5700
caaccaagcc tagatctctt gaatagattc atgttaatta tggatttaca taggatataa    5760
ataaataatt aaaacttgaa gagatctaaa tgaaaccttc tcgtacatat taaatcgaat    5820
gatcttccat cattgtagat atacggatac tctactgatg ttgatgattt tcgactagat    5880
atagtacttt ggttgcatcg aaaaagtaca accactttat aacatgagat gttgcagggt    5940
agagatgggg ttgggcccaa taattgttag gtgaggatcc aaatgatggc tgcacttgcg    6000
tgtgaatggc gagtctgact taattaagaa atagagctaa taactattag atgaggcttc    6060
aggacttaga gacttatgac cactacaact tacttgagaa gcaatggata aagagtcgtc    6120
tatttatcaa ctgacgcatc accaataact atcagatgga gtgatgtata attagtggga    6180
ctatagtatc cacttgaaat cttaatcgta aaaattttg tttctccacc tgaagagcat      6240
gggagattcg aaaaaatagt gggggtagtt tattttaaa ataaagctcc taaaataaac      6300
taaaataagt aaaatacaaa gtctaactag aatcttcttc tctctgtaga aaatatctgc    6360
ttccaacctc tatttcatat ccttaagact aattgtttga ctagacccag ttataaagat    6420
tgactctaaa acttaaagat agtccttgagt tttgaaaaga tgagctatgt cctggatcaa    6480
gatatcctct ctctaccagc ttgtcccacc cctaatcaag gggcatccta tgaaaagtgg    6540
ttaaacgatg ataacaaggc ttggtgctgt gtgctgacat ctatgtccat tgaactccaa    6600
tgccagcata agggtacaaa ctgtccaagg tatattgact catctacaag agttatatag    6660
```

-continued

```
tgagtagagc catgtatctc actaggaagt atttaagaga ctct              6704
```

<210> SEQ ID NO 64
<211> LENGTH: 4741
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (3017)..(3951)
<223> OTHER INFORMATION: n is a, c, g, or t

<400> SEQUENCE: 64

```
cagattatca atataattga taattggact aacttgtaat tattataagt agcaaagatt    60
taattgctaa aggttagcag attcaaggag gacttatgtg taaataatgt acatcttaat   120
ttgattggat caacttagtt atggctaaat ttaagatgaa tcaaacaggg atttagttta   180
atcgaatttg ggtcaagctt tgggcttagg tcacatgcac tcaaagggt ttggatacat    240
caagtgtgtg acacccaaac caagcctccc taaactattt tgagttggtt ttgaccaagt   300
caaaagggtc cacaccctag ggtttcttga ataaaaccct aggtgccaca ttgaggacca   360
attaggaaac tttgacattc tttcacacgg agcagcacac tagggtttca tgaaaaccct   420
aggcacccat tttagccata aaaggaaagc tccaagggat gggatggtgc catgaagaat   480
ccctggccat tgggactcca ttcaaaagtt ctctaggttt tgggctctta tagagcccta   540
gggtttgttt gcctataaat aggtcgctac cccaaggctt tagataatgc tagaggcttg   600
tgaagctctc tcctttctct tgtttgccat cccaccttct ctcctctctc ctccatgcct   660
caagacttct ttcttctctc catcatcttg ttgaaattta gatttcaatg agaaggatca   720
agtagagtca gagttctact gcagttctca aggtgttgag aactttcttc atcaggcaaa   780
gattctgcaa aggagttagc acctcaaaga accagaaaag ttgctaatct gccctcatct   840
ccatgtggat acttatagag gccaagcatg acgagaagag ccttatcacg atcatcactc   900
gtggagatca tctacccgcg caaaggtatg agataagaaa aaaatatttt tcttatcatg   960
attcatgaat cctttgctta tgttacattg agactcttgg attagatttt ttctctaata  1020
aaatttcaaa gattagatct cgaagtcttc ttcacctaaa ggtattgaaa gttctttata  1080
ttttcgctac tttgattcaa aatagattag atttgttttg cctttcaatt tttctcatat  1140
ttattgagat atgaagcttt aattaatgag attaataaaa agcatatgtg aaatactgag  1200
aacatcctaa caatttgagc ttacaattca cttaaacaac taatgatcaa attaataatc  1260
acaatgcaca ataaaaattc atgataaatc ttttttgttgt tacttttagat caaaatccaa  1320
ctaatcataa catgatccac ggattgccta tcatatatca aaccctctga attattaatc  1380
ttaaacgatc ttttcattca tgatcataag atttagttaa aaatcatgaa gacaacttat  1440
attgtaatca tcatagatct gtatcttaac atccttagtg tttacctacc tatactcatc  1500
ctatgtttga ttctatatat cataatttat tcactaaatac tttgatatca tataaattat  1560
cgcatcccca atctaagatc atattggtac tttaatatttt cattagtggg ggttatgcat  1620
tagtactttg atacccttatc agttgaatgg ttaaacactg gtactttgat atcctatcag  1680
tggaggttat acgctggtac tttaatatcc tatcagtaag atggttaaat actgatactt  1740
tgataacctc ccagtgggtg ttgtatgcta gtacttttatt atcctaccaa tggggcagtt  1800
aaatgctact actttgatac gctaccaatg ggatagttaa acgctagtaa tctaatctta  1860
gcttgacata aagtaacgtc gactcgagtt tagggtcgac tcgagagaat gttagggtta  1920
```

```
gcttgatatg aaagagggtc gctcgtcaat attttggagt caactcttgt ttatggacga    1980
tctagaaagt gtcagagtga gctcgagtac tgcatatttc tgatacattg tctatgctag    2040
aatgtgctag aactgattat cttctttatc aaagttgatt tttgagtaac ttgatgatca    2100
atttttctag gctagacttg ctttgtcaaa atgagcactt gttagtttag agaatcttca    2160
cctacacatg atctcaagca ttcattagta ccaaaaatac ttaagtattt tgatatcatc    2220
aaaatcaatt cttgggttaa cacaatactt ttcaaataat aagcatacag atataatcct    2280
ataacaattt aaattttgtt catatatcaa tttctttaaa aatattatat tcatcttgat    2340
agctatgaac taaatcaaaa tacatactag tatacaactt ttactgggag agtattagat    2400
taccagcatt taaccatccc actggcaagg tatcaaatta ccaatacaca acccctattt    2460
ataaagtatc aaagtaccag tgttcaactg cctcactggc aggatatcat agtactagta    2520
tttaactacc acattgacag gatatggaat tatcagtatt taaccatcat tagtagaatt    2580
ttgatgcata gtcaggctgc gagtcaaaat ctatctcaaa tcaaaatatt gatcacatgt    2640
ctaattctgt atcataattc attcccttat gctctaatat tatattaatt gtcatacttc    2700
tagctcgaga tcatgagcca aggattgcag taactaccgc atacttatag agaactcttt    2760
ctataagcat acaagatatt ctaaatatac tatcaatata tcatagagaa attaatttaa    2820
ataactaaaa gttaatattc aattaataaa ttcaactggc aaatgtattt aaaaatttta    2880
catcaaataa atcttgatta ataaatatta attaataaca atagatttaa atcgaaacaa    2940
ggttgatatt gttagaattt gatgcctcaa gattcagccc acattgagtc cacagtgagg    3000
ttcgcgacga aaaatgnnnn nnnnnnnnnn nnnnnnnnnn nnnnnnnnnn nnnnnnnnnn    3060
nnnnnnnnnn nnnnnnnnnn nnnnnnnnnn nnnnnnnnnn nnnnnnnnnn nnnnnnnnnn    3120
nnnnnnnnnn nnnnnnnnnn nnnnnnnnnn nnnnnnnnnn nnnnnnnnnn nnnnnnnnnn    3180
nnnnnnnnnn nnnnnnnnnn nnnnnnnnnn nnnnnnnnnn nnnnnnnnnn nnnnnnnnnn    3240
nnnnnnnnnn nnnnnnnnnn nnnnnnnnnn nnnnnnnnnn nnnnnnnnnn nnnnnnnnnn    3300
nnnnnnnnnn nnnnnnnnnn nnnnnnnnnn nnnnnnnnnn nnnnnnnnnn nnnnnnnnnn    3360
nnnnnnnnnn nnnnnnnnnn nnnnnnnnnn nnnnnnnnnn nnnnnnnnnn nnnnnnnnnn    3420
nnnnnnnnnn nnnnnnnnnn nnnnnnnnnn nnnnnnnnnn nnnnnnnnnn nnnnnnnnnn    3480
nnnnnnnnnn nnnnnnnnnn nnnnnnnnnn nnnnnnnnnn nnnnnnnnnn nnnnnnnnnn    3540
nnnnnnnnnn nnnnnnnnnn nnnnnnnnnn nnnnnnnnnn nnnnnnnnnn nnnnnnnnnn    3600
nnnnnnnnnn nnnnnnnnnn nnnnnnnnnn nnnnnnnnnn nnnnnnnnnn nnnnnnnnnn    3660
nnnnnnnnnn nnnnnnnnnn nnnnnnnnnn nnnnnnnnnn nnnnnnnnnn nnnnnnnnnn    3720
nnnnnnnnnn nnnnnnnnnn nnnnnnnnnn nnnnnnnnnn nnnnnnnnnn nnnnnnnnnn    3780
nnnnnnnnnn nnnnnnnnnn nnnnnnnnnn nnnnnnnnnn nnnnnnnnnn nnnnnnnnnn    3840
nnnnnnnnnn nnnnnnnnnn nnnnnnnnnn nnnnnnnnnn nnnnnnnnnn nnnnnnnnnn    3900
nnnnnnnnnn nnnnnnnnnn nnnnnnnnnn nnnnnnnnnn nnnnnnnnnn nagatattac    3960
taaattttgc ttctaatctc actcttaaat agtacttacc tttgaaacta ggcatttgaa    4020
tctgaaaaag aaagaggaga ttatgagctt gatagttcag taaatcatga ataaattagc    4080
taaataaatc tatgaataat agtatattaa aaataaatat gtaagataca ataattcaaa    4140
aatgaattca tatatataat actttccaaa taataagtat gtggctgcaa tcctttcgta    4200
attcaaattt tgttcattaa ttatttttt caaaacatca catggatagt catgaactaa     4260
```

```
atcaaagtac cagtgcataa cccctattga taaagaatca aataacaagt gtttgactgc    4320
ctcattatca ggatatcaaa ttattaatgc ataacctcca ctgctagggt atcaaagtag    4380
caacctcaat cacctcactg aagggcatc tagtttcagt atttaactac tccactggca    4440
aggtgttaaa ttatcaatat ttaacctcca ctgataggat tttgatatat agtcagactg    4500
cgagccaaaa ttcatttcaa accaaaatat ttttctcaaa gacatatttt atgtttcaca    4560
ttgaaaaatt cacaaaaatt atgcgatatt gaaatcaatt ggataaaatc cacgtcaaat    4620
ttagtatatt caatcataaa tcatttacta ttctagaaaa ggtatattaa agtataatg     4680 catcaatttc ataaatcata aatatctcaa tataaaaaat attttattat ttattaataa    4740
a                                                                    4741

<210> SEQ ID NO 65
<211> LENGTH: 5462
<212> TYPE: DNA
<213> ORGANISM: Artificial Sequence
<220> FEATURE:
<223> OTHER INFORMATION: synthetic

<400> SEQUENCE: 65
agtatattca atcataaatc atttactatt ctagaaaagg tatattaaaa gtataatgca      60
tcaatttcat aaatcataaa tatctcaata taaaaatat tttattattt attaataaat     120
ctaggagaag tgaagcatta cttatcttgt aagtaaaact aaccaactga tcaaattaat    180
tctgagaatc tttctcaaaa ctcatcacca ctatatcaaa aacttgtgct tcttgctatg    240
taagagcata gacccttcct tcgatctggg gttccaagtt tctattttat tttgttcaac    300
tatcaaatta gactgacttt tcatttttt gtggatattc agctatttta tggccttct     360 aacaataacc aaagtatgta ccaatattcc aacaataatc atttattgca tgattttcac    420
cgcatcgaaa tatttgatat tatcaatcaa tccaaacttg ttattcactg acctcttatt    480 caaacccta gtatatttaa tattctacct ttgtgattca ttcaatcgat ttctttttt      540 tattttcttt cccttctctat atgctcttca ttaactttc tttcaattat caatgcttta    600
ttcaatacat ctgtataagt agttaactca tatagtacca tttatttct aatttctatc     660 ctcaattcca actcaaattt atctactcag tcacattcat cttcaaccaa tctcgaagca    720
aacttgacaa gctccataaa tttagcttca tattctacaa ctattatatt tctttatttc    780
agataaataa attttttattc tttctgaatc ctcatactct aagaaaaata ttttatcat    840 aaaatatctt tgaaatcac tcccaagcga gttgttctcc atcttgttca tatttaggtt     900
tcattctcta ttatcaatta aatgtctcat ctttcaacat gtatgatgca tataagattt    960
tttcatcatc atggtatctc ttaacaataa atgctttctc catctccata agctaatttt    1020
tagctcctat ttcatagttt tcttaaaagt caatggagac aacttcttaa attctatgat    1080
attactttat tgctcctatt gctcttatgt ccttgtggtg acaatattta ttgttgcact    1140
tgctgtagag gcagttactg ttactgcaat tgctattacg attccatcaa gccgactagt    1200
gtctgcatta tttggataat agttgatttt tgctacttta tttagatgtt ggtggcaaaa    1260
tcaatgactt cttttgctg agagatgcca ccaacctact aagtatcatc atcttattgg     1320
ttgatacctt tagcagcacc tcgagtggtt cttttatct gatatggaac catcttaatc     1380
ttgcatgaaa acaaacttc gcaaaatttt cttttaaaat ctaatatcta atattatact    1440
tttattaaaa tttaattatg attattttaa gaataaaaaa tttaaatttt gaatcctca     1500 caaggctggc caagagataa tgaccatcat cctagtcggt ttgacgtagg acatccaaag    1560
```

```
atcaactata attcaagcat catattgaga tgctaggata taatcgatgg tgaaatttaa    1620
tgatgctcga ctgatcaaga tgggggccgg cccgatggcc tgttcaacaa tcattgatca    1680 aaattttta accaaggtct atcaagatca ttaaaaagtc tttctaagat ctataaattg     1740
taataaagag acacaatcta gagagagaca cttttacat aaagaaagta gaaatttag      1800 ggagagaaat tagagagaaa ggggaaagag agaggaagct gagaggaaga aagaaaagag    1860
aaagactctc tctctttttc ttttctttct tttctttctt ttcttttct tttctttttt     1920 tcttccttt ctttctttct ttctttggct cattagaaaa ataggggacc tattgatccc     1980
cttgtttcct aaataggga ggaatctcat cttggtagct atggccggcg atgtgagcca     2040
aagtggcaaa atcatgaatc tcccaacttg cagccgacat tgactttgg cactggaaaa    2100 tcaaagaaat ttgacaaaaa atgggaaaaa attgaaacca aaatagggac caaaatccgg    2160
taatagctag ccaaaaatcc ttgatctttg ctcatggagg ataggaaaaa agattattca    2220
agagattaag ggaatcttat ctcattttt tgctgtgctt cggccatggt ggttgcagaa     2280
atcgtttgtg aaagctcgac aaactctgca atttcctcgg gcttgggcct cgatctttaa    2340
taggagaaga gagaagtcct cttttcttta aatagagtcg gagggaagga gtttgatttc    2400
ctccttatgg tggtttcaaa ctctgatcgg aagtccattg gaaagaaga ctcccattag     2460 ttttaaaatc taataagatt tattgattag aaaattgata aaaaatgatt attaaaaaag    2520
tagcataatt atttaaatca atgatgctta gattgttgga ggtaaatagt aataaaatca    2580
aaaaattaaa attcatggga ccaaaaaata atgaacaaga tttgaaagaa atgtctataa    2640
ataagaattt atgaaacagg ggaacattga tcaaggtgt gttaaatagt gtccttaaag     2700
tgttattgtc cctctcacgt agactttgtg tgttgggaga gaacatagta attctctcaa    2760
cctatgcaac ctaaatcttt tgaaagaaa tttaaaatta tagaaaaatt ggcaaactag    2820
aattttggtc attttctta ttagtaaaaa atatactaag ttatatgtct ttatttatac    2880
tagtgaggtc tatctttgca caattcagac caaatttata ttctagttaa aagaggtata    2940 gatttttaa aatagatata actagtggaa atagtcatag aaaagttaaa aatcaatgaa    3000
aggtagattt cacttctata ttggctttat ttgtggtcac tttatctaat tctttttttt    3060
gatggagcaa tataccctgt taaaatcttc tcgattttt tttcacttta agcaacctat    3120
ttcgatgcct aaacaatgga atttagttta accacttaat atgctacact tttaaaagga    3180
gcaccatatt gtagggcttg aaaagttact tgatttaaaa aaagagcatc ttaattggac    3240
atcatacaag taagttatga cctctgaaaa tttgatacat gatttatcat cttgatatgg    3300
taaatcttgt taagatttcc tcatggtgtc taaagtggcc ggttcatact gagtttggtg    3360
attcttctgg tcaatggtta attgctcgaa tattttaag atataactaa tctccaactc     3420
tgccgactcc ttagtagtat gagcacatgg aaagcttgac ctaattgatt tcttaaattg    3480
cttgaaatca gtacttagaa aatatgcaaa atggatgaaa tgtttattgc agcgagagct    3540
ttctgatctg tacgaccgag agcttactag tttttatga gctatacgtt ttgcacttaa     3600
gcctaattta aatagtgaaa tagttttgca acaattcaaa acaattaaaa tcaaagaca     3660 agctgctatg catgttcaac tgactcggct ttcaatcgca atatgtcaca taggctggcc    3720
tagaatgcag atgcgtgcgt ggtgagcatc ctaaaaacct acatatccaa taaattccca    3780
ctagttggtg aagtattaaa tgtaactcgt attaacttt taatgtagga ctaaagttta     3840
ttcgactaat taagaactaa atactttaat aattgaactt ttccaaccag aaatcagaaa    3900
```

```
atatttaagt aattaaatat tacataataa ctagatcaaa atatcatggt tcctctctcg    3960
ctcgagatca attgggatgt tggtttatct tggtcatcca tcgagatgac tctatcttag    4020
cctttcaaaa cggcgcggta ccacgggtct caccgcttcg ttacatcgaa tgccaccatc    4080
cctttttttt tttttttat ttatttatgc tttcttgctc ctagattggt gcggcctcat    4140
tacaactcca ctgctacttg atgcttccct ctagcatctc ctttgcagct ctctcacttc    4200
caccactctt cggcctaatg ttgggaaacg acgaaggggc cttacaaaaa tgtcatccat    4260
gatggcagtg gagaagaaaa catcgctggg gctttccttc gatatccttc gcagccaaag    4320
ctcttatagg gttatatggg agaacgctgc attatttggg tgatcttttt ggatggtgtt    4380
gttgactgat gctagttttg cttcatgaat tgaatattta cacaagatga gaatacaatc    4440
tagtacaatt ggtaccaatt acctgggttt gactcctgct cgcatctgat tgaagcttgg    4500
ttaatgtgca tctcaattaa ttcagaaaga tcatcggact tcatgtgaat tattttgact    4560
agcatgaata gggctaaata aggctgaaat atgtgttaaa ttttttaaaat tataacttga    4620
tcatatgatg tccaattgag atgttttcaa atcaaaaatt ttttttcgaga tttatcactt    4680
aatgttaaac tcttagaagg tcgaaacaga ctgaaagttt tcttttcaag atgtattttg    4740
accgagtata taacttgatg atcatatgat gcccaattga gatgttttca aatgaaaatt    4800
tttttttgaga tttatgactt aatgttaaac tcttaaaagg tcgaaacaga ctgaaagttt    4860
tcttttcaag atgtattttg accaaatata tctcataatc tataaagaat atatttcata    4920
atctatgaat aattagatag agcgacagaa gataatgcta atgtaaaaat cacgatctat    4980
tttttataaa atttaatatt tttatataat cacttttact atagtcatat ttattttaaa    5040
aaatttagtt atatttaaaa tatcaaaaaa atttgacttg aattatataa gaaaggatct    5100
tcctactatt atagatagaa gcttatatc atagttaca gtgtatggat catcaatgaa    5160
agaaagaggg atgtaaacct tacttttgaa attttttctat ttgtttctaa atttttttaaa    5220
ggatccaagt tgagaattga gagaattctt tcttttctgca aatcaaatca ttagtataat    5280
ccacatggag acgttgtaat agaaagtaga aactatattt tatgaataat agaaagggag    5340
ttgatttacg ccaagccttt tgtttgcttg attaattatt tatttttatg gtgttagctg    5400
gaccccatga atagcaacca tcgttgggtc agggtcgtgt atttgttttg gggtcttcat    5460
ta                                                                    5462
```

<210> SEQ ID NO 66
<211> LENGTH: 8953
<212> TYPE: DNA
<213> ORGANISM: Artificial Sequence
<220> FEATURE:
<223> OTHER INFORMATION: synthetic

<400> SEQUENCE: 66

```
caagtactcc agaatcaaaa ttgtgaaaga aaaataggat aaatctggtt aagctgtaat      60
ttatttactt actttctatc tatattaaaa ttattcagat tattttgcaa atttatggat     120
atgcttgaat cacgtatctg atactttctc ttcatctgga tggcagtacc atgtgatcac     180
cacgcagacg gatacctaca agaaaaaggc aaggctaaca tgctttctta ccatcattct     240
ttacggtctt tgatccggtt ttgcgtgtcc acttcttacg tagtcttttt caaacattcc     300
tatctaagac tgaaggtaat gatttgcaaa ggaatagctt tactgttttc ctctaagtag     360
atgaaatatt actcacgtag aaaggagcca tcataattgc agaagaata aaactgaatg     420
gaatatgagt agaattgtca aaatcttggt ttaagggttt taatagccag atgagaaagc     480
```

```
aacctacttt tcttgaacaa cttgtttgtg actgtcttgt tgctcccatc ttgcatctat    540
gattagcaaa atatatgata aatagatatt cagatttgat cgaaaagaag gaagattttc    600
tttaatccat ttaatttgaa tctcacaaaa aaaagtaga agatttggac acgatcgctg     660
ggggcagcac gctcttaata gaatggtgtc acgttgcaga tctcgaaaaa ttattcaatt   720
ttttttaaaa aaaagagtc attgaaatta gacgttgtat gaccatgtta tgatctctga    780
aagtttgact tctgactcaa cttcccaatg tagcagattt tactcctgaa ccatgtttaa   840
cctcctgact catagtggcc aaagtatcta catcgagttc actggtcttc ttggatcaca   900
ttcataagaa tacttcccat aattttgctc aacgttgttt ttctcatcaa ccaaaggtat   960
atgcttttta aaattgaaat gcccatgaat attatggcat tcttttatttt gacattttgg  1020
ttgatcctat attgtttgtt tggcattcaa cacttcttca tgggaacctt tgaaatgagg  1080
taggtgctag gattttttctt tttacctatc catatcatat ttccaatgtc ttcttttaca  1140
ttaggttctt tagtgacaat aggggaaacg acccaatata ataccttga aaatttgggc   1200
aatatctact aaaactaact tgaataaaat attaacataa aagggatttt agtaacataa  1260
aagcataact caaatcact caccttgtgt gccacgttct cattgcccctt attatttttg  1320
cattgtgaat tgtgtcccccc aataaagcaa cgtgaatggt ggaagagagt tgaatggctt  1380
tgttgagtaa ttgttttgag ttactatagc attgctctac taaaattgaa atcttgctgt  1440
gaggctatgt atgagaagca agttcatgct ttttgactgt tgggatggaa gtatgagcaa   1500
tctttttaat agaaaatgga cgaatcatga agttttttcct ttttattgaa aaagatgatc  1560
gaaaaatatg tgcaagatag aaaaacactg aaaagataaa atgagaagta aaagtggaag  1620
tctaggagaa gaaaatttaa gagaaatatc ttcaatgaga ggatgtgtgc accaacaaag   1680
ccaactttca ctaaagaatg taatgactca cctctacttt cttcgaataa ggggttccca   1740
gttgtggaaa gtatatagaa tcttctgaaa gactgagtaa atggagcaat tccttctaag  1800
aaatattatg gcatttctct cccacgaaat ttcaaagcaa agagcagcta gtagttgatc  1860
ctctaatctc ttaattgaag tttgaatttt ctcttgcctc tatttggccc aaaggtcatg  1920
aagatctacc ggccaacctc ttaagttgaa ttagatctta atagaagtcc aaatgcttct  1980
tgtagaagaa catctaataa ataaatgagt gatagattct aatccagaga caaagagcac  2040
acctcgaatt cacttgccat cctttttctag ctagaacttc tctagcatga aacttgttcc  2100
ttaaggcaag ccaaataaat actcacattt taggaatgac tgccttccaa ataattttat   2160
aatatgaca aattagacca ccattattga taaacttgca atgaacaatt ataaatgagt   2220
tttcaggttg gcacattagc aatataggat ggtttgatta ttaaaaggat gatatgaagg   2280
gtttcaaggt ggtttgcctc gttcaaatca aaggattttg aagattaata ttccaagata   2340
aggttctcca actccattag gaaagtgtct tcatgtcatc ttagagaagc agctcgtacc   2400
aaacttgaca gatgttttat ttatttagag tgacacagat acccctttggc aatactctcc  2460
atccttgtcc gaacaacttc taatcacacc tcacttatct tgcatctaac tcagaggcta   2520
caagttacac ctttcaacaa acctttttcgg tttgaaaatt tgtgatttca ttatttagag  2580
ttcgaagagc atatcaagta ttggtcggag ttggcaccca aagcaaacga aacagttact   2640
gacatggtcc aaaagctgag atttctaaga tcccaactta agcactgaat aaagccatta   2700
tgggaaatat catttttaacg aaagaggaat ttagagtaag aattgattct cttgataccg   2760
aagaagaact aatacagctt tcatcacttc aaaatgatga acagatgcat ctcaagtcag   2820
```

```
cactagacca tcttctaaaa taggaagatc tatggaagca acactcccaa atgcagtggc    2880
ttcaaaatgg ggattgcaat acgaagttta tccatgtttg ggcaagtaac aggaaaaaaa    2940
gaatactatc actgaactct agcaaggcga tcagaagatt atcgaatagc agcaaatcca    3000
atccacattc tacaactttt tttctaccct actaggctcg actgaggaat gactcatcca    3060
agctgattgg aagattcttt atccagaagg acctctggat cttgctgaca ttgagtatcc    3120
atttatggag aaagaaatcc atgatacagt gtatgacttg gctttggaaa agtcacccgg    3180
atgatatttt cccattctcc ttctataagc acttctagtg tatcatcaaa catgacctga    3240
tgaacctact gtaaaatcag ctaatgtaga ccatctgaac tacttgttca tcacccttat    3300
cccaaaaaaa aattggtgtg tattcagtta gagacttcag gccaataagc ctgattaatg    3360
gagtaataaa aaatatttca aaactctat cgaaaaggct cccacagaaa atgaatttgt    3420
taattttatc cacagagctt gctttcaaca gaggaagaaa tatctctgaa tattttgtaa    3480
tgactatgga aactatacac ttctgcaaag ctgaagtaca caaggatctc aattataaag    3540
tcgacttcga gaaagctttt gacaatgtgg attggagctt tctattgaaa ttgctatcca    3600
gcacggggct ttgattcgag gtggtgtcaa tggatagaat atctgattta tacagctaaa    3660
ttctcagtcc ttattaatgg tgataaaggt aaacttttta aattgaggaa agatctcagg    3720
caaggagatc ctctattcgc ctagctcttt ctcttagttg ttgatataga atgatcaagg    3780
gagcaagtag gttcaatctt tttgttggaa ttggatcata taatatcatg ggataacttc    3840
aaagctttta gttcactgat gacacactta tattttgcag atatgatcta aaatacatca    3900
aaactcttaa atttttactc tatagttatg agctactgat gggtctcaaa attaactttg    3960
aaaaattcca attttttggc ttgagaattg caaagatgtc agtacagcaa gttgcatcta    4020
tcctagaaag caaggtggct acatttttcca ttacttattt gggtctccca ctccatcatt    4080
ctaaactgag gaaaacttat tggaatccac tccttgagaa ggttcagaag aaattgatcg    4140
ggtagaaagg taaacttctt aacctctagg gtaggcttat actaactaat gcagtgctta    4200
cagggatccc actactctgg agggatacat tccttctccc tcaattcatt atcaaataaa    4260
ttgataaaat ccatcgatca ttcatttgga gaggaaacga ggagtataac taagggcact    4320
ctagaatatg ttggtcgaat atttgtcgat caaaaaaatt tggaggactg ggggttcctc    4380
aatctaaaaa ttttcaatac aattcttctt tgtaaatggt ggtggaagct ctactctaat    4440
gctggtgacc cgtggtgtag ttttattgcc actgtccacc caacttcaca ctagagatct    4500
aaaggtatac acaaatcaac ctcttcattt tggaatggtt tacagcacac atgaaatatt    4560
tctactccta atccactttc aagttagcaa ctagtattat tttggaaaga tagttggtta    4620
cataatcatc cactgaagga tcgatttcct cacctttaca caatagcatt gaagtgcaac    4680
aactcagtgg caaaggtatt aagcaatcta cttgataata gctcttttag tactcctctt    4740
cctcaaagat accaagaaga ttttcagagt ctataggaaa gcattgaaca aattacatta    4800
acggaacgac ctgatactat acaatggaaa tggtttagta gcaatatttt tttggcatga    4860
aggatctact attttctgca agatggagga gtttggcctc tactgagtaa tattatataa    4920
aaactcctaa taccaagaa agccaagtta tttgcttggc taagtgctca caacaaaatc    4980
ccaatgaaag ctaatcttct taatagagga ataattggaa ctgattactg tacactttgc    5040
gatgacttat cagaaactaa tgatcatcta atgctcatct atacttttc aaaagcaatt    5100 tggaatcaag tactttcaga cctgcaattg tcgaaacttt tatgcatgct taacacccta    5160
tgggatactt ggagactcat caatatgcaa cacgatagaa gacctaaact agctgctcta    5220
```

```
ttcgtaattg gtcaatggtg tctttggaag gaaagaaata aaagattatt cgacttctat    5280 acttttatc cacgatcgat tgctgaaact gtgtcacttt ttctttcttg ggcatcacac    5340
ctaacaacgg agcaactaaa gatgttagct cctgttcgag aagttctctt atctaagaat    5400
gaaaacacac aatctttagt gagaattaca gatgctaaca ggcgcagatg aatgttttat    5460
gagcattttt atagctgcag cttatatgtg atctatggtg caaggagtta attataacca    5520
tggatattag ttaggttgac tatcagaaat catctccaat acattctatg taaccactga    5580
tcaattccat gttcaactag ataggaacct gcctatatac aggtatgtcc ctgatgtaac    5640
tatagtatac tattattcat aaataaataa cgaaggtttt accttcttct cataaaaaaa    5700
aagtatcttc atgtcatcct atatgtcatg catctccttt gctacttctt ttatttactt    5760
cttaaacttg gttctaccat atattatcag ccccttttaa atttgctttt ggatattgca    5820
tattccactc ttcaatcacc tcatgccaag caaaacattt attcacactt gaaaaccaat    5880
ataagaatac caagaatttt atccatgaaa ttctagaaac tttggtttta ctcctttctc    5940
catcattcaa aaaggttcaa aatgatgata actctatata gcttatttat caaatttacg    6000
aggttggtgt tcaatgtttt tgtgaaaaaa atatcttgct atccacatag tttgaatcca    6060
tacttttgct atcttgagtt tcaaaaattt taatttgcta caatttgttg ctattagcat    6120
atgactactt ttaagaagat aagccaatat actattttcc taagaattta aaaaatcaaa    6180
aataaaaatt tttatttaag attttttaag ggttgttttc caaatgtgca atggggctta    6240
atcttggcat cattttctaa cttgtagaat tttgacccaa gtaacatttg tccaatcact    6300
tagaacttct ataacttcgt acaatcattt gttaatgttg ttcatctatt tatctatatt    6360
atctatctgg aatatagttg ctcttaatta tttttatata tcgcctatta tccaccctaa    6420
gctttcatgt tcatcctcat gttgttggag gtgcatgtct tattccaaac tatttaccat    6480
tgctgtagat tttaaaaaat ttgctagttt aggactttt aatcttttga tatcatgttg    6540
atgtaagcta accctctaag gctagtcata atacatttta aggatttatg ttatatgaga    6600
ccaaaatttt aacaaaatga agtgttggaa attggtagaa tggaagtgta agatgctta    6660 gagacataga actagccctg gccatgtaa atcttccaaa agaagaagaa ataataaaa    6720 ttaagatcat attcaatctc tacagaaaag ttggtctttg ttgtataata agccatctta    6780
acatatgatg gacaataaaa tatataaact tatgagtttt aatacttaga tggaagaaaa    6840
gggacagata tgtcacaccc catcctacta gcatgagtag gcacatgata cacggttgca    6900
tgccctgcag agtttgactc atgaggcatg caaggtattg aatagtagtc taggtaaaat    6960
taaaaaactt ggagcattct aaaaataaat caagttcatt ttataaaatc aatatttatt    7020
atggactcca tcaaatatta tgcgcataac attttatttg caaatagaag aagataagtc    7080
ctagatccta agtctcctac tcttagtctc ataattcatc caagctatcc accaaatatc    7140
taaaacgaaa aagaaaaacg atagtatgct aatagctttg taagtcacct tttatctcta    7200
attagatcaa gcatattaga tataaaacaa taattttcaa agtatatgat ttgcaattag    7260 gaataaaatat ttgataaata cagaataaat tttcataaag catatttact aacattattt    7320
ataaaatata taatgcttat atcaataaat taatttctaa atcaatatat ataaactatc    7380
cattctgtct tagccttaca actattgcta ccattccctg tagcatggtt aggaagagac    7440
tagctcttga atactcatgt catttatcaa catatgcgaa tgatcattcg actaatatag    7500
tcaaaaaaaa attactctga tttatataaa ttaaaaatta gtaaataata tatgctagta    7560
```

```
atcaccttac cagctaagct ctaaagaaaa ttagcttttg aatatacatc atgctattga    7620
ttattatatg tcagtgcttg tctcattttg tggcatgcaa gaagactaga tcctaaactt    7680
atatgcatag tcagattaaa gagcaaatgt tgcatctgat tatatgaaca tctattatga    7740
tgtagagttt gtatcatgta tatttaattt aaacacaaat ataattatac ataaataata    7800
ttcatatttt aaattttaaa tatttagata attattctag tgcaggtata aaaataagca    7860
atataaaatt ttaaatcgat ttatataaca tgcataataa aaaaaattaa ggatagaggt    7920
acttactgct caactcataa aacataagaa atctctttaa ctaactttag tgcaacctag    7980
atagaacata ttaatgatta agttttcatc taaaataaac atagatatca ttttaaaatc    8040
ttaggcattt aaatggtctc atgatttgtg aggctttctt cagattctac aattttgaaa    8100
ttttttcaaa ttataatttt tttaccttga ttgataacaa agccaataat acacctcaaa    8160
tccaaatgta ttcctaatag ttttcaataa atctaatatc aataaatcat aattaagata    8220
tcaatccatt ctatgaattt gaccataaat cctacttgtt tctctgacct tcactataaa    8280
ttaatcatca aactaaataa gtgagggat cataattctt ttacgacaat ccaagaattc    8340
aagtctagca tccacattag atggcttcct gtccagatat ttgcgcctct ccaaaattga    8400
gattatcaga ttaagaaaaa taaaataaga gagagggtta aaggacaatg ccttctaggt    8460
agtgatgtcc gacatcataa tttttgatcaa atctatgggg caaccaataa tattagggaa    8520
agaggattgg atttgagcaa gaatagcaaa gtcattgtca tcaatggcct gattcattga    8580
gttcaatgaa ggattggtgg ttgagtggtg gaggtggcat ctaggaagga gagagaaaga    8640 aaagataga gagaaagaga taagaaaaat agagagaagg tggcagttaa gatcccttt    8700 tgtgattaat atatagccgt aagatactca aagatctcac cttatcgacc tcaaacacta    8760
agggaggtgg aaggagggac tactacccat gaagctagaa aaagggatga tgatgattgg    8820
aggaaggaag aaggaaaaat agtagactcg atgatgataa gactaaaaga aaagggtttg    8880
acttagccac ttggtatata atgaggtttg gtatggagtc aatagcttga gtaatagcat    8940
ggaaagagag aag                                                      8953
```

<210> SEQ ID NO 67
<211> LENGTH: 6021
<212> TYPE: DNA
<213> ORGANISM: Artificial Sequence
<220> FEATURE:
<223> OTHER INFORMATION: synthetic

<400> SEQUENCE: 67

```
aaatatctaa aacgaaaaag aaaaacgata gtatgctaat agctttgtaa gtcaccttt      60 atctctaatt agatcaagca tattagatat aaaacaataa ttttcaaagt atatgatttg    120
caattaggaa taaatatttg ataaatacag aataaatttt cataaagcat atttactaac    180
attatttata aaatatataa tgcttatatc aataaattaa tttctaaatc aatatatata    240
aactatccat tctgtcttag ccttacaact attgctacca ttccctgtag catggttagg    300
aagagactag ctcttgaata ctcatgtcat ttatcaacat atgcgaatga tcattcgact    360
aatatagtca aaaaaaaatt actctgattt atataaatta aaaattagta ataataata    420 gctagtaatc accttaccag ctaagctcta agaaaatta gcttttgaat atacatcatg    480
ctattgatta ttatatgtca gtgcttgtct cattttgtgg catgcaagaa gactagatcc    540
taaacttata tgcatagtca gattaaagag caaatgttgc atctgattat atgaacatct    600
attatgatgt agagtttgta tcatgtatat ttaatttaaa cacaaatata attatacata    660
```

```
aataatattc atattttaaa ttttaaatat ttagataatt attctagtgc aggtataaaa      720
ataagcaata taaaatttta aatcgattta tataacatgc ataataaaaa aaattaagga      780
tagaggtact tactgctcaa ctcataaaac ataagaaatc tctttaacta actttagtgc      840
aacctagata gaacatatta atgattaagt tttcatctaa aataaacata gatatcattt      900
taaaatctta ggcatttaaa tggtctcatg atttgtgagg ctttcttcag attctacaat      960
tttgaaattt tttcaaatta taattttttt accttgattg ataacaaagc caataataca     1020
cctcaaatcc aaatgtattc ctaatagttt tcaataaatc taatatcaat aaatcataat     1080
taagatatca atccattcta tgaatttgac cataaatcct acttgtttct ctgaccttca     1140
ctataaatta atcatcaaac taaataagtg agggggatcat aattcttttta cgacaatcca    1200 agaattcaag tctagcatcc acattagatg gcttcctgtc cagatatttg cgcctctcca     1260
aaattgagat tatcagatta agaaaaataa aataagagag agggttaaag gacaatgcct     1320
tctaggtagt gatgtccgac atcataattt tgatcaaatc tatggggcaa ccaataatat     1380
tagggaaaga ggattggatt tgagcaagaa tagcaaagtc attgtcatca atggcctgat     1440
tcattgagtt caatgaagga ttggtggttg agtggtggag gtggcatcta ggaaggagag     1500
agaaagaaaa agatagagag aaagagataa gaaaaataga gagaaggtgg cagttaagat     1560 cccttttgt gattaatata tagccgtaag atactcaaag atctcacctt atcgacctca      1620
aacactaagg gaggtggaag gagggactac tacccatgaa gctagagaaa gggatgatga     1680
tgattggagg aaggaagaag gaaaaatagt agactcgatg atgataagac taaaagaaaa     1740
gggtttgact tagccacttg gtatataatg aggtttggta tggagtcaat agcttgagta     1800
atagcatgga aagagagaag gagctgaaga gagtactaag tcttattaga ataaagaaag     1860
atagaatctt agcgaaaaat agggcctcaa atctttcagg tagaggaaaa agagggatca     1920
acgaatgaaa gactaaggaa aaggtgtgga gtaggatata ctctcgatta gtctctcaat     1980
catggattct agtagggctt cgtcagctgc tcaatcatgg attctgatag ctcaaatggt     2040
ggtaagtaga aagagagaga tctaaagaga ttgatagtgg ccttaaaacc agcacggtca     2100
aggataggca tgccttagag agaggaaaag agagagagat taatgaaat aagcgagaaa      2160 aatatattct tagagaatag attggcgata agaagaggag gtggttgggg catgcttaaa     2220
gaaataaaga aaattgagta ggcggaaagt ggtgatgctt ggcgatgaga agatttgaga     2280
gagagagcaa aaaaatgtgg atgatggtca taggataggg aaaggaaaga acaaagaagg     2340
gggtgctaag ctaactcttt ctaccttcct cacaccctga agcaaaggat ttggccaagg     2400
atggacaaat gggcgagggc tttggtggat ccatgcctac cctttctccc tctcacgatg     2460
attctagtca agctatctat ctttgatagc ttgagccaag ccaattgact tgatccaatc     2520
tctctaaatc catacaaact taagagagtg tattgattca cttattctct tctaagttga     2580
taagaaacat aattaagtgg agctcattaa gtatttcagg tagttgctaa cttggcaaaa     2640
tggaagcaat aataaatctt aaaagactat agcttggtat aatctcaacc atccatgatt     2700
tagaaagatc ttcagactca atatagatta ctttggctac tacaggtaag agctaaaatag    2760 gatccaaaag taagatccat cacattagta agtcaaatta tatgtcaaat tttagtaggt     2820
atacttagtc ctacgatgcc taattaaaat gatcatcatt tgaaccttaa aatggactag     2880
tcaactaaaa ttttctttt tgaagaagat ttagaccata aaatatcttc taatctgtga      2940
agaattagat agagcgagga atataaaatt gatgtagaaa tcaagatcta tcatatatac     3000
```

```
aattttaata ttttttttcat aatttttaaa tatttatctt cttttttttat aggtctagtc    3060
ctatttaaac taggaagagg agtccaactt gacttatgca ataggggatg tccttctaga    3120
agataagaat aatttgatca gaattatata agagcaaacc tcattattat aaatagggc     3180
tatatacatc aatttatgag atagagaatc aatgaaacaa aagtagactt aagttttatt    3240
ttcataattc ttctatcttc tacttttttt ctaggagatt caagttgagt ggattgaaga    3300
aaatctttca tcttctcgat cggatcatat tggtattaga gcgttggtct tctatattta    3360
tggagagctt taatgtattg tttaaatacg tgaacaatac aaacaatcaa gagaagtgct    3420
atccatgctt caaatacatc gaaatataaa agcaaatatg gctactaatt cttttcaat    3480
ggacaatgag ataaaaggat gtcttacaca actcaaggag aagattgtgc aactcatgaa    3540
gattgtctcc agattgaaga taatttcaat acaagcacaa acaccagcaa ctcatgttgt    3600
gaaactgttt cctatgtttg gagatgaaga tcttctatct agtgaggaga ttgaattacc    3660
taaaagtatg aaaaatcttt cttcaatcat tgaaagttaa agcttgaatt gagatcccca    3720
tatataatgg aaccattgat gaaaaaaagc tagataattg gctaaactaa ttacaaacct    3780
attttattat ctatagatat tatggcatct agaagatagc ttttacttat ctcaagcttt    3840
ctagccatgc tcttatctga tgaaattcat atatgagaaa taataatatt tttaatatgg    3900
tgcagagcca attcaaaggt ttaatcaaga agtaattta tctaattggc cataaggaag    3960
atcggtggat caaatgataa tacttatgat agaaacataa tcaatccact taggactata    4020
ccaccaagtt ccacaaacag gcaatctgcc ttggaatctt tatcaacaat tatacaattt    4080
ttataaagta tgttgaaagt cttcatgaga gcatctaaaa aaagatgaaa ctcttttaagg   4140
ttgatgatat cagtaaagct aacatgaaag tcatagagat tgaggagaaa aatcaaatta    4200
gagaagataa ggaaggcaaa aagcatatca acataactca aaaaaaaaaa ttatgatcat    4260
tgaaatctttt gaaaatacat caaggagaag tattgaaagt ttcatcctga attggagcta    4320
aagtagaaga agcccaagga tgataatttt aagaaaaata aaaagtggtc ctcaattcta    4380
tagagattga ggagctatct gaacttgagt aagcaaactt caaattgagc ttgatggtga    4440
gaaaacctaa tacaacaatt aaaacggatc tagaggtaca tgacaactca cccacttaaa    4500
gattcaagtg aagcagagta tcattaaggc tattataaat ctttgaagct agaagaacct    4560
cattttccaa tatttggttc agaaatcgag gttgtagatc aagcctcatc catatcctta    4620
tcctcttagt tggattcaga aggatgtcaa gttaaaaatt atgagatagt gtaccttcaa    4680
gttagccatc actgagaggt ttatttgtga ggtaactttt gaaatagttt ctttggatat    4740
ttgtcaagtt atccttagaa atgtgtacct ttagaatcaa gatgcaattt tctatagacg    4800
atagagaaag tatcatctta taagggatga gaaaaagttc atgatcaaca cctcaagaac    4860
ataaggtaac tttgaccttg caactgttgc ccaagtgaag tgatttgtta atgtttgtga    4920
tgagtgcatg atgatggtat aaagaaccga tatcactcat gagaggtcaa ggccttgtcc    4980
tttggttcca tcaatcgatc aatagagatt gagattaagg aggagtcact atagtccttg    5040
tcgatgagga aggatgacaa caagcattcc taccatgaag tctagatttg agagcaaatg    5100
aaagtaatcc actgagacct gagagcaaaa aaaggcgaga ccaaaaatca tcttcaagta    5160
aagtcaaatg gttcaaccat gagatgggga agtaagtatt tcccaccttt caattctaac    5220
tttgtagaaa ctaaatccct taaacagggg agccctaatt taagaggatc ctcagattca    5280
ttgtggacta ctttggctat tacaataaga gctggatagg aatcgaaagc aaaattcacc    5340
acattaggaa gccaaattgt atggcaaact tcaagagacc ataacttgat cacatgaaat    5400
```

| | |
|---|---|
| ccaattaaga tgattttatt tttgaatttg aatatttttt tgagatctat aactttagat | 5460 |
| ctaaatcaag ctaaaatttt attgcttatg ccttcaaaat aggctagtca aatcaaaact | 5520 |
| tttcttttca aaaagactt tgactgaaag atatctttca atctatgaag aatcaagtag | 5580 |
| agtgatgaaa gataaagttg atataaaaat tgagatctat ctcttataaa attttagtaa | 5640 |
| ttttattttt tttaatattt atctttattt agagatctat tcctatttaa actagaaaga | 5700 |
| attgtccaac ctaacttgtt caatgatcaa catcctccta aaagataaaa agaagaatct | 5760 |
| gactcaaatt ataaaagggc ggacctttt ttttgatgaa agggaggaa aaaatccat | 5820 |
| caaaatttat taagaaaaaa agagtacaag aaaagaagga tatgaaagag taagagaagc | 5880 |
| cccacaacat ccatcaatat ttaaaattta aatttaaatc tcccccatca ttctatcaat | 5940 |
| atttgatatt caaattttaaa ttcttcgcag catcccacca catttgaaaa ttcaaatcct | 6000 |
| ttcatacaaa caaaataata t | 6021 |

<210> SEQ ID NO 68
<211> LENGTH: 5329
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (4258)..(4985)
<223> OTHER INFORMATION: n is a, c, g, or t

<400> SEQUENCE: 68

| | |
|---|---|
| atattttcgt agtctctaaa ggcttcttcc agattggcaa tatactgatc tgactcagta | 60 |
| tttttttacta atatatcatc aacataaact ttgatattaa tttcaatttg ttacttaaaa | 120 |
| atcttattaa tcaagtatta gtatgtagca cctacatttt taagatcaaa agacatcatt | 180 |
| ttataacaat gcaaatcttt ttcagtgatg aaggccatat tttcttcatc ctcaagtgcc | 240 |
| attttgatct gatataacca gaaaaagtat ccataaagct tagtaatttg tgtcttgaag | 300 |
| tagcatcaac aagctgatca ttttttgaga gagaaaaact atcttttagg caagctttat | 360 |
| tgagatcggt ataatcaaca tagatccttc attttttcatt agccttttta accatgacaa | 420 |
| catttacaat ccactttgga tattatgctt ctctgatgaa tttgtctttc aagagtttgt | 480 |
| cgacttcctc atctattatt ttttatcttt tcggggtgaa acttcttttc ttctgttgca | 540 |
| ttggtttatg ctttggatca acattcagct tatgtacaat aagatcagtt aaaatctcag | 600 |
| gcatattaga gactgactaa acaaagacat cggcattcat ccgaagaaaa gatattaatt | 660 |
| tctccctcag atcaggcttc aatagagatc caatttggac agttttttt ggatcatcac | 720 |
| acaaaagaac aataataagt ttctcgactg gttctcctcg attttgatg atatcaactt | 780 |
| tactttcttg atcaagtatt ttaattggta gagcttccac agaccttttc attttacag | 840 |
| ctatcagaaa atactactta gcaagtatct gatttcctca tatttctcca actccatact | 900 |
| tagtttggaa ttggattagt aaatgataag tgaagactat agccttaagg gcgttgagcc | 960 |
| taggtcggtc aagaatagca ttataagctg atggtatttt gacaataaaa aaagtgagtc | 1020 |
| ttacagttga ctggcatggt tctatccctg cagtgacgga caaagtgacc tctccttcca | 1080 |
| cagctacagg atttctagaa atccaatta cggggggtacc aacctattta gctaatttat | 1140 |
| catattcatt ctttggaatg tatcatagaa caatatatta gcagagcttt cattatcaat | 1200 |
| aagtattctt tttatatcat atttggctat tgccataaag atgacaacag catcattacg | 1260 |

```
aggagtttga actctaacat catcatcgaa aaatgaaatt atgtgatcca tgcactgatg    1320
ctttggaagg ctttcagtaa tctcagccac ctcctcagtt ccgtcgagat ctgagatcat    1380
attgatgact gcagcagtag acttgttgtg atcattctca ttgttgggct tctatcattg    1440
gtcagtagct tgacttgccc gatctcgaac atatttacta aagtaacatt agtggatcaa    1500
tacttcaatt ttatctttta attatcgatg ctcctcagta tcatggccat agtctcgatg    1560
gaaatgacag tattttctct tatctctctt tgctggaggg gctttcatag gattaggttg    1620
gcgaatatat cctaaatcct cgatttctat cagtatctga gctcgaggag tagatagtga    1680
ggtatagatg tcgaatcacc gaggtgggct tttgaacttc agattcttct gaggtcgttc    1740
agagttatcc tgttggtttt tatgatcttc ttcctagggc cacttttttc catctctttt    1800
tttcttcacc taacgaagta tgcatgctct ctttctttc agcttgagca tacttacaaa     1860
cctagatcaa tatttgttca taattgtttg ggtagttctt attaagagag aagatcaggc    1920
gattactctt gagtccttgc ttcaaagctg ccattgcaat ggactcattg aagttcttca    1980
ctttcagtat ggcggcatta aagcatgcca catattcttg aagagattca ccttcctact    2040
atttgatagt aaaagattg ctagtatttt tcaaatgaat ccatttatta tcaaaatacg     2100
tgatgaatat ttgctaactg tgtgaaagat gaaatagatc atgtctggag gtcagagaac    2160
tagattcttg cagatgtttt gagagtgatt ggaaaagtga tgcaaaatag ggcattagat    2220
accccttgta gtcttataat ggctctgaag ccttcaagat gatttaaggg attgatggag    2280
ccatcgaatg tttccaatgt aggtatcttg aatcgaggag gaactgattt accaagaatt    2340
ttttgagaaa aaagagatcg taagttgaaa tctcttctac cttgagaatg gcttccaatc    2400
tatatctcca tcattttctt ctcaagattt tgaatctttt gtccaagacc ctcctccata    2460
catggcttct tatgtggagc agatttcact tcccaagagt gatcagtatg gtcaagaaga    2520
tgatcatgat gaagatcttg aggagttggt tgctaagtgt gatgtgattg gactacttgg    2580
ggggctactt tttgctaccg ttctgtcgta tactacagca gtaagagctt ggacctgctg    2640
aaccaagaga ctaaactatt gtggatcaat aataattgaa ggttaggtat tctcctgaac    2700
atcttcagga gaagatgaag taggtaaagg atgatttggt gccttcttgt tcaccatttc    2760
tactaaaata ttttaagtgc ccttcctcta acactaatct attactgcaa ggcttcaaaa    2820
gacaggcaac gagatgggtc ttgaatcgaa ctagaatgtt tcttggttga atttggcgaa    2880
gtctgtaaca aatcttgcaa agaaaatctc gaaacctacg ggtaccttct ggttcaagat    2940
cctctgatgg ataagttagg taaagtcttg agaataggt gtgaaaatag aagaatagaa     3000
ggatgagaag agagattgtc ggtaaatgga gagatgactc ttatttcttt caatggggga    3060
gctgaaaata attcagcaga gtttccactc tatcaatcct gacttatttt gtggagggta    3120
ccttggcccc ttcatatata ggggatgaag aggcctggta aggttgttag actattagga    3180
gagtttgtta gatcgttaat ttattataat agaatgacca gctatataaa aatcatggag    3240
tatttaccca catggtgatt gactgtagta taactgaaag atagctaatg cttagctgga    3300
tgactgctgt tagataactg tctgcattct tacggtacat tgatatttta ccaatgtgac    3360
atagcttaaa tcggcaactg gctgaactaa atattatgta tccctttagt taacaatcat    3420
gtcggttaga gatcaatgta attcgcagca gatcgatcat aagctgagat gagtatcata    3480
ttttaagaac aacgctgggc gagttaggcc gatcaaatgt cagactgaaa aagcagatca    3540
ataaacctct gatgtgatct gaagaatat ttatgattta aataataatc tatcaccacg      3600
tatccagata atgaggtcat ataacatgta ccaacagtgc attttttccat ctagttaaga    3660
```

```
ggttggttag tggcatttgt cttcgatatg taatgttcac ataactaatg tgcttagtag    3720
cattcttttg taaggttaaa tcttcaatga tcttaagttc acataattgc ctttgtgccc    3780
tattagttta tagttgacct tttaattcaa gagacagtca ccttagcaat cgatgtctgc    3840
ttagattggg ccaattaggt actcacatta atatattgaa tcatgtttga atataaagga    3900
ttagattgat ttataagttt cctttattg tttacatact gatacttaga ttgacttact     3960
acattatttg atatgttatg ttctaatttt tggattaaaa ttgttgtttc tgatttctcc    4020
ttacatctaa tactttgtat aatttattat tttttagcat gattgagtgt agaggattag    4080 attgatttt aagtttattt tgattattta catgcccata cttaaattga cttactacat     4140
tattcaatat gttatgtttc aattattgag ttaaaattt tatttctgat ttctactgat     4200
gtccagtgtg tgtgtgtgta cgtatgtgtg tatatattta tttacatata tatgtatnnn    4260
nnnnnnnnnn nnnnnnnnnn nnnnnnnnnn nnnnnnnnnn nnnnnnnnnn nnnnnnnnnn    4320
nnnnnnnnnn nnnnnnnnnn nnnnnnnnnn nnnnnnnnnn nnnnnnnnnn nnnnnnnnnn    4380
nnnnnnnnnn nnnnnnnnnn nnnnnnnnnn nnnnnnnnnn nnnnnnnnnn nnnnnnnnnn    4440
nnnnnnnnnn nnnnnnnnnn nnnnnnnnnn nnnnnnnnnn nnnnnnnnnn nnnnnnnnnn    4500
nnnnnnnnnn nnnnnnnnnn nnnnnnnnnn nnnnnnnnnn nnnnnnnnnn nnnnnnnnnn    4560
nnnnnnnnnn nnnnnnnnnn nnnnnnnnnn nnnnnnnnnn nnnnnnnnnn nnnnnnnnnn    4620
nnnnnnnnnn nnnnnnnnnn nnnnnnnnnn nnnnnnnnnn nnnnnnnnnn nnnnnnnnnn    4680
nnnnnnnnnn nnnnnnnnnn nnnnnnnnnn nnnnnnnnnn nnnnnnnnnn nnnnnnnnnn    4740
nnnnnnnnnn nnnnnnnnnn nnnnnnnnnn nnnnnnnnnn nnnnnnnnnn nnnnnnnnnn    4800
nnnnnnnnnn nnnnnnnnnn nnnnnnnnnn nnnnnnnnnn nnnnnnnnnn nnnnnnnnnn    4860
nnnnnnnnnn nnnnnnnnnn nnnnnnnnnn nnnnnnnnnn nnnnnnnnnn nnnnnnnnnn    4920
nnnnnnnnnn nnnnnnnnnn nnnnnnnnnn nnnnnnnnnn nnnnnnnnnn nnnnnnnnnn    4980
nnnnnatgta tacatataca tgtatacata catatataga tatatatata tacatatatg    5040
tatatatata tatatatata cacatatata ggttatttgg aacctaagaa acttgcaaag    5100
ttactagatg caatgttcgg aaaccatgga ccgtaacaac tggagtagta tttgggtcat    5160
gaattcatgg ctagatcatg aattgagtgg gagtcaaccg aagtagggcc agctcagaca    5220
cttgtattta ggtcccatgc ttgcgtgcat tctcttccct gatatccttt ggctttgctg    5280
cctcaaatcc tcgagctatc ttatcatcat cgcattgagc tccatacct               5329
```

<210> SEQ ID NO 69
<211> LENGTH: 6061
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (5947)..(6061)
<223> OTHER INFORMATION: n is a, c, g, or t

<400> SEQUENCE: 69

```
cagtttggac ttcaatgtta acccaatatt gattttaaat ccaacattgg tccacttaga     60
cttatttatt tatttttatc aatttaatat aaaaaagatc taaacctcat aagtcataaa    120
ttttggattt attttgaac atgtacaaaa taaaacagaa aaagaaaaa attacttatc      180 taaaagtaac tatatctgaa aactttcact ttagaattgt cttaaattaa tgtacttcca    240
```

```
tcaacaattc aatgttaata tttttatgaa tccaaatgga tgatagagta ttttttagaa    300
tgaagtattg aagtctaaat gacatcgtcc caaaataaaa gtgaatttat gaaatactac    360
atctgtcgga ttcggtttca tacggattaa aagtgtagga atagaatccg attataaata    420
attatttttt tataaattct aattcaattt tattcgattt atattttta accggtcaaa     480 attaatattt attaagtagg attggatgga tttattcgta tctcgattat ttgctcagcc    540
cattgccaaa tctaaactct tttcagatag gttccatgtg aacatgatac atgagatgca    600
gtgtgatagt acacaccatt gctaagaaaa ctttggagtt tgcgtaacaa tatctgttta    660
ccatttaaaa aatggcagtt ttgaatttta acacgctctc ctccagattc agcttatgaa    720
cttttcgaat aaaaatacc ctggactatt ttccaaaaa gtaccagcat cttttgaact     780
tgaatggaaa ttcggccaat aaaatgtttt catttattga agaaataaac agggtaacgc    840
agtagctcta tttcctctgc ttttcttttc tatattaata acatgattat tcatctctct    900
cggatcacaa aaaattaag ctattcaagc tttatttata tttcattttt aaatttttta    960
cttaaataca aaatctccca tcccactact acggcagcat gttttctatg tatgattatt    1020
ttcattcaaa tgatatcatt ttttataatt tatattgtat gtaattaatt catttatagt    1080
tcttacattt tcctgtttct agtagataca ataaagcggt tttggactag tagcttgttc    1140
tctgtatcga gtttaacta aagctttgac aataatatat gaatccatat cactgggtag    1200
gagaggaata tgttgggtat aaaggattta aggaattaga tattttcata caattgtatt    1260
gcattgcaga cagtaattag attactatgc aattattctc tctctccatg tttgttgcag    1320
ttgaagaact ctaatgaagc tcacaaaaat ttactgcatg aacttgtaag tggaattaga    1380
cgactccgtt gtcctccatt ttcttttatt ttctttaaaa tcatctgcca ttcaaataga    1440
cagaaaaaaa aggattgatt agctattgga tgcctcttga attcaggaaa tgaaggacga    1500
gcacccagtt tatggttttg tggatgatga ccctagcaac tacgcaggtg cactagctct    1560
tgccaatggg gcttcccaca tgtatgcttt ccgtgttcag ccgagccagc cgaatctcca    1620
tcgaatgggg tttggctccc atgacctgcg ccttgcttga ttttattgta gcttaaagac    1680
cttacaactt ccagagtggt gttatatatt agtatcttaa gctatgacag tggtaagcct    1740
ctctatccgc tacttgttat cctttaggta ctttgcatgt ggtgcaaggt tataattgcc    1800 ttgtgttct attgtcttcc tcatggtact tactggactg atgatgtcaa gtgaaatgga    1860
gttgtttgaa tcctgactga aatttctctt ggtccatcaa gtgcaagagt aagtttagac    1920
atcactcgca agcttttgct aggaaataag tagtttcatt gcactaatga tttcgaattt    1980
ttgttttcgg gttagagaaa cctagattaa tgctgttatt ggatgctggc agtcagatga    2040
agattatgtt tgattgtacc tcgttggaca gatgctcatg cgtagatcca taactctatt    2100
tcatttcatt tccctgtaca caattgaaac agggcatata tgaataggta tagaacagat    2160
gattcctgca atattggagg tggctagctc agcttagact aaagttggtc tagctgggat    2220
attctgaaca cctgagatgt tcaaataatg tgggataact tggcccaact caactaaaca    2280
ttggctcaaa gcatagtcaa ggtaaagctt gagcaagctc ttttgagctt ggttcgagtc    2340
cgagctgagc ccgggccgct tgtttagctg atgaactgaa ttcaaatagc cggtactcag    2400
cttggctcca ctcgattcat gagttcgaat cccctcaagt tcaacctcga acttgacggt    2460
gtagtcccac aaccatggcc accttataat gtgggacggc cattatgcat tcctctagtg    2520
cctgctccat atgactttg ttctcattat accatgcacc taaatgagtg ctcatagtga    2580
caatgtttag cctccacgta taatgtgtgc cagctaacta gaagcctaaa ctttggtgaa    2640
```

```
atttctgcaa tgttgtggtt gtaaaacgct cctacgttga gacatgatgg tatctaagat    2700
tatagacaaa ctatcatgct gaatcaaccc aaatccaagg tgaataaaac ttgatacaaa    2760
gccgagctcc attgaaatag tacaatggat tctgcacttg aagaacatta caaaatcatt    2820
ttttcccaaa aagaaacatt gcgaacagac caaagcgtaa agaaattaca tgattcaact    2880
aattcaagct ttccatgatg taggcactcg ctagatgtag tagggtgata acttgctttg    2940
tgagggtgga tcataagctt aacctcaatc tatcccaatc tatcctttcc cttgacctat    3000
ccatgccaat ctaggccatt tctgcataaa tataacttaa tcccagtgga tccggcctag    3060
tttcactcac tccaacacat tcctactcaa tggtagccaa tcctttcttt agccctcaaa    3120
tataatccta atctagcata gccaaccatc aatcatgcct aataaagccc gactacacca    3180
acccgatcat tcctgatcgt acacaatcaa gacttatcct aattgatcct agctttttt    3240 aggcctctct tatagaacct gtgccaattc tggacaagct aatccaatct tagcagccaa    3300
aaatattaca tgtttaatta gccaaatcga acctatcata aacccaatat ataatcggac    3360
cataccaaga tcatcatcct atatttcctt ctcttgttat aactacacct aaaaaggaat    3420
ttcttcatac ttatgagggg tatattatga taaaaattcc ttcattttag ccctccatcc    3480
ttgtctattt ttgggaccac tagccaagta acaccttaag agccctccat cttaatattc    3540
cctctaacta gctcgatttc ttcttcattc tttctttgcg atgtgtcccc tccaatttaa    3600
ttcttacatg ttgggatttg agtactgaaa ataatagat aaagagaaag taaaaactat    3660
gctaatgata ataccaaagg cataagaaa tcacagcagt cgcaaaaaca tcaaattttt    3720
ttatggttcg gcctaagcct atatctacat agggacgaga gtaagaagaa gcttccacta    3780
taataatagt ttagagtaca aaaacttctc tgacaccatg tagggaacat cgcttctaat    3840
acaagaaaga agaaatccaa gattaaacaa acctctagaa aaattcttct cgatggaata    3900
actctaatct gagattgaac aatcttctcc aatcgatgat ctccaatctt cttttcttaa    3960
atgaagcacc cttcaagcct ctcttctttt ctctcttcct atcctctttt gtggctcaca    4020
acctcctctc cttttatgt tctatgttcc tcacatcaca tccacagact cattttata    4080 gataaaaaat tagagtctat ttcggactcc ttttccacac acaagatggc ttcccacgcc    4140
attggttccg tgcgcatgac ttttttcatg ccacaaagga ttccgtgctg caaaagtttt    4200
ccatatccat gcagtttcca cacaccacaa aaactttcgc acacttctcg aaggcttttc    4260
atgctcgacc cttttggtt ttcaattaaa ttgatggatc ccatatgagg agggaccaca    4320
ccaataaatc tcctccttct aactcatatg gtaggttcca tcaagcctgt agcaccttttg   4380 cattttatca gttttgttcc tgaagccggc ttcatcaata tattagaact attttcttca    4440
gtgtcaactt ttttaagctt gaaccacttc atctctagca tattgacatg cttttggaaa    4500
gtatgtcaaa ttgctcaaaa ttaatcttac ggttctcttt ttcgttagat tctagtgcat    4560
attacgcact ttaacataag atctaaggaa ggaagaggac tgaggtaagg tgaagtgatt    4620
ttttttgagt tggtaatggt acaaaagtta tactagaccg tgggtaccta atctcggaga    4680
ttaccattta gatttggttc ttgatcattt gtatagtgat gcatttaaaa aattatttga    4740
gcaaaacagt gaatgccatt gggtctgaga gatccaaaac caaataacct aaagtatata    4800
gatggttcct ttagctagat catgtatgag aaaaaatgat ctgccgactg aaaaaatag    4860 atctttgagc tcattgattg ttaagtcata tctagtctgt gaatcatctc tttgaggatt    4920
aatgatcaag ctatcttttta tgggttaaaa gaataggatc actgaaatac ttatcctagt    4980
```

```
atacatataa tgtgcatggc ctatttgatg agtcagacta gaaggttatc actacttcat    5040
cacctttact gatgagcaat catgatatag atatgtatgt gagatacaaa tctaaaagat    5100
tttgaatggt tcaaagaatt cagatatgaa gtagaaaaga taaatcaaaa aattttttaaa   5160 ggtacttgat cggatctaga atgcaatacc aaataaaaaa tttgttgatt atctaaaaaa    5220
agtgatatag tttcatgatg gaattcttct tgtacacctc agctcaacgg tatatatatg    5280
aggagcaata gcactatatg agatatggtc cggtccatca tgaatatcac taatttaatt    5340
attatttatt taagagcaag atttaatttt taaaatttaa attagatttt ttctaaaatt    5400
ggtttcaccg caccatatga gatatgattt ggtggataag ttagaggata ggtctgtgag    5460
aactcattta tagggtatcc caaaaggtat ttaaaatatt acttttctt tctagtagtt     5520 gacaatatga ttgtgagcaa tcatactgtt ttcttaaaaa cagtggaagg atgaactcaa    5580
aaagaaagtc tctaaagaac aacgagtcac aagacctata caacctattt aagatgagcc    5640
agtatatgta gtacttcctt cacctcatca atttagtagg atctcctatc ctttagaaag    5700
atactcggta ttcttacaaa ggatttagag aaagtgtttc ttgagggaga ttgagaatat    5760
agggatgatc tcaaaaccta caatgacata atataaggaa tcatgtagtt acatgaaggt    5820
cagtgggagg gttccatact gacatcgatt atgatgtggt tacatataga attttttttt    5880
caaagatcta gatcaaacat tctgaaaata aaggtctat  agagataaat ccgaaaagga    5940
tgtttgnnnn nnnnnnnnn  nnnnnnnnnn nnnnnnnnnn nnnnnnnnnn nnnnnnnnnn    6000
nnnnnnnnnn nnnnnnnnnn nnnnnnnnnn nnnnnnnnnn nnnnnnnnnn nnnnnnnnnn    6060 n                                                                   6061

<210> SEQ ID NO 70
<211> LENGTH: 14226
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (1949)..(2907)
<223> OTHER INFORMATION: n is a, c, g, or t
<220> FEATURE:
<221> NAME/KEY: misc_feature
<222> LOCATION: (3857)..(4532)
<223> OTHER INFORMATION: n is a, c, g, or t

<400> SEQUENCE: 70
atcctctttt gtggctcaca acctcctctc cttttatgt tctatgttcc tcacatcaca       60
tccacagact catttttata gataaaaaat tagagtctat ttcggactcc ttttccacac     120
acaagatggc ttcccacgcc attggttccg tgcgcatgac ttttttcatg ccacaaagga    180
ttccgtgctg caaaagtttt ccatatccat gcagtttcca cacaccacaa aaactttcgc    240
acacttctcg aaggcttttc atgctcgacc ctttttggtt ttcaattaaa ttgatggatc    300
ccatatgagg agggaccaca ccaataaatc tcctccttct aactcatatg gtaggttcca    360
tcaagcctgt agcacctttg cattttatca gttttgttcc tgaagccggc ttcatcaata    420
tattagaact attttcttca gtgtcaactt ttttaagctt gaaccacttc atctctagca    480
tattgacatg cttttggaaa gtatgtcaaa ttgctcaaaa ttaatcttac ggttctcttt    540
ttcgttagat tctagtgcat attacgcact ttaacataag atctaaggaa ggaagaggac    600
tgaggtaagg tgaagtgatt ttttttttgag ttggtaatgg tacaaaagtt atactagacc   660
gtgggtacct aatctcggag attaccattt agatttggtt cttgatcatt tgtatagtga    720
```

```
tgcatttaaa aaattatttg agcaaaacag tgaatgccat tgggtctgag agatccaaaa      780
tcaaataacc taaagtatat agatggttcc tttagctagg tcatgtatga gaaaaaatga      840
tctgccgact ggagaaaata gatctttgag ctcattgact gttaagtcat atctagtctg      900
tgaatcatct ctttgaggat taatgatcaa gctatccttt atgggttaaa agaataggat      960
cactgaaata cttatcctag tatacatata atgtgcatgg cctatttgat gagtcagact     1020
agaaggttat cactacttca tcacctttac tgatgagcaa tcatgatatg gatatgtatg     1080
tgagatacaa atctaaaaga ttttgaatgg ttcaaagaat tcagatatga agtagaaaag     1140
ataaatcaaa aaatttttaa aggtacttga tcggatctag aatgcaatac caaataaaaa     1200
atttgttgat tatctaaaaa aagtgatata gtttcatgat ggaattcttc ttgtacacct     1260
cagctcaacg gtatatatat gaggagcaat agcactatat gagatatggt ccggtccatc     1320
atgaatatca ctaatttaat tattatttat ttaagagcaa gatttaattt ttaaaattta     1380
aattagattt tttctaaaat tggtttcacc gcaccatatg agatatgatt tggtggataa     1440
gttagaggat agatctgtga gaactcattt atagggtatc ccaaaaggta tttaaaatat     1500
tacttttcct ttccagtagt tgacaatatg attgtgagca atcatactgt tttcttaaaa     1560
atagtggaag gatgaactca aaaagaaagt ctctaaagaa caacgagtca caagacctat     1620
acaacctatt taagatgagc cagtatatgt agtacttcct tcacctcatc aatttagtag     1680
gatctcctat cttttagaaa gatactcggt attcttacaa aggatttaga gaaagtgttt     1740
cttgagggag attgagaata tagggatgat ctcaaaacct acaatgacat aatataagga     1800
atcatgtagt tacatgaagg tcagtgggag ggttccatac tgacatcgat tatgatgtgg     1860
ttacatatag aattttttt tcaaagatct agatcaaaca ttctgaaaat aaaaggtcta     1920
tagagataaa tccgaaaagg atgtttgann nnnnnnnnnn nnnnnnnnnn nnnnnnnnnn     1980
nnnnnnnnnn nnnnnnnnnn nnnnnnnnnn nnnnnnnnnn nnnnnnnnnn nnnnnnnnnn     2040
nnnnnnnnnn nnnnnnnnnn nnnnnnnnnn nnnnnnnnnn nnnnnnnnnn nnnnnnnnnn     2100
nnnnnnnnnn nnnnnnnnnn nnnnnnnnnn nnnnnnnnnn nnnnnnnnnn nnnnnnnnnn     2160
nnnnnnnnnn nnnnnnnnnn nnnnnnnnnn nnnnnnnnnn nnnnnnnnnn nnnnnnnnnn     2220
nnnnnnnnnn nnnnnnnnnn nnnnnnnnnn nnnnnnnnnn nnnnnnnnnn nnnnnnnnnn     2280
nnnnnnnnnn nnnnnnnnnn nnnnnnnnnn nnnnnnnnnn nnnnnnnnnn nnnnnnnnnn     2340
nnnnnnnnnn nnnnnnnnnn nnnnnnnnnn nnnnnnnnnn nnnnnnnnnn nnnnnnnnnn     2400
nnnnnnnnnn nnnnnnnnnn nnnnnnnnnn nnnnnnnnnn nnnnnnnnnn nnnnnnnnnn     2460
nnnnnnnnnn nnnnnnnnnn nnnnnnnnnn nnnnnnnnnn nnnnnnnnnn nnnnnnnnnn     2520
nnnnnnnnnn nnnnnnnnnn nnnnnnnnnn nnnnnnnnnn nnnnnnnnnn nnnnnnnnnn     2580
nnnnnnnnnn nnnnnnnnnn nnnnnnnnnn nnnnnnnnnn nnnnnnnnnn nnnnnnnnnn     2640
nnnnnnnnnn nnnnnnnnnn nnnnnnnnnn nnnnnnnnnn nnnnnnnnnn nnnnnnnnnn     2700
nnnnnnnnnn nnnnnnnnnn nnnnnnnnnn nnnnnnnnnn nnnnnnnnnn nnnnnnnnnn     2760
nnnnnnnnnn nnnnnnnnnn nnnnnnnnnn nnnnnnnnnn nnnnnnnnnn nnnnnnnnnn     2820
nnnnnnnnnn nnnnnnnnnn nnnnnnnnnn nnnnnnnnnn nnnnnnnnnn nnnnnnnnnn     2880
nnnnnnnnnn nnnnnnnnnn nnnnnnnact atgtatgttg gctatgtagg ttccgattcg     2940
ctgtttggaa tatgatatac ctagatgaaa tctatcgatc ttgatagaaa aagagaagtc     3000
ctatgtgatt cgtaagactg agttcagaaa aatctctgac cagagtaagt gtgaatattg     3060
```

```
aaaaattttt tttacgaaat tcacaaatga actcgagtcg agccaatgta gcatatgact    3120
gatgatagag tttgacgagt tctcaatgac ctccgtcaaa ttgggactct cgatagaggg    3180
attgtatcac acgataactg cacctaggga ttcacttttc tattttgcta gcttgccact    3240
atatgttgct agacgtcact ggtggatcgt gagaactcac taaaatcatt ttcggatcaa    3300
cgatctttgc tgaggtaagt tggaatcgtt tcagtccatc gaaaagagtt tcgatgatac    3360
tgtgatggag atcacgatat gtctcactat caaacagaat agaacctgag gagtcacata    3420 caaaagagc ttaacctgat caatggcttg gattatattt gaattatcaa ttagattgat    3480
agtttgaata ttagaaactg ctaatttgta accgttacag ttttgacaac tactaattgt    3540
tagcgcaagg acttaattgc aagtattata attttttga ggctgattaa attataaatt    3600 aaatttaat taatttaatt cagatttaat ttaattagac ttaatttaat ttaatattaa    3660
ttggattcaa ttatccaaat cagatttgga tttcaagcct gattggatca ggcttgacag    3720 cctttttcgaa tttggctcat tttagactcg atttgaatcc gtttgaggtt ctatttggat    3780
cagataaacc atgacttaga gagctcaagt ttttgggac tctctttaga aatcatgtca    3840
aaaggagaag tagagcnnnn nnnnnnnnnn nnnnnnnnnn nnnnnnnnnn nnnnnnnnnn    3900
nnnnnnnnnn nnnnnnnnnn nnnnnnnnnn nnnnnnnnnn nnnnnnnnnn nnnnnnnnnn    3960
nnnnnnnnnn nnnnnnnnnn nnnnnnnnnn nnnnnnnnnn nnnnnnnnnn nnnnnnnnnn    4020
nnnnnnnnnn nnnnnnnnnn nnnnnnnnnn nnnnnnnnnn nnnnnnnnnn nnnnnnnnnn    4080
nnnnnnnnnn nnnnnnnnnn nnnnnnnnnn nnnnnnnnnn nnnnnnnnnn nnnnnnnnnn    4140
nnnnnnnnnn nnnnnnnnnn nnnnnnnnnn nnnnnnnnnn nnnnnnnnnn nnnnnnnnnn    4200
nnnnnnnnnn nnnnnnnnnn nnnnnnnnnn nnnnnnnnnn nnnnnnnnnn nnnnnnnnnn    4260
nnnnnnnnnn nnnnnnnnnn nnnnnnnnnn nnnnnnnnnn nnnnnnnnnn nnnnnnnnnn    4320
nnnnnnnnnn nnnnnnnnnn nnnnnnnnnn nnnnnnnnnn nnnnnnnnnn nnnnnnnnnn    4380
nnnnnnnnnn nnnnnnnnnn nnnnnnnnnn nnnnnnnnnn nnnnnnnnnn nnnnnnnnnn    4440
nnnnnnnnnn nnnnnnnnnn nnnnnnnnnn nnnnnnnnnn nnnnnnnnnn nnnnnnnnnn    4500
nnnnnnnnnn nnnnnnnnnn nnnnnnnnnn nnccccatcg aaaagagttt cgatgatact    4560
gtgatggaga tcacgatatg tctcactatc aaacagaata gaacctgagg agtcatatac    4620
aaaaggagct taacctgatc aatggcttgg attatatttg aattatcaat tagattgata    4680
gtttgaatat tagaaactgc taatttgtaa ccgttacagt tttgacaact actaattgtt    4740
agcgcaagga cttaattgca agtattgtat ttttttgag gctgattaaa ttataaatta    4800
aattttaatt aatttaattc agatttaatt taattagact taatttaatt taatattaat    4860
taggttcaat tatccaaatc agatttggat ttcaagcctg attggatcag gcttgacagt    4920
cttttcgaat ttggctcatt ttagactcga tttgaatccg tttgaggttc tatttggatc    4980
agatgaacca tgacttagag agctcaagtt ttttgggact ctctctagaa atcatgtcaa    5040
aaggagaagt agagtattat ttttttcatc cttctttctt cacacgcatg aaaggagagg    5100
gggcaccaat agttggtgcc ctgccttatc tggatgtctt tttcatccaa ttttttttttt    5160 aattgaattt gatttaaaat agaatagaaa tatcttagat taaggtatag aagtactttt    5220
tttatgtgat aaaaaaaata gagaaagagg acgtgcgcta attattggcg tgagacatct    5280
ttccttcttt cttcccttat ctcaacgcac atctatcctt tgatttgttt ttgaacacct    5340
tggattaaaa gagatgagat ctcttgggca ttaagaagga gttgtgcgtg ggatttgaga    5400
tgtggtgcga caaaaaatta aaagaggatg catgaaggga ggtggcgtgc gttagatgcg    5460
```

```
agaggcttct ttcttacatc tttctctcct ccccaatgcc tcttccttcc ttctccactt    5520
cacgtccatg cccagattca ataaagatca gatctaagaa aagaaaagag agagaaaaag    5580
agaagaagaa gggttcttct tttcttcatg gtgatctggt atagatcctg ttggatttgt    5640
gcgaaagagt ttgagcaacg atctgcttct ttaagatctg aaagaaaaga tcaagatcca    5700
tggatgaaga gtgagatctg caaggtgcta gcacaccagt gatctcggtg ctccgatcaa    5760
atggctccgt gtggatatca gctgaggtcg aacgcgtgca tggctacgat cagaatctgc    5820
gatatctgca ggatccgaga tatggagatt cgatctccat tttattttc taacagttta    5880 tttttctatt tcagatatca gatcgtgggt acatatttgt atcaagatct ttactatggt    5940
tttcagatct gatttgatac gtaaataaat taaaattatt ttaatttatt tattttcact    6000
gtgtagatgt ctagaaaaaa ttttaaacta cacgtacgaa atcgaagcat tttctaacaa    6060
ctctgactat caccatagac gacgtatatc tcttgcttcc caccaaactt ctttaataag    6120
ttctttagcc atagcatttc tttatcgacc tttgttatgg tgatgtattc aacctccatc    6180
gacgataatg tgacacttt atgactttga ttgccacaac accgctccct ctgagaatat    6240
catcagataa tctgacgtgg atttctgtat gtccacatca tcgatcatgt ccgtatctgt    6300
gtaagcctgt agcataggat ctccactatc atggcataaa tatatcctgg atatctattt    6360
aagatatctt attttccact tcattgcttt ccggtgctcc tttccaaagt ttgaaagaaa    6420
ccgattgacc ataccatcca cttgagcaat attagacctg gtgtacacca tagcatacat    6480
aagactcccc accacttagt ccttctcact ctttctgctt tgctctttaa tcaatgtaaa    6540
gtgtcctaca agcagacacc accggcttca ctctactcat gttgaatcaa tccagcacct    6600
tctcaacata ggcctcctat gacaaccata ggacctggat ctcctatctc tagcaattct    6660
tatccttaat atcattttga cctatcccaa gtcttccgtc ataaatgttc gatccaactt    6720
taccttcaaa tcattgattt tggtaatgtg catcccaca atcagcatgt catcaacata    6780
tagcaaaaat ttgataaaat tattgtcaaa atatttttc atgaacatgc aatggtcaga    6840
acttactttc ttatatccat tctccattat gatggaatca acttcttgt actactatca    6900 tggtgcctgc ttcagttcat aaagattttt cttcaagcaa cacactatgt tctcattaac    6960
ctttcatttc aaactcttct agttactcta tatattctcc tcctccaagt cgccatgaag    7020
gaatgccatc ttcacatcaa attgttccac ctcaacatct aaacagccag cgagatcgag    7080
gataactcga gtagacgtga gctttacaac gattgagaaa atctcttcaa aatcgatact    7140
ttttctctga ccaaaatctt tcacaactaa tctcatcttg taccttggtt ataaactatt    7200
ctcctatggc ttcaatctga acatctattt atttttgagt gcttgctttt tcttaggtat    7260 attaccaac tcatatgtat tatttttcta taaagaattc atctcctctt tcattgcctt    7320
catccactcc tcactatgct ggagctctat ggcttcagag taggactcaa gctcttccac    7380
atctgttaat agcacataat cctatggtgg atatcttatg gatggcgtcc actctcttgt    7440
gaatctctgg acctcttatg caggtggttc aacatgcaac tcaatttgaa caccatccgc    7500
actctcctca gcctcatgac tatcatatgt accgtcatct gtagttgctc tcctgttatc    7560
aagacttctc gaagaggtat ctgggcataa gtctataggc tgctcggggg ttgacttcgg    7620
cttcttaggc ttcttaaaat catcgatcgt ctgatcctcc aaaaaaataa tgtcatagtt    7680
gcacacgatc ttccactcca tagaatccca caatcgatag ttgaactctc cgtcctcact    7740
atagctcagg aatatgcact gcttcacctt gacatctagt ttggatctct catctttagg    7800
```

```
aatatgcacg aatgtcctgc atccaaagat tttcaaataa tcataagaaa tatctttctc    7860
caacaatatt ctctatagtg tatcacactt aagagtataa gaaaaaaaaa gattaatgct    7920
atggatcaca gtcatcaatg cctccctcca gaatgccttc gatagtttag cataagagcg    7980
catgctcccg atcctctcgc aaatcatcct gttcaccctc tcaacaatct cattttgttg    8040
tggcatctta ggcactgtct tctctagtct gatgccattt cattgatagt attttttgaa    8100
agaaccctg  tattcacccc tgttgtccgt ccaaatatac ttcagctttt gcccagtctt    8160
tctttcaaca gagatgtcaa attacttgaa tattatcgag cacttgatcc ttcatttta    8220
aaatatatgt ccaaattttt tagaagtgat catcaataaa agtcatgaag taagaacatc    8280
cataaaaaat tttatcactc agagaacaaa catcactgtg aataagatct aatgcaccaa    8340
tttttctttt agaaaaaaat tctaaaaaga aacttggatt tgcttaccca tcaagcaact    8400
ttcatatatc ttcaatccaa aactatgaat aggaagagca ttcttcttag tcaaaattga    8460
cattcctttt tggcttatat gtcccagtcg tcaatgccat aattctaagg tagaagattc    8520
ttccactaca ttcacctccc ctttaccgag cttggcttgt atgaagtaga gaaagccttg    8580
cttgatactt ttggctacta ctagcgattt tttggttagc ttctatttgc tgtctccaaa    8640
tatattgtag tagtcctcct catctaatac ccctatcgat aacaagttca gatgaatatc    8700
tagtacatgt cgaatatttt tcaaaaatag cctgtacccc aagctcgtga tcagcataat    8760
atctccaata tcaaggattt ttaattctcc atcattctcc atctttattg tcccaaagtt    8820
actgaaatga caagatgaga ataattttca cctcactgta acatgatacg aagtggccaa    8880
atcgatcacc cagatagagt ctcaaccaat agtacttgca agatcatcat ttgttgtgcc    8940
acaagcaacg atcatctctc catccgtagc tactgctatc atcttattgt tcgagctgga    9000
gtcatcactt gattattttt tgacttctcc ttttttagta atcggtagtc tttcttaaag    9060
tgatcctttt tgccgtagtt gtaatatcta tcacttcgag acttggatct cttccgtaat    9120
ttagtggggc catcattcaa gttagattgg gagtccttgt gcttgtttct tccctttctt    9180
tctatgatga gagcctcatg gtggctcgag acaccttgct cctttctcct agcctcctca    9240
ttaagcatat agtctttcac cattgccaag gctatcgaac tatctggtga agaattgctt    9300
agagacacca ccaaagtctc ctaactatcg agtaagaaac ttaacaatag taaagcctag    9360
agctcctcat ctaacagcat cttcatcaca gtaagctggt tcaccacgtt ctaaaagttg    9420
cttagatgct ccaccatata agctccctcc ttatatttca tatttatcag tttgtgaatt    9480
aggaacacct tgttctatac catctctctt gtatagactt tttagtttca accaaaggcc    9540
atgagcatta acctccattg aaatatggtg gaagatgcta tcatcaatcc actgttggat    9600
aatcccaacg attttatgat tcaatttctc ccattcttta tttgacatct tatcaaactg    9660
aataataaca tcctcgattg gatcatgaaa atcttagcag taaggaggt cttccatgta    9720
aggattccag attgagtagt tagttaatgt cagcttgatc gtagtgcccg acgaagattg    9780
gttctccatc tattagcatc ttaatttctt tttgaatact ttagattttg taaaatttgg    9840
ctctgatacc acttattggg atttgagtac taaaagataa tagaaaaagc aaaagcaaaa    9900
atcacgccaa cgataatacc aaaggcacaa agaatcatag caatcgcaag agcactagaa    9960
tttttatgg ctcgatcaaa gtctatgtct gcacagggat gaaaataaaa agaaacttt    10020
actataataa tagtttagag tataaaaact tctctgacac tacgccgaca atactacttc    10080
taatacaaga aagaagaaat tcaagattaa acaaacctcc agaagaatcc ttttgatggc    10140
aatatgaaag aataatattc tacaagtcaa tcgcatgagt aatgcaataa gatattgttc    10200
```

```
tatattttat cttccaaatt catatatttg atattaatta ttaataaaat tagatatttt   10260
atttcattat atgctgcatt ttaatacttg tttaaaatta taatgaactc cataggttag   10320
gacaataatt ttaaggtcat gatgagatca taccagtgag atttaaatct ttgataacct   10380
taatctaaaa tattctcaat agtaggatca ttaagtcaaa aatcaatgat actgataaaa   10440
ctggtacatc ctatatattc tcgacagaga gggtggttga tgtcataatc acttgtgtgg   10500
agacactaat acgaagatgt ggtgctcatt agagaataag ttcattgaat ttactgatcg   10560
agagaatata tgatgcaagt gatcctttga cctaagatca ccatggtgcc ttgtatatat   10620
gaatctatgt tttggttcat tctttagctt cattttttga gccttgtgtg gggtgctccg   10680
gacatggtgc agtatgtatg gaggttgtga gtggtcaaca aaaaatcaat cactccttgt   10740
aaaaggagcg aatatcttat gtgatcttat aggttgatcc aaaaaatctt tgaccaaagc   10800
agaatgataa ttagaaagag ttttaatat atcattaact gaatcaatat cttctgatcg   10860
agatacatat aaataagtat ttgaatttga catgattttta tatccataac taatctgaaa   10920
tattgtatga ttgaagaatt gaattgtaca attttttacc attgaaaaaa attttttgata   10980 ttttttttca aatttaatat cttttttgata gtcatgacat gttgctagac atcaatcttg   11040
acttgtgggc tcacaaaaat taaaaagatt ttatttgaaa gttaattaga aagtattctg   11100
attaattgat gtatttggac tgacctaatc taattggatt gatttaggtc atgagcttga   11160
gcccactgct ggctagatga tcgctgtcgt aggcagtcaa gaataaaaat caactcaaac   11220
tatatagata gggtgagtag ggatcatttc tatggagatc taggatgatt atctttttt   11280 ttaagaaaaa ataaaagag aattgattgt agaagaatta aaagaaatag aatagcaaga   11340
attaaattaa aagtatgaat taatttatga aaaaaaataa gtcagagaaa taactcagaa   11400
attttgaatc caccatgcaa attagattta ttttcttctt tttttatgt tgcaacatta   11460 attcttgtga ttaaggtatt agtatagctt atctctaaga gatacggact gtatcagtag   11520
attacaactc gtcctgttga agtataaact atctaaattc aattacaaaa tataagattc   11580
aatctaacat actacgatct atctctccaa agcacgtatc gtatctaggg atcacgatac   11640
gtcaatagag ggtataagcc gtgtaggctg gatcaatacc tcaaaaaaaa ataaaaagat   11700
atgaaataaa agtataattt tattacataa aaatttaata taaaaaaaaa ccgtttacag   11760
gctttatcat atttctggat tgaagagatt tagccacgca tcaagctctc tagctccata   11820
atctctcaat aattgatccc taaagctctt taatttttt ttttattatt tttttgtttt   11880
ttctttaatt ttttctcttt cttatttttg ctgccatctg ctgcctctgt tttctctgct   11940
cctgctgcct ccttttatag agcacagctt cttcgaatta taagcatcta tggactttca   12000
attcccacta tcttttattt tgattgggat tttaaaactt tatccgcatc ccagcatctt   12060
gtttcacgcg agatcctagc gtccacatgt gttttgaatt ccttatgggc cacagaccat   12120
ttaaaccacc aaagaccact ttactatttt gatttgaatc ccatggaagc cggctgcctc   12180
tggtctcatt caccctccca gtgcttcaca tgggtcccat taatttgaat tcctatgagc   12240
cacatccaag cttttgaatc caagccttcc ttattttta aatcaattaa aactttgctt   12300
taaatgcctt gtagaccctc ctatttgcat gctacgtgag aacattgtta agctcctctt   12360
ggcccactta agaacttcta tgggctacat gcttttggct agctttaaaa tggttttggg   12420
cctaactttg gatcaccatt cgaagtccat tttgaattca attttatttt atttttttt   12480 ttaacctaca aatcgagctc ttttattggt gatcattttt cctataaaac aaaaacaaaa   12540
```

```
agcatcaagt cttaagaaat aaaagttaat taatatatat tttgatactt ttattgggat    12600
atttaatgta cttatcacta gatatgaaat ccaatgggtc acacactttg aaatttgatc    12660
ttagtctaat ctaactagga tttattataa atcttatggg ttaaatttac atgctagcac    12720
atgaattaac tcaagttttc aattggattt agttctaagg tgtttgagct aaccctatcc    12780
tgatacctta aacctaatta gattagattt gaacctatgg ttttcttgat gccttatgct    12840
tattacatga aagagtttca tgtgacttaa attcctccat gccaccacat cttcatccat    12900
gccaaattaa tatggaacac cccatttaat tgtgcattta agaaggaata gtccttctta    12960
aacactcctc ttaatttccc acactttcct ttgttctaca caccatcaaa tggcttttgg    13020
aaatatgcgg gcgcagaagt ggaggtgtcc tatatgaagg ctcttccaca ttataagtta    13080
tcacatggtg aattaaatta ttgtgtgaga aaatcatgcg ccaagagttg cacccttg     13140 ggagttttag gcactccttc ttatcctata ataaggggc acccatatg gataaataca    13200 agggaattca agtttaggca tgagattgag aggagaaaaa gacacaaaaa tctgaaaaaa    13260
agataagaaa aaaaagaga gaaaatagaa agaaaagac gagagaaaac gaaaggcaag     13320
ggttgctaat cctagggttc aattttcaa tagttggatt tctgaatcaa tttggggtgg     13380
tgagattttt tgagaaaaag tttctgatgt ggccctagta aagattgaa ggcattcaga     13440 tgatggtgca atccgttttt gaaaagaaa agtgagtagt atacttgtga agaaagctgc    13500
aacactacat caaattggaa aggaccttga tcaaacccat atggatcacc gttgcaggat    13560
atctactttg gtatcttgtg aaggttattt tttttatcag atcatcatct tcaaaaaggt    13620
ataattttct acctaatatg catgcttgat ttgtttgatt aaaatctata aagtgttcat    13680
aaggtttgtg ttctgattgt attgttttaa gtattaaaac ttactttaaa aatataaaaa    13740
aatttgaaaa ctatcttcta ctgtgcaact aaaatccaac agaataaccc taatatgaga    13800
ttgagcgatc tccgtcaacc gatgttctct gatcttcttt tcttgaatga agcctcttca    13860
agcctttctt cttctctctc tctccctatc ttcttttgtg gcccacggcc tcctcttctt    13920
tttatgtttt gtatttctca tgtcacatcc ataaactccc ttttatagat aaaaaattag    13980
agtccatttt ggactccttt tccatgcttc ccacgccatt ggttctgtgc acacgacttt    14040
ttccatgcta caaagttttt tcatgtctca cgtagtttcc atgcgccata aaattttgca    14100
tacttctcca agacttttta tgctcgaccc ttttggttt tcatttaaat cagtgggtcc     14160
catatgacga gggatcacac caacatcata tgctctcctc accataccaa atggtatccc    14220
caacta                                                               14226
```

<210> SEQ ID NO 71
<211> LENGTH: 61
<212> TYPE: DNA
<213> ORGANISM: Artificial Sequence
<220> FEATURE:
<223> OTHER INFORMATION: synthetic

<400> SEQUENCE: 71

```
tttgggtcaa gctttaggct taggtcacat atacccaaaa tcatttggat gcatcaggtg    60
t                                                                   61
```

<210> SEQ ID NO 72
<211> LENGTH: 61
<212> TYPE: DNA
<213> ORGANISM: Artificial Sequence
<220> FEATURE:
<223> OTHER INFORMATION: synthetic

<400> SEQUENCE: 72

```
ttggctttgc tgcctcaaat cctcgagcta tcttatcatc atcgcattga gctccatacc    60
t                                                                    61
```

<210> SEQ ID NO 73
<211> LENGTH: 4061
<212> TYPE: DNA
<213> ORGANISM: Artificial Sequence
<220> FEATURE:
<223> OTHER INFORMATION: synthetic

<400> SEQUENCE: 73

```
atcaaatcat atgatccatc ttaaattttt aactcaaaaa attaatattg caaactagct    60
caaaataatt ttgatcacta catttctgct gtgcattcta atttaaaccg ttcacatttt   120
ttagattcat gaaataattt tgaccaaagt attactccat actatagtca aaaaagatta   180
aaatattaga ttctaattaa agccaaagat aaacttttga ttctcatcct taattttgcc   240
taaagtataa ttattttgat taacccttaa gcgcaataac acattcaaaa ccaacagata   300
ggtttactat aatccaaatg aattaaatct taattctttt atcaattcat ttagacaatt   360
tcaaatcaaa attctataag taatatcaat aaaaaaaatt tttgatgctc caataagtta   420
gaacttaaat caaatatat aagtaaaatt gatttaatca tctcttctaa agtttcttct    480
attaagatct ttaatatcta tcaaatacat tccacaataa tcatgcaaac cttttaaaaa   540
ttaaattctc aatgccttta ctacatttta acaccaagct cgataatagt gataaagaaa   600
catctagatc agctttataa tcaaaaattt tgacttacaa ttttacgtgt gtctcaaaat   660
cttgaataaa tataaataag atctttatc ttgatccaaa aatagtaatc aaggatttca    720
ttagtaactt caacaacaat ggtaaaaaaa ttttctatcc attgataaac ccaaattttg   780
aattgaagtt tcatgcatac catatagcct ttaataagat ctattatttg gatctaaaga   840
tagtaattaa aattgttaat gattccacta agatgaatac tttacaatct cataattaat   900
ttcttcaata aaaatagact tcttgataat gtctccaatt gtatatttt ttttatttct    960
acaagaaaac ttcatacatt ttttacgttc caatataaat cttaaaaagt tattccaatc  1020
aaatatcata aaagatcttc ttagtccaac cttaaataac ttttatgaat gaatctttat  1080
cttgccacta aataatgaat tttaaaatca agagcaacat cacagcattc tgtcatgtca  1140
aatttgtgtt agatgtatgt cctagaaatc aattagattg acaatgtaaa ttttttaagg  1200
atataattta tatattttga tttattaata aaataaaatt taaattaatt tttattcata  1260
ttttttatc tatgaatcat ctaaagaatt aataagatga tgatacatat tcttaagagt   1320
tcaaatttg aaatatatgt cattgatgat taatttctga atactttga attcttaaga    1380
gtttagaaga tcttgaccca agtagtgtga atagtgaaaa aaagttttca catacttcac  1440
atcaaaaatt taagttgaat aaattgtaca tatgacaggt attatagttt gacgagtaat  1500
ctataacctc tatcttatca aaattctgat agaaagattg tattgtatga taactgtact  1560
tagaggttca ccttttattt tactggatta ccactacatg ttgctagatg tcactggtgg  1620
attgtgagat ctacgaagat tatcttgatg atcgataatt ctcattgaaa agattgaaac  1680
tattttaatg atgttgtgat agagatcata atatatctta ttatcagaca gaatagaatt  1740
ctatgggatc atacacaata ggagattaag actgatcaaa tagttgaatg atgattaaga  1800
atcattacgg agttcagatt atcaatataa ttgataatta gactaactta taattgttac  1860
```

```
aagtagcaag gacttaactg ctaaaggtta ataggttcaa aaagaactta tgtataaatg    1920
ttgtgcatct taatttgatt ggatcaaatt agttatggct gaattcaaga tgaatcaaat    1980
aggaatttgg ttcaattgaa tttgggtcaa gctttaggct taggtcacat atacccaaaa    2040
tcatttggat gcatcaggtg tgtgacacct gaatcaggcc tttctaaact attttgagta    2100
agtttgatca agtcaaaagg atccacaccc taaggtttct tgaataaaac cttaggcacc    2160
acattgagga cctataggaa actttgaccc tctctcatat ggggtggcac actgaggttt    2220
tataaaaacc ttaggcaccc attttagcca taaaaaaaaa gctccaaggg atggggcagt    2280
agccatgaag aatccttggc tgtcaggact ctattcaaaa gagttctcaa ggttttggac    2340
tcttatggag ccctaggatt tgtttgccta taaatagatg gccaccccaa ggctttagat    2400
aatgttagag acttgtgaag ctctcccctt tctcttggtt gccggcccac cctctctcct    2460
ctctcttcca tgccccaaga cttctttctt gtctccatca tcttgctgaa atttagattt    2520
cagcaagaaa agtcaagtag aagtcaaagt tctaatgtag ctcacaagat gttgagaact    2580
tcctccatct ggcaaaggtt ctgcaagaga gctagcatcc tgagaaacaa aaagattgct    2640
gatcagccct catctccata tggatatttg tagagatcaa atgcatgcat agctagaaga    2700
gaatcttatc acgatcatca ctcgtgaaga tcatctacct gtgcaaaggt atgagataag    2760
aaaaatattt tttttatcat aattcatgaa tcctttgctt atattatact gagattcttg    2820
gaatggattt tttctctagt aaaactctag agatcagatc tcaaagtctt cttcacataa    2880
aggttttgaa agttctttat atttccgctg ctttgattca aaataaatta gatctatttt    2940
gcctttcaac ctttctcata tttattgaca tataaagctt taattaatga gattaatgaa    3000
aagcatgtgc gaaatactga gaaaatccta acagtgatat cagagctact tttgtacata    3060
agaaaaggat tcaagttaaa taaaatatgt ttgatttaag taaatgaatc aatcaaaatt    3120
tatcctaaca taagtttgtc ctggtataat ggtcaagacc attatgttga aaggttatcc    3180
taggacaaaa agtctaagta aaatctattt tatttaagta aatgaatcaa ttaaagttta    3240
ttctaatata agattgcctt agcataatgg tgaagaccct tatgttgaaa ggttgtccta    3300
ggatggaaag tgattgatga gacaaatata tcatgaaagt attttttcaca gatggaataa    3360 aatatatata ttttgtttgt gaaaatgaga tttcatgaat gtgtttgtca ttcaatatgt    3420
gtggtgatca tcttgaattg ccacaaatcc ttttttggatt agggttgtat catgactcac    3480
aaatcctgat ggttttgcaaa attttgcatt ctgtagtgat agaaaccaaa agttaatcca    3540
attttggaat aagattgatc aattggtatc taaggcaagt attttataat ggtggttact    3600
taattagtta taaaagtacg aagagtctcc taccaatctt acacttatct agccaatttg    3660
gttgattgaa ttctgaattt gggttgctta agtgttaagt tcactacaaa tatattgcaa    3720
ccatgattcc gacttagtca accaagccta gatctcttga atagattcat gttaattatg    3780
gatttacata ggatataaat aaataattaa aacttgaaga gatctaaatg aaaccttctc    3840
gtacatatta aatcgaatga tcttccatca ttgtagatat acggatactc tactgatgtt    3900
gatgattttc gactagatat agtactttgg ttgcatcgaa aaagtacaac cactttataa    3960
catgagatgt tgcagggtag agatgggggtt gggcccaata attgttaggt gaggatccaa    4020
atgatggctg cacttgcgtg tgaatggcga gtctgactta a                        4061
```

<210> SEQ ID NO 74
<211> LENGTH: 4061
<212> TYPE: DNA
<213> ORGANISM: Artificial Sequence

```
<220> FEATURE:
<223> OTHER INFORMATION: synthetic
<220> FEATURE:
<221> NAME/KEY: misc_feature
<222> LOCATION: (990)..(1717)
<223> OTHER INFORMATION: n is a, c, g, or t

<400> SEQUENCE: 74
tataactgaa agatagctaa tgcttagctg gatgactgct gttagataac tgtctgcatt      60
cttacggtac attgatattt taccaatgtg acatagctta aatcggcaac tggctgaact     120
aaatattatg tatcccttta gttaacaatc atgtcggtta gagatcaatg taattcgcag     180
cagatcgatc ataagctgag atgagtatca tattttaaga acaacgctgg gcgagttagg     240
ccgatcaaat gtcagactga aaaagcagat caataaacct ctgatgtgat ctgaaagaat     300
atttatgatt taaataataa tctatcacca cgtatccaga taatgaggtc atataacatg     360
taccaacagt gcattttttcc atctagttaa gaggttggtt agtggcattt gtcttcgata     420
tgtaatgttc acataactaa tgtgcttagt agcattcttt tgtaaggtta aatcttcaat     480
gatcttaagt tcacataatt gcctttgtgc cctattagtt tatagttgac ctttttaattc     540
aagagacagt caccttagca atcgatgtct gcttagattg ggccaattag gtactcacat     600
taatatattg aatcatgttt gaatataaag gattagattg atttataagt ttcctttttat     660
tgtttacata ctgatactta gattgactta ctacattatt tgatatgtta tgttctaatt     720
tttggattaa aattgttgtt tctgatttct ccttacatct aatactttgt ataatttatt     780
atttttttagc atgattgagt gtagaggatt agattgattt taagtttat tttgattatt      840
tacatgccca tacttaaatt gacttactac attattcaat atgttatgtt tcaattattg     900
agttaaaatt tttattctg atttctactg atgtccagtg tgtgtgtgtg tacgtatgtg      960
tgtatatatt tatttacata tatatgtatn nnnnnnnnnn nnnnnnnnnn nnnnnnnnnn    1020
nnnnnnnnnn nnnnnnnnnn nnnnnnnnnn nnnnnnnnnn nnnnnnnnnn nnnnnnnnnn    1080
nnnnnnnnnn nnnnnnnnnn nnnnnnnnnn nnnnnnnnnn nnnnnnnnnn nnnnnnnnnn    1140
nnnnnnnnnn nnnnnnnnnn nnnnnnnnnn nnnnnnnnnn nnnnnnnnnn nnnnnnnnnn    1200
nnnnnnnnnn nnnnnnnnnn nnnnnnnnnn nnnnnnnnnn nnnnnnnnnn nnnnnnnnnn    1260
nnnnnnnnnn nnnnnnnnnn nnnnnnnnnn nnnnnnnnnn nnnnnnnnnn nnnnnnnnnn    1320
nnnnnnnnnn nnnnnnnnnn nnnnnnnnnn nnnnnnnnnn nnnnnnnnnn nnnnnnnnnn    1380
nnnnnnnnnn nnnnnnnnnn nnnnnnnnnn nnnnnnnnnn nnnnnnnnnn nnnnnnnnnn    1440
nnnnnnnnnn nnnnnnnnnn nnnnnnnnnn nnnnnnnnnn nnnnnnnnnn nnnnnnnnnn    1500
nnnnnnnnnn nnnnnnnnnn nnnnnnnnnn nnnnnnnnnn nnnnnnnnnn nnnnnnnnnn    1560
nnnnnnnnnn nnnnnnnnnn nnnnnnnnnn nnnnnnnnnn nnnnnnnnnn nnnnnnnnnn    1620
nnnnnnnnnn nnnnnnnnnn nnnnnnnnnn nnnnnnnnnn nnnnnnnnnn nnnnnnnnnn    1680
nnnnnnnnnn nnnnnnnnnn nnnnnnnnnn nnnnnnnatg tatacatata catgtataca    1740
tacatatata gatatatata tatacatata tgtatatata tatatatata tacacatata    1800
taggttattt ggaacctaag aaacttgcaa agttactaga tgcaatgttc ggaaaccatg    1860
gaccgtaaca actggagtag tatttgggtc atgaattcat ggctagatca tgaattgagt    1920
gggagtcaac cgaagtaggg ccagctcaga cacttgtatt taggtcccat gcttgcgtgc    1980
attctcttcc ctgatatcct ttggctttgc tgcctcaaat cctcgagcta tcttatcatc    2040
atcgcattga gctccatacc ttgctctttc ctaactgccc ccatcaaacc tccggagatc    2100
```

| | |
|---|---|
| ctctttcttc tccaatgttg agatttgttg gagtcttccc accttctcac ttcaatgggt | 2160 |
| ggcaatttca agtgccagtt cccttatttg tcccagctat attgacaatg gggcttattc | 2220 |
| tagggtttct catggacata gtgataataa taatcaaggg accaagagag aaaaatcttt | 2280 |
| ctagtctgtg ttctttaagt ttgagagata ggcagcacat ttttttaata agcctttttc | 2340 |
| actcatcgga tcctgatttt cagttgttcg acctgaacag ttcaagcaat tgaactgctt | 2400 |
| gggtcactat tttggacgat tttcagccat ttttaagtat tgtttgactg gatccacgct | 2460 |
| gcgtagtggg cattgcgttg atcaagtaga cctgtaaggg tcaacaaggt ctgagaacac | 2520 |
| tgaatggatg ctccataatc ctcttgttat ctgtcaacca tttggaatct tttaaaacaa | 2580 |
| catgtggtga taatatatat gataaactgt gatagattca tgtatagatt atacatatga | 2640 |
| aaatgtagag tgcttagtaa aagtgatgaa gagcaatgcg ttagaatgtg ctagcctttg | 2700 |
| acctaaaaat tggaatgccc aatgatgagt tatgataaaa ttgtgacgtg atttatgaag | 2760 |
| tctaatgttt agttggcttg cagtttcaga tgcgataaag aattttatga tttagctctt | 2820 |
| tggtttttta acatgcaaac atttaattgt actgaaaaac atttatttcg aaacatgtag | 2880 |
| gagactattg gatattgaaa ttaaaattga cttttggtg tttcacaata tttcttaata | 2940 |
| aacactacga ctatgtaaat aggtggtgga tcaaagggaa agaaatgttt ggtgattatt | 3000 |
| tttagaaaag acaagaagta tttgataaat ggttatttt caaccgatta atgagagaat | 3060 |
| gactatgaac ctatgaggtg cacctcttat gatgttgcat ggatgaagca tctaatccat | 3120 |
| gggtacaatt tactaaaata taggcccaat tctgagacag gaacatttac aactcatgta | 3180 |
| caaagaagaa acttaaagta tcatggatgc cgggatattt ccttcttcaa atctttcaaa | 3240 |
| agctgtagtt ttcattataa ggaaaaatga ttataactaa catcttctat aggtgatgag | 3300 |
| tggacactag aaggctttcc tataataaca gtagagagag tagaaaagcc tgtcagcatg | 3360 |
| cggtccataa gtatatatac atattttcag cgcttaaagt aaattttctt gtaccaaaaa | 3420 |
| aagataaatt ttcaaaataa aaactaaaat caactgaaat gtttgaaatc tgattcgtag | 3480 |
| gtacatggag aagagtgtaa gacagcaaat atcataagg cagaataaga gctggtaatc | 3540 |
| ttgtaacctg gcgcaactat gttatgcatg tctatatgtg tgcatgttta tgtataacaa | 3600 |
| gtaatatttc ttttcttatt tactcacttc agttaggaag tcaatccaat ctccctttgc | 3660 |
| ttgggtgtgt tcagattatc aagggccata acagtagtgc tggtaagcac ctgtttaatg | 3720 |
| gataaatggc gacaaattct ctccccttct gctcactcta ttatcatacc ttccgtctta | 3780 |
| cccatctgct atatcttata aggaaacataa ggatcgacat agcttcatgc tatcacatta | 3840 |
| caagctaaga tcggaataat acctaatctt ttcgatctac tattaggtat tactataggg | 3900 |
| ttgtaaattg ggtttaggtt ttgaactata ttatattttg gtgtaagaat atagtgccac | 3960 |
| actatcttga accagactag ctgttgcact ttttttgcag gcatcaatat tttgttcatc | 4020 |
| caaaaaaaaa tattgcacat gcacagatga agtatgaggg c | 4061 |

<210> SEQ ID NO 75
<211> LENGTH: 680
<212> TYPE: DNA
<213> ORGANISM: Artificial Sequence
<220> FEATURE:
<223> OTHER INFORMATION: synthetic

<400> SEQUENCE: 75

| | |
|---|---|
| atggggaggg ggaagataga gatcaagaag atagagaatc ctacaaacag gcaggtgacc | 60 |
| tactccaaga ggaggacggg gatcatgaag aaggctaagg aactgacggt gctttgcgat | 120 |

```
gctgaggtct cgcttatcat gttctccagc accggcaagt tctccgagta ttgcagcccc       180
ctttccgaca ccaagaccat atttgatcgc taccagcagg tgtcagggat caacctgtgg       240
agcgcccaat acgagaaaat gcaaacact tgaaccatc tgagggagat caaccagaac         300
ctccgcagag aaataaggca gcggatgggt gaagatctcg acagtttggg catccatgaa       360
ctgcgcggtc ttgagcaaaa tttagatgag ctttgaagg ttgttcgtca cagaaaatac        420
catgtgatca ccacgcagac ggatacctac aagaaaagg caaggctaac atgctttctt       480
accatcattc tttacggtct tgatccggt tttgcgtgtc cacttcttac gtagtctttt        540
tcaaacattc ctatctaaga ctgaaggtaa tgatttgcaa aggaatagct ttactgtttt       600
cctctaagta gatgaaatat tactcacgta gaaggagcc atcataattg cagaaagaat       660
aaaactgaat ggaatatgag                                                   680

<210> SEQ ID NO 76
<211> LENGTH: 167
<212> TYPE: PRT
<213> ORGANISM: Artificial Sequence
<220> FEATURE:
<223> OTHER INFORMATION: synthetic predicted sequence of tDEF1

<400> SEQUENCE: 76

Met Gly Arg Gly Lys Ile Glu Ile Lys Ile Glu Asn Pro Thr Asn
1               5                   10                  15

Arg Gln Val Thr Tyr Ser Lys Arg Arg Thr Gly Ile Met Lys Lys Ala
            20                  25                  30

Lys Glu Leu Thr Val Leu Cys Asp Ala Glu Val Ser Leu Ile Met Phe
        35                  40                  45

Ser Ser Thr Gly Lys Phe Ser Glu Tyr Cys Ser Pro Leu Ser Asp Thr
    50                  55                  60

Lys Thr Ile Phe Asp Arg Tyr Gln Gln Val Ser Gly Ile Asn Leu Trp
65                  70                  75                  80

Ser Ala Gln Tyr Glu Lys Met Gln Asn Thr Leu Asn His Leu Arg Glu
                85                  90                  95

Ile Asn Gln Asn Leu Arg Arg Glu Ile Arg Gln Arg Met Gly Glu Asp
            100                 105                 110

Leu Asp Ser Leu Gly Ile His Glu Leu Arg Gly Leu Glu Gln Asn Leu
        115                 120                 125

Asp Glu Ala Leu Lys Val Val Arg His Arg Lys Tyr His Val Ile Thr
    130                 135                 140

Thr Gln Thr Asp Thr Tyr Lys Lys Lys Ala Arg Leu Thr Cys Phe Leu
145                 150                 155                 160

Thr Ile Ile Leu Tyr Gly Leu
                165

<210> SEQ ID NO 77
<211> LENGTH: 1850
<212> TYPE: DNA
<213> ORGANISM: Elaeis guineensis

<400> SEQUENCE: 77
aaatcagcta atgtagacca tctgaactac ttgttcatca cccttatccc aaaaaaaaat       60
tggtgtgtat tcagttagag acttcaggcc aataagcctg attaatggag taataaaaaa     120
tatttcaaaa actctatcga aaggctctc acagaaaatg aatttgttaa ttttatccac      180
agagcttgct ttcaacaaag gaagaaatat ctctgaatat tttgtaatga ctatggaaac      240
```

```
tatacacttc tgcaaagctg aagtacacaa ggatctcaat tataaagtcg acttcgagaa    300
agcttttgac aatgtggatt ggagctttct attgaaattg ctatccagca cggggctttg    360
attcgaggtg gtgtcaatgg atagaatatc tgatttatac agctaaattc tcagtcctta    420
ttaatggtga taaaggtaaa cttttaaat tgaggaaaga tctcaggcaa ggagatcctc    480
tattcgccta gctctttctc ttagttgttg atatagaatg atcaagggag caagtaggtt    540
caatcttttt gttggaattg gatcatataa tatcatggga taacttcaaa gcttttagtt    600
cactgatgac acacttatat tttgcagata tgatctaaaa tacatcaaaa ctcttaaatt    660
tttactctat agttatgagc tactgatggg tctcaaaatt aactttgaaa aattccaatt    720
ttttggcttg agaattgcaa agatgtcagt acagcaagtt gcatctatcc tagaaagcaa    780
ggtggctaca ttttccatta cttatttggg tctcccactc catcattcta aactgaggaa    840
aacttattgg aatccactcc ttgagaaggt tcagaagaaa ttgatcgggt agaaaggtaa    900
acttcttaac ctctagggta ggcttatact aactaatgca gtgcttacag ggatcccact    960
actctggagg gatacattcc ttctcccctca attcattatc aaataaattg ataaaatcca   1020
tcgatcattc atttggagag gaaacgagga gtataactaa gggcactcta gaatatgttg   1080
gtcgaatatt tgtcgatcaa aaaaatttgg aggactgggg gttcctcaat ctaaaaattt   1140
tcaatacaat tcttctttgt aaatggtggt ggaagctcta ctctaatgct ggtgacccgt   1200
ggtgtagttt tattgccact atccacccaa cttcacacta gagatctaaa ggtatacaca   1260
aatcaacctc ttcattttgg aatggtttac agcacacatg aaatatttct actcctaatc   1320
cactttcaag ttagcaacta gtattatttt ggaaagatag ttggttacat aatcatccac   1380
tgaaggatcg atttcctcac ctttacacaa tagcattgaa gtgcaacaac tcagtggcaa   1440
aggtattaag caatctactt gataatagct cttttagtac tcctcttcct caaagatacc   1500
aagaagattt tcagagtcta taggaaagca ttgaacaaat tacattaacg gaacgacctg   1560
atactataca atggaaatgg tttagtagca atatttttt ggcatgaagg atctactatt   1620
ttctgcaaga tggaggagtt tggcctctac tgagtaatat tatataaaaa ctcctaatac   1680
caaagaaagc caagttattt gcttggctaa gtgctcacaa caaaatccca atgaaagcta   1740
atcttcttaa tagaggaata attggaactg attactgtac actttgcgat gacttatcag   1800
aaactaatga tcatctaatg ctcatctata cttttttcaaa agcaatttgg              1850
```

<210> SEQ ID NO 78
<211> LENGTH: 498
<212> TYPE: DNA
<213> ORGANISM: Artificial Sequence
<220> FEATURE:
<223> OTHER INFORMATION: synthetic

<400> SEQUENCE: 78

```
atggggaggg ggaagataga gatcaagaag atagagaatc ctaccaacag gcaggtgacc     60
tactccaaga ggaggacggg gatcatgaag aaggctaagg agctgacggt gctttgcgat    120
gctgaggtct cgcttatcat gttctccagc accggcaagt tctccgagta ttgcagcccc    180
ctttccgaca ccaagaccat atttgatcgc taccagcagg tgtcagggat caacctgtgg    240
agcgcccaat acgagaaaat gcaaaacact ttgaaccatc tgagggagat caaccagaac    300
ctccgcagag aaataaggca gcggatgggg aagatctcg acagtttggg catccatgaa    360
ctgcgcggtc ttgagcaaaa tttagatgag gctttgaagg ttgttcgtca cagaaaatac    420
```

```
catgtgatca ccacgcagac ggatacctac aagaaaaaga tgcatctcaa gtcagcacta    480
gaccatcttc taaaatag                                                  498
```

<210> SEQ ID NO 79
<211> LENGTH: 165
<212> TYPE: PRT
<213> ORGANISM: Artificial Sequence
<220> FEATURE:
<223> OTHER INFORMATION: synthetic

<400> SEQUENCE: 79

```
Met Gly Arg Gly Lys Ile Glu Ile Lys Ile Glu Asn Pro Thr Asn
1               5                   10                  15

Arg Gln Val Thr Tyr Ser Lys Arg Arg Thr Gly Ile Met Lys Lys Ala
            20                  25                  30

Lys Glu Leu Thr Val Leu Cys Asp Ala Glu Val Ser Leu Ile Met Phe
        35                  40                  45

Ser Ser Thr Gly Lys Phe Ser Glu Tyr Cys Ser Pro Leu Ser Asp Thr
    50                  55                  60

Lys Thr Ile Phe Asp Arg Tyr Gln Gln Val Ser Gly Ile Asn Leu Trp
65              70                  75                  80

Ser Ala Gln Tyr Glu Lys Met Gln Asn Thr Leu Asn His Leu Arg Glu
                85                  90                  95

Ile Asn Gln Asn Leu Arg Arg Glu Ile Arg Gln Arg Met Gly Glu Asp
            100                 105                 110

Leu Asp Ser Leu Gly Ile His Glu Leu Arg Gly Leu Glu Gln Asn Leu
        115                 120                 125

Asp Glu Ala Leu Lys Val Val Arg His Arg Lys Tyr His Val Ile Thr
    130                 135                 140

Thr Gln Thr Asp Thr Tyr Lys Lys Lys Met His Leu Lys Ser Ala Leu
145                 150                 155                 160

Asp His Leu Leu Lys
                165
```

<210> SEQ ID NO 80
<211> LENGTH: 459
<212> TYPE: DNA
<213> ORGANISM: Artificial Sequence
<220> FEATURE:
<223> OTHER INFORMATION: synthetic

<400> SEQUENCE: 80

```
atggggaggg ggaagataga gatcaagaag atagagaatc ctacaaacag gcaggtgacc     60
tactccaaga ggaggacggg gatcatgaag aaggctaagg aactgacggt gctttgcgat    120
gctgaggtct cgcttatcat gttctccagc accggcaagt tctccgagta ttgcagcccc    180
ctttccgaca ccaagaccat atttgatcgc taccagcagg tgtcagggat caacctgtgg    240
agcgcccaat acgagaaaat gcaaaacact ttgaaccatc tgaggagat caaccagaac    300 ctccgcagag aaataaggca gcggatgggt gaagatctcg acagtttggg catccatgaa    360
ctgcgcggtc ttgagcaaaa tttagatgag gctttgaagg ttgttcgtca cagaaaatac    420
catgtgatca ccacgcagac ggatacctac aagaaaaag                          459
```

<210> SEQ ID NO 81
<211> LENGTH: 153
<212> TYPE: PRT
<213> ORGANISM: Artificial Sequence
<220> FEATURE:

<223> OTHER INFORMATION: synthetic

<400> SEQUENCE: 81

| Met | Gly | Arg | Gly | Lys | Ile | Glu | Ile | Lys | Lys | Ile | Glu | Asn | Pro | Thr | Asn |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Arg | Gln | Val | Thr | Tyr | Ser | Lys | Arg | Arg | Thr | Gly | Ile | Met | Lys | Lys | Ala |
|     |     |     | 20  |     |     |     |     | 25  |     |     |     |     | 30  |     |     |

| Lys | Glu | Leu | Thr | Val | Leu | Cys | Asp | Ala | Glu | Val | Ser | Leu | Ile | Met | Phe |
|     |     |     | 35  |     |     |     |     | 40  |     |     |     |     | 45  |     |     |

| Ser | Ser | Thr | Gly | Lys | Phe | Ser | Glu | Tyr | Cys | Ser | Pro | Leu | Ser | Asp | Thr |
|     |     |     | 50  |     |     |     |     | 55  |     |     |     |     | 60  |     |     |

| Lys | Thr | Ile | Phe | Asp | Arg | Tyr | Gln | Gln | Val | Ser | Gly | Ile | Asn | Leu | Trp |
| 65  |     |     |     |     | 70  |     |     |     |     | 75  |     |     |     |     | 80  |

| Ser | Ala | Gln | Tyr | Glu | Lys | Met | Gln | Asn | Thr | Leu | Asn | His | Leu | Arg | Glu |
|     |     |     |     | 85  |     |     |     |     | 90  |     |     |     |     | 95  |     |

| Ile | Asn | Gln | Asn | Leu | Arg | Arg | Glu | Ile | Arg | Gln | Arg | Met | Gly | Glu | Asp |
|     |     |     |     | 100 |     |     |     |     | 105 |     |     |     |     | 110 |     |

| Leu | Asp | Ser | Leu | Gly | Ile | His | Glu | Leu | Arg | Gly | Leu | Glu | Gln | Asn | Leu |
|     |     |     | 115 |     |     |     |     | 120 |     |     |     |     | 125 |     |     |

| Asp | Glu | Ala | Leu | Lys | Val | Val | Arg | His | Arg | Lys | Tyr | His | Val | Ile | Thr |
|     | 130 |     |     |     |     | 135 |     |     |     |     | 140 |     |     |     |     |

| Thr | Gln | Thr | Asp | Thr | Tyr | Lys | Lys | Lys |
| 145 |     |     |     |     | 150 |     |     |     |

<210> SEQ ID NO 82
<211> LENGTH: 21
<212> TYPE: DNA
<213> ORGANISM: Artificial Sequence
<220> FEATURE:
<223> OTHER INFORMATION: synthetic

<400> SEQUENCE: 82
tgatatgaag ggtttcaagg t                                              21

<210> SEQ ID NO 83
<211> LENGTH: 25
<212> TYPE: DNA
<213> ORGANISM: Artificial Sequence
<220> FEATURE:
<223> OTHER INFORMATION: synthetic

<400> SEQUENCE: 83
tcctatttta gaagatggtc tagtg                                          25

<210> SEQ ID NO 84
<211> LENGTH: 576
<212> TYPE: DNA
<213> ORGANISM: Artificial Sequence
<220> FEATURE:
<223> OTHER INFORMATION: synthetic

<400> SEQUENCE: 84
tgatatgaag ggtttcaagg tggtttgcct cgttcaaatc aaaggatttt gaagattaat    60
attccaagat aaggttctcc aactccatta ggaaagtgtc ttcatgtcat cttagagaag   120
cagctcgtac caaacttgac agatgtttta tttatttaga gtgacacaga taccctttgg   180
caatactctc catccttgtc cgaacaactt ctaatcacac ctcacttatc ttgcatctaa   240
ctcagaggct acaagttaca cctttcaaca aaccttttcg gtttgaaaat ttgtgatttc   300
attatttaga gttcgaagag catatcaagt attggtcgga gttggcaccc aaagcaaacg   360

```
aaacagttac tgacatggtc caaaagctga gatttctaag atcccaactt aagcactgaa    420
taaagccatt atgggaaata tcattttaac gaaagaggaa tttagagtaa gaattgattc    480
tcttgatacc gaagaagaac taatacagct ttcatcactt caaaatgatg aacagatgca    540
tctcaagtca gcactagacc atcttctaaa atagga                              576
```

<210> SEQ ID NO 85
<211> LENGTH: 22
<212> TYPE: DNA
<213> ORGANISM: Artificial Sequence
<220> FEATURE:
<223> OTHER INFORMATION: synthetic

<400> SEQUENCE: 85

```
agaattgatt ctcttgatac cg                                             22
```

<210> SEQ ID NO 86
<211> LENGTH: 24
<212> TYPE: DNA
<213> ORGANISM: Artificial Sequence
<220> FEATURE:
<223> OTHER INFORMATION: synthetic

<400> SEQUENCE: 86

```
ttttattact ccattaatca ggct                                           24
```

<210> SEQ ID NO 87
<211> LENGTH: 633
<212> TYPE: DNA
<213> ORGANISM: Artificial Sequence
<220> FEATURE:
<223> OTHER INFORMATION: synthetic

<400> SEQUENCE: 87

```
agaattgatt ctcttgatac cgaagaagaa ctaatacagc tttcatcact tcaaaatgat    60
gaacagatgc atctcaagtc agcactagac catcttctaa aataggaaga tctatggaag    120
caacactccc aaatgcagtg gcttcaaaat ggggattgca atacgaagtt tatccatgtt    180
tgggcaagta acaggaaaaa agaatactat cactgaact ctagcaaggc gatcagaaga    240
ttatcgaata gcagcaaatc caatccacat tctacaactt ttttctacc ctactaggct    300 cgactgagga atgactcatc caagctgatt ggaagattct ttatccagaa ggacctctgg    360
atcttgctga cattgagtat ccatttatgg agaaagaaat ccatgataca gtgtatgact    420
tggctttgga aaagtcaccc ggatgatatt ttcccattct ccttctataa gcacttctag    480
tgtatcatca acatgaccct gatgaaccta ctgtaaaatc agctaatgta gaccatctga    540
actacttgtt catcaccctt atcccaaaaa aaaattggtg tgtattcagt tagagacttc    600
aggccaataa gcctgattaa tggagtaata aaa                                 633
```

<210> SEQ ID NO 88
<211> LENGTH: 20
<212> TYPE: DNA
<213> ORGANISM: Artificial Sequence
<220> FEATURE:
<223> OTHER INFORMATION: synthetic

<400> SEQUENCE: 88

```
gcaaggagat cctctattcg                                                20
```

<210> SEQ ID NO 89

```
<211> LENGTH: 20
<212> TYPE: DNA
<213> ORGANISM: Artificial Sequence
<220> FEATURE:
<223> OTHER INFORMATION: synthetic

<400> SEQUENCE: 89
gatcgacaaa tattcgacca                                                   20

<210> SEQ ID NO 90
<211> LENGTH: 632
<212> TYPE: DNA
<213> ORGANISM: Artificial Sequence
<220> FEATURE:
<223> OTHER INFORMATION: synthetic

<400> SEQUENCE: 90
gcaaggagat cctctattcg cctagctctt tctcttagtt gttgatatag aatgatcaag        60
ggagcaagta ggttcaatct ttttgttgga attggatcat ataatatcat gggataactt       120
caaagctttt agttcactga tgacacactt atattttgca gatatgatct aaaatacatc       180
aaaactctta aattttact ctatagttat gagctactga tgggtctcaa aattaacttt        240 gaaaattcc aattttttgg cttgagaatt gcaaagatgt cagtacagca agttgcatct        300
atcctagaaa gcaaggtggc tacattttcc attacttatt tgggtctccc actccatcat       360
tctaaactga ggaaaactta ttggaatcca ctccttgaga aggttcagaa gaaattgatc       420
gggtagaaag gtaaacttct taacctctag ggtaggctta tactaactaa tgcagtgctt       480
acagggatcc cactactctg gagggataca ttccttctcc ctcaattcat tatcaaataa       540
attgataaaa tccatcgatc attcatttgg agaggaaacg aggagtataa ctaagggcac       600
tctagaatat gttggtcgaa tatttgtcga tc                                     632

<210> SEQ ID NO 91
<211> LENGTH: 24
<212> TYPE: DNA
<213> ORGANISM: Elaeis guineensis

<400> SEQUENCE: 91
ctctagcaag gcgatcagaa gatt                                              24

<210> SEQ ID NO 92
<211> LENGTH: 24
<212> TYPE: DNA
<213> ORGANISM: Elaeis guineensis

<400> SEQUENCE: 92
tcaggtgtta tgtcagtttg gact                                              24

<210> SEQ ID NO 93
<211> LENGTH: 24
<212> TYPE: DNA
<213> ORGANISM: Elaeis guineensis

<400> SEQUENCE: 93
aagtctccac tctatctatc ccga                                              24

<210> SEQ ID NO 94
<211> LENGTH: 24
<212> TYPE: DNA
<213> ORGANISM: Elaeis guineensis

<400> SEQUENCE: 94
```

```
gggtcaacaa ggtctgagaa cact                                              24

<210> SEQ ID NO 95
<211> LENGTH: 24
<212> TYPE: DNA
<213> ORGANISM: Elaeis guineensis

<400> SEQUENCE: 95
cgcaatcaga atcaactggc caat                                              24

<210> SEQ ID NO 96
<211> LENGTH: 24
<212> TYPE: DNA
<213> ORGANISM: Elaeis guineensis

<400> SEQUENCE: 96
atgatacacg gttgcatgcc ctgc                                              24

<210> SEQ ID NO 97
<211> LENGTH: 24
<212> TYPE: DNA
<213> ORGANISM: Elaeis guineensis

<400> SEQUENCE: 97
gatctatggt gcaaggagtt aatt                                              24

<210> SEQ ID NO 98
<211> LENGTH: 24
<212> TYPE: DNA
<213> ORGANISM: Elaeis guineensis

<400> SEQUENCE: 98
agagagaggg ttaaaggaca atgc                                              24

<210> SEQ ID NO 99
<211> LENGTH: 24
<212> TYPE: DNA
<213> ORGANISM: Elaeis guineensis

<400> SEQUENCE: 99
atagggagaa tagcttggct tcga                                              24

<210> SEQ ID NO 100
<211> LENGTH: 24
<212> TYPE: DNA
<213> ORGANISM: Elaeis guineensis

<400> SEQUENCE: 100
tcgggttctt ttattcgtgg attt                                              24

<210> SEQ ID NO 101
<211> LENGTH: 24
<212> TYPE: DNA
<213> ORGANISM: Elaeis guineensis

<400> SEQUENCE: 101
aggggagatt gttggcttag cttg                                              24

<210> SEQ ID NO 102
<211> LENGTH: 24
<212> TYPE: DNA
<213> ORGANISM: Elaeis guineensis
```

-continued

```
<400> SEQUENCE: 102
agtagactcg atgatgataa gact                                          24

<210> SEQ ID NO 103
<211> LENGTH: 24
<212> TYPE: DNA
<213> ORGANISM: Elaeis guineensis

<400> SEQUENCE: 103
accagcacgg tcaaggatag gcat                                          24

<210> SEQ ID NO 104
<211> LENGTH: 24
<212> TYPE: DNA
<213> ORGANISM: Elaeis guineensis

<400> SEQUENCE: 104
atagtagact cgatgatgat aaga                                          24

<210> SEQ ID NO 105
<211> LENGTH: 24
<212> TYPE: DNA
<213> ORGANISM: Elaeis guineensis

<400> SEQUENCE: 105
cctccaacat cggccaagtt agtt                                          24

<210> SEQ ID NO 106
<211> LENGTH: 24
<212> TYPE: DNA
<213> ORGANISM: Elaeis guineensis

<400> SEQUENCE: 106
aaatcctact tgtttctctg acct                                          24

<210> SEQ ID NO 107
<211> LENGTH: 24
<212> TYPE: DNA
<213> ORGANISM: Elaeis guineensis

<400> SEQUENCE: 107
catgaggcat gcaaggtatt gaat                                          24

<210> SEQ ID NO 108
<211> LENGTH: 24
<212> TYPE: DNA
<213> ORGANISM: Elaeis guineensis

<400> SEQUENCE: 108
aaggctggct aactcaaaga agag                                          24

<210> SEQ ID NO 109
<211> LENGTH: 24
<212> TYPE: DNA
<213> ORGANISM: Elaeis guineensis

<400> SEQUENCE: 109
aatgatcgag aagggctgga gaca                                          24

<210> SEQ ID NO 110
<211> LENGTH: 24
<212> TYPE: DNA
<213> ORGANISM: Elaeis guineensis
```

```
<400> SEQUENCE: 110
tgacccacca tcgagaagga ccga                                          24

<210> SEQ ID NO 111
<211> LENGTH: 24
<212> TYPE: DNA
<213> ORGANISM: Elaeis guineensis

<400> SEQUENCE: 111
ataactgaca agtggcattg atct                                          24

<210> SEQ ID NO 112
<211> LENGTH: 24
<212> TYPE: DNA
<213> ORGANISM: Elaeis guineensis

<400> SEQUENCE: 112
agaaggatga gaagagagat tgtc                                          24

<210> SEQ ID NO 113
<211> LENGTH: 24
<212> TYPE: DNA
<213> ORGANISM: Elaeis guineensis

<400> SEQUENCE: 113
aaagatgtta gctcctgttc gaga                                          24

<210> SEQ ID NO 114
<211> LENGTH: 24
<212> TYPE: DNA
<213> ORGANISM: Elaeis guineensis

<400> SEQUENCE: 114
aaaggctggc taactcaaag aaga                                          24

<210> SEQ ID NO 115
<211> LENGTH: 24
<212> TYPE: DNA
<213> ORGANISM: Elaeis guineensis

<400> SEQUENCE: 115
agagattgtg aacaaatgga gaga                                          24

<210> SEQ ID NO 116
<211> LENGTH: 24
<212> TYPE: DNA
<213> ORGANISM: Elaeis guineensis

<400> SEQUENCE: 116
atattgtctg ctcttcacca aaga                                          24

<210> SEQ ID NO 117
<211> LENGTH: 24
<212> TYPE: DNA
<213> ORGANISM: Elaeis guineensis

<400> SEQUENCE: 117
ctcgtaaggc ccaagggtag tcat                                          24

<210> SEQ ID NO 118
<211> LENGTH: 24
<212> TYPE: DNA
```

```
<213> ORGANISM: Elaeis guineensis

<400> SEQUENCE: 118
aaaatagctt gacccaccat cgag                                              24

<210> SEQ ID NO 119
<211> LENGTH: 24
<212> TYPE: DNA
<213> ORGANISM: Elaeis guineensis

<400> SEQUENCE: 119
atagaatagg gagaatagct tggc                                              24

<210> SEQ ID NO 120
<211> LENGTH: 24
<212> TYPE: DNA
<213> ORGANISM: Elaeis guineensis

<400> SEQUENCE: 120
tcctgtccag atatttgcgc ctct                                              24

<210> SEQ ID NO 121
<211> LENGTH: 24
<212> TYPE: DNA
<213> ORGANISM: Elaeis guineensis

<400> SEQUENCE: 121
acaactagcc aatgatcgag aagg                                              24

<210> SEQ ID NO 122
<211> LENGTH: 24
<212> TYPE: DNA
<213> ORGANISM: Elaeis guineensis

<400> SEQUENCE: 122
aacacactgc tgaaaggac tagg                                               24

<210> SEQ ID NO 123
<211> LENGTH: 24
<212> TYPE: DNA
<213> ORGANISM: Elaeis guineensis

<400> SEQUENCE: 123
aaactcatgg tgtcaaggga cgtg                                              24

<210> SEQ ID NO 124
<211> LENGTH: 24
<212> TYPE: DNA
<213> ORGANISM: Elaeis guineensis

<400> SEQUENCE: 124
gctacacagg cacaatctcg attt                                              24

<210> SEQ ID NO 125
<211> LENGTH: 19
<212> TYPE: DNA
<213> ORGANISM: Artificial Sequence
<220> FEATURE:
<223> OTHER INFORMATION: synthetic

<400> SEQUENCE: 125
ctttccgaca ccaagacca                                                    19
```

```
<210> SEQ ID NO 126
<211> LENGTH: 24
<212> TYPE: DNA
<213> ORGANISM: Artificial Sequence
<220> FEATURE:
<223> OTHER INFORMATION: synthetic

<400> SEQUENCE: 126
caagtagcgg atagagaggc ttac                                    24

<210> SEQ ID NO 127
<211> LENGTH: 23
<212> TYPE: DNA
<213> ORGANISM: Artificial Sequence
<220> FEATURE:
<223> OTHER INFORMATION: synthetic

<400> SEQUENCE: 127
gttcgtcaca gaaaatacca tgt                                     23

<210> SEQ ID NO 128
<211> LENGTH: 21
<212> TYPE: DNA
<213> ORGANISM: Artificial Sequence
<220> FEATURE:
<223> OTHER INFORMATION: synthetic

<400> SEQUENCE: 128
tcttctgatc gccttgctag a                                       21

<210> SEQ ID NO 129
<211> LENGTH: 21
<212> TYPE: DNA
<213> ORGANISM: Artificial Sequence
<220> FEATURE:
<223> OTHER INFORMATION: synthetic

<400> SEQUENCE: 129
accggatcaa agaccgtaaa g                                       21

<210> SEQ ID NO 130
<211> LENGTH: 24
<212> TYPE: DNA
<213> ORGANISM: Elaeis guineensis

<400> SEQUENCE: 130
aaattcttac ttctgagcat actt                                    24

<210> SEQ ID NO 131
<211> LENGTH: 24
<212> TYPE: DNA
<213> ORGANISM: Elaeis guineensis

<400> SEQUENCE: 131
cgaggtggtg tcaatggata gaat                                    24

<210> SEQ ID NO 132
<211> LENGTH: 24
<212> TYPE: DNA
<213> ORGANISM: Elaeis guineensis

<400> SEQUENCE: 132
ctctttgtta tacaatcacg gtgt                                    24

<210> SEQ ID NO 133
```

```
<211> LENGTH: 24
<212> TYPE: DNA
<213> ORGANISM: Elaeis guineensis

<400> SEQUENCE: 133
caaggcgatc agaagattat cgaa                                          24

<210> SEQ ID NO 134
<211> LENGTH: 24
<212> TYPE: DNA
<213> ORGANISM: Elaeis guineensis

<400> SEQUENCE: 134
gtgccatatg tcatagtcaa ctgt                                          24

<210> SEQ ID NO 135
<211> LENGTH: 24
<212> TYPE: DNA
<213> ORGANISM: Elaeis guineensis

<400> SEQUENCE: 135
aatctgatat tggcatccac atga                                          24

<210> SEQ ID NO 136
<211> LENGTH: 24
<212> TYPE: DNA
<213> ORGANISM: Elaeis guineensis

<400> SEQUENCE: 136
cctgactttc ggttggctgt ctct                                          24

<210> SEQ ID NO 137
<211> LENGTH: 24
<212> TYPE: DNA
<213> ORGANISM: Elaeis guineensis

<400> SEQUENCE: 137
aatcctactt gtttctctga cctt                                          24

<210> SEQ ID NO 138
<211> LENGTH: 24
<212> TYPE: DNA
<213> ORGANISM: Elaeis guineensis

<400> SEQUENCE: 138
ctctagcaag gcgatcagaa gatt                                          24

<210> SEQ ID NO 139
<211> LENGTH: 24
<212> TYPE: DNA
<213> ORGANISM: Elaeis guineensis

<400> SEQUENCE: 139
aaatggcata ctctggcaat tcga                                          24

<210> SEQ ID NO 140
<211> LENGTH: 24
<212> TYPE: DNA
<213> ORGANISM: Elaeis guineensis

<400> SEQUENCE: 140
tctatctcat ccctctcaac caat                                          24
```

```
<210> SEQ ID NO 141
<211> LENGTH: 24
<212> TYPE: DNA
<213> ORGANISM: Elaeis guineensis

<400> SEQUENCE: 141
gtagcccatg tctttgtttt ccct                                      24

<210> SEQ ID NO 142
<211> LENGTH: 24
<212> TYPE: DNA
<213> ORGANISM: Elaeis guineensis

<400> SEQUENCE: 142
tgtggatggc taacgatatg gact                                      24

<210> SEQ ID NO 143
<211> LENGTH: 24
<212> TYPE: DNA
<213> ORGANISM: Elaeis guineensis

<400> SEQUENCE: 143
actagcacca tgtgtcgtta tggg                                      24

<210> SEQ ID NO 144
<211> LENGTH: 24
<212> TYPE: DNA
<213> ORGANISM: Elaeis guineensis

<400> SEQUENCE: 144
ttcagtcaga gacttcaggc caat                                      24

<210> SEQ ID NO 145
<211> LENGTH: 24
<212> TYPE: DNA
<213> ORGANISM: Elaeis guineensis

<400> SEQUENCE: 145
aggctctcac agaaaatgaa tttg                                      24

<210> SEQ ID NO 146
<211> LENGTH: 24
<212> TYPE: DNA
<213> ORGANISM: Elaeis guineensis

<400> SEQUENCE: 146
ttatacagct aaattctcag tcct                                      24

<210> SEQ ID NO 147
<211> LENGTH: 24
<212> TYPE: DNA
<213> ORGANISM: Elaeis guineensis

<400> SEQUENCE: 147
tatacagcta aattctcagt cctt                                      24

<210> SEQ ID NO 148
<211> LENGTH: 24
<212> TYPE: DNA
<213> ORGANISM: Elaeis guineensis

<400> SEQUENCE: 148
acagctaaat tctcagtcct tatt                                      24
```

<210> SEQ ID NO 149
<211> LENGTH: 24
<212> TYPE: DNA
<213> ORGANISM: Elaeis guineensis

<400> SEQUENCE: 149
gctaaattct cagtccttat taat                                    24

<210> SEQ ID NO 150
<211> LENGTH: 24
<212> TYPE: DNA
<213> ORGANISM: Elaeis guineensis

<400> SEQUENCE: 150
cattctaaac tgaggaaaac ttat                                    24

<210> SEQ ID NO 151
<211> LENGTH: 24
<212> TYPE: DNA
<213> ORGANISM: Elaeis guineensis

<400> SEQUENCE: 151
aggttcagaa gaaattgatc gggt                                    24

<210> SEQ ID NO 152
<211> LENGTH: 24
<212> TYPE: DNA
<213> ORGANISM: Elaeis guineensis

<400> SEQUENCE: 152
attgatcggg tagaaaggta aact                                    24

<210> SEQ ID NO 153
<211> LENGTH: 24
<212> TYPE: DNA
<213> ORGANISM: Elaeis guineensis

<400> SEQUENCE: 153
tgcagtgctt acagggatcc cact                                    24

<210> SEQ ID NO 154
<211> LENGTH: 24
<212> TYPE: DNA
<213> ORGANISM: Elaeis guineensis

<400> SEQUENCE: 154
acgaggagta taactaaggg cact                                    24

<210> SEQ ID NO 155
<211> LENGTH: 24
<212> TYPE: DNA
<213> ORGANISM: Elaeis guineensis

<400> SEQUENCE: 155
aagggcactc tagaatatgt tggt                                    24

<210> SEQ ID NO 156
<211> LENGTH: 24
<212> TYPE: DNA
<213> ORGANISM: Elaeis guineensis

<400> SEQUENCE: 156
aagggcactt tagaatatgt tggt                                    24

```
<210> SEQ ID NO 157
<211> LENGTH: 24
<212> TYPE: DNA
<213> ORGANISM: Elaeis guineensis

<400> SEQUENCE: 157
tggtttacag cacacatgaa atat                                              24

<210> SEQ ID NO 158
<211> LENGTH: 24
<212> TYPE: DNA
<213> ORGANISM: Elaeis guineensis

<400> SEQUENCE: 158
ggcatgaagg atctactatt ttct                                              24

<210> SEQ ID NO 159
<211> LENGTH: 24
<212> TYPE: DNA
<213> ORGANISM: Elaeis guineensis

<400> SEQUENCE: 159
ggcatgaagg atctactatt ttct                                              24

<210> SEQ ID NO 160
<211> LENGTH: 24
<212> TYPE: DNA
<213> ORGANISM: Elaeis guineensis

<400> SEQUENCE: 160
acttttatgc atgcttaaca ccct                                              24

<210> SEQ ID NO 161
<211> LENGTH: 24
<212> TYPE: DNA
<213> ORGANISM: Elaeis guineensis

<400> SEQUENCE: 161
atgcatgctt aacaccctat ggga                                              24
```